(12) United States Patent
Apt et al.

(10) Patent No.: US 12,203,075 B2
(45) Date of Patent: *Jan. 21, 2025

(54) POLYUNSATURATED FATTY ACID SYNTHASE NUCLEIC ACID MOLECULES AND POLYPEPTIDES, COMPOSITIONS, AND METHODS OF MAKING AND USES THEREOF

(71) Applicant: DSM IP Assets B.V., Heerlen (NL)

(72) Inventors: Kirk E. Apt, Ellicott City, MD (US);
Leslie Richter, Broomfield, CO (US);
David Simpson, Boulder, CO (US);
Ross Zirkle, Mt. Airy, MD (US)

(73) Assignee: DSM IP Assets B.V., Maastricht (NL)

( * ) Notice: Subject to any disclaimer, the term of this patent is extended or adjusted under 35 U.S.C. 154(b) by 1389 days.

This patent is subject to a terminal disclaimer.

(21) Appl. No.: 16/700,009

(22) Filed: Dec. 2, 2019

(65) Prior Publication Data
US 2020/0199598 A1 Jun. 25, 2020

Related U.S. Application Data

(62) Division of application No. 15/371,410, filed on Dec. 7, 2016, now Pat. No. 10,538,772, which is a division of application No. 14/566,458, filed on Dec. 10, 2014, now Pat. No. 9,540,666, which is a division of application No. 12/727,851, filed on Mar. 19, 2010, now Pat. No. 8,940,884.

(60) Provisional application No. 61/296,460, filed on Jan. 19, 2010, provisional application No. 61/161,742, filed on Mar. 19, 2009.

(51) Int. Cl.
| C12N 15/52 | (2006.01) |
| A61K 38/00 | (2006.01) |
| C12N 9/02 | (2006.01) |
| C12N 9/04 | (2006.01) |
| C12N 9/10 | (2006.01) |
| C12N 9/88 | (2006.01) |
| C12N 15/82 | (2006.01) |
| C12P 7/6432 | (2022.01) |
| C12P 7/6434 | (2022.01) |
| C12P 7/6472 | (2022.01) |

(52) U.S. Cl.
CPC ........... *C12N 15/52* (2013.01); *C12N 9/0006* (2013.01); *C12N 9/001* (2013.01); *C12N 9/1029* (2013.01); *C12N 9/88* (2013.01); *C12N 15/8247* (2013.01); *C12P 7/6432* (2022.01); *C12P 7/6434* (2022.01); *C12P 7/6472* (2013.01); *C12Y 101/01* (2013.01); *C12Y 203/01039* (2013.01); *C12Y 402/01059* (2013.01); *A61K 38/00* (2013.01); *C12Y 103/01* (2013.01); *C12Y 402/01* (2013.01); *Y02P 20/52* (2015.11)

(58) Field of Classification Search
None
See application file for complete search history.

(56) References Cited

U.S. PATENT DOCUMENTS

| 4,721,626 | A | 1/1988 | Rule |
| 5,601,860 | A | 2/1997 | Lien et al. |
| 5,952,544 | A | 9/1999 | Browse et al. |
| 5,981,781 | A | 11/1999 | Knowlton |
| 6,036,992 | A | 3/2000 | Borror et al. |
| 6,051,754 | A | 4/2000 | Knutzon |
| 6,160,007 | A | 12/2000 | DeMichele |
| 6,372,965 | B1 | 4/2002 | Lightner et al. |
| 6,432,684 | B1 | 8/2002 | Mukerji et al. |
| 6,566,583 | B1 | 5/2003 | Facciotti et al. |
| 7,211,418 | B2 | 5/2007 | Metz et al. |
| 7,217,856 | B2 * | 5/2007 | Weaver ............. C12P 7/62 |
| | | | 800/278 |
| 7,247,461 | B2 | 7/2007 | Metz et al. |
| 7,256,023 | B2 | 8/2007 | Metz et al. |
| 7,700,320 | B2 | 4/2010 | Metz et al. |
| 8,003,772 | B2 | 8/2011 | Weaver et al. |
| 8,426,686 | B2 | 4/2013 | Metz et al. |
| 8,829,274 | B2 | 9/2014 | Facciotti et al. |
| 9,994,828 | B2 | 6/2018 | Walsh et al. |
| 2002/0194641 | A1 | 12/2002 | Metz et al. |
| 2003/0101486 | A1 | 5/2003 | Facciotti et al. |
| 2004/0235127 | A1 | 11/2004 | Metz et al. |

(Continued)

FOREIGN PATENT DOCUMENTS

| AU | 2007226510 | 9/2007 |
| AU | 2013251201 | 11/2013 |

(Continued)

OTHER PUBLICATIONS

Hauvermale et al., Fatty acid production in *Schizochytrium* sp., Lipids 41, 2006, 739-47. (Year: 2006).*
Tonan et al, XP002635611 (2005).
Witkowski et al, "*Conversion of a β-Ketoacyl Synthase to a Malonyl Decarboxylase by Replacement of the Active-Site Cysteine with Glutamine,*" Biochemistry 1999, 38, 11643-11650.
Tonan et al, "*Identification of a Long-Chain Polyunsaturated Fatty Acid Acyl-Coenzyme A Synthetase from the Diatom Thalassiosira pseudonana,*" Plant Physiology, May 2005, vol. 138, pp. 402-408.
Shockey et al, "*Arabidopsis Contains Nine Long-Chain Acyl-Coenzyme A Synthetase Genes That Participate in Fatty Acid and Glycerolipid Metabolism,*" Plant Physiology, vol. 129, 2002, pp. 1710-1722.

(Continued)

*Primary Examiner* — Todd M Epstein
(74) *Attorney, Agent, or Firm* — Jed C. Benson

(57) ABSTRACT

The present invention is directed to isolated nucleic acid molecules and polypeptides of thraustochytrid polyunsaturated fatty acid (PUFA) synthases involved in the production of PUFAs, including PUFAs enriched in docosahexaenoic acid (DHA), eicosapentaenoic acid (EPA), or a combination thereof. The present invention is directed to vectors and host cells comprising the nucleic acid molecules, polypeptides encoded by the nucleic acid molecules, compositions comprising the nucleic acid molecules or polypeptides, and methods of making and uses thereof.

11 Claims, 68 Drawing Sheets

Specification includes a Sequence Listing.

(56) References Cited

U.S. PATENT DOCUMENTS

| | | |
|---|---|---|
| 2005/0014231 A1 | 1/2005 | Mukerji et al. |
| 2005/0100995 A1 | 5/2005 | Weaver et al. |
| 2005/0255440 A1 | 11/2005 | Downing |
| 2005/0273883 A1 | 12/2005 | Metz et al. |
| 2005/0273884 A1 | 12/2005 | Metz et al. |
| 2007/0244192 A1 | 10/2007 | Metz et al. |
| 2007/0266455 A1 | 11/2007 | Weaver et al. |
| 2008/0038794 A1 | 2/2008 | Metz et al. |
| 2008/0044871 A1 | 2/2008 | Metz et al. |
| 2008/0144473 A1 | 6/2008 | Morimoto et al. |
| 2018/0282711 A1 | 10/2018 | Walsh et al. |

FOREIGN PATENT DOCUMENTS

| | | |
|---|---|---|
| CA | 2646317 | 9/2007 |
| CA | 2755639 | 9/2010 |
| CN | 1535312 | 10/2004 |
| CN | 104073505 | 10/2014 |
| EP | 0913473 | 5/1999 |
| WO | WO1998/044917 | 10/1998 |
| WO | WO2002/094861 | 11/2002 |
| WO | WO2004/087879 | 10/2004 |
| WO | WO2005/097982 | 10/2005 |
| WO | WO2006/037947 | 4/2006 |
| WO | WO2006/125231 | 11/2006 |
| WO | WO2006/135866 | 12/2006 |
| WO | WO2007/106903 | 9/2007 |
| WO | WO2007/106908 | 9/2007 |
| WO | WO2010/108114 | 9/2010 |

OTHER PUBLICATIONS

Seffernick et al, *Melamine Deaminase and Atrazine Chlorohydrolase: 98 Percent Identical but Functionally Different*, Journal of Bacteriology, Apr. 2001, pp. 2405-2410.

Old, R.W., "Principles of gene manipulation: an introduction to genetic engineering", Studies in Microbiology, v. 2, 3rd ed., 1985.

Kendrick et al, *"Lipids of Selected Molds Grown for Production of n-3 and n-6 Polyunsaturated Fatty Acids"*, Lipids, vol. 27, No. 1 (1992).

Ivanova et al, "*Shewanella japonica* sp. nov.", Int'l Journal of Systematic and Evolutionary Microbiology (2001) 51,1027-1033.

Branden et al, *"Introduction to Protein Structure"*, Chapter 16, ISBN 0-8153-0344-0, p. 247 1991.

Skerratt et al, "*Shewanella olleyana* sp. nov., *a marine species isolated from a temperate estuary which roduces high levels of polyunsaturated fatty acids*", International Journal of Systematic and Evolutionary Microbiology (2002), 52, 2101-2106.

* cited by examiner

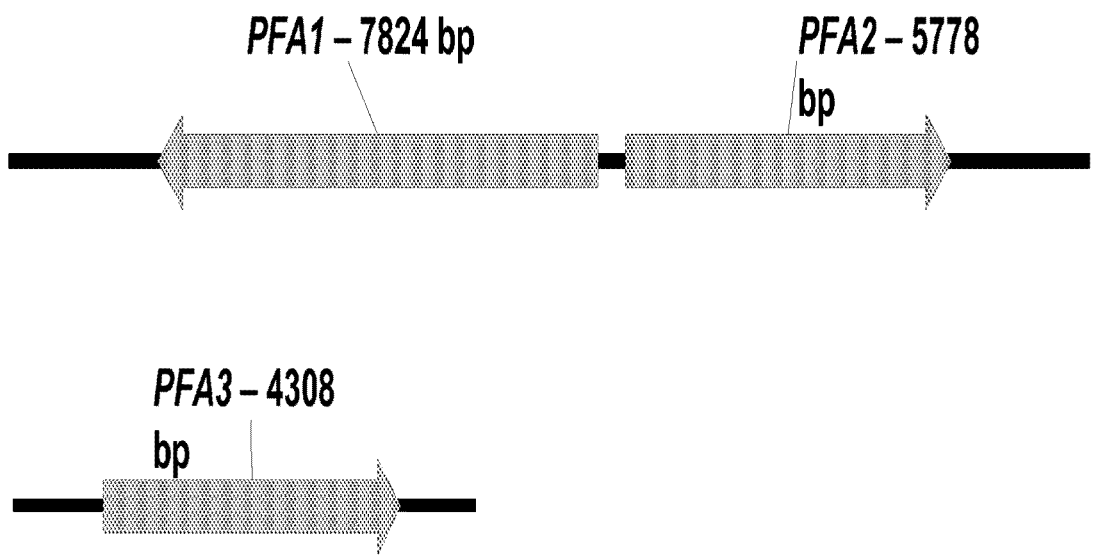
Figure 1. *Schizochytrium sp.* ATCC PTA-9695 Gene architecture

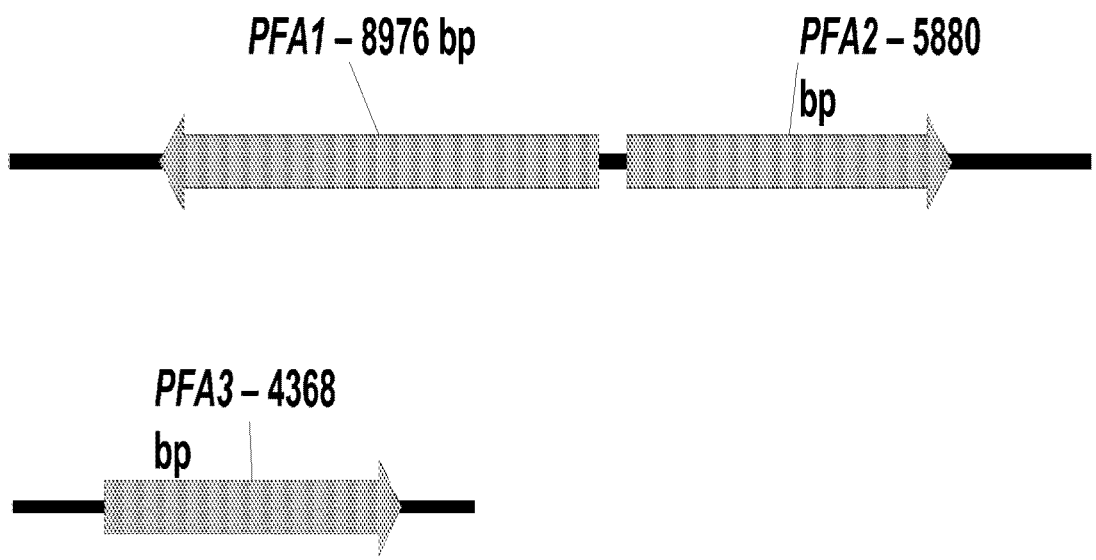
Figure 2. *Thraustochutrium sp.* ATCC PTA-10212 Gene architecture

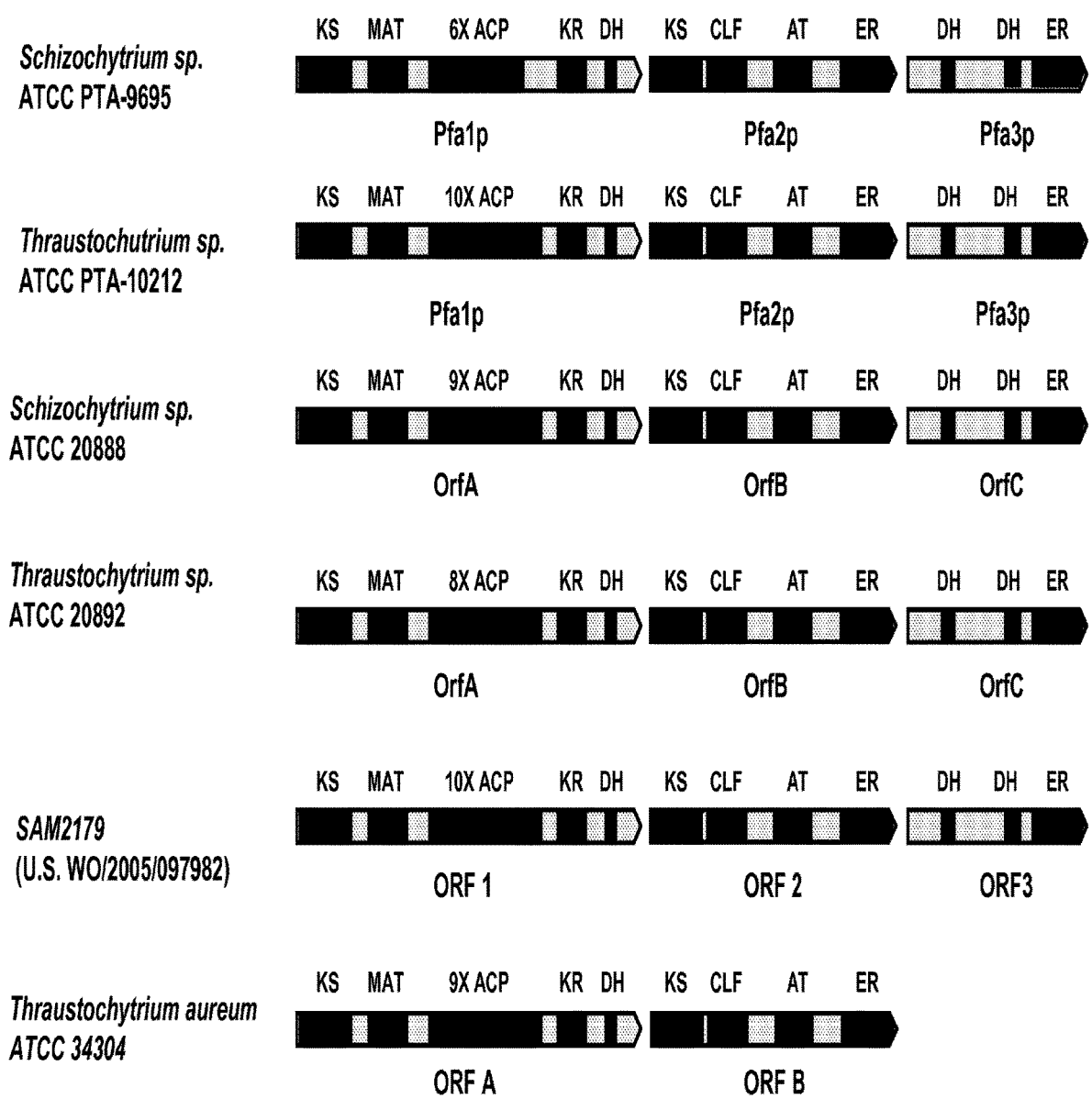
Figure 3. Domain architecture:

Figure 4.

```
                              1                                                  50
Sch_sp_9695_Pfa1p    (1)      --------------------------------------------------
Thr_aureum_ORF1      (1)      RKCIRPSLGHHWAIIGVLGRALRIVRPIRYEATNLRRLPRSGWLVALGLF
Sch_sp_2088_OrfA     (1)      --------------------------------------------------
Thr_sp_10212_Pfa1p   (1)      --------------------------------------------------
Thr_sp_20892_OrfA    (1)      --------------------------------------------------

51                                                 100
Sch_sp_9695_Pfa1p    (1)      -------------------------------------------------M
Thr_aureum_ORF1      (51)     CDLSSCAGKLDLQTRDTAKDPCCKRKWSASRAPPRPRAEADKASNEMETK
Sch_sp_2088_OrfA     (1)      ---------------------------------------MAARLQEQKGGEM
Thr_sp_10212_Pfa1p   (1)      ------------------------------------------------ME
Thr_sp_20892_OrfA    (1)      ----------------------------------------------MKDME 101                                                150
Sch_sp_9695_Pfa1p    (2)      DTRIAIVGMSAILPSGENVRESWEAIRDGLDCLSDLPADRVDVTAYYNPE
Thr_aureum_ORF1      (101)    DDRVAIVGMSAILPCGESVRESWEAIREGLDCLQDLPADRVDITAYYDPN
Sch_sp_2088_OrfA     (14)     DTRIAIIGMSAILPCGTTVRESWETIRAGIDCLSDLPEDRVDVTAYFDPV
Thr_sp_10212_Pfa1p   (3)      DQRIAIVGLSAILPSGENVRESWEAIRDGLNCLSDLPADRVDVTAYYNPT
Thr_sp_20892_OrfA    (6)      DRRVAIVGMSAHLPCGTDVKESWQAIRDGIDCLSDLPADRLDVTAYYNPN
```

Figure 4. cont.

```
                              151                                            200
Sch_sp_9695_Pfa1p   (52)      KTTKDKIYCKRGGFIPEYDFDAREFGLNMFQMEDSDANQTISLLKVKEAL
Thr_aureum_ORF1     (151)     KTTKDKIYCKRGGFIPEYDFDAREFGLNMFQMEDSDANQTVTLLKVKEAL
Sch_sp_2088_OrfA    (64)      KTTKDKIYCKRGGFIPEYDFDAREFGLNMFQMEDSDANQTISLLKVKEAL
Thr_sp_10212_Pfa1p  (53)      KGVKDKIYCKRGGFIPEYEFDSREFGLNMLQMEDSDANQTLTLLKVKEAL
Thr_sp_20892_OrfA   (56)      KATKDKIYCKRGGFIPNYDFDPREFGLNMFQMEDSDANQTLTLLKVKQAL 201                                            250
Sch_sp_9695_Pfa1p   (102)     TDANIPAFSSGKKNIGCVLGIGGGQKASHEFYSRLNYVVVDKVLRKMGLP
Thr_aureum_ORF1     (201)     EDAGVEPFTKKKKNIGCVLGIGGGQKASHEFYSRLNYVVVEKVLRKMNLP
Sch_sp_2088_OrfA    (114)     QDAGIDALGKEKKNIGCVLGIGGGQKSSHEFYSRLNYVVVEKVLRKMGMP
Thr_sp_10212_Pfa1p  (103)     DDANIPAFTNEKKNIGCVLGIGGGQKASHEFYSRLNYVVVDKVLRKMGLP
Thr_sp_20892_OrfA   (106)     EDASIEPFTKEKKNIGCVLGIGGGQKASHEFYSRLNYVVVEKVLRKMGLP 251                                            300
Sch_sp_9695_Pfa1p   (152)     EEDVAAAVDKYKASFPEWRLDSFPGFLGNVTAGRCCNTFNMEGMNCVVDA
Thr_aureum_ORF1     (251)     DEVVEAAVEKYKANFPEWRLDSFPGFLGNVTAGRCSNVFNMEGMNCVVDA
Sch_sp_2088_OrfA    (164)     EEDVKVAVEKYKANFPEWRLDSFPGFLGNVTAGRCTNTFNLDGMNCVVDA
Thr_sp_10212_Pfa1p  (153)     DEDVETAVEKFKANFPEWRLDSFPGFLGNVTAGRCTNTFNMEGMNCVVDA
Thr_sp_20892_OrfA   (156)     DADVEEAVEKYKANFPEWRLDSFPGFLGNVTAGRCSNTFNMEGMNCVVDA
```

Figure 4. cont.

```
                          301                                              350
Sch_sp_9695_Pfa1p  (202)  ACASSLIAVKVAIEELLYGDCDAMIAGATCTDNSIGMYMAFSKTPVFSTD
Thr_aureum_ORF1    (301)  ACASSLIAIKVAIDELLHGDCDTMIAGATCTDNSIGMYMAFSKTPVFSTD
Sch_sp_2088_OrfA   (214)  ACASSLIAVKVAIDELLYGDCDMMVTGATCTDNSIGMYMAFSKTPVFSTD
Thr_sp_10212_Pfa1p (203)  ACASSLIAIKVAIDELLHGDCDAMIAGATCTDNALGMYMAFSKTPVFSTD
Thr_sp_20892_OrfA  (206)  ACASSLIAIKVAVEELLFGDCDTMIAGATCTDNSLGMYMAFSKTPVFSTD 351                                              400
Sch_sp_9695_Pfa1p  (252)  PSVKAYDAATKGMLIGEGSAMLVLKRYADAVRDGDTVHAVIKGCASSSDG
Thr_aureum_ORF1    (351)  QSVKAYDAKTKGMLIGEGSAMVVLKRYADAVRDGDEIHAVIRACASSSDG
Sch_sp_2088_OrfA   (264)  PSVRAYDEKTKGMLIGEGSAMLVLKRYADAVRDGDEIHAVIRGCASSSDG
Thr_sp_10212_Pfa1p (253)  QSCLAYDEKTKGMLIGEGSAMFVLKRYADAVRDGDTVHAVIRSCSSSSDG
Thr_sp_20892_OrfA  (256)  PSVRAYDEKTKGMLIGEGSAMFVLKRYADAVRDGDTIHAVLRSCSSSSDG 401                                              450
Sch_sp_9695_Pfa1p  (302)  KAAGIYTPTISGQEEALRRAYARANVDPATVTLVEGHGTGTPVGDKIELT
Thr_aureum_ORF1    (401)  KAAGIYAPTVSGQEEALRRAYARAGVDPSTVTLVEGHGTGTPVGDRIELT
Sch_sp_2088_OrfA   (314)  KAAGIYTPTISGQEEALRRAYNRACVDPATVTLVEGHGTGTPVGDRIELT
Thr_sp_10212_Pfa1p (303)  KASGIYTPTISGQEEAILRAYRRAGVSPNTITLVEGHGTGTPVGDKIELT
Thr_sp_20892_OrfA  (306)  KAAGIYTPTISGQEEALRRAYARAGVCPSTIGLVEGHGTGTPVGDRIELT
```

Figure 4. cont.

```
                        451                                          500
Sch_sp_9695_Pfa1p  (352) ALSNLFSKAFSANGGGAEEAEQVAVGSIKSQIGHLKAVAGLAGLVKVVLA
Thr_aureum_ORF1    (451) ALRNVFDAANKGR------KETVAVGSIKSQIGHLKAVAGFAGLVKVVMA
Sch_sp_2088_OrfA   (364) ALRNLFDKAYGEG-----NTEKVAVGSIKSSIGHLKAVAGLAGMIKVIMA
Thr_sp_10212_Pfa1p (353) ALRNVFDKAYGPG-----HKEEVAVGSIKSQIGHLKAVAGCAGLVKLVMA
Thr_sp_20892_OrfA  (356) ALRNLFDKAFGSK------KEQIAVGSIKSQIGHLKSVAGFAGLVKAVLA 501                                          550
Sch_sp_9695_Pfa1p  (402) LKHKTLPQTINVDKPPSLVDGTPIQQSPLYVNTMNRPWFTPVGVPRRAGV
Thr_aureum_ORF1    (495) LKHKTLPQTINVHDPPALHDGSPIQDSSLYINTMNRPWFTAPGVPRRAGI
Sch_sp_2088_OrfA   (409) LKHKTLPGTINVDNPPNLYDNTPINESSLYINTMNRPWFPPPGVPRRAGI
Thr_sp_10212_Pfa1p (398) LKHKTLPQSINVENPPNLVDGTVISDTTLYINTMNRPWITKPGVPRRAGI
Thr_sp_20892_OrfA  (400) LKHKTLPGSINVDQPPLLYDGTQIQDSSLYINKTNRPWFTQNKLPRRAGV 551                                          600
Sch_sp_9695_Pfa1p  (452) SSFGFGGANYHAVLEEFEPEHESAYRYNNLPQVALLHAGDVATLAATVRA
Thr_aureum_ORF1    (545) SSFGFGGANYHAVLEEAEPEHAKPYRMNQVPQPVLLHASSASALASICDA
Sch_sp_2088_OrfA   (459) SSFGFGGANYHAVLEEAEPEHTTAYRLNKRPQPVLMMAATPAALQSLCEA
Thr_sp_10212_Pfa1p (448) SSFGFGGANYHAVLEEFEPEQTKPYRLNVSAQPMLLHAVNANSLQKLCED
Thr_sp_20892_OrfA  (450) SSFGFGGANYHAVLEEFEPEHEKPYRLNTVGHPVLLYAPSVEALKVLCND
```

Figure 4. cont.

```
                              601                                              650
Sch_sp_9695_Pfa1p    (502)    KLALATAEQEEARVVKNADYIAYHRFLDECKLRGAVPQAHARVGLLVRDL
Thr_aureum_ORF1      (595)    QADALQAAVSP-EASKHADYRAIVAFHEAFKLRAGVPAGHARIGFVSGSA
Sch_sp_2088_OrfA     (509)    QLKEFEAAIKENETVKNTAYIKCVKFGEQFKFPGSIPATNARLGFLVKDA
Thr_sp_10212_Pfa1p   (498)    QLKLLKESREKCVNTKNTDYVAFSKFQDSFKLKGSVPSQHARVGFASKSI
Thr_sp_20892_OrfA    (500)    QLAELTIALEEAKTHKNVDKVCGYKFIDEFQLQGSCPPENPRVGFLATLP 651                                              700
Sch_sp_9695_Pfa1p    (552)    SSLIAVLEAAAAKLAGEESATEWTVSVATGEAAFRVRGVATEANVAALFS
Thr_aureum_ORF1      (644)    AATLAVLRAASAKLKQSSATLEWTLLRE--GVTYRSAAMHTPGSVAALFA
Sch_sp_2088_OrfA     (559)    EDACSTLRAICAQFAKDVTKEAWRLPRE-GVSFRAKGIATN-GAVAALFS
Thr_sp_10212_Pfa1p   (548)    EDTISILSAIVNRFQKDITTTSWALPKE-GAIFRSTALINDNKSVAALFS
Thr_sp_20892_OrfA    (550)    TSNIIVALKAILAQLDAKPDAKKWDLPHKKAFGATFASSSVKGSVAALFA 701                                              750
Sch_sp_9695_Pfa1p    (602)    GQGAQYTHMFSDVAMNWPPFRESVAAMDRAQRERFG--RPAKRVSSVLYP
Thr_aureum_ORF1      (692)    GQGAQYTHMFADVAMNWPPFRSAVQEMDAAQVTAAAP----KRLSEVLYP
Sch_sp_2088_OrfA     (607)          GQGAQYTHMFSEVAMNWPQFRQSIAAMDAAQSKVAGSDKDFERVSQVLYP
Thr_sp_10212_Pfa1p   (597)    GQGAQYTHMFNDVAMQWPQFRLCVNDMEKAQEEVIN-DKSVKRISQVMFP
Thr_sp_20892_OrfA    (600)    GQGTQYLNMFSDVAMNWPPFRDSIVAMEEAQTEVFEG--QVEPISKVLFP
```

Figure 4. cont.

```
                             751                                          800
Sch_sp_9695_Pfa1p    (650)   RKPYGDEPRQDHKEISQTRYSQPATLACSVGAFDIFKAAGLAPSFAAGHS
Thr_aureum_ORF1      (738)   RKPYAAEPEQDNKAISMTINSQPALMACAAGAFEVFRQAGLAPDHVAGHS
Sch_sp_2088_OrfA     (657)   RKPYEREPEQNPKKISLTAYSQPSTLACALGAFEIFKEAGFTPDFAAGHS
Thr_sp_10212_Pfa1p   (646)   RKPYARESPLDNKEISKTEYSQTTTVASSVGLFEIFRDAGFAPAFVAGHS
Thr_sp_20892_OrfA    (648)   RERYASESEQGNELLCLTEYSQPTTIAAAVGAFDIFKAAGFKPDMVGGHS 801                                          850
Sch_sp_9695_Pfa1p    (700)   LGEFAALYAAGSLDRDAVFDLVCARAKAMSDFTAQASSSGGAMAAVIGAK
Thr_aureum_ORF1      (788)   LGEFGALLAAGCASREELFRLVCSRAKAMQDVPQG---------------
Sch_sp_2088_OrfA     (707)   LGEFAALYAAGCVDRDELFELVCRRARIMGGKDAP-ATPKGCMAAVIGPN
Thr_sp_10212_Pfa1p   (696)   LGEFSALYAAGLIDREDLFKLVCNRAMAMRDAPK--KSADGAMAAVIGPN
Thr_sp_20892_OrfA    (698)   LGEFAALYAAGSISRDDLYKLVCKRAKAMANASDG------AMAAVIGPD 851                                          900
Sch_sp_9695_Pfa1p    (750)   ADQLSLGGAPDVWLANSNSPSQTVITGTAEAVAAASDKLRCSGNFRVVPL
Thr_aureum_ORF1      (823)   ---------DGAWLANCNSPSQVVISGDKTAVERESSRLAGLG-FRIIPL
Sch_sp_2088_OrfA     (756)   AENIKVQ-AANVWLGNSNSPSQTVITGSVEGIQAESARLQKEG-FRVVPL
Thr_sp_10212_Pfa1p   (744)   ASSIKLS-APEVWVANNNSPSQTVITGANSGVQAETSKLKTQG-FRVVHL
Thr_sp_20892_OrfA    (742)   ARLVTPQ-NSDVYVANFNSATQVVISGTVQGVKEESKLLISKG-FRVLPL
```

Figure 4. cont.

```
                           901                                          950
Sch_sp_9695_Pfa1p  (800)   ACEAAFHSPHMRGAEQTFASALAQAPVSAPAAARFYSNVTGGAAVTSPAD
Thr_aureum_ORF1    (863)   ACEGAFHSPHMTAAQATFQAALDSLKISTPTNGARLYNNVSGKTCRSLGE
Sch_sp_2088_OrfA   (804)   ACESAFHSPQMENASSAFKDVISKVSFRTPKAE--TKLFSNVSGETYPTD
Thr_sp_10212_Pfa1p (792)   ACDGAFHSPHMENAEKQFQKALSAVKFNKPTGS--SPKIFSNVTGGVFTD
Thr_sp_20892_OrfA  (790)   KCQGAFHSPLMGPSEDSFKSLVETCTISPPKNVK-FFCNVSGKESP---N 951                                         1000
Sch_sp_9695_Pfa1p  (850)   VKTNLGKHMTSPVQFVQQVRAMHAAGARVFVEFGPKQVLSRLVKETLGEA
Thr_aureum_ORF1    (913)   LRDCLGKHMTSPVLFQAQVENMYAAGARIFVEFGPKQVLSKLVGEILADK
Sch_sp_2088_OrfA   (852)   AREMLTQHMTSSVKFLTQVRNMHQAGARIFVEFGPKQVLSKLVSETLKDD
Thr_sp_10212_Pfa1p (840)   PKTALSRHMTSSVQFLTQIKNMYAAGARVFIEFGPKQVLSKLVNEIFPGD
Thr_sp_20892_OrfA  (836)   PKQTLKSHMTSSVQFEEQIRNMYDAGARVFLEFGPRQVLAKLIAEMFP--

1001                                        1050
Sch_sp_9695_Pfa1p  (900)   GDVVTVAVNPDSAKDSDTQLRQAALTLAVAGVPLKDFDRWQLPDATRLEP
Thr_aureum_ORF1    (963)   SDFVTVAVNSSSSKDSDVQLREAAAKLAVLGVPLANFDPWELCDARRLRE
Sch_sp_2088_OrfA   (902)   PSVVTVSVNPASGTDSDIQLRDAAVQLVVAGVNLQGFDKWDAPDATRMQA
Thr_sp_10212_Pfa1p (890)   TSVLTVSVNPASAKDSDIQLRQAAVQMAVAGVALTDFDKWELKDPTRMKE
Thr_sp_20892_OrfA  (884)   -SCTAISVNPASSGDSDVQLRLAAVKFAVSGAALSTFDPWEYRKPQDLLI
```

Figure 4. cont.

```
                              1051                                          1100
Sch_sp_9695_Pfa1p    (950)    VKKKKTTLRLSAATYVSAKTLRQREAVLNDGYTVSGAT----------AV
Thr_aureum_ORF1      (1013)   CPRSKTTLRLSAATYVSNKTLAAREKVMEDNCDFSSLFASG--------P
Sch_sp_2088_OrfA     (952)    IKKKRTTLRLSAATYVSDKTKKVRDAAMNDGRCVTYLKGAAPLIKAPEPV
Thr_sp_10212_Pfa1p   (940)    FPRKKTTLTLSAATYVSKKTLQERERIMNDGRTVSCVQ-----------R
Thr_sp_20892_OrfA    (933)    RKPRKTALVLSAATYVSPKTLAERKKAMEDIKLVSITPR----------D 1101                                         1150
Sch_sp_9695_Pfa1p    (990)    VKEVDTANEERLVRQAQDLQRQLAEASTAAQAAQSKVAELERTIQDLERK
Thr_aureum_ORF1      (1055)   ASQEMEREIANLRAELEAAQRQLDTAKTQLARKQVQDPTADRQRDMIAKH
Sch_sp_2088_OrfA     (1002)   VDEAAKREAERLQKELQDAQRQLDDAKRAAAEANSKLAAAKEEAKTAAAS
Thr_sp_10212_Pfa1p   (979)    IENTNTGELEKLKKQLQDKENEVVRVQALATQASADLQNTKAELQKAQAT
Thr_sp_20892_OrfA    (973)    SMVSIGKIAQEVRTAKQPLETEIRRLNKELEHLKRELAAAKASVKSASKS 1151                                         1200
Sch_sp_9695_Pfa1p    (1040)   ----------------------------------VQQQQQE--------
Thr_aureum_ORF1      (1105)   RSTLAAMVKEFEALAS---------GSPCAVPFAPVVDTAVEDVPFADKV
Sch_sp_2088_OrfA     (1052)   -AKPAVDTAVVEKHRAILKSMLAELDGYGSVDASSLQQQQQQQTAPAPVK
Thr_sp_10212_Pfa1p   (1029)   KSSNAASDAVVAKHKAILLAMLEELETGKAVDYSSFSKGQVASPATVRVV
Thr_sp_20892_OrfA    (1023)   ----SKERSVLSKHRALLQNILQDYDDLRVVPFAVRSVAVDNTAPYADQV
```

Figure 4. cont.

```
                               1201                              1250
Sch_sp_9695_Pfa1p   (1047)  ----------------------------K-GEN--S--------
Thr_aureum_ORF1     (1146)  STPPPQ---------VTSAPIAELARAEAVVMEVLAAKTGYEVDMIEADM
Sch_sp_2088_OrfA    (1101)  AAAPAAP---VASAPAPAVSNELLEKAETVVMEVLAAKTGYETDMIEADM
Thr_sp_10212_Pfa1p  (1079)  SAPVQAA---APVQVSASVDSGLLAKAEQVVLEVLASKTGYETELIELDM
Thr_sp_20892_OrfA   (1069)  STPASERSASPLFEKRSSVSSARLAEAEAAVLSVLADKTGYDSSMIEMDM 1251                              1300
Sch_sp_9695_Pfa1p   (1052)  -------------------DSNAAAEVLRRHKELLQRMLQDCDEQAVPVAT
Thr_aureum_ORF1     (1187)  LLDAELGIDSVKRIEILAAVQAQLGVEAKDVDALSRTRTVGEVVDAMKAE
Sch_sp_2088_OrfA    (1148)  ELETELGIDSIKRVEILSEVQAMLNVEAKDVDALSRTRTVGEVVNAMKAE
Thr_sp_10212_Pfa1p  (1126)  ELETELGIDSIKRVEILSEVQAQLNVEAKDVDALSRTRTVGEVIDAMKAE
Thr_sp_20892_OrfA   (1119)  DLESELGVDSIKRVEIMSEVQTLLSVEVSDVDALSRTKTVGDVIEAMKLE 1301                              1350
Sch_sp_9695_Pfa1p   (1084)  VVPTPTSSPTPTSSPVSGN-----------SKSTRGSADLQALLAKAETV
Thr_aureum_ORF1     (1237)  IGGQATSAPSPMAQPQASAPSPSPTASVLPKPVALPASVDPAKLARAEAV
Sch_sp_2088_OrfA    (1198)  IAGSSAPAPAAAAPAPAKA-----------APAAAAPAVSNELLEKAETV
Thr_sp_10212_Pfa1p  (1176)  IAGGQPAAPVQVAAPTQVV-----------APVQASAPVDSGLLAKAEQV
Thr_sp_20892_OrfA   (1169)  LGGPQGQTLTAESIRQPPVSEPAVPTS----SSSSIANVSSARLAEAEAA
```

Figure 4. cont.

```
                           1351                                          1400
Sch_sp_9695_Pfa1p  (1123)  VMAVLAAKTGYEADMVEADMDLEAELGIDSIKRVEILSEVQGQLGVEAKD
Thr_aureum_ORF1    (1287)  VMEVLAAKTGYEVDMIEADMLLDAELGIDSVKRIEILAAVQAQLGVEAKD
Sch_sp_2088_OrfA   (1237)  VMEVLAAKTGYETDMIESDMELETELGIDSIKRVEILSEVQAMLNVEAKD
Thr_sp_10212_Pfa1p (1215)  VLEVLASKTGYETELIELDMELETELGIDSIKRVEILSEVQAQLSVEAKD
Thr_sp_20892_OrfA  (1215)  VLSVLADKTGYDSSMIEMDMDLESELGVDSIKRVEIMSEVQTLLSVEVSD
                           1401                                          1450
Sch_sp_9695_Pfa1p  (1173)  VDALSRTRTVGEVVDAMKAEIVAAS-------------------------
Thr_aureum_ORF1    (1337)  VDALSRTRTVGEVVDAMKAEIGGQATSAPASVAQPQASAPSPSATTASVL
Sch_sp_2088_OrfA   (1287)  VDALSRTRTVGEVVNAMKAEIAGGSAPAPAAAAPGPAAAA----------
Thr_sp_10212_Pfa1p (1265)  VDALSRTRTVGEVIDAMKAEIAGGQPAAPVQVAAPTQVVA----------
Thr_sp_20892_OrfA  (1265)  VDALSRTKTVGDVIEAMKLELGGPQGQTLTAESIRQPPVSEPAVPTS---
                           1451                                          1500
Sch_sp_9695_Pfa1p  (1198)  --------------------------------------------------
Thr_aureum_ORF1    (1387)  PKPVAAPTSADPAKLARAEAVVMEVLAAKTGYEVDMIEADMLLDAELGID
Sch_sp_2088_OrfA   (1327)  PAPAAAAPAVSNELLEKAETVVMEVLAAKTGYETDMIESDMELETELGID
Thr_sp_10212_Pfa1p (1305)  PVQASAP--VDSGLLAKAEQVVLEVLASKTGYETELIELDMELETELGID
Thr_sp_20892_OrfA  (1312)  -S-SSSIANVSSARLAEAEAAVLSVLADKTGYDSSMIEMDMDLESELGVD
```

Figure 4. cont.

```
                              1501                                    1550
Sch_sp_9695_Pfa1p    (1198)   ----------------------------------GGSAPAV
Thr_aureum_ORF1      (1437)   SVKRIEILAAVQAQLGVEAKDVDALSRTRTVGEVVEAMKAEIGGQATSAP
Sch_sp_2088_OrfA     (1377)   SIKRVEILSEVQAMLNVEAKDVDALSRTRTVGEVVDAMKAEIAGGSAPAP
Thr_sp_10212_Pfa1p   (1353)   SIKRVEILSEVQAQLSVEAKDVDALSRTRTVGEVIDAMKAEISGGQPAAP
Thr_sp_20892_OrfA    (1360)   SIKRVEIMSEVQTLLSVEVSDVDALSRTKTVGDVIEAMKLELGGPQGQTL 1551                                    1600
Sch_sp_9695_Pfa1p    (1205)   PSAPAASAAPTPAASTAPSA-----DLQALLSKAETVVMAVLAAKTGYEA
Thr_aureum_ORF1      (1487)   ASVAQPQISVSPTPLAASPS-----ADPAKLARAEAVVMEVLAAKTGYEV
Sch_sp_2088_OrfA     (1427)   AAAAPAPAAAAPAPAAPAPA-----VSSELLEKAETVVMEVLAAKTGYET
Thr_sp_10212_Pfa1p   (1403)   VQVAAPTQIVAPVQVSAP-------VDSGLLAKAEQVVLEVLASKTGYET
Thr_sp_20892_OrfA    (1410)   TAESIRQPPVSEPAVPTSSSSSIANVLSARLAEAEAAVLSVLADKTGYDS 1601                                    1650
Sch_sp_9695_Pfa1p    (1250)   DMVEADMDLEAELGIDSIKRVEILSEVQGQLGVEAKDVDALSRTRTVGEV
Thr_aureum_ORF1      (1532)   DMIEADMLDAELGIDSVKRIEILAAVQAQLGVEAKDVDALSRTRTVGEV
Sch_sp_2088_OrfA     (1472)   DMIESDMELETELGIDSIKRVEILSEVQAMLNVEAKDVDALSRTRTVGEV
Thr_sp_10212_Pfa1p   (1446)   ELIELDMELETELGIDSIKRVEILSEVQAQLSVEAKDVDALSRTRTVGEV
Thr_sp_20892_OrfA    (1460)   SMIEMDMDLESELGVDSIKRVEIMSEVQTLLSVEVSDVDALSRTKTVGDV
```

Figure 4. cont.

```
                              1651                                          1700
Sch_sp_9695_Pfa1p   (1300)    VDAMKAEIVAASAGSAP----APAVPSAPAASAAPTPAASTAPSADLQAL
Thr_aureum_ORF1     (1582)    VDAMKAEIGGQATSAPASVAQPQASAPSPSATASVLPKPVAAPTSADPAK
Sch_sp_2088_OrfA    (1522)    VDAMKAEIAGGSAPAPA----AAAPAPAAAAPAPAAPAPAAPAPAVSSEL
Thr_sp_10212_Pfa1p  (1496)    IDAMKAEISGGQP-----------TAPVQVAAPTQIVAPVQVSAPVDSGL
Thr_sp_20892_OrfA   (1510)    IEAMKLELGGPQG-Q---TLTAESIRQPPVSEPAVPTSSSSSIANVSSAR 1701                                          1750
Sch_sp_9695_Pfa1p   (1346)    LSKAETVVMAVLAAKTGYEADMVEADMDLEAELGIDSIKRVEILSEVQGQ
Thr_aureum_ORF1     (1632)    LARAEAVVMEVLAAKTGYEVDMIEADMLLDAELGIDSVKRIEILAAVQAQ
Sch_sp_2088_OrfA    (1568)    LEKAETVVMEVLAAKTGYETDMIESDMELETELGIDSIKRVEILSEVQAM
Thr_sp_10212_Pfa1p  (1535)    LAKAEQVVLEVLASKTGYETELIELDMELETELGIDSIKRVEILSEVQAQ
Thr_sp_20892_OrfA   (1556)    LAEAEAAVLSVLADKTGYDSSMIEMDMDLESELGVDSIKRVEIMSEVQTL 1751                                          1800
Sch_sp_9695_Pfa1p   (1396)    LGVEAKDVDALSRTRTVGEVVDAMKAEIVAASGGSAPAPAVPSAPAASAA
Thr_aureum_ORF1     (1682)    LGVEAKDVDALSRTRTVGEVVEAMKAEIGGQAT-----SAPASMAQPQIS
Sch_sp_2088_OrfA    (1618)    LNVEAKDVDALSRTRTVGEVVDAMKAEIAGSS-----ASAPAAAAPAPAA
Thr_sp_10212_Pfa1p  (1585)    LSVEAKDVDALSRTRTVGEVIDAMKAEISGGQ-----PAAPVQVAAPTQI
Thr_sp_20892_OrfA   (1606)    LSVEVSDVDALSRTKTVGDVIEAMKLELGGPQGQTLTSEPIHQPPVSEPA
```

Figure 4. cont.

```
                          1801                                              1850
Sch_sp_9695_Pfa1p  (1446) PTPAAATAPSADLQALLAKAETVVMAVLAAKTGYEADMVEADMDLEAELG

Thr_aureum_ORF1    (1727) VSPTPLAASPSADPAKLARAEAVVMEVLAAKTGYEVDMIEADMLLDAELG

Sch_sp_2088_OrfA   (1663) AAPAPAAAAPAVSNELLEKAETVVMEVLAAKTGYETDMIESDMELETELG

Thr_sp_10212_Pfa1p (1630) VAPVQASAP--VDSGLLAKAEQVVLEVLASKTGYETELIELDMELETELG

Thr_sp_20892_OrfA  (1656) VPTSSSSSIANVSSARLAEAEAAVLSVLADKTGYDSSMIEMDMDLESELG 1851                                              1900
Sch_sp_9695_Pfa1p  (1496) IDSIKRVEILSEVQGQLGVEAKDVDALSRTRTVGEVVDAMKAEIVAASAG

Thr_aureum_ORF1    (1777) IDSVKRIEILAAVQAQLGVEAKDVDALSRTRTVGEVVDAMKAEIGGQATS

Sch_sp_2088_OrfA   (1713) IDSIKRVEILSEVQAMLNVEAKDVDALSRTRTVGEVVDAMKAEIAGGSAP

Thr_sp_10212_Pfa1p (1678) IDSIKRVEILSEVQAQLSVEAKDVDALSRTRTVGEVIDAMKAEISGGQPA

Thr_sp_20892_OrfA  (1706) VDSIKRVEIMSEVQTLLSVEVSDVDALSRTKTVGDVIEAMKMELGGPQGQ 1901                                              1950
Sch_sp_9695_Pfa1p  (1546) SAPAPAVP-----------------------------------------

Thr_aureum_ORF1    (1827) APASVAQP-----------------------------------------

Sch_sp_2088_OrfA   (1763) APAAAAPA-----PAAAAPAVSNELLEKAETVVMEVLAAKTGYETDMIES

Thr_sp_10212_Pfa1p (1728) APVQVAAPTQIVAPVQVSAPVDSGLLAKAEQVVLEVLASKTGYETELIEL

Thr_sp_20892_OrfA  (1756) TLTAESIR-----------------------------------------
```

Figure 4. cont.

```
                             1951                                           2000
Sch_sp_9695_Pfa1p    (1554)  --------------------------------------------------
Thr_aureum_ORF1      (1835)  ----------------------------------------QASAP-----
Sch_sp_2088_OrfA     (1808)  DMELETELGIDSIKRVEILSEVQAMLNVEAKDVDALSRTRTVGEVVDAMK
Thr_sp_10212_Pfa1p   (1778)  DMELETELGIDSIKRVEILSEVQAQLNVEAKDVDALSRTRTVGEVIDAMK
Thr_sp_20892_OrfA    (1764)  --------------------------------------------------

2001                                           2050
Sch_sp_9695_Pfa1p    (1554)  -------------SAPAASAAPTPAASTAPSADLQALLSKAETVVMAVLAA
Thr_aureum_ORF1      (1840)  -------------SPSATASAPVTPLAAPASVDPAKLARAEAVVMEVLAA
Sch_sp_2088_OrfA     (1858)  AEIAGSSAPAPAAAAPAPAAAAPAPAAAAPAVSSELLEKAETVVMEVLAA
Thr_sp_10212_Pfa1p   (1828)  AEIAGGQP--AAPVQVAAPAPVVAPVQVSTPVDSGLLAKAEQVVLEVLAC
Thr_sp_20892_OrfA    (1764)  ------------QPPVSEPAVPTSSSSSIANVSSARLAEAEAAVLSVLAD 2051                                           2100
Sch_sp_9695_Pfa1p    (1592)  KTGYEADMVEADMDLEAELGIDSIKRVEILSEVQGQLGVEAKDVDALSRT
Thr_aureum_ORF1      (1877)  KTGYEVDMIEADMLLDAELGIDSVKRIEILAAVQAQLGVEAKDVDALSRT
Sch_sp_2088_OrfA     (1908)  KTGYETDMIESDMELETELGIDSIKRVEILSEVQAMLNVEAKDVDALSRT
Thr_sp_10212_Pfa1p   (1876)  KTGYETELIELDMELETELGIDSIKRVEILSEVQAQLSVEAKDVDALSRT
Thr_sp_20892_OrfA    (1802)  KTGYDSSMIEMDMDLESELGVDSIKRVEIMSEVQALLSVEVSDVDALSRT
```

Figure 4. cont.

```
                              2101                                    2150
Sch_sp_9695_Pfa1p    (1642)   RTVGEVVDAMKAEIVAASGGSAPAAAVPSAPAASA------APTPATAPS
Thr_aureum_ORF1      (1927)   RTVGEVVDAMKAEIGGQATSAPASVAQPQASAPSPSATASVLPKPVASPA
Sch_sp_2088_OrfA     (1958)   RTVGEVVDAMKAEIAGGS-----APAPAAAAP----------APAAAAP
Thr_sp_10212_Pfa1p   (1926)   RTVGEVIDAMKAEISGGQ-----PTAPVQVAAPTQ------VVAPVKVST
Thr_sp_20892_OrfA    (1852)   KTVGDVIEAMKMELGGPQG----QTLTAESIREPPVSEPAVPTSSSSSIA 2151                                    2200
Sch_sp_9695_Pfa1p    (1686)   ADLQALLSKAETVVMAVLAAKTGYEADMVEADMDLEAELGIDSIKRVEIL
Thr_aureum_ORF1      (1977)   SVDPAKLARAEAVVMEVLAAKTGYEVDMIDADMLLDAELGIDSVKRIEIL
Sch_sp_2088_OrfA     (1992)   AVSNELLEKAETVVMEVLAAKTGYETDMIESDMELETELGIDSIKRVEIL
Thr_sp_10212_Pfa1p   (1965)   PVDSGLLAKAEQVVLEVLASKTGYETELIELDMELETELGIDSIKRVEIL
Thr_sp_20892_OrfA    (1898)   NVSSARLAEAEAAVLSVLADKTGYDSSMIEMDMDLESELGVDSIKRVEIM 2201                                    2250
Sch_sp_9695_Pfa1p    (1736)   SEVQGQLGVEAKDVDALSRTRTVGEVVDAMKAEIVAASGGSAPAAPSAPA
Thr_aureum_ORF1      (2027)   AAVQAQLGVEAKDVDALSRTRTVGEVVEAMKAEIGAAGPNDAQAAS----
Sch_sp_2088_OrfA     (2042)   SEVQAMLNVEAKDVDALSRTRTVGEVVDAMKAEIAGGSAPAPAAAAPASA
Thr_sp_10212_Pfa1p   (2015)   SEVQAQLNVEAKDVDALSRTRTVGEVIDAMKAEIAGDQPAPAVVPVQAKS
Thr_sp_20892_OrfA    (1948)   SEVQTLLSVEVSDVDALSRTKTVGDVIEAMKLELGESSSIETLNCTEVEH
```

Figure 4. cont.

```
                              2251                                          2300
Sch_sp_9695_Pfa1p    (1786)   LLPT--------------------------------------------
Thr_aureum_ORF1      (2073)   ------------------------------------------------
Sch_sp_2088_OrfA     (2092)   GAAP--------------------------------------------
Thr_sp_10212_Pfa1p   (2065)   GVANPALLAKAEQVVLEVLASKTGYETELIELDMELETELGIDSIKRVEI
Thr_sp_20892_OrfA    (1998)   TSYKS-------------------------------------------

2301                                          2350
Sch_sp_9695_Pfa1p    (1790)   --------------------------------------------------
Thr_aureum_ORF1      (2073)   -----------------------------G--------------------
Sch_sp_2088_OrfA     (2096)   --------------------------------------------------
Thr_sp_10212_Pfa1p   (2115)   LSEVQAELSVEAKDVDALSRTRTVGEVIDAMKAEIAGSAVTVATLDDSTI
Thr_sp_20892_OrfA    (2003)   --------------------------------------------------

2351                                          2400
Sch_sp_9695_Pfa1p    (1790)   ----------------LFGSECEDLSLTFPVITTLPLPAELVLAEGGARP
Thr_aureum_ORF1      (2074)   ----------------HLFGTGCEDLSLCSASVVEIARCSELALERPMDRP
Sch_sp_2088_OrfA     (2096)   ----------AVKIDSVHGADCDDLSLMHAKVVDIRRPDELILERPENRP
Thr_sp_10212_Pfa1p   (2165)   MEETDDEDEDFILYDHVYGSECEDLSLSFSSVKSIPRADKLLLDNIAERP
Thr_sp_20892_OrfA    (2003)   ----------------VKASGCENVDTRFAKVVQISLPSKLKSTVSHDRP
```

Figure 4. cont.

```
                              2401                                              2450
Sch_sp_9695_Pfa1p   (1824)    VVVVDDGSALTSSLVSSLGDRAVLLQVQSSSACSPR-STTHKLVTVADRS
Thr_aureum_ORF1     (2109)    ILIVSDGSALPAALASRLGSCAVILTTAGETDQSVR---STKHVDMEGWG
Sch_sp_2088_OrfA    (2136)    VLVVDDGSELTLALVRVLGACAVVLTFEGLQLAQRAGAAAIRHVLAKDLS
Thr_sp_10212_Pfa1p  (2215)    IVIVDCGTKLTTELAKAIGERAVVATFSAQSLVSRG--FVGKSFTLGNTE
Thr_sp_20892_OrfA   (2037)    VIVVDDGTPLTTELCKILGGNIVVLSYQGKPAGPRG-------VEVPDLS 2451                                              2500
Sch_sp_9695_Pfa1p   (1873)    EAALQAALTSVEAQFGKVGGFVFQFG-DDDVQAQLGWALLAAKHLKTSLS
Thr_aureum_ORF1     (2156)    EADLVRALEAVESRFGVPGGVVVLERASETARDQLGFALLLAKHSSKALN
Sch_sp_2088_OrfA    (2186)    AESAEKAIKEAEQRFGALGGFISQQAERFEPAEILGFTLMCAKFAKASLC
Thr_sp_10212_Pfa1p  (2263)    ESEIEKMVSSIESSYGKIGGFVYQHFHDSDYGMQLGWALMAAKHLKESLN
Thr_sp_20892_OrfA   (2080)    EEALIQALALIRSTYGVPIGFICQQVSNVSTKAQLCWALLAAKHLKKDLN 2501                                              2550
Sch_sp_9695_Pfa1p   (1922)    EQIEGGRTFFVAVARLDGQLGLSG--K---STTATVDLSRAQQGSVFGLC
Thr_aureum_ORF1     (2206)    QQIPGGRACFVGVSRIDGKLGLSG--ACAKGKGWAEAAEIAQQGAVAGLC
Sch_sp_2088_OrfA    (2236)    TAVAGGRPAFIGVARLDGRLGFT-------SQGTSDALKRAQRGAIFGLC
Thr_sp_10212_Pfa1p  (2313)    DPIKNGRTFFLAVARMNGKLGMDN--ASVHDQGIVESCGIAERGAIFGLC
Thr_sp_20892_OrfA   (2130)    AVLPDSRSFFVGVVRLNGKLGTFENISDFSKFDLTKALDYGQRGSLLGLC
```

Figure 4. cont.

```
                              2551                                          2600
Sch_sp_9695_Pfa1p   (1967)   KTLDLEWPA--VFCRGIDLAADLDAAQAARCLLGELSDPDVAVRESGYSA
Thr_aureum_ORF1     (2254)   KTLDLEWPH--VFARSIDIELGANEETAAQAIFEELSCPDLTVREAGYTK
Sch_sp_2088_OrfA    (2279)   KTIGLEWSESDVFSRGVDIAQGMHPEDAAVAIVREMACADIRIREVGIGA
Thr_sp_10212_Pfa1p  (2361)   KTLDLEWPN--VFARGVDIAEGMSYSLAAELIVDEISCANLSIRESGYTI
Thr_sp_20892_OrfA   (2180)   KSLDLEWEQ--VFCRGIDLACDLMPLQAARILRNELQCPNMRLREVGYDI 2601                                          2650
Sch_sp_9695_Pfa1p   (2015)   SGQRCTTTTKSLTTGKPHQPISSSDLFLVSGGARGITPLCVRELAQRVGG
Thr_aureum_ORF1     (2302)   DGKRWTTEARPVGLGKPKQALRSSDVFLVSGGARGITPVCVRELAKSISG
Sch_sp_2088_OrfA    (2329)   NQQRCTIRAAKLETGNPQRQIAKDDVLLVSGGARGITPLCIREITRQIAG
Thr_sp_10212_Pfa1p  (2409)   SGERFTTEAHKLVTGKPHAPIKKKDAFLVSGGARGITPLCIREIAKAVKG
Thr_sp_20892_OrfA   (2228)   SGARYTISTDDLLCGPSKAKVEAADLFLVTGGARGITPHCVREIASRSPG 2651                                          2700
Sch_sp_9695_Pfa1p   (2065)   GTYVLIGRSELPTTEPAWAVGVESGKPLEKAALAFLKAEFAAGRGAKPTP
Thr_aureum_ORF1     (2352)   GTFVLLGRS-PLADDPAWACGV-EEANIGTAAMAHLKAEFAAGRGPKPTP
Sch_sp_2088_OrfA    (2379)   GKYILLGRSKVSASEPAWCAGITDEKAVQKAATQELKRAFSAGEGPKPTP
Thr_sp_10212_Pfa1p  (2459)   GTYILMGRS-ALADEPLWANGK-SGKDLDKAGLAFLKEEFAAGRGSKPTP
Thr_sp_20892_OrfA   (2278)   TTFVLVGRS-EMSDEPDWAVGH-YNKDLDQSTMKHLKATHAAG-GVKPTP
```

Figure 4. cont.

```
                              2701                                              2750
Sch_sp_9695_Pfa1p   (2115)    MLHKKLVGAVVGAREVRASLAEITAQGATAVYESCDVSSAAKVREMVERV
Thr_aureum_ORF1     (2400)    KAHKALVGSVLGAREVLGSLESIRAQGARAEYVSCDVSCAERVKAVVDDL
Sch_sp_2088_OrfA    (2429)    RAVTKLVGSVLGAREVRSSIAAIEALGGKAIYSSCDVNSAADVAKAVRDA
Thr_sp_10212_Pfa1p  (2507)    KVHKSLIDKVLGIREVRASIANIEAHGAKAIYLSCDVSSAEKVKAAVQKV
Thr_sp_20892_OrfA   (2325)    KAHRALVNRVTGSREVRESLRAIQEAGANVEYIACDVSDENKVRQLVQRV 2751                                              2800
Sch_sp_9695_Pfa1p   (2165)    QQQGGRRVSGVFHASGVLRDKLVENKSLADFSAVYDTKVGGLINLLACVD
Thr_aureum_ORF1     (2450)    ERRVG-AVTGVVHASGVLRDKSVERLELADFEVVYGTKVDGLLNLLQAVD
Sch_sp_2088_OrfA    (2479)    ESQLGARVSGIVHASGVLRDRLIEKKLPDEFDAVFGTKVTGLENLLAAVD
Thr_sp_10212_Pfa1p  (2557)    EKEHLVRITGIVHASGVLRDKLVENKTLDDFNAVYGTKVTGLVNLLSAVN
Thr_sp_20892_OrfA   (2375)    EQKYGCEITGIWHASGVLRDKLVEQKTTDDFEAVFGTKVTGLVNIVSQVN 2801                                              2850
Sch_sp_9695_Pfa1p   (2215)    LAQLRHLVLFSSLAGFHGNVGQSDYAMANEALNKLAAHLSAVHPQLCARS
Thr_aureum_ORF1     (2499)    RPKLRHLVLFSSLAGFHGNTGQAVYAMANEALNKMAFHLETAMPGLSVKT
Sch_sp_2088_OrfA    (2529)    RANLKHMVLFSSLAGFHGNVGQSDYAMANEALNKMGLELAKDVS---VKS
Thr_sp_10212_Pfa1p  (2607)    MNFVRHLVMFSSLAGYHGNVGQSDYAMANESLNKIGFRLGAAYSQLCVKS
Thr_sp_20892_OrfA   (2425)    MSKLRHFILFSSLAGFHGNKGQTDYAIANEALNKIAHTLSAFLPKLNAKV
```

Figure 4. cont.

```
                             2851                                              2900
Sch_sp_9695_Pfa1p   (2265)   ICFGPWDG-GMVTPALKANFIRMGIQIIPRQGGAQTVANMLVSSSPGQLL
Thr_aureum_ORF1     (2549)   IGFGPWDG-GMVNDALKAHFASMGVQIIPLDGGAETVSRIIGACSPTQVL
Sch_sp_2088_OrfA    (2576)   ICFGPWDG-GMVTPQLKKQFQEMGVQIIPREGGADTVARIVLGSSPAEIL
Thr_sp_10212_Pfa1p  (2657)   ICFGPWDG-GMVTPALKKQFQSMGVQIIPREGGAETVARIVLSSNPSQVL
Thr_sp_20892_OrfA   (2475)   LDFGPWVGSGMVTETLEKHFKAMGVQTIPLEPGARTVAQIILASSPPQSL 2901                                              2950
Sch_sp_9695_Pfa1p   (2314)   VGNWGVPPVVPSATEHTVLQTLRQS-DNPFLDSHVIQGRRVLPMTLAVGY
Thr_aureum_ORF1     (2598)   VGNWGLPPVVPNASVHKITVRLGGESANPFLSSHTIQGRKVLPMTVALGL
Sch_sp_2088_OrfA    (2625)   VGNWRTPSKKVGSDTITLHRKISAK-SNPFLEDHVIQGRRVLPMTLAIGS
Thr_sp_10212_Pfa1p  (2706)   VGNWGVPPVSPLSKSATIVQTFTPE-LNPFLKSHQIHGKNVLPMTVAIGY
Thr_sp_20892_OrfA   (2525)   LGNWGFPATKPLQRSNVVTGTLSPE-EIEFIADHKIQGRKVLPMMAAIGF 2951                                              3000
Sch_sp_9695_Pfa1p   (2363)   MAHQAQSIYAGHQLWAVEDAQLFKGIAIDNGADVPVRVELSRRKEEQEDA
Thr_aureum_ORF1     (2648)   LAEAARGLYVGHQVVGIEDAQVFQGVVLDKGATCEVQLRRESSTASP---
Sch_sp_2088_OrfA    (2674)   LAETCLGLFPGYSLWAIDDAQLFKGVTVDGDVNCEVTLTPSTAPSG----
Thr_sp_10212_Pfa1p  (2755)   LAHLVKNFYAGHHLWGVEDAQLFSGVVIDHAVQAQVKLTEQSLDDDG---
Thr_sp_20892_OrfA   (2574)   MASIAEGLYPGYNLQGVENAQLFQGLTINQETKFQITLIEEHNSEEN---
```

Figure 4. cont.

```
                          3001                                          3050
Sch_sp_9695_Pfa1p  (2413) GKVKVKVQVLLKSQVN-GKSVPAYKATVVLS-PAPRPSVITRDFDLT---
Thr_aureum_ORF1    (2695) ---SEVVLSASLNVFAAGKVVPAYRAHVVLGASGPRTGGVQLELKDLGVD
Sch_sp_2088_OrfA   (2720) ---RVNVQATLKTFSS-GKLVPAYRAVIVLSNQGAPPANATMQPPSL---
Thr_sp_10212_Pfa1p (2802) ---KVKVQAVLTASNDNGKMVPAYKAVIVLG-KTSRPAFILKDFSLQ---
Thr_sp_20892_OrfA  (2621) ----LDVLTSLGVMLESGKVLPAYRCVVCLNTTQQQPKLSPKILNLEVDP 3051                                          3100
Sch_sp_9695_Pfa1p  (2458) --PDPACTEHDLYDGKTLFHGKAFQGIEQVLSATPKQLTAKCRNLPLTPE
Thr_aureum_ORF1    (2742) ADPACSVGKGALYDGRTLFHGPAFQYMDEVLRCSPAELAVRCRVVPSAAQ
Sch_sp_2088_OrfA   (2763) --DADPALQGSVYDGKTLFHGPAFRGIDDVLSCTKSQLVAKCSAVPGSDA
Thr_sp_10212_Pfa1p (2845) --ESNSRSADELYDGKTLFHGPLFRGITKLLNVSDTSLTTQCTNIDLTAT
Thr_sp_20892_OrfA  (2667) ------ACEVNPYDGKSLFHGPLLQFVQQVLHSSTKGLVAKCRALPIKEA 3101                                          3150
Sch_sp_9695_Pfa1p  (2506) QRGQFVVNLSQQDPFQADIAFQAMLVWARMLRQSAALPNNCERFDFYKPM
Thr_aureum_ORF1    (2792) DRGQFVSRGVLYDPFLNDTVFQALLVWARLVRDSASLPSNVERISFHGQP
Sch_sp_2088_OrfA   (2811) ARGEFATDTDAHDPFVNDLAFQAMLVWVRRTLGQAALPNSIQRIVQHRPV
Thr_sp_10212_Pfa1p (2893) ER-GQFADIEPVNPFMADAAFQAMLVWVRNLRNSASLPNNCERVDIYKPI
Thr_sp_20892_OrfA  (2711) IR-GPFIKQTLHDPILDDVIFQLMLVWCRNALGSASLPNRIEKMSYFGNV
```

Figure 4. cont.

```
                                   3151                                              3200
Sch_sp_9695_Pfa1p   (2556)   AP-GATYYTSVKLASASP-LVDSVCKCTVAMHDEQGEVYFSARASVVLNK

Thr_aureum_ORF1     (2842)   PSEGEVFYTTLKLDSAASGPLDPIAKAQFFLHRACGAVFASGRASVVLNK

Sch_sp_2088_OrfA    (2861)   PQ-DKPFYITLRSNQSG---GHSQHKHALQFHNEQGDLFIDVQASVIATD

Thr_sp_10212_Pfa1p  (2942)   AP-GEKYYTTLQALGNT---SGSVLKSVFYMHDEQGEVFLSGRASVVVND

Thr_sp_20892_OrfA   (2760)   SE-GSTFFASVTPVGPR-VPKDPVIKMQFLLQDESGNTFSSGEGSVVLSD

3201
Sch_sp_9695_Pfa1p   (2604)   TLTY

Thr_aureum_ORF1     (2892)   ALSF

Sch_sp_2088_OrfA    (2907)   SLAF

Thr_sp_10212_Pfa1p  (2988)   KMEF

Thr_sp_20892_OrfA   (2808)   ELVF
```

Figure 5.

```
                             1                                                50
Sch_sp_9659_Pfa2p    (1)     ---------------------------------------MPCDNI
Sch_sp_2088_OrfB     (1)     --------------------------------MAARNVSAAHEMHDEKRI
Thr_sp_10212_Pfa2p   (1)     ----------------------------------MVKLSVGDNICHDQRV
Thr_aureum_ORF2      (1)     QAIGHRAARWSCRSKSKARGHKAQKEMNQGGRNDEGVSVARADPCPDTRI
Thr_sp_20892_OrfB    (1)     -----------------------------------MQLPPAHSADENRI 51                                              100
Sch_sp_9659_Pfa2p    (7)     AVVGMAVQYAGCKNQDEFWDTLMRKEINSSPISAERLGTRYRDLHFHPQR
Sch_sp_2088_OrfB     (19)    AVVGMAVQYAGCKTKDEFWEVLMNGKVESKVISDKRLGSNYRAEHYKAER
Thr_sp_10212_Pfa2p   (17)    AVVGMAVMYAGCQNQHEFWQSLQGKNMNSKSISQNRLGSEYREEHFKPER
Thr_aureum_ORF2      (51)    AVVGMAVEYAGCRGKEAFWDTLMNGKINSACISDDRLGSARREEHYAPER
Thr_sp_20892_OrfB    (15)    AVVGMAVKYAGCDNKEEFWKTLMNGSINTKSISAARLGSNKRDEHYVPER 101                                             150
Sch_sp_9659_Pfa2p    (57)    SKYADTFCNDRYGCVDASVDN-EHDLLADLARRALLDAGIN--LDDASTT
Sch_sp_2088_OrfB     (69)    SKYADTFCNETYGTLDENEIDNEHELLLNLAKQALAETS----------V
Thr_sp_10212_Pfa2p   (67)    SKYSDTFCNERYGCIDENVQS-EHELLLKLAKDAIADTKG---------S
Thr_aureum_ORF2      (101)   SKYADTFCNERYGCIDPKVDN-EHDLLLGLAAAALQDAQDRRSDGGKFDP
Thr_sp_20892_OrfB    (65)    SKYADTFCNERYGCIQQGTDN-EHDLLLGLAQEALADAAGRMEKQ-PSEA
```

Figure 5. cont.

```
                              151                                       200
Sch_sp_9659_Pfa2p    (104)    ANLRDFGIVSGCLSFPMDNLQGELLNLYQVHVENRVGAQRFRDSR-PWSE
Sch_sp_2088_OrfB     (109)    KDSTRCGIVSGCLSFPMDNLQGELLNVYQNHVEKKLGARVFKDAS-HWSE
Thr_sp_10212_Pfa2p   (107)    IDLNKTGIVSGCLSFPMDNLQGDLLNLYQCHIEKKIGPNALKDVN-LWSK
Thr_aureum_ORF2      (150)    AQLKRCGIVSGCLSFPMDNLQGELLNLYQAHAERRIGKHCFADQT-PWST
Thr_sp_20892_OrfB    (113)    FDLENTGIVSGCLSFPMDNLQGELLNLYQSHVEKQLPPSALVEAVKLWSE 201                                       250
Sch_sp_9659_Pfa2p    (153)    RPRAVSPEASDPRVYSDPASFVANQLGLGPVRYSLDAACASALYCLKLAS
Sch_sp_2088_OrfB     (158)    REQSNKPEAGDRRIFMDPASFVAEELNLGALHYSVDAACATALYVLRLAQ
Thr_sp_10212_Pfa2p   (156)    RTTNG---KDDKKAYFDPASFVAEQLDMGPLHYSLDAACASALYVLRLAQ
Thr_aureum_ORF2      (199)    RTRALHPLPGDPRTHRDPASFVAGQLGLGPLHYSLDAACASALYVLRLAQ
Thr_sp_20892_OrfB    (163)    RQKSTKAHAGDKRRFIDPASFVADKLNLGPLHYAIDAACASALYVLKLAQ 251                                       300
Sch_sp_9659_Pfa2p    (203)    DHLLSRSADVMLCGATCFPDPFFILSGFSTFQAMPLGGPDDNPLSVPLRQ
Sch_sp_2088_OrfB     (208)    DHLVSGAADVMLCGATCLPEPFFILSGFSTFQAMPVGTGQ--NVSMPLHK
Thr_sp_10212_Pfa2p   (203)    DHLLSGAADTMLCGASCLPEPFFILSGFSTFHAMPLSG----DVSAPLHK
Thr_aureum_ORF2      (249)    DHLLSGEADLMLCGATCFPEPFFILTGFSTFHAMPVGEN---GVSMPFHP
Thr_sp_20892_OrfB    (213)    DHLVSGAVDMMLCGATCFPEPFFILSGFSTFQAMPVGAD---GVSLPLHK
```

Figure 5. cont.

|  |  | 301 | 350 |
|---|---|---|---|
| Sch_sp_9659_Pfa2p | (253) | GSQGLTPGEGGAIMVLKRLEDAVRDGDRIYGTLLGTSLSNAGCGLPLSPH | |
| Sch_sp_2088_OrfB | (256) | DSQGLTPGEGGSIMVLKRLDDAIRDGDHIYGTLLGANVSNSGTGLPLKPL | |
| Thr_sp_10212_Pfa2p | (249) | TSQGLTPGEGGAIMVLKRLNDAIRDGDRIYGTLLGAELSNAGCGLPLSPH | |
| Thr_aureum_ORF2 | (296) | DTQGLTPGEGGSVMVLKRLADAERDGDHIYGTLLGASLSNAGCGLPLKPH | |
| Thr_sp_20892_OrfB | (260) | TSAGLTPGEGGSIMVLKRLKDAIRDGNHIYGVLLEANLSNAGCGLPLSPH | |

|  |  | 351 | 400 |
|---|---|---|---|
| Sch_sp_9659_Pfa2p | (303) | LPSEKSCMEDLYTSVGIDP-SEVQYVECHATGTPQGDVVEVEALRHCFRG | |
| Sch_sp_2088_OrfB | (306) | LPSEKKCLMDTYTRINVHP-HKIQYVECHATGTPQGDRVEIDAVKACFEG | |
| Thr_sp_10212_Pfa2p | (299) | MPSEFDCMEKALQRVHRLP-SSIQYVECHATGTPQGDKVEIDAMTKCFGE | |
| Thr_aureum_ORF2 | (346) | QPSEEACLKATYELVGVPP-RDVQYVECHATGTPQGDTVELQAVKACFEG | |
| Thr_sp_20892_OrfB | (310) | LPSEESCIRDTYRRAGVAADQSIQYIECHATGTPRGDVVEIEAVERVFKK | |

|  |  | 401 | 450 |
|---|---|---|---|
| Sch_sp_9659_Pfa2p | (352) | NTDHPPRMGSTKGNFGHTLVAAGFAGMAKVLLSMQHGTIPPTPGVDRSN- | |
| Sch_sp_2088_OrfB | (355) | ---KVPRFGTTKGNFGHTLVAAGFAGMCKVLLSMKHGIIPPTPGIDDETK | |
| Thr_sp_10212_Pfa2p | (348) | ---HLPRFGSTKGNFGHTLVAAGFAGMCKVLLSMQYGEIPPTPGLENPDN | |
| Thr_aureum_ORF2 | (395) | ---ASPRIGSTKGNFGHTLVAAGFAGMCKVLLAMERGVIPPTPGVDSGT- | |
| Thr_sp_20892_OrfB | (360) | ---NVPRLGSTKGNFGHSLVAAGFAGMAKLLLAMEHGVIPPTPGLDASN- | |

Figure 5. cont.

```
                              451                                               500
Sch_sp_9659_Pfa2p    (401)    CIDPLVVDEAIPWPYSSAQARAGKPGDELKCASLSAFGFGGTNAHCVFRE
Sch_sp_2088_OrfB     (402)    MDPLVVSGEAIPWPETNGEPKR---------AGLSAFGFGGTNAHAVFEE
Thr_sp_10212_Pfa2p   (395)    IMHDLVVTETIPWPNTNGDLKR---------ACLSAFGFGGTNAHAVFEE
Thr_aureum_ORF2      (441)    QIDPLVVTAALPWPDTRGGPKR---------AGLSAFGFGGTNAHAVFEE
Thr_sp_20892_OrfB    (406)    QASEHVVTKAITWPETHGAPKR---------AGLSAFGFGGTNAHALFEE 501                                               550
Sch_sp_9659_Pfa2p    (451)    HRQIAATATASPVLP-------EVTPGPIAIIGMDATFGTLKGLDAFEQA
Sch_sp_2088_OrfB     (443)    HDPSNAACTGHDSISALSARCGGESNMRIAITGMDATFGALKGLDAFERA
Thr_sp_10212_Pfa2p   (436)    YRSDLQANKTLENE--S-KSHEIFSSFKIAIVGMESEFGTLKGLQEFERA
Thr_aureum_ORF2      (482)    HIPSRAPPAVLCQPRLG-----SGPNRKLAIVGMDATFGSLKGLSALEAA
Thr_sp_20892_OrfB    (447)    FNAEGISYRPGKPP------VESNTRPSVVITGMDCTFGSLEGIDAFETA 551                                               600
Sch_sp_9659_Pfa2p    (494)    IYKGTDGASDLPSKRWRFLGADTDFLTAMGLDAVPRGCYVRDVDVDYKRL
Sch_sp_2088_OrfB     (493)    IYTGAHGAIPLPEKRWRFLGKDKDFLDLCGVKATPHGCYIEDVEVDFQRL
Thr_sp_10212_Pfa2p   (483)    IYNGGHGACDLPENRWRFLGEDKEFLQACGLQKLPRGCYIKEVETDFKRL
Thr_aureum_ORF2      (527)    LYEARHAARPLPAKRWRFLGGDESFLHEIGLECSPHGCYIEDVDVDFKRL
Thr_sp_20892_OrfB    (491)    LYEGRDAARDLPAKRWRFLGEDLEFLRAIRLKEKPRGCFVESVDVNFRRL
```

Figure 5. cont.

```
                                      601                                              650
Sch_sp_9659_Pfa2p     (544)   RSPMIPEDVLRPQQLLAVATMDRALQDAGMATGGKVAVLVGLGTDTELYR
Sch_sp_2088_OrfB      (543)   RTPMTPEDMLLPQQLLAVTTIDRAILDSGMKKGGNVAVFVGLGTDLELYR
Thr_sp_10212_Pfa2p    (533)   RLPMIQEDILRPLQLLAVSIIDRALNASGVKPNGKVAVLVGLGTDLELYR
Thr_aureum_ORF2       (577)   RTPMVPEDLLRPQQLLAVSTIDKAILDSGLAKGGNVAVLVGLGTDLELYR
Thr_sp_20892_OrfB     (541)   KTPLTPEDMLRPQQLLAVSTMDRAIIDAGLKKGQHVAVLVGLGTDLELYR 651                                              700
Sch_sp_9659_Pfa2p     (594)   HRARVTLKERLDP---AAFSPEQVQEMMDYINDCGTSTSYTSYIGNLVAT
Sch_sp_2088_OrfB      (593)   HRARVALKERVR-----PEASKKLNDMMQYINDCGTSTSYTSYIGNLVAT
Thr_sp_10212_Pfa2p    (583)   HRARVALKERLQTAV--KEDIPLLEKLMNYVNDRGTSTSYTSYIGNLVAT
Thr_aureum_ORF2       (627)   HRARVALKERLQGLVRSAEGGALTSRLMNYINDSGTSTSYTSYIGNLVAT
Thr_sp_20892_OrfB     (591)   HRARVALKEVLHPSL--KSDTAILQKIMQYVNDAGTSTSYTSYIGNLVAT 701                                              750
Sch_sp_9659_Pfa2p     (641)   RVSSQWGFTGPSFTVTEGANSVYRCLELGKFLLDTHQVDAVVVAGVDLCA
Sch_sp_2088_OrfB      (638)   RVSSQWGFTGPSFTITEGNNSVYRCAELGKYLLETGEVDGVVVAGVDLCG
Thr_sp_10212_Pfa2p    (631)   RVSSLWGFTGPSFTITEGENSVYRCLDLGRWFLANGEVDAVVVAGVDLCG
Thr_aureum_ORF2       (677)   RVSSQWGFTGPSFTVTEGANSVHRCAQLAKYMLDRGEVDAVVVAGVDLCG
Thr_sp_20892_OrfB     (639)   RISSQWGFTGPSFTVTEGNNSVYRCAQLAKDMLQVNRVDAVVIAGVDLNG
```

Figure 5. cont.

```
                             751                                              800
Sch_sp_9659_Pfa2p    (691)   TAENLYLKARRSAISRQDHPRANFEASADGYFAGEGSGALVLKRQADVGS
Sch_sp_2088_OrfB     (688)   SAENLYVKSRRFKVSTSDTPRASFDAAADGYFVGEGCGAFVLKRETSCTK
Thr_sp_10212_Pfa2p   (681)   SAENLFVKSRRSKVSTQNEPFANFESNADGYFAGDGCGALVLKRLSDCTD
Thr_aureum_ORF2      (727)   SAEAFFVRSRRMQISKSQRPAAPFDRAADGFFAGEGCGALVFKRLTDCVS
Thr_sp_20892_OrfB    (689)   SAESFFVRANRQKISKLSHPCASFDRDADGFFAGEGCGALVFKRLEDCAP 801                                              850
Sch_sp_9659_Pfa2p    (741)   -DDKVYASVAGLTCAAQPAEAVSPLLLQVHNDDNEKRVVEMVELAADSGR
Sch_sp_2088_OrfB     (738)   -DDRIYACMDAIVPGNVPSACLREALDQARVKPGD---IEMLELSADSAR
Thr_sp_10212_Pfa2p   (731)   STEKIYATVDSIAVGDEVGPTIKQALKNASIAAKD---IELAELSASSGK
Thr_aureum_ORF2      (777)   -GERIYASLDSVVVATTPRAALRAAAGSARVDPAS---IDMVELSADSHR
Thr_sp_20892_OrfB    (739)   -QEKIYASIDSIAIDKEPTSSAVKAVYQSDSSLSD---IELLEISGDSKR 851                                              900
Sch_sp_9659_Pfa2p    (790)   HAPHLANSPLSAESQLEQVSKLLAHQVPG----SVAIGSVRANVGDVGYA
Sch_sp_2088_OrfB     (784)   HLKDPSVLPKELTAEEEIGGLQTILRDDDKLPRNVATGSVKATVGDTGYA
Thr_sp_10212_Pfa2p   (778)   HHSGRITCEDELNELGEIFNEG---------IQRVAIGSVKANVGDVGYA
Thr_aureum_ORF2      (823)   FVRAPGTVAQPLTAEVEVGAVREVIGTAGRGSRSVAVGSVRANVGDAGFA
Thr_sp_20892_OrfB    (785)   FAAFEGAVEIQSSVEAQLKGLSKVLEPAK--GQGVAVGSTRATVGDIGYA
```

Figure 5. cont.

```
                              901                                              950
Sch_sp_9659_Pfa2p    (836)    SGAASLIKTALCLHNRYLP---ANPQWERPVAPVSEALFTCPRSRAWLKN
Sch_sp_2088_OrfB     (834)    SGAASLIKAALCIYNRYLPSNGDDWDEPAPEAPWDSTLFACQTSRAWLKN
Thr_sp_10212_Pfa2p   (819)    SGAASLIKTALCLYNRYLP-KLPNWNKPTKDVEWSKSFFVCEHSRAWLKN
Thr_aureum_ORF2      (873)    SGAAALVKTALCLHNRYLA-ATPGWDAPAAGVDFGAELYVCRESRAWVKN
Thr_sp_20892_OrfB    (833)    TGAASLIKTALCLYNRYLP-ALANWSGPCEQSAWGSNMFVCHETRPWMKN 951                                             1000
Sch_sp_9659_Pfa2p    (883)    PGESRLAAVASASESGSCFGVLLTDEYATHESSNRLSLDDAAPKLIAIRG
Sch_sp_2088_OrfB     (884)    PGERRYAAVSGVSETRSCYSVLLSEAEGHYERENRISLDEEAPKLIVLRA
Thr_sp_10212_Pfa2p   (868)    VDENRHAVVSGVCENGSCYGIVMSDVQGHHEESNLVSLDKNEPKVLGIYG
Thr_aureum_ORF2      (922)    AGVARHAAISGVDEGGSCYGLVLSDVPGQYETGNRISLQAESPKLLLLSA
Thr_sp_20892_OrfB    (882)    QNEKRCALISGTDPSHTCFSLVLSDTG-CYEEHNRTCFDVQAPQLVLIHG 1001                                            1050
Sch_sp_9659_Pfa2p    (933)    DTVDDIMAKVNAELALLRAHAETGSATDDDPAAAVAFTAHRLRFLRLVGE
Sch_sp_2088_OrfB     (934)    DSHEEILGRLDKIRERFLQPTGAAPRESELKAQARRIFLE--LLGETLAQ
Thr_sp_10212_Pfa2p   (918)    DSVDDILVQLNKYLEKFLQETGTAAAAQKVKSPTIDIDSN--VFAEMLNL
Thr_aureum_ORF2      (972)    PDHAALLDKVAAELAALEQADGLSAAAAVDR----------LLGESLVG
Thr_sp_20892_OrfB    (931)    FDGKTIVRRLEGYLLELVEGHASPS----------EYFHK--LIGQSLLE
```

Figure 5. cont.

```
                               1051                                          1100
Sch_sp_9659_Pfa2p    (983)    TVASHGATATLCLALLTTPEKLEKELELAAKGVPRSAKAGRNWMSPSGSA
Sch_sp_2088_OrfB     (982)    DAASSGSQKPLALSLVSTPSKLQREVELAAKGIPRCLKMRRDWSSPAGSR
Thr_sp_10212_Pfa2p   (966)    PQDKN---KKFAVALVTTPNKLQREIELAVKGIPRCVKAKRDWCSPSGSI
Thr_aureum_ORF2     (1012)    CAAGS---GGLTLCLVASPASLHKELALAHRGIPRCIKARRDWASPAGSY
Thr_sp_20892_OrfB    (969)    NSKES---KLTLSLVCNPNQLQKELMLAIKGVQRSMLTGKDWVSPSGSCF 1101                                          1150
Sch_sp_9659_Pfa2p   (1033)    FAPTPVTSDRVAFMYGEGRSPYYGVGLDLHRLWPALHERINDKTAALWEN
Sch_sp_2088_OrfB    (1032)    YAPEPLASDRVAFMYGEGRSPYYGITQDIHRIWPELHEVINEKTNRLWAE
Thr_sp_10212_Pfa2p  (1013)    FACNPLKSDNIAFMYGEGRSPYAGLGYDLHRIWPMLHELVNNRTTELWDQ
Thr_aureum_ORF2     (1059)    FAPEPIASDRVAFMYGEGRSPYCGVGRDLHRIWPALHERVNAKTVNLWGD
Thr_sp_20892_OrfB   (1015)    APNPLSSAKVAFMYGEGRSPYCGVGLGLHRLWPGLHENVNNKTVDLWTEG 1151                                          1200
Sch_sp_9659_Pfa2p   (1083)    GDSWLMPRAVDADSQRAVQTAFDADQIEMFRTGIFVSICLTDYARDVLGV
Sch_sp_2088_OrfB    (1082)    GDRWVMPRASFKSELESQQQEFDRNMIEMFRLGILTSIAFTNLARDVLNI
Thr_sp_10212_Pfa2p  (1063)    GDSWYLPRSSSVAEKEKVFGDFDKNQIEMFRLGIFVSMCFTDMATELLGL
Thr_aureum_ORF2     (1109)    GDAWLLPRATSAEEEEQLCRNFDSNQVEMFRTGVYISMCLTDLARSLIGL
Thr_sp_20892_OrfB   (1065)    DGWLYPRTLTREEHTKAIESFNANQIEMFRAGIFISMCQTDYVMNVLGVQ
```

Figure 5. cont.

```
                            1201                                              1250
Sch_sp_9659_Pfa2p    (1133) QPKACFGLSLGEISMLFALSRRNCGLSDQLTQRLRTSPVWSTQLAVEFQA
Sch_sp_2088_OrfB     (1132) TPKAAFGLSLGEISMIFAFSKKNGLISDQLTKDLRESDVWNKALAVEFNA
Thr_sp_10212_Pfa2p   (1113) KPKAAFGLSLGEISMLFAFSKKNTKLSKELTRRLKEAKVWASQLAVEFAA
Thr_aureum_ORF2      (1159) GPKASFGLSLGEVSMLFALSESNCRLSEEMTRRLRASPVWNSELAVEFNA
Thr_sp_20892_OrfB    (1115) PKAGFGLSLGEISMLFAMSKENCRQSQEMTNRLRGSPVWSNELAINFNAI 1251                                              1300
Sch_sp_9659_Pfa2p    (1183) LRKLWNVPADAPVESFWQGYLVRASRAEIEKAIGPDNRFVRLLIVNDSSS
Sch_sp_2088_OrfB     (1182) LREAWGIPQSVPKDEFWQGYIVRGTKQDIEAAIAPDSKYVRLTIINDANT
Thr_sp_10212_Pfa2p   (1163) IRDLWNIPADKSIDEFWQGYFVYANRTLVENTIG-ENKFVRLLIVNDSQS
Thr_aureum_ORF2      (1209) LRKLWGVAPGAPVDSFWQGYVVRATRAQVEQAIGEDNQFVRLLIVNDSQS
Thr_sp_20892_OrfB    (1165) RKLWKIPRGAPLESFWQGYLVHGTREEVEHAIGLSEPYVRLLIVNDSRSA 1301                                              1350
Sch_sp_9659_Pfa2p    (1233) ALIAGKPAECLRVLERLGGRLPPMPVKQGMIGHCPEVAPYTPGIAHIHEI
Sch_sp_2088_OrfB     (1232) ALISGKPDACKAAIARLGGNIPALPVTQGMCGHCPEVGPYTKDIAKIHAN
Thr_sp_10212_Pfa2p   (1212) CLIAGKPDECQKVIEKLHLKLPAVPVTQGMIGHCPEAIPYLDQISHIHEM
Thr_aureum_ORF2      (1259) VLIAGKPAACEAVIARIGSILPPLQVSQGMVGHCAEVLPYTSEIGRIHNM
Thr_sp_20892_OrfB    (1215) LIAGKPDACQAVISRLNSKFPSLPVKQGMIGHCPEVRAFIKDIGYIHETL
```

Figure 5. cont.

```
                             1351                                         1400
Sch_sp_9659_Pfa2p   (1283)   LEIPDSPVKMYTSVTNAELRG----------------GSNSSITEFVQKL
Sch_sp_2088_OrfB    (1282)   LEFPVVDGLDLWTTINQKRLV-------PRATGAKDEWAPSSFGEYAGQL
Thr_sp_10212_Pfa2p  (1262)   LEIPKPENVKLFTTSENR--------------ELVSMKDSVSKLVAEI
Thr_aureum_ORF2     (1309)   LRFPSQDETGGCKMYSSVSNSRIGPVEESQMGPGTELVFSPSMEDFVAQL
Thr_sp_20892_OrfB   (1265)   RISNDYSDCQLFSAVTKG---------------ALDSSTMEIKHFVGEV 1401                                         1450
Sch_sp_9659_Pfa2p   (1317)   YTRIADFPGIVDKVSRDG-HDVFVEVGPNNMRSAAVSDILGKAATPHVSV
Sch_sp_2088_OrfB    (1325)   YEKQANFPQIVETIYKQN-YDVFVEVGPNNHRSTAVRTTLGPQR-NHLAG
Thr_sp_10212_Pfa2p  (1296)   YQHVADFPNIVNKVKETCKTDIFIELGSNNYRSGAVKTILGP---EIVSV
Thr_aureum_ORF2     (1359)   YSRVADFPAITEAVYQQG-HDVFVEVGPDHSRSAAVRSTLGPTR-RHIAV
Thr_sp_20892_OrfB   (1300)   YSRIADFPQIVNTVHSAG-YDVFLELGCDASRSAAVQNILGGQG-KFLST 1451                                         1500
Sch_sp_9659_Pfa2p   (1366)   ALDRPSESAWTQTLKSLALLTAHRVPLHNPTLFADLYHPTFLTAIDSAMQ
Sch_sp_2088_OrfB    (1373)   AIDKQNEDAWTTIVKLVASLKAHLVPGVTISPLYHSKLVAEAQACYAALC
Thr_sp_10212_Pfa2p  (1343)   AIDRQNETAWGQLMKMVASLISHRVPGVELKKLYHPELLKFDPQAKPNRF
Thr_aureum_ORF2     (1407)   AMDRKGESAWSQLLKMLATLASHRVPGLDLSSMYHPAVVERCRLALAAQR
Thr_sp_20892_OrfB   (1348)   AIDKKGHSAWSQVLRATASLAAHRVPGISILDLFHPNFREMCCTMATT--
```

Figure 5. cont.

```
                             1501                                              1550
Sch_sp_9659_Pfa2p    (1416)  E-PPPKPNRFLRSVEVNGYFCPDGISKQVAAASAKPSTHCMVRLHPAKAV
Sch_sp_2088_OrfB     (1423)  KGEKPKKNKFVRKIQLNGRFNSKADPISSADLASFPPADPAIEAAISSRI
Thr_sp_10212_Pfa2p   (1393)  IRNIELNGFFDRTNIIVDKQLSPADPKLAEIVNNRNMPKDNVYVPIERVK
Thr_aureum_ORF2      (1457)  SGQPEQRNKFLRTIEVNGFYDPADATIPEAVATILPATAAISPPKLGAPH
Thr_sp_20892_OrfB    (1396)  --PKVEDKFLRTIQINGRFEKEMIHLEDTTLSCLPAPSEANIAAIQSRSI 1551                                              1600
Sch_sp_9659_Pfa2p    (1465)  VVAAAGAVVADSTPVVKAKQTSSS--------------------------
Sch_sp_2088_OrfB     (1473)  MKPVAPKFYARLNIDEQDETRDPILNKDNAPSSSSSSSSSSSSSSSPSPA
Thr_sp_10212_Pfa2p   (1443)  TMIKAEPANLQVSVGSKPVVTERISSDDNLFEKLSEITKSFDG-------
Thr_aureum_ORF2      (1507)  DSQPEAEARPVGEASVPRRATSSSKLARTLAIDACDSDVRAALLDLDAPI
Thr_sp_20892_OrfB    (1443)  RSAAARSGQSHDCASHSHEENKDSCPEKLKLDSVSVAINFDN--------

1601                                              1650
Sch_sp_9659_Pfa2p    (1489)  --------------------------------------------------
Sch_sp_2088_OrfB     (1523)  PSAPVQKKAAPAAETKAVASADALRSALLDLDSMLALSSASASGNLVETA
Thr_sp_10212_Pfa2p   (1486)  ------------------------VN------------------------
Thr_aureum_ORF2      (1557)  AVG----------------G------------------------------
Thr_sp_20892_OrfB    (1486)  --------------------------------------------------
```

Figure 5. cont.

```
                            1651                                          1700
Sch_sp_9659_Pfa2p   (1489)  --------------LLVGDDAFLRCYDVDWPLYMGAMAEGISSVDLVVAAA
Sch_sp_2088_OrfB    (1573)  PSDASVIVPPCNIADLGSRAFMKTYGVSAPLYTGAMAKGIASADLVIAAG
Thr_sp_10212_Pfa2p  (1488)  ------ACTEAMLGDSG---FLKTYEVDYPLYTGAMAKGIASADLVIAAG
Thr_aureum_ORF2     (1561)  --SSRAQVPPCPVSALGSAAFRAAHGVDYALYMGAMAKGVASAEMVIAAG
Thr_sp_20892_OrfB   (1486)  ----------DDRIQLGHAGFREMYNTRYSLYTGAMAKGIASADLVIAAG 1701                                          1750
Sch_sp_9659_Pfa2p   (1526)  EARMLASFGAARLPMDQVELQIREIQQRTSN-AFAVNLMPGPDEAAT---
Sch_sp_2088_OrfB    (1623)  RQGILASFGAGGLPMQVVRESIEKIQAALPNGPYAVNLIHSPFDSNLEKG
Thr_sp_10212_Pfa2p  (1529)  KSKILASFGAGGLALQVVEDAIKQIKAELGNGPFAVNLIHSPFDPSLEKG
Thr_aureum_ORF2     (1609)  KARMLASFGAGGLPLGEVEEALDKIQAALPEGPFAVNLIHSPFDPNLEEG
Thr_sp_20892_OrfB   (1526)  KEGILASYGAGGLPLATVRKGIDKIQQALPSGPYAVNLIHSPFDGNLEQG 1751                                          1800
Sch_sp_9659_Pfa2p   (1572)  -VDALLRTGVSIVEASGYTGALSADLVRYRVTGLRRTSCGASVSATHRVV
Sch_sp_2088_OrfB    (1673)  NVDLFLEKGVTFVEASAFM-TLTPQVVRYRAAGLTRNAD-GSVNIRNRII
Thr_sp_10212_Pfa2p  (1579)  NVDLFLKYNVRFVEVSAFM-SLTPQVVRYRAAGLAKARD-GSVKIQNRII
Thr_aureum_ORF2     (1659)  NVELFLRRGIRLVEASAFM-SVTPSLVRYRVAGLERGPG-GTARVLNRVI
Thr_sp_20892_OrfB   (1576)  NVDLFLEKNVRVAECSAFT-TLTVPVVHYRAAGLVRRQD-GSILIKNRII
```

Figure 5. cont.

```
                                     1801                                          1850
Sch_sp_9659_Pfa2p    (1621)   AKVSRTEVAEHFLRPAPAAVLEALVAAKQITPEQAALASRVAMADDVAVE
Sch_sp_2088_OrfB     (1721)   GKVSRTELAEMFMRPAPEHLLQKLIASGEINQEQAELARRVPVADDIAVE
Thr_sp_10212_Pfa2p   (1627)   AKISRTELAELFLKPAPKNILDALVADGSISQEQAQLALLVPMADDITVE
Thr_aureum_ORF2      (1707)   GKVSRAELAEMFMRPPPAAIVSKLLAQGLVTEEQASLAEIVPLVDDVAIE
Thr_sp_20892_OrfB    (1624)   AKVSRTELAEMFLRPAPQIILEKLVAAEIISSDQARMAAKVPMADDIAVE 1851                                          1900
Sch_sp_9659_Pfa2p    (1671)   ADSGGHTDNRPIHVLLPLVVAQRNR----WRHLVDTPVRVGAGGGIACPR
Sch_sp_2088_OrfB     (1771)   ADSGGHTDNRPIHVILPLIINLRDRLHRECGYPANLRVRVGAGGGIGCPQ
Thr_sp_10212_Pfa2p   (1677)   ADSGGHTDNRPIHVLLPLIIQQRN--RICKQYPKHLKVRIGAAGGIGCPK
Thr_aureum_ORF2      (1757)   ADSGGHTDNRPIHVVLPVVLALRDRVMRECKYPAANRVRVGAGGGIGCPA
Thr_sp_20892_OrfB    (1674)   ADSGGHTDNRPMHVILPLIIQLRNTILAEYGCATAFRTRIGAGGGIGCPS 1901                                          1950
Sch_sp_9659_Pfa2p    (1717)   AALLAFSLGAAFVVTGSVNQLAREAGTSDAVRLLLATATYSDVAMAPGG-
Sch_sp_2088_OrfB     (1821)   AALATFNMGASFIVTGTVNQVAKQSGTCDNVRKQLAKATYSDVCMAPAAD
Thr_sp_10212_Pfa2p   (1725)   AAFAAFEMGAAYIATGTVNQLSKEAGTCDYVRKVLNKATYSDVTMAPAAD
Thr_aureum_ORF2      (1807)   AARAAFDMGAAFVLTGSINQLTRQAGTSDSVRAALARATYSDVTMAPAAD
Thr_sp_20892_OrfB    (1724)   AALAAFDMGASFVVTGSINQICREAGTCDTVRELLANSSYSDVTMAPAAD
```

Figure 5. cont.

```
                          1951                                              2000
Sch_sp_9659_Pfa2p    (1766)   -------VQVLKKQTMFAARATMLAQLQAKFGSFDAVPEPQLRKLERSVF

Sch_sp_2088_OrfB     (1871)   MFEEGVKLQVLKKGTMFPSRANKLYELFCKYDSFESMPPAELARVEKRIF

Thr_sp_10212_Pfa2p   (1775)   MFDHGVELQVLKKGTMFPSRAKKLYDLFKKYKSIEELPADEVKKLEQKVF

Thr_aureum_ORF2      (1857)   MFDQGVKLQVLKRGTMFPARANKLYELFTTYQSLDAIPRAELARLEKRVF Thr_sp_20892_OrfB    (1774)   MFDQGVKLQVLKRGTMFPSRANKLRKLFVNYESLETLPSKELKYLENIIF 2001                                              2050
Sch_sp_9659_Pfa2p    (1809)   KQSVADVWAAAREKFGVDATAAS--------PQERMALCVRWYMSQSSRW Sch_sp_2088_OrfB     (1921)   SRALEEVWDETKNFYINRLHNPEKIQRAERDPKLKMSLCFRWYLSLASRW Thr_sp_10212_Pfa2p   (1825)   KKSFDEVWDETKNYYINRLHSPEKIERAERDAKLKMSLCFRWYLSKSSRW Thr_aureum_ORF2      (1907)   RMSIDEVWNETKQFYETRLNNPAKVARAERDPKLKMSLCFRWYLSKSSKW Thr_sp_20892_OrfB    (1824)   KQAVDQVWEETKRFYCEKLNNPDKIARAMKDPKLKMSLCFRWYLSKSSGW 2051                                              2100
Sch_sp_9659_Pfa2p    (1851)   ATEATSARKADYQIWCGPAIGSFNDFVRGTKLDATAGTGEFPRVVDINQH Sch_sp_2088_OrfB     (1971)   ANTGASDRVMDYQVWCGPAIGSFNDFIKG-TYLDPAVANEYPCVVQINKQ Thr_sp_10212_Pfa2p   (1875)   ANTGESGRVQDYQIWCGPAIGSYNDFAKGSPCLDPEILGSFPSVVQINKH Thr_aureum_ORF2      (1957)   ASTGQVGRELDYQVWCGPTIGAFNEFVKGSSLDAEACGGRFPCVVRVNQE Thr_sp_20892_OrfB    (1874)   ANAGIKSRALDYQIWCGPAMGSFNNFASG-TSLDWKVTGVFPGVAEVNMA
```

Figure 5. cont.

```
                            2101                                    2140
Sch_sp_9659_Pfa2p   (1901)  ILLGASHYRRVQQQQQDDDVEYIIV---------------
Sch_sp_2088_OrfB    (2020)  ILRGACFLRRLEILRNARLSDGAAALVASIDDTYVPAEKL
Thr_sp_10212_Pfa2p  (1925)  ILRGACFYQRLSQLKYLNFNYEELDTLTYSASNFI-----
Thr_aureum_ORF2     (2007)  ILCGAAYEQRLARFMLLAGRESADALAYTVAEAR------
Thr_sp_20892_OrfB   (1923)  ILDGARELAAKRN---------------------------
```

Figure 6.

```
                              1                                                  50
Sch_sp_9659_Pfa3p    (1)   ---MTSSKKTPVWEMSKEELLDGKTVVFDYNELLEFAEGDVGQVFGPEFD
Sch_sp_2088_OrfC     (1)   MALRVKTNKKPCWEMTKEELTSGKTEVFNYEELLEFAEGDIAKVFGPEFA
Thr_sp_20892_OrfC    (1)   MGPRVASGKVPAWEMSKSELCDDRTVVFDYEELLEFAEGDISKVFGPEFK
Thr_sp_10212_Pfa3p   (1)   -MVGLQMKKKPVWEMSKEEQSSGKNVVFDYDELLEFAEGDIGKVFGPKFD 51                                                 100
Sch_sp_9659_Pfa3p    (48)  IIDKYRRRVRLPAREYLLVSRVTLMDAEVNNFRVGSRMVTEYDVPVNGEL
Sch_sp_2088_OrfC     (51)  VIDKYPRRVRLPAREYLLVTRVTLMDAEVNNYRVGARMVTEYDLPVNGEL
Thr_sp_20892_OrfC    (51)  VVDGFRRRVRLPAREYLLVTRVTLMDAEVGNFRVGARMVTEYDVPVNGEL
Thr_sp_10212_Pfa3p   (50)  IIDKYSRRVRLPAREYLLVTRVTLMDAEVGNFRVGSRMVTEYDVPVNGEL 101                                                150
Sch_sp_9659_Pfa3p    (98)  SEGGDVPWAVLVESGQCDLMLISYMGIDFQCKGDRVYRLLNTSLTFFGVA
Sch_sp_2088_OrfC    (101)  SEGGDCPWAVLVESGQCDLMLISYMGIDFQNQGDRVYRLLNTTLTFYGVA
Thr_sp_20892_OrfC   (101)  SEGGDVPWAVLVEAGQCDLLLISYMGIDFQCKGERVYRLLNTTLTFFGVA
Thr_sp_10212_Pfa3p  (100)  SQGGDVPWAVLVESGQCDLMLISYMGIDFQCKGDRVYRLLNTTLTFYGVA 151                                                200
Sch_sp_9659_Pfa3p   (148)  HEGETLVYDIRVTGFAKGAGGEISMFFFEYDCFVDGRLLIEMRDGCAGFF
Sch_sp_2088_OrfC    (151)  HEGETLEYDIRVTGFAKRLDGGISMFFFEYDCYVNGRLLIEMRDGCAGFF
Thr_sp_20892_OrfC   (151)  KEGETLVYDIRVTGFAKRPDGDISMFFFEYDCYCNGKLLIEMRDGSAGFF
Thr_sp_10212_Pfa3p  (150)  HEGETLVYDIRVTGFAKGMHGEISMFFFEYDCYVNGRLLIEMRDGCAGFF
```

Figure 6. cont.

```
                              201                                              250
Sch_sp_9659_Pfa3p   (198)  TDAELAAGKGVLKTKAELAARAQIQKQDIAPFAPAPCSHKTSLDAREMRL
Sch_sp_2088_OrfC    (201)  TNEELDAGKGVVFTRGDLAARAKIPKQDVSPYAVAPCLHKTKLNEKEMQT
Thr_sp_20892_OrfC   (201)  TDEELAAGKGVVVTRAQQNMRDKIVRQSIEPFALAACTHKTTLNESDMQS
Thr_sp_10212_Pfa3p  (200)  TDEELAAGKGVIKTVAELHKRKSIVPKSIKPFALNPAVHKTMFSENDMEK 251                                              300
Sch_sp_9659_Pfa3p   (248)  LVDRQWARVFG--SGMAGIDYKLCARKMLMIDRVTHLDPRGGAHGLGLLI
Sch_sp_2088_OrfC    (251)  LVDKDWASVFGSKNGMPEINYKLCARKMLMIDRVTSIDHKGGVYGLGQLV
Thr_sp_20892_OrfC   (251)  LVERNWANVFGTSNKMAELNYKICARKMLMIDRVTHIDHHGGAYGLGLLV
Thr_sp_10212_Pfa3p  (250)  LCERQWENVLG--SGLQGIDYKLCARKMLMIDRITKIQHNGGAYGLGLLV 301                                              350
Sch_sp_9659_Pfa3p   (296)  GEKVLERDHWYFPCHFVRDEVMAGSLVSDGCSQLLKVYMLWLGLHTTVGA
Sch_sp_2088_OrfC    (301)  GEKILERDHWYFPCHFVKDQVMAGSLVSDGCSQMLKMYMIWLGLHLTTGP
Thr_sp_20892_OrfC   (301)  GEKILDRNHWYFPCHFVNDQVMAGSLVSDGCSQLLKLYMIWLGLHLKMEE
Thr_sp_10212_Pfa3p  (298)  GEKILERDHWYFPCHFVKDQVMAGSLVSDGCSQLLKLYMLWLGLHDVVPD 351                                              400
Sch_sp_9659_Pfa3p   (346)  FDFRPVSGHANKVRCRGQISPHKGKLVYVMEIKEMGFDAKTGDPFAIADV
Sch_sp_2088_OrfC    (351)  FDFRPVNGHPNKVRCRGQISPHKGKLVYVMEIKEMGFDEDN-DPYAIADV
Thr_sp_20892_OrfC   (351)  FDFLPVSGHKNKVRCRGQISPHKGKLVYVMEIKKMGYDQASGSPYAIADV
Thr_sp_10212_Pfa3p  (348)  FQFRPVPGQPNKVRCRGQISPHRGKLVYVMEIREMGFNESTGQPYAIADV
```

Figure 6. cont.

```
                           401                                              450
Sch_sp_9659_Pfa3p   (396)  DIIDVNFEEGQAFAGVEDLHSYGQGDLRKKIVVDFKGIALSLQKRKEQQK
Sch_sp_2088_OrfC    (400)  NIIDVDFEKGQDFS-LDRISDYGKGDLNKKIVVDFKGIALKMQKRSTNKN
Thr_sp_20892_OrfC   (401)  DIIDVNEELGQSFD-INDLASYGKGDLSKKIVVDFKGIALQLKGRAFSRM
Thr_sp_10212_Pfa3p  (398)  DIIDVNYELGQSFD-MADIDSYGRGNLSKKIVVDFKGIALQMEGTVKSSN 451                                              500
Sch_sp_9659_Pfa3p   (446)  ES--------------------------------MTVTTTTTTTSRVIA
Sch_sp_2088_OrfC    (449)  PSKVQPVFANGAATVGPEASKASSGASASASAAPAKPAFSADVLAPKPVA
Thr_sp_20892_OrfC   (450)  SS-------------------------SSSLNEGWQCVPKPSQRMEHEQ
Thr_sp_10212_Pfa3p  (447)  -----------------------------------IIDSSP--KSTIIQ 501                                              550
Sch_sp_9659_Pfa3p   (463)  PPSGCLKGDPTAPTSVTWHPMAEGNGGPGPTPSFSPSAYPPRAVCFSPFP
Sch_sp_2088_OrfC    (499)  LPEHILKGDALAPKEMSWHPMARIPG--NPTPSFAPSAYKPRNIAFTPFP
Thr_sp_20892_OrfC   (474)  PPAHCLASDPEAPSTVTWHPMSKLPG--NPTPFFSPSSYPPRAICFIPFP
Thr_sp_10212_Pfa3p  (459)  PPPNCLRGDPLAPSQVTWHPMAGVNG--APAPSFSPSDYPPRAVCFKPFP 551                                              600
Sch_sp_9659_Pfa3p   (513)  NNPLDNDHTPGQMPLTWFNMSEFMCGKVSNCLGPEFARFDASKTSRSPAF
Sch_sp_2088_OrfC    (547)  GNPNDNDHTPGKMPLTWFNMAEFMAGKVSMCLGPEFAKFDDSNTSRSPAW
Thr_sp_20892_OrfC   (522)  GNPLDNNCKAGEMPLNWYNMSEFMCGKVSNCLGPEFARFDKSNTSRSPAF
Thr_sp_10212_Pfa3p  (507)  GNPLDNDHTPGKMPLTWFNMSEFMCGKVSNCLGPEFKRFDNSKTSRSPAF
```

Figure 6. cont.

```
                           601                                              650
Sch_sp_9659_Pfa3p   (563)  DLALVTRVTSVADMEHGPFYNVDVNPGQGTMVGEFDCPADAWFFGASSRD
Sch_sp_2088_OrfC    (597)  DLALVTRAVSVSDLKHVNYRNIDLDPSKGTMVGEFDCPADAWFYKGACND
Thr_sp_20892_OrfC   (572)  DLALVTRVVEVTNMEHGKFLNVDCNPSKGTMVGEFDCPQDAWFFDGSCND
Thr_sp_10212_Pfa3p  (557)  DLALVTRVVSVSDMEFKPHLNIDVNPSKGTMIGEFDCPADAWFFQGSCND 651                                              700
Sch_sp_9659_Pfa3p   (613)  DHMPYSILMEIALQTSGVLTSVLKAPLTMDKDDILFRNLDADAELVGDAM
Sch_sp_2088_OrfC    (647)  AHMPYSILMEIALQTSGVLTSVLKAPLTMEKDDILFRNLDANAEFVR-AD
Thr_sp_20892_OrfC   (622)  GHMPYSIIMEIGLQTSGVLTSVLKAPLTMDKDDILFRNLDASAEMVR-PD
Thr_sp_10212_Pfa3p  (607)  GHMPYSIVMEIALQTSGVLTSVLKAPLTMDKDDILFRNLDATAEMVR-SD 701                                              750
Sch_sp_9659_Pfa3p   (663)  PDVRGKTIRNFTKCTGYSMLGKMGIHRFTFELSVDGAVFYKGSTSFGWFV
Sch_sp_2088_OrfC    (696)  LDYRGKTIRNVTKCTGYSMLGEMGVHRFTFELYVDDVLFYKGSTSFGWFV
Thr_sp_20892_OrfC   (671)  VDVRGKTIRNVTKCTGYAMLGKMGIHRFTFELSVDGVVFYKGSTSFGWFT
Thr_sp_10212_Pfa3p  (656)  VDCRGKTIKNFTQCTGYSMLGKMGIHRFTFELSVDDVVFYKGSTSFGWFT 751                                              800
Sch_sp_9659_Pfa3p   (713)  PEVFESQTGLDNGKPRLPWYREN----------NVAVDTLSAPASASSAQ
Sch_sp_2088_OrfC    (746)  PEVFAAQAGLDNGRKSEPWFIENKVPASQVSSFDVRPNGSGRTAIFANAP
Thr_sp_20892_OrfC   (721)  PEVFAQQAGLDNGKKTEPWCKTNN--TSVRRVEIASAKGKEQLTEKLPDA
Thr_sp_10212_Pfa3p  (706)  PEVFESQVGLDNGKKVQPWYLEQKS--SNVVTYDVASTAGKDKLFSKIGS
```

Figure 6. cont.

```
                              801                                              850
Sch_sp_9659_Pfa3p   (753) GQLQLQRRGSQAQFLDTIHLAGSGAGVHGQGYAHGEKAVNKQDWFFSCHF
Sch_sp_2088_OrfC    (796) SGAQLNRRTDQGQYLDAVDIVSG-SGKKSLGYAHGSKTVNPNDWFFSCHF
Thr_sp_20892_OrfC   (769) TNAQVLRRSEQCEYLDYLNIAPD-SGLHGKGYAHGHKDVNPQDWFFSCHF
Thr_sp_10212_Pfa3p  (754) KDAQVQRRNTQCEFLDTMHIIPN-TGKYNKGYAHGEKKVNPNDWFFSCHF 851                                              900
Sch_sp_9659_Pfa3p   (803) WFDPVMPGSLGIESMFQLVEAWCVKQGLAARHGIAHPVFAHAP-GATSWK
Sch_sp_2088_OrfC    (845) WFDSVMPGSLGVESMFQLVEAIAAHEDLAGKARHCQPHLCARPRARSSWK
Thr_sp_20892_OrfC   (818) WFDPVMPGSLGIESMFQLIEAFAVDQNIPGEYNVSNPTFAHAP-GKTAWK
Thr_sp_10212_Pfa3p  (803) WFDPVMPGSLGIESMFQLIEAFSIDQGIASKHGIVNPTFAHSN-GKTSWK 901                                              950
Sch_sp_9659_Pfa3p   (852) YRGQLTPKNDRMDSEVHIKSVAAFSS---WVDVVADGFLFVDGLRVYSAD
Sch_sp_2088_OrfC    (895) YRGQLTPKSKKMDSEVHIVSVDAHDG---VVDLVADGFLWADSLRVYSVS
Thr_sp_20892_OrfC   (867) YRGQLTPKNRAMDCEVHIVSITASPENGGYVDIVADGALWVDGLRVYEAK
Thr_sp_10212_Pfa3p  (852) YRGQLNNKGKRMDSEIHIKDIVKNADG--TVDLIADGFLLVDSLRVYSAD 951                                             1000
Sch_sp_9659_Pfa3p   (899) NLRVRIQTGAGHVEEQEVAAKATTKN----------SSIADVDVADLQAL
Sch_sp_2088_OrfC    (942) NIRVRIASGEAPAAASSAASVGSSASSVERTRSSPAVASGPAQTIDLKQL
Thr_sp_20892_OrfC   (917) ELRVRVVSAKPQAIPDVQQQPPSAKADPG----------KTGVALSPTQL
Thr_sp_10212_Pfa3p  (900) DLRVKIVPGTKAAPKSVAAAPRHVATPIPGV-----PSNTSSVEISLESL
```

Figure 6. cont.

```
                                 1001                                              1050
Sch_sp_9659_Pfa3p   (939)  KQALLTLERPLQLDAG-----------------SEVPACAVSDLGDRGFM
Sch_sp_2088_OrfC    (992)  KTELLELDAPLYLSQDPTSGQLKKHTDVASGQATIVQPCTLGDLGDRSFM
Thr_sp_20892_OrfC   (957)  RDVLLEVDNPLYLGVENSNLVQFESKPATSSRIVSIKPCSISDLGDKSFM
Thr_sp_10212_Pfa3p  (945)  KKELLNLEKPLYLETSNHI--VKQFGDVNNGQASVIPPCTINDLGERSFM 1051                                              1100
Sch_sp_9659_Pfa3p   (972)  ETYGVVAPLYSGAMAKGIASADLVIAMGQRKMLGSFGAGGLPMHVVRAGI
Sch_sp_2088_OrfC   (1042)  ETYGVVAPLYTGAMAKGIASADLVIAAGKRKILGSFGAGGLPMHHVRAAL
Thr_sp_20892_OrfC  (1007)  ETYNVSAPLYTGAMAKGIASADLVIAAGKRKILGSFGAGGLPISIVREAL
Thr_sp_10212_Pfa3p (0993)  ETYNVVAPLYTGAMAKGIASADLVIAAGKRKILGSFGAGGLPMHLVRASV 1101                                              1150
Sch_sp_9659_Pfa3p  (1022)  EKIQAALPAGPYAVNLIHSPFDANLEKGNVDLFLEKGVRVVEASAFMELT
Sch_sp_2088_OrfC   (1092)  EKIQAALPQGPYAVNLIHSPFDSNLEKGNVDLFLEKGVTVVEASAFMTLT
Thr_sp_20892_OrfC  (1057)  EKIQQHLPHGPYAVNLIHSPFDSNLEKGNVDLFLEMGVTVVECSAFMELT
Thr_sp_10212_Pfa3p (1043)  EKIQAALPEGPYAVNLIHSPFDSNLEKGNVDLFLEKGVHVVEASAFTALT 1151                                              1200
Sch_sp_9659_Pfa3p  (1072)  PQVVRYRATGLSRDARGGSVRTAHKIIGKVSRTELAEMFIRPAPQAILDK
Sch_sp_2088_OrfC   (1142)  PQVVRYRAAGLSRNADG-SVNIRNRIIGKVSRTELAEMFIRPAPEHLLEK
Thr_sp_20892_OrfC  (1107)  AQVVRYRASGLSKSADG-SIRIAHRIIGKVSRTELAEMFIRPAPQHLLQK
Thr_sp_10212_Pfa3p (1093)  TQVVRYRACGLSRAKDG-SVLIKNRIIGKVSRTELAEMFFRPAPQNLLDK
```

Figure 6. cont.

```
                              1201                                              1250
Sch_sp_9659_Pfa3p   (1122)   LVASGEITPEQAALALEVPMADDIAVEADSGGHTDNRPIHVILPLILSLR
Sch_sp_2088_OrfC    (1191)   LIASGEITQEQAELARRVPVADDIAVEADSGGHTDNRPIHVILPLIINLR
Thr_sp_20892_OrfC   (1156)   LVASGELTAEQAELATQVPVADDIAVEADSGGHTDNRPIHVILPLIINLR
Thr_sp_10212_Pfa3p  (1142)   LIASGEITKEQASLALEVPMADDVAVEADSGGHTDNRPIHVILPLIINLR 1251                                              1300
Sch_sp_9659_Pfa3p   (1172)   NRLQRELKYPARHRVRVGAGGGIGCPQAALGAFHMGAAFVVTGTVNQLSR
Sch_sp_2088_OrfC    (1241)   NRLHRECGYPAHLRVRVGAGGGVGCPQAAAAALTMGAAFIVTGTVNQVAK
Thr_sp_20892_OrfC   (1206)   NRLHKELDYPSHLRVRVGAGGGIGCPQAALAAFQMGAAFLITGTVNQLAR
Thr_sp_10212_Pfa3p  (1192)   NRIHKECGFPAALRVRVGAGGGIGCPSAVAAFNMGAAFLITGSVNQVSK 1301                                              1350
Sch_sp_9659_Pfa3p   (1222)   QAGTCDNVRRQLSRATYSDITMAPAADMFEQGVELQVLKKGTMFPSRAKK
Sch_sp_2088_OrfC    (1291)   QSGTCDNVRKQLSQATYSDICMAPAADMFEEGVKLQVLKKGTMFPSRANK
Thr_sp_20892_OrfC   (1256)   ESGTCDNVRLQLSKATYSDVCMAPAADMFDQGVELQVLKKGTLFPSRAKK
Thr_sp_10212_Pfa3p  (1242)   QSGTCDIVRKQLSEASYSDITMAPAADMFDQGVELQVLKKGTMFPSRAKK 1351                                              1400
Sch_sp_9659_Pfa3p   (1272)   LFELFHKYDSFEAMPADELARVEKRIFSKSLAEVWAETKDFYITRLNNPE
Sch_sp_2088_OrfC    (1341)   LYELFCKYDSFDSMPPAELERIEKRIFKRALQEVWEETKDFYINGLKNPE
Thr_sp_20892_OrfC   (1306)   LYELFCKYDSFEAMPAEELQRVEKRIFQKSLAEVWQETSDFYIHRIKNPE
Thr_sp_10212_Pfa3p  (1292)   LYELFCMYNSFDDMPKSELQRLEKRIFQKSLAEVWEETKDFYINRLNNPE
```

Figure 6. cont.

```
                              1401                                          1450
Sch_sp_9659_Pfa3p   (1322)    KIRKAENEDPKLKMSLCFRWYLGLSSFWANNGIADRTMDYQIWCGPAIGA
Sch_sp_2088_OrfC    (1391)    -KIQRAEHDPKLKMSLCFRWYLGLASRWANMGAPDRVMDYQVWCGPAIGA
Thr_sp_20892_OrfC   (1356)    -KINRAASDGKLKMSLCFRWYLGLSSFWANSGAQDRVMDYQIWCGPAIGA
Thr_sp_10212_Pfa3p  (1342)    KIEHAEKKDPKLKMSLCFRWYLGLSSFWANNGIKERSMDYQIWCGPAIGS 1451                                          1500
Sch_sp_9659_Pfa3p   (1372)    FNDFIADSYLDVAVSGEFPDVVQINLQILSGAAYLQRLLSVKLA--PRID
Sch_sp_2088_OrfC    (1440)    FNDFIKGTYLDPAVSNEYPCVVQINLQILRGACYLRRLNALRND--PRID
Thr_sp_20892_OrfC   (1405)    FNDFTKGTYLDVTVAKSYPCVAQINLQILQGAAYLKRLGVIRFDRMLLQA
Thr_sp_10212_Pfa3p  (1392)    YNDFVKGTYLDPAVAGSYPCVVQINMQILRGACFLQRVRAIKHD--PRLD 1501      1517
Sch_sp_9659_Pfa3p   (1420)    VDTEDDLFTYRPDHAL
Sch_sp_2088_OrfC    (1488)    LETEDAAFVYEPTNAL
Thr_sp_20892_OrfC   (1455)    VDIDDPVFTYVPTQPL
Thr_sp_10212_Pfa3p  (1440)    IDVDEDVFTYRPESTL
```

FIG. 7

(SEQ ID NO:1)

FIG.8

MDTRIAIVGMSAILPSGENVRESWEAIRDGLDCLSDLPADRVDVTAYYNPEKTTKDKIYCKRGGFIPEYDFDAREFGLNMFQMEDSDANQTISLLKV
KEALTDANIPAFSSGKKNIGCVLGIGGGQKASHEFYSRLNYVVVDKVLRKMGLPEEDVAAAVDKYKASFPEWRLDSFPGFLGNVTAGRCCNTFNM
EGMNCVVDAACASSLIAVKVAIEELLYGDCDAMIAGATCTDNSIGMYMAFSKTPVFSTDPSVKA YDAATKGMLIGEGSAMLVLKRYADAVRDGD
TVHAVIKGCASSSDGKAAGIYTPTISGQEEALRRAYARANVDPATVILVEGHGTGTPVGDKIELTALSNLFSKAFSANGGGAEEAEQVAVGSIKSQI
GHLKAVAGLAGLVKVVLALKHKTLPQTINVDKPPSLVDGTPIQQSPLYVNTMNRPWFTPVGVPRRAGVSSFGFGGANYHAVLEEFEPEHESAYRY
NNLPQVALLHAGDVATLAATVRAKLALATAEQEEARVVKNADYIAYHRFLDECKLRGAVPQAHARVGLLVRDLSSLIAVLEAAAAKLAGEESAT
EWTVSVATGEAAFRVRGVATEANVAALFSGQGAQYTHMFSDVAMNWPPFRESV AAMDRAQRERFGRPAKRVSSVLYPRKPYGDEPRQDHKEIS
QTRYSQPATLACSVGAFDIFKAAGLAPSFAAGHSLGEF AALYAAGSLDRDAVFDLVCARAKAMSDFTAQASSSGGAMAAVIGAKADQLSLGGAPD
VWLANSNSPSQTVITGTAEAVAAASDKLRCSGNFRVVPLACEAAFHSPHMRGAEQTFASALAQAPVSAPAAARFYSNVTGGAAVTSPADVKTNLG
KHMTSPVQFVQQVRAMHAAGARVFVEFGPKQVLSRLVKETLGEAGDVVTVAVNPDSAKDSDTQLRQAALTLAVAGVPLKDFDRWQLPDATRLE
PVKKKKTTLRLSAATYVSAKTLRQREAVLNDGYTVSGATAVVKEVDTANEERLVRQAQDLQRQLAEASTAAQAAQSKVAELERTIQDLERKVQQ
QQQEKGENSDSNAAAEVLRRHKELLQRMLQDCDEQAVPVATVVPTPTSSPTPTSSPVSGNSKSTRGSADLQALLAKAETVVMAVLAAKTGYEAD
MVEADMDLEAELGIDSIKRVEILSEVQGQLGVEAKDVDALSRTRTVGEVVDAMKAEIVAASGGSAPAVPSAPAASAAPTPAASTAPSADLQALLSK
AETVVMAVLAAKTGYEADMVEADMDLEAELGIDSIKRVEILSEVQGQLGVEAKDVDALSRTRTVGEVVDAMKAEIVAASAGSAPAPAVPSAPAA
SAAPTP AASTAPSADLQALLSKAETVVMAVLAAKTGYEADMVEADMDLEAELGIDSIKRVEILSEVQGQLGVEAKDVDALSRTRTVGEVVDAMK
AEIVAASGGSAPAPAVPSAPAASAAPTPAAATAPSADLQALLAKAETVVMAVLAAKTGYEADMVEADMDLEAELGIDSIKRVEILSEVQGQLGVE
AKDVDALSRTRTVGEVVDAMKAEIVAASAGSAPAPAVPSAPAASAAPTPAASTAPSADLQALLSKAETVVMAVLAAKTGYEADMVEADMDLEA
ELGIDSIKRVEILSEVQGQLGVEAKDVDALSRTRTVGEVVDAMKAEIVAASGGSAPAAAVPSAPAASAAPTPATAPSADLQALLSKAETVVMAVLA
AKTGYEADMVEADMDLEAELGIDSIKRVEILSEVQGQLGVEAKDVDALSRTRTVGEVVDAMKAEIVAASGGSAP AAPSAPALLPTLFGSECEDLSL
TFPVITTLPLPAELVLAEGGARPVVVVDDGSALTSSLVSSLGDRAVLLQVQSSSACSPRSTTHKLVTVADRSEAALQAALTSVEAQFGKVGGFVFQF
GDDDVQAQLGWALLAAKHLKTSLSEQIEGGRTFFVAVARLDGQLGLSGKSTTATVDLSRAQQGSVFGLCKTLDLEWPAVFCRGIDLAADLDAAQ
AARCLLGELSDPDVAVRESGYSASGQRCTTTTKSLTTGKPHQPISSSDLFLVSGGARGITPLCVRELAQRVGGGTYVLIGRSELPTTEPAWAVGVESG
KPLEKAALAFLKAEFAAGRGAKPTPMLHKKLVGAVVGAREVRASLAEITAQGATAVYESCDVSSAAKVREMVERVQQQGGRRVSGVFHASGVL
RDKLVENKSLADFSAVYDTKVGGLINLLACVDLAQLRHLVLFSSLAGFHGNVGQSDYAMANEALNKLAAHLSAVHPQLCARSICFGPWDGGMVT
PALKANFIRMGIQIIPRQGGAQTVANMLVSSSPGQLLVGNWGVPPVVPSATEHTVLQTLRQSDNPFLDSHVIQGRRVLPMTLAVGYMAHQAQSIYA
GHQLWAVEDAQLFKGIAIDNGADVPVRVELSRRKEEQEDAGKVKVKVQVLLKSQVNGKSVPAYKATVVLSPAPRPSVITRDFDLTPDPACTEHDL
YDGKTLFHGKAFQGIEQVLSATPKQLTAKCRNLPLTPEQRGQFVVNLSQQDPFQADIAFQAMLVWARMLRQSAALPNNCERFDFYKPMAPGATY
YTSVKLASASPLVDSVCKCTVAMHDEQGEVYFSARASVVLNKTLTY (SEQ ID NO:2)

FIG.9 atgccgtgcgataacattgccgtcgtgggcatggcggtgcagtatgccggatgcaagaaccaggacga tctgggatacgctgatgcgtaaggagatcaactcgagcccgatctcggcggagcgcctcg acgcgctaccgcgacctccacttccaccc gcagcgcagcaa acgccgacaccttctgcaacgatcgctacggctgc cgatgccagcgtcgacaacgagcacgaccctcgccgacctggcccggcgcgccctgctcgacgccggaattaacctcgacgacgccagccaccaccgccaacctacg cgacttcggcatcgtgagcggctgcct c tcccccatggacaatctgcagggcgagctgctcaatctgtaccaa gcat ggagaaccgcgtgggcgcccagcgcttccgcgactcgcgccctg cggagcgccgcgcgctgtctcgcccgagg ccagcgacccgcgc gtactccgacccggccgtccttcgtggccaaccagctcggcctggggccgtgcgctacagcctcgatgcagcctgcgcgtcggcgctgtactgcctcaagctggcgtccgaccacttgctctcgcgcagcgcggac gatgctg tgccgcgccacatgctttccggaccccgttcttcattctctcggggttctccacccttccaggcgatgccgctgggccggaccggacgataacccact ccgtgccgctgccggcagggcagccagggcctgacgcccgagagggcggcgccatcatggtgct gaagcgcctcgaggacgccgtgcgcgacggcgaccgcatctacggcaccttgctcggcacgagtctgagcaacgccgggtgccgcctgccgctgagcccgcacctgccgagcgagaagtcgtgcatggaggacct acacgagcgtcggcatcgac ccaagcgaggtgcagtac ggagtgccacgccacgggcactccgcagggcgac cgtggag agaggcgctgcgccactgcttcgag aacacggaccaccgccgcgcatgggctccaccaaggggcaactttggccacactctc ggcggc cgg tcgcaggcatggccaag gctgctgtcgatgcagcacggcacgatcccgcccacgcccggt cgaccgctcaactgcatcgacccgctc c ggacgaggccatcccttggccgtactcgtcggcgcaggcgcgggcaggcaaaccagg cgatgagctcaa gcgcctcgctctccgcctttggctttggtggaaccaacgcgcactgt cttcc gagcaccgccaaattgctgctactgcgacagcctcgccggtgcttcccgag gactcctggaccgattgccatcatcgggatggacgcgac t tggtaccctcaagggcctggacgc ttgagcaggccatctacaagggcacggacggcgccagcgacctgccgagcaagcgctggccgttcctgggcgccgacacggacttcttgaccgccatgggcctcgacgccgtgccgcgcgg gctacgtgc gcgac ggac ggactacaagcggctgcg cgccgatgatccctgaggacgtcctgcgccccgcaacagctgctggcggtggctacgatggaccgcgcgctgcaggacgctggaatggcgacggaggaagcaag ggcggtgctggtggggctcgg cacggacaccgagctgtaccggcaccgcgcgcgc gacactcaaggagcggctcgaccgcccgcgtctcgcccgagcaggtgcaggagatgatggactacatcaacgactgccgcacctcgacgtcgtacac c acatcggcaacctc ggc cacgcgcgtcctcgcagtcgggcctttacgggccccttcaccgtcaccgaaggcgcaaactcg ctaccgctgcctcgagctgggcaatcctgctcgacacgcaccaggtggacgccc ggtggccggccgtcgacctctgccaccgccg agaacctttacctcaaggcgcgccgctccgccatcagccgacaggaccaccctcgccgccaactttgaggccagccgccgacgggtactttgccggcgagggcagcggcgccctggtcctcaagcgccaggccgac tggctcagacgacaag ctacg ccagtgtcgcgggcctcacgtgccgccgcgcagcccgctgaagcc gtcgccgctactactccaagtccacaacgacgacaacgagaagagggtggtggagatg ggagctcgccgccgactcgg cgccatgcgccgcacttggccaactcgccg ctgagcgccgagtcgcagctggagcaa gtccaagttgctcgccgcaccaggtgccgggctcggtggccatcggcagcgtgccgcgccaac gggagacgtcgg acgcctcgggcgccgcgagcctcatcaagacggcgctgtgcctccacaaccg ctacctcccggccaacccgcagtgggaacggccggtggccgcg ctccgaggcgctgtttacttgccgcgcctcgc gcctggctgaagaacccgggcga cgcgactggcggct cgcca gcctccgagagcgg cctgctttggcgtgctc ctcacagacga acgccactcatgagagcagcaaccgcctctcgctggatgacgccgccccaagctcatcgcgatcc ggcgacaccgttgacgatatcatggccaaggtcaacgccgagctggcgctcctccgagcgcacgccgaaaccgggtctg ctactgacgacgacccagctgctgct cgctttcactgctcatcgcttgccgcttttgcggctcgtaggggagacg ggctagtcacg gccaccggcgacctt gtttggccctgctgacaacgccggagaagctggagaaggagttggagctggcagcc aagggt accgcgaagcgccaaggccggcgcaactggat cgccatcgggcagcgccttttgcgccgacacct gaccagcgaccgccgc tcatgtacggcgagggccgcagcccctactacggc cggcctcgacctgcaccgcct g gccggcttttgcagagcgcatcaacgacaagaccgcgcgctgtgggagaacggcgactcgttggctcatgccgcgcgcggtggatgccgactcgcagcgcgcc gcagacggccttttgacgcggaccagatcgaaggt tccgcacgggcatcttcgt ccatctgcctcaccgactacgcgcgcgac gctcgggggtgcagcccaaggccgtgcttcggcctcagcctcggcgagatctccatgctctttgcgctgtcgcgacgcaactgcggcct cggaccagctcacgcagcgcctacgcacctcgccg gtg cgacacagctggcg ggagttccaggccttgcgcaagctatggaacgtgccggcggacgccccc ggagtccttctggcagggctacttggttcgcgccagccgcgccgaaatcgagaaggcgatcgggcccgacaaccgcttcgtgcgcctgctg atcgtcaacgactcgagcagcgcgctgatcgccggcaaacctgccga gtctgcgc gctggagcgcctgggccggcg tgccgccgatgcccgtcaagcaaggcatgattggcgcactgccccgaagtggcgccctacacgccgggcatcgcgca catccacgagattttggagattccggacagcccc caagat acacctcg caccaacgccgagctgcgcggggcagcaacagcagcatcaccgagttc gcagaa t acacgcgcatcgccgactttccggcatcgtcgacaaggtcagcc gacggccacgatgtcttcgtcgaggtggggccgaacaacatgcgctccgccgcg cagtgacattcttggcaaggctgccaccccgcatgtctccgtggccgctggaccgccccagtga cggc ggacgcagaccctcaa cgctggcgctgctg accgccaccgcgtgcccctgcacaaccccgactctgtttgcggacct accaccccacgttcctgacggctatcgactctgcgatgcaggacccccgcccaagcccaaccgcttcctcgcagcgtagaggtcaacgg acttttgccccgacggcatca gcaagcag tgctgctgcaa gccaaaccctcgacgcattgcatggttc ttgcacccagccaaggca t g tgctgctgctggtgct ggttgctgattcgacgcccgtggtcaaggccaagcagac cgtcgtcgttgttg tggggatgacg cctttctgcgctgctacgacgtggactggccgctctacatgggcgccatggccggaaggcatctcgtcggtagacctg ggtcgctgccgccgaggcccgcatgctggcatcattcggagcggcccgcttgcctatggaccaggtggaactccagatccgtg agatccagcaacgcacctccaacgcctttgctgtcaacctgatgccgggtcctgacgaggccgcgacggtggacgcgctgctgcgcacggc ctcaatcgtcgaggcatcgggctacaccggcgctctctgcagacctggtgcgctaccgt cacg ggtctgcgacgaactagttgcg gcttct gtcggcgactcacc gtggtcgccaag gtcgcgcaccgag ggccgagcacttctgcgcccggccgccgccgcctactagaggcttg cgccgccaaacagattacgcccgagcaggccgc gctggccagccgc cgccatggccgacgac cgccgggtggaggccgactcggccgggcacacacgacaaccgacccgatccac gctgctgccgctcgtggtggcgcagcgcaaccgctggcgccacctg ggacacgcca gcgccgtcggcgc cggcggcgggatcgcct ccgcgcgccgcgctgctcgccttttccctgggcgccgcctt ggtcaccgggtcc caaccaactggcccgcgaggctggcaccagcgacgcg ccgactactgctggcgacggccacctactcggac ggccatg gcgccgggcggc ccag gctcaagaagcagaccattgttcgccgcgcgggccacgatgctcgcccagctgcaggccaagttcggctccttgacgcc gccggagccgcagctgcgcaagctcgagcgctccgttcaagcagtcc ggcggac gtgtggctgctgcacgcgaaaagtttggtgtcgacgctaccgctgcaagtccgcaggagaggatggcgctctgtgcgcgctgatacatgtcgcagtc cgcgatgggctaccgaggcgacgtccgcgcgcaaggcggactaccagatctggtgcggcc ccgccatcggcacgcttcaacgacttc tcgccggcaccaagctggacgcgaccgctggaccggcgagtttccgcgcgtcgtggacatcaaccagcacatcctcctcggagcctcgcactaccgccgcgtgcagcaacaacaggacgacgcgtag aatacatcatcgtataa (SEQ ID NO:3)

FIG.10

MPCDNIAVVGMAVQYAGCKNQDEFWDTLMRKEINSSPISAERLGTRYRDLHFHPQRSKYADTFCNDRYGCVDASVDNEHDLLADLARRALLDAG
INLDDASTTANLRDFGIVSGCLSFPMDNLQGELLNLYQVHVENRVGAQRFRDSRPWSERPRAVSPEASDPRVYSDPASFVANQLGLGPVRYSLDAA
CASALYCLKLASDHLLSRSADVMLCGATCFPDPFFILSGFSTFQAMPLGGPDDNPLSVPLRQGSQGLTPGEGGAIMVLKRLEDAVRDGDRIYGTLLG
TSLSNAGCGLPLSPHLPSEKSCMEDLYTSVGIDPSEVQYVECHATGTPQGDVVEVEALRHCFRGNTDHPPRMGSTKGNFGHTLVAAGFAGMAKVL
LSMQHGTIPPTPGVDRSNCIDPLVVDEAIPWPYSSAQARAGKPGDELKCASLSAFGFGGTNAHCVFREHRQIAATATASPVLPEVTPGPIAIIGMDAT
FGTLKGLDAFEQAIYKGTDGASDLPSKRWRFLGADTDFLTAMGLDAVPRGCYVRDVDVDYKRLRSPMIPEDVLRPQQLLAVATMDRALQDAGM
ATGGKVAVLVGLGTDTELYRHRARVTLKERLDPAAFSPEQVQEMMDYINDCGTSTSYTSYIGNLVATRVSSQWGFTGPSFTVTEGANSVYRCLEL
GKFLLDTHQVDAVVVAGVDLCATAENLYLKARRSAISRQDHPRANFEASADGYFAGEGSGALVLKRQADVGSDDKVYASVAGLTCAAQPAEAV
SPLLLQVHNDDNEKRVVEMVELAADSGRHAPHLANSPLSAESQLEQVSKLLAHQVPGSVAIGSVRANVGDVGYASGAASLIKTALCLHNRYLPAN
PQWERPVAPVSEALFTCPRSRAWLKNPGESRLAA VASASESGSCFGVLLTDEYATHESSNRLSLDDAAPKLIAIRGDTVDDIMAKVNAELALLRAH
AETGSATDDDP AAAVAFTAHRLRFLRLVGETVASHGATATLCLALLTTPEKLEKELELAAKGVPRSAKAGRNWMSPSGSAFAPTPVTSDRVAFMY
GEGRSPYYGVGLDLHRLWPALHERINDKTAALWENGDSWLMPRAVDADSQRAVQTAFDADQIEMFRTGIFVSICLTDYARDVLGVQPKACFGLSL
GEISMLFALSRRNCGLSDQLTQRLRTSPVWSTQLAVEFQALRKLWNVPADAPVESFWQGYLVRASRAEIEKAIGPDNRFVRLLIVNDSSSALIAGKP
AECLRVLERLGGRLPPMPVKQGMIGHCPEVAPYTPGIAHIHEILEIPDSPVKMYTSVTNAELRGGSNSSITEFVQKLYTRIADFPGIVDKVSRDGHDVF
VEVGPNNMRSAA VSDILGKAATPHVSVALDRPSESAWTQTLKSLALLTAHRVPLHNPTLFADLYHPTFLTAIDSAMQEPPPKPNRFLRSVEVNGYFC
PDGISKQV AAASAKPSTHCMVRLHPAKAVVVAAAGAVVADSTPVVKAKQTSSSLLVGDDAFLRCYDVDWPLYMGAMAEGISSVDLVVAAAEAR
MLASFGAARLPMDQVELQIREIQQRTSNAFAVNLMPGPDEAATVDALLRTGVSIVEASGYTGALSADLVRYRVTGLRRTSCGASVSATHRVVAKV
SRTEVAEHFLRP APAAVLEALVAAKQITPEQAALASRVAMADDVAVEADSGGHTDNRPIHVLLPLVVAQRNRWRHLVDTPVRVGAGGGIACPRA
ALLAFSLGAAFVVTGSVNQLAREAGTSDAVRLLLATATYSDVAMAPGGVQVLKKQTMFAARATMLAQLQAKFGSFDAVPEPQLRKLERSVFKQS
VADVWAAAREKFGVDATAASPQERMALCVRWYMSQSSRWATEATSARKADYQIWCGPAIGSFNDFVRGTKLDATAGTGEFPRVVDINQHILLGA
SHYRRVQQQQQDDDVEYIIV (SEQ ID N0:4)

FIG.11 atgacatcatcgaagaagactcccgtgtgggagatgagcaaggaggagctgctggacggcaagacggtggtcttcgactacaacgagctgctcgaattcgccgagggcgacgtgggccaagtgttcggacccgagttcgacatcat
cgacaagtaccggcgtcgcgtgcggctgccggccgcgcgagtacctgctcgtgtcgcgcgtgacgctgatggacgccgaggtgaacaacttccgcgtcgggtcgcgcatggtgaccgagtacgacgtgcccgtgaacggggagct
gtcggagggcggggacgtgccgtgggccggtgctggtggagtcggggcagtgcgacctgatgctcatctcgtacatgggcatcgacttccagtgcaaggggcgaccgcgtgtaccgcctgctcaacacatcgctcaccttcttcgggagt
ggcgcacgagggcgagacgctggtgtacgacatccgcgtcacggggttcgccaagggcgcggggcggggagatctcgatgttcttcttcgagtacgactgcttcgtggacggccgcctgctgatcgagatgcgcgacgggtgcgcc
gggttcttcacggacgccgagctggccgccggcaagggcgtgcttaagaccaaggcggagctggcggcgcgcgcagatccagaagcaggacatcgcgcccttcgccggccgccgtgctcgcacaagacctcgctggacgc
gcgcgagatgcggctgctcgtggaccgccagtgggcgcgcgtcttcggcagccggcatggcgggcatcgactacaagttgtgcgctcgcaagatgctcatgatcgaccgcgtcacgcacctcgacccgccgggcggcgcacgg
cctcgggctgctgatcggggagaaggtgctggagcgcgaccactggtacttccctgccactttgtgcgcgacgaggtgatggcccgggtcgctggtcagcgacggctgctcgcagctcctcaaggtgtacatgctgtgctcggcct
gcacacgaccgtgggcgcgttcgactttcgtcccgtgagcgggcacgccaacaagtgcggtgccgcgggcagatctcaccgcacaagggcaagctcgtgtacgtgatggagatcaaggaaatgggctttgacgcgaagacggg
cgatccgtttgcgatcgcggacgtggacatcatcgacgtcaacttcgaggagggacaggcgtttgcggggagtggaagacctgcacagctacggccagggcgacctccgcaagaagatcgtcgtcgacttcaagggcatcgcgctct
ccctgcagaagcggaaggagcagcagaaggaaagcatgaccgtgactacgacgacgacgacgagccgggtgattgccgccgcccagcgggtgcctcaagggcgacccgacggccgccgacgagcgtgacgtggcacccg
atggcggagggcaacggcgggcccggaccgacgccgtcgtctcgccgtccgcgtaccccgccgcgggccgtgtgcttctcgccgttccccaacaaccccgcttgacaacgaccacacgccgggccagatgccgttgacctggtca
acatgtccgaattcatgtgcggcaaagtgtccaactgcctgggccccgagtttgcgcgcttcgacgcgagcaagacgagccgcagcccggccttgacctggccgctcgtgacgcgggtgacgagcgtggcggacatggagcacgg
gccgttctacaacgtggacgtcaaccccgggccagggcacgatggtgggcgagttcgactgtcccgcgacgcgtggttcttcggccgcctcgagccgcgacgaccacatgccgtactcgatcctgatggagatcgcgctgcagacgt
cgggcgtcctcacctcggtgctcaaggcgccgctgacgatggacaaggacgacatcctcttccgcaacctcgacgcagacgccgagtcgtgggcgacgccatgccggacgtgcgcgcaagacgatccgcaacttcaccaagt
gcacaggctacagcatgctcggcaagatgggcatccaccgcttcacctttgagctcagcgtcgacggcgccgtcttctacaagggcagcacctcgtttggctggttcgtccccgaggtcttcgagtcgcagaccggtctcgacaacgg
caagccgccgcctgccttggtaccgcgagaacaacgtcgccgtcgacacgctctccgcgcccgcctccgcttcctccgcgcaaggtcagctgcagctgcagcgacgcgggtcgcaggcgcagttcctggacacaatccacctggcg
ggcagcggcgccggcgtgcacggccagggctacgcgcacggggagaaggccgtgaacaagcaagattggttcttctcgtgccacttctggttcgaccccgtgatgcccgggtcctgggcatcgagtcgatgttccagctcgtcga
ggcgtggtgcgtgaagcagggactcgccggcgcggcacggcatcgctcacccagtgttcgcgcacgcgccggggccacgagctggaagtaccgcgggcagctaaccccaagaacgaccgcatggacagcgaggtgcacatc
aagtcggtggcggccttctcctcctgggtcgacgtcgtcgcggacggggttcctcttcgtcgacggcctccgcgtctactcggcagacaactccgcgtccgcatccagaccggcgccggccacgttgaagagcaagaggttgctgcc
aaggccacaaccaagaacagcagtattgctgatgtggacgtggccggacctgcaagcgctcaagcaggccgttgctgacgctggagcgaccgctgcagctggacgcggggagcgaggtgcccgcctgccggtgagcgacctggg
cgataggggcttcatggagacgtacgggtggtggccgccgctgtacagcggggcgatggccaaggcatcgcgtcggccgacctggtgatcgcgatgggccagcgcaagatgctggggtcgtttggcgcggcggggctccga
tgcacgtcgtgcgcgcggggattgagaagatccaggcagcgctgccagcggggccatacgcggtcaacctgattcactcgccttttgacgccaacctggagaagggcaacgtggacctcttcctggagaagggcgtgcgcgtcgtg
gaggcgtcggccttcatggagctcacgccccaggtggtgcgctaccgcgcgacgggcctctctcgcgacgcgcgcgcggctccgtgcgcacggcccacaagatcatcggcaagtcagccgcaccgagctggccgagatgttt
atccggcccgcgccgcaagccattctcgcaagcttgtggcgtccggcgagatcaccccgagcaggcgcgcgctggcgctcgaggtgcccatggccgacgacatcgccgtcgaggccgattcgggcgggcacaccgacaaccg
ccccatccacgtcatcctgccctcatcctcagcctgcgcaaccgcctccagcgcgagctcaagtaccctgcgcgacaccgcgtgcgcgtcggccgccggggcggcatcgggtgcccgcaagcggctctgggcgccttccacatg
ggccgccgcgtttgtggtgacgggcacggtcaaccagctgagccggcaggccgggacatgcgacaatgtgccgccggcagctgtcgcgcgcgacgtactcggacatcacgatggcgccggccggcgacatgttcgagcagggcgt
cgagctgcaggtgctcaagaagggcacgatgtttccctcgcgccgccaagaagctgttcgagctgtttcacaagtacgactcgttcgaggcgatgccggccggacgagctggccgcgctcgagaagcgcatcttcagcaagtcactcgc
cgaggtgtgggccgagaccaaggacttctacatcacgcgcggctcaacaaccccgagaagatccgcaaggccggagaacgaggaccccaagctcaagatgtcactctgcttccgctggtacctcgggctcagtcgttctgggccaaca
acggcatcgcgaccgcgcacgatggactaccagatctggtgcgcgccctgccatcggcgccttcaacgacttcatcgccgactcgtacctcgacgtgcccgtctcgggcgagttcccccgacgtcgtgcagatcaacctgcagatcctgtc
gggcgcagcctacctccagcgcctcctctccgtcaagctcgcaccgcggatcgacgtcgacaccgaggacgacctcttcacctaccgccccgaccacgcactctaa (SEQ ID NO:5)

FIG.12

MTSSKKTPVWEMSKEELLDGKTVVFDYNELLEFAEGDVGQVFGPEFDIIDKYRRRVRLPAREYLLVSRVTLMDAEVNNFRVGSRMVTEYDVPVNG
ELSEGGDVPWAVLVESGQCDLMLISYMGIDFQCKGDRVYRLLNTSLTFFGVAHEGETLVYDIRVTGFAKGAGGEISMFFFEYDCFVDGRLLIEMRD
GCAGFFTDAELAAGKGVLKTKAELAARAQIQKQDIAPFAPAPCSHKTSLDAREMRLLVDRQWARVFGSGMAGIDYKLCARKMLMIDRVTHLDPR
GGAHGLGLLIGEKVLERDHWYFPCHFVRDEVMAGSLVSDGCSQLLKVYMLWLGLHTTVGAFDFRPVSGHANKVRCRGQISPHKGKLVYVMEIKE
MGFDAKTGDPFAIADVDIIDVNFEEGQAFAGVEDLHSYGQGDLRKKIVVDFKGIALSLQKRKEQQKESMTVTTTTTTTSRVIAPPSGCLKGDPTAPT
SVTWHPMAEGNGGPGPTPSFSPSAYPPRAVCFSPFPNNPLDNDHTPGQMPLTWFNMSEFMCGKVSNCLGPEFARFDASKTSRSPAFDLALVTRVTS
VADMEHGPFYNVDVNPGQGTMVGEFDCPADAWFFGASSRDDHMPYSILMEIALQTSGVLTSVLKAPLTMDKDDILFRNLDADAELVGDAMPDVR
GKTIRNFTKCTGYSMLGKMGIHRFTFELSVDGAVFYKGSTSFGWFVPEVFESQTGLDNGKPRLPWYRENNVAVDTLSAPASASSAQGQLQLQRRG
SQAQFLDTIHLAGSGAGVHGQGYAHGEKAVNKQDWFFSCHFWFDPVMPGSLGIESMFQLVEAWCVKQGLAARHGIAHPVFAHAPGATSWKYRG
QLTPKNDRMDSEVHIKSVAAFSSWVDVVADGFLFVDGLRVYSADNLRVRIQTGAGHVEEQEVAAKATTKNSSIADVDVADLQALKQALLTLERPL
QLDAGSEVPACAVSDLGDRGFMETYGVVAPLYSGAMAKGIASADLVIAMGQRKMLGSFGAGGLPMHVVRAGIEKIQAALPAGPYAVNLIHSPFD
ANLEKGNVDLFLEKGVRVVEASAFMELTPQVVRYRATGLSRDARGGSVRTAHKIIGKVSRTELAEMFIRPAPQAILDKLVASGEITPEQAALALEVP
MADDIAVEADSGGHTDNRPIHVILPLILSLRNRLQRELKYPARHRVRVGAGGGIGCPQAALGAFHMGAAFVVTGTVNQLSRQAGTCDNVRRQLSR
ATYSDITMAPAADMFEQGVELQVLKKGTMFPSRAKKLFELFHKYDSFEAMPADELARVEKRIFSKSLAEVWAETKDFYITRLNNPEKIRKAENEDP
KLKMSLCFRWYLGLSSFWANNGIADRTMDYQIWCGPAIGAFNDFIADSYLDVAVSGEFPDVVQINLQILSGAAYLQRLLSVKLAPRIDVDTEDDLF
TYRPDHAL (SEQ ID NO:6)

FIG.13

```
ATGGAAGATCAAAGAATTGCTATTGTTGGATTATCTGCGATTTTACCAAGTGGTGAAAATGTTAGAGAATCTTGGGAAGCAATACGTGATGGTTTGAATTGTTTAAGTGATTTA
CCTGCGGATCGTGTTGATGTTACTGCGTATTATAATCCAACAAAAGGTGTAAAGGATAAAATTTATTGTAAACGTGGTGGGTTTATTCCTGAATATGAATTTGATTCTAGAGAA
TTTGGACTTAATATGTTACAAATGGAAGATTCTGATGCTAATCAAACGTTAACTTTATTAAAAGGTTAAAGAAGCATTAGATGATGCTAATATACCTGCATTTACTAATGAGAAA
AAAAATATTGGTTGTGTTCTTGGTATTGGTGGTGGTCAAAAAGCATCTCATGAATTTTATTCAAGACTTAATTATGTTGTTGTCGATAAAGTTTTAAGAAAAATGGGATTACCT
GATGAGGATGTTGAAACTGCTGTTGAAAAGTTTAAAGCTAATTTTCCTGAATGGAGATTAGATTCCTTTCCTGGTTTTCTTGGTAATGTTACTGCTGGCCGTTGTACTAATACAT
TCAATATGGAAGGTATGAATTGTGTTGTAGATGCTGCTTGTGCTAGTTCTTTAATTGCTATTAAAGTTGCTATTGATGAATTATTACATGGTGATTGTGATGCAATGATTGCTGG
TGCAACTTGTACTGATAACGCTCTTGGTATGTATATGGCATTTTCAAAAACACCTGTTTTTTCAACTGATCAAAGTTGTCTTGCATATGATGAAAAAACAAAAGGTATGCTTATT
GGTGAAGGTTCAGCTATGTTTGTTTTAAAACGTTATGCTGACGCAGTGAGAGATGGTGATACTGTACATGCTGTTATACGTTCATGTTCATCATCATCTGACGGTAAAGCATCT
GGTATTTATACACCAACTATTTCTGGTCAAGAAGAAGCTATTCTTAGAGCATATCGTAGAGCTGGTGTATCACCAAATACTATTACTTTAGTTGAAGGACATGGTACTGGTACA
CCAGTGGGTGATAAAATTGAATTAACAGCTTTACGCAATGTATTTGATAAAGCATATGGTCCTGGTCATAAGGAAGAAGTTGCTGTTGGAAGTATTAAAAGTCAAATTGGTCA
TTTGAAAGCTGTTGCTGGTTGTGCTGGTCTTGTGAAATTGGTTATGGCATTGAAACATAAAACACTACCTCAAAGTATTAATGTTGAAAATCCACCTAATTTAGTGGATGGTAC
TGTCATTAGTGATACTACTTTATATATTAATACAATGAATCGTCCATGGATTACTAAGCCTGGTGTTCCAAGAAGAGCTGGTATATCTAGTTTCGGATTTGGTGGTGCAAATTAT
CATGCTGTTTTAGAAGAATTTGAGCCGGAACAAACTAAACCATATAGATTGAATGTATCTGCACAACCAATGCTTCTTCATGCCGGTAAATGCAAATTCATTACAAAAGCTATGT
GAAGATCAATTAAAACTTTTGAAAGAATCAAGAGAAAAATGTGTCAACACCAAAAACACTGATTATGTTGCGTTTTCAAAATTTCAAGATTCTTTTAAATTGAAAGGTTCTGTT
CCATCACAACATGCTAGAGTTGGTTTTGCATCAAAATCTATTGAAGATACTATTTCTATTTTATCTGCTATCGTTAATAGATTTCAAAAAGATATTACAACAACTAGTTGGGCTT
TACCAAAAGAAGGTGCTATTTTTAGATCTACTGCATTGATTAATGACAATAAAAGTGTAGCTGCTTTATTTTCTGGACAAGGCGCCACAATATACCCATATGTTTAATGATGTTG
CAATGCAATGGCCACAATTTCGTTTATGTGTAAATGATATGGAGAAAGCACAGGAAGAAGTTATCAATGATAAAAGTGTGAAACGTATCAGTCAAGTTATGTTTCCTCGTAAA
CCATATGCAAGAGAATCACCTTTAGACAATAAAGAAATCTCTAAGACTGAATATTCTCAAACAACAACTGTCGCTAGTTCAGTAGGTTTATTTGAAATTTTCCGTGATGCTGGT
TTCGCTCCTGCTTTTGTTGCTGGTCATTCTTTAGGTGAATTTAGTGCATTGTATGCAGCTGGATTGATTGATCGCGAAGATTTATTCAAGTTGGTATGTAATCGTGCAATGGCTA
TGAGAGATGCACCAAAAAAATCTGCTGATGGAGCAATGGCTGCTGTTATTGGTCCAAATGCTTCTTCAATTAAGCTTTCAGCTCCTGAAGTATGGGTTGCTAACAATAACTCTC
CATCTCAAACTGTTATTACCGGTGCAAATTCTGGTGTACAAGCTGAAACAAGTAAATTGAAAACTCAAGGTTTCCGTGTGGTTCATTTGGCATGTGATGGGGCATTTCATTCGC
CTCATATGGAAAATGCTGAAAAGCAATTTCAAAAAGCTCTTTCAGCAGTTAAGTTTAATAAACCAACTGGTTCTTCTCCAAAAATTTTCAGCAATGTAACTGGTGGTGTATTTA
CGGATCCAAAAACTGCTTTGTCAAGACATATGACTAGTTCTGTACAATTTCTTACTCAAATTAAGAATATGTACGCGGCTGGAGCTCGTGTCTTTATTGAATTTGGACCAAAAC
AAGTACTTTCCAAATTGGTCAATGAAATTTTTCCTGGTGATACAAGCGTTTTAACTGTTTCGGTGAATCCAGCTAGTGCTAAAGATAGTGACATTCAATTGCGTCAAGCTGCAG
TTCAAATGGCCGTTGCTGGTGTAGCTCTTACCGATTTTGATAAATGGGAACTCAAAGATCCTACCCGTATGAAGGAATTCCCACGTAAGAAGACTACTTTGACTTTGTCTGCAG
CAACTTATGTCTCCAAGAAAACTCTACAGGAGCGTGAACGAATCATGAATGATGGGCGAACTGTTTCATGTGTTCAACGTATTCAAAACACTAATACTGGTGAGTTGGAGAAA
TTGAAGAAGCAATTGCAAGATAAAGAAAATGAGGTTGTAAGAGTTCAAGCTCTTGCAACTCAAGCTTCAGCTGATTTGCAAAATACCAAAGCAGAATTACAAAAAGCTCAAG
CAACAAAATCTAGTAATGCAGCATCTGATGCGGTGGTGGCAAAACATAAGGCAATTTTATTGGCAATGTTAGAAGAACTTGAAACCGGCAAGGCTGTAGATTATTCTTCATTT
TCGAAAGGTCAAGTTGCAAGTCCAGCTACCGTTCGTGTCGTTTCAGCTCCTGTTCAAGCGGCTGCTCCTGTGCAGGTATCTGCTTCTGTTGATTCTGGTTTGTTGGCAAAAGCGG
AACAAGTTGTATTGGAAGTATTGGCATCGAAGACTGGTTATGAGACTGAGTTGATTGAATTGGATATGGAATTGGAAACTGAACTTGGTATTGATTCTATCAAGAGAGTAGAA
ATTCTTTCTGAAGTTCAAGCTCAATTGAATGTTGAAGCTAAAGATGTAGATGCTCTTAGTAGAACTCGTACTGTTGGTGAAGTCATTGATGCAATGAAAGCCGAAATTGCTGGT
GGTCAACCAGCTGCTCCTGTTCAAGTTGCAGCTCCTACTCAAGTAGTTGCTCCTGTTCAAGCATCTGCTCCTGTTGATTCTGGTTTGTTAGCAAAAGCGGAACAAGTTGTATTGG
AAGTATTGGCATCGAAGACTGGTTATGAGACTGAGTTGATTGAATTGGATATGGAATTGGAAACCGAACTTGGTATTGATTCTATCAAGAGAGTAGAAATTCTTTCTGAAGTT
CAAGCTCAATTGAGTGTTGAAGCTAAAGATGTAGATGCTCTTAGTAGAACTCGTACTGTTGGTGAAGTGATTGATGCAATGAAAGCCGAAATTGCTGGTGGTCAACCAGCTGC
TCCTGTTCAAGTTGCAGCTCCTACTCAAGTAGTTGCTCCTGTTCAAGCATCTGCTCCTGTTGATTCTGGTTTGTTAGCAAAAGCGGAACAAGTTGTATTGGAAGTATTGGCATCG
AAGACTGGTTATGAGACTGAGTTGATTGAATTGGATATGGAATTGGAAACCGAACTTGGTATTGATTCTATCAAGAGAGTAGAAATTCTTTCTGAAGTTCAAGCTCAATTGAG
TGTTGAAGCTAAAGATGTAGATGCTCTTAGTAGAACTCGTACTGTTGGTGAAGTGATTGATGCAATGAAAGCTGAAATTTCTGCTGGTCAGCCAGCTGCTCCTGTTCAAGTTGC
AGCTCCTACTCAAATAGTTGCTCCTGTTCAAGTATCCGCTCCTGTTGATTCTGGTTTGTTAGCAAAAGGCGGAACAAGTAGTATTGGAAGTATTGGCATCCAAGACTGGTTATGA
GACTGAGTTGATTGAATTGGATATGGAATTGGAAACTGAACTTGGTATTGATTCTATCAAGAGAGTAGAAATTCTTTCTGAAGTTCAAGCTCAATTGAGTGTTGAAGCTAAAG
ATGTAGATGCTCTTAGTAGAACTCGTACTGTTGGTGAAGTGATTGATGCAATGAAAGCTGAAATTTCTGGTGGTCAACCAACTGCTCCTGTTCAAGTTGCAGCTCCTACTCAAA
TAGTTGCTCCTGTTCAAGTATCTGCTCCTGTTGATTCTGGTTTGTTAGCAAAGGCGGAACAAGTTGTATTGGAAGTATTGGCATCGAAGACTGGTTATGAGACTGAGTTGATTG
```

FIG.13 (cont'd)

```
AATTGGATATGGAATTGGAAACCGAACTTGGTATTGATTCTATCAAGAGAGTAGAAATTCTTTCTGAAGTTCAAGCTCAATTGAGTGTTGAAGCTAAAGATGTAGATGCTCTTA
GTAGAACTCGTACTGTTGGTGAAGTGATTGATGCAATGAAAGCCGAAATTTCTGGTGGTCAGCCAGCTGCTCCTGTTCAAGTTGCAGCTCCTACTCAAATAGTTGCTCCTGTTC
AAGCATCTGCTCCTGTTGATTCTGGTTTGTTGGCAAAAGCGGAACAAGTTGTATTGGAAGTGTTAGCATCCAAGACTGGTTATGAAACTGAGTTGATTGAATTAGATATGGAAT
TGGAAACCGAACTTGGTATTGATTCTATCAAGAGAGTAGAAATTCTTTCTGAAGTTCAAGCTCAATTGAGTGTTGAAGCTAAAGATGTAGATGCTCTTAGTAGAACTCGTACTG
TTGGTGAAGTGATTGATGCAATGAAAGCTGAAATTTCTGGTGGTCAACCAGCTGCTCCTGTTCAAGTTGCAGCTCCTACTCAAATAGTTGCTCCTGTTCAAGTATCTGCTCCTGT
TGATTCTGGTTTGTTAGCAAAGGCGGAACAAGTTGTATTGGAAGTATTGGCATCTAAGACTGGTTATGAGACTGAGTTGATTGAATTGGATATGGAATTGGAAACTGAACTTG
GTATTGATTCTATCAAGAGAGTAGAAATTCTTTCTGAAGTTCAAGCTCAATTGAATGTTGAAGCTAAAGATGTAGATGCTCTTAGTAGAACTCGTACTGTTGGTGAAGTGATTG
ATGCAATGAAAGCCGAAATTGCTGGTGGTCAACCAGCTGCTCCTGTTCAAGTTGCAGCTCCTGCTCCAGTAGTTGCTCCTGTTCAAGTATCTACTCCTGTTGATTCTGGTTTGTT
GGCAAAAGCGGAACAAGTTGTATTGGAAGTGTTAGCATGCAAGACTGGTTATGAAACTGAGTTGATTGAATTGGATATGGAATTGGAAACTGAACTTGGTATTGATTCTATCA
AGAGAGTAGAAATTCTTTCTGAAGTTCAAGCTCAATTGAGTGTTGAAGCTAAAGATGTAGATGCTCTTAGTAGAACTCGTACTGTTGGTGAAGTGATTGATGCAATGAAAGCC
GAAATTTCTGGTGGTCAACCAACTGCTCCTGTTCAAGTTGCAGCTCCTACTCAAGTAGTTGCTCCTGTTAAAGTATCTACTCCTGTTGATTCTGGTTTGTTAGCAAAGGCGGAAC
AAGTAGTATTGGAAGTATTGGCATCTAAGACTGGTTATGAAACTGAGTTGATTGAATTAGATATGGAATTGGAAACTGAACTTGGTATTGATTCTATCAAGAGAGTAGAAATT
CTTTCTGAAGTTCAAGCTCAATTGAATGTGGAAGCTAAAGATGTGGATGCTCTTAGTAGAACTCGTACTGTTGGTGAAGTGATTGATGCAATGAAAGCCGAAATTGCTGGTGA
TCAACCTGCTCCAGCTGTAGTTCCAGTTCAAGCTAAGAGTGGTGTAGCCAACCCTGCACTTTTGGCAAAGGCGGAACAAGTAGTATTGGAAGTATTGGCATCCAAGACCGGTT
ATGAAACTGAGCTGATTGAATTGGATATGGAATTGGAAACTGAACTTGGTATTGATTCAATCAAGAGAGTAGAAATTCTGTCCGAAGTTCAAGCAGAATTGAGTGTTGAAGCA
AAAGATGTAGACGCTCTAAGTAGAACCCGTACTGTTGGGGAAGTGATCGATGCAATGAAAGCTGAAATTGCTGGCAGTGCTGTCACGGTTGCAACTTTGGATGATTCAACAAT
TATGGAGGAGACAGATGATGAAGATGAAGACTTTATTTTATACGATCATGTATACGGAAGCGAATGTGAAGATCTTAGTCTGAGTTTTTCATCCGTAAAGAGCATCCCGCGCG
CTGATAAACTTTTGTTGGATAACATTGCTGAAAGGCCAATTGTTATTGTGGATTGTGGAACAAAGCTTACAACTGAACTTGCAAAAGCTATTGGAGAACGTGCCGTGGTTGCTA
CATTCAGTGCACAGAGCTTGGTATCCCGTGGATTCGTTGGTAAATCATTTACTCTAGGAAATACAGAAGAAAGTGAGATCGAAAAGATGGTTTCAAGCATTGAATCTTCGTAT
GGAAAAATTGGTGGCTTTGTTTATCAACATTTTCATGATAGCGACTATGGTATGCAACTTGGATGGGCGTTAATGGCAGCGAAACATTTGAAAGAGTCCCTCAACGACCCGAT
TAAGAATGGAAGAACCTTCTTTTTGGCTGTTGCGCGTATGAATGGTAAACTTGGTATGGACAATGCTTCAGTTCATGATCAAGGAATAGTGGAATCATGCGGTATCGCCGAAC
GTGGTGCTATCTTTGTTTGTGCAAAACTTTGGATTTGGAATGGCCTAATGTTTTTGCTCGTGGTGTTGATATTGCTGAAGGTATGAGTTATAGTTTGGCTGCGGAATTGATTGT
TGATGAGATTTCTTGTGCAAATCTTTCCATTCGGGAATCTGGTTACACGATTAGCGGAGAAAGATTCACAACTGAAGCTCACAAATTGGTTACTGGAAAGCCTCATGCTCCGAT
TAAGAAGAAGGATGCTTTCCTAGTATCTGGTGGTGCTCGTGGTATTACTCCACTTTGTATTCGTGAAATTGCTAAAGCAGTGAAAGGTGGCACTTACATTTTGATGGGTCGATC
AGCTTTGGCTGATGAACCCTTGTGGGCTAATGGTAAATCCGGAAAAGATTTAGATAAAGCTGGTTTGGCATTTTTGAAGGAAGAGTTTGCAGCTGGGCGTGGTAGTAAACCAA
CTCCAAAAGTTCACAAATCTTTGATTGATAAAGTGCTCGGTATTAGGGAGGTTAGAGCATCTATTGCAAATATAGAAGCCCATGGAGCAAAAGCTATATATTTGTCTTGCGAT
GTATCTTCCGCTGAGAAAGTAAAGGCTGCAGTGCAAAAAGTTGAAAAGGAGCATCTAGTTCGTATTACTGGTATTGTGCATGCATCAGGCGTTTTGAGGGATAAATTGGTTGA
GAACAAAACTTTGGATGATTTCAACGCAGTATATGGAACCAAAGTAACTGGACTAGTAAACTTGCTGTCAGCAGTGAACATGAATTTTGTTCGTCATTTGGTTATGTTTAGTTC
TTTGGCTGGATATCATGGAAATGTTGGTCAATCTGATTATGCAATGGCTAACGAATCACTTAACAAGATTGGTTTTAGATTGGGTGCAGCTTATTCTCAATTGTGTGTTAAATCT
ATTTGTTTTGGACCTTGGGATGGTGGAATGGTAACTCCAGCTTTGAAAAAACAATTTCAATCAATGGGTGTCCAGATTATTCCTCGTGAAGGTGGCGCGGAGACTGTTGCAAG
AATAGTCTTATCTTCAAATCCTTCTCAAGTTTTAGTTGGCAACTGGGGTGTTCCTCCAGTTTCACCTTTGTCAAAATCGGCAACTATTGTTCAAACTTTTACCCCTGAGTTAAATC
CATTTCTAAAGTCTCATCAAATTCATGGTAAAAATGTTTTGCCTATGACTGTAGCAATTGGATATCTTGCTCACTTGGTTAAGAATTTTTATGCTGGTCATCATTTGTGGGGAGT
TGAAGATGCTCAATTGTTCAGTGGTGTTGTAATTGACCATGCGGTGCAAGCTCAAGTGAAATTAACGGAACAGAGTTTGGATGATGATGGCAAGGTAAAAGTTCAAGCTGTTC
TGACTGCTTCAAACGATAATGGAAAAATGGTACCTGCATACAAAGCAGTGATTGTTTGGGAAAAACAAGTAGACCTGCGTTTATTTTGAAAGATTTTTCATTGCAAGAATCT
AATTCTCGCAGTGCTGATGAGTTGTATGATGGTAAAACTTTGTTTCATGGTCCATTATTTCGTGGAATTACCAAGTTGTTGAATGTATCTGATACTTCACTAACAACTCAATGTA
CCAATATTGATTTGACTGCTACTGAACGTGGTCAATTTGCGGATATCGAACCTGTGAATCCTTTTATGGCGGATGCTGCATTTCAAGCTATGCTTGTATGGGTTAGAAATTTAA
GGAATAGTGCATCTTTACCAAACAATTGTGAAAGAGTAGATATCTATAAACCAATAGCACCTGGTGAAAAGTATTACACTACTTTGCAAGCTTTGGGTAATACCTCCGGTTCTG
TTCTCAAGTCTGTATTTTATATGCACGATGAACAAGGAGAAGTATTTCTATCTGGAAGAGCTAGTGTTGTTGTGAATGACAAGATGGAGTTTTAG
```

(SEQ ID NO:68)

FIG.14

```
ATGGAGGACCAGCGTATTGCGATCGTTGGCCTTAGCGCGATCCTTCCCTCGGGCGAGAACGTCCGCGAGTCGTGGGAGGCGATCCGTGACGGCCTCAACTGCCTTTCCGACCT
GCCCGCCGACCGCGTTGACGTCACTGCCTACTACAACCCCACGAAGGGCGTCAAGGACAAGATCTACTGCAAGCGTGGTGGCTTCATCCCCGAGTACGAGTTTGACTCGCGCG
AGTTCGGCCTCAACATGCTTCAGATGGAGGACTCGGACGCCAACCAGACCCTCACCCTGCTCAAGGTTAAGGAGGCCCTCGACGACGCCAACATTCCCGCGTTTACCAACGAG
AAGAAGAACATCGGTTGCGTCCTCGGTATTGGCGGTGGTCAGAAGGCCTCGCATGAGTTCTACAGCCGGCCTCAACTACGTCGTCGTGGATAAGGTCCTCCGCAAGATGGGCCT
CCCGGACGAGGACGTCGAGACTGCTGTCGAGAAGTTCAAGGCCAACTTTCCCGAGTGGCGCCTTGACTCCTTCCCCGGCTTTCTCGGTAACGTCACTGCGGGCCGCTGCACCA
ACACCTTCAACATGGAGGGCATGAACTGCGTGGTCGATGCCGCCTGCGCCTCGTCCCTCATCGCTATCAAGGTCGCCATCGATGAGCTGCTCCACGGCGATTGCGACGCGATG
ATTGCTGGCGCGACGTGCACCGACAACGCCCTTGGCATGTACATGGCCTTTTCCAAGACCCCCGTCTTTTCCACGGACCAGAGCTGCCTCGCCTACGACGAGAAAACCAAGGG
TATGCTCATTGGCGAGGGTTCCGCCATGTTCGTCCTTAAGCGCTACGCCGACGCCGTCCGCGATGGCGACACCGTCCACGCCGTCATCCGCTCGTGCTCGTCCTCCTCCGACGG
CAAGGCGTCGGGTATCTACACCCCGACCATCTCGGGCCAGGAGGAGGCCATCCTTCGCGCCTACCGTCGTGCCGGCGTGAGCCCGAACACGATCACCCTTGTGGAGGGCCATG
GCACCGGCACCCCCGTCGGCGACAAGATCGAGCTGACCGCCCTCCGCAACGTCTTTGACAAGGCCTACGGCCCTGGCCACAAGGAGGAGGTCGCTGTGGGCTCCATCAAGTC
GCAGATCGGTCACCTCAAGGCCGTCGCCGGCTGCGCTGGCCTCGTCAAGCTCGTGATGGCTCTCAAGCATAAGACGCTCCCGCAGTCCATCAACGTCGAGAACCCGCCCAACC
TCGTCGATGGCACTGTCATCTCGGACACCACGCTCTACATCAACACCATGAACCGCCCGTGGATCACCAAGCCGGGCGTCCCCCGTCGTGCGGGCATCTCCAGCTTCGGCTTTG
GCGGCGCTAACTACCACGCTGTCCTTGAGGAGTTCGAGCCCGAGCAGACCAAGCCCTACCGCCTGAACGTTTCGGCCCAGCCGATGCTCCTCCACGCCGTCAACGCGAACTCG
CTCCAGAAGCTCTGCGAGGACCAGCTCAAGCTCCTCAAGGAGTCCCGCGAGAAGTGCGTCAACACGAAGAACACCGACTACGTCGCTTTTTCCAAGTTTCAGGACTCCTTTAA
GCTCAAGGGCTCCGTCCCCAGCCAGCACGCTCGCGTGGGCTTTGCTTCCAAGAGCATCGAGGACACGATTTCCATTCTTAGCGCCATTGTCAACCGCTTCCAGAAGGACATCAC
GACCACCAGCTGGGCGCTCCCGAAGGAGGGCGCCATCTTTCGCAGCACCGCCCTCATCAACGACAACAAGTCCGTGGCCGCCCTGTTCTCGGGTCAGGGCGCTCAGTACACCC
ACATGTTCAACGACGTCGCGATGCAGTGGCCGCAGTTCCGCCTCTGCGTTAACGATATGGAGAAGGCCCAGGAGGAGGTGATCAACGACAAGTCGGTTAAGCGCATTAGCCA
GGTCATGTTTCCCCGCAAGCCCTACGCGCGCGAGAGCCCCCTCGACAACAAGGAGATCAGCAAGACCGAGTACTCGCAGACGACGACCGTCGCCTCGTCCGTCGGCCTCTTTG
AGATTTTCCGCGACGCCGCTTTGCCCCGGCTTTTGTTGCGGGCCACTCGCTCGGTGAGTTCTCCGCCCTTTACGCCGCTGGCCTCATCGACCGCGAGGACCTCTTTAAGCTCGT
GTGCAACCGCGCCATGGCTATGCGCGACGCCCCCAAGAAGTCCGCTGACGGCGCCATGGCTGCCGTCATCGGTCCGAACGCCTCGTCCATCAAGCTCTCGGCTCCCGAGGTTT
GGGTCGCGAACAACAACTCGCCCTCGCAGACCGTCATCACTGGTGCCAACAGCGGCGTCCAGGCCGAGACTTCGAAGCTCAAGACGCAGGGTTTCCGCGTGGTCCACCTCGCC
TGCGACGGCGCGTTTCACAGCCCGCACATGGAGAACGCCGAGAAGCAGTTTCAGAAGGCCCTCTCGGCCGTCAAGTTCAACAAGCCCACCGGCTCGTCCCCAAGATTTTCAG
CAACGTCACCGGCGGTGTCTTTACCGATCCTAAGACGGGCCCTCTCCCGCCACATGACTAGCTCGGTCCAGTTTCTCACCCAGATCAAGAACATGTACGCCGCTGGCGCCCGCGT
TTTCATCGAGTTCGGCCCCAAGCAGGTCCTCTCGAAGCTCGTCAACGAGATTTTCCCGGGCGACACCAGCGTCCTCACTGTTAGCGTGAACCCTGCCTCCGCCAAGGACTCGGA
CATCCAGCTCCGCCAGGCGGCCGTGCAGATGGCGGTCGCTGGCGTCGCTCTCACCGACTTTGATAAGTGGGAGCTTAAGGACCCGACCCGCATGAAGGAGTTCCCTCGCAAGA
AAACGACCCTCACCCTCTCCGCCGCTACCTACGTTAGCAAGAAAACGCTCCAGGAGCGCGAGCGTATCATGAACGACGGTCGCACTGTCAGCTGCGTGCAGCGCATCGAGAA
CACGAACACGGGCGAGCTTGAGAAGCTCAAGAAGCAGCTCCAGGACAAGGAGAACGAGGTTGTCCGCGTCCAGGCCCTTGCCACCCAGGCCAGCGCCGACCTTCAGAACACC
AAGGCTGAGCTTCAGAAGGCTCAGGCCACCAAGTCGTCGAACGCTGCCTCGGACGCCGTCGTCGCCAAGCACAAGGCCATCCTCCTCGCTATGCTGGAGGAGCTGGAGACTG
GCAAGGCCGTCGATTACTCCAGCTTTTCCAAGGGTCAGGTTGCCTCCCCTGCGACCGTTCGTGTCGTGTCGGCTCCCGTGCAGGCTGCCGCACCGGTTCAGGTCAGCGCCTCCG
TGGACTCGGGCCTGCTCGCGAAGGCGGAGCAGGTCGTGCTTGAGGTCCTCGCCTCCAAGACCGGCTACGAGACTGAGCTTATCGAGCTGGACATGGAGCTTGAGACTGAGCTT
GGTATCGATTCGATCAAGCGCGTCGAGATTCTTTCGGAGGTCCAGGCCCAGCTCAACGTCGGAGGCCAAGGACGTTGACGCCCTGTCGCGCACCCGTACGGTCGGCGAGGTCAT
CGATGCCATGAAGGCGGAGATTGCCGGCGGTCAGCCTGCTGCCCCCGTCCAGGTCGCTGCGCCGACGCAGGTCGTCGCCCCGGTCCAGGCCTCCGCGCCTGTCGATAGCGGCC
TCCTCGCCAAGGCGGAGCAGGTCGTCCTTGAGGTGCTCGCTTCCAAGACTGGTTACGAGACTGAGCTTATTGAGCTTGACATGGAGCTGGAGACTGAGCTTGGCATTGACTCC
ATCAAGCGCGTGGAGATTCTGAGCGAGGTCCAGGCCCAGCTCAGCGTGGAGGCCAAGGATGTCGATGCCCTCTCCCGTACGCGCACCGTCGGCGAGGTCATTGACGCGATGA
AGGCCGAGATCGCGGGTGGTCAGCCGGCCGCCCCCGTCCAGGTCGCTGCCCCTACGCAGGTCGTCGCTCCCGTCCAGGCCAGCGCTCCCGTCGACTCGGGCCTTCTTGCTAAG
GCCGAGCAGGTCGTCCTTGAGGTCCTTGCCAGCAAGACTGGCTACGAGACTGAGCTTATTGAGCTTGACATGGAGCTTGAGACTGAGCTTGGCATCGACTCGATTAAGCGCGT
CGAGATCCTCAGCGAGGTCCAGGCCCAGCTCTCCGTCGAGGCTAAGGATGTGGATGCTCTCAGCCGCACGCGCACGGTGGGCGAGGTCATTGATGCCATGAAGGCGGAGATT
TCCGGCGGTCAGCCCGCTGCCCCCGTCCAGGTCGCTGCTCCGACCCAGATCGTCGCCCCGGTCCAGGTTTCGGCTCCGGTGGACAGCGGCCTCCTTGCCAAGGCCGAGCAGGT
CGTCCTTGAGGTCCTCGCCAGCAAGACCGGCTACGAGACTGAGCTGATCGAGCTTGACATGGAGCTTGAGACTGAGCTGGGCATCGATTCCATTAAGCGCGTCGAGATCCTCT
CGGAGGTCCAGGCCCAGCTCAGCGTGGAGGCCAAGGATGTCGATGCCCTCTCGCGCTACCCGTACCGTCGGCGAGGTTATCGATGCTATGAAGGCCGAGATCAGCGGCGGTCA
GCCCACGGCGCCCGTTCAGGTCGCTGCCCCTACGCAGATCGTTGCCCCTGTCCAGGTCAGCGCTCCCGTGGACAGCGGCCTCCTCGCTAAGGCTGAGCAGGTGGTGCTGGAGG
TCCTGGCCTCCAAGACCGGCTACGAGACTGAGCTTATCGAGCTTGACATGGAGCTTGAGACTGAGCTTGGCATTGACAGCATCAAGCGTGTCGAGATCCTCTCCGAGGTGCAG
```

FIG.14 (cont'd)

```
GCCCAGCTCAGCGTGGAGGCCAAGGACGTTGACGCGCTCAGCCGTACGCGCACCGTTGGCGAGGTGATCGACGCCATGAAGGCCGAGATTAGCGGTGGTCAGCCCGCTGCCC
CGGTTCAGGTGGCTGCCCCTACGCAGATCGTCGCCCCCGTGCAAGCTTCCGCCCCTGTGGACAGCGGCCTTCTCGCCAAGGCCGAGCAGGTCGTCCTTGAGGTGCTGGCCTCCA
AGACCGGCTACGAGACTGAGCTGATCGAGCTTGACATGGAGCTGGAGACTGAGCTTGGCATCGACTCGATCAAGCGCGTGGAGATTCTCTCGGAGGTCCAGGCCCAGCTCTCG
GTCGAGGCCAAGGACGTCGATGCGCTCTCCCGCACCCGCACCGTGGGCGAGGTCATCGACGCTATGAAGGCGGAGATCAGCGGCGGTCAGCCGGCGGCCCCTGTGCAGGTGG
CCGCTCCGACCCAGATCGTCGCTCCTGTCCAGGTTTCCGCCCCGGTGGACTCGGGCCTCCTGGCTAAGGCCGAGCAGGTCGTCCTTGAGGTCCTCGCTTCCAAGACCGGCTACG
AGACTGAGCTGATCGAGCTGGACATGGAGCTTGAGACTGAGCTGGGCATCGATTCGATCAAGCGCGTCGAGATTCTCTCGGAGGTCCAGGCCCAGCTCAACGTTGAGGCCAA
GGACGTGGACGCCCTCTCGCGTACTCGCACCGTTGGCGAGGTTATTGATGCTATGAAGGCCGAGATCGCCGGTGGTCAGCCGGCTGCCCCTGTTCAGGTTGCTGCCCCTGCGCC
GGTGGTCGCCCCGGTCCAGGTGTCCACCCCGGTTGACAGCGGCCTCCTTGCCAAGGCCGAGCAGGTTGTGCTGGAGGTCCTCGCCTGCAAGACGGGCTACGAGACTGAGCTTA
TCGAGCTTGACATGGAGCTGGAGACTGAGCTTGGCATCGACTCCATCAAACGCGTCGAGATTCTTTCGGAGGTCCAGGCCCAGCTGTCGGTGGAGGCTAAGGATGTCGATGCC
CTCAGCCGCACGCGCACGGTCGGTGAGGTCATCGATGCTATGAAGGCCGAGATTTCGGGCGGTCAGCCCACCGCCCCGTGCAGGTCGCCGCGCCCACCCAGGTCGTGGCCCC
GGTCAAGGTTTCCACGCCCGTGGACTCGGGCCTTCTCGCCAAGGCCGAGCAGGTCGTGCTGGAGGTTCTCGCCTCCAAGACGGGTTACGAGACTGAGCTGATTGAGCTTGACA
TGGAGCTGGAGACTGAGCTGGGCATTGACTCCATCAAGCGCGTCGAGATCCTCTCGGAGGTCCAGGCCCAGCTCAACGTCGAGGCCAAGGACGTCGATGCCCTCTCGCGCACC
CGCACCGTCGGCGAGGTCATTGATGCCATGAAGGCCGAGATCGCTGGCGATCAGCCTGCCCCGGCTGTGGTCCCGGTGCAGGCCAAGTCGGGTGTCGCGAACCCCGCCCTCCT
CGCCAAGGCGGAGCAGGTCGTGCTGGAGGTCCTGGCCAGCAAGACGGGCTACGAGACTGAGCTTATCGAGCTTGACATGGAGCTTGAGACTGAGCTTGGTATTGACTCGATT
AAGCGCGTTGAGATCCTTTCCGAGGTCCAGGCCGAGCTGTCCGTGGAGGCCAAGGATGTCGATGCGCTCTCCCGCACCCGCACGGTGGGCGAGGTCATCGACGCTATGAAGGC
CGAGATTGCCGGCTCCGCGGTCACTGTCGCTACCCTTGACGACTCGACCATTATGGAGGAGACTGACGACGAGGACGAGGACTTTATCCTGTACGACCACGTCTACGGCTCCG
AGTGCGAGGATCTCTCGCTCTCGTTCTCGTCGGTCAAGTCGATTCCTCGCGCGGACAAGCTCCTGCTGGACAACATTGCCGAGCGCCCCATTGTCATTGTCGATTGCGGCACGA
AGCTCACGACCGAGCTGGCGAAGGCCATCGGCGAGCGCGCTGTCGTTGCCACGTTCTCGGCCCAGTCGCTCGTGTCCCGTGGCTTCGTGGGCAAGAGCTTCACCCTCGGCAAC
ACCGAGGAGTCGGAGATCGAGAAGATGGTGTCCTCCATCGAGTCGTCCTACGGCAAGATCGGCGGCTTTGTCTACCAGCACTTTCATGACAGCGACTACGGTATGCAGCTCGG
CTGGGCTCTCATGGCCGCGAAGCACCTCAAGGAGTCCCTCAACGACCCGATCAAGAACGGCCGCACCTTTTTCCTGGCTGTCGCCCGCATGAACGGCAAGCTCGGCATGGACA
ACGCCTCCGTCCACGACCAGGGCATCGTCGAGAGCTGCGGTATCGCTGAGCGTGGTGCCATCTTTGGCCTCTGCAAGACCCTGGACCTGGAGTGGCCTAACGTGTTTGCGCGC
GGTGTGGACATCGCGGAGGGCATGTCCTACTCCCTCGCGGCCGAGCTGATCGTCGATGAGATCAGCTGCGCCAACCTTTCGATCCGCGAGAGCGGCTACACTATTAGCGGCGA
GCGCTTCACCACGGAGGCGCACAAGCTCGTCACGGGCAAGCCTCACGCGCCCATCAAGAAGAAGGACGCCTTTCTCGTGTCGGGTGGTGCTCGCGGCATCACGCCCCTGTGCA
TTCGCGAGATTGCCAAGGCCGTCAAGGGTGGCACCTACATTCTCATGGGCCGCTCGGCGCTCGCGGACGAGCCCCTCTGGGCTAACGGCAAGAGCGGCAAGGACCTCGACAA
GGCCGGCCTCGCCTTCCTTAAGGAGGAGTTCGCTGCCGGCCGTGGCTCGAAGCCCACCCCCAAGGTCCACAAGTCGCTCATCGACAAGGTCCTCGGCATCCGCGAGGTTCGCG
CGTCCATCGCCAACATCGAGGCGCACGCGCTAAGGCCATCTACCTCTCGTGCGATGTGTCGAGCGCCGAGAAGGTCAAGGCTGCCGTCCAGAAGGTCGAGAAGGAGCATCT
CGTCCGCATCACGGGCATCGTGCACGCCTCCGGCGTCCTGCGCGACAAGCTCGTCGAGAACAAGACCCTCGACGACTTTAACGCTGTGTACGGCACGAAGGTCACGGGCCTCG
TCAACCTCCTTAGCGCCGTCAACATGAACTTCGTCCGCCACCTGGTGATGTTCTCGTCGCTCGCTGGTTACCACGGCAACGTCGGCCAGTCGGACTACGCTATGGCCAACGAGA
GCCTTAACAAGATCGGCTTCCGTCTTGGTGCCGCGTACTCCCAGCTCTGCGTCAAGTCCATCTGCTTCGGCCCTTGGGATGGCGGCATGGTGACGCCGGCGCTCAAGAAGCAGT
TCCAGTCCATGGGCGTTCAGATCATCCCTCGCGAGGGTGGCGCCGAGACTGTCGCTCGCATTGTGCTCTCGTCCAACCCCAGCCAGGTCCTCGTCGGCAACTGGGGCGTCCCGC
CCGTCAGCCCCCTCTCCAAGTCGGCCACCATCGTCCAGACCTTTACCCCTGAGCTTAACCCCTTCCTCAAGTCCCACCAGATCCACGGCAAGAACGTCCTGCCCATGACGGTCG
CCATTGGTTACCTCGCCCACCTCGTGAAGAACTTTTACGCCGGCCACCACCTCTGGGGCGTGGAGGACGCGCAGCTCTTCTCCGGCGTCGTCATCGACCACGCCGTGCAGGCCC
AGGTCAAGCTCACTGAGCAGAGCCTGGATGACGATGGCAAGGTCAAGGTCCAGGCGGTGCTCACCGCCTCGAACGACAACGGCAAGATGGTGCCGGCCTACAAGGCCGTCAT
CGTGCTCGGCAAGACTTCCCGTCCGGCCTTCATCCTCAAGGACTTTTCGCTCCAGGAGTCCAACTCGCGCTCGGCCGACGAGCTGTACGACGGCAAGACCCTGTTCCACGGCCC
GCTGTTCCGTGGCATCACCAAGCTCCTCAACGTGTCCGACACTAGCCTCACGACCCAGTGCACCAACATCGATCTCACCGCCACTGAGCGCGGCCAGTTTGCCGACATCGAGC
CGGTCAACCCTTTCATGGCGGACGCCGCCTTCCAGGCCATGCTCGTCTGGGTCCGCAACCTCCGTAACTCCGCCAGCCTTCCGAACAACTGCGAGCGCGTCGATATCTACAAGC
CCATCGCGCCCGGCGAGAAGTACTACACCACGCTGCAGGCCCTCGGCAACACCTCCGGCTCGGTTCTCAAGTCCGTTTTCTACATGCATGACGAGCAGGGCGAGGTGTTCCTC
TCGGGCCGCGCCAGCGTCGTGGTCAACGATAAGATGGAATTCTAA(SEQ ID NO:120)
```

FIG.15

MEDQRIAIVGLSAILPSGENVRESWEAIRDGLNCLSDLPADRVDVTAYYNPTKGVKDKIYCKRGGFIPEYEFDSREFGLNMLQMEDSDANQTLTLLKVKEALDDANIPAFTNEKKNIG
CVLGIGGGQKASHEFYSRLNYVVVDKVLRKMGLPDEDVETAVEKFKANFPEWRLDSFPGFLGNVTAGRCTNTFNMEGMNCVVDAACASSLIAIKVAIDELLHGDCDAMIAGATCTD
NALGMYMAFSKTPVFSTDQSCLAYDEKTKGMLIGEGSAMFVLKRYADAVRDGDTVHAVIRSCSSSSDGKASGIYTPTISGQEEAILRAYRRAGVSPNTITLVEGHGTGTPVGDKIELT
ALRNVFDKAYGPGHKEEVAVGSIKSQIGHLKAVAGCAGLVKLVMALKHKTLPQSINVENPPNLVDGTVISDTTLYINTMNRPWITKPGVPRRAGISSFGFGGANYHAVLEEFEPEQTK
PYRLNVSAQPMLLHAVNANSLQKLCEDQLKLLKESREKCVNTKNTDYVAFSKFQDSFKLKGSVPSQHARVGFASKSIEDTISILSAIVNRFQKDITTTSWALPKEGAIFRSTALINDNKS
VAALFSGQGAQYTHMFNDVAMQWPQFRLCVNDMEKAQEEVINDKSVKRISQVMFPRKPYARESPLDNKEISKTEYSQTTTVASSVGLFEIFRDAGFAPAFVAGHSLGEFSALYAAGL
IDREDLFKLVCNRAMAMRDAPKKSADGAMAAVIGPNASSIKLSAPEVWVANNNSPSQTVITGANSGVQAETSKLKTQGFRVVHLACDGAFHSPHMENAEKQFQKALSAVKFNKPTG
SSPKIFSNVTGGVFTDPKTALSRHMTSSVQFLTQIKNMYAAGARVFIEFGPKQVLSKLVNEIFPGDTSVLTVSVNPASAKDSDIQLRQAAVQMAVAGVAL TDFDKWELKDPTRMKEFP
RKKTTLTLSAATYVSKKTLQERERIMNDGRTVSCVQRIENTNTGELEKLKKQLQDKENEVVRVQALATQASADLQNTKAELQKAQATKSSNAASDAVVAKHKAILLAMLEELETGK
AVDYSSFSKGQVASPATVRVVSAPVQAAAPVQVSASVDSGLLAKAEQVVLEVLASKTGYETELIELDMELETELGIDSIKRVEILSEVQAQLNVEAKDVDALSRTRTVGEVIDAMKAE
IAGGQPAAPVQVAAPTQVVAPVQASAPVDSGLLAKAEQVVLEVLASKTGYETELIELDMELETELGIDSIKRVEILSEVQAQLSVEAKDVDALSRTRTVGEVIDAMKAEIAGGQPAAP
VQVAAPTQVVAPVQASAPVDSGLLAKAEQVVLEVLASKTGYETELIELDMELETELGIDSIKRVEILSEVQAQLSVEAKDVDALSRTRTVGEVIDAMKAEISGGQPAAPVQVAAPTQI
VAPVQVSAPVDSGLLAKAEQVVLEVLASKTGYETELIELDMELETELGIDSIKRVEILSEVQAQLSVEAKDVDALSRTRTVGEVIDAMKAEISGGQPTAPVQVAAPTQIVAPVQVSAPV
DSGLLAKAEQVVLEVLASKTGYETELIELDMELETELGIDSIKRVEILSEVQAQLSVEAKDVDALSRTRTVGEVIDAMKAEISGGQPAAPVQVAAPTQIVAPVQASAPVDSGLLAKAEQ
VVLEVLASKTGYETELIELDMELETELGIDSIKRVEILSEVQAQLSVEAKDVDALSRTRTVGEVIDAMKAEISGGQPAAPVQVAAPTQIVAPVQVSAPVDSGLLAKAEQVVLEVLASKT
GYETELIELDMELETELGIDSIKRVEILSEVQAQLNVEAKDVDALSRTRTVGEVIDAMKAEIAGGQPAAPVQVAAPAPVVAPVQVSTPVDSGLLAKAEQVVLEVLACKTGYETELIELD
MELETELGIDSIKRVEILSEVQAQLSVEAKDVDALSRTRTVGEVIDAMKAEISGGQPTAPVQVAAPTQVVAPVKVSTPVDSGLLAKAEQVVLEVLASKTGYETELIELDMELETELGID
SIKRVEILSEVQAQLNVEAKDVDALSRTRTVGEVIDAMKAEIAGDQPAPAVVPVQAKSGVANPALLAKAEQVVLEVLASKTGYETELIELDMELETELGIDSIKRVEILSEVQAELSVE
AKDVDALSRTRTVGEVIDAMKAEIAGSAVTVATLDDSTIMEETDDEDEDFILYDHVYGSECEDLSLSFSSVKSIPRADKLLLDNIAERPIVIVDCGTKLTTELAKAIGERAVVATFSAQS
LVSRGFVGKSFTLGNTEESEIEKMVSSIESSYGKIGGFVYQHFHDSDYGMQLGWALMAAKHLKESLNDPIKNGRTFFLAVARMNGKLGMDNASVHDQGIVESCGIAERGAIFGLCKT
LDLEWPNVFARGVDIAEGMSYSLAAELIVDEISCANLSIRESGYTISGERFTTEAHKLVTGKPHAPIKKKDAFLVSGGARGITPLCIREIAKAVKGGTYILMGRSALADEPLWANGKSGK
DLDKAGLAFLKEEFAAGRGSKPTPKVHKSLIDKVLGIREVRASIANIEAHGAKAIYLSCDVSSAEKVKAAVQKVEKEHLVRITGIVHASGVLRDKLVENKTLDDFNAVYGTKVTGLVN
LLSAVNMNFVRHLVMFSSLAGYHGNVGQSDYAMANESLNKIGFRLGAAYSQLCVKSICFGPWDGGMVTPALKKQFQSMGVQIIPREGGAETVARIVLSSNPSQVLVGNWGVPPVSP
LSKSATIVQTFTPELNPFLKSHQIHGKNVLPMTVAIGYLAHLVKNFYAGHHLWGVEDAQLFSGVVIDHAVQAQVKLTEQSLDDDGKVKVQAVLTASNDNGKMVPAYKAVIVLGKTS
RPAFILKDFSLQESNSRSADELYDGKTLFHGPLFRGITKLLNVSDTSLTTQCTNIDLTATERGQFADIEPVNPFMADAAFQAMLVWVRNLRNSASLPNNCERVDIYKPIAPGEKYYTTLQ
ALGNTSGSVLKSVFYMHDEQGEVFLSGRASVVVNDKMEF (SEQ ID NO:69)

FIG.16

```
ATGGTGAAATTAAGTGTTGGTGATAATATTTGTCATGATCAACGTGTTGCTGTTGTTGGTATGGCTGTTATGTATGCTGGTTGTCAAAATCAACATGAATTTTGGCAATCTTTAC
AAGGTAAAAATATGAATTCAAAATCGATTTCACAAAATCGTTTAGGTTCTGAGTATAGAGAAGAACATTTTAAACCTGAAAGAAGTAAATATTCCGATACCTTTTGTAATGAA
AGATATGGTTGTATTGATGAGAATGTTCAAAGTGAACATGAACTTTTATTAAAACTTGCAAAAGATGCTATTGCGGATACAAAAGGTTCTATTGATTTGAATAAAACCGGAAT
CGTTAGTGGTTGCTTATCTTTTCCAATGGATAATTTACAAGGTGATTTATTAAATTTGTATCAATGTCACATTGAAAAGAAAATTGGGCCAAATGCATTAAAAGATGTGAATTT
ATGGTCTAAAAGAACCACCAACGGAAAAGATGATAAAAAAGCTTATTTTGATCCTGCCTCTTTCGTAGCTGAACAATTAGATATGGGACCATTACATTATAGTTTAGATGCTG
CTTGTGCGTCTGCACTTTATGTATTAAGACTTGCTCAAGATCATTTATTAAGTGGTGCTGCTGATACAATGTTATGTGGTGCATCTTGTTTACCTGAACCTTTTTTTATTTTATCT
GGTTTTTCTACTTTTCATGCAATGCCATTATCTGGTGATGTTTCTGCTCCTTTGCATAAAACTTCACAAGGTCTTACACCTGGTGAAGGTGGTGCTATTATGGTACTTAAACGAT
TAAATGATGCAATCCGTGATGGTGATAGAATTTATGGTACTTTACTTGGTGCTGAATTAAGTAATGCTGGTTGTGGTTTACCATTGAGTCCACATATGCCAAGTGAATTTGATT
GTATGGAAAAAGCTTTACAAAGAGTACACAGATTACCATCATCTATTCAATATGTTGAGTGTCATGCAACTGGTACACCACAAGGTGATAAAGTTGAAATTGATGCTATGACA
AAATGTTTTGGTGAACATTTACCAAGGTTTGGTTCAACGAAAGGGAATTTTGGTCATACACTTGTTGCTGCTGGTTTTGCTGGTATGTGTAAAGTTTTATTATCAATGCAATATG
GTGAAATACCACCAACTCCAGGTCTTGAAAATCCAGACAATATTATGCATGATTTAGTTGTTACTGAAACAATTCCATGGCCTAATACAAATGGTGATTTGAAACGTGCATGTT
TATCTGCTTTTGGATTCGGTGGTACTAATGCACATGCTGTATTTGAAGAGTATCGTTCAGATTTACAAGCAAATAAAACTCTTGAAAATGAAAGTAAAAGTCATGAAATCTTTT
CTTCATTTAAAATTGCTATTGTTGGTATGGAATCTGAATTTGGTACTTTGAAAGGATTACAAGAATTTGAACGTGCTATTTACAATGGTGGTCATGGTGCATGTGATTTACCTGA
AAATAGATGGAGATTTCTTGGAGAAGATAAAGAATTTTTACAAGCTTGTGGTTTACAAAAATTACCAAGAGGTTGTTATATTAAAGAAGTGGAAACTGATTTTAAAAGGTTAC
GTTTACCAATGATACAGGAGGTATTCTAAGACCTTTACAGTTGTTAGCTGTTTCGATTATCGACAGAGCACTTAACGCATCTGGTGTTAAACCAAATGGCAAAGTTGCAGTTT
TAGTTGGATTAGGTACTGATCTTGAATTATATCGTCATCGTGCTCGTGTTGCATTAAAGGAACGCCTCCAAACTGCGGTCAAAGAAGATATTCCTTTACTTGAAAAGTTAATGA
ACTATGTCAATGATGAGGTACAAGTACATCATATACATCTTATATTGGAAATTTGGTTGCAACTCGAGTTTCATCATTATGGGGTTTTACTGGTCCATCATTCACGATTACTGA
AGGTGAAAATTCCGTATATCGTTGTCTTGATTTGGGAAGATGGTTCTTAGCTAATGGTGAAGTAGATGCTGTTGTTGTTGCCGGGGTTGATTTATGTGGTAGTGCTGAAAATCT
TTTTGTAAAATCTCGTAGAAGTAAAGTTTCCACACAAAATGAACCATTTGCAAATTTTGAATCAAATGCTGATGGATATTTTGCTGGAGATGGTTGTGGAGCTTTGGTTTTGAA
ACGATTGAGTGATTGTACGGATTCAACTGAAAAAATTTATGCAACGGTGGATTCAATTGCTGTTGGTGATGAAGTTGGCCCAACTATTAAACAAGCTTTGAAGAATGCATCCA
TAGCAGCGAAAGATATTGAACTGGCAGAGCTATCAGCAAGTTCAGGCAAACATCATTCTGGTAGAATCACTTGTGAAGATGAACTAAATGAACTGGGTGAAATTTTCAATGA
AGGTATACAAAGAGTTGCAATTGGTAGTGTGAAAGCTAATGTTGGAGATGTTGGATATGCATCTGGTCAGCAAGTTTAATCAAAACGGCTTTGTGCCTGTACAACCGATATT
TACCAAAGTTACCAAATTGGAATAAGCCAACGAAAGATGTTGAATGGTCCAAATCATTTTTTGTATGTGAACATTCTAGAGCATGGTTGAAAAATGTTGATGAAAATAGACAT
GCTGTCGTTTCTGGAGTTTGCGAAAATGGTTCGTGTTATGGAATCGTAATGTCTGATGTACAAGGACATCATGAAGAATCGAATCTTGTTAGTTTAGACAAAAATGAACCAAA
AGTACTGGGTATTTACGGAGATTCAGTTGATGATATCCTAGTTCAGCTCAACAAATATCTTGAAAAATTCCTTCAAGAAACTGGAACGGCTGCGGCTGCACAAAAAGTTAAAT
CACCTACAATAGATATTGACTCCAATGTGTTTGCTGAGATGCTTAATCTACCGCAGGATAAAAACAAAAATTTGCGGTCGCATTGGTTACCACACCAAATAAACTCCAGCGT
GAAATAGAACTTGCTGTGAAGGGTATTCCACGTTGCGTAAAAGCAAAAGAGATTGGTGTTCTCCATCTGGAAGTATTTTTGCTTGTAATCCACTCAAAAGTGATAATATTGCA
TTTATGTATGGTGAAGGCCGAAGCCCATATGCTGGACTGGGATATGATTTTGCATCGAATTTGGCCTATGCTACACGAGTTGGTTAACAATAGAACTACAGAACTTTGGGATCA
AGGTGATAGTTGGTATTTACCTCGATCTAGCTCTGTTGCTGAAAAAGAAAAAGTCTTCGGAGATTTTGATAAGAATCAAATTGAAATGTTTAGATTGGGTATTTTTGTATCAAT
GTGTTTCACTGATATGGCCACTGAACTTTTGGGTTTAAAACCCAAAGCCGCGTTTGGTTTAAGTTTGGGTGAAATATCTATGCTTTTTGCATTTTCTAAAAAGAATACCAAGTTG
TCCAAAGAATTGACCCGTCGTCTAAAAGAAGCAAAAGTTTGGGCATCACAATTAGCTGTTGAATTTGCAGCTATTCGAGATTTGTGGAATATTCCAGCTGATAAATCTATTGAT
GAATTTTGGCAAGGGTATTTTGTTTACGCAAATCGAACCCTGGTCGAGAACACAATTGGGGAGAATAAATTTGTTCGTTTGTTGATTGTAAATGATTCGCAAAGTTGTCTAATT
GCCGGGAAACCAGATGAATGTCAAAAAGTTATTGAGAAGCTTCATTTGAAGCTACCGGCGGTTCCAGTAACTCAGGGTATGATCGGTCATTGCCCAGAAGCAATTCCTTATCT
AGATCAAATCAGTCATATTCATGAAATGCTTGAAATTCCAAAACCCGAAAATGTGAAATTGTTTACAACTAGTGAAAACAGAGAATTAGTGTCGATGAAAGATTCCGTGTCAA
AATTGGTTGCTGAGATTTATCAGCATGTTGCTGATTTTCCAAACATCGTGAACAAGGTTAAAGAAACTTGCAAAACTGATATATTTATTGAATTGGGATCGAACAATTATCGAT
CTGGAGCTGTCAAAACAATTTTAGGTCCAGAAATCGTTTCTGTTGCAATTGATAGGCAAAATGAAACTGCATGGGGTCAACTAATGAAGATGGTTGCATCGTTGATAAGTCAT
CGAGTTCCGGGTGTTGAATTGAAAAAACTCTATCATCCTGAATTGCTGAAATTTGATCCACAGGCAAAACCGAATCGTTTCATCAGAAATATAGAACTGAATGGATTTTTTGAT
CGTACGAATATTATTGTTGATAAGCAACTATCCCCTGCGGATCCGAAACTCGCTGAAATTGTGAACAATCGAAATATGCCTAAAGATAATGTTTATGTACCAATTGAACGGGT
GAAAACGATGATAAAGGCGGAACCAGCTAATTTACAAGTCAGCGTGGGAAGTAAACCAGTTGTTACTGAAAGAATTAGTTCGGACGATAATCTATTTGAAAAGTTGTCAGAA
ATTACAAAATCTTTTGATGGTGTAAATGCGTGTACTGAAGCAATGTTGGGAGACTCTGGATTTCTCAAAACATATGAGGTTGACTATCCTTTGTACACAGGTGCCATGGCTAAA
GGAATTGCGTCTGCTGATTTGGTTATTGCTGCTGGTAAATCAAAGATCTTGGCATCATTTGGAGCTGGTGGGTTGGCCTTACAAGTGGTAGAAGATGCCATTAAACAAATTAAA
GCTGAATTGGGGAACGGTCCGTTTGCTGTAAATTTGATTCATTCACCATTCGATCCTAGCTTGGAGAAGGGTAACGTTGATCTTTTTCTAAAATATAACGTTCGATTTGTTGAAG
```

FIG.16 (cont'd)

TATCCGCATTTATGTCATTAACCCCTCAGGTTGTACGATACAGAGCCGCTGGTTTGGCCAAAGCAAGAGATGGATCTGTGAAAATTCAAAATCGTATTATTGCCAAAATTTCAA
GAACAGAGTTAGCGGAACTGTTCTTGAAACCAGCACCCAAAAATATTTTAGATGCATTGGTTGCGGATGGATCTATTAGTCAAGAACAAGCCCAACTTGCATTACTTGTGCCA
ATGGCTGATGATATTACTGTGGAAGCTGATTCTGGTGGGCATACTGACAATCGACCAATTCATGTTTTGTTACCTTTGATAATTCAGCAAAGAAATAGAATTTGTAAACAATAC
CCAAAACATTTAAAAGTTCGAATCGGAGCAGCTGGTGGTATTGGATGCCCGAAGGCAGCATTTGCTGCGTTTGAGATGGGTGCTGCATACATTGCAACTGGAACGGTAAATCA
ACTTTCAAAGGAAGCAGGTACTTGTGACTATGTACGTAAAGTATTGAATAAAGCTACATATTCGGATGTTACCATGGCTCCAGCCGCAGATATGTTCGATCATGGTGTTGAATT
ACAAGTTTTGAAGAAAGGTACTATGTTTCCTTCACGTGCTAAAAAACTATACGATTTGTTCAAAAAATACAAATCGATTGAGGAATTACCAGCAGATGAGGTGAAAAAACTTG
AGCAAAAAGTTTTCAAAAAGTCGTTTGATGAAGTATGGGATGAGACCAAGAATTACTATATTAATCGTTTACATTCTCCCGAAAAAATTGAACGTGCTGAAAGAGATGCAAAA
CTTAAAATGTCGTTATGTTTTCGTTGGTATTTGTCGAAGTCTTCCAGATGGGCTAATACCGGTGAATCTGGAAGAGTGCAGGATTATCAAATTTGGTGTGGTCCAGCAATTGGG
TCATATAATGATTTTGCGAAAGGATCACCATGTTTGGATCCTGAGATTTTGGGTAGTTTTCCAAGTGTTGTTCAGATTAATAAACATATTTTACGTGGTGCTTGTTTCTATCAAA
GACTCTCTCAGTTGAAATATCTGAATTTTAACTATGAGGAATTAGATACGTTAACATACTCTGCATCGAATTTTATTTAA (SEQ ID NO:70)

FIG.17

```
ATGGTGAAGCTTTCCGTTGGTGACAACATTTGCCACGATCAGCGCGTCGCCGTGGTCGGCATGGCCGTCATGTACGCCGGCTGCCAGAACCAGCACGAGTTTTGGCAGAGCCT
CCAGGGTAAGAACATGAACAGCAAGAGCATCAGCCAGAACCGCCTGGGCTCCGAGTACCGCGAGGAGCACTTTAAGCCGGAGCGCTCGAAGTACAGCGACACCTTCTGCAAC
GAGCGTTACGGCTGCATCGACGAGAACGTCCAGAGCGAGCATGAGCTCCTCCTGAAGCTCGCTAAGGACGCGATCGCCGATACCAAGGGCAGCATCGACCTTAACAAGACCG
GCATTGTCTCCGGCTGCCTCTCGTTCCCTATGGATAACCTCCAGGGCGACCTTCTCAACCTCTACCAGTGCCATATTGAGAAGAAGATCGGCCCGAACGCCCTCAAGGATGTCA
ACCTCTGGTCGAAGCGCACGACCAACGGTAAGGACGATAAGAAGGCCTACTTCGATCCCGCCAGCTTCGTCGCTGAGCAGCTTGACATGGGTCCCCTCCACTACTCGCTCGAC
GCTGCCTGCGCCTCCGCTCTCTACGTCCTCCGCCTCGCCCAGGACCACCTCCTCAGCGGTGCCGCCGACACCATGCTCTGCGGCGCCTCGTGCCTCCCGGAGCCCTTTTTCATCC
TTTCGGGCTTTTCGACCTTCCACGCCATGCCCCTTTCGGGTGACGTGTCGGCCCTCTTCACAAGACGAGCCAGGGCCTCACTCCGGGCGAGGGCGGTGCTATCATGGTCCTGA
AGCGCCTCAACGATGCCATTCGCGACGGCGACCGCATCTACGGCACGCTCCTGGGCGCCGAGCTTTCCAACGCGGGTTGCGGCCTCCCGCTCTCCCCGCACATGCCGTCCGAG
TTCGACTGCATGGAGAAGGCCCTCCAGCGCGTTCACCGCCTCCCGTCCTCCATCCAGTACGTGGAGTGCCACGCCACTGGCACCCCGCAGGGCGACAAGGTCGAGATCGACGC
CATGACGAAGTGCTTCGGCGAGCATCTGCCTCGCTTCGGCTCCACCAAGGGTAACTTCGGCCACACCCTCGTGGCTGCTGGCTTTGCGGGCATGTGCAAGGTCCTCCTCTCGAT
GCAGTACGGTGAGATTCCTCCTACGCCTGGCCTGGAGAACCCCGACAACATTATGCACGATCTTGTCGTTACCGAGACTATTCCCTGGCCGAACACCAACGGCGATCTTAAGC
GTGCGTGCCTCAGCGCCTTTGGCTTTGGCGGTACTAACGCCCACGCCGTGTTCGAGGAGTACCGCAGCGACCTTCAGGCCAACAAGACCCTTGAGAACGAGAGCAAGTCCCAC
GAGATCTTTTCCTCCTTTAAGATTGCCATTGTTGGCATGGAGTCCGAGTTTGGCACTCTCAAGGGCCTCCAGGAGTTCGAGCGTGCCATCTACAACGGCGGCCACGGCGCGTGC
GACCTTCCGGAGAACCGCTGGCGCTTTCTCGGTGAGGACAAGGAGTTTCTCCAGGCCTGCGGCCTCCAGAAGCTCCCGCGTGGCTGCTACATCAAGGAGGTCGAGACTGACTT
TAAGCGCCTTCGCCTCCCCATGATCCAGGAGGACATCCTCCGCCCCCTCCAGCTCCTCGCCGTGTCGATCATCGACCGCGCCCTCAACGCCAGCGGCGTTAAGCCCAACGGCA
AGGTCGCCGTCCTCGTGGGCCTCGGCACCGATCTTGAGCTCTACCGCCACCGCGCTCGCGTCGCCCTGAAGGAGCGCCTTCAGACCGCCGTCAAGGAGGACATCCCCCTGCTG
GAGAAGCTCATGAACTACGTGAACGACCGCGGCACCTCCACGTCCTACACCTCGTACATCGGCAACCTCGTTGCGACCCGCGTCAGCTCGCTCTGGGGCTTCACCGGCCCTAG
CTTCACGATCACGGAGGGCGAGAACTCGGTTTACCGTTGCCTCGACCTCGGCCGCTGGTTCCTCGCCAACGGTGAGGTCGATGCCGTGGTTGTCGCTGGCGTGGATCTCTGCGG
CTCGGCCGAGAACCTGTTCGTCAAGTCGCGCCGCTCCAAGGTGTCCACCCAGAACGAGCCCTTTGCTAACTTTGAGTCGAACGCCGACGGCTACTTCGCCGGCGACGGCTGCG
GTGCCCTCGTTCTCAAGCGCCTTTCGGACTGCACTGACTCCACCGAGAAGATCTACGCGACCGTGGACAGCATTGCTGTCGGCGACGAGGTGGGCCCGACTATTAAGCAGGCC
CTGAAGAACGCCCTCGATCGCCGCGAAGGACATCGAGCTCGCGGAGCTCTCCGCCTCCAGCGGCAAGCACCACTCCGGCCGCATCACCTGCGAGGACGAGCTTAACGAGCTCG
GCGAGATCTTCAACGAGGGCATTCAGCGCGTGCCCATCGGCAGCGTCAAGGCCAACGTCGGCGACGTCGGCTACGCCTCCGGTGCTGCCAGCCTCATCAAGACGGCCCTCTGC
CTCTACAACCGCTACCTCCCCAAGCTCCCCAACTGGAACAAGCCGACCAAGGACGTCGAGTGGTCGAAGAGCTTCTTTGTCTGCGAGCACTCGCGCGCCTGGCTCAAGAACGT
GGACGAGAACCGCCACGCGGTCGTGAGCGGCGTCTGCGAGAACGGCTCCTGCTACGGCATCGTCATGAGCGACGTCCAGGGCCACCATGAGGAGTCGAACCTCGTGTCCCTC
GATAAGAACGAGCCCAAGGTGCTCGGTATCTACGGCGATTCCGTGGACGATATTCTGGTCCAGCTGAACAAGTACCTGGAGAAGTTCCTTCAGGAGACTGGCACTGCTGCGGC
TGCGCAGAAGGTGAAGAGCCCTACCATTGACATCGACTCGAACGTCTTTGCCGAGATGCTGAACCTTCCCCAGGACAAGAACAAGAAGTTTGCCGTCGCTCTGGTCACGACCC
CCAACAAGCTCCAGCGCGAGATTGAGCTCGCCGTTAAGGGCATCCCTCGCTGCGTGAAGGCCAAGCGCGACTGGTGCTCCCCCTCCGGCAGCATCTTTGCGTGCAACCCGCTC
AAGTCGGACAACATTGCCTTTATGTACGGCGAGGGCCGCTCGCCTTACGCCGGCCTCGGCTACGATCTCCACCGCATCTGGCCCATGCTTCACGAGCTCGTGAACAACCGCAC
GACTGAGCTGTGGGACCAGGGTGACTCGTGGTACCTGCCGCGCAGCTCCTCCGTGGCCGAGAAGGAGAAGGTCTTTGGCGACTTCGACAAGAACCAGATCGAGATGTTCCGC
CTCCGGTATTTTCGTCAGCATGTGCTTTACCGACATGGCGACGGAGCTCCTCGGCCTTAAGCCGAAGGCCGCTTTCGGCCTCTCCCTCGGCGAGATCAGCATGCTCTTTGCTTTCT
CGAAGAAGAACACCAAGCTCTCCAAGGAGCTTACTCGCCGCCTCAAGGAGGCCAAGGTGTGGGCGTCGCAGCTGGCCGTCGAGTTCGCCGCCATCCGCGACCTTTGGAACAT
CCCGGCCGACAAGTCCATCGATGAGTTCTGGCAGGGTTACTTCGTTTACGCCAACCGTACGCTCGTGGAGAACACCATTGGCGAGAACAAGTTCGTCCGCCTCCTTATCGTCAA
CGACTCCCAGTCCTGCCTCATTGCCGGTAAGCCCGATGAGTGCCAGAAGGTCATCGAGAAGCTCCACCTTAAGCTCCCCGCCGTCCCCGTCACCCAGGGCATGATTGGCCACT
GCCCGGAGGCCATTCCCTACCTCGACCAGATCAGCCACATCCACGAGATGCTTGAGATCCCGAAGCCTGAGAACGTCAAGCTCTTCACGACGTCCGAGAACCGCGAGCTTGTC
TCGATGAAGGACTCCGTTAGCAAGCTCGTCGCGGAGATCTACCAGCACGTCGCTGACTTCCCCAACATTGTCAACAAGGTCAAGGAGACTTGCAAGACGGACATTTTCATCGA
GCTGGGCAGCAACAACTACCGTTCCGGTGCCGTCAAGACTATCCTCGGTCCGGAGATCGTGAGCGTTGCCATCGACCGTCAGAACGAGACTGCCTGGGGCCAGCTCATGAAGA
TGGTCGCCAGCCTGATCTCCCACCGCGTCCCCGGCGTCGAGCTCAAGAAGCTGTACCATCCGGAGCTCCTGAAGTTCGATCCCCAGGCCAAGCCCAACCGCTTTATCCGCAAC
ATCGAGCTCAACGGCTTTTCGACCGCACGAACATCATCGTCGATAAGCAGCTTTCCCCTGCGGACCCGAAGCTCGCCGAGATCGTCAACAACCGCAACATGCCGAAGGATAA
CGTGTACGTCCCCATTGAGCGCGTCAAGACGATGATCAAGGCCGAGCCCGCTAACCTCCAGGTGTCCGTCGGCTCGAAGCCCGTGGTCACCGAGCGTATCTCGTCGGACGACA
ACCTCTTTGAGAAGCTCTCGGAGATCACTAAGTCCTTCGACGGTGTCAACGCCTCGACCGAGGCCATGCTCGGCGATTCGGGCTTTCTCAAGACGTACGAGGTTGACTACCCGC
TCTACACCGGCGCTATGGCCAAGGGTATCGCCTCCGCCGACCTCGTCATTGCGGCGGGTAAGTCGAAGATCCTTGCGTCCTTTGGTGCTGGCGGCCTCGCTCTCCAGGTGGTCG
```

FIG.17 (cont'd)

```
AGGATGCCATTAAGCAGATCAAGGCTGAGCTTGGCAACGGTCCCTTTGCCGTCAACCTCATCCACTCGCCTTTCGACCCCTCGCTTGAGAAGGGCAACGTTGACCTTTTCCTCA
AGTACAACGTCCGCTTTGTCGAGGTGAGCGCGTTCATGAGCCTCACCCCCAGGTCGTTCGCTACCGCGCTGCCGGCCTTGCCAAGGCCCGTGACGGCTCGGTCAAGATTCAG
AACCGCATCATCGCCAAGATTTCGCGCACGGAGCTGGCCGAGCTCTTCCTCAAGCCCGCTCCGAAGAACATCCTCGATGCCCTCGTTGCCGACGGCTCGATTTCCCAGGAGCA
GGCTCAGCTCGCGCTCCTCGTCCCTATGGCCGATGACATCACCGTTGAGGCCGACTCCGGTGGCCACACCGACAACCGCCCCATTCATGTGCTCCTCCCCCTCATCATCCAGCA
GCGCAACCGCATTTGCAAGCAGTACCCGAAGCACCTCAAGGTCCGCATCGGCGCTGCCGGTGGCATCGGTTGCCCTAAGGCGGCTTTTGCCGCCTTTGAGATGGGTGCGGCCT
ACATCGCCACGGGCACCGTTAACCAGCTCTCGAAGGAGGCCGGCACCTGCGACTACGTGCGCAAGGTGCTCAACAAGGCCACCTACTCCGACGTCACGATGGCTCCCGCTGCC
GACATGTTCGACCACGGTGTCGAGCTCCAGGTTCTCAAGAAGGGCACCATGTTTCCGTCGCGCGCCAAGAAGCTCTACGACCTCTTTAAGAAGTACAAGTCGATCGAGGAGCT
CCCTGCCGACGAGGTCAAGAAGCTGGAGCAGAAGGTTTTTAAGAAGTCGTTCGACGAGGTCTGGGACGAGACTAAGAACTACTACATTAACCGCCTCCACTCCCTGAGAAG
ATCGAGCGCGCGGAGCGTGACGCCAAGCTGAAGATGTCGCTCTGCTTTCGTTGGTACCTGAGCAAGTCGTCCCGCTGGGCCAACACCGGCGAGTCGGGCCGTGTCCAGGACTA
CCAGATCTGGTGCGGCCCCGCCATCGGCTCGTACAACGACTTCGCGAAGGGCTCGCCCTGCCTTGACCCTGAGATCCTTGGCTCGTTCCCGTCGGTTGTCCAGATCAACAAGCA
TATTCTGCGCGGCGCTTGCTTCTACCAGCGTCTTTCGCAGCTCAAGTACCTTAACTTCAACTACGAGGAGCTCGATACGCTCACCTACAGCGCTAGCAACTTTATCTAA
```

(SEQ ID NO: 121)

FIG.18

MVKLSVGDNICHDQRVAVVGMAVMY AGCQNQHEFWQSLQGKNMNSKSISQNRLGSEYREEHFKPERSKYSDTFCNERYGCIDENVQSEHELLLKLAKDAIADTKGSIDLNKTGIVS
GCLSFPMDNLQGDLLNLYQCHIEKKIGPNALKDVNLWSKRTTNGKDDKKAYFDPASFVAEQLDMGPLHYSLDAACASALYVLRLAQDHLLSGAADTMLCGASCLPEPFFILSGFSTF
HAMPLSGDVSAPLHKTSQGLTPGEGGAIMVLKRLNDAIRDGDRIYGTLLGAELSNAGCGLPLSPHMPSEFDCMEKALQRVHRLPSSIQYVECHATGTPQGDKVEIDAMTKCFGEHLPR
FGSTKGNFGHTLV AAGFAGMCKVLLSMQYGEIPPTPGLENPDNIMHDLVVTETIPWPNTNGDLKRACLSAFGFGGTNAHAVFEEYRSDLQANKTLENESKSHEIFSSFKIAIVGMESEF
GTLKGLQEFERAIYNGGHGACDLPENRWRFLGEDKEFLQACGLQKLPRGCYIKEVETDFKRLRLPMIQEDILRPLQLLAVSIIDRALNASGVKPNGKVAVLVGLGTDLELYRHRARVA
LKERLQTAVKEDIPLLEKLMNYVNDRGTSTSYTSYIGNLVATRVSSLWGFTGPSFTITEGENSVYRCLDLGRWFLANGEVDAVVVAGVDLCGSAENLFVKSRRSKVSTQNEPFANFES
NADGYFAGDGCGALVLKRLSDCTDSTEKIYATVDSIAVGDEVGPTIKQALKNASIAAKDIELAELSASSGKHHSGRITCEDELNELGEIFNEGIQRVAIGSVKANVGDVGYASGAASLI
KTALCLYNRYLPKLPNWNKPTKDVEWSKSFFVCEHSRAWLKNVDENRHA VVSGVCENGSCYGIVMSDVQGHHEESNLVSLDKNEPKVLGIYGDSVDDILVQLNKYLEKFLQETGT
AAAAQKVKSPTIDIDSNVFAEMLNLPQDKNKKFAVALVTTPNKLQREIELAVKGIPRCVKAKRDWCSPSGSIFACNPLKSDNIAFMYGEGRSPYAGLGYDLHRIWPMLHELVNNRTTE
LWDQGDSWYLPRSSSVAEKEKVFGDFDKNQIEMFRLGIFVSMCFTDMATELLGLKPKAAFGLSLGEISMLFAFSKKNTKLSKELTRRLKEAKVWASQLAVEFAAIRDLWNIPADKSID
EFWQGYFVY ANRTLVENTIGENKFVRLLIVNDSQSCLIAGKPDECQKVIEKLHLKLPAVPVTQGMIGHCPEAIPYLDQISHIHEMLEIPKPENVKLFTTSENRELVSMKDSVSKLVAEIY
QHVADFPNIVNKVKETCKTDIFIELGSNNYRSGAVKTILGPEIVSVAIDRQNETAWGQLMKMVASLISHRVPGVELKKLYHPELLKFDPQAKPNRFIRNIELNGFFDRTNIIVDKQLSPA
DPKLAEIVNNRNMPKDNVYVPIERVKTMIKAEPANLQVSVGSKPVVTERISSDDNLFEKLSEITKSFDGVNACTEAMLGDSGFLKTYEVDYPLYTGAMAKGIASADLVIAAGKSKILA
SFGAGGLALQVVEDAIKQIKAELGNGPFAVNLIHSPFDPSLEKGNVDLFLKYNVRFVEVSAFMSLTPQVVRYRAAGLAKARDGSVKIQNRIIAKISRTELAELFLKPAPKNILDALVAD
GSISQEQAQLALLVPMADDITVEADSGGHTDNRPIHVLLPLIIQQRNICKQYPKHLKVRIGAAGGIGCPKAAFAAFEMGAAYIATGTVNQLSKEAGTCDYVRKVLNKATYSDVTMAP
AADMFDHGVELQVLKKGTMFPSRAKKLYDLFKKYKSIEELPADEVKKLEQKVFKKSFDEVWDETKNYYINRLHSPEKIERAERDAKLKMSLCFRWYLSKSSRWANTGESGRVQDY
QIWCGPAIGSYNDFAKGSPCLDPEILGSFPSVVQINKHILRGACFYQRLSQLKYLNFNYEELDTLTYSASNFI (SEQ ID NO:71)

FIG.19

```
ATGGTTGGTTTACAAATGAAAAGAAACCAGTATGGGAGATGAGTAAGGAAGAACAAAGTTCTGGAAAGAATGTTGTATTTGACTATGATGAATTGTTGGAATTTGCTGAAG
GTGATATTGGTAAAGTCTTTGGACCTAAGTTTGATATTATCGATAAGTATAGTCGACGTGTACGTTTACCTGCGAGAGAATATCTTCTAGTTACCAGAGTTACTTTGATGGATG
CTGAAGTTGGGAATTTCAGAGTTGGATCTAGAATGGTTACTGAATATGATGTTCCAGTAAATGGTGAACTTTCACAAGGTGGTGATGTTCCATGGGCTGTTCTTGTTGAATCTG
GACAATGTGATCTTATGTTAATATCTTATATGGGTATTGATTTTCAATGTAAAGGTGATCGTGTCTATCGATTATTAAATACTACGTTGACGTTTTACGGTGTTGCTCATGAGGG
TGAAACACTAGTATACGATATTCGTGTAACTGGATTTGCAAAAGGTATGCACGGTGAAATCTCCATGTTTTTTTTTGAATATGATTGTTATGTGAATGGACGATTATTAATCGA
AATGAGAGATGGTTGTGCGGGATTTTTTACTGATGAAGAACTTGCAGCAGGTAAAGGAGTTATTAAAACTGTTGCTGAACTTCATAAAAGAAAATCTATTGTTCCAAAATCCA
TTAAACCTTTTGCTCTAAATCCAGCAGTACACAAAACAATGTTTTCTGAAAATGATATGGAAAAATTGTGTGAGCGTCAATGGGAAAATGTATTGGGTAGTGGACTTCAAGGT
ATTGACTACAAGTTATGTGCACGGAAAATGCTTATGATTGATCGTATTACTAAAATACAACATAATGGTGGTGCATATGGTCTTGGATTATTGGTTGGCGAAAAAATTCTTGAA
CGTGATCATTGGTATTTTCCATGCCATTTTGTAAAGGATCAAGTTATGGCTGGCTCACTTGTTAGTGATGGTTGCAGTCAGCTACTAAAACTTTATATGTTATGGTTGGGTTTAC
ATGATGTGGTTCCAGATTTTCAATTTCGTCCAGTTCCTGGACAACCAAATAAAGTTCGTTGCCGTGGACAAATTAGTCCACATCGTGGTAAACTTGTTTATGTTATGGAAATAA
GAGAAATGGGATTCAATGAATCAACTGGACAACCATATGCTATTGCTGATGTTGATATTATTGATGTAAACTATGAACTTGGTCAATCATTTGATATGGCTGATATTGATAGTT
ATGGACGTGGTAATTTGTCAAAGAAAATTGTGGTTGATTTTAAAGGAATTGCTTTGCAAATGGAAGGTACCGTGAAATCATCAAATATCATTGATTCTTCACCAAAATCAACTA
TTATACAACCACCTCCAAATTGTCTTCGTGGTGATCCACTGGCACCATCACAAGTTACATGGCATCCAATGGCAGGAGTTAATGGGGCACCAGCTCCTTCATTTAGTCCATCTG
ATTATCCACCACGTGCTGTTTGCTTCAAACCATTTCCTGGTAATCCTTTAGATAACGATCATACACCTGGTAAAATGCCTTTAACATGGTTTAATATGTCCGAGTTTATGTGTGG
TAAAGTATCAAATTGTCTTGGACCAGAATTTAAGAGATTTGATAACTCTAAAACATCCAGAAGTCCTGCCTTTGATCTTGCACTTGTTACACGTGTTGTGAGTGTATCAGATAT
GGAATTTAAACCTCATTTAAATATTGATGTTAATCCAAGTAAGGGTACAATGATAGGTGAATTTGATTGCCCTGCAGATGCGTGGTTTTTTCAAGGATCATGTAACGATGGTCA
TATGCCGTATTCTATTGTTATGGAAATTGCTCTTCAAACTTCTGGTGTATTAACTTCAGTTTTGAAAGCACCTTTGACTATGGATAAAGATGATATTCTTTTCCGCAATTTGGAT
GCCACTGCTGAAATGGTTCGAAGTGATGTTGATTGTAGAGGTAAAACTATCAAAAACTTTACTCAATGTACCGGTTACAGTATGCTCGGAAAAATGGGAATTCATAGATTCAC
ATTTGAATTATCTGTTGATGATGTAGTTTTCTACAAAGGATCAACATCTTTTGGTTGGTTCACCCCTGAAGTATTCGAGTCACAAGTTGGTCTTGATAATGGTAAAAAAGTACA
ACCATGGTATTTGGAACAAAAATCATCTAATGTAGTAACTTATGACGTTGCGTCCACTGCTGGCAAGGATAAGTTATTTTCAAAGATTGGATCTAAGGATGCACAAGTTCAAA
GAAGAAATACACAATGTGAGTTTCTAGATACTATGCATATTATTCCAAATACTGGAAAGTACAACAAAGGTTATGCTCATGGAGAAAAGAAAGTTAATCCAAACGACTGGTTC
TTTTCCTGTCATTTCTGGTTTGATCCTGTGATGCCTGGTTCATTAGGTATTGAAAGTATGTTTCAACTCATTGAAGCATTTTCAATTGATCAAGGAATCGCTTCAAAACATGGTA
TTGTGAATCCAACTTTTGCTCATTCCAATGGAAAAACTTCTTGGAAATACAGAGGTCAATTGAATAACAAAGGTAAACGAATGGATAGTGAAATTCATATCAAAGATATTGTC
AAAAATGCTGATGGTACTGTTGATTTGATTGCTGATGGATTTTTATTGGTTGATTCACTAAGAGTATACTCTGCAGATGATCTTCGCGTAAAAATTGTACCGGGAACCAAAGCT
GCACCTAAATCAGTAGCTGCTGCTCCAAGACATGTTGCAACACCAATTCCAGGAGTGCCTTCGAATACAAGCAGTGTTGAAATCAGTTTGGAATCTTTGAAGAAAGAATTGTT
AAATCTTGAGAAACCATTGTATCTTGAAACTTCCAATCATATTGTAAAACAATTCGGTGACGTTAACAATGGCCAAGCATCCGTTATTCCACCATGCACCATCAATGATTTGGG
TGAGCGTAGTTTTATGGAAACATACAATGTTGTTGCACCACTTTACACTGGAGCCATGGCTAAAGGTATTGCATCTGCTGATTTGGTAATTGCAGCTGGTAAAAGAAAAATTTT
GGGTTCTTTTGGCGCTGGAGGCTTACCAATGCACTTGGTTCGTGCTTCTGTTGAAAAAAATCCAAGCCGCACTTCAGAAGGTCCATACGCTGTCAACTTGATTCATAGTCCATT
CGACTCAAATCTTGAAAAGGGAAATGTAGATCTATTTTTGGAAAAAGGTGTTCATGTTGTTGAAGCATCTGCATTCACTGCTCTGACCACTCAAGTAGTTCGTTACCGTGCATG
TGGTTTATCTCGGGCTAAAGACGGATCTGTATTGATCAAAAATAGAATCATCGGTAAAGTTTCAAGAACCGAATTGGCTGAAATGTTTTTCAGACCTGCACCACAAAACTTGCT
TGACAAGCTTATTGCTAGTGGAGAAATCACTAAAGAACAAGCTTCATTGGCTTTGGAAGTACCAATGGCTGATGATGTAGCTGTTGAAGCTGATAGCGGTGGACATACTGATA
ATAGACCAATTCATGTAATCCTACCTTTGATTATCAATCTACGAAATAGAATTCATAAAGAATGTGGTTTTCCTGCTGCTTTGAGAGTTCGCGTTGGTGCTGGTGGTGGAATTG
GTTGTCCAAGTGCTGCAGTTGCTGCATTCAATATGGGAGCTGCATTCTTGATTACTGGCAGCGTCAACCAAGTTAGCAAACAATCTGGTACGTGTGATATCGTTAGAAAGCAAT
TATCTGAAGCTTCGTATTCAGATATTACCATGGCACCAGCGGCTGATATGTTTGATCAAGGAGTCGAGCTTCAAGTATTAAAAAAAGGAACTATGTTTCCATCTCGTGCAAAGA
AATTGTATGAATTATTCTGTATGTACAACTCATTTGATGACATGCCAAAAAGCGAACTTCAAAGACTAGAAGCGAATTTTTCAAAAATCGCTTGCCGGAAGTTTGGGAAGAA
ACTAAAGATTTTTATATCAATCGTTTGAATAATCCTGAGAAGATTGAACATGCTGAGAAGAAAGATCCAAAGTTGAAGATGTCATTATGCTTTAGATGGTATTTGGGTTTAAGT
TCATTTTGGGCAAACAATGGAATTAAAGAAAGATCAATGGACTATCAAATTTGGTGTGGTCCAGCGATTGGTTCATACAATGATTTTGTAAAAGGAACTTATTTGGATCCTGCA
GTAGCAGGTTCATATCCATGTGTTGTTCAAATTAACATGCAAATTCTACGCGGTGCTTGTTTTCTTCAACGAGTTCGTGCAATCAAGCACGATCCACGATTGGATATTGATGTC
GATGAAGATGTATTTACCTATCGTCCAGAATCAACCCTATAG
```
(SEQ ID NO:72)

FIG. 20

ATGGTTGGCCTGCAGATGAAGAAGAAGCCTGTGTGGGAGATGTCGAAGGAGGAGCAGTCGTCCGGCAAGAACGTCGTCTTTGACTACGACGAGCTCCTCGAATTCGCGGAGG
GTGACATCGGCAAGGTGTTCGGCCCCAAGTTTGACATCATCGACAAGTACAGCCGCCGTGTGCGCCTCCCGGCCCGCGAGTACCTCCTCGTCACCCGTGTCACGCTCATGGAT
GCCGAGGTCGGCAACTTCCGCGTCGGCTCGCGCATGGTCACCGAGTACGACGTCCCGGTGAACGGCGAGCTTTCCCAGGGCGGCGACGTTCCCTGGGCCGTCCTCGTCGAGTC
GGGCCAGTGCGACCTCATGCTTATCTCGTACATGGGCATTGACTTTCAGTGCAAGGGTGACCGCGTTTACCGCCTTCTCAACACGACCCTCACGTTCTACGGTGTCGCCCACGA
GGGCGAGACTCTCGTTTACGACATCCGCGTCACTGGTTTCGCCAAGGGCATGCACGGCGAGATTAGCATGTTCTTCTTCGAGTACGACTGCTACGTCAACGGCCGCCTGCTCAT
CGAGATGCGCGACGGTTGCGCTGGCTTCTTCACGGACGAGGAGCTCGCCGCGGGCAAGGGCGTCATCAAGACCGTCGCTGAGCTCCACAAGCGCAAGTCGATTGTGCCCAAG
TCGATCAAGCCTTTTGCCCTCAACCCCGCCGTCCACAAGACGATGTTCAGCGAGAACGACATGGAGAAGCTTTGCGAGCGCCAGTGGGAGAACGTCCTCGGCTCCGGCCTCCA
GGGCATCGACTACAAGCTGTGCGCCCGCAAGATGCTCATGATCGACCGCATCACGAAGATCCAGCACAACGGCGGTGCGTACGGCCTCGGCCTCCTCGTTGGCGAGAAGATTC
TTGAGCGCGACCATTGGTACTTCCCTTGCCACTTCGTCAAGGACCAGGTGATGGCGGGCTCCCTCGTTAGCGACGGCTGCTCGCAGCTGCTCAAGCTTTACATGCTTTGGCTCG
GCCTCCACGACGTGGTCCCCGATTTCCAGTTCCGTCCTGTCCCTGGCCAGCCCAACAAGGTGCGCTGCCGTGGCCAGATCAGCCCCCATCGTGGCAAGCTCGTGTACGTGATGG
AGATTCGCGAGATGGGTTTCAACGAGTCCACCGGCCAGCCCTACGCGATCGCTGACGTTGACATTATCGATGTGAACTACGAGCTCGGCCAGTCCTTTGACATGGCCGACATC
GACTCGTACGGCCGTGGCCAACCTCTCCAAGAAGATTGTCGTCGATTTCAAGGGCATTGCGCTCCAGATGGAGGGCACCGTCAAGAGCTCCAACATCATCGATTCGTCCCCCAA
GTCCACGATTATCCAGCCGCCGCCCAACTGCCTCCGCGGCGATCCTCTCGCCCCCTCGCAGGTCACCTGGCACCCGATGGCCGGTGTCAACGCGCCCCCGCCCCCTCCTTCAG
CCCGTCGGATTACCCTCCTCGTGCCGTTTGCTTTAAGCCCTTCCCTGGCAACCCCCTCGACAACGATCATACGCCGGGCAAGATGCCGCTGACCTGGTTTAACATGTCGGAGTT
TATGTGCGGCAAGGTCAGCAACTGCCTTGGCCCTGAGTTTAAGCGCTTCGACAACTCCAAGACGAGCCGCTCCCCGGCCTTCGACCTGGCCCTGGTTACGCGCGTGGTGTCGGT
CAGCGATATGGAGTTCAAGCCCCACCTCAACATCGACGTCAACCCGTCGAAGGGCACGATGATTGGCGAGTTCGACTGCCCCGCTGACGCCTGGTTCTTTCAGGGCTCCTGCA
ACGACGGCCACATGCCGTACAGCATCGTCATGGAGATCGCCCTTCAGACCAGCGGTGTCCTCACCTCCGTCCTCAAGGCCCCGCTCACTATGGACAAGGACGACATTCTCTTTC
GCAACCTCGACGCCACCGCCGAGATGGTCCGTTCCGACGTCGATTGCCGCGGTAAGACCATCAAGAACTTCACCCAGTGCACCGGCTACAGCATGCTTGGCAAGATGGGCATC
CACCGCTTCACTTTTGAGCTCTCGGTCGATGACGTCGTGTTTTACAAGGGCTCGACCAGCTTTGGTTGGTTCACGCCGGAGGTGTTTGAGTCGCAGGTCGGCCTCGATAACGGC
AAGAAGGTCCAGCCGTGGTATCTGGAGCAGAAGTCGTCGAACGTGGTGACGTACGATGTCGCCTCGACCGCCGGCAAGGACAAGCTCTTCTCGAAGATCGGCTCGAAGGACG
CTCAGGTCCAGCGTCGCAACACCCAGTGCGAGTTTCTCGACACGATGCACATTATTCCGAACACCGGCAAGTACAACAAGGGCTACGCGCACGGTGAGAAGAAGGTCAACCC
CAACGACTGGTTCTTCTCCTGCCACTTTTGGTTCGACCCGGTGATGCCCGGCTCCCTCGGTATTGAGTCCATGTTCCAGCTCATCGAGGCCTTTTCGATTGACCAGGGTATCGCG
TCCAAGCATGGCATCGTGAACCCTACCTTCGCGCACTCGAACGGCAAGACCTCGTGGAAGTACCGCGGCCAGCTCAACAACAAGGGCAAGCGCATGGACAGCGAGATTCACA
TCAAGGATATTGTCAAGAACGCCGACGGTACTGTCGATCTCATCGCCGATGGTTTTCTTCGTGGACTCGCTTCGCGTTTACAGCGCCGATGACCTCCGCGTCAAGATCGTCC
CCGGCACTAAGGCTGCTCCCAAGAGCGTCGCGGCCGCTCCGCGCCATGTGGCCACTCCGATCCCCGGCGTCCCCTCCAACACCTCCTCGGTGGAGATCTCGCTTGAGTCCCTTA
AGAAGGAGCTCCTCAACCTGGAGAAGCCCCTCTACCTTGAGACTTCCAACCACATCGTCAAGCAGTTCGGCGACGTTAACAACGGCCAGGCCTCCGTCATCCCTCCGTGCACC
ATTAACGATCTCGGTGAGCGCTCGTTTATGGAGACTTACAACGTCGTCGCTCCCCTCTACACCGGCGCGATGGCGAAGGGCATCGCTTCGGCGGACCTCGTCATCGCTGCCGGT
AAGCGCAAGATCCTCGGCAGCTTCGGCGCCGGTGGCCTCCCGATGCACCTCGTGCGCGCCTCGGTCGAGAAGATCCAGGCCGCCCTCCCGGAGGGCCCGTACGCGGTCAACCT
CATCCACTCGCCTTTCGACTCGAACCTTGAGAAGGGTAACGTGGACCTCTTTCTGGAGAAGGGCGTCCACGTGGTCGAGGCCTCCGCCTTTACCGCCCTCACGACCCAGGTCGT
TCGCTACCGCGCCTGCCGCCTCTCGCGTGCTAAGGACGGTTCCGTGCTGATTAAGAACCGCATCATCGGTAAGGTCAGCCGCACGGAGCTTGCCGAGATGTTCTTTCGCCCTGC
CCCCCAGAAACCTCCTCGATAAGCTCATCGCCAGCGGCGAGATCACCAAGGAGCAGGCGTCCCTCGCTCTTGAGGTTCCTATGGCCGACGATGTCGCTGTTGAGGCCGACTCCG
GCGGCCACACCGATAACCGTCCCATCCACGTCATCCTCCCGCTGATTATTAACCTCCGCAACCGTATCCACAAGGAGTGCGGCTTTCCTGCCGCTCTCCGCGTCCGCGTCGGCG
CTGGTGGTGGCCATCGGTTGCCCCTCGGCCGCTGTCGCCGCCTTCAACATGGGCGCGGCCTTCCTGATCACCGGCTCCGTTAACCAGGTGAGCAAGCAGTCCGGCACGTGCGAC
ATTGTGCGCAAGCAGCTTAGCGAGGCCAGCTACTCCGACATCACGATGGCTCCCGCCGCTGACATGTTCGACCAGGGCGTGGAGCTCCAGGTCCTCAAGAAGGGTACGATGTT
TCCCTCGCGCGCCAAGAAGCTCTACGAGCTCTTTTGCATGTACAACAGCTTTGACGACATGCCGAAGTCCGAGCTCCAGCGCCTGGAGAAGCGCATTTTCCAGAAGAGCCTCG
CCGAGGTCTGGGAGGAGACTAAGGACTTTTACATCAACCGCCTCAACAACCCGGAGAAGATCGAGCACGCCGAGAAGAAGGACCCCAAGCTCAAGATGTCCCTTTGCTTTCG
CTGGTATCTCGGCCTTTCGAGCTTTTGGGCCAACAACGGCATCAAGGAGCGCAGCATGGATTACCAGATTTGGTGCGGCCCGGCCATTGGCAGCTACAACGACTTCGTGAAGG
GCACCTACCTCGACCCCGCCGTCGCCGGTTCGTACCCCTGCGTGGTCCAGATCAACATGCAGATCCTCCGCGGTGCGTGCTTCCTCCAGCGCGTCCGCGCCATTAAGCACGACC
CGCGCCTCGATATCGACGTTGATGAGGACGTCTTTACCTACCGCCCCGAGAGCACCCTCTAA     (SEQ ID NO:122)

FIG. 21

MVGLQMKKKPVWEMSKEEQSSGKNVVFDYDELLEFAEGDIGKVFGPKFDIIDKYSRRVRLPAREYLLVTRVTLMDAEVGNFRVGSRMVTEYDVPVNGELSQGGDVPWAVLVESGQ
CDLMLISYMGIDFQCKGDRVYRLLNTTLTFYGVAHEGETLVYDIRVTGFAKGMHGEISMFFFEYDCYVNGRLLIEMRDGCAGFFTDEELAAGKGVIKTVAELHKRKSIVPKSIKPFAL
NPAVHKTMFSENDMEKLCERQWENVLGSGLQGIDYKLCARKMLMIDRITKIQHNGGAYGLGLLVGEKILERDHWYFPCHFVKDQVMAGSLVSDGCSQLLKLYMLWLGLHDVVPD
FQFRPVPGQPNKVRCRGQISPHRGKLVYVMEIREMGFNESTGQPYAIADVDIIDVNYELGQSFDMADIDSYGRGNLSKKIVVDFKGIALQMEGTVKSSNIIDSSPKSTIIQPPPNCLRGDP
LAPSQVTWHPMAGVNGAPAPSFSPSDYPPRAVCFKPFPGNPLDNDHTPGKMPLTWFNMSEFMCGKVSNCLGPEFKRFDNSKTSRSPAFDLALVTRVVSVSDMEFKPHLNIDVNPSKG
TMIGEFDCPADAWFFQGSCNDGHMPYSIVMEIALQTSGVLTSVLKAPLTMDKDDILFRNLDATAEMVRSDVDCRGKTIKNFTQCTGYSMLGKMGIHRFTFELSVDDVVFYKGSTSFG
WFTPEVFESQVGLDNGKKVQPWYLEQKSSNVVTYDVASTAGKDKLFSKIGSKDAQVQRRNTQCEFLDTMHIIPNTGKYNKGYAHGEKKVNPNDWFFSCHFWFDPVMPGSLGIESMF
QLIEAFSIDQGIASKHGIVNPTFAHSNGKTSWKYRGQLNNKGKRMDSEIHIKDIVKNADGTVDLIADGFLLVDSLRVYSADDLRVKIVPGTKAAPKSVAAAPRHVATPIPGVPSNTSSV
EISLESLKKELLNLEKPLYLETSNHIVKQFGDVNNGQASVIPPCTINDLGERSFMETYNVVAPLYTGAMAKGIASADLVIAAGKRKILGSFGAGGLPMHLVRASVEKIQAALPEGPYAV
NLIHSPFDSNLEKGNVDLFLEKGVHVVEASAFTALTTQVVRYRACGLSRAKDGSVLIKNRIIGKVSRTELAEMFFRPAPQNLLDKLIASGEITKEQASLALEVPMADDVAVEADSGGHT
DNRPIHVILPLIINLRNRIHKECGFPAALRVRVGAGGGIGCPSAAVAAFNMGAAFLITGSVNQVSKQSGTCDIVRKQLSEASYSDITMAPAADMFDQGVELQVLKKGTMFPSRAKKLYE
LFCMYNSFDDMPKSELQRLEKRIFQKSLAEVWEETKDFYINRLNNPEKIEHAEKKDPKLKMSLCFRWYLGLSSFWANNGIKERSMDYQIWCGPAIGSYNDFVKGTYLDPAVAGSYPC
VVQINMQILRGACFLQRVRAIKHDPRLDIDVDEDVFTYRPESTL (SEQ ID NO:73)

FIG.22

*Schizochytrium* Codon Usage

| AA* | Codon | Fraction | AA* | Codon | Fraction | AA* | Codon | Fraction | AA* | Codon | Fraction |
|---|---|---|---|---|---|---|---|---|---|---|---|
| Ala | GCC | 0.64 | End | TAA | 0.34 | Leu | CTT | 0.16 | Ser | TCG | 0.33 |
| Ala | GCA | 0.03 | End | TGA | 0.33 | Leu | TTG | 0.02 | Ser | TCC | 0.31 |
| Ala | GCT | 0.18 | End | TAG | 0.33 | Leu | CTG | 0.12 | Ser | AGT | 0.03 |
| Ala | GCG | 0.16 | Gln | CAA | 0.08 | Leu | CTC | 0.69 | Ser | TCA | 0 |
| Arg | CGG | 0.01 | Gln | CAG | 0.92 | Leu | TTA | 0 | Ser | TCT | 0.09 |
| Arg | AGA | 0 | Glu | GAA | 0.09 | Leu | CTA | 0 | Thr | ACG | 0.3 |
| Arg | CGC | 0.8 | Glu | GAG | 0.91 | Lys | AAA | 0.04 | Thr | ACC | 0.54 |
| Arg | CGA | 0.01 | Gly | GGA | 0.1 | Lys | AAG | 0.96 | Thr | ACA | 0.02 |
| Arg | AGG | 0 | Gly | GGT | 0.2 | Met | ATG | 1 | Thr | ACT | 0.14 |
| Arg | CGT | 0.17 | Gly | GGG | 0 | Phe | TTT | 0.45 | Trp | TGG | 1 |
| Asn | AAC | 0.94 | Gly | GGC | 0.7 | Phe | TTC | 0.55 | Tyr | TAC | 0.94 |
| Asn | AAT | 0.06 | His | CAC | 0.83 | Pro | CCT | 0.21 | Tyr | TAT | 0.06 |
| Asp | GAT | 0.24 | His | CAT | 0.17 | Pro | CCG | 0.34 | Val | GTC | 0.62 |
| Asp | GAC | 0.76 | Ile | ATC | 0.7 | Pro | CCC | 0.43 | Val | GTA | 0 |
| Cys | TGC | 0.95 | Ile | ATA | 0 | Pro | CCA | 0.02 | Val | GTT | 0.14 |
| Cys | TGT | 0.05 | Ile | ATT | 0.3 | Ser | AGC | 0.24 | Val | GTG | 0.24 |

* AA=Amino Acid

POLYUNSATURATED FATTY ACID SYNTHASE NUCLEIC ACID MOLECULES AND POLYPEPTIDES, COMPOSITIONS, AND METHODS OF MAKING AND USES THEREOF

CROSS-REFERENCE TO RELATED APPLICATION

This application is a divisional of U.S. application Ser. No. 15/371,410, filed Dec. 7, 2016, which is a divisional application of U.S. application Ser. No. 14/566,458, filed on Dec. 10, 2014 and now issued as U.S. Pat. No. 9,540,666B2, which is a divisional application of U.S. application Ser. No. 12/727,851, filed Mar. 19, 2010 and now issued as U.S. Pat. No. 8,940,884B2, which application claims the benefit of the filing date of U.S. Appl. No. 61/161,742, filed Mar. 19, 2009, and U.S. Appl. No. 61/296,460, filed Jan. 19, 2010, which are hereby incorporated by reference in their entireties for all purposes. A copy of the sequence listing which contains all the sequences mentioned in this application was filed with the present application on the filing date of Dec. 2, 2019 is hereby incorporated by reference in its entirety.

REFERENCE TO A SEQUENCE LISTING SUBMITTED ELECTRONICALLY

The content of the electronically submitted sequence listing ("sequence listing.txt", 507,769 bytes, created on Mar. 12, 2010) filed with the application is incorporated herein by reference in its entirety.

BACKGROUND OF THE INVENTION

Field of the Invention

The present invention is directed to isolated nucleic acid molecules and polypeptides of polyunsaturated fatty acid (PUPA) synthases involved in the production of PUFAs, including PUFAs enriched in docosahexaenoic acid (DHA), eicosapentaenoic acid (EPA), or a combination thereof. The present invention is directed to vectors and host cells comprising the nucleic acid molecules, polypeptides encoded by the nucleic acid molecules, compositions comprising the nucleic acid molecules or polypeptides, and methods of making and uses thereof.

Background of the Invention

Thraustochytrids are microorganisms of the order Thraustochytriales, including members of the genus *Thraustochytrium* and the genus *Schizochytrium*, and have been recognized as an alternative source of PUFAs. See, e.g., U.S. Pat. No. 5,130,242. It has recently been shown that polyketide synthase (PKS)-like systems in marine bacteria and thraustochytrids are capable of synthesizing polyunsaturated fatty acids (PUFAs) from acetyl-CoA and malonyl-CoA. These PKS synthase-like systems are also refelTed to herein as PUPA synthase systems. PUPA synthase systems in the marine bacteria *Shewanella* and *Vibrio marinus* are described in U.S. Pat. No. 6,140,486. A PUPA synthase system in a thraustochytrid of the genus *Schizochytrium* is described in U.S. Pat. No. 6,566,583. PUPA synthase systems in thraustochytrids of the genus *Schizochytrium* and the genus *Thraustochytrium* are also described in U.S. Pat. No. 7,247,461. U.S. Pat. No. 7,211,418 describes a PUPA synthase system in a thraustochytrid of the genus *Thraustochytrium* and the production of eicosapentaenoic acid (C20:5, omega-3) (EPA) and other PUFAs using the system. U.S. Pat. No. 7,217,856 describes PUPA synthase systems in *Shewanella olleyana* and *Shewanella japonica*. WO 2005/097982 describes a PUPA synthase system in strain SAM2179. U.S. Pat. Nos. 7,208,590 and 7,368,552 describe PUPA synthase genes and proteins from *Thraustochytrium aureum*.

PKS systems have been traditionally described in the literature as falling into one of three basic types, typically referred to as Type I (modular or iterative), Type II, and Type III. The Type I modular PKS system has also been referred to as a "modular" PKS system, and the Type I iterative PKS system has also been referred to as a "Type I" PKS system. The Type II system is characterized by separable proteins, each of which carries out a distinct enzymatic reaction. The enzymes work in concert to produce the end product and each individual enzyme of the system typically participates several times in the production of the end product. This type of system operates in a manner analogous to the fatty acid synthase (FAS) systems found in plants and bacteria. Type I iterative PKS systems are similar to the Type II system in that the enzymes are used in an iterative fashion to produce the end product. The Type I iterative system differs from the Type II system in that enzymatic activities, instead of being associated with separable proteins, occur as domains of larger proteins. This system is analogous to the Type I FAS systems found in animals and fungi.

In contrast to the Type II systems, each enzyme domain in the Type I modular PKS systems is used only once in the production of the end product. The domains are found in very large proteins and the product of each reaction is passed on to another domain in the PKS protein.

Type III systems have been more recently discovered and belong to the plant chalcone synthase family of condensing enzymes. Type III PKSs are distinct from Type I and Type II PKS systems and utilize free CoA substrates in iterative condensation reactions to usually produce a heterocyclic end product.

In the conventional or standard pathway for PUPA synthesis, medium chain-length saturated fatty acids (products of a fatty acid synthase (FAS) system) are modified by a series of elongation and desaturation reactions. The substrates for the elongation reaction are fatty acyl-CoA (the fatty acid chain to be elongated) and malonyl-CoA (the source of the two carbons added dming each elongation reaction). The product of the elongase reaction is a fatty acyl-CoA that has two additional carbons in the linear chain. The desaturases create cis double bonds in the preexisting fatty acid chain by extraction of two hydrogens in an oxygen-dependent reaction. The substrates for the desaturases are either acyl-CoA (in some animals) or the fatty acid that is esterified to the glycerol backbone of a phospholipid (e.g., phosphatidylcholine).

Fatty acids are classified based on the length and saturation characteristics of the carbon chain. Fatty acids are termed short chain, medium chain, or long chain fatty acids based on the number of carbons present in the chain, are termed saturated fatty acids when no double bonds are present between the carbon atoms, and are termed unsaturated fatty acids when double bonds are present. Unsaturated long chain fatty acids are monounsaturated when only one double bond is present and are polyunsaturated when more than one double bond is present.

PUFAs are classified based on the position of the first double bond from the methyl end of the fatty acid: omega-3 (n-3) fatty acids contain a first double bond at the third carbon, while omega-6 (n-6) fatty acids contain a first double bond at the sixth carbon. For example, docosahexaenoic acid ("DHA") is an omega-3 PUFA with a chain length of 22 carbons and 6 double bonds, often designated as "22:6 n-3." Other omega-3 PUFAs include eicosapentaenoic acid ("EPA"), designated as "20:5 n-3," and omega-3 docosapentaenoic acid ("DPA n-3"), designated as "22:5 n-3." DHA and EPA have been termed "essential" fatty acids. Omega-6 PUFAs include arachidonic acid ("ARA"), designated as "20:4 n-6," and omega-6 docosapentaenoic acid ("DPA n-6"), designated as "22:5 n-6."

Omega-3 fatty acids are biologically important molecules that affect cellular physiology due to their presence in cell membranes, regulate production and gene expression of biologically active compounds, and serve as biosynthetic substrates. Roche, H. M., *Proc. Nutr. Soc.* 58: 397-401 (1999). DHA, for example, accounts for approximately 15%-20% of lipids in the human cerebral cortex, and 30%-60% of lipids in the retina, is concentrated in the testes and sperm, and is an important component of breast milk. Berge, J. P., and Barnathan, G. *Adv. Biochem. Eng. Biotechnol.* 96:49-125 (2005). DHA accounts for up to 97% of the omega-3 fatty acids in the brain and up to 93% of the omega-3 fatty acids in the retina. Moreover, DHA is essential for both fetal and infant development, as well as maintenance of cognitive functions in adults. Id. Because omega-3 fatty acids are not synthesized de nova in the human body, these fatty acids must be derived from nutritional sources.

Flaxseed oil and fish oils are considered good dietary sources of omega-3 fatty acids. Flaxseed oil contains no EPA, DHA, DPA, or ARA but rather contains linolenic acid (C18:3 n-3), a building block enabling the body to manufacture EPA. There is evidence, however, that the rate of metabolic conversion can be slow and variable, particularly among those with impaired health. Fish oils vary considerably in the type and level of fatty acid composition depending on the particular species and their diets. For example, fish raised by aquaculture tend to have a lower level of omega-3 fatty acids than those in the wild. Furthermore, fish oils carry the risk of containing environmental contaminants and can be associated with stability problems and a fishy odor or taste.

Oils produced from thraustochytlids often have simpler polyunsaturated fatty acid profiles than corresponding fish or microalgal oils. Lewis, T. E., *Mar. Biotechnol.* 1: 580-587 (1999). Strains of thraustrochytlid species have been reported to produce omega-3 fatty acids as a high percentage of the total fatty acids produced by the organisms. U.S. Pat. No. 5,130,242; Huang, J. et al., *J. Am. Oil. Chem. Soc.* 78: 605-610 (2001); Huang, J. et al., *Mar. Biotechnol.* 5: 450-457 (2003). However, isolated thraustochytrids vary in the identity and amounts of PUFAs produced, such that some previously described strains can have undesirable PUFA profiles.

Efforts have been made to produce PUFAs in oil-seed crop plants by modification of the endogenously-produced fatty acids. Genetic modification of these plants with various individual genes for fatty acid elongases and desaturases has produced leaves or seeds containing measurable levels of PUFAs such as EPA, but also containing significant levels of mixed shorter-chain and less unsaturated PUFAs (Qi et al., *Nature Biotech.* 22:739 (2004); PCT Publ. No. WO 04/071467; Abbadi et al., *Plant Cell* 16:1 (2004)); Napier and Sayanova, *Proc. Nutrition Society* 64:387-393 (2005); Robert et al., *Functional Plant Biology* 32:473-479 (2005); and U.S. Appl. Publ. No. 2004/0172682).

As such, a continuing need exists for the isolation of nucleic acid molecules and polypeptides associated with desirable PUFA profiles and methods to produce desirable PUFA profiles through use of such nucleic acid molecules and polypeptides.

BRIEF SUMMARY OF THE INVENTION

The present invention is directed to an isolated nucleic acid molecule selected from the group consisting of: (a) a nucleic acid molecule comprising a polynucleotide sequence at least 80% identical to SEQ ID NO:1, wherein the polynucleotide sequence encodes a polypeptide comprising PUFA synthase activity selected from the group consisting of beta-ketoacyl-ACP synthase (KS) activity, malonyl-CoA: ACP acyltransferase (MAT) activity, acyl carrier protein (ACP) activity, ketoreductase (KR) activity, beta-hydroxyacyl-ACP dehydrase (DH) activity, and combinations thereof; (b) a nucleic acid molecule comprising a polynucleotide sequence at least 80% identical to SEQ ID NO:7, wherein the polynucleotide sequence encodes a polypeptide comprising KS activity; (c) a nucleic acid molecule comprising a polynucleotide sequence at least 80% identical to SEQ ID NO:9, wherein the polynucleotide sequence encodes a polypeptide comprising MAT activity; (d) a nucleic acid molecule comprising a polynucleotide sequence at least 80% identical to any one of SEQ ID NOs:13, 15, 17, 19, 21, or 23, wherein the polynucleotide sequence encodes a polypeptide comprising ACP activity; (e) a nucleic acid molecule comprising a polynucleotide sequence at least 80% identical to SEQ ID NO:11, wherein the polynucleotide sequence encodes a polypeptide comprising ACP activity; (f) a nucleic acid molecule comprising a polynucleotide sequence at least 80% identical to SEQ ID NO:25, wherein the polynucleotide sequence encodes a polypeptide comprising KR activity; and (g) a nucleic acid molecule comprising a polynucleotide sequence at least 80% identical to SEQ ID NO:27, wherein the polynucleotide sequence encodes a polypeptide comprising DH activity. In some embodiments, the polynucleotide sequences are at least 90% identical or at least 95% identical to SEQ ID NOs:1, 7, 9, 11, 13, 15, 17, 19, 21, 23, 25, and 27, respectively. In some embodiments, the nucleic acid molecules comprise the polynucleotide sequences of SEQ ID NOs:1, 7, 9, 11, 13, 15, 17, 19, 21, 23, 25, and 27, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:2, and wherein the polypeptide comprises a PUFA synthase activity selected from the group consisting of KS activity, MAT activity, ACP activity, KR activity, DH activity, and combinations thereof; (b) a nucleic acid molecule comprising a polynucleotide sequence encoding a polypeptide, wherein the polypeptide comprises an amino acid sequence at least 80% identical to SEQ ID NO:8, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:10, and wherein the polypeptide comprises MAT activity; (d) a nucleic acid molecule comprising a polynucleotide sequence encoding a polypeptide, wherein the polypeptide comprises an amino acid sequence at least 80% identical to any one of SEQ ID NOs:14, 16, 18, 20, 22, or 24, and wherein the polypeptide comprises ACP activity; (e) a nucleic acid molecule comprising a polynucleotide sequence encoding a polypeptide, wherein the polypeptide comprises an amino acid sequence at least 80% identical to SEQ ID NO:12, and wherein the polypeptide comprises ACP activity; (f) a nucleic acid molecule comprising a polynucleotide sequence encoding a polypeptide, wherein the polypeptide comprises an amino acid sequence at least 80% identical to SEQ ID NO:26, and wherein the polypeptide comprises KR activity; and (g) a nucleic acid molecule comprising a polynucleotide sequence encoding a polypeptide, wherein the polypeptide comprises an amino acid sequence at least 80% identical to SEQ ID NO:28, and wherein the polypeptide comprises DH activity. In some embodiments, the amino acid sequences are at least 90% identical or at least 95% identical to SEQ ID NOs:2, 8, 10, 12, 14, 16, 18, 20, 22, 24, 26, and 28, respectively. In some embodiments, the polypeptides comprise the amino acid sequences of SEQ ID NOs:2, 8, 10, 12, 14, 16, 18, 20, 22, 24, 26, and 28, respectively.

The present invention is directed to an isolated nucleic acid molecule selected from the group consisting of: (a) a nucleic acid molecule comprising a polynucleotide sequence at least 80% identical to SEQ ID NO:3, wherein the polynucleotide sequence encodes a polypeptide comprising PUFA synthase activity selected from the group consisting of KS activity, chain length factor (CLP) activity, acyltransferase (AT) activity, enoyl-ACP reductase (ER) activity, and combinations thereof; (b) a nucleic acid molecule comprising a polynucleotide sequence at least 80% identical to SEQ ID NO:29, wherein the polynucleotide sequence encodes a polypeptide comprising KS activity; (c) a nucleic acid molecule comprising a polynucleotide sequence at least 80% identical to SEQ ID NO:31, wherein the polynucleotide sequence encodes a polypeptide comprising CLP activity; (d) a nucleic acid molecule comprising a polynucleotide sequence at least 80% identical to SEQ ID NO:33, wherein the polynucleotide sequence encodes a polypeptide comprising AT activity; and (e) a nucleic acid molecule comprising a polynucleotide sequence at least 80% identical to SEQ ID NO:35, wherein the polynucleotide sequence encodes a polypeptide comprising ER activity. In some embodiments, the polynucleotide sequences are at least 90% identical or at least 95% identical to SEQ ID NOs:3, 29, 31, 33, and 35, respectively. In some embodiments, the nucleic acid molecules comprise the polynucleotide sequences of SEQ ID NOs:3, 29, 31, 33, and 35, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:4, and wherein the polypeptide comprises a PUPA synthase activity selected from the group consisting of KS activity, CLP activity, AT activity, ER activity, and combinations thereof; (b) a nucleic acid molecule comprising a polynucleotide sequence encoding a polypeptide, wherein the polypeptide comprises an amino acid sequence at least 80% identical to SEQ ID NO:30, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:32, and wherein the polypeptide comprises CLP activity; (d) a nucleic acid molecule comprising a polynucleotide sequence encoding a polypeptide, wherein the polypeptide comprises an amino acid sequence at least 80% identical to SEQ ID NO:34, and wherein the polypeptide comprises AT activity; and (e) a nucleic acid molecule comprising a polynucleotide sequence encoding a polypeptide, wherein the polypeptide comprises an amino acid sequence at least 80% identical to SEQ ID NO:36, and wherein the polypeptide comprises ER activity. In some embodiments, the amino acid sequences are at least 90% identical or at least 95% identical to SEQ ID NOs:4, 30, 32, 34, and 36, respectively. In some embodiments, the polypeptides comprise the amino acid sequence of SEQ ID NOs:4, 30, 32, 34, and 36, respectively.

The present invention is directed to an isolated nucleic acid molecule selected from the group consisting of: (a) an nucleic acid molecule comprising a polynucleotide sequence at least 80% identical to SEQ ID NO:5, wherein the polynucleotide sequence encodes a polypeptide comprising PUPA synthase activity selected from the group consisting of DH activity, ER activity, and combinations thereof; (b) a nucleic acid molecule comprising a polynucleotide sequence at least 80% identical to SEQ ID NO:37, wherein the polynucleotide sequence encodes a polypeptide comprising DH activity; (c) a nucleic acid molecule comprising a polynucleotide sequence at least 80% identical to SEQ ID NO:39, wherein the polynucleotide sequence encodes a polypeptide comprising DH activity; and (d) a nucleic acid molecule comprising a polynucleotide sequence at least 80% identical to SEQ ID NO:41, wherein the polynucleotide sequence encodes a polypeptide comprising ER activity. In some embodiments, the polynucleotide sequences are at least 90% identical or at least 95% identical to SEQ ID NOs:5, 37, 39, and 41, respectively. In some embodiments, the nucleic acid molecules comprise the polynucleotide sequences of SEQ ID NOs:5, 37, 39, and 41, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:6, wherein the polypeptide comprises PUPA synthase activity selected from the group consisting of DH activity, ER activity, and combinations thereof; (b) a nucleic acid molecule comprising a polynucleotide sequence encoding a polypeptide, wherein the polypeptide comprises an amino acid sequence at least 80% identical to SEQ ID NO:38, and wherein the polypeptide comprises DH activity; (c) a nucleic acid molecule comprising a polynucleotide sequence encoding a polypeptide, wherein the polypeptide comprises an amino acid sequence at least 80% identical to SEQ ID NO:40, and wherein the polypeptide comprises DH activity; and (d) a nucleic acid molecule comprising a polynucleotide sequence encoding a polypeptide, wherein the polypeptide comprises an amino acid sequence at least 80% identical to SEQ ID NO:42, and wherein the polypeptide comprises ER activity. In some embodiments, the amino acid sequences are at least 90% identical or at least 95% identical to SEQ ID NOs:6, 38, 40, and 42, respectively. In some embodiments, the polypeptides comprise the amino acid sequences of SEQ ID NOs:6, 38, 40, and 42, respectively.

The present invention is directed to an isolated nucleic acid molecule selected from the group consisting of: (a) a nucleic acid molecule comprising a polynucleotide sequence at least 80% identical to SEQ ID NO:68 or SEQ ID NO:120, wherein the polynucleotide sequence encodes a polypeptide comprising PUPA synthase activity selected from the group consisting of KS activity, MAT activity, ACP activity, KR activity, DH activity, and combinations thereof; (b) a nucleic acid molecule comprising a polynucleotide sequence at least 80% identical to SEQ ID NO:74, wherein the polynucleotide sequence encodes a polypeptide comprising KS activity; (c)

a nucleic acid molecule comprising a polynucleotide sequence at least 80% identical to SEQ ID NO:76, wherein the polynucleotide sequence encodes a polypeptide comprising MAT activity; (d) a nucleic acid molecule comprising a polynucleotide sequence at least 80% identical to any one of SEQ ID NOs: 80, 82, 84, 86, 88, 90, 92, 94, 96, or 98, wherein the polynucleotide sequence encodes a polypeptide comprising ACP activity; (e) a nucleic acid molecule comprising a polynucleotide sequence at least 80% identical to SEQ ID NO:78, wherein the polynucleotide sequence encodes a polypeptide comprising ACP activity; (f) a nucleic acid molecule comprising a polynucleotide sequence at least 80% identical to SEQ ID NO:100, wherein the polynucleotide sequence encodes a polypeptide comprising KR activity; and (g) a nucleic acid molecule comprising a polynucleotide sequence at least 80% identical to SEQ ID NO:118, wherein the polynucleotide sequence encodes a polypeptide comprising DH activity. In some embodiments, the polynucleotide sequences are at least 90% identical or at least 95% identical to SEQ ID NOs:68, 74, 76, 78, 80, 82, 84, 86, 88, 90, 92, 94, 96, 98, 100, 118, and 120, respectively. In some embodiments, the nucleic acid molecules comprise the polynucleotide sequences of SEQ ID NOs:68, 74, 76, 78, 80, 82, 84, 86, 88, 90, 92, 94, 96, 98, 100, 118, and 120, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:69, and wherein the polypeptide comprises a PUPA synthase activity selected from the group consisting of KS activity, MAT activity, ACP activity, KR activity, DH activity, and combinations thereof; (b) a nucleic acid molecule comprising a polynucleotide sequence encoding a polypeptide, wherein the polypeptide comprises an amino acid sequence at least 80% identical to SEQ ID NO:75, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:77, and wherein the polypeptide comprises MAT activity; (d) a nucleic acid molecule comprising a polynucleotide sequence encoding a polypeptide, wherein the polypeptide comprises an amino acid sequence at least 80% identical to any one of SEQ ID NOs:81, 83, 85, 87, 89, 91, 93, 95, 97, or 99, and wherein the polypeptide comprises ACP activity; (e) a nucleic acid molecule comprising a polynucleotide sequence encoding a polypeptide, wherein the polypeptide comprises an amino acid sequence at least 80% identical to SEQ ID NO:79, and wherein the polypeptide comprises ACP activity; (f) a nucleic acid molecule comprising a polynucleotide sequence encoding a polypeptide, wherein the polypeptide comprises an amino acid sequence at least 80% identical to SEQ ID NO:101, and wherein the polypeptide comprises KR activity; and (g) a nucleic acid molecule comprising a polynucleotide sequence encoding a polypeptide, wherein the polypeptide comprises an amino acid sequence at least 80% identical to SEQ ID NO:119, and wherein the polypeptide comprises DH activity. In some embodiments, the amino acid sequences are at least 90% identical or at least 95% identical to SEQ ID NOs:69, 75, 77, 79, 81, 83, 85, 87, 89, 91, 93, 95, 97, 99, 101, and 119, respectively. In some embodiments, the polypeptides comprise the amino acid sequences of SEQ ID NOs:69, 75, 77, 79, 81, 83, 85, 87, 89, 91, 93, 95, 97, 99, 101, and 119, respectively.

The present invention is directed to an isolated nucleic acid molecule selected from the group consisting of: (a) a nucleic acid molecule comprising a polynucleotide sequence at least 80% identical to SEQ ID NO:70 or SEQ ID NO:121, wherein the polynucleotide sequence encodes a polypeptide comprising PUPA synthase activity selected from the group consisting of KS activity, chain length factor (CLP) activity, acyltransferase (AT) activity, enoyl-ACP reductase (ER) activity, and combinations thereof; (b) a nucleic acid molecule comprising a polynucleotide sequence at least 80% identical to SEQ ID NO:102, wherein the polynucleotide sequence encodes a polypeptide comprising KS activity; (c) a nucleic acid molecule comprising a polynucleotide sequence at least 80% identical to SEQ ID NO:104, wherein the polynucleotide sequence encodes a polypeptide comprising CLP activity; (d) a nucleic acid molecule comprising a polynucleotide sequence at least 80% identical to SEQ ID NO:106, wherein the polynucleotide sequence encodes a polypeptide comprising AT activity; and (e) a nucleic acid molecule comprising a polynucleotide sequence at least 80% identical to SEQ ID NO:108, wherein the polynucleotide sequence encodes a polypeptide comprising ER activity. In some embodiments, the polynucleotide sequences are at least 90% identical or at least 95% identical to SEQ ID NOs:70, 102, 104, 106, 108, and 121, respectively. In some embodiments, the nucleic acid molecules comprise the polynucleotide sequences of SEQ ID NOs:70, 102, 104, 106, 108, and 121, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:71, and wherein the polypeptide comprises a PUPA synthase activity selected from the group consisting of KS activity, CLP activity, AT activity, ER activity, and combinations thereof; (b) a nucleic acid molecule comprising a polynucleotide sequence encoding a polypeptide, wherein the polypeptide comprises an amino acid sequence at least 80% identical to SEQ ID NO:103, and wherein the polypeptide comprises KS activity; (c) a nucleic acid molecule comprising a polynucleotide sequence encoding a polypeptide, wherein the polypeptide comprises an amino acid sequence at least 80% identical to SEQ ID NO:105, and wherein the polypeptide comprises CLP activity; (d) a nucleic acid molecule comprising a polynucleotide sequence encoding a polypeptide, wherein the polypeptide comprises an amino acid sequence at least 80% identical to SEQ ID NO:107, and wherein the polypeptide comprises AT activity; and (e) a nucleic acid molecule comprising a polynucleotide sequence encoding a polypeptide, wherein the polypeptide comprises an amino acid sequence at least 80% identical to SEQ ID NO:109, and wherein the polypeptide comprises ER activity. In some embodiments, the amino acid sequences are at least 90% identical or at least 95% identical to SEQ ID NOs:71, 103, 105, 107, and 109, respectively. In some embodiments, the polypeptides comprise the amino acid sequence of SEQ ID NOs:71, 103, 105, 107, and 109, respectively.

The present invention is directed to an isolated nucleic acid molecule selected from the group consisting of: (a) an nucleic acid molecule comprising a polynucleotide sequence at least 80% identical to SEQ ID NO:72 or SEQ ID NO:122, wherein the polynucleotide sequence encodes a polypeptide comprising PUPA synthase activity selected from the group consisting of DH activity, ER activity, and combinations thereof; (b) a nucleic acid molecule comprising a polynucleotide sequence at least 80% identical to SEQ ID NO:110, wherein the polynucleotide sequence encodes a polypeptide comprising DH activity; (c) a nucleic acid molecule comprising a polynucleotide sequence at least 80% identical to SEQ ID NO:112, wherein the polynucleotide sequence encodes a polypeptide comprising DH activity; and (d) a nucleic acid molecule comprising a polynucleotide sequence at least 80% identical to SEQ ID NO:114, wherein the polynucleotide sequence encodes a polypeptide comprising ER activity. In some embodiments, the polynucleotide sequences are at least 90% identical or at least 95% identical to SEQ ID NOs:72, 110, 112, 114, and 122, respectively. In some embodiments, the nucleic acid molecules comprise the polynucleotide sequences of SEQ ID NOs:72, 110, 112, 114, and 122, respectively.

The present invention is directed to an isolated nucleic acid molecule selected from the group consisting of: (a) a nucleic acid molecule comprising a polynucleotide sequence encoding a polypeptide, wherein the polypeptide comprises an amino acid sequence at least 80% identical to SEQ ID NO:73, wherein the polypeptide comprises PUPA synthase activity selected from the group consisting of DH activity, ER activity, and combinations thereof; (b) a nucleic acid molecule comprising a polynucleotide sequence encoding a polypeptide, wherein the polypeptide comprises an amino acid sequence at least 80% identical to SEQ ID NO:111, and wherein the polypeptide comprises DH activity; (c) a nucleic acid molecule comprising a polynucleotide sequence encoding a polypeptide, wherein the polypeptide comprises an amino acid sequence at least 80% identical to SEQ ID NO:113, and wherein the polypeptide comprises DH activity; and (d) a nucleic acid molecule comprising a polynucleotide sequence encoding a polypeptide, wherein the polypeptide comprises an amino acid sequence at least 80% identical to SEQ ID NO:115, and wherein the polypeptide comprises ER activity. In some embodiments, the amino acid sequences are at least 90% identical or at least 95% identical to SEQ ID NOs:73, 111, 113, and 115, respectively. In some embodiments, the polypeptides comprise the amino acid sequences of SEQ ID NOs:73, 111, 113, and 115, respectively.

The present invention is directed to an isolated nucleic acid molecule comprising a polynucleotide sequence encoding a polypeptide comprising PUFA synthase activity selected from the group consisting of KS activity, MAT activity, ACP activity, KR activity, CLF activity, AT activity, ER activity, DH activity, and combinations thereof, wherein the polynucleotide hybridizes under stringent conditions to the complement of any of the polynucleotide sequences described above.

The present invention is directed to an isolated nucleic acid molecule comprising a polynucleotide sequence that is fully complementary to any of the polynucleotide sequences described above.

The present invention is directed to a recombinant nucleic acid molecule comprising any of the nucleic acid molecules described above or combinations thereof and a transcription control sequence. In some embodiments, the recombinant nucleic acid molecule is a recombinant vector.

The present invention is directed to a host cell that expresses any of the nucleic acid molecules described above, any of the recombinant nucleic acid molecules described above, and combinations thereof. In some embodiments, the host cell is selected from the group consisting of a plant cell, a microbial cell, and an animal cell. In some embodiments, the microbial cell is a bacterium. In some embodiments, the bacterium is E. coli. In some embodiments, the bacterium is a marine bacterium. In some embodiments, the microbial cell is a thraustochytrid. In some embodiments, the thraustochytrid is a Schizochytrium. In some embodiments, the thraustochytrid is a Thraustochytrium. In some embodiments, the thraustochytrid is an Ulkenia.

The present invention is directed to a method to produce at least one PUFA, comprising: expressing a PUFA synthase gene in a host cell under conditions effective to produce PUFA, wherein the PUFA synthase gene comprises any of the isolated nucleic acid molecules described above, any of the recombinant nucleic acid molecules described above, or combinations thereof, and wherein at least one PUFA is produced. In one aspect of this embodiment, the host cell is selected from the group consisting of a plant cell, an isolated animal cell, and a microbial cell. In another aspect of this embodiment, the at least one PUPA comprises docosahexaenoic acid (DHA) or eicosapentaenoic acid (EPA).

The present invention is directed to a method to produce lipids enriched for DHA, EPA, or a combination thereof, comprising: expressing a PUPA synthase gene in a host cell under conditions effective to produce lipids, wherein the PUPA synthase gene comprises any of the isolated nucleic acid molecules described above, any of the recombinant nucleic acid molecules described above, or combinations thereof in the host cell, and wherein lipids enriched with DHA, EPA, or a combination thereof are produced. The present invention is directed to a method for making a recombinant vector comprising inserting any one of the isolated nucleic acid molecules described above into a vector.

The present invention is directed to a method of making a recombinant host cell comprising introducing a recombinant vector as described above into a host cell. In some embodiments, the host cell is selected from the group consisting of a plant cell, an isolated animal cell, and a microbial cell.

The present invention is directed to an isolated polypeptide encoded by any of the polynucleotide sequences described above.

The present invention is directed to an isolated polypeptide selected from the group consisting of: (a) a polypeptide comprising an amino acid sequence at least 80% identical to SEQ ID NO:2, wherein the polypeptide comprises a PUPA synthase activity selected from the group consisting of KS activity, MAT activity, ACP activity, KR activity, DH activity, and combinations thereof; (b) a polypeptide comprising an amino acid sequence at least 80% identical to SEQ ID NO:8, wherein the polypeptide comprises KS activity; (c) a polypeptide comprising an amino acid sequence at least 80% identical to SEQ ID NO:10, wherein the polypeptide comprises MAT activity; (d) a polypeptide comprising an amino acid sequence at least 80% identical to any one of SEQ ID NOs:14, 16, 18, 20, 22, or 24, wherein the polypeptide comprises ACP activity; (e) a polypeptide comprising an amino acid sequence at least 80% identical to SEQ ID NO:12, wherein the polypeptide comprises ACP activity; (f) a polypeptide comprising an amino acid sequence at least 80% identical to SEQ ID NO:26, wherein the polypeptide comprises KR activity; and (g) a polypeptide comprising an amino acid sequence at least 80% identical to SEQ ID NO:28, wherein the polypeptide comprises DH activity. In some embodiments, the amino acid sequences are at least 90% identical or at least 95% identical to SEQ ID NOs:2, 8, 10, 12, 14, 16, 18, 20, 22, 24, 26, and 28, respectively. In some embodiments, the polypeptides comprise the amino acid sequences of SEQ ID NOs:2, 8, 10, 12, 14, 16, 18, 20, 22, 24, 26, and 28, respectively.

The present invention is directed to an isolated polypeptide selected from the group consisting of: (a) a polypeptide comprising an amino acid sequence at least 80% identical to SEQ ID NO:4, wherein the polypeptide comprises a PUPA synthase activity selected from the group consisting of KS activity, CLP activity, AT activity, ER activity, and combinations thereof; (b) a polypeptide comprising an amino acid sequence at least 80% identical to SEQ ID NO:30, wherein the polypeptide comprises KS activity; (c) a polypeptide comprising an amino acid sequence at least 80% identical to SEQ ID NO:32, wherein the polypeptide comprises CLP activity; (d) a polypeptide comprising an amino acid sequence at least 80% identical to SEQ ID NO:34, wherein the polypeptide comprises AT activity; and (e) a polypeptide comprising an amino acid sequence at least 80% identical to SEQ ID NO:36, wherein the polypeptide comprises ER activity. In some embodiments, the amino acid sequences are at least 90% identical or at least 95% identical to SEQ ID NOs:4, 30, 32, 34, and 36, respectively. In some embodiments, the polypeptides comprise the amino acid sequence of SEQ ID NOs:4, 30, 32, 34, and 36, respectively.

The present invention is directed to an isolated polypeptide selected from the group consisting of: (a) a polypeptide comprising an amino acid sequence at least 80% identical to SEQ ID NO:6, wherein the polypeptide comprises a PUPA synthase activity selected from the group consisting of DH activity, ER activity, and combinations thereof; (b) a polypeptide comprising an amino acid sequence at least 80% identical to SEQ ID NO:38, wherein the polypeptide comprises DH activity; (c) a polypeptide comprising an amino acid sequence at least 80% identical to SEQ ID NO:40, wherein the polypeptide comprises DH activity; and (d) a polypeptide comprising an amino acid sequence at least 80% identical to SEQ ID NO:42, wherein the polypeptide comprises ER activity. In some embodiments, the amino acid sequences are at least 90% identical or at least 95% identical to SEQ ID NOs:6, 38, 40, and 42, respectively. In some embodiments, the polypeptides comprise the amino acid sequences of SEQ ID NOs:6, 38, 40, and 42, respectively.

The present invention is directed to an isolated polypeptide selected from the group consisting of: (a) a polypeptide comprising an amino acid sequence at least 80% identical to SEQ ID NO:69, wherein the polypeptide comprises a PUPA synthase activity selected from the group consisting of KS activity, MAT activity, ACP activity, KR activity, DH activity, and combinations thereof; (b) a polypeptide comprising an amino acid sequence at least 80% identical to SEQ ID NO:75, wherein the polypeptide comprises KS activity; (c) a polypeptide comprising an amino acid sequence at least 80% identical to SEQ ID NO:77, wherein the polypeptide comprises MAT activity; (d) a polypeptide comprising an amino acid sequence at least 80% identical to any one of SEQ ID NOs:81, 83, 85, 87, 89, 91, 93, 95, 97, or 99, wherein the polypeptide comprises ACP activity; (e) a polypeptide comprising an amino acid sequence at least 80% identical to SEQ ID NO:79, wherein the polypeptide comprises ACP activity; (f) a polypeptide comprising an amino acid sequence at least 80% identical to SEQ ID NO:101, wherein the polypeptide comprises KR activity; and (g) a polypeptide comprising an amino acid sequence at least 80% identical to SEQ ID NO:119, wherein the polypeptide comprises DH activity. In some embodiments, the amino acid sequences are at least 90% identical or at least 95% identical to SEQ ID NOs:69, 75, 77, 79, 81, 83, 85, 87, 89, 91, 93, 95, 97, 99, 101, and 119, respectively. In some embodiments, the polypeptides comprise the amino acid sequences of SEQ ID NOs:69, 75, 77, 79, 81, 83, 85, 87, 89, 91, 93, 95, 97, 99, 101, and 119, respectively.

The present invention is directed to an isolated polypeptide selected from the group consisting of: (a) a polypeptide comprising an amino acid sequence at least 80% identical to SEQ ID NO:71, wherein the polypeptide comprises a PUPA synthase activity selected from the group consisting of KS activity, CLP activity, AT activity, ER activity, and combinations thereof; (b) a polypeptide comprising an amino acid sequence at least 80% identical to SEQ ID NO:103, wherein the polypeptide comprises KS activity; (c) a polypeptide comprising an amino acid sequence at least 80% identical to SEQ ID NO:105, wherein the polypeptide comprises CLP activity; (d) a polypeptide comprising an amino acid sequence at least 80% identical to SEQ ID NO:107, wherein the polypeptide comprises AT activity; and (e) a polypeptide comprising an amino acid sequence at least 80% identical to SEQ ID NO:109, wherein the polypeptide comprises ER activity. In some embodiments, the amino acid sequences are at least 90% identical or at least 95% identical to SEQ ID NOs:71, 103, 105, 107, and 109, respectively. In some embodiments, the polypeptides comprise the amino acid sequence of SEQ ID NOs:71, 103, 105, 107, and 109, respectively.

The present invention is directed to an isolated polypeptide selected from the group consisting of: (a) a polypeptide comprising an amino acid sequence at least 80% identical to SEQ ID NO:73, wherein the polypeptide comprises a PUFA synthase activity selected from the group consisting of DH activity, ER activity, and combinations thereof; (b) a polypeptide comprising an amino acid sequence at least 80% identical to SEQ ID NO:111, wherein the polypeptide comprises DH activity; (c) a polypeptide comprising an amino acid sequence at least 80% identical to SEQ ID NO:113, wherein the polypeptide comprises DH activity; and (d) a polypeptide comprising an amino acid sequence at least 80% identical to SEQ ID NO:115, wherein the polypeptide comprises ER activity. In some embodiments, the amino acid sequences are at least 90% identical or at least 95% identical to SEQ ID NOs:73, 111, 113, and 115, respectively. In some embodiments, the polypeptides comprise the amino acid sequences of SEQ ID NOs:73, 111, 113, and 115, respectively.

In some embodiments, any of the isolated polypeptides of the invention can be a fusion polypeptide.

The present invention is directed to a composition comprising any of the polypeptides described above and a biologically acceptable carrier.

The present invention is directed to a method of increasing production of DHA, EPA, or a combination thereof in an organism having PUFA synthase activity, comprising: expressing any of the isolated nucleic acid molecules described above, any of the recombinant nucleic acid molecules described above, or combinations thereof in the organism under conditions effective to produce DHA, EPA, or a combination thereof, wherein the PUFA synthase activity replaces an inactive or deleted activity, introduces a new activity, or enhances an existing activity in the organism, and wherein production of DHA, EPA, or a combination thereof in the organism is increased.

The present invention is directed to a method of isolating lipids from a host cell, comprising: (a) expressing a PUFA synthase gene in the host cell under conditions effective to produce lipids, wherein the PUFA synthase gene comprises any of the isolated nucleic acid molecules described above, any of the recombinant nucleic acid molecules described above, or combinations thereof in the host cell, and (b) isolating lipids from the host cell. In some embodiments, the host cell is selected from the group consisting of a plant cell, an isolated animal cell, and a microbial cell. In some embodiments, the lipids comprise DHA, EPA, or a combination thereof.

BRIEF DESCRIPTION OF THE DRAWINGS/FIGURES

FIG. 1 shows the gene architecture of the *Schizochytrium* sp. ATCC PTA-9695 PUPA synthases of the invention.

FIG. 2 shows the gene architecture of the *Thraustochytrium* sp. ATCC PTA-10212 PUPA synthases of the invention.

FIG. 3 shows the domain architecture of the *Schizochytrium* sp. ATCC PTA-9695 and *Thraustochytrium* sp. ATCC PTA-10212 PUPA synthases of the invention and synthases from *Schizochytrium* sp. ATCC 20888, *Thraustochytrium* sp. ATCC 20892, *Thraustochytrium aureum*, and SAM2179.

FIG. 4 shows an alignment of a *Schizochytrium* sp. ATCC PTA-9695 Pfa1p amino acid sequence (SEQ ID NO:2) and a *Thraustochytrium* sp. ATCC PTA-10212 Pfa1 p amino acid sequence (SEQ ID NO:69) of the invention with the OrfA sequences from *Schizochytrium* 0.5p. ATCC 20888 (SEQ ID NO:54) and *Thraustochytrium* sp. ATCC 20892 (SEQ ID NO:56) and the ORF A sequence from *Thraustochytrium aureum* (SEQ ID NO:55).

FIG. 5 shows an alignment of a *Schizochytrium* sp. ATCC PTA-9695 Pfa2p amino acid sequence (SEQ ID NO:4) and a *Thraustochytrium* sp. ATCC PTA-10212 Pfa2p amino acid sequence (SEQ ID NO:71) of the invention with the OrfB sequences from *Schizochytrium* sp. ATCC 20888 (SEQ ID NO:57) and *Thraustochytrium* sp. ATCC 20892 (SEQ ID NO:58) and the ORF B sequence from *Thraustochytrium aureum* (SEQ ID NO:59).

FIG. 6 shows an alignment of a *Schizochytrium* sp. ATCC PTA-9695 Pfa3p amino acid sequence (SEQ ID NO:6) and a *Thraustochytrium* sp. ATCC PTA-10212 Pfa3p amino acid sequence (SEQ ID NO:73) of the invention with the OrfC sequences from *Schizochytrium* sp. ATCC 20888 (SEQ ID NO:61) and *Thraustochytrium* sp. ATCC 20892 (SEQ ID NO:60).

FIG. 7 shows the *Schizochytrium* sp. ATCC PTA-9695 PFAJ polynucleotide sequence (SEQ ID NO:1).

FIG. 8 shows the *Schizochytrium* sp. ATCC PTA-9695 Pfa1p amino acid sequence (SEQ ID NO:2).

FIG. 9 shows the *Schizochytrium* sp. ATCC PTA-9695 PFA2 polynucleotide sequence (SEQ ID NO:3).

FIG. 10 shows the *Schizochytrium* sp. ATCC PTA-9695 Pfa2p amino acid sequence (SEQ ID NO:4).

FIG. 11 shows the *Schizochytrium* sp. ATCC PTA-9695 PFA3 polynucleotide sequence (SEQ ID NO:5).

FIG. 12 shows the *Schizochytrium* sp. ATCC PTA-9695 Pfa3p amino acid sequence (SEQ ID NO:6).

FIG. 13 shows the *Thraustochytrium* sp. ATCC PTA-10212 PFAJ polynucleotide sequence (SEQ ID NO:68).

FIG. 14 shows a *Thraustochytrium* sp. ATCC PTA-10212 PFAJ polynucleotide sequence (SEQ ID NO:120) that has been codon-optimized for expression in *Schizochytrium*.

FIG. 15 shows the *Thraustochytrium* sp. ATCC PTA-10212 Pfa1p amino acid sequence (SEQ ID NO: 69).

FIG. 16 shows the *Thraustochytrium* sp. ATCC PTA-10212 PFA2 polynucleotide sequence (SEQ ID NO:70).

FIG. 17 shows a *Thraustochytrium* sp. ATCC PTA-10212 PFA2 polynucleotide sequence (SEQ ID NO:121) that has been codon-optimized for expression in *Schizochytrium*.

FIG. 18 shows the *Thraustochytrium* sp. ATCC PTA-10212 Pfa2p amino acid sequence (SEQ ID NO:71).

FIG. 19 shows the *Thraustochytrium* sp. ATCC PTA-10212 PFA3 polynucleotide sequence (SEQ ID NO:72).

FIG. 20 shows a *Thraustochytrium* sp. ATCC PTA-10212 PFA3 polynucleotide sequence (SEQ ID NO:122) that has been codon-optimized for expression in *Schizochytrium*.

FIG. 21 shows the *Thraustochytrium* sp. ATCC PTA-10212 Pfa3p amino acid sequence (SEQ ID NO:73).

FIG. 22 shows a codon usage table for *Schizochytrium*.

DETAILED DESCRIPTION OF THE INVENTION

The present invention is directed to isolated nucleic acid molecules and polypeptides of polyunsaturated fatty acid (PUPA) synthases involved in the production of PUFAs, including PUFAs enriched in docosahexaenoic acid (DHA), eicosapentaenoic acid (EPA), or a combination thereof. The present invention is directed to vectors and host cells comprising the nucleic acid molecules, polypeptides encoded by the nucleic acid molecules, compositions comprising the nucleic acid molecules or polypeptides, and methods of making and uses thereof.

PUPA Synthases

As used herein, the term "PUPA synthase" refers to an enzyme that is involved in the production of polyunsaturated fatty acids. See, e.g., Metz et al., *Science* 293:290-293 (2001).

The present invention is directed in pail to three PUPA synthase subunits termed Pfa1p (SEQ ID NO:2 or SEQ ID NO:69), Pfa2p (SEQ ID NO:4 or SEQ ID NO:71), and Pfa3p (SEQ ID NO:6 or SEQ ID NO:73), as well as the genes that encode the subunits termed PFAJ (SEQ ID NO:1, SEQ ID NO:68, or SEQ ID NO:120), PFA2 (SEQ ID NO:3, SEQ ID NO:70, or SEQ ID NO:121), and PFA3 (SEQ ID NO:5, SEQ ID NO:72, or SEQ ID NO:122). See, FIGS. 1-3 and 7-21. PUPA synthases in other thraustochytrids have also been designated as ORF 1, ORF 2, and ORF 3, respectively, or as OrfA, OrfB, and OrfC, respectively. See, e.g., *Schizochytrium* sp. (ATCC 20888) and *Thraustochytrium* sp. (ATCC 20892) in U.S. Pat. Nos. 7,247,461 and 7,256,022, refelTing to orfA, oifB, and orfC genes and colTesponding OrfA, OrfB, and OrfC proteins, and *Thraustochytrium aureum* (ATCC 34304) in U.S. Pat. No. 7,368,552, referring to ORF A, ORF B, and ORF C genes and proteins. See also, strain SAM2179 in WO/2005/097982, referring to ORF 1, ORF 2, and ORF 3 genes and proteins.

Nucleic Acid Molecules

The present invention is directed to isolated nucleic acid molecules comprising polynucleotide sequences for PUPA synthase genes and domains derived from an isolated microorganism that is the subject of co-pending U.S. application Ser. No. 12/407,687, filed on Mar. 19, 2009, incorporated herein by reference in its entirety. The microorganism was deposited under the Budapest Treaty at the American Type Culture Collection, Patent Depository, 10801 University Boulevard, Manassas, VA 20110-2209, on Jan. 7, 2009, and given ATCC Accession No. PTA-9695, and is also referred to as *Schizochytrium* sp. ATCC PTA-9695. When expressed, these genes produce unique fatty acid profiles, characterized in part by high levels of omega-3 fatty acids, in particular high levels of DHA.

The present invention is directed to isolated nucleic acid molecules comprising polynucleotide sequences for PUPA synthase genes and domains derived from an isolated microorganism that is the subject of U.S. Appl. No. 61/296,456, filed on Jan. 19, 2010, incorporated herein by reference in its entirety. The microorganism was deposited under the Budapest Treaty at the American Type Culture Collection, Patent Depository, 10801 University Boulevard, Manassas, VA 20110-2209, on Jul. 14, 2009, and given ATCC Accession No. PTA-10212, and is also referred to as *Thraustochytrium* sp. ATCC PTA-10212. When expressed, these genes produce unique fatty acid profiles, characterized in part by high levels of omega-3 fatty acids, in particular high levels of DHA, EPA, or a combination thereof.

As used herein, a "polynucleotide" can comprise a conventional phosphodiester bond or a non-conventional bond (e.g., an amide bond, such as found in peptide nucleic acids (PNA)). A polynucleotide can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotides can be composed of triple-stranded regions comprising RNA or DNA or both RNA and DNA. Polynucleotides can contain ribonucleosides (adenosine, guanosine, uridine, or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters. Polynucleotides can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms. The term nucleic acid molecule refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

The terms "isolated" nucleic acid molecule refers to a nucleic acid molecule, DNA or RNA, which has been removed from its native environment. Further examples of isolated nucleic acid molecules include nucleic acid molecules comprising recombinant polynucleotides maintained in heterologous host cells or purified (partially or substantially) polynucleotides in solution. Isolated RNA molecules include in vivo or in vitro RNA transcripts of polynucleotides of the present invention. Isolated nucleic acid molecules according to the present invention further include such molecules produced synthetically. In addition, a nucleic acid molecule or polynucleotide can include a regulatory element such as a promoter, ribosome binding site, or a transcription terminator.

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

The present invention is directed to isolated nucleic acid molecules comprising polynucleotide sequences at least 80% identical to the polynucleotide sequences of *Schizochytrium* sp. ATCC PTA-9695 PFAJ (SEQ ID NO:1), *Schizochytrium* sp. ATCC PTA-9695 PFA2 (SEQ ID NO:3), *Schizochytrium* sp. ATCC PTA-9695 PFA3 (SEQ ID NO:5), *Thraustochytrium* sp. ATCC PTA-10212 PFAJ (SEQ ID NO:68 or SEQ ID NO:120), *Thraustochytrium* sp. ATCC PTA-10212 PFA2 (SEQ ID NO:70 or SEQ ID NO:121), *Thraustochytrium* sp. ATCC PTA-10212 PFA3 (SEQ ID NO:72 or SEQ ID NO:122), and combinations thereof, wherein the polynucleotides encode polypeptides comprising one or more PUFA synthase activities.

The PUFA synthase activities are associated with one or more domains in each synthase polypeptide, wherein the domains can be identified by their conserved structural or functional motifs based on their homology to known motifs and can also be identified based upon their specific biochemical activities. See, e.g., U.S. Pat. No. 7,217,856, incorporated by reference herein in its entirety. Examples of PUFA synthase domains include: the beta-ketoacyl-ACP synthase (KS) domain, malonyl-CoA:ACP acyltransferase (MAT) domain, acyl carrier protein (ACP) domains, ketoreductase (KR) domain, and beta-hydroxyacyl-ACP dehydrase (DH) domain in Pfa1 p; the KS domain, chain length factor (CLF) domain, acyltransferase (AT) domain, and enoyl-ACP reductase (ER) domain in Pfa2p; and the DH domains and the ER domain in Pfa3p.

A polypeptide or domain of a polypeptide having beta-ketoacyl-ACP synthase (KS) biological activity (function) has been previously shown to be capable of carrying out the initial step of the fatty acid elongation reaction cycle. The term "beta-ketoacyl-ACP synthase" has been used interchangeably with the terms "3-keto acyl-ACP synthase," "beta-ketoacyl-ACP synthase," and "keto-acyl ACP synthase." In other systems, it has been shown that the acyl group for elongation is linked to a cysteine residue at the active site of KS by a thioester bond, and the acyl-KS undergoes condensation with malonyl-ACP to form -ketoacyl-ACP, $CO_2$, and unbound ("free") KS. In such systems, KS has been shown to possess greater substrate specificity than other polypeptides of the reaction cycle. Polypeptides (or domains of polypeptides) can be readily identified as belonging to the KS family by homology to known KS sequences.

A polypeptide or a domain of a polypeptide having malonyl-CoA:ACP acyltransferase (MAT) activity has been previously shown to be capable of transferring the malonyl moiety from malonyl-CoA to ACP. The term "malonyl-CoA:ACP acyltransferase" has been used interchangeably with "malonyl acyltransferase." In addition to the active site motif (GxSxG), MATs have been shown to possess an extended motif (R and Q amino acids in key positions). Polypeptides (or domains of polypeptides) can be readily identified as belonging to the MAT family by their homology to known MAT sequences and by their extended motif structure.

A polypeptide or a domain of a polypeptide having acyl carrier protein (ACP) activity has been previously shown to be capable of functioning as a carrier for growing fatty acyl chains via a thioester linkage to a covalently bound co-factor. ACPs are typically about 80 to about 100 amino acids long and have been shown to be converted from inactive apo-forms to functional holo-forms by transfer of the phosphopantetheinyl moiety of CoA to a highly conserved seline residue of the ACP. It has also been shown that acyl groups are attached to ACPs by a thioester linkage at the free terminus of the phosphopantetheinyl moiety. The presence of valiations of an active site motif (LGIDS*) has also been recognized as a signature of ACPs. The functionality of the active site serine (S*) has been demonstrated in a bacterial PUFA synthase (Jiang et al., *J. Am. Chem. Soc.* 130:6336-7 (2008)). Polypeptides (or domains of polypeptides) can be readily identified as belonging to the ACP family by labeling with radioactive pantetheine and by sequence homology to known ACPs.

A polypeptide or a domain of a polypeptide having dehydrase or dehydratase (DH) activity has been previously shown to be capable of catalyzing a dehydration reaction. Reference to DH activity typically refers to FabA-like beta-hydroxyacyl-ACP dehydrase biological activity. FabA-like beta-hydroxyacyl-ACP dehydrase biological activity removes HOH from a beta-ketoacyl-ACP and initially produces a trans double bond in the carbon chain. The term "FabA-like beta-hydroxyacyl-ACP dehydrase" has been used interchangeably with the terms "FabA-like beta-hydroxy acyl-ACP dehydrase," "beta-hydroxyacyl-ACP dehydrase," and "dehydrase." The DH domains of PUFA synthase systems have previously been demonstrated as showing homology to bacterial DH enzymes associated with FAS systems (rather than to the DH domains of other PKS systems). See, e.g., U.S. Pat. No. 7,217,856, incorporated by reference herein in its entirety. A subset of bacterial DHs, the PabA-like DHs, possesses cis-trans isomerase activity (Heath et al., *J. Biol. Chem.*, 271, 27795 (1996)). Based on homology to the PabA-like DH proteins, one or all of the PUPA synthase system DH domains can be responsible for insertion of cis double bonds in the PUPA synthase products. A polypeptide or domain can also have non-PabA-like DH activity, or non-PabA-like beta-hydroxyacyl-ACP dehydrase (DH) activity. More specifically, a conserved active site motif of about 13 amino acids in length has been previously identified in PUPA synthase DH domains: LxxHxxxGxxxxP (the L position can also be an I in the motif). See, e.g., U.S. Pat. No. 7,217,856, and Donadio S, Katz L., *Gene* 111(1): 51-60 (1992), each of which is incorporated by reference herein in its entirety. This conserved motif is found in a similar region of all known PUPA synthase sequences and could be responsible for a non-PabA like dehydration.

A polypeptide or a domain of a polypeptide having beta-ketoacyl-ACP reductase (KR) activity has been previously shown to be capable of catalyzing the pyridine-nucleotide-dependent reduction of 3-ketoacyl forms of ACP. The term "beta-ketoacyl-ACP reductase" has been used interchangeably with the terms "ketoreductase," "3-ketoacyl-ACP reductase," and "keto-acyl ACP reductase." It has been determined in other systems that KR function involves the first reductive step in the de novo fatty acid biosynthesis elongation cycle. Polypeptides (or domains of polypeptides) can be readily identified as belonging to the KR family by sequence homology to known PUPA synthase KRs.

A polypeptide or a domain of a polypeptide having chain length factor (CLP) activity has been previously defined as having one or more of the following activities or characteristics: (1) it can determine the number of elongation cycles and hence chain length of the end product, (2) it has homology to KS, but lacks the KS active site cysteine, (3) it can heterodimerize with KS, (4) it can provide the initial acyl group to be elongated, or (5) it can decarboxylate malonate (as malonyl-ACP), thus forming an acetate group that can be transferred to the KS active site and that can act as the 'priming' molecule that undergoes the initial elongation (condensation) reaction. A CLP domain is found in all currently identified PUPA synthase systems and in each case is found as part of a multidomain protein. Polypeptides (or domains of polypeptides) can be readily identified as belonging to the CLP family by sequence homology to known PUPA synthase CLPs.

A polypeptide or a domain of a polypeptide having acyltransferase (AT) activity has been previously defined as having one or more of the following activities or characteristics: (1) it can transfer the fatty acyl group from the ACP domain(s) to water (i.e., a thioesterase), releasing the fatty acyl group as a free fatty acid, (2) it can transfer a fatty acyl group to an acceptor such as CoA, (3) it can transfer the acyl group among the various ACP domains, or (4) it can transfer the fatty acyl group to a lipophilic acceptor molecule (e.g. to lysophosphadic acid). Polypeptides (or domains of polypeptides) can be readily identified as belonging to the AT family by sequence homology to known PUPA synthase ATs.

A polypeptide or a domain of a polypeptide having enoyl-ACP reductase (ER) biological activity has been previously shown to be capable of reducing the trans-double bond (introduced by the DH activity) in the fatty acyl-ACP, resulting in saturation of the associated carbons. The ER domain in PUPA synthase systems has previously been shown to have homology to a family of ER enzymes (Heath et al., *Nature* 406: 145-146 (2000), incorporated by reference herein in its entirety), and an ER homolog has been shown to function as an enoyl-ACP reductase in vitro (Bumpus et al. *J. Am. Chem. Soc.*, 130: 11614-11616 (2008), incorporated by reference herein in its entirety). The term "enoyl-ACP reductase" has been used interchangeably with "enoyl reductase," "enoyl ACP-reductase," and "enoyl acyl-ACP reductase." Polypeptides (or domains of polypeptides) can be readily identified as belonging to the ER family by sequence homology to known PUPA synthase ERs.

In some embodiments, the present invention is directed to nucleic acid molecules comprising a polynucleotide sequence at least 80% identical to a polynucleotide sequence within PFAJ (SEQ ID NO:1, SEQ ID NO:68, or SEQ ID NO:120) that encodes one or more PUPA synthase domains. In some embodiments, the nucleic acid molecule comprises a polynucleotide sequence at least 80% identical to a polynucleotide sequence within PFAJ (SEQ ID NO:1, SEQ ID NO:68, or SEQ ID NO:120) that encodes one or more PUPA synthase domains such as a KS domain (SEQ ID NO:7 or SEQ ID NO:74), a MAT domain (SEQ ID NO:9 or SEQ ID NO:76), an ACP domain (such as any one of SEQ ID NOs:13, 15, 17, 19, 21, 23, 80, 82, 84, 86, 88, 90, 92, 94, 96, or 98), a combination of two or more ACP domains, such as two, three, four, five, six, seven, eight, nine, or ten ACP domains, including tandem domains (SEQ ID NO:11 or SEQ ID NO:78, and portions thereof), a KR domain (SEQ ID NO:25 or SEQ ID NO:100), a DH domain (SEQ ID NO:27 or SEQ ID NO:118), and combinations thereof. In some embodiments, the nucleic acid molecule comprises two or more polynucleotide sequences, wherein each of the at least two or more polynucleotide sequences is 80% identical to a polynucleotide sequence within PFAJ (SEQ ID NO:1, SEQ ID NO:68, or SEQ ID NO:120) that encodes one or more PUFA synthase domains. In some embodiments, the at least two or more polynucleotide sequences are 80% identical to the same polynucleotide sequence within SEQ ID NO:1, SEQ ID NO:68, or SEQ ID NO:120 that encodes one or more PUFA synthase domains. In some embodiments, the at least two or more polynucleotide sequences are 80% identical to different polynucleotide sequences within SEQ ID NO:1, SEQ ID NO:68, or SEQ ID NO:120 that each encode one or more PUFA synthase domains. In some embodiments, the at least two or more polynucleotide sequences are 80% identical to different polynucleotide sequences within SEQ ID NO:1, SEQ ID NO:68, or SEQ ID NO:120, wherein the at least two or more polynucleotide sequences are located in the same order or a different order in the nucleic acid molecule as compared to the order of the corresponding sequences within SEQ ID NO:1, SEQ ID NO:68, or SEQ ID NO:120. In some embodiments, each of the at least two or more polynucleotide sequences are 80% identical to a polynucleotide sequence within PFAJ (SEQ ID NO:1, SEQ ID NO:68, or SEQ ID NO:120) that encodes one or more PUFA synthase domains such as a KS domain (SEQ ID NO:7 or SEQ ID NO:74), a MAT domain (SEQ ID NO:9 or SEQ ID NO:76), an ACP domain (such as any one of SEQ ID NOs:13, 15, 17, 19, 21, 23, 80, 82, 84, 86, 88, 90, 92, 94, 96, or 98), a combination of two, three, four, five, six, seven, eight, nine, or ten ACP domains, including tandem domains (SEQ ID NO:11 or SEQ ID NO:78, and portions thereof), a KR domain (SEQ ID NO:25 or SEQ ID NO:100), a DH domain (SEQ ID NO:27 or SEQ ID NO:118), and combinations thereof. In some embodiments, the nucleic acid molecule comprises one or more polynucleotide sequences within PFAJ (SEQ ID NO:1, SEQ ID NO:68, or SEQ ID NO:120) that encodes one or more PUFA synthase domains, including one or more copies of any individual domain in combination with one or more copies of any other individual domain.

In some embodiments, the present invention is directed to nucleic acid molecules comprising a polynucleotide sequence at least 80% identical to a polynucleotide sequence within PFA2 (SEQ ID NO:3, SEQ ID NO:70, or SEQ ID NO:121) that encodes one or more PUPA synthase domains. In some embodiments, the nucleic acid molecule comprises a polynucleotide sequence at least 80% identical to the polynucleotide sequence within PFA2 (SEQ ID NO:3, SEQ ID NO:70, or SEQ ID NO:121) that encodes one or more PUPA synthase domains such as a KS domain (SEQ ID NO:29 or SEQ ID NO:102), a CLP domain (SEQ ID NO:31 or SEQ ID NO:104), an AT domain (SEQ ID NO:33 or SEQ ID NO:106), an ER domain (SEQ ID NO:35 or SEQ ID NO:108), and combinations thereof. In some embodiments, the nucleic acid molecule comprises two or more polynucleotide sequences, wherein each of the at least two or more polynucleotide sequences is 80% identical to a polynucleotide sequence within PFA2 (SEQ ID NO:3, SEQ ID NO:70, or SEQ ID NO:121) that encodes one or more PUPA synthase domains. In some embodiments, the at least two or more polynucleotide sequences are 80% identical to the same polynucleotide sequence within SEQ ID NO:3, SEQ ID NO:70, or SEQ ID NO:121 that encodes one or more PUPA synthase domains. In some embodiments, the at least two or more polynucleotide sequences are 80% identical to different polynucleotide sequences within SEQ ID NO:3, SEQ ID NO:70, or SEQ ID NO:121 that each encode one or more PUPA synthase domains. In some embodiments, the at least two or more polynucleotide sequences are 80% identical to different polynucleotide sequences within SEQ ID NO:3, SEQ ID NO:70, or SEQ ID NO:121, wherein the at least two or more polynucleotide sequences are located in the same order or a different order in the nucleic acid molecule as compared to the order of the corresponding sequences within SEQ ID NO:3, SEQ ID NO:70, or SEQ ID NO:121. In some embodiments, each of the at least two or more polynucleotide sequences are 80% identical to a polynucleotide sequence within PFA2 (SEQ ID NO:3, SEQ ID NO:70, or SEQ ID NO:121) that encodes one or more PUPA synthase domains such as a KS domain (SEQ ID NO:29 or SEQ ID NO:102), a CLP domain (SEQ ID NO:31 or SEQ ID NO:104), an AT domain (SEQ ID NO:33 or SEQ ID NO:106), an ER domain (SEQ ID NO:35 or SEQ ID NO:108), and combinations thereof. In some embodiments, the nucleic acid molecule comprises one or more polynucleotide sequences within PFA2 (SEQ ID NO:3, SEQ ID NO:70, or SEQ ID NO:121) that encodes one or more PUPA synthase domains, including one or more copies of any individual domain in combination with one or more copies of any other individual domain.

In some embodiments, the present invention is directed to nucleic acid molecules comprising a polynucleotide sequence at least 80% identical to a polynucleotide sequence within PFA3 (SEQ ID NO:5, SEQ ID NO:72, or SEQ ID NO:122) that encodes one or more PUFA synthase domains. In some embodiments, the nucleic acid molecule comprises a polynucleotide sequence at least 80% identical to a polynucleotide sequence within PFA3 (SEQ ID NO:5, SEQ ID NO:72, or SEQ ID NO:122) that encodes one or more PUFA synthase domains such as a DH domain (such as SEQ ID NO:37, SEQ ID NO:39, SEQ ID NO:110, or SEQ ID NO:112), an ER domain (SEQ ID NO:41 or SEQ ID NO:114), and combinations thereof. In some embodiments, the nucleic acid molecule comprises two or more polynucleotide sequences, wherein each of the at least two or more polynucleotide sequences is 80% identical to a polynucleotide sequence within PFA. 3 (SEQ ID NO:5, SEQ ID NO:72, or SEQ ID NO:122) that encodes one or more PUFA synthase domains. In some embodiments, the at least two or more polynucleotide sequences are 80% identical to the same polynucleotide sequence within SEQ ID NO:5, SEQ ID NO:72, or SEQ ID NO:122 that encodes one or more PUFA synthase domains. In some embodiments, the at least two or more polynucleotide sequences are 80% identical to different polynucleotide sequences within SEQ ID NO:5, SEQ ID NO:72, or SEQ ID NO:122 that each encode one or more PUFA synthase domains. In some embodiments, the at least two or more polynucleotide sequences are 80% identical to different polynucleotide sequences within SEQ ID NO:5, SEQ ID NO:72, or SEQ ID NO:122, wherein the at least two or more polynucleotide sequences are located in the same order or a different order in the nucleic acid molecule as compared to the order of the corresponding sequences within SEQ ID NO:5, SEQ ID NO:72, or SEQ ID NO:122. In some embodiments, each of the at least two or more polynucleotide sequences is 80% identical to a polynucleotide sequence within PFA3 (SEQ ID NO:5, SEQ ID NO:72, or SEQ ID NO:122) that encodes one or more PUFA synthase domains such as a DH domain (such as SEQ ID NO:37, SEQ ID NO:39, SEQ ID NO:110, or SEQ ID NO:112), an ER domain (SEQ ID NO:41 or SEQ ID NO:114), and combinations thereof. In some embodiments, the nucleic acid molecule comprises one or more polynucleotide sequences within PFA3 (SEQ ID NO:5, SEQ ID NO:72, or SEQ ID NO:122) that encodes one or more PUFA synthase domains, including one or more copies of any individual domain in combination with one or more copies of any other individual domain.

In some embodiments, the present invention is directed to a nucleic acid molecule comprising a polynucleotide sequence at least 80% identical to SEQ ID NO:1, SEQ ID NO:68, or SEQ ID NO:120, wherein the polynucleotide sequence encodes apolypeptide comprising PUPA synthase activity selected from the group consisting of KS activity, MAT activity, ACP activity, KR activity, DH activity, and combinations thereof.

In some embodiments, the present invention is directed to a nucleic acid molecule comprising a polynucleotide sequence at least 80% identical to SEQ ID NO:7 or SEQ ID NO:74, wherein the polynucleotide sequence encodes a polypeptide comprising KS activity.

In some embodiments, the present invention is directed to a nucleic acid molecule comprising a polynucleotide sequence at least 80% identical to SEQ ID NO:9 or SEQ ID NO:76, wherein the polynucleotide sequence encodes a polypeptide comprising MAT activity.

In some embodiments, the present invention is directed to a nucleic acid molecule comprising a polynucleotide sequence at least 80% identical to any one of SEQ ID NOs:13, 15, 17, 19, 21, 23, 80, 82, 84, 86, 88, 90, 92, 94, 96, or 98, wherein the polynucleotide sequence encodes a polypeptide comprising ACP activity.

In some embodiments, the present invention is directed to a nucleic acid molecule comprising a polynucleotide sequence at least 80% identical to SEQ ID NO:11 or SEQ ID NO:78, wherein the polynucleotide sequence encodes a polypeptide comprising ACP activity.

In some embodiments, the nucleic acid molecule comprises a polynucleotide sequence at least 80% identical to a polynucleotide sequence within SEQ ID NO:11 that encodes one, two, three, four, five, or six ACP domains, wherein the polynucleotide sequence encodes a polypeptide comprising ACP activity associated with one or more ACP domains. SEQ ID NOs:13, 15, 17, 19, 21, and 23 are representative polynucleotides sequence that each encode a single ACP domain within SEQ ID NO:11.

In some embodiments, the nucleic acid molecule comprises a polynucleotide sequence at least 80% identical to a polynucleotide sequence within SEQ ID NO:78 that encodes one, two, three, four, five, six, seven, eight, nine, or ten ACP domains, wherein the polynucleotide sequence encodes a polypeptide comprising ACP activity associated with one or more ACP domains. SEQ ID NOs:80, 82, 84, 86, 88, 90, 92, 94, 96, and 98 are representative polynucleotides sequence that each encode a single ACP domain within SEQ ID NO:78.

In some embodiments, the present invention is directed to a nucleic acid molecule comprising a polynucleotide sequence at least 80% identical to SEQ ID NO:25 or SEQ ID NO:100, wherein the polynucleotide sequence encodes a polypeptide comprising KR activity.

In some embodiments, the present invention is directed to a nucleic acid molecule comprising a polynucleotide sequence at least 80% identical to SEQ ID NO:27 or SEQ ID NO:118, wherein the polynucleotide sequence encodes a polypeptide comprising DH activity.

In some embodiments, the present invention is directed to a nucleic acid molecule comprising a polynucleotide sequence at least 80% identical to SEQ ID NO:3, SEQ ID NO:70, or SEQ ID NO:121, wherein the polynucleotide sequence encodes a polypeptide comprising PUPA synthase activity selected from the group consisting of KS activity, CLP activity, AT activity, ER activity, and combinations thereof.

In some embodiments, the present invention is directed to a nucleic acid molecule comprising a polynucleotide sequence at least 80% identical to SEQ ID NO:29 or SEQ ID NO:102, wherein the polynucleotide sequence encodes a polypeptide comprising KS activity.

In some embodiments, the present invention is directed to a nucleic acid molecule comprising a polynucleotide sequence at least 80% identical to SEQ ID NO:31 or SEQ ID NO:104, wherein the polynucleotide sequence encodes a polypeptide comprising CLP activity.

In some embodiments, the present invention is directed to a nucleic acid molecule comprising a polynucleotide sequence at least 80% identical to SEQ ID NO:33 or SEQ ID NO:106, wherein the polynucleotide sequence encodes a polypeptide comprising AT activity.

In some embodiments, the present invention is directed to a nucleic acid molecule comprising a polynucleotide sequence at least 80% identical to SEQ ID NO:35 or SEQ ID NO:108, wherein the polynucleotide sequence encodes a polypeptide comprising ER activity.

In some embodiments, the present invention is directed to a nucleic acid molecule comprising a polynucleotide sequence at least 80% identical to SEQ ID NO:5, SEQ ID NO:72, or SEQ ID NO:122, wherein the polynucleotide sequence encodes apolypeptide comprising PUFA synthase activity selected from the group consisting of DH activity, ER activity, and combinations thereof.

In some embodiments, the present invention is directed to a nucleic acid molecule comprising a polynucleotide sequence at least 80% identical to SEQ ID NO:37, wherein the polynucleotide sequence encodes a polypeptide comprising DH activity.

In some embodiments, the present invention is directed to a nucleic acid molecule comprising a polynucleotide sequence at least 80% identical to SEQ ID NO:39, wherein the polynucleotide sequence encodes a polypeptide comprising DH activity.

In some embodiments, the present invention is directed to a nucleic acid molecule comprising a polynucleotide sequence at least 80% identical to SEQ ID NO:110, wherein the polynucleotide sequence encodes a polypeptide comprising DH activity.

In some embodiments, the present invention is directed to a nucleic acid molecule comprising a polynucleotide sequence at least 80% identical to SEQ ID NO:112, wherein the polynucleotide sequence encodes a polypeptide comprising DH activity.

In some embodiments, the present invention is directed to a nucleic acid molecule comprising a polynucleotide sequence at least 80% identical to SEQ ID NO:41 or SEQ ID NO:114, wherein the polynucleotide sequence encodes a polypeptide comprising ER activity.

The present invention is directed to isolated nucleic acid molecules comprising polynucleotide sequences encoding polypeptides, wherein the polypeptides comprise amino acid sequences that are at least 80% identical to the amino acid sequences of Pfa1p (SEQ ID NO:2 or SEQ ID NO:69), Pfa2p (SEQ ID NO:4 or SEQ ID NO:71), or Pfa3p (SEQ ID NO:6 or SEQ ID NO:73), wherein the polynucleotides encode polypeptides comprising one or more PUFA synthase activities.

The present invention is directed to nucleic acid molecules comprising a polynucleotide sequence encoding a polypeptide, wherein the polypeptide comprises an amino acid sequence at least 80% identical to the amino acid sequences of one or more PUFA synthase domains of the PUF A synthases of the invention.

In some embodiments, the present invention is directed to nucleic acid molecules comprising a polynucleotide sequence encoding a polypeptide, wherein the polypeptide comprises an amino acid sequence at least 80% identical to an amino acid sequence within Pfa1p (SEQ ID NO:2 or SEQ ID NO:69) comprising one or more PUFA synthase domains. In some embodiments, the polypeptide comprises an amino acid sequence at least 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO:77), an ACP domain (such as any one of SEQ ID NOs:14, 16, 18, 20, 22, 24, 81, 83, 85, 87, 89, 91, 93, 95, 97, or 99), a combination of two or more ACP domains, such as two, three, four, five, six, seven, eight, nine, or ten ACP domains, including tandem domains (SEQ ID NO:12 or SEQ ID NO:79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises two or more amino acid sequences, wherein each of the at least two or more amino acid sequences is 80% identical to an amino acid sequence within Pfa1 p (SEQ ID NO:2 or SEQ ID NO:69) comprising one or more PUFA synthase domains. In some embodiments, the at least two or more amino acid sequences are 80% identical to the same amino acid sequence within Pfa1 p (SEQ ID NO:2 or SEQ ID NO:69) comprising one or more PUFA synthase domains. In some embodiments, the at least two or more amino acid sequences are 80% identical to different amino acid sequences within Pfa1 p (SEQ ID NO:2 or SEQ ID NO: 69) that each comprise one or more PUFA synthase domains. In some embodiments, the at least two or more amino acid sequences are 80% identical to different amino acid sequences within Pfa1p (SEQ ID NO:2 or SEQ ID NO:69), wherein the at least two or more amino acid sequences are located in the same order or a different order in the polypeptide as compared to the order of the corresponding domains within Pfa1p (SEQ ID NO:2 or SEQ ID NO:69). In some embodiments, the at least two or more amino acid sequences are 80% identical to an amino acid sequence within Pfa1p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO: 77), an ACP domain (such as any one of SEQ ID NOs:14, 16, 18, 20, 22, 24, 81, 83, 85, 87, 89, 91, 93, 95, 97, or 99), a combination of two, three, four, five, six, seven, eight, nine, or ten ACP domains, including tandem domains (SEQ ID NO:12 or SEQ ID NO: 79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises one or more amino acid sequences within Pfa1p (SEQ ID NO:2 or SEQ ID NO:69) comprising one or more PUFA synthase domains, including one or more copies of any individual domain in combination with one or more copies of any other individual domain.

In some embodiments, the present invention is directed to nucleic acid molecules comprising a polynucleotide sequence encoding a polypeptide, wherein the polypeptide comprises an amino acid sequence at least 80% identical to an amino acid sequence within Pfa2p (SEQ ID NO:4 or SEQ ID NO:71) comprising one or more PUFA synthase domains. In some embodiments, the polypeptide comprises an amino acid sequence at least 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLF domain (SEQ ID NO:32 or SEQ ID NO:105), an AT domain (SEQ ID NO:34 or SEQ ID NO:107), an ER domain (SEQ ID NO:36 or SEQ ID NO:109), and combinations thereof. In some embodiments, the polypeptide comprises two or more amino acid sequences, wherein each of the at least two or more amino acid sequences is 80% identical to an amino acid sequence within Pfa2p (SEQ ID NO:4 or SEQ ID NO:71) comprising one or more PUFA synthase domains. In some embodiments, the at least two or more amino acid sequences are 80% identical to the same amino acid sequence within Pfa2p (SEQ ID NO:4 or SEQ ID NO:71). In some embodiments, the at least two or more amino acid sequences are 80% identical to different amino acid sequences within Pfa2p (SEQ ID NO:4 or SEQ ID NO:71) that each comprise one or more PUFA synthase domains. In some embodiments, the at least two or more amino acid sequences are 80% identical to different amino acid sequences within Pfa2p (SEQ ID NO:4 or SEQ ID NO:71), wherein the at least two or more amino acid sequences are located in the same order or a different order in the polypeptide as compared to the order of the corresponding domains within Pfa2p (SEQ ID NO:4 or SEQ ID NO:71). In some embodiments, the at least two or more amino acid sequences are 80% identical to an amino acid sequence within Pfa2p (SEQ ID NO:4 or SEQ ID NO:71) comprising one or more PUFA synthase domains such as a KS domain (SEQ ID NO:30 or SEQ ID NO:103), a CLP domain (SEQ ID NO:32 or SEQ ID NO:105), an AT domain (SEQ ID NO:34 or SEQ ID NO:107), an ER domain (SEQ ID NO:36 or SEQ ID NO:109), and combinations thereof. In some embodiments, the polypeptide comprises one or more amino acid sequences within Pfa2p (SEQ ID NO:4 or SEQ ID NO:71) comprising one or more PUPA synthase domains, including one or more copies of any individual domain in combination with one or more copies of any other individual domain.

In some embodiments, the present invention is directed to nucleic acid molecules comprising a polynucleotide sequence encoding a polypeptide, wherein the polypeptide comprises an amino acid sequence at least 80% identical to an amino acid sequence within Pfa3p (SEQ ID NO:6 or SEQ ID NO:73) comprising one or more PUPA synthase domains. In some embodiments, the polypeptide comprises an amino acid sequence at least 80% identical to an amino acid sequence within Pfa3p (SEQ ID NO:6 or SEQ ID NO:73) comprising one or more PUPA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises two or more amino acid sequences, wherein each of the at least two or more amino acid sequences is 80% identical to an amino acid sequence within Pfa3p (SEQ ID NO:6 or SEQ ID NO:73) comprising one or more PUPA synthase domains. In some embodiments, the at least two or more amino acid sequences are 80% identical to the same amino acid sequence within Pfa3p (SEQ ID NO:6 or SEQ ID NO:73) comprising one or more PUPA synthase domains. In some embodiments, the at least two or more amino acid sequences are 80% identical to different amino acid sequences within Pfa3p (SEQ ID NO:6 or SEQ ID NO:73) that each comprise one or more PUPA synthase domains. In some embodiments, the at least two or more amino acid sequences are 80% identical to different amino acid sequences within Pfa3p (SEQ ID NO:6 or SEQ ID NO:73), wherein the at least two or more amino acid sequences are located in the same order or a different order in the polypeptide as compared to the order of the corresponding domains within Pfa3p (SEQ ID NO:6 or SEQ ID NO:73). In some embodiments, the at least two or more amino acid sequences are 80% identical to an amino acid sequence within Pfa3p (SEQ ID NO:6 or SEQ ID NO:73) comprising one or more PUPA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises one or more amino acid sequences within Pfa3p (SEQ ID NO:6 or SEQ ID NO:73) comprising one or more PUFA synthase domains, including one or more copies of any individual domain in combination with one or more copies of any other individual domain.

In some embodiments, the present invention is directed to a nucleic acid molecule comprising a polynucleotide sequence encoding a polypeptide, wherein the polypeptide comprises an amino acid sequence at least 80% identical to SEQ ID NO:2 or SEQ ID NO:69, and wherein the polypeptide comprises a PUFA synthase activity selected from the group consisting of KS activity, MAT activity, ACP activity, KR activity, DH activity, and combinations thereof.

In some embodiments, the present invention is directed to a nucleic acid molecule comprising a polynucleotide sequence encoding a polypeptide, wherein the polypeptide comprises an amino acid sequence at least 80% identical to SEQ ID NO:8 or SEQ ID NO:75, and wherein the polypeptide comprises KS activity.

In some embodiments, the present invention is directed to a nucleic acid molecule comprising a polynucleotide sequence encoding a polypeptide, wherein the polypeptide comprises an amino acid sequence at least 80% identical to SEQ ID NO:10 or SEQ ID NO:77, and wherein the polypeptide comprises MAT activity.

In some embodiments, the present invention is directed to a nucleic acid molecule comprising a polynucleotide sequence encoding a polypeptide, wherein the polypeptide comprises an amino acid sequence at least 80% identical to any one of SEQ ID NOs:14, 16, 18, 20, 22, 24, 81, 83, 85, 87, 89, 91, 93, 95, 97, or 99, and wherein the polypeptide comprises ACP activity.

In some embodiments, the present invention is directed to a nucleic acid molecule comprising a polynucleotide sequence encoding a polypeptide, wherein the polypeptide comprises an amino acid sequence at least 80% identical to SEQ ID NO:12 or SEQ ID NO:79, and wherein the polypeptide comprises ACP activity.

In some embodiments, the present invention is directed to nucleic acid molecules comprising a polynucleotide sequence encoding a polypeptide, wherein the polypeptide comprises an amino acid sequence at least 80% identical to an amino acid sequence within SEQ ID NO:12, wherein the polypeptide comprises ACP activity. In some embodiments, the amino acid sequence is at least 80% identical to an amino acid sequence within SEQ ID NO:12 comprising one, two, three, four, five, or six ACP domains, wherein the polypeptide comprises ACP activity associated with one or more ACP domains. SEQ ID NOs:14, 16, 18, 20, 22 and 24 are representative amino acid sequences, each comprising a single ACP domain within SEQ ID NO: 12.

In some embodiments, the present invention is directed to nucleic acid molecules comprising a polynucleotide sequence encoding a polypeptide, wherein the polypeptide comprises an amino acid sequence at least 80% identical to an amino acid sequence within SEQ ID NO:79, wherein the polypeptide comprises ACP activity. In some embodiments, the amino acid sequence is at least 80% identical to an amino acid sequence within SEQ ID NO:79 comprising one, two, three, four, five, six, seven, eight, nine, or ten ACP domains, wherein the polypeptide comprises ACP activity associated with one or more ACP domains. SEQ ID NOs:81, 83, 85, 87, 89, 91, 93, 95, 97, and 99 are representative amino acid sequences, each comprising a single ACP domain within SEQ ID NO:79.

In some embodiments, the present invention is directed to a nucleic acid molecule comprising a polynucleotide sequence encoding a polypeptide, wherein the polypeptide comprises an amino acid sequence at least 80% identical to SEQ ID NO:26 or SEQ ID NO:101, and wherein the polypeptide comprises KR activity.

In some embodiments, the present invention is directed to a nucleic acid molecule comprising a polynucleotide sequence encoding a polypeptide, wherein the polypeptide comprises an amino acid sequence at least 80% identical to SEQ ID NO:28 or SEQ ID NO:119, and wherein the polypeptide comprises DH activity.

In some embodiments, the present invention is directed to nucleic acid molecules comprising a polynucleotide sequence encoding a polypeptide, wherein the polypeptide comprises an amino acid sequence at least 80% identical to SEQ ID NO:4 or SEQ ID NO:71, wherein the polypeptide comprises a PUPA synthase activity selected from the group consisting of KS activity, CLF activity, AT activity, ER activity, and combinations thereof.

In some embodiments, the present invention is directed to a nucleic acid molecule comprising a polynucleotide sequence encoding a polypeptide, wherein the polypeptide comprises an amino acid sequence at least 80% identical to SEQ ID NO:30 or SEQ ID NO:103, and wherein the polypeptide comprises KS activity.

In some embodiments, the present invention is directed to a nucleic acid molecule comprising a polynucleotide sequence encoding a polypeptide, wherein the polypeptide comprises an amino acid sequence at least 80% identical to SEQ ID NO:32 or SEQ ID NO:105, and wherein the polypeptide comprises CLF activity.

In some embodiments, the present invention is directed to a nucleic acid molecule comprising a polynucleotide sequence encoding a polypeptide, wherein the polypeptide comprises an amino acid sequence at least 80% identical to SEQ ID NO:34 or SEQ ID NO:107, and wherein the polypeptide comprises AT activity.

In some embodiments, the present invention is directed to a nucleic acid molecule comprising a polynucleotide sequence encoding a polypeptide, wherein the polypeptide comprises an amino acid sequence at least 80% identical to SEQ ID NO:36 or SEQ ID NO:109, and wherein the polypeptide comprises ER activity.

In some embodiments, the present invention is directed to a nucleic acid molecule comprising a polynucleotide sequence encoding a polypeptide, wherein the polypeptide comprises an amino acid sequence at least 80% identical to SEQ ID NO:6 or SEQ ID NO:73, wherein the polypeptide comprises a PUFA synthase activity selected from the group consisting of DH activity, ER activity, and combinations thereof.

In some embodiments, the present invention is directed to a nucleic acid molecule comprising a polynucleotide sequence encoding a polypeptide, wherein the polypeptide comprises an amino acid sequence at least 80% identical to SEQ ID NO:38, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:40, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO: 111, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:113, and wherein the polypeptide comprises DH activity.

In some embodiments, the present invention is directed to a nucleic acid molecule comprising a polynucleotide sequence encoding a polypeptide, wherein the polypeptide comprises an amino acid sequence at least 80% identical to SEQ ID NO:42 or SEQ ID NO:115, and wherein the polypeptide comprises ER activity.

In some embodiments, the nucleic acid molecules comprise polynucleotide sequences at least about 80%, 85%, or 90% identical to the polynucleotide sequences reported herein, or at least about 95%, 96%, 97%, 98%, 99%, or 100% identical to the polynucleotide sequences reported herein. The term "percent identity," as known in the art, is a relationship between two or more amino acid sequences or two or more polynucleotide sequences, as determined by comparing the sequences. In the art, "identity" also means the degree of sequence relatedness between amino acid or polynucleotide sequences, as the case may be, as determined by the match between strings of such sequences.

By a nucleic acid molecule having a polynucleotide sequence at least, for example, 95% "identical" to a reference polynucleotide sequence of the present invention, it is intended that the polynucleotide sequence of the nucleic acid molecule is identical to the reference sequence except that the polynucleotide sequence can include up to five nucleotide differences per each 100 nucleotides of the reference polynucleotide sequence. In other words, to obtain a nucleic acid molecule having a polynucleotide sequence at least 95% identical to a reference polynucleotide sequence, up to 5% of the nucleotides in the reference sequence can be deleted or substituted with another nucleotide, or a number of nucleotides up to 5% of the total nucleotides in the reference sequence can be inserted into the reference sequence.

As a practical matter, whether any particular polynucleotide sequence or amino acid sequence is at least 80%, 85%, 90%, 95%, 96%, 97%, 98% or 99% identical to a polynucleotide sequence or amino acid sequence of the present invention can be determined conventionally using known computer programs. A method for determining the best overall match between a query sequence (a sequence of the present invention) and a subject sequence can be determined using the alignment of sequences and calculation of identity scores. The alignments were done using the computer program AlignX, which is a component of the Vector NTI Suite 10.0 package from Invitrogen (www.invitrogen.com). The alignments were performed using a ClustalW alignment (Thompson, J. D., et al. *Nucl. Acids Res.* 22: 4673-4680 (1994)) for both amino acid and polynucleotide sequence alignments. The default scoring matrices Blosum62mt2 and swgapdnamt were used for amino acid and polynucleotide sequence alignments, respectively. For amino acid sequences, the default gap opening penalty is 10 and the gap extension penalty 0.1. For polynucleotide sequences, the default gap opening penalty is 15 and the gap extension penalty is 6.66.

The present invention is directed to an isolated nucleic acid molecule comprising a polynucleotide sequence encoding a polypeptide comprising PUPA synthase activity selected from the group consisting of KS activity, MAT activity, ACP activity, KR activity, CLF activity, AT activity, ER activity, DH activity, and combinations thereof, wherein the polynucleotide hybridizes under stringent conditions to the complement of any of the polynucleotide sequences described above.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified. See, e.g., Sambrook J. and Russell D. 2001. Molecular cloning: A laboratory manual, 3rd edition. Cold Spring Harbor Laboratory Press, Cold Spring Harbor, New York. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

The present invention is directed to an isolated nucleic acid molecule comprising a polynucleotide sequence that is fully complementary to any of the polynucleotide sequences described above. The term "complementary" is used to describe the relationship between nucleotide bases that are capable to hybridizing to one another. For example, with respect to DNA, adenosine is complementary to thymine and cytosine is complementary to guanine.

In certain embodiments, the polynucleotide or nucleic acid is DNA. In the case of DNA, a nucleic acid molecule comprising a polynucleotide sequence which encodes a polypeptide can normally include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a polynucleotide sequence encoding a polypeptide if the promoter was capable of effecting transcription of that polynucleotide sequence. The promoter can be a cell-specific promoter that directs substantial transcription of the DNA only in predetermined cells. In general, a coding region is located 3' to a promoter. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths can have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

Suitable regulatory regions include nucleic acid regions located upstream (5' non-coding sequences), within, or downstream (3' non-coding sequences) of a coding region, and which influence the transcription, RNA processing or stability, or translation of the associated coding region. Regulatory regions can include promoters, translation leader sequences, RNA processing sites, effector binding sites, and stem-loop structures. Other transcription control elements, besides a promoter, for example enhancers, operators, repressors, and transcription termination signals, can be operably associated with the polynucleotide to direct cell-specific transcription. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

In certain aspects of the invention, polynucleotide sequences having at least 20 bases, at least 30 bases, or at least 50 bases and that hybridize to a polynucleotide sequence of the present invention can be employed as PCR primers. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. Generally two short segments of the instant sequences can be used in polymerase chain reaction (PCR) protocols to amplify longer nucleic acid fragments encoding homologous genes from DNA or RNA. The polymerase chain reaction can also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence can be based upon sequences derived from the cloning vector.

In addition, specific primers can be designed and used to amplify a part of or full-length of the instant sequences. The resulting amplification products can be labeled directly dming amplification reactions or labeled after amplification reactions, and used as probes to isolate full length DNA fragments under conditions of appropriate stringency.

Therefore, the nucleic acid molecules of the present invention can be used to isolate genes encoding homologous proteins from the same or other species or bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, Mullis et al., U.S. Pat. No. 4,683,202; ligase chain reaction (LCR) (Tabor, S. et al., *Proc. Acad. Sci. USA* 82: 1074 (1985)); or strand displacement amplification (SDA; Walker, et al., *Proc. Natl. Acad. Sci. U.S.A.* 89: 392 (1992)).

In some embodiments, the isolated nucleic acid molecules of the present invention are used to isolate homologous nucleic acid molecules from other organisms in order to identify PUPA synthases that produce similar or improved PUPA profiles. In some embodiments, the isolated nucleic acid molecules of the present invention are used to isolate homologous nucleic acid molecules from other organisms that are involved in producing high amounts of DHA.

The nucleic acid molecules of the present invention also comprise polynucleotide sequences encoding a PUPA synthase gene, a domain of a PUPA synthase gene, or a fragment of the PUPA synthase gene fused in frame to a marker sequence which allows for detection of the polypeptide of the present invention. Marker sequences include auxotrophic or dominant markers known to one of ordinary skill in the art such as ZEO (zeocin), NEO (0418), hygromycin, arsenite, HPH, NAT, and the like.

The present invention also encompasses variants of the PUPA synthase gene. Variants can contain alterations in the coding regions, non-coding regions, or both. Examples are polynucleotide sequence variants containing alterations which produce silent substitutions, additions, or deletions, but do not alter the properties or activities of the encoded polypeptide. In certain embodiments, polynucleotide sequence variants are produced by silent substitutions due to the degeneracy of the genetic code. In further embodiments, polynucleotide sequence variants can be produced for a variety of reasons, e.g., to optimize codon expression for a particular host (e.g., changing codons in the thraustochytrid mRNA to those preferred by other organisms such as *E. coli* or *Saccharomyces cerevisiae*).

Also provided in the present invention are allelic variants, orthologs, and/or species homologs. Procedures known in the art can be used to obtain full-length genes, allelic variants, splice variants, full-length coding portions, orthologs, and/or species homologs of the genes described herein using information from the sequences disclosed herein. For example, allelic variants and/or species homologs can be isolated and identified by making suitable probes or primers from the sequences provided herein and screening a suitable nucleic acid source for allelic variants and/or the desired homologue.

The present invention is directed to a recombinant nucleic acid molecule comprising any of the nucleic acid molecules described above or combinations thereof and a transcription control sequence. In some embodiments, the recombinant nucleic acid molecule is a recombinant vector.

The present invention is directed to a method for making a recombinant vector comprising inserting one or more isolated nucleic acid molecules as described herein into a vector.

The vectors of this invention can be, for example, a cloning vector or an expression vector. The vector can be, for example, in the form of a plasmid, a viral particle, a phage, etc.

The polynucleotide sequences of the invention can be included in any one of a variety of expression vectors for expressing a polypeptide. Such vectors include chromosomal, nonchromosomal, and synthetic DNA or RNA sequences, e.g., derivatives of SV40; bacterial plasmids; and yeast plasmids. However, any other appropriate vector known to one of ordinary skill in the art can be used.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the ail.

The present invention also includes recombinant constructs comprising one or more of the polynucleotide sequences described above. The constructs comprise a vector, such as a plasmid or viral vector, into which one or more sequences of the invention has been inserted, in a forward or reverse orientation. In one aspect of this embodiment, the construct further comprises regulatory sequences, including, for example, a promoter, operably associated to the sequence. Large numbers of suitable vectors and promoters are known to those of skill in the art, and are commercially available.

Polypeptides

The present invention is directed to isolated polypeptides comprising amino acid sequences for PUFA synthase proteins and domains derived from the isolated microorganisms deposited as ATCC Accession Nos. PTA-9695 and PTA-10212.

As used herein, the term "polypeptide" is intended to encompass a singular "polypeptide" as well as plural "polypeptides" and refers to a molecule composed of monomers (amino acids) linearly linked by amide bonds (also known as peptide bonds). The term "polypeptide" refers to any chain or chains of two or more amino acids and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids.

Polypeptides as described herein can include fragment, variant, or derivative molecules thereof without limitation. The terms "fragment," "variant," "derivative" and "analog" when referring to a polypeptide include any polypeptide which retains at least some biological activity. Polypeptide fragments can include proteolytic fragments, deletion fragments, and fragments which more easily reach the site of action when delivered to an animal. Polypeptide fragments further include any portion of the polypeptide which comprises an antigenic or immunogenic epitope of the native polypeptide, including linear as well as three-dimensional epitopes. Polypeptide fragments can comprise variant regions, including fragments as described above, and also polypeptides with altered amino acid sequences due to amino acid substitutions, deletions, or insertions. Variants can occur naturally, such as an allelic variant. By an "allelic variant" is intended alternate forms of a gene occupying a given locus on a chromosome of an organism. Non-naturally occurring variants can be produced using art-known mutagenesis techniques. Polypeptide fragments of the invention can comprise conservative or non-conservative amino acid substitutions, deletions, or additions. Variant polypeptides can also be referred to herein as "polypeptide analogs." Polypeptide fragments of the present invention can also include derivative molecules. As used herein a "derivative" of a polypeptide or a polypeptide fragment refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and omithine can be substituted for lysine.

Polypeptides of the invention can be encoded by any of the nucleic acid molecules of the invention.

The present invention is directed to isolated polypeptides comprising amino acid sequences that are at least 80% identical to the amino acid sequences of Pfa1p (SEQ ID NO:2 or SEQ ID NO:69), Pfa2p (SEQ ID NO:4 or SEQ ID NO:71), Pfa3p (SEQ ID NO:6 or SEQ ID NO:73), and combinations thereof, wherein the polypeptides comprise one or more PUFA synthase activities.

The present invention is directed to polypeptides comprising amino acid sequences that are at least 80% identical to the amino acid sequences of one or more PUFA synthase domains of the PUF A synthases of the invention.

In some embodiments, the present invention is directed to polypeptides comprising amino acid sequences that are at least 80% identical to an amino acid sequence within Pfa1p (SEQ ID NO:2 or SEQ ID NO:69) comprising one or more PUFA synthase domains. In some embodiments, the polypeptide comprises an amino acid sequence at least 80% identical to an amino acid sequence within Pfa1 p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO:77), an ACP domain (such as any one of SEQ ID NOs:14, 16, 18, 20, 22, 24, 81, 83, 85, 87, 89, 91, 93, 95, 97, or 99), a combination of two or more ACP domains such as two, three, four, five, six, seven, eight, nine, or ten ACP domains, including tandem domains (SEQ ID NO:12 or SEQ ID NO:79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises two or more amino acid sequences, wherein each of the at least two or more amino acid sequences is 80% identical to an amino acid sequence within Pfa1 p (SEQ ID NO:2 or SEQ ID NO:69) comprising one or more PUFA synthase domains. In some embodiments, the at least two or more amino acid sequences are 80% identical to the same amino acid sequence within Pfa1p (SEQ ID NO:2 or SEQ ID NO:69) comprising one or more PUFA synthase domains. In some embodiments, the at least two or more amino acid sequences are 80% identical to different amino acid sequences within Pfa1p (SEQ ID NO:2 or SEQ ID NO:69) that each comprise one or more PUFA synthase domains. In some embodiments, the at least two or more amino acid sequences are 80% identical to different amino acid sequences within Pfa1 p (SEQ ID NO:2 or SEQ ID NO:69), wherein the at least two or more amino acid sequences are located in the same order or a different order in the polypeptide as compared to the order of the corresponding domains within Pfa1p (SEQ ID NO:2 or SEQ ID NO:69). In some embodiments, the at least two or more amino acid sequences are 80% identical to an amino acid sequence within Pfa1 p (SEQ ID NO:2 or SEQ ID NO:69) comprising one or more PUFA synthase domains such as a KS domain (SEQ ID NO:8 or SEQ ID NO:75), a MAT domain (SEQ ID NO:10 or SEQ ID NO:77), an ACP domain (such as any one of SEQ ID NOs:14, 16, 18, 20, 22, 24, 81, 83, 85, 87, 89, 91, 93, 95, 97, or 99), a combination of two, three, four, five, six, seven, eight, nine, or ten ACP domains, including tandem domains (SEQ ID NO:12 or SEQ ID NO:79, and portions thereof), a KR domain (SEQ ID NO:26 or SEQ ID NO:101), a DH domain (SEQ ID NO:28 or SEQ ID NO:119), and combinations thereof. In some embodiments, the polypeptide comprises one or more amino acid sequences within Pfa1p (SEQ ID NO:2 or SEQ ID NO:69) comprising one or more PUPA synthase domains, including one or more copies of any individual domain in combination with one or more copies of any other individual domain.

In some embodiments, the present invention is directed to polypeptides comprising amino acid sequences that are at least 80% identical to an amino acid sequence within Pfa2p (SEQ ID NO:4 or SEQ ID NO:71) comprising one or more PUPA synthase domains. In some embodiments, the polypeptide comprises an amino acid sequence at least 80% identical to an amino acid sequence within Pfa2p (SEQ ID NO:4 or SEQ ID NO:71) comprising one or more PUPA synthase domains such as a KS domain (SEQ ID NO:30 or SEQ ID NO:103), a CLP domain (SEQ ID NO:32 or SEQ ID NO:105), an AT domain (SEQ ID NO:34 or SEQ ID NO:107), an ER domain (SEQ ID NO:36 or SEQ ID NO:109), and combinations thereof. In some embodiments, the polypeptide comprises two or more amino acid sequences, wherein each of the at least two or more amino acid sequences is 80% identical to an amino acid sequence within Pfa2p (SEQ ID NO:4 or SEQ ID NO:71) comprising one or more PUPA synthase domains. In some embodiments, the at least two or more amino acid sequences are 80% identical to the same amino acid sequence within Pfa2p (SEQ ID NO:4 or SEQ ID NO:71). In some embodiments, the at least two or more amino acid sequences are 80% identical to different amino acid sequences within Pfa2p (SEQ ID NO:4 or SEQ ID NO:71) that each comprise one or more PUPA synthase domains. In some embodiments, the at least two or more amino acid sequences are 80% identical to different amino acid sequences within Pfa2p (SEQ ID NO:4 or SEQ ID NO:71), wherein the at least two or more amino acid sequences are located in the same order or a different order in the polypeptide as compared to the order of the corresponding domains within Pfa2p (SEQ ID NO:4 or SEQ ID NO:71). In some embodiments, the at least two or more amino acid sequences are 80% identical to an amino acid sequence within Pfa2p (SEQ ID NO:4 or SEQ ID NO:71) comprising one or more PUPA synthase domains such as a KS domain (SEQ ID NO:30 or SEQ ID NO:103), a CLP domain (SEQ ID NO:32 or SEQ ID NO:105), an AT domain (SEQ ID NO:24 or SEQ ID NO:107), an ER domain (SEQ ID NO:36 or SEQ ID NO:109), and combinations thereof. In some embodiments, the polypeptide comprises one or more amino acid sequences sequence within Pfa2p (SEQ ID NO:4 or SEQ ID NO:71) comprising one or more PUPA synthase domains, including one or more copies of any individual domain in combination with one or more copies of any other individual domain.

In some embodiments, the present invention is directed to polypeptides comprising amino acid sequences that are at least 80% identical to an amino acid sequence within Pfa3p (SEQ ID NO:6 or SEQ ID NO:73) comprising one or more PUPA synthase domains. In some embodiments, the polypeptide comprises an amino acid sequence at least 80% identical to an amino acid sequence within Pfa3p (SEQ ID NO:6 or SEQ ID NO:73) comprising one or more PUPA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises two or more amino acid sequences, wherein each of the at least two or more amino acid sequences is 80% identical to an amino acid sequence within Pfa3p (SEQ ID NO:6 or SEQ ID NO:73) comprising one or more PUPA synthase domains. In some embodiments, the at least two or more amino acid sequences are 80% identical to the same amino acid sequence within Pfa3p (SEQ ID NO:6 or SEQ ID NO:73) comprising one or more PUPA synthase domains. In some embodiments, the at least two or more amino acid sequences are 80% identical to different amino acid sequences within Pfa3p (SEQ ID NO:6 or SEQ ID NO:73) that each comprise one or more PUPA synthase domains. In some embodiments, the at least two or more amino acid sequences are 80% identical to different amino acid sequences within Pfa3p (SEQ ID NO:6 or SEQ ID NO:73), wherein the at least two or more amino acid sequences are located in the same order or a different order in the polypeptide as compared to the order of the corresponding domains within Pfa3p (SEQ ID NO:6 or SEQ ID NO:73). In some embodiments, the at least two or more amino acid sequences are 80% identical to an amino acid sequence within Pfa3p (SEQ ID NO:6 or SEQ ID NO:73) comprising one or more PUPA synthase domains such as a DH domain (such as SEQ ID NO:38, SEQ ID NO:40, SEQ ID NO:111, or SEQ ID NO:113), an ER domain (SEQ ID NO:42 or SEQ ID NO:115), and combinations thereof. In some embodiments, the polypeptide comprises one or more amino acid sequences within Pfa3p (SEQ ID NO:6 or SEQ ID NO:73) comprising one or more PUPA synthase domains, including one or more copies of any individual domain in combination with one or more copies of any other individual domain.

In some embodiments, the present invention is directed to a polypeptide comprising an amino acid sequence at least 80% identical to SEQ ID NO:2 or SEQ ID NO:69, wherein the polypeptide comprises a PUPA synthase activity selected from the group consisting of KS activity, MAT activity, ACP activity, KR activity, DH activity, and combinations thereof.

In some embodiments, the present invention is directed to a polypeptide comprising an amino acid sequence at least 80% identical to SEQ ID NO:8 or SEQ ID NO:75, wherein the polypeptide comprises KS activity.

In some embodiments, the present invention is directed to a polypeptide comprising an amino acid sequence at least 80% identical to SEQ ID NO:10 or SEQ ID NO:77, wherein the polypeptide comprises MAT activity.

In some embodiments, the present invention is directed to a polypeptide comprising an amino acid sequence at least 80% identical to such as any one of SEQ ID NOs:14, 16, 18, 20, 22, 24, 81, 83, 85, 87, 89, 91, 93, 95, 97, or 99, wherein the polypeptide comprises ACP activity.

In some embodiments, the present invention is directed to a polypeptide comprising an amino acid sequence at least 80% identical to SEQ ID NO:12 or SEQ ID NO:79, wherein the polypeptide comprises ACP activity.

In some embodiments, the present invention is directed to a polypeptide comprising an amino acid sequence at least 80% identical to an amino acid sequence within SEQ ID NO:12, wherein the polypeptide comprises ACP activity. In some embodiments, the amino acid sequence is at least 80% identical to an amino acid sequence within SEQ ID NO:12 comprising one, two, three, four, five, or six ACP domains, wherein the polypeptide comprises ACP activity associated with one or more ACP domains. SEQ ID NOs:14, 16, 18, 20, 22, and 24 are representative amino acid sequences comprising a single ACP domain within SEQ ID NO: 12.

In some embodiments, the present invention is directed to a polypeptide comprising an amino acid sequence at least 80% identical to an amino acid sequence within SEQ ID NO:79, wherein the polypeptide comprises ACP activity. In some embodiments, the amino acid sequence is at least 80% identical to an amino acid sequence within SEQ ID NO:79 comprising one, two, three, four, five, six, seven, eight, nine, or ten ACP domains, wherein the polypeptide comprises ACP activity associated with one or more ACP domains. SEQ ID NOs:81, 83, 85, 87, 89, 91, 93, 95, 97, and 99 are representative amino acid sequences comprising a single ACP domain within SEQ ID NO:79.

In some embodiments, the present invention is directed to a polypeptide comprising an amino acid sequence at least 80% identical to SEQ ID NO:26 or SEQ ID NO:101, wherein the polypeptide comprises KR activity.

In some embodiments, the present invention is directed to a polypeptide comprising an amino acid sequence at least 80% identical to SEQ ID NO:28 or SEQ ID NO:119, wherein the polypeptide comprises DH activity.

In some embodiments, the present invention is directed to a polypeptide comprising an amino acid sequence at least 80% identical to SEQ ID NO:4 or SEQ ID NO:71, wherein the polypeptide comprises a PUPA synthase activity selected from the group consisting of KS activity, CLP activity, AT activity, ER activity, and combinations thereof.

In some embodiments, the present invention is directed to a polypeptide comprising an amino acid sequence at least 80% identical to SEQ ID NO:30 or SEQ ID NO:103, wherein the polypeptide comprises KS activity.

In some embodiments, the present invention is directed to a polypeptide comprising an amino acid sequence at least 80% identical to SEQ ID NO:32 or SEQ ID NO:105, wherein the polypeptide comprises CLP activity.

In some embodiments, the present invention is directed to a polypeptide comprising an amino acid sequence at least 80% identical to SEQ ID NO:34 or SEQ ID NO:107, wherein the polypeptide comprises AT activity.

In some embodiments, the present invention is directed to a polypeptide comprising an amino acid sequence at least 80% identical to SEQ ID NO:36 or SEQ ID NO:109, wherein the polypeptide comprises ER activity.

In some embodiments, the present invention is directed to a polypeptide comprising an amino acid sequence at least 80% identical to SEQ ID NO:6 or SEQ ID NO:73, wherein the polypeptide comprises a PUPA synthase activity selected from the group consisting of DH activity, ER activity, and combinations thereof.

In some embodiments, the present invention is directed to a polypeptide comprising an amino acid sequence at least 80% identical to SEQ ID NO:38, wherein the polypeptide comprises DH activity.

In some embodiments, the present invention is directed to a polypeptide comprising an amino acid sequence at least 80% identical to SEQ ID NO:40, wherein the polypeptide comprises DH activity.

In some embodiments, the present invention is directed to a polypeptide comprising an amino acid sequence at least 80% identical to SEQ ID NO:111, wherein the polypeptide comprises DH activity.

In some embodiments, the present invention is directed to a polypeptide comprising an amino acid sequence at least 80% identical to SEQ ID NO:113, wherein the polypeptide comprises DH activity.

In some embodiments, the present invention is directed to a polypeptide comprising an amino acid sequence at least 80% identical to SEQ ID NO:42 or SEQ ID NO:115, wherein the polypeptide comprises ER activity.

In some embodiments, the polypeptides comprise amino acid sequences at least about 80%, 85%, or 90% identical to the amino acid sequences reported herein, or at least about 95%, 96%, 97%, 98%, 99%, or 100% identical to the amino acid sequences reported herein.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide having an amino acid sequence that is at least 80%, 85%, 90%, 95%, 96%, 97%, 98% or 99% identical to, for instance, the amino acid sequence of the present invention can be determined conventionally using known computer programs. As discussed above, a method for determining the best overall match between a query sequence (a sequence of the present invention) and a subject sequence can be determined using the alignment of sequences and calculation of identity scores. The alignments were done using the computer program AlignX, which is a component of the Vector NTI Suite 10.0 package from Invitrogen (www.invitrogen.com). The alignments were performed using a ClustalW alignment (J. Thompson et al., *Nucleic Acids Res.* 22(22): 4673-4680 (1994). The default scoring matrix Blosum62mt2 was used. The default gap opening penalty is 10 and the gap extension penalty O.I.

In further aspects of the invention, nucleic acid molecules having polynucleotide sequences at least 80%, 85%, 90%, 95%, 96%, 97%, 98% or 99% identical to the polynucleotide sequences disclosed herein, encode a polypeptide having one or more PUPA synthase activities. Polypeptides having one or more PUPA synthase activities exhibit one or more activities similar to, but not necessarily identical to, one or more activities of a PUPA synthase of the present invention.

Of course, due to the degeneracy of the genetic code, one of ordinary skill in the art will immediately recognize that a large portion of the nucleic acid molecules having a polynucleotide sequence at least 80%, 85%, 90%, 95%, 96%, 97%, 98%, or 99% identical to the polynucleotide sequences described herein will encode polypeptides "having PUPA synthase functional activity." In fact, since degenerate variants of any of these polynucleotide sequences all encode the same polypeptide, in many instances, it can be predicted by the skilled artisan based on knowledge of conservative substitutions as well as conserved functional domains, which polypeptides will exhibit activity. In certain aspects of the invention, the polypeptides and polynucleotides of the present invention are provided in an isolated form, e.g., purified to homogeneity. Alternatively, the polypeptides and polynucleotides of the invention can be synthetically produced by conventional synthesizers.

As known in the art "similarity" between two polypeptides is determined by comparing the amino acid sequence and conserved amino acid substitutes thereto of the polypeptide to the sequence of a second polypeptide.

In some embodiments, a polypeptide of the invention is a fusion polypeptide.

As used herein, "fusion polypeptide" means a polypeptide comprising a first polypeptide linearly connected, via peptide bonds, to a second polypeptide. The first polypeptide and the second polypeptide can be identical or different, and they can be directly connected, or connected via a peptide linker. As used herein, the terms "linked," "fused," or "fusion" are used interchangeably. These terms refer to the joining together of two more elements or components by any means including chemical conjugation or recombinant means. An "in-frame fusion" refers to the joining of two or more open reading frames to form a continuous longer open reading frame, in a manner that maintains the correct reading frame of the original open reading frames. Thus, the resulting recombinant fusion protein is a single protein containing two or more segments that correspond to polypeptides encoded by the original open reading frames (which segments are not normally so joined in nature). Although the reading frame is thus made continuous throughout the fused segments, the segments can be physically or spatially separated by, for example, in-frame linker sequence. A "linker" sequence is a series of one or more amino acids separating two polypeptide coding regions in a fusion protein.

The invention is directed to a composition comprising one or more polypeptides of the invention and a biologically acceptable carrier.

In some embodiments, the composition includes a biologically acceptable "excipient," wherein the excipient is a component, or mixture of components, that is used in a composition of the present invention to give desirable characteristics to the composition, and also include carriers. "Biologically acceptable" means a compound, material, composition, salt, and/or dosage form which is, within the scope of sound medical judgment, suitable for contact with the tissues of living cells without excessive toxicity, irritation, inflammatory response, or other problematic complications over the desired duration of contact commensurate with a reasonable benefit/risk ratio. Various excipients can be used. In some embodiments, the excipient can be, but is not limited to, an alkaline agent, a stabilizer, an antioxidant, an adhesion agent, a separating agent, a coating agent, an exterior phase component, a controlled-release component, a solvent, a surfactant, a humectant, a buffering agent, a filler, an emollient, or combinations thereof. Excipients in addition to those discussed herein can include excipients listed in, though not limited to, *Remington: The Science and Practice of Pharmacy*, $21^{st}$ ed. (2005). Inclusion of an excipient in a particular classification herein (e.g., "solvent") is intended to illustrate rather than limit the role of the excipient. A particular excipient can fall within multiple classifications.

The present invention further relates to a fragment, variant, derivative, or analog of any of the polypeptide disclosed herein.

The polypeptide of the present invention can be a recombinant polypeptide, a natural polypeptide, or a synthetic polypeptide.

Host Cells

The present invention is directed to a host cell that expresses any of the nucleic acid molecules and recombinant nucleic acid molecules described above as well as combinations thereof.

The term "expression" as used herein refers to a process by which a gene produces a biochemical, for example, a RNA or polypeptide. The process includes any manifestation of the functional presence of the gene within the cell including, without limitation, gene knockdown as well as both transient expression and stable expression. It includes, without limitation, transcription of the gene into messenger RNA (mRNA), transfer RNA (tRNA), small hairpin RNA (shRNA), small interfering RNA (siRNA), or any other RNA product, and the translation of such mRNA into polypeptide(s). If the final desired product is biochemical, expression includes the creation of that biochemical and any precursors.

To produce one or more desired polyunsaturated fatty acids, a host cell can be genetically modified to introduce a PUPA synthase system of the present invention into the host cell.

When genetically modifying organisms to express a PUPA synthase system according to the present invention, some host organisms can endogenously express accessory proteins that are required in conjunction with a PUPA synthase system in order to produce PUPAs. However, it may be necessary to transform some organisms with nucleic acid molecules encoding one or more accessory protein(s) in order to enable or to enhance production of PUPAs by the organism, even if the organism endogenously produces a homologous accessory protein. Some heterologous accessory proteins can operate more effectively or efficiently with the transformed PUPA synthase proteins than the host cells' endogenous accessory protein(s).

Accessory proteins are defined herein as proteins that are not considered to be part of the core PUPA synthase system (i.e., not part of the PUPA synthase enzyme complex itself) but which may be necessary for PUFA production or efficient PUFA production using the core PUPA synthase enzyme complex of the present invention. For example, in order to produce PUFAs, a PUPA synthase system must work with an accessory protein that transfers a 4'-phosphopantetheinyl moiety from coenzyme A to the acyl carrier protein (ACP) domain(s). Therefore, a PUPA synthase system can be considered to include at least one 4'-phosphopantetheinyl transferase (PPTase) domain, or such a domain can be considered to be an accessory domain or protein to the PUFA synthase system. Structural and functional characteristics of PPTases have been described in detail, e.g., in U.S. Appl. Publ. Nos. 2002/0194641; 2004/0235127; and 2005/0100995.

A domain or protein having 4'-phosphopantetheinyl transferase (PPTase) biological activity (function) is characterized as the enzyme that transfers a 4'-phosphopantetheinyl moiety from Coenzyme A to the acyl carrier protein (ACP). This transfer to an invariant serine reside of the ACP activates the inactive apo-form to the holo-form. In both polyketide and fatty acid synthesis, the phosphopanthetheine group forms thioesters with the growing acyl chains. The PPTases are a family of enzymes that have been well characterized in fatty acid synthesis, polyketide synthesis, and non-ribosomal peptide synthesis. The sequences of many PPTases are known, crystal structures have been determined (e.g., Reuter K., et al., *EMBO J.* 18(23):6823-31 (1999)), and mutational analysis has identified amino acid residues important for activity (Mofid M. R., et al., *Biochemistry* 43(14):4128-36 (2004)).

One heterologous PPTase which has been previously demonstrated to recognize *Schizochytrium* ACP domains as substrates is the Het I protein of *Nostoc* sp. PCC 7120 (formerly called *Anabaena* sp. PCC 7120). Het I is present in a cluster of genes in *Nostoc* known to be responsible for the synthesis of long chain hydroxy-fatty acids that are a component of a glyco-lipid layer present in heterocysts of that organism (Black and Wolk, *J. Bacterial.* 176: 2282-2292 (1994); Campbell et al., *Arch. Microbial.* 167: 251-258 (1997)). Het I is likely to activate the ACP domains of a protein, Hgl E, present in that cluster. Sequences and constructs containing Het I have been described in, e.g., U.S. Appl. Publ. No. 2007/0244192, incorporated by reference herein in its entirety.

Another heterologous PPTase which has been demonstrated previously to recognize the *Schizochytrium* ACP domains is Sfp, derived from *Bacillus subtilis*. Sfp has been well characterized and is widely used due to its ability to recognize a broad range of substrates. Based on published sequence information (Nakana, et al., *Molecular and General Genetics* 232: 313-321 (1992)), an expression vector was previously produced for Sfp by cloning the coding region, along with defined up- and downstream flanking DNA sequences, into a pACYC-184 cloning vector. This construct encodes a functional PPTase as demonstrated by its ability to be co-expressed with *Schizochytrium* Orfs in *E. coli* which, under appropriate conditions, resulted in the accumulation of DHA in those cells (see, U.S. Appl. Publ. No. 2004/0235127, incorporated by reference herein in its entirety).

Host cells can include microbial cells; animal cells; plant cells; and insect cells. Representative examples of appropriate hosts include bacterial cells; thermophilic or mesophlic bacteria; marine bacteria; thraustochytrids; fungal cells, such as yeast; plant cells; insect cells; and isolated animal cells. Host cells can be either untransfected cells or cells that are already transfected with at least one other recombinant nucleic acid molecule. Host cells can also include transgenic cells that have been engineered to express a PUFA synthase. The selection of an appropriate host is deemed to be within the scope of those skilled in the art from the teachings herein.

Host cells include any microorganism of the order *Thraustochytriales*, such as microorganisms from a genus including, but not limited to: *Thraustochytrium, Labyrinthuloides, Japonochytrium*, and *Schizochytrium*. Species within these genera include, but are not limited to: any *Schizochytrium* species, including *Schizochytrium aggregatum, Schizochytrium limacinum, Schizochytrium minutum*; any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Strains of *Thraustochytriales* include, but are not limited to: *Schizochytrium* sp. (S31) (ATCC 20888); *Schizochytrium* sp. (S8) (ATCC 20889); *Schizochytrium* sp. (LC-RM) (ATCC 18915); *Schizochytrium* sp. (SR21); *Schizochytrium aggregatum* (Goldstein et Belsky) (ATCC 28209); *Schizochytrium limacinum* (Honda et Yokochi) (IFO 32693); *Thraustochytrium* sp. (23B) (ATCC 20891); *Thraustochytrium striatum* (Schneider) (ATCC 24473); *Thraustochytrium aureum* (Goldstein) (ATCC 34304); *Thraustochytrium roseum* (Goldstein) (ATCC 28210); and *Japonochytrium* sp. (L1) (ATCC 28207). Other examples of suitable host microorganisms for genetic modification include, but are not limited to, yeast including *Saccharomyces cerevisiae, Saccharomyces carlsbergensis*, or other yeast such as *Candida, Kluyveromyces*, or other fungi, for example, filamentous fungi such as *Aspergillus, Neurospora, Penicillium*, etc. Bacterial cells also can be used as hosts. This includes *Escherichia coli*, which can be useful in fermentation processes. Alternatively, a host such as a *Lactobacillus* species or *Bacillus* species can be used as a host.

Plant host cells include, but are not limited to, any higher plants, including both dicotyledonous and monocotyledonous plants, and consumable plants, including crop plants and plants used for their oils. Such plants can include, for example: canola, soybeans, rapeseed, linseed, corn, safflowers, sunflowers, and tobacco. Other plants include those plants that are known to produce compounds used as pharmaceutical agents, flavoring agents, neutraceutical agents, functional food ingredients, cosmetically active agents, or plants that are genetically engineered to produce these compounds/agents. Thus, any plant species or plant cell can be selected. Examples of plants and plant cells, and plants grown or derived therefrom, include, but are not limited to, plants and plant cells obtainable from canola (*Brassica rapa* L.); canola cultivars NQC02CNX12 (ATCC PTA-6011), NQC02CNX21 (ATCC PTA-6644), and NQC02CNX25 (ATCC PTA-6012) as well as cultivars, breeding cultivars, and plant parts derived from canola cultivars NQC02CNX12, NQC02CNX21, and NQC02CNX25 (see, U.S. Pat. Nos. 7,355,100, 7,456,340, and 7,348,473, respectively); soybean (*Glycine max*); rapeseed (*Brassica* spp.); linseed/flax (*Linum usitatissimum*); maize (corn) (*Zea mays*); safflower (*Carthamus tinctorius*); sunflower (*Helianthus annuus*); tobacco (*Nicotiana tabacum*); *Arabidopsis thaliana*, Brazil nut (*Betholettia excelsa*); castor bean (*Ricinus communis*); coconut (*Cocus nucifera*); coriander (*Coriandrum sativum*); cotton (*Gossypium* spp); groundnut (*Arachis hypogaea*); jojoba (*Simmondsia chinensis*); mustard (*Brassica* spp. and *Sinapis alba*); oil palm (*Elaeis guineeis*); olive (*Olea eurpaea*); lice (*Oryza sativa*); squash (*Cucurbita maxima*); barley (*Hordeum vulgare*); wheat (*Traeticum aestivum*); and duckweed (*Lemnaceae* sp). Plant lines from these and other plants can be produced, selected, or optimized for a desirable trait such as or associated with, but not limited to, seed yield, lodging resistance, emergence, disease resistance or tolerance, maturity, late season plant intactness, plant height, shattering resistance, ease of plant transformation, oil content, or oil profile. Plant lines can be selected through plant breeding such as pedigree breeding, recurrent selection breeding, intercross and backcross breeding, as well as methods such as marker assisted breeding and tilling. See, e.g., U.S. Pat. No. 7,348,473.

Animal cells include any isolated animal cells.

The present invention is directed to a host cell that expresses one or more nucleic acid molecules or recombinant nucleic acid molecules, including vectors, of the invention.

The present invention is directed to a method for making a recombinant host cell comprising introducing a recombinant vector into a host cell.

Host cells can be genetically engineered (transduced or transformed or transfected) with the vectors of this invention that can be, for example, a cloning vector or an expression vector. The vector can be, for example, in the form of a plasmid, a viral pmiicle, a phage, etc. The vector containing a polynucleotide sequence as described herein, as well as an appropriate promoter or control sequence, can be employed to transform an appropriate host to permit expression of the polypeptide encoded by the polynucleotide sequence. The genetic modification of host cells can also include the optimization of genes for preferred or optimal host codon usage.

The engineered host cells can be cultured in conventional nutrient media modified as appropriate for activating promoters, selecting transformants, or amplifying the genes of the present invention. The culture conditions, such as temperature, pH, and the like, are those previously used with the host cell selected for expression, and will be apparent to the ordinarily skilled artisan.

In some embodiments, the present invention is directed to genetically modifying a plant or part of a plant to express a PUFA synthase system described herein, which includes at least the core PUFA synthase enzyme complex. A "part of a plant" or "plant part" as defined herein includes any pmi of a plant, such as, but not limited to, seeds (immature or mature), oils, pollen, embryos, flowers, fruits, shoots, leaves, roots, stems, explants, etc. In some embodiments, the genetically modified plant or part of a plant produces one or more PUFAs, such as EPA, DHA, DPA (n-3 or n-6), ARA, GLA, SDA, other PUFAs, and combinations thereof. Plants are not known to endogenously contain a PUPA synthase system; therefore, the PUPA synthase systems of the present invention can be used to engineer plants with unique fatty acid production capabilities. In a further embodiment, the plant or part of a plant is further genetically modified to express at least one PUPA synthase accessory protein, (e.g., a PPTase). In some embodiments, the plant is an oil seed plant, wherein the oil seeds, and/or the oil in the oil seeds, contain PUPAs produced by the PUPA synthase system. In some embodiments, the genetically modified plants, parts of plants, oil seeds, and/or oils in the oil seeds contain a detectable amount of at least one PUPA that is the product of the PUPA synthase system. In further embodiments, such plants, parts of plants, oil seeds, and/or oils in the oil seeds can be substantially free of intermediate or side products that are not the primary PUPA products of the introduced PUPA synthase system and that are not naturally produced by the endogenous FAS system in the wild-type plants. While wild-type plants produce some short or medium chain PUPAs, such as 18 carbon PUPAs via the FAS system, new or additional PUFAs will be produced in the plant, parts of plants, oil seeds, and/or oils in the oil seeds as a result of genetic modification with a PUPA synthase system described herein.

Genetic modification of a plant can be accomplished using classical strain development and/or molecular genetic techniques. See, U.S. Appl. Publ. No. 2007/0244192. Methods for producing a transgenic plant, wherein a recombinant nucleic acid molecule encoding a desired amino acid sequence is incorporated into the genome of the plant, are known in the art. For example, viral vectors can be used to produce transgenic plants, such as by transformation of a monocotyledonous plant with a viral vector using the methods described in U.S. Pat. Nos. 5,569,597; 5,589,367; and 5,316,931. Methods for the genetic engineering or modification of plants by transformation are also well known in the art, including biological and physical transformation protocols. See, e.g., B. L. Miki et al., *Procedures for Introducing Foreign DNA into Plants*, in METHODS IN PLANT MOLECULAR BIOLOGY AND BIOTECHNOLOGY 67-88 (Glick, B. R. and Thompson, J. E. eds., CRC Press, Inc., Boca Raton, 1993). In addition, vectors and in vitro culture methods for plant cell or tissue transformation and regeneration of plants are available. See, e.g., M. Y. Gruber et al., *Vectors for Plant Transformation*, in METHODS IN PLANT MOLECULAR BIOLOGY AND BIOTECHNOLOGY 89-119 (Glick, B. R. and Thompson, J. E. eds., CRC Press, Inc., Boca Raton, 1993).

A widely utilized method for introducing an expression vector into plants is based on the natural transformation system of *Agrobacterium*. See, e.g., Horsch et al., *Science* 227:1229 (1985) and U.S. Pat. No. 6,051,757. *A. tumefaciens* and *A. rhizogenes* are plant pathogenic soil bacteria which genetically transform plant cells. The Ti and Ri plasmids of *A tumefaciens* and *A. rhizogenes*, respectively, carry genes responsible for genetic transformation of the plant. See, e.g., Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra; Miki et al., supra; Moloney et al., *Plant Cell Reports* 8:238 (1989); U.S. Pat. Nos. 5,177,010; 5,104,310; 5,149,645; 5,469,976; 5,464,763; 4,940,838; 4,693,976; 5,591,616; 5,231,019; 5,463,174; 4,762,785; 5,004,863; and 5,159,135; and European Patent Appl. Nos. 0131624, 120516, 159418, 176112, 116718, 290799, 320500, 604662, 627752, 0267159, and 0292435.

Other methods of plant transformation include microprojectile-mediated transformation, wherein DNA is carried on the surface of microprojectiles. The expression vector is introduced into plant tissues with a biolistic device that accelerates the microprojectiles to speeds sufficient to penetrate plant cell walls and membranes. See, e.g., Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992), and U.S. Pat. Nos. 5,015,580 and 5,322,783. Techniques for accelerating genetic material coated onto microparticles directed into cells is also described, e.g., in U.S. Pat. Nos. 4,945,050 and 5,141,141. Another method for physical delivery of DNA to plants is sonication of target cells. See, e.g., Zhang et al., *Bio/Technology* 9:996 (1991). Alternatively, liposome or spheroplast fusion have been used to introduce expression vectors into plants. See, e.g., Deshayes et al., *EMBO J.*, 4:2731 (1985), Christou et al., *Proc Natl. Acad. Sci. USA* 84:3962 (1987). Direct uptake of DNA into protoplasts using $CaCl_2$ precipitation, DNA injection, polyvinyl alcohol or poly-L-omithine have also been reported. See, e.g., Hain et al., *Mol. Gen. Genet.* 199:161 (1985) and Draper et al., *Plant Cell Physiol.* 23:451 (1982). Electroporation of protoplasts and whole cells and tissues has also been described. See, e.g., Donn et al., in Abstracts of VIIth International Congress on Plant Cell and Tissue Culture IAPTC, A2-38, p. 53 (1990); D'Halluin et al., *Plant Cell* 4:1495-1505 (1992); Spencer et al., *Plant Mol. Biol.* 24:51-61 (1994); International Appl. Publ. Nos. WO 87/06614, WO 92/09696, and WO 93/21335; and U.S. Pat. Nos. 5,472,869 and 5,384,253.

Other transformation technology includes whiskers technology, see, e.g., U.S. Pat. Nos. 5,302,523 and 5,464,765.

Chloroplasts or plastids can also be directly transformed. As such, recombinant plants can be produced in which only the chloroplast or plastid DNA has been modified with any of the nucleic acid molecules and recombinant nucleic acid molecules described above as well as combinations thereof. Promoters which function in chloroplasts and plastids are known in the art. See, e.g., Hanley-Bowden et al., *Trends in Biochemical Sciences* 12:67-70 (1987). Methods and compositions for obtaining cells containing chloroplasts into which heterologous DNA has been inserted have been described, e.g., in U.S. Pat. Nos. 5,693,507 and 5,451,513.

Any other methods which provide for efficient transformation can also be employed.

Vectors suitable for use in plant transformation are known in the art. See, e.g., U.S. Pat. Nos. 6,495,738; 7,271,315; 7,348,473; 7,355,100; 7,456,340; and references disclosed therein.

Expression vectors can include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which can be an antibiotic or an herbicide, or genes that encode an altered target which is insensitive to the inhibitor. Selectable markers suitable for use in plant transformation include, but are not limited to, the aminoglycoside phosphotransferase gene of transposon Tn5 (Aph II) which encodes resistance to the antibiotics kanamycin, neomycin, and G418, as well as those genes which encode for resistance or tolerance to glyphosate, hygromycin, methotrexate, phosphinothricin (bialophos), imidazolinones, sulfonylureas and triazolopyrimidine herbicides, such as chlorsulfuron, bromoxynil, dalapon, and the like. One commonly used selectable marker gene for plant transformation is the neomycin phosphotransferase II (nptII) gene under the control of plant regulatory signals which confers resistance to kanamycin. See, e.g., Fraley et al., *Proc. Natl. Acad. Sci. U.S.A.* 80: 4803 (1983). Another commonly used selectable marker gene is the hygromycin phosphotransferase gene which confers resistance to the antibiotic hygromycin. See, e.g., Vanden Elzen et al., *Plant Mol. Biol.* 5:299 (1985). Additional selectable marker genes of bacterial origin that confer resistance to antibiotics include gentamycin acetyl transferase, streptomycin phosphotransferase, aminoglycoside-3'-adenyl transferase, and the bleomycin resistance determinant. See, e.g., Hayford et al., *Plant Physiol.* 86:1216 (1988), Jones et al., *Mol. Gen. Genet.* 210: 86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate, or bromoxynil. See, e.g., Comai et al., *Nature* 317:741-744 (1985), Gordon-Kamm et al., *Plant Cell* 2:603-618 (1990) and Stalker et al., *Science* 242:419-423 (1988). Other selectable marker genes for plant transformation are not of bacterial origin. These genes include, for example, mouse dihydrofolate reductase, plant 5-enolpyruvylshikimate-3-phosphate synthase and plant acetolactate synthase. See, e.g., Eichholtz et al., *Somatic Cell Mol. Genet.* 13:67 (1987), Shah et al., *Science* 233:478 (1986), Charest et al., *Plant Cell Rep.* 8:643 (1990).

A reporter gene can be used with or without a selectable marker. Reporter genes are genes which are typically not present in the recipient organism or tissue and typically encode for proteins resulting in some phenotypic change or enzymatic property. See, e.g., K. Weising et al., *Ann. Rev. Genetics* 22: 421 (1988). Reporter genes include, but are not limited to, beta-glucuronidase (GUS), beta-galactosidase, chloramphenicol acetyltransferase, green fluorescent protein, and luciferase genes. See, e.g., Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), and Chalfie et al., *Science* 263:802 (1994). An assay for detecting reporter gene expression can be performed at a suitable time after the gene has been introduced into recipient cells. One such assay entails the use of the gene encoding beta-glucuronidase (GUS) of the uida locus of *E. coli* as described by Jefferson et al., *Biochem. Soc. Trans.* 15: 17-19 (1987).

Promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter, as well as promoters of viral origin, such as the cauliflower mosaic virus (35S and 19S), 35T (which is a re-engineered 35S promoter, see International Appl. Publ. No. WO 97/13402) can be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Matrix attachment regions, scaffold attachment regions, introns, enhancers, and polyadenylation sequences can also be used to improve transcription efficiency or DNA integration. Such elements can be included to obtain optimal performance of the transformed DNA in the plant. Typical elements include, but are not limited to, Adh-intron 1, Adh-intron 6, the alfalfa mosaic virus coat protein leader sequence, the maize streak virus coat protein leader sequence, as well as others available to a skilled artisan. Constitutive promoter regulatory elements can also be used to direct continuous gene expression. Constitutive promoters include, but are not limited to, promoters from plant viruses such as the 35S promoter from CaMV (Odell et al., *Nature* 313:810-812 (1985)), and promoters from such genes as rice actin (McElroy et al., *Plant Cell* 2:163-171 (1990)), ubiquitin (Christensen et al., *Plant Mol. Biol.* 12:619-632 (1989) and Christensen et al., *Plant Mol. Biol.* 18:675-689 (1992)), pEMU (Last et al., *Theor. Appl. Genet.* 81:581-588 (1991)), MAS (Velten et al., *EMBO J.* 3:2723-2730 (1984)), maize H3 histone (Lepetit et al., *Mol. Gen. Genetics* 231:276-285 (1992) and Atanassova et al., *Plant Journal* 2(3): 291-300 (1992)), and the ALS promoter, XbaI/NcoI fragment 5' to the *Brassica napus* ALS3 structural gene (or a nucleotide sequence similar to the XbaI/NcoI fragment) (International Appl. Publ. No. WO 96/30530). Tissue-specific promoter regulatory elements can also be used for gene expression in specific cell or tissue types, such as leaves or seeds (e.g., zein, oleosin, napin, ACP, globulin, and the like). Tissue-specific or tissue-preferred promoters include, but are not limited to, a root-preferred promoter, such as from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as from cab or rubisco (Simpson et al., *EMBO J.* 4(11):2723-2729 (1985) and Timko et al., *Nature* 318:579-582 (1985)); an antherspecific promoter such as from LAT52 (Twell et al., *Mol. Gen. Genetics* 217:240-245 (1989)); a pollen-specific promoter such as from Zm13 (Guerrero et al., *Mol. Gen. Genetics* 244:161-168 (1993)); or a microspore-preferred promoter such as from apg (Twell et al., *Sex. Plant Reprod.* 6:217-224 (1993)). Promoter regulatory elements can also be active during a certain stage of a plants' development as well as plant tissues and organs, including, but not limited to, pollen-specific, embryo specific, corn silk specific, cotton fiber specific, root specific, and seed endosperm specific promoter regulatory elements. An inducible promoter regulatory element can be used, which is responsible for expression of genes in response to a specific signal, such as: physical stimulus (heat shock genes); light (RUBP carboxylase); hormone (Em); metabolites; chemicals; and stress. Inducible promoters include, but are not limited to, a promoter from the ACEI system which responds to copper (Mett et al., *PNAS* 90:4567-4571 (1993)); from the In2 gene from maize which responds to benzenesulfonamide herbicide safeners (Hershey et al., *Mol. Gen Genetics* 227:229-237 (1991) and Gatz et al., *Mol. Gen. Genetics* 243: 32-38 (1994)), from the Tet repressor from Tn10 (Gatz et al., *Mol. Gen. Genetics* 227:229-237 (1991)); and from a steroid hormone gene, the transcriptional activity of which is induced by a glucocorticosteroid hormone (Schena et al., *Proc. Natl. Acad. Sci. U.S.A.* 88:0421 (1991).

Signal sequences can also be used to direct a polypeptide to either an intracellular organelle or subcellular compartment or for secretion to the apoplast. See, e.g., Becker et al., *Plant Mol. Biol.* 20:49 (1992), Knox, C., et al., *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., *Cell* 39:499-509 (1984), and Steifel et al., *Plant Cell* 2:785-793 (1990). Such targeting sequences provide for the desired expressed protein to be transferred to the cell structure in which it most effectively functions or to areas of the cell in which cellular processes necessary for desired phenotypic functions are concentrated.

In some embodiments, signal sequences are used to direct proteins of the invention to a subcellular compartment, for example, to the plastid or chloroplast. Gene products, including heterologous gene products, can be targeted to the plastid or chloroplast by fusing the gene product to a signal sequence which is cleaved during chloroplast import yielding the mature protein. See, e.g., Comai et al., *J. Biol. Chem.* 263: 15104-15109 (1988) and van den Broeck et al., *Nature* 313: 358-363 (1985). DNA encoding for appropriate signal sequences can be isolated from cDNAs encoding the RUBISCO protein, the CAB protein, the EPSP synthase enzyme, the GS2 protein, or from any naturally occurring chloroplast targeted protein that contains a signal sequence (also termed a chloroplast transit peptide (CTP)) that directs the targeted protein to the chloroplast. Such chloroplast targeted proteins are well known in the art. The chloroplast targeted proteins are synthesized as larger precursor proteins that contain an amino-terminal CTP, which directs the precursor to the chloroplast import machinery. CTPs are generally cleaved by specific endoproteases located within the chloroplast organelle, thus releasing the targeted mature protein, including active proteins such as enzymes, from the precursor into the chloroplast milieu. Examples of sequences encoding peptides suitable for targeting a gene or gene product to the chloroplast or plastid of the plant cell include the *petunia* EPSPS CTP, the *Arabidopsis* EPSPS CTP2 and intron, and other sequences known in the art.

Specific examples of CTPs include, but are not limited to, the *Arabidopsis thaliana* ribulose bisphosphate carboxylase small subunit ats1A transit peptide, an *Arabidopsis thaliana* EPSPS transit peptide, and a *Zea* maize ribulose bisphosphate carboxylase small subunit transit peptide. An optimized transit peptide is described, e.g., by Van den Broeck et al., *Nature* 313:358-363 (1985). Prokaryotic and eukaryotic signal sequences are disclosed, e.g., by Michaelis et al., *Ann. Rev. Microbial.* 36: 425 (1982). Additional examples of transit peptides that can be used in the invention include chloroplast transit peptides described in Von Heijne et al., *Plant Mol. Biol. Rep.* 9:104-126 (1991); Mazur et al., *Plant Physiol.* 85: 1110 (1987); Vorst et al., *Gene* 65: 59 (1988); Chen & Jagendorf, *J. Biol. Chem.* 268: 2363-2367 (1993); a transit peptide from the rbcS gene from *Nicotiana plumbaginifolia* (Poulsen et al. *Mol. Gen. Genet.* 205: 193-200 (1986)); and a transit peptide derived from *Brassica napus* acyl-ACP thioesterase (Loader et al., *Plant Mol. Biol.* 23: 769-778 (1993); Loader et al., *Plant Physiol.* 110:336-336 (1995).

Genetically modified plants of the invention can be further modified to delete or inactivate an endogenous fatty acid synthase, to reduce endogenous competition with the exogenous PUPA synthase system for malonyl CoA, to increase the level of malonyl CoA in the organism, and combinations thereof. See, e.g., U.S. Appl. Publ. No. 2007/0245431.

A genetically modified plant can be cultured in a fermentation medium or grown in a suitable medium such as soil. A suitable growth medium for higher plants includes any growth medium for plants, such as, but not limited to, soil, sand, any other particulate media that support root growth (e.g. vermiculite, perlite, etc.) or hydroponic culture as well as suitable light, water, and nutritional supplements which optimize the growth of the higher plant. PUPAs can be recovered from the genetically modified plants through purification processes which extract the compounds from the plant. PUPAs can be recovered by harvesting the plant as well as by harvesting the oil from the plant (e.g., from the oil seeds). The plant can also be consumed in its natural state or further processed into consumable products. In some embodiments, the present invention is directed to a genetically modified plant, wherein the plant produces at least one PUPA as a result of the genetic modification, and wherein the total fatty acid profile in the plant, or the part of the plant that accumulates PUPAs, comprises a detectable amount of the PUPA produced as a result of genetic modification of the plant. In some embodiments, the plant is an oil seed plant. In some embodiments, the oil seed plant produces PUPAs in its mature seeds or contains the PUPAs in the oil of its seeds.

Various mammalian cell culture systems can also be employed to express recombinant protein. Expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences.

Methods Involving Heterologous Expression

The present invention is directed to a method to produce at least one PUPA comprising expressing a PUPA synthase system in a host cell under conditions effective to produce PUPA, wherein the PUPA synthase system comprises any of the isolated nucleic acid molecules and recombinant nucleic acid molecules described herein as well as combinations thereof, wherein at least on PUPA is produced. In some embodiments, the at least one PUPA includes DHA, EPA, or a combination thereof. In some embodiments, the host cell is a plant cell, an isolated animal cell, or a microbial cell. In some embodiments the host cell is a thraustochytrid.

The present invention is directed to a method to produce lipids enriched for DHA, EPA, or a combination thereof, comprising expressing a PUFA synthase gene in a host cell under conditions effective to produce lipids, wherein the PUFA synthase gene comprises any of the isolated nucleic acid molecules and recombinant nucleic acid molecules described herein as well as combinations thereof in the host cell, wherein lipids enriched with DHA, EPA, or a combination thereof are produced.

The invention is directed to a method of isolating lipids from a host cell, comprising expressing a PUFA synthase gene in the host cell under conditions effective to produce lipids, and isolating lipids from the host cell, wherein the PUFA synthase system in the host cell comprises any of the isolated nucleic acid molecules and recombinant nucleic acid molecules described herein as well as combinations thereof.

In some embodiments, one or more lipid fractions containing PUFAs are isolated from the host cells. In some embodiments, the one or more fractions isolated from the host cell includes the total fatty acid fraction, the sterol esters fraction, the triglyceride fraction, the free fatty acid fraction, the sterol fraction, the diglycerol fraction, the phospholipid fraction, or combination thereof. In some embodiments, PUFAs are isolated from the host cells, wherein the PUFAs are enriched for omega-3 fatty acids omega-6 fatty acids, or combinations thereof based on the composition of the PUF A synthase system introduced into a host cell. In some embodiments, the PUFAs are enriched for DHA, EPA, DPA n-6, ARA, or combinations thereof based on the composition of the PUFA synthase system introduced into a host cell. In some embodiments, the PUFAs are enriched for DHA, EPA, or a combination thereof. In some embodiments, the PUFA profile of PUFAs isolated from a host cell include high concentrations of DHA and lower concentrations of EPA, ARA, DPA n-6, or combinations thereof. In some embodiments, the PUFA profile of PUFAs isolated from a host cell include high concentrations of DHA and EPA, and lower concentrations of ARA, DPA n-6, or combinations thereof. In some embodiments, the PUFA profile of PUF As isolated from a host cell include high concentrations of EPA and lower concentrations of DHA, ARA, DPA n-6, or combinations thereof.

The invention is directed to a method of replacing an inactive or deleted PUFA synthase activity, introducing a new PUFA synthase activity, or enhancing an existing PUFA synthase activity in an organism having PUFA synthase activity, comprising expressing any of the isolated nucleic acid molecules and recombinant nucleic acid molecules described herein as well as combinations thereof in the organism under conditions effective to express the PUFA synthase activity. In some embodiments, the nucleic acid molecule comprises one or more PFAJ, PFA2, or PFA3 PUPA synthase polynucleotide sequences described herein that encode one or more PUFA synthase domains. In some embodiments, the PUFA profiles of the organisms are altered by the introduction of the one or more nucleic acid molecules of the invention. In some embodiments, the altered PUFA profiles include an increase in omega-3 fatty acids and a decrease in omega-6 fatty acids. In some embodiments, the altered PUFA profiles include an increase in omega-6 fatty acids and a decrease in omega-3 fatty acids. In some embodiments, both omega-3 and omega-6 fatty acids are increased. In some embodiments, the amount of DHA is increased while the amounts of one or more of EPA, ARA, DPA n-6, or combinations thereof are maintained or decrease. In some embodiments, the amounts of EPA and DHA are increased while the amounts of ARA, DPA n-6, or a combination thereof are maintained or decrease. In some embodiments, the amount of EPA is increased while the amounts of one or more of EPA, ARA, DPA n-6, or combinations thereof are maintained or decrease. In some embodiments, the nucleic acid molecule comprises the polynucleotide sequence of PFA3 or one or more domains therein. In some embodiments, the nucleic acid molecule comprises the polynucleotide sequence of PFA3 or one or more domains therein and the amount of omega-3 fatty acids in the organism is increased while the amount of omega-6 fatty acids is decreased. In some embodiments, the nucleic acid molecule comprises the polynucleotide sequence of PFA.2 or one or more domains therein and the amount of DHA in the organism is increased while the amount of EPA is decreased.

The invention is directed to methods of increasing production of DHA, EPA, or a combination thereof in an organism having PUFA synthase activity, comprising expressing any of the isolated nucleic acid molecules and recombinant nucleic acid molecules described herein as well as combinations thereof in the organism under conditions effective to produce DHA, EPA, or a combination thereof, wherein the PUFA synthase activity replaces an inactive or deleted activity, introduces a new activity, or enhances an existing activity in the organism, and wherein production of DHA, EPA, or a combination thereof in the organism is increased.

Having generally described this invention, a further understanding can be obtained by reference to the examples provided herein. These examples are for purposes of illustration only and are not intended to be limiting.

Example 1

Degenerate primers for the KS and DH PUPA synthase domains were designed in order to isolate the corresponding sequences from the isolated microorganism deposited under ATCC Accession No. PTA-9695, also known as *Schizochytrium* sp. ATCC PTA-9695.

Degenerate primers for the KS region of *Schizochytrium* sp. ATCC PTA-9695 PFA.1 (i.e., the region containing the KS domain) were designed based on the published PFAJ (previously termed oifA or ORF 1) sequences for *Shewanella japonica*, *Schizochytrium* sp. ATCC 20888, *Thraustochytrium aureum* (ATCC 34304), and *Thraustochytrium* sp. 23B ATCC 20892:

```
prDS173 (forward):
                                    (SEQ ID NO: 62)
GATCTACTGCAAGCGCGGNGGNTTYAT,
and prDS174 (reverse):
                                    (SEQ ID NO: 63)
GGCGCAGGCGGCRTCNACNAC.
```

Degenerate primers for the DH region of *Schizochytrium* sp. ATCC PTA-9695 PFA3 (previously termed orfC or ORF 3) were designed based on the published sequences for *Moritella marina*; *Schizochytrium* sp. ATCC 20888; *Shewanella* sp. SCRC-2738; *Photobacter profundum*; and *Thraustochytrium* sp. 23B ATCC 20892:

```
JGM190 (forward):
                                    (SEQ ID NO: 64)
CAYTGGTAYTTYCCNTGYCAYTT;
and BLR242 (reverse):
                                    (SEQ ID NO: 65)
CCNGGCATNACNGGRTC.
```

The PCR conditions with chromosomal DNA template were as follows: 0.2 µM dNTPs, 0.1 uM each primer, 8% DMSO, 200 ng chromosomal DNA, 2.5 U Herculase® II fusion polymerase (Stratagene), and 1× Herculase® buffer (Stratagene) in a 50 µL total volume. The PCR Protocol included the following steps: (1) 98° C. for 3 minutes; (2) 98° C. for 30 seconds; (3) 50° C. for 30 seconds; (4) 72° C. for 2 minutes; (5) repeat steps 2-4 for 40 cycles; (6) 72° C. for 5 minutes; and (7) hold at 6° C.

For both primer pairs, PCR yielded distinct DNA products with the expected sizes using chromosomal templates from *Schizochytrium* sp. ATCC Accession No. PTA-9695. The respective PCR products were cloned into the vector pJET1.2/blunt (Fermentas) according to the manufacturer's instructions, and the insert sequence was determined using supplied standard primers.

The DNA sequences obtained from the PCR products were compared with known sequences available from the NCBI GenBank in a standard BLASTx search (BLASTx parameters: Low complexity filter on; Matrix: BLOSUM62; Gap cost; Existence 11, ExtenstionI. Stephen F. Altschul, Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", *Nucleic Acids Res.* 25:3389-3402.).

At the amino acid level, the sequences with the highest level of homology to deduced amino acid sequence derived from the cloned DNA containing the KS fragment from *Schizochytrium* sp. ATCC PTA-9695 were: *Schizochytrium* sp. ATCC 20888 "polyunsaturated fatty acid synthase subunit A" (Identity=87%; positives=92%); *Shewanella oneidensis* MR-1 "multi-domain beta-ketoacyl synthase" (Identity=49%; positives=64%); and *Shewanella* sp. MR-4 "beta-ketoacyl synthase" (Identity=49%; positives=64%).

At the amino acid level, the sequences with the highest level of homology to the deduced amino acid sequence derived from the cloned DNA containing the DH fragment from *Schizochytrium* sp. ATCC PTA-9695 were: *Schizochytrium* sp. ATCC 20888 "polyunsaturated fatty acid synthase subunit C" (Identity=61%; positives=71%); *Shewanella pealeana* ATCC 700345 "Beta-hydroxyacyl-(acyl-cairier-protein) dehydratase FabA/FabZ" (Identity=35%; positives=50%); and *Shewanella sediminis* HAW-EB3 "omega-3 polyunsaturated fatty acid synthase PfaC" (Identity=34%; positives=50%).

Example 2

PUPA synthase genes were identified from *Schizochytrium* sp. ATCC PTA-9695.

Genomic DNA was prepared from the microorganism by standard procedures. See, e.g., Sambrook J. and Russell D. 2001. *Molecular cloning: A laboratory manual,* 3rd edition. Cold Spring Harbor Laboratory Press, Cold Spring Harbor, New York. Briefly: (1) 500 µL of cells were pelleted from mid-log culture. The cells were Re-spun, and all traces of liquid were removed from the cell pellet with a small-bore tip; (2) pellets were resuspended with 200 µL lysis buffer (20 mM Tris pH 8.0, 125 µg/mL Proteinase K, 50 mM NaCl, 10 mM EDTA pH 8.0, 0.5% SDS); (3) cells were lysed at 50° C. for 1 hour; (4) the lysis mixture was pipetted into phase-lock gel (PLG-Eppendorf) 2 mL tubes; (5) equal volume of P:C:I was added and allowed to mix for 1.5 hours; (6) the tubes were centrifuged at 12 k×g for 5 minutes; (7) the aqueous phase was removed from above the gel within the PLG tube and an equal volume of chloroform was added to the aqueous phase, and mixed for 30 minutes; (8) the tubes were centrifuged at 14 k for approximately 5 minutes; (9) the top layer (aqueous phase) was pipetted away from the chloroform, and placed in a new tube; (10) 0.1 volume of 3M NaOAC was added and mixed (inverted several times); (11) 2 volumes of 100% EtOH were added and mixed (inverted several times) with genomic DNA precipitant forming at this stage; (12) the tubes were spun at 4° C. in a microcentrifuge at 14 k for approximately 15 minutes; (13) the liquid was gently poured off with genomic DNA remaining at the bottom of the tube; (14) the pellet was washed with 0.5 mL 70% EtOH; (15) the tubes were spun at 4° C. in a microcentrifuge at 14 k for approximately 5 minutes; (16) the EtOH was gently poured off and the genomic DNA pellet was dried; and (17) a suitable volume of $H_2O$ and RNase was added directly to the genomic DNA pellet.

The isolated genomic DNA was used to generate recombinant libraries consisting of large fragments (approximately 40 kB) according to the manufacturer's instructions in the cosmid pWEB-TNC™ (Epicentre). The cosmid libraries were screened by standard colony hybridization procedures using $^{32}P$ radioactively labeled probes (Sambrook J. and Russell D. 2001. *Molecular cloning: A laboratory manual,* 3rd edition. Cold Spring Harbor Laboratory Press, Cold Spring Harbor, New York). The probes contained DNA homologous to published PUFA synthase sequences from other organisms as described in Example 1. These probes were generated by a DNA restriction digest of the cloned fragments from respective clones from pJET1 0.2/blunt described above and labeled by standard methods. In all cases, strong hybridization of the individual probes to certain cosmids indicated clones containing DNA homologous to PUFA synthase genes.

Cosmid clone pDS115 demonstrated strong hybridization of probe to the KS region and was selected for DNA sequencing of the *Schizochytrium* sp. ATCC PTA-9695 PFA.1 gene. Cosmid clone pDS115, containing the *Schizochytrium* sp. ATCC PTA-9695 PFA.1 and PFA2 genes, was deposited under the Budapest Treaty, at the American Type Culture Collection, Patent Depository, 10801 University Boulevard, Manassas, VA 20110-2209, on Jan. 27, 2009, and given ATCC Accession No. PTA-9737. Sequencing primers to the DNA sequence of the KS region determined in Example 1 were designed using standard methods. To determine the DNA sequence of *Schizochytrium* sp. ATCC PTA-9695 PFAJ, successive rounds of DNA sequencing, involving subsequent sequencing primer design by standard methods, was carried out in order to "walk" the cosmid clone.

In previously published thraustochytrid PUPA synthase systems, the PUPA synthase genes PFAJ and PFA2 have been clustered together and arranged as to be divergently transcribed. This is also the case for PFAJ and PFA2 from *Schizochytrium* sp. ATCC PTA-9695. Through the "walking" of DNA sequence from cosmid clone pDS1 15, the conceptual start of PFA2 was found to be 493 nucleotides from the start of PFA.1 and divergently transcribed. Each nucleotide base pair of the *Schizochytrium* sp. ATCC PTA-9695 PFAJ and PFA2 PUPA synthase genes were covered by at least two separate DNA sequencing reactions with high-quality with at least a minimum aggregated Phred score of 40 (confidence level of 99.99%).

Cosmid clone pBS4 demonstrated strong hybridization of probe to the DH region and was selected for DNA sequencing of the *Schizochytrium* sp. ATCC PTA-9695 PFA3 gene. Cosmid clone pBS4, containing the *Schizochytrium* sp. ATCC PTA-9695 PFA3 gene, was deposited under the Budapest Treaty, at the American Type Culture Collection, Patent Depository, 10801 University Boulevard, Manassas, VA 20110-2209, on Jan. 27, 2009, and given ATCC Accession No. PTA-9736. Sequencing primers were designed using standard methods to the DH region DNA sequence determined in Example 1. To determine the DNA sequence of the *Schizochytrium* sp. ATCC PTA-9695 PFA3 gene, successive rounds of DNA sequencing, involving subsequent sequencing primer design by standard methods, was carried out in order to "walk" the cosmid clone. Each nucleotide base pair of the *Schizochytrium* sp. ATCC PTA-9695 PFA3 gene was covered by at least two separate DNA sequencing reactions of high-quality with at least a minimum aggregated Phred score of 40 (confidence level of 99.99%).

Table 1 shows identities for the *Schizochytrium* sp. ATCC PTA-9695 PFAJ (SEQ ID NO:1), PFA2 (SEQ ID NO:3), and PFA3 (SEQ ID NO:5) polynucleotide sequences as compared to previously published sequences. Identities were determined by the scoring matrix "swgapdnamt" within the "AlignX" program of the VectorNTI program, a standard for DNA alignment.

TABLE 1

PERCENT IDENTITY TO PFAJ, PFA2, AND PFA3 POLYNUCLEOTIDE Sequences

| Source of Published PFAJ, PFA2, and PFA3 Sequences | % Identity of published PFAJ (orfA) toPFAJ (SEQ ID NO: 1) | % Identity of published PFA2 (orfB) toPFA2 (SEQ ID NO: 3) | % Identity of published PFA3 (orfC) toPFA3 (SEQ ID NO: 5) |
|---|---|---|---|
| *Schizochytrium* sp. ATCC 20888 | 70 | 66 | 75 |
| *Thraustochytrium aureum* ATCC 34304 | 65 | 62 | not published |
| *Thraustochytrium* sp. 23B ATCC 20892 | 56 | 55 | 67 |

Table 2 shows identities for the *Schizochytrium* sp. ATCC PTA-9695 Pfa1p (SEQ ID NO:2), Pfa2p (SEQ ID NO:4), and Pfa3p (SEQ ID NO:6) amino acid sequences as compared to previously published PUFA synthase amino acid sequences. Identities were determined through use of the sc0 ling matrix "blosum62mt2" within the "AlignX" program of the VectorNTI program, a standard for protein alignment.

TABLE 2

Percent Identity to Pfa1p, Pfa2p, and Pfa3p Amino Acid Sequences

| Source of Published Pfa1p, Pfa2p, and Pfa3p Sequences | % Identity of published Pfa1p (OrfA) to Pfa1p (SEQ ID NO: 2) | % Identity of published Pfa2p (OrfB) to Pfa2p (SEQ ID NO: 4) | % Identity of published Pfa3p (OrfC) to Pfa3p (SEQ ID NO: 6) |
|---|---|---|---|
| *Schizochytrium* sp. ATCC 20888 | 60 | 53 | 70 |
| *Thraustochytrium aureum* ATCC 34304 | 60 | 54 | not published |
| *Thraustochytrium* sp. 23B ATCC 20892 | 52 | 52 | 70 |

Example 3

Domain analysis was performed to annotate the sequence coordinates for the PUFA synthase domains and active sites of *Schizochytrium* sp. ATCC PTA-9695 PFAJ, PFA2, and PFA3, respectively. Domains were identified based on homology to known PUPA synthase, fatty acid synthase, and polyketide synthase domains.

Table 3 shows the domains and active sites associated with *Schizochytrium* sp. ATCC PTA-9695 PFAJ.

TABLE 3

*Schizochytrium* sp. ATCC PTA-9695 PFAJ Domain Analysis

| Domain | DNA position | AA position | Sites | DNA position | AA position |
|---|---|---|---|---|---|
| KS | 7-1401 of SEQ ID NO: 1 (SEQ ID NO: 7) | 3-467 of SEQ ID NO: 2 (SEQ ID NO: 8) | Active - DXAC* (SEQ ID NO: 43) | 607-609 of SEQ ID NO: 1 | C203 of SEQ ID NO: 2 |
| | | | End-GFGG (SEQ ID NO: 44) | 1363-1374 of SEQ ID NO: 1 (SEQ ID NO: 45) | 455-458 of SEQ ID NO: 2 |
| MAT | 1798-2700 of SEQ ID NO: 1 (SEQ ID NO: 9) | 600-900 of SEQ ID NO: 2 (SEQ ID NO: 10) | Active GHS*LG (SEQ ID NO: 46) | 2095-2097 of SEQ ID NO: 1 | S699 of SEQ ID NO: 2 |
| ACT | 3298-5400 of SEQ ID NO: 1 (SEQ ID NO: 11) | 1100-1800 of SEQ ID NO: 2 (SEQ ID NO: 12) | ACP1 domain | 3325-3600 of SEQ ID NO: 1 (SEQ ID NO: 13) | 1109-1200 of SEQ ID NO: 2 (SEQ ID NO: 14) |
| | | | ACP1 Active LGIDS* (SEQ ID NO: 47) | 3454-3456 of SEQ ID NO: 1 | S1152 of SEQ ID NO: 2 |
| | | | ACP2 domain | 3667-3942 of SEQ ID NO: 1 (SEQ ID NO: 15) | 1223-1314 of SEQ ID NO: 2 (SEQ ID NO: 16) |
| | | | ACP2 Active LGIDS* (SEQ ID NO: 47) | 3796-3798 of SEQ ID NO: 1 | S1266 of SEQ ID NO: 2 |
| | | | ACP3 domain | 4015-4290 of SEQ ID NO: 1 (SEQ ID NO: 17) | 1339-1430 of SEQ ID NO: 2 (SEQ ID NO: 18) |
| | | | ACP3 Active LGIDS* (SEQ ID NO: 47) | 4144-4146 of SEQ ID NO: 1 | S1382 of SEQ ID NO: 2 |
| | | | ACP4 domain | 4363-4638 of SEQ ID NO: 1 (SEQ ID NO: 19) | 1455-1546 of SEQ ID NO: 2 (SEQ ID NO: 20) |
| | | | ACP4 Active LGIDS* (SEQ ID NO: 47) | 4492-4494 of SEQ ID NO: 1 | S1498 of SEQ ID NO: 2 |
| | | | ACP5 domain | 4711-4986 of SEQ ID NO: 1 (SEQ ID NO: 21) | 1571-1662 of SEQ ID NO: 2 (SEQ ID NO: 22) |
| | | | ACP5 Active LGIDS* (SEQ ID NO: 47) | 4840-4842 of SEQ ID NO: 1 | S1614 of SEQ ID NO: 2 |
| | | | ACP6 domain | 5053-5328 of SEQ ID NO: 1 (SEQ ID NO: 23) | 1685-1776 of SEQ ID NO: 2 (SEQ ID NO: 24) |
| | | | ACP6 Active LGIDS* (SEQ ID NO: 47) | 5182-5184 of SEQ ID NO: 1 | S1728 of SEQ ID NO: 2 |
| KR | 5623-7800 of SEQ ID NO: 1 (SEQ ID NO: 25) | 1875-2600 of SEQ ID NO: 2 (SEQ ID NO: 26) | "core region" | 5998-6900 of SEQ ID NO: 1 (SEQ ID NO:48) | 2000-2300 of SEQ ID NO: 2 (SEQ ID NO: 49) |
| DH Motif | 7027-7065 of SEQ ID NO: 1 (SEQ ID NO: 27) | 2343-2355 of SEQ ID NO: 2 (SEQ ID NO: 28) | LxxHxxxGxxxxP (SEQ ID NO: 50) | 7027-7065 of SEQ ID NO: 1 (SEQ ID NO: 27) | 2343-2355 of SEQ ID NO: 2 (SEQ ID NO: 28) |

The first domain in *Schizochytrium* sp. ATCC PTA-9695 Pfa1 is a KS domain. The nucleotide sequence containing the sequence encoding the *Schizochytrium* sp. ATCC PTA-9695 Pfa1 KS domain is represented herein as SEQ ID NO:7, corresponding to positions 7-1401 of SEQ ID NO:1. The amino acid sequence containing the *Schizochytrium* sp. ATCC PTA-9695 Pfa1 KS domain is represented herein as SEQ ID NO:8, corresponding to positions 3-467 of SEQ ID NO:2. The KS domain contains an active site motif: DXAC* (SEQ ID NO:43), with an *acyl binding cite corresponding to C203 of SEQ ID NO:2. Also, a characteristic motif is present at the end of the KS domain: GFGG (SEQ ID NO:44), corresponding to positions 455-458 of SEQ ID NO:2 and positions 453-456 of SEQ ID NO:8.

The second domain in *Schizochytrium* sp. ATCC PTA-9695 Pfa1 is a MAT domain. The nucleotide sequence containing the sequence encoding the *Schizochytrium* sp. ATCC PTA-9695 Pfa1 MAT domain is represented herein as SEQ ID NO:9, coIresponding to positions 1798-2700 of SEQ ID NO: 1. The amino acid sequence containing the *Schizochytrium* sp. ATCC PTA-9695 Pfa1 MAT domain is represented herein as SEQ ID NO:10, coITesponding to positions 600-900 of SEQ ID NO:2. The MAT domain contains an active site motif: GHS*XG (SEQ ID NO:46), with an *acyl binding cite coITesponding to S699 of SEQ ID NO:2.

The third through eighth domains of *Schizochytrium* sp. ATCC PTA-9695 Pfa1 are six tandem ACP domains, also referred to herein as ACP1, ACP2, ACP3, ACP4, ACP5, and ACP6. The nucleotide sequence containing the first ACP domain, ACP1, is represented herein as SEQ ID NO:13 and is contained within the nucleotide sequence spanning from about position 3325 to about position 3600 of SEQ ID NO:1. The amino acid sequence containing ACP1, represented herein as SEQ ID NO:14, is contained within the amino acid sequence spanning from about position 1109 to about position 1200 of SEQ ID NO:2. The nucleotide sequence containing ACP2, represented herein as SEQ ID NO:15, is contained within the nucleotide sequence spanning from about position 3667 to about position 3942 of SEQ ID NO:1.

The amino acid sequence containing ACP2, represented herein as SEQ ID NO:16, is contained within the amino acid sequence spanning from about position 1223 to about position 1314 of SEQ ID NO:2. The nucleotide sequence containing ACP3, represented herein as SEQ ID NO:17, is contained within the nucleotide sequence spanning from about position 4015 to about position 4290 of SEQ ID NO:1. The amino acid sequence containing ACP3, represented herein as SEQ ID NO:18, is contained within the amino acid sequence spanning from about position 1339 to about position 1430 of SEQ ID NO:2. The nucleotide sequence containing ACP4, represented herein as SEQ ID NO:19, is contained within the nucleotide sequence spanning from about position 4363 to about position 4638 of SEQ ID NO:1. The amino acid sequence containing ACP4, represented herein as SEQ ID NO:20, is contained within the amino acid sequence spanning from about position 1455 to about position 1546 of SEQ ID NO:2. The nucleotide sequence containing ACP5, represented herein as SEQ ID NO:21, is contained within the nucleotide sequence spanning from about position 4711 to about position 4986 of SEQ ID NO:1. The amino acid sequence containing ACP5, represented herein as SEQ ID NO:22, is contained within the amino acid sequence spanning from about position 1571 to about position 1662 of SEQ ID NO:2. The nucleotide sequence containing ACP6, represented herein as SEQ ID NO:23, is contained within the nucleotide sequence spanning from about position 5053 to about position 5328 of SEQ ID NO:1. The amino acid sequence containing ACP6, represented herein as SEQ ID NO:24, is contained within the amino acid sequence spanning from about position 1685 to about position 1776 of SEQ ID NO:2. All six ACP domains together span a region of Schizochytrium sp. ATCC PTA-9695 Pfa1 of from about position 3298 to about position 5400 of SEQ ID NO:1, corresponding to amino acid positions of about 1100 to about 1800 of SEQ ID NO:2. The nucleotide sequence for the entire ACP region containing all six domains is represented herein as SEQ ID NO:11; while the amino acid sequence for the entire ACP region containing all six domains is represented herein as SEQ ID NO:12. The repeat interval for the six ACP domains within SEQ ID NO:11 was found to be approximately every 342 nucleotides (the actual number of amino acids measured between adjacent active site serines ranges from 114 to 116 amino acids). Each of the six ACP domains contains a pantetheine binding motif LGIDS* (SEQ ID NO:47) wherein S* is the pantetheine binding site serine (S). The pantetheine binding site serine (S) is located near the center of each ACP domain sequence. The locations of the active site serine residues (i.e., the pantetheine binding site) for each of the six ACPD domains, with respect to the amino acid sequence of SEQ ID NO:2 are: ACP1=S1152, ACP2=S1266, ACP3=S1382, ACP4=S1498, ACP5=S1614, and ACP6=S1728.

The ninth domain in Schizochytrium sp. ATCC PTA-9695 Pfa1 is a KR domain. The nucleotide sequence containing the sequence encoding the Schizochytrium sp. ATCC PTA-9695 Pfa1 KR domain is represented herein as SEQ ID NO:25, corresponding to positions 5623-7800 of SEQ ID NO: 1. The amino acid sequence containing the Schizochytrium sp. ATCC PTA-9695 Pfa1 KR domain is represented herein as SEQ ID NO:26, corresponding to positions 1875-2600 of SEQ ID NO:2. Within the KR domain is a core region (contained within the nucleotide sequence of SEQ ID NO:48, and the amino acid sequence of SEQ ID NO:49) with homology to short chain aldehyde-dehydrogenases (KR is a member of this family). This core region spans from about position 5998 to about 6900 of SEQ ID NO:1, which corresponds to amino acid positions 2000-2300 of SEQ ID NO:2.

The tenth domain in Schizochytrium sp. ATCC PTA-9695 Pfa1 is a DH domain. The nucleotide sequence containing the sequence encoding the Schizochytrium sp. ATCC PTA-9695 Pfa1 DH domain is represented herein as SEQ ID NO:27, corresponding to positions 7027-7065 of SEQ ID NO: 1. The amino acid sequence containing the Schizochytrium sp. ATCC PTA-9695 Pfa1 DH domain is represented herein as SEQ ID NO:28, corresponding to positions 2343-2355 of SEQ ID NO:2. The DH domain contains a conserved active site motif (See, Donadio, S. and Katz., L., Gene 111(1): 51-60 (1992)): LxxHxxxGxxxxP (SEQ ID NO: 50).

Table 4 shows the domains and active sites associated with Schizochytrium sp. ATCC PTA-9695 PFA2.

TABLE 4

Schizochytrium sp. ATCC PTA-9695 PFA2 Domain Analysis

| Domain | DNA positions | AA positions | Sites | DNA positions | AA positions |
|---|---|---|---|---|---|
| KS | 10-1350 of SEQ ID NO: 3 (SEQ ID NO: 29) | 4-450 of SEQ ID NO: 4 (SEQ ID NO: 30) | DXAC* (SEQ ID NO: 43) | 571-573 of SEQ ID NO: 3 | C191 of SEQ ID NO: 4 |
| | | | End-GFGG (SEQ ID NO: 44) | 1312-1323 of SEQ ID NO: 3 (SEQ ID NO: 51) | 438-441 of SEQ ID NO: 4 |
| CLF | 1408-2700 of SEQ ID NO: 3 (SEQ ID NO: 31) | 470-900 of SEQ ID NO: 4 (SEQ ID NO: 32) | | | |
| AT | 2998-4200 of SEQ ID NO: 3 (SEQ ID NO: 33) | 1000-1400 of SEQ ID NO: 4 (SEQ ID NO: 34) | GxS*xG (SEQ ID NO: 52) | 3421-3423 of SEQ ID NO: 3 | S1141 of SEQ ID NO: 4 |
| ER | 4498-5700 of SEQ ID NO: 3 (SEQ ID NO: 35) | 1500-1900 of SEQ ID NO: 4 (SEQ ID NO: 36) | | | |

The first domain in Schizochytrium sp. ATCC PTA-9695 Pfa2 is a KS domain. The nucleotide sequence containing the sequence encoding the Schizochytrium sp. ATCC PTA-9695 Pfa2 KS domain is represented herein as SEQ ID NO:29, corresponding to positions 10-1350 of SEQ ID NO:3. The amino acid sequence containing the Schizochytrium sp. ATCC PTA-9695 Pfa2 KS domain is represented herein as SEQ ID NO:30, corresponding to positions 4-450 of SEQ ID NO:4. The KS domain contains an active site motif: DXAC* (SEQ ID NO:43), with an *acyl binding cite corresponding to C191 of SEQ ID NO:4. Also, a characteristic motif is present at the end of the KS domain: GFGG (SEQ ID NO:44), corresponding to positions 438-441 of SEQ ID NO:4 and positions 435-438 of SEQ ID NO:30.

The third domain in *Schizochytrium* sp. ATCC PTA-9695 Pfa2 is a CLF domain. The nucleotide sequence containing the sequence encoding the *Schizochytrium* sp. ATCC PTA-9695 Pfa2 CLF domain is represented herein as SEQ ID NO:31, corresponding to positions 1408-2700 of SEQ ID NO:3. The amino acid sequence containing the *Schizochytrium* sp. ATCC PTA-9695 Pfa2 CLF domain is represented herein as SEQ ID NO:32, corresponding to positions 470-900 of SEQ ID NO:4.

The third domain in *Schizochytrium* sp. ATCC PTA-9695 Pfa2 is an AT domain. The nucleotide sequence containing the sequence encoding the *Schizochytrium* sp. ATCC PTA-9695 Pfa2 AT domain is represented herein as SEQ ID NO:33, corresponding to positions 2998-4200 of SEQ ID NO:3. The amino acid sequence containing the *Schizochytrium* sp. ATCC PTA-9695 Pfa2 AT domain is represented herein as SEQ ID NO:34, corresponding to positions 1000-1400 of SEQ ID NO:4. The AT domain contains an active site motif of GxS*xG (SEQ ID NO:52) that is characteristic of acyltransferse (AT) proteins, with an active site serine residue corresponding to S1 141 of SEQ ID NO:4.

The fourth domain of *Schizochytrium* sp. ATCC PTA-9695 Pfa2 is an ER domain. The nucleotide sequence containing the sequence encoding the *Schizochytrium* sp. ATCC PTA-9695 Pfa2 ER domain is represented herein as SEQ ID NO:35, corresponding to positions 4498-5700 of SEQ ID NO:3. The amino acid sequence containing the Pfa2 ER domain is represented herein as SEQ ID NO:36, corresponding to positions 1500-1900 of SEQ ID NO:4.

Table 5 shows the domains and active sites associated with *Schizochytrium* sp. ATCC PTA-9695 PFA3.

TABLE 5

*Schizochytrium* sp. ATCC PTA-9695 PFA3 Domain Analysis

| Domain | DNA positions | AA positions | Sites | DNA positions | AA positions |
| --- | --- | --- | --- | --- | --- |
| DH1 | 1-1350 of SEQ ID NO: 5 (SEQ ID NO: 37) | 1-450 of SEQ ID NO: 6 (SEQ ID NO: 38) | FxxH*F (SEQ ID NO: 53) | 931-933 of SEQ ID NO: 5 | H310 of SEQ ID NO: 6 |
| DH2 | 1501-2700 of SEQ ID NO: 5 (SEQ ID NO: 39) | 501-900 of SEQ ID NO: 6 (SEQ ID NO: 40) | FxxH*F (SEQ ID NO: 53) | 2401-2403 of SEQ ID NO: 5 | H801 of SEQ ID NO: 6 |
| ER | 2848-4200 of SEQ ID NO: 5 (SEQ ID NO: 41) | 950-1400 of SEQ ID NO: 6 (SEQ ID NO: 42) | | | |

The first and second domains of *Schizochytrium* sp. ATCC PTA-9695 Pfa3 are DH domains, referred to herein as DH1 and DH2, respectively. The nucleotide sequence containing the sequence encoding the *Schizochytrium* sp. ATCC PTA-9695 Pfa3 DH1 domain is represented herein as SEQ ID NO:37, corresponding to positions 1-1350 of SEQ ID NO:5. The amino acid sequence containing the *Schizochytrium* sp. ATCC PTA-9695 Pfa3 DH1 domain is represented herein as SEQ ID NO:38, corresponding to positions 1-450 of SEQ ID NO:6. The nucleotide sequence containing the sequence encoding the *Schizochytrium* sp. ATCC PTA-9695 Pfa3 DH2 domain is represented herein as SEQ ID NO:39, corresponding to positions 1501-2700 of SEQ ID NO:5. The amino acid sequence containing the *Schizochytrium* sp. ATCC PTA-9695 Pfa3 DH2 domain is represented herein as SEQ ID NO:40, corresponding to positions 501-900 of SEQ ID NO:6. The DH domains contain an active site motif: FxxH*F (SEQ ID NO:53). The nucleotide sequence containing the active site motif in DH1 corresponds to positions 931-933 of SEQ ID NO:5, while the nucleotide sequence containing the active site motif in DH2 corresponds to positions 2401-2403 of SEQ ID NO:5. The active site H* in the motif FxxH*F is based on data from Leesong et al., *Structure* 4:253-64 (1996) and Kimber et al. *J Biol Chem.* 279:52593-602 (2004), with the active site H* in DH1 corresponding to H310 of SEQ ID NO:6 and the active site H* in DH2 corresponding to H801 of SEQ ID NO:6.

The third domain of *Schizochytrium* sp. ATCC PTA-9695 Pfa3 is an ER domain. The nucleotide sequence containing the sequence encoding the *Schizochytrium* sp. ATCC PTA-9695 Pfa3 ER domain is represented herein as SEQ ID NO:41, corresponding to positions 2848-4200 of SEQ ID NO:5. The amino acid sequence containing the *Schizochytrium* sp. ATCC PTA-9695 Pfa3 ER domain is represented herein as SEQ ID NO:42, coITesponding to positions 950-1400 of SEQ ID NO:6.

Example 4

Degenerate primers for the KS, ER, and DH PUPA synthase domains were designed in order to isolate the coITesponding sequences from the isolated microorganism deposited under ATCC Accession No. PTA-10212, also known as *Thraustochytrium* sp. ATCC PTA-10212.

Degenerate primers for the KS region of *Thraustochytrium* sp. ATCC PTA-10212 PFAJ (i.e., the region containing the KS domain) were designed based on the published PFAJ (previously termed orfA or ORF 1) sequences for *Schizochytrium* sp. ATCC 20888, *Thraustochytrium aureum* (ATCC 34304), and *Thraustochytrium* sp. 23B ATCC 20892:

prDS233 (forward):

(SEQ ID NO: 123)

TGATATGGGAGGAATGAATTGTGTNGTNGA YGC prDS235 (reverse):

(SEQ ID NO: 124)

TTCCATAACAAAATGATAATTAGCTCCNCCRAANCC.

Degenerate primers for the ER region of *Thraustochytrium* sp. ATCC PTA-10212 PFA2 (i.e., the region containing the ER domain) were designed based on the published PFA.2 (previously termed orfB or ORF 2) sequences for *Shewanella japonica, Schizochytrium* sp. ATCC 20888, *Thraustochytrium aureum* (ATCC 34304), and *Thraustochytrium* sp. 23B ATCC 20892:

```
prDS183 (forward):
                        (SEQ ID NO: 125)
GGCGGCCACACCGAYAAYMGNCC prDS184 (reverse):
                        (SEQ ID NO: 126)
CGGGGCCGCACCANAYYTGRTA.
```

Degenerate primers for the ER region of *Thraustochytrium* sp. ATCC PTA-10212 PFA3 (i.e., the region containing the ER domain) were designed based on the published PFA3 (previously termed orfC or ORF 3) sequences for *Shewanella japonica, Schizochytrium* sp. ATCC 20888, *Thraustochytrium aureum* (ATCC 34304), and *Thraustochytrium* sp. 23B ATCC 20892:

```
prDS181 (forward):
                        (SEQ ID NO: 127)
TCCTTCGGNGCNGSNGG prDS184 (reverse):
                        (SEQ ID NO: 126)
CGGGGCCGCACCANAYYTGRTA.
```

Degenerate primers JGM190 (forward, SEQ ID NO:64) and BLR242 (reverse, SEQ ID NO:65), as described above, were used to amplify the DH region of PFA3 from *Thraustochytrium* sp. ATCC PTA-10212.

The PCR conditions with chromosomal DNA template were as follows: 0.2 µM dNTPs, 0.1 uM each primer, 6% DMSO, 200 ng chromosomal DNA, 2.5 U Herculase® II fusion polymerase (Stratagene), and 1× Herculase® buffer (Stratagene) in a 50 µL total volume. The PCR Protocol included the following steps: (1) 98° C. for 3 minutes; (2) 98° C. for 30 seconds; (3) 54° C. for 45 seconds; (4) 72° C. for 1 minutes; (5) repeat steps 2-4 for 40 cycles; (6) 72° C. for 5 minutes; and (7) hold at 6° C.

For all primer pairs, PCR yielded distinct DNA products with the expected sizes using chromosomal templates from *Thraustochytrium* sp. ATCC PTA-10212. The respective PCR products were cloned into the vector pJET1 0.2/blunt (Fermentas) according to the manufacturer's instructions, and the insert sequence was determined using supplied standard primers.

The DNA sequences obtained from the PCR products were compared with known sequences available from the NCBI GenBank as described in Example 1.

At the amino acid level, the sequences with the highest level of homology to deduced amino acid sequence derived from the cloned DNA containing the KS fragment from PFAJ from *Thraustochytrium* sp. ATCC PTA-10212 were: *Schizochytrium* sp. ATCC 20888 "polyunsaturated fatty acid synthase subunit A" (Identity=80%; positives=90%); *Shewanella benthica* KT99 "omega-3 polyunsaturated fatty acid synthase PfaA" (Identity=51%; positives=67%); *Shewanella loihica* PV-4 "beta-ketoacyl synthase" (Identity=50%; positives=67%); *Shewanella woodyi* ATCC 51908 "polyketide-type polyunsaturated fatty acid synthase PfaA" (Identity=51%; positives=66%).

At the amino acid level, the sequences with the highest level of homology to deduced amino acid sequence derived from the cloned DNA containing the ER fragment from PFA2 from *Thraustochytrium* sp. ATCC PTA-10212 were: *Schizochytrium* sp. ATCC 20888 "polyunsaturated fatty acid synthase subunit B" (Identity=70%; positives=85%); *Schizochytrium* sp. ATCC 20888 "polyunsaturated fatty acid synthase subunit C" (Identity=66%; positives=83%); *Nodularia spumigena* CCY9414 "2-nitropropane dioxygenase" (Identity=57%; positives=74%); *Moritella* sp. PE36 "polyunsaturated fatty acid synthase PfaD" (Identity=57%; positives=71%).

At the amino acid level, the sequences with the highest level of homology to deduced amino acid sequence derived from the cloned DNA containing the ER fragment from PFA3 from *Thraustochytrium* sp. ATCC PTA-10212 were: *Schizochytrium* sp. ATCC 20888 "polyunsaturated fatty acid synthase subunit C" (Identity=80%; positives=90%); *Schizochytrium* sp. ATCC 20888 "polyunsaturated fatty acid synthase subunit B" (Identity=78%; positives=89%); *Moritella* sp. PE36 "polyunsaturated fatty acid synthase PfaD" (Identity=56%; positives=71%); *Shewanella amazonensis* SB2B "omega-3 polyunsaturated fatty acid synthase PfaD" (Identity=55%; positives=73%).

At the amino acid level, the sequences with the highest level of homology to deduced amino acid sequence derived from the cloned DNA containing the DH fragment from PFA3 from *Thraustochytrium* sp. ATCC PTA-10212 were: *Schizochytrium* sp. ATCC 20888 "polyunsaturated fatty acid synthase subunit C" (Identity=63%; positives=76%); *Shewanella pealeana* ATCC 700345 "B eta-hydroxyacyl-(acyl-carrier-protein) dehydratase FabA/FabZ" (Identity=35%; positives=53%); *Shewanella piezotolerans* WP3 "Multi-domain beta-ketoacyl synthase" (Identity=36%; positives=52%); *Shewanella benthica* KT99 "omega-3 polyunsaturated fatty acid synthase PfaC" (Identity=35%; positives=51%).

EXAMPLES

PUPA synthase genes were identified from *Thraustochytrium* sp. ATCC PTA-10212.

From a −80° C. cyrovial, 1 mL of cells were thawed at room temperature and added to 50 mL of liquid HSFM media (below) in a 250 mL non-baffled flask. The flask was incubated at 23° C. for 3 days. Cells were collected and utilized for standard Bacterial Artificial Chromosome (BAC) library construction (Lucigen Corporation, Middleton, Vv'J USA).

TABLE 6

| HSFM Media | | | |
|---|---|---|---|
| Ingredient | | concentration | ranges |
| Na2S04 | g/L | 31.0 | 0-50, 15-45, or 25-35 |
| NaCl | g/L | 0.625 | 0-25, 0.1-10, or 0.5-5 |
| KCl | g/L | 1.0 | 0-5, 0.25-3, or 0.5-2 |
| MgS04•7H2O | g/L | 5.0 | 0-10, 2-8, or 3-6 |
| (NH4)2S04 | g/L | 0.44 | 0-10, 0.25-5, or 0.05-3 |
| MSG*IH2O | g/L | 6.0 | 0-10, 4-8, or 5-7 |

TABLE 6-continued

HSFM Media

| Ingredient | concentration | | ranges |
|---|---|---|---|
| CaCh | g/L | 0.29 | 0.1-5, 0.15-3, or 0.2-1 |
| T 154 (yeast extract) | g/L | 6.0 | 0-20, 0.1-10, or 1-7 |
| KH2PO4 | g/L | 0.8 | 0.1-10, 0.5-5, or 0.6-1.8 |
| Post autoclave (Metals) | | | |
| Citric acid | mg/L | 3.5 | 0.1-5000, 10-3000, or 3-2500 |
| $FeSO_4 \cdot 7H_2O$ | mg/L | 10.30 | 0.1-100, 1-50, or 5-25 |
| MnCh—4H2O | mg/L | 3.10 | 0.1-100, 1-50, or 2-25 |
| $ZnSO_4 \cdot 7H_2O$ | mg/L | 3.10 | 0.01-100, 1-50, or 2-25 |
| COCh•6H2O | mg/L | 0.04 | 0-1, 0.001-0.1, or 0.01-0.1 |
| $Na_2MoO_4 \cdot 2H_2O$ | mg/L | 0.04 | 0.001-1, 0.005-0.5, or 0.01-0.1 |
| CuSO4•5H2O | mg/L | 2.07 | 0.1-100, 0.5-50, or 1-25 |
| $NiSO_4 \cdot 6H_2O$ | mg/L | 2.07 | 0.1-100, 0.5-50, or 1-25 |
| Post autoclave (Vitamins) | | | |
| Thiamine | mg/L | 9.75 | 0.1-100, 1-50, or 5-25 |
| Vitamin B12 | mg/L | 0.16 | 0.01-100, 0.05-5, or 0.1-1 |
| Ca½-pantothenate | mg/L | 2.06 | 0.1-100, 0.1-50, or 1-10 |
| Biotin | mg/L | 3.21 | 0.1-100, 0.1-50, or 1-10 |
| Post autoclave (Carbon) | | | |
| Glycerol | g/L | 30.0 | 5-150, 10-100, or 20-50 |
| Nitrogen Feed: | | | |
| MSG•1H2O | g/L | 17 | 0-150, 10-100, or 15-50 |

Typical Cultivation Conditions would Include the Following:
   pH about 6.5-about 9.5, about 6.5-about 8.0, or about 6.8-about 7.8;
   temperature: about 15-about 30 degrees Celsius, about 18-about 28 degrees Celsius, or about 21 to about 23 degrees Celsius;
   dissolved oxygen: about 0.1-about 100% saturation, about 5-about 50% saturation, or about 10-about 30% saturation; and/or
   glycerol controlled @: about 5-about 50 g/L, about 10-about 40 g/L, or about 15-about 35 g/L.

The recombinant BAC libraries, consisting of large fragments (average of approximately 120 kB) were handled according to the manufacturer's instructions in the BAC vector pSMART® (Lucigen Corporation). The BAC libraries were screened by standard colony hybridization procedures using $^{32}P$ radioactively labeled probes (Sambrook J. and Russell D. 2001. Molecular cloning: A laboratory manual, 3rd edition. Cold Spring Harbor Laboratory Press, Cold Spring Harbor, New York). The probes contained DNA homologous to published PUPA synthase sequences from other organisms as described in Example 4. These probes were generated by a DNA restriction digest of the cloned fragments from respective clones from pJET1 0.2/blunt described above and labeled by standard methods. In all cases, strong hybridization of the individual probes to certain BACs indicated clones containing DNA homologous to PUPA synthase genes.

BAC clone pLR130 (also known as LuMaBAC 2M23) demonstrated strong hybridization of probe to both the KS region and ER region, indicating that it contained the PFAJ and PFA2 genes, and was selected for DNA sequencing of the Thraustochytrium sp. ATCC PTA-10212 PFAJ and PFA2 genes. The BAC was sequenced by standard procedures (Eurofins MWG Operon, Huntsville, AL). BAC clone pLR130, containing the PFAJ and PFA2 genes, was deposited under the Budapest Treaty, at the American Type Culture Collection, Patent Depository, 10801 University Boulevard, Manassas, VA 20110-2209, on Dec. 1, 2009, and given ATCC Accession No. PTA-10511.

In previously published thraustochytrid PUPA synthase systems, the PUPA synthase genes PFAJ and PFA2 have been clustered together and arranged as to be divergently transcribed. This is also the case for PFAJ and PFA2 from Thraustochytrium 5p. ATCC PTA-10212. The conceptual start of PFA2 was found to be 693 nucleotides from the start of PFAJ and divergently transcribed.

BAC clone pDS127 (also known as LuMaBAC 9K1 7) demonstrated strong hybridization of probe to both the DH region and ER region of PFA3 and was selected for DNA sequencing of the PFA3 gene. BAC clone pDS127, containing the PFA3 gene, was deposited under the Budapest Treaty, at the American Type Culture Collection, Patent Depository, 10801 University Boulevard, Manassas, VA 20110-2209, on Dec. 1, 2009, and given ATCC Accession No. PTA-10510. Sequencing primers were designed using standard methods to the DH region and ER region and the DNA sequence determined in Example 4. To determine the DNA sequence of the Thraustochytrium sp. ATCC PTA-10212 PFA3 gene, successive rounds of DNA sequencing, involving subsequent sequencing primer design by standard methods, was carried out in order to "walk" the BAC clone. Each nucleotide base pair of the PFA3 gene was covered by at least two separate DNA sequencing reactions of high-quality with at least a minimum aggregated Phred score of 40 (confidence level of 99.99%).

Table 7 shows identities for the Thraustochytrium sp. ATCC PTA-10212 PFAJ (SEQ ID NO:68), PFA2 (SEQ ID NO:70), and PFA3 (SEQ ID NO:72) polynucleotide sequences as compared to previously published sequences and the sequences from Schizochytrium sp. PTA-9695. Identities were determined by the scoring matrix "swgapdnamt" within the "AlignX" program of the VectorNTI program, a standard for DNA alignment.

TABLE 7

Percent Identity to PFAJ, PFA2, and PFA3 Polynucleotide Sequences

| Source of Comparison PFAl, PFA2, and PFA3 Sequences | % Identity of Comparison PFAJ (or/A) to PFAJ | % Identity of Comparison PFA2 (orfB) to PFA2 | % Identity of Comparison PFA3 (orfC) to PFA3 |
|---|---|---|---|
| *Schizochytrium* sp. ATCC 20888 | 55 | 54 | 59 |
| *Thraustochytrium aureum* ATCC 34304 | 55 | 53 | not published |
| *Thraustochytrium* sp. 23B ATCC 20892 | 55 | 57 | 62 |
| Schizochytriumsp. PTA-9695 | 55 | 52 | 59 |

Table 8 shows identities for the *Thraustochytrium* sp. ATCC PTA-10212 Pfa1p (SEQ ID NO:69), Pfa2p (SEQ ID NO:71), and Pfa3p (SEQ ID NO:73) amino acid sequences as compared to previously published PUPA synthase amino acid sequences and the sequences from *Schizochytrium* sp. PTA-9695. Identities were determined through use of the scoring matrix "blosum62mt2" within the "AlignX" program of the VectorNTI program, a standard for protein alignment.

TABLE 8

Percent Identity to Pfa1p, Pfa2p, and Pfa3p Amino Acid Sequences

| Source of Comparison Pfa1p, Pfa2p, and Pfa3p Sequences | % Identity of Comparison Pfa1p (OrfA) to Pfa1p | % Identity of Comparison Pfa2p (Orfi) to Pfa2p | % Identity of Comparison Pfa3p (OrfC) to Pfa3p |
|---|---|---|---|
| *Schizochytrium* sp. ATCC 20888 | 62 | 57 | 69 |
| *Thraustochytrium aureum* ATCC 34304 | 58 | 54 | not published |
| *Thraustochytrium* sp. 23B ATCC 20892 | 54 | 54 | 71 |
| Schizochytriumsp. PTA-9695 | 59 | 53 | 73 |

Example 6

Domain analysis was performed to annotate the sequence coordinates for the PUPA synthase domains and active sites of *Thraustochytrium* sp. ATCC PTA-10212 PFA.1, PFA2, and PFA3, respectively. Domains were identified based on homology to known PUPA synthase, fatty acid synthase, and polyketide synthase domains.

Table 9 shows the domains and active sites associated with *Thraustochytrium* sp. ATCC PTA-10212 PFAJ.

TABLE 9

*Thraustochytrium* sp. ATCC PTA-10212 PFAJ Domain Analysis

| Domain | DNA position | AA position | Sites | DNA position | AA position |
|---|---|---|---|---|---|
| KS | 13-1362 of SEQ ID NO: 68 (SEQ ID NO: 74) | 5-545 of SEQ ID NO: 69 (SEQ ID NO: 75) | Active - DXAC* (SEQ ID NO: 43) | 601-612 of SEQ ID NO: 68 | C204 of SEQ ID NO: 69 |
|  |  |  | End-GFGG (SEQ ID NO: 44) | 1351-1362 of SEQ ID NO: 68 (SEQ ID NO: 45) | 451-454 of SEQ ID NO: 69 |
| MAT | 1783-2703 of SEQ ID NO: 68 (SEQ ID NO: 76) | 595-901 of SEQ ID NO: 69 (SEQ ID NO: 77) | Active GHS*LG (SEQ ID NO: 46) | 2083-2085 of SEQ ID NO: 68 (SEQ ID NO: 116) | S695 of SEQ ID NO: 69 |
| ACP | 3208-6510 of SEQ ID NO: 68 (SEQ ID NO: 78) | 1070-2170 of SEQ ID NO: 69 (SEQ ID NO: 79) | ACPl domain | 3280-3534 of SEQ ID NO: 68 (SEQ ID NO: 80) | 1094-1178 of SEQ ID NO: 69 (SEQ ID NO: 81) |

TABLE 9-continued

*Thraustochytrium* sp. ATCC PTA-10212 PFAJ Domain Analysis

| Domain | DNA position | AA position | Sites | DNA position | AA position |
|---|---|---|---|---|---|
| | | | ACP1 Active LGIDS* (SEQ ID NO: 47) | 3403-3405 of SEQ ID NO: 68 | S1135 of SEQ ID NO: 69 |
| | | | ACP2 domain | 3607-3861 of SEQ ID NO: 68 (SEQ ID NO: 82) | 1203-1287 of SEQ ID NO: 69 (SEQ ID NO: 83) |
| | | | ACP2 Active LGIDS* (SEQ ID NO: 47) | 3730-3732 of SEQ ID NO: 68 | S1244 of SEQ ID NO: 69 |
| | | | ACP3 domain | 3934-4185 of SEQ ID NO: 68 (SEQ ID NO: 84) | 1312-1396 of SEQ ID NO: 69 (SEQ ID NO: 85) |
| | | | ACP3 Active LGIDS* (SEQ ID NO: 47) | 4057-4059 of SEQ ID NO: 68 | S1353 of SEQ ID NO: 69 |
| | | | ACP4 domain | 4261-4515 of SEQ ID NO: 68 (SEQ ID NO: 86) | 1421-1505 of SEQ ID NO: 69 (SEQ ID NO: 87) |
| | | | ACP4 Active LGIDS* (SEQ ID NO: 47) | 4384-4386 of SEQ ID NO: 68 | S1462 of SEQ ID NO: 69 |
| | | | ACP5 domain | 4589-4842 of SEQ ID NO: 68 (SEQ ID NO: 88) | 1530-1614 of SEQ ID NO: 69 (SEQ ID NO: 89) |
| | | | ACP5 Active LGIDS* (SEQ ID NO: 47) | 4711-4713 of SEQ ID NO: 68 | S1571 of SEQ ID NO: 69 |
| | | | ACP6 domain | 4915-5169 of SEQ ID NO: 68 (SEQ ID NO: 90) | 1639-1723 of SEQ ID NO: 69 (SEQ ID NO: 91) |
| | | | ACP6 Active LGIDS* (SEQ ID NO: 47) | 5038-5040 of SEQ ID NO: 68 | S1680 of SEQ ID NO: 69 |
| | | | ACP7 domain | 5242-5496 of SEQ ID NO: 68 (SEQ ID NO: 92) | 1748-1832 of SEQ ID NO: 69 (SEQ ID NO: 93) |
| | | | ACP7 Active LGIDS* (SEQ ID NO: 47) | 5365-5367 of SEQ ID NO: 68 | S1789 of SEQ ID NO: 69 |
| | | | ACP8 domain | 5569-5823 of SEQ ID NO: 68 (SEQ ID NO: 94) | 1857-1941 of SEQ ID NO: 69 (SEQ ID NO: 95) |
| | | | ACP8 Active LGIDS* (SEQ ID NO: 47) | 5692-5694 of SEQ ID NO: 68 | S1898 of SEQ ID NO: 69 |
| | | | ACP9 domain | 5896-6150 of SEQ ID NO: 68 (SEQ ID NO: 96) | 1966-2050 of SEQ ID NO: 69 (SEQ ID NO: 97) |
| | | | ACP9 Active LGIDS* (SEQ ID NO: 47) | 6019-6021 of SEQ ID NO: 68 | S2007 of SEQ ID NO: 69 |
| | | | ACP10 domain | 6199-6453 of SEQ ID NO: 68 (SEQ ID NO: 98) | 2067-2151 of SEQ ID NO: 69 (SEQ ID NO: 99) |
| | | | ACP10 Active LGIDS* (SEQ ID NO: 47) | 6322-6324 of SEQ ID NO: 68 | S2108 of SEQ ID NO: 69 |
| KR | 6808-8958 of SEQ ID NO: 68 (SEQ ID NO: 100) | 2270-2986 of SEQ ID NO: 69 (SEQ ID NO: 101) | "core region" | 7198-8100 of SEQ ID NO: 68 (SEQ ID NO: 116) | 2400-2600 of SEQ ID NO: 69 (SEQ ID NO: 117) |
| DH Motif | 8203-8241 of SEQ ID NO: 68 (SEQ ID NO: 118) | 2735-2747 of SEQ ID NO: 69 (SEQ ID NO: 119) | LxxHxxxGxxxxP (SEQ ID NO: 50) | 8203-8241 of SEQ ID NO: 68 (SEQ ID NO: 118) | 2735-2747 of SEQ ID NO: 69 (SEQ ID NO: 119) |

The first domain in *Thraustochytrium* sp. ATCC PTA-10212 Pfa1 is a KS domain. The nucleotide sequence containing the sequence encoding the *Thraustochytrium* sp. ATCC PTA-10212 Pfa1 KS domain is represented herein as SEQ ID NO:74, corresponding to positions 13-1362 of SEQ ID NO:68. The amino acid sequence containing the *Thraustochytrium* sp. ATCC PTA-10212 Pfa1 KS domain is represented herein as SEQ ID NO:75, corresponding to positions 5-454 of SEQ ID NO:69. The KS domain contains an active site motif: DXAC* (SEQ ID NO:43), with an *acyl binding cite corresponding to C204 of SEQ ID NO:69. Also, a characteristic motif is present at the end of the KS domain: GFGG (SEQ ID NO:44), corresponding to positions 451-454 of SEQ ID NO:69 and positions 447-450 of SEQ ID NO:75.

The second domain in *Thraustochytrium* sp. ATCC PTA-10212 Pfa1 is a MAT domain. The nucleotide sequence containing the sequence encoding the *Thraustochytrium* sp. ATCC PTA-10212 Pfa1 MAT domain is represented herein as SEQ ID NO:76, corresponding to positions 1783-2703 of SEQ ID NO:68. The amino acid sequence containing the *Thraustochytrium* sp. ATCC PTA-10212 Pfa1 MAT domain is represented herein as SEQ ID NO:77, corresponding to positions 595-901 of SEQ ID NO:69. The MAT domain contains an active site motif: GHS*XG (SEQ ID NO:46), with an *acyl binding cite corresponding to 5695 of SEQ ID NO:69.

The third through twelfth domains of *Thraustochytrium* sp. ATCC PTA-10212 Pfa1p are ten tandem ACP domains, also referred to herein as ACP1, ACP2, ACP3, ACP4, ACP5, ACP6, ACP7, ACP8, ACP9, and ACP1O. The nucleotide sequence containing the first ACP domain, ACP1, is represented herein as SEQ ID NO:80 and is contained within the nucleotide sequence spanning from about position 3280 to about position 3534 of SEQ ID NO:68. The amino acid sequence containing ACP1, represented herein as SEQ ID NO:81, is contained within the amino acid sequence spanning from about position 1094 to about position 1178 of SEQ ID NO:69. The nucleotide sequence containing ACP2, represented herein as SEQ ID NO:82, is contained within the nucleotide sequence spanning from about position 3607 to about position 3861 of SEQ ID NO:68. The amino acid sequence containing ACP2, represented herein as SEQ ID NO:83, is contained within the amino acid sequence spanning from about position 1203 to about position 1287 of SEQ ID NO:69. The nucleotide sequence containing ACP3, represented herein as SEQ ID NO:84, is contained within the nucleotide sequence spanning from about position 3934 to about position 4185 of SEQ ID NO:68. The amino acid sequence containing ACP3, represented herein as SEQ ID NO:85, is contained within the amino acid sequence spanning from about position 1312 to about position 1396 of SEQ ID NO:69. The nucleotide sequence containing ACP4, represented herein as SEQ ID NO:86, is contained within the nucleotide sequence spanning from about position 4261 to about position 4515 of SEQ ID NO:68. The amino acid sequence containing ACP4, represented herein as SEQ ID NO:87, is contained within the amino acid sequence spanning from about position 1421 to about position 1505 of SEQ ID NO:69. The nucleotide sequence containing ACP5, represented herein as SEQ ID NO:88, is contained within the nucleotide sequence spanning from about position 4589 to about position 4842 of SEQ ID NO:68. The amino acid sequence containing ACP5, represented herein as SEQ ID NO:89, is contained within the amino acid sequence spanning from about position 1530 to about position 1614 of SEQ ID NO:69. The nucleotide sequence containing ACP6, represented herein as SEQ ID NO:90, is contained within the nucleotide sequence spanning from about position 4915 to about position 5169 of SEQ ID NO:68. The amino acid sequence containing ACP6, represented herein as SEQ ID NO:91, is contained within the amino acid sequence spanning from about position 1639 to about position 1723 of SEQ ID NO:69. The nucleotide sequence containing ACP7, represented herein as SEQ ID NO:92, is contained within the nucleotide sequence spanning from about position 5242 to about position 5496 of SEQ ID NO:68. The amino acid sequence containing ACP7, represented herein as SEQ ID NO:93, is contained within the amino acid sequence spanning from about position 1748 to about position 1832 of SEQ ID NO:69. The nucleotide sequence containing ACP8, represented herein as SEQ ID NO:94, is contained within the nucleotide sequence spanning from about position 5569 to about position 5832 of SEQ ID NO:68. The amino acid sequence containing ACP8, represented herein as SEQ ID NO:95, is contained within the amino acid sequence spanning from about position 1857 to about position 1941 of SEQ ID NO:69. The nucleotide sequence containing ACP9, represented herein as SEQ ID NO:96, is contained within the nucleotide sequence spanning from about position 5896 to about position 6150 of SEQ ID NO:68. The amino acid sequence containing ACP9, represented herein as SEQ ID NO:97, is contained within the amino acid sequence spanning from about position 1966 to about position 2050 of SEQ ID NO:69. The nucleotide sequence containing ACP1O, represented herein as SEQ ID NO:98, is contained within the nucleotide sequence spanning from about position 6199 to about position 6453 of SEQ ID NO:68. The amino acid sequence containing ACP1O, represented herein as SEQ ID NO:99, is contained within the amino acid sequence spanning from about position 2067 to about position 2151 of SEQ ID NO:69. All ten ACP domains together span a region of *Thraustochytrium* sp. ATCC PTA-10212 Pfa1 of from about position 3208 to about position 6510 of SEQ ID NO:68, corresponding to amino acid positions of about 1070 to about 2170 of SEQ ID NO:69. The nucleotide sequence for the entire ACP region containing all 10 domains is represented herein as SEQ ID NO:78; while the amino acid sequence for the entire ACP region containing all six domains is represented herein as SEQ ID NO:79. The repeat interval for the 10 ACP domains within SEQ ID NO:78 was found to be approximately every 327 nucleotides (the actual number of amino acids measured between adjacent active site serines ranges from 101 to 109 amino acids). Each of the ten ACP domains contains a pantetheine binding motif LGIDS* (SEQ ID NO:47) wherein S* is the pantetheine binding site serine (S). The pantetheine binding site serine (S) is located near the center of each ACP domain sequence. The locations of the active site serine residues (i.e., the pantetheine binding site) for each of the six ACPD domains, with respect to the amino acid sequence of SEQ ID NO:69 are: ACP1=S1135, ACP2=S1244, ACP3=S1353, ACP4=S1462, ACP5=S1571, ACP6=S1680, APC7=S1789, ACP7=S1789, ACP8=S1898, ACP9=S=2007, and ACP1O=S2108.

The thirteenth domain in *Thraustochytrium* sp. ATCC PTA-10212 Pfa1 is a KR domain. The nucleotide sequence containing the sequence encoding the Pfa1 KR domain is represented herein as SEQ ID NO:100, corresponding to positions 6808-8958 of SEQ ID NO:68. The amino acid sequence containing the Pfa1 KR domain is represented herein as SEQ ID NO:101, corresponding to positions 2270-2986 of SEQ ID NO:69. Within the KR domain is a core region (contained within the nucleotide sequence of SEQ ID NO:116, and the amino acid sequence of SEQ ID NO: 117) with homology to short chain aldehyde-dehydrogenases (KR is a member of this family). This core region spans from about position 5998 to about 6900 of SEQ ID NO:68, which corresponds to amino acid positions 2000-2300 of SEQ ID NO:69.

The fourteenth domain in *Thraustochytrium* sp. ATCC PTA-10212 Pfa1 is a DH domain. The nucleotide sequence containing the sequence encoding the Pfa1 DH domain is represented herein as SEQ ID NO:118, corresponding to positions 7027-7065 of SEQ ID NO:68. The amino acid sequence containing the Pfa1 DH domain is represented herein as SEQ ID NO:119, corresponding to positions 2343-2355 of SEQ ID NO:69. The DH domain contains a conserved active site motif (see, Donadio, S. and Katz., L., Gene 111(1): 51-60 (1992)): LxxHxxxGxxxxP (SEQ ID NO:50).

Table 10 shows the domains and active sites associated with *Thraustochytrium* sp. ATCC PTA-10212 PFA2.

The second domain in *Thraustochytrium* sp. ATCC PTA-10212 Pfa2 is a CLP domain. The nucleotide sequence containing the sequence encoding the *Thraustochytrium* sp. ATCC PTA-10212 Pfa2 CLP domain is represented herein as SEQ ID NO:104, corresponding to positions 1378-2700 of SEQ ID NO:70. The amino acid sequence containing the *Thraustochytrium* sp. ATCC PTA-10212 Pfa2 CLP domain is represented herein as SEQ ID NO:105, corresponding to positions 460-900 of SEQ ID NO:71.

The third domain in *Thraustochytrium* sp. ATCC PTA-10212 Pfa2 is an AT domain. The nucleotide sequence containing the sequence encoding the *Thraustochytrium* sp. ATCC PTA-10212 Pfa2 AT domain is represented herein as SEQ ID NO:106, corresponding to positions 2848-4200 of SEQ ID NO:70. The amino acid sequence containing the *Thraustochytrium* sp. ATCC PTA-10212 Pfa2 AT domain is represented herein as SEQ ID NO:107, corresponding to positions 950-1400 of SEQ ID NO:71. The AT domain contains an active site motif of GxS*xG (SEQ ID NO:50)

TABLE 10

*Thraustochytrium* sp. ATCC PTA-10212 PFA2 Domain Analysis

| Domain | DNA positions | AA positions | Sites | DNA positions | AA positions |
| --- | --- | --- | --- | --- | --- |
| KS | 10-1320 of SEQ ID NO: 70 (SEQ ID NO: 102) | 4-440 of SEQ ID NO: 71 (SEQ ID NO: 103) | DXAC* (SEQ ID NO: 43) | 571-573 of SEQ ID NO: 70 | C191 of SEQ ID NO: 71 |
|  |  |  | End-GFGG (SEQ ID NO: 44) | 1267-1278 of SEQ ID NO: 70 | 423-426 of SEQ ID NO: 71 |
| CLF | 1378-2700 of SEQ ID NO: 70 (SEQ ID NO: 104) | 460-900 of SEQ ID NO: 71 (SEQ ID NO: 105) |  |  |  |
| AT | 2848-4200 of SEQ ID NO: 70 (SEQ ID NO: 106) | 950-1400 of SEQ ID NO: 71 (SEQ ID NO: 107) | GxS*xG (SEQ ID NO: 52) | 3361-3363 of SEQ ID NO: 70 | S1121 of SEQ ID NO: 71 |
| ER | 4498-5700 of SEQ ID NO: 70 (SEQ ID NO: 108) | 1500-1900 of SEQ ID NO: 71 (SEQ ID NO: 109) |  |  |  |

The first domain in *Thraustochytrium* sp. ATCC PTA-10212 Pfa2 is a KS domain. The nucleotide sequence containing the sequence encoding the *Thraustochytrium* sp. ATCC PTA-10212 Pfa2 KS domain is represented herein as SEQ ID NO:102, coITesponding to positions 10-1320 of SEQ ID NO:70. The amino acid sequence containing the *Thraustochytrium* sp. ATCC PTA-10212 Pfa2 KS domain is represented herein as SEQ ID NO:103, corresponding to positions 4-440 of SEQ ID NO:71. The KS domain contains an active site motif: DXAC* (SEQ ID NO:43), with an *acyl binding cite corresponding to C191 of SEQ ID NO:71. Also, a characteristic motif is present at the end of the KS domain: GPGG (SEQ ID NO:44), corresponding to positions 423-426 of SEQ ID NO:71 and positions 1267-1278 of SEQ ID NO:70.

that is characteristic of acyltransferse (AT) proteins, with an active site seline residue corresponding to S1121 of SEQ ID NO:71.

The fourth domain of *Thraustochytrium* sp. ATCC PTA-10212 Pfa2 is an ER domain. The nucleotide sequence containing the sequence encoding the *Thraustochytrium* sp. ATCC PTA-10212 Pfa2 ER domain is represented herein as SEQ ID NO:108, corresponding to positions 4498-5700 of SEQ ID NO:70. The amino acid sequence containing the *Thraustochytrium* sp. ATCC PTA-10212 Pfa2 ER domain is represented herein as SEQ ID NO:109, corresponding to positions 1500-1900 of SEQ ID NO:71.

Table 11 shows the domains and active sites associated with *Thraustochytrium* sp. ATCC PTA-10212 PFA.3.

TABLE 11

*Thraustochytrium* sp. ATCC PTA-10212 PFA3 Domain Analysis

| Domain | DNA positions | AA positions | Sites | DNA positions | AA positions |
| --- | --- | --- | --- | --- | --- |
| DH1 | 1-1350 of SEQ ID NO: 72 | 1-450 of SEQ ID NO: 73 | FxxH*F (SEQ ID NO: 53) | 934-936 of SEQ ID | H312 of SEQ ID NO: 73 |

TABLE 11-continued

Thraustochytrium sp. ATCC PTA-10212 PFA3 Domain Analysis

| Domain | DNA positions | AA positions | Sites | DNA positions | AA positions |
|---|---|---|---|---|---|
| | (SEQ ID NO: 110) | (SEQ ID NO: 111) | | NO: 72 | |
| DH2 | 1501-2700 of SEQ ID NO: 72 (SEQ ID NO: 112) | 501-900 of SEQ ID NO: 73 (SEQ ID NO: 113) | FxxH*F (SEQ ID NO: 53) | 2401-2403 of SEQ ID NO: 72 | H801 of SEQ ID NO: 73 |
| ER | 2848-4212 of SEQ ID NO: 72 (SEQ ID NO: 114) | 950-1404 of SEQ ID NO: 73 (SEQ ID NO: 115) | | | |

The first and second domains of *Thraustochytrium* sp. ATCC PTA-10212 Pfa3 are DH domains, referred to herein as DH1 and DH2, respectively. The nucleotide sequence containing the sequence encoding the *Thraustochytrium* sp. ATCC PTA-10212 Pfa3 DH1 domain is represented herein as SEQ ID NO:110, corresponding to positions 1-1350 of SEQ ID NO:72. The amino acid sequence containing the *Thraustochytrium* sp. ATCC PTA-10212 Pfa3 DH1 domain is represented herein as SEQ ID NO:111, corresponding to positions 1-450 of SEQ ID NO:73. The nucleotide sequence containing the sequence encoding the *Thraustochytrium* 5p. ATCC PTA-10212 Pfa3 DH2 domain is represented herein as SEQ ID NO:112, corresponding to positions 1501-2700 of SEQ ID NO:72. The amino acid sequence containing the *Thraustochytrium* sp. ATCC PTA-10212 Pfa3 DH2 domain is represented herein as SEQ ID NO:113, corresponding to positions 501-900 of SEQ ID NO:73. The DH domains contain an active site motif: PxxH*P (SEQ ID NO:53). The nucleotide sequence containing the active site motif in DH1 corresponds to positions 934-936 of SEQ ID NO:72, while the nucleotide sequence containing the active site motif in DH2 corresponds to positions 2401-2403 of SEQ ID NO:72. The active site H* in the motif PxxH*P is based on data from Leesong et al., Structure 4:253-64 (1996) and Kimber et al. J Biol Chem. 279:52593-602 (2004), with the active site H* in DH1 corresponding to H312 of SEQ ID NO:73 and the active site H* in DH2 corresponding to H801 of SEQ ID NO:73.

The third domain of *Thraustochytrium* sp. ATCC PTA-10212 Pfa3 is an ER domain. The nucleotide sequence containing the sequence encoding the *Thraustochytrium* sp. ATCC PTA-10212 Pfa3 ER domain is represented herein as SEQ ID NO:114, corresponding to positions 2848-4200 of SEQ ID NO:72. The amino acid sequence containing the *Thraustochytrium* sp. ATCC PTA-10212 Pfa3 ER domain is represented herein as SEQ ID NO:115, corresponding to positions 950-1400 of SEQ ID NO:73.

Example 7

The inactivation of native PUPA synthase genes in *Schizochytrium* sp. ATCC 20888, to generate PUPA auxotrophs, and the replacement of such inactivated genes with exogenously introduced homologous genes to restore PUPA synthesis has been previously demonstrated and described. See, e.g., U.S. Pat. No. 7,217,856, incorporated by reference herein in its entirety. The three PUPA synthase genes from *Schizochytrium* sp. ATCC 20888 have been previously termed oifA, oifB, and 01fC, corresponding to the PFAJ, PFA2, and PPA3 nomenclature used herein, respectively. Id.

The native orfA gene in *Schizochytrium* sp. ATCC 20888 was replaced by homologous recombination following transformation with a vector containing the Zeocin$_{1M}$ resistance marker surrounded by sequences from the oifA flanking region. A mutant strain was generated lacking a functional orfA gene. The mutant strain was auxotrophic and required PUFA supplementation for growth.

*Schizochytrium* sp. ATCC PTA-9695 PFAJ (SEQ ID NO:1) was cloned into expression vector pREZ37 to generate pREZ345. The expression vector contained approximately 2 kb of DNA from the flanking region of the native oifA gene locus from *Schizochytrium* sp. ATCC 20888. The *Schizochytrium* sp. ATCC 20888 mutant lacking functional oifA was transformed via electroporation with enzyme pretreatment (see below) with pREZ345 containing PFAJ. Based on homologous regions flanking the Zeocin™ resistance marker in the mutant and flanking the PFAJ gene in pREZ345, double-crossover recombination occurred such that PFAJ was inserted into the native 011,4 locus. Recombination with *Schizochytrium* sp. ATCC PTA-9695 PFAJ (SEQ ID NO:1) restored PUPA production in the *Schizochytrium* sp. ATCC 20888 mutant lacking 01fA. In brief, cells were grown in M2B liquid media (see following paragraph) at 30° C. with 200 rpm shaking for 3 days. Cells were harvested and the fatty acids were converted to methyl-esters using standard techniques. Fatty acid profiles were determined using gas chromatography with flame ionization detection (GC-FID) as fatty acid methyl esters (FAME). The native *Schizochytrium* sp. ATCC 20888 strain containing a functional orfA gene produced DHA and DPA n-6 in a ratio of 2.3:1. The recombinant strain containing *Schizochytrium* sp. ATCC PTA-9695 PFAJ (SEQ ID NO:1) in place of the inactivated orfA gene also produced DHA and DPA n-6 in a ratio of 2.4:1. The EPA content of the recombinant strain was 2.7% of fatty acid methyl-esters (FAME), the DPA n-3 content was 0.7%, the DPA n-6 content was 8.8%, and the DHA content was 21.2%.

M2B Medium—10 g/L glucose, 0.8 g/L (NH4)2SO4, 5 g/L Na2SO4, 2 g/L MgSO4·7H2O, 0.5 g/L KH2PO4, 0.5 g/L KCl, 0.1 g/L CaCh·2H2O, 0.1 M MES (pH 6.0) 0.1% PB26 metals, and 0.1% PB26 Vitamins (v/v). PB26 vitamins consisted of 50 mg/mL vitamin B12, 100 µg/mL thiamine, and 100 µg/mL Ca-pantothenate. PB26 metals were adjusted to pH 4.5 and consisted of 3 g/L FeSO$_4$·7H$_2$O, 1 g/L MnCh·4H$_2$O, 800 mg/mL ZnSO4.7H2O, 20 mg/mL COCh·6H$_2$O, 10 mg/mL Na2MoO4.2H2O, 600 mg/mL CuSO$_4$·5 H$_2$O, and 800 mg/mL NiSO$_4$·6H$_2$O. PB26 stock solutions were filter-sterilized separately and added to the broth after autoclaving. Glucose, KH$_2$PO$_4$, and CaCh·2H$_2$O were each autoclaved separately from the remainder of the broth ingredients before mixing to prevent salt precipitation and carbohydrate caramelizing. All medium ingredients were purchased from Sigma Chemical (St. Louis, MO).

Electroporation—with Enzyme Pretreatment—Cells were grown in 50 mL of M50-20 media (see U.S. Publ. No. 2008/0022422) on a shaker at 200 rpm for 2 days at 30° C. The cells were diluted at 1:100 into M2B media and grown overnight (16-24 h), attempting to reach mid-log phase growth (OD600 of 1.5-2.5). The cells were centrifuged in a 50 mL conical tube for 5 min at about 3000×g. The supernatant was removed and the cells were resuspended in 1 M mannitol, pH 5.5, in a suitable volume to reach a final concentration of 2 $OD_{600}$ units. 5 mL of cells were aliquoted into a 25 mL shaker flask and amended with 10 mM CaCh (1.0 M stock, filter sterilized) and 0.25 mg/mL Protease XIV (10 mg/mL stock, filter sterilized; Sigma-Aldrich, St. Louis, MO). Flasks were incubated on a shaker at 30° C. and about 100 rpm for 4 h. Cells were monitored under the microscope to determine the degree of protoplasting, with single cells desired. The cells were centrifuged for 5 min at about 2500×g in round-bottom tubes (i.e., 14 mL Falcon™ tubes, BD Biosciences, San Jose, CA). The supernatant was removed and the cells were gently resuspended with 5 mL of ice cold 10% glycerol. The cells were re-centrifuged for 5 min at about 2500×g in round-bottom tubes. The supernatant was removed and the cells were gently resuspended with 500 μL of ice cold 10% glycerol, using wide-bore pipette tips. 90 μL of cells were aliquoted into a prechilled electro-cuvette (Gene Pulser® cuvette—0.1 cm gap or 0.2 cm gap, Bio-Rad, Hercules, CA). One μg to 5 μg of DNA (in less than or equal to a 10 μL volume) was added to the cuvette, mixed gently with a pipette tip, and placed on ice for 5 min. Cells were electroporated at 200 ohms (resistance), 25 μF (capacitance), and either 250V (for 0.1 cm gap) or 500V (0.2 cm gap). 0.5 mL of M50-20 media was added immediately to the cuvette. The cells were then transferred to 4.5 mL of M50-20 media in a 25 mL shaker flask and incubated for 2-3 h at 30° C. and about 100 rpm on a shaker. The cells were centrifuged for 5 min at about 2500×g in round bottom tubes. The supernatant was removed and the cell pellet was resuspended in 0.5 mL of M50-20 media. Cells were plated onto an appropriate number (2 to 5) of M2B plates with appropriate selection and incubated at 30° C.

The *Schizochytrium* sp. ATCC 20888 mutant lacking functional orfA is also transformed with pREZ345 containing PFA1, such that PFA1 is randomly integrated in the mutant and restores PUPA production.

EXAMPLES

*Thraustochytrium* sp. ATCC PTA-10212 PFA1 (SEQ ID NO:68) was re-synthesized (DNA2.0) and codon-optimized for expression in *Schizochytrium* (SEQ ID NO:120) and was cloned into an expression vector to generate pLR95. Codon-optimization occurred using the *Schizochytrium* codon usage table in FIG. 22. The expression vector contained approximately 2 kb of DNA from the flanking region of the native orfA gene locus from *Schizochytrium* sp. ATCC 20888.

The *Schizochytrium* sp. ATCC 20888 mutant lacking functional orfA from Example 7 was transformed via electroporation with enzyme pretreatment (See Example 7) with pLR95 containing codon-optimized *Thraustochytrium* sp. ATCC PTA-10212 PFA1 (SEQ ID NO:120). Based on homologous regions flanking the Zeocin™ resistance marker in the mutant and flanking the PFA1 gene in pLR95, double-crossover recombination occurred such that codon-optimized *Thraustochytrium* sp. ATCC PTA-10212 PFA1 was inserted into the native 01fA locus. Recombination with codon-optimized *Thraustochytrium* sp. ATCC PTA-10212 PFA1 (SEQ ID NO:120) restored PUPA production in the *Schizochytrium* sp. ATCC 20888 mutant lacking orfA. Cells were grown and analyzed for FAMEs as described in Example 7. The native *Schizochytrium* sp. ATCC 20888 strain containing a functional orfA gene produced DHA and EPA in a ratio of 25:1. The recombinant strain containing codon-optimized *Thraustochytrium* sp. ATCC PTA-10212 PFA1 (SEQ ID NO:120) in place of the inactivated orfA gene produced DHA and EPA in a ratio of 5.4:1, further demonstrating that the PUPA profile of *Schizochytrium* can be altered by the nucleic acid molecules described herein. The EPA content of the recombinant strain was 4.4% of FAME, the DPA n-3 content was 2.3%, the DPA n-6 content was 4.9%, and the DHA content was 24.0%.

The *Schizochytrium* sp. ATCC 20888 mutant lacking functional orfA is also transformed with pLR95 containing PFA.1J, such that PFAJ is randomly integrated in the mutant and restores PUPA production.

Example 9

The native 01fB gene in *Schizochytrium* sp. ATCC 20888 was replaced by homologous recombination following transformation via electroporation with enzyme pretreatment (See Example 7) with a vector containing the $Zeocin_{1M}$ resistance marker surrounded by sequences from the orfB flanking region. A mutant strain was generated lacking a functional orfB gene. The mutant strain was auxotrophic and required PUPA supplementation for growth.

*Schizochytrium* sp. ATCC PTA-9695 PFA2 (SEQ ID NO:3) was cloned into expression vector pDS04 to generate pREZ331. The expression vector contained approximately 2 kb of DNA from the flanking region of the native orfB gene locus from *Schizochytrium* sp. ATCC 20888.

The *Schizochytrium* sp. ATCC 20888 mutant lacking functional orfB was transformed with pREZ331 containing PFA2. Based on random integration in the mutant, PUPA production was restored by *Schizochytrium* sp. ATCC PTA-9695 PFA2 (SEQ ID NO:3). Cells were grown and analyzed for FAMEs as described in Example 7. The native *Schizochytrium* sp. ATCC 20888 strain containing a functional orfB gene produced DHA and DPA n-6 in a ratio of 2.3:1. The recombinant strain containing *Schizochytrium* sp. ATCC PTA-9695 PFA2 (SEQ ID NO:3) as a replacement of the inactivated orfB gene produced DHA and DPA n-6 in a ratio of 3.5:1. The EPA content of the recombinant strain was 0.8% of FAME, the DPA n-3 content was 0.1%, the DPA n-6 content was 7.1%, and the DHA content was 25.1%.

The *Schizochytrium* sp. ATCC 20888 mutant lacking functional orfB is also transformed with pREZ331 containing PFA2, such that PFA2 is inserted into the native orfB locus and restores PUPA production.

Example 10

*Thraustochytrium* sp. ATCC PTA-10212 PFA2 (SEQ ID NO:70) was re-synthesized (DNA2.0) and codon-optimized for expression in *Schizochytrium* (SEQ ID NO:121) and was cloned into an expression vector to generate pLR85. Codon-optimization occurred using the *Schizochytrium* codon usage table in FIG. 22. The expression vector contained approximately 2 kb of DNA from the flanking region of the native orfB gene locus from *Schizochytrium* sp. ATCC 20888.

Replacement of orf genes was also studied in a daughter strain of *Schizochytrium* sp. ATCC 20888 having improved DHA productivity. The native orfB gene in the daughter strain was replaced by homologous recombination following transformation via electroporation with enzyme pretreatment (See Example 7) with a vector containing the Zeocin™ resistance marker surrounded by sequences from the orfB flanking region. A mutant strain was generated lacking a functional o,jB gene. The mutant strain was auxotrophic and required PUPA supplementation for growth. The mutant strain was transformed via electroporation with enzyme pretreatment (see Example 8) with pLR85 containing codon-optimized *Thraustochytrium* sp. ATCC PTA-10212 PFA2 (SEQ ID NO:121). Based on homologous regions flanking the Zeocin™ resistance marker in the mutant and flanking the PFA2 gene in pLR85, double-crossover recombination occurred such that codon-optimized *Thraustochytrium* sp. ATCC PTA-10212 PFA2 (SEQ ID NO:121) was inserted into the native o,jB locus of the mutant strain. Recombination with codon-optimized *Thraustochytrium* sp. ATCC PTA-10212 PFA2 (SEQ ID NO:121) restored PUPA production in the daughter strain mutant lacking o,jB. Cells were grown and analyzed for FAMEs as described in Example 7. The EPA content of the recombinant strain was 1.0% of FAME, the DPA n-3 content was 0.3%, the DPA n-6 content was 7.0%, and the DHA content was 31.0%.

In an experiment to be performed, the *Schizochytrium* sp. ATCC 20888 mutant lacking functional o,jB from Example 9 is transformed via electroporation with enzyme pretreatment (see Example 8) with pLR85 containing codon-optimized *Thraustochytrium* 5p. ATCC PTA-10212 PFA2 (SEQ ID NO:121). Based on homologous regions flanking the Zeocin™ resistance marker in the mutant and flanking the PFA2 gene in pLR85, double-crossover recombination occurs such that codon-optimized *Thraustochytrium* sp. ATCC PTA-10212 PFA2 (SEQ ID NO:121) is inserted into the native orfB locus. Recombination with codon-optimized *Thraustochytrium* sp. ATCC PTA-10212 PFA2 (SEQ ID NO:121) restores PUPA production in the *Schizochytrium* sp. ATCC 20888 mutant lacking orfB.

The *Schizochytrium* sp. ATCC 20888 and daughter strain mutants lacking functional oifB are also transformed with pLR85 containing PFA2, such that PFA2 is randomly integrated in the mutants and restores PUPA production in each of the mutants.

Example 11

A plasmid containing a paromomycin resistance marker cassette functional in *Schizochytrium* was developed for *Schizochytrium* sp. ATCC 20888 by replacement of the bleomycin/Zeocin™ resistance gene (ble) coding region in pMON50000/pTUBZEOll-2 (U.S. Pat. No. 7,001,772 B2) with that of neomycin phosphotransferase II (npt), originally from bacterial transposon Tn5. In pMON50000, the ble resistance gene is driven by the *Schizochytrium* a-tubulin promoter and is followed by the SV40 transcription terminator. The ble region in pMON50000 encompasses a NcoI restriction site at the ATG start codon and a PmlI restriction site immediately following the TGA stop signal. PCR was used to amplify the npt coding region present in pCaMVnpt (Shimizu et al., *Plant J.* 26(4):375 (2001)) such that the product included a BspHI restriction site (underlined below, primer CAX055) at the start ATG (bold) and a PmlI restriction site (underlined below, primer CAX056) immediately following the stop signal (bold-reverse complement):

```
CAX055 (forward):
                                    (SEQ ID NO: 66)
GTCATGATTGAACAAGATGGATTGCAC CAX056 (reverse):
                                    (SEQ ID NO: 67)
CCACGTGTCAGAAGAACTCGTCAAGAA.
```

PCR was carried out with the TaqMaster polymerase kit (5Prime), products were cloned into pCR4-TOPO (Invitrogen), and resulting plasmids were transformed into *E. coli* TOP1O (Invitrogen). DNA sequence analysis using vector primers identified multiple clones containing the desired 805 bp structure (i.e., the sequences match those of the source template plus the engineered restriction sites). The modified npt coding region was isolated by digestion with BspHI plus PmlI restriction enzymes, and the purified DNA fragment was ligated with a pMON50000 vector fragment generated by digestion with NcoI plus Pm/I enzymes. Restriction enzymes B.spHI and NcoI leave compatible overlapping ends, and Pm/I leaves blunt ends. The resulting plasmid, pTS-NPT, contains the npt neomycin/paromomycin resistance gene in the identical context as that of the original ble gene in pMON50000.

Particle bombardment of *Schizochytrium* (U.S. Pat. No. 7,001,772 B2) was used to evaluate the function of the novel paromomycin resistance cassette in pTS-NPT. Selection for paromomycin (PAR) resistance was carried out on agar plates containing 50 µg/mL paromomycin sulfate (Sigma). Paromomycin-resistant *Schizochytrium* transformants were found at frequencies similar to those for Zeocinncresistance from pMON50000. The "a-tubulin promoter/npt/SV40 terminator" cassette can be freed from pTS-NPT with various restriction enzymes for subsequent use in other development efforts.

Example 12

The native orfC gene in *Schizochytrium* sp. ATCC 20888 was replaced by homologous recombination following transformation with a vector containing the paromomycin resistance marker surrounded by sequences from the orfC flanking region. A mutant strain was generated lacking a functional orfC gene. The mutant strain was auxotrophic and required PUFA supplementation for growth.

*Schizochytrium* sp. ATCC PTA-9695 PFA3 (SEQ ID NO:5) was cloned into expression vector pREZ22 to generate pREZ324. The expression vector contained approximately 2 kb of DNA from the flanking region of the native orfC gene locus from *Schizochytrium* sp. ATCC 20888.

The *Schizochytrium* sp. ATCC 20888 mutant lacking functional orfC was transformed with pREZ324 containing *Schizochytrium* sp. ATCC PTA-9695 PFA3. Based on homologous regions flanking the paromomycin resistance marker in the mutant and flanking the *Schizochytrium* sp. ATCC PTA-9695 PFA3 gene in pREZ324, double-crossover recombination occurred such that *Schizochytrium* sp. ATCC PTA-9695 PFA3 was inserted into the native orfC locus. Homologous recombination with *Schizochytrium* sp. ATCC PTA-9695 PFA3 (SEQ ID NO:5) restored PUPA production in the *Schizochytrium* sp. ATCC 20888 mutant lacking orfC. Cells were grown and analyzed for FAMEs as described in Example 7. The native *Schizochytrium* sp. ATCC 20888 strain containing a functional orfC gene produced DHA and DPA n-6 in a ratio of 2.3:1. The recombinant strain containing Schizochytrium sp. ATCC PTA-9695 PFA3 (SEQ ID NO:5) in place of the inactivated orfC gene produced DHA and DPA n-6 in a ratio of 14:9, further demonstrating that the PUFA profile of Schizochytrium can be altered by the nucleic acid molecules described herein. The EPA content of the recombinant strain was 1.2% of FAME, the DPA n-3 content was 0.2%, the DPA n-6 content was 2.9%, and the DHA content was 43.4%.

The Schizochytrium sp. ATCC 20888 mutant lacking functional orfC was also transformed with pREZ324 containing PFA3, such that PFA3 was randomly integrated in the mutant and restored PUFA production. The EPA content of the recombinant strain was 1.2% of FAME, the DPA n-3 content was 0.2%, the DPA n-6 content was 2.5%, and the DHA content was 39.1%.

The native orfC gene in the daughter strain discussed in Example 10 was replaced by homologous recombination following transformation with a vector containing the paromomycin resistance marker surrounded by sequences from the orfC flanking region. A mutant strain was generated lacking a functional orfC gene. The mutant strain was auxotrophic and required PUFA supplementation for growth. The mutant lacking functional 01fC was transformed with pREZ324. Double-crossover recombination occurred such that Schizochytrium sp. ATCC PTA-9695 PFA3 was inserted into the native 01fC locus of the mutant strain. Homologous recombination with Schizochytrium sp. ATCC PTA-9695 PFA3 (SEQ ID NO:5) restored PUFA production in the the daughter strain mutant lacking orfC. Cells were grown and analyzed for FAMEs as described in Example 7. The EPA content of the recombinant strain was 1.2% of FAME, the DPA n-3 content was 0.3%, the DPA n-6 content was 2.8%, and the DHA content was 43.1%.

The daughter strain mutant lacking functional orfB is also transformed with pREZ324 containing PFA3, such that PFA3 is randomly integrated in the mutant and restores PUFA production.

Example 13

Thraustochytrium sp. ATCC PTA-10212 PFA3 (SEQ ID NO:72) was re-synthesized (DNA2.0) and codon-optimized for expression in Schizochytrium (SEQ ID NO:122) and was cloned into expression vector pREZ22 to generate pREZ337. Codon-optimization occurred using the Schizochytrium codon usage table in FIG. 22. The expression vector contained approximately 2 kb of DNA from the flanking region of the native orfC gene locus from Schizochytrium sp. ATCC 20888.

The daughter strain mutant lacking functional oifC from Example 12 was transformed via electroporation with enzyme pretreatment (see Example 8) with pREZ337 containing codon-optimized Thraustochytrium sp. ATCC PTA-10212 PFA3 (SEQ ID NO:122). Based on homologous regions flanking the Zeocin™ resistance marker in the mutant and flanking the PFA3 gene in pREZ337, double-crossover recombination occurred such that codon-optimized Thraustochytrium sp. ATCC PTA-10212 PFA3 (SEQ ID NO:122) was inserted into the native oifC locus. Recombination with codon-optimized Thraustochytrium sp. ATCC PTA-10212 PFA3 (SEQ ID NO:122) restored PUPA production in the daughter strain mutant lacking oifC. Cells were grown and analyzed for FAMEs as described in Example 7. The EPA content of the recombinant strain was 1.3% of FAME, the DPA n-3 content was 0.4%, the DPA n-6 content was 2.7%, and the DHA content was 50.2%.

In an experiment to be performed, the Schizochytrium sp. ATCC 20888 mutant lacking functional orfC from Example 12 is transformed via electroporation with enzyme pretreatment (see Example 8) with pREZ337 containing codon-optimized Thraustochytrium sp. ATCC PTA-10212 PFA3 (SEQ ID NO:122). Based on homologous regions flanking the Zeocin™ resistance marker in the mutant and flanking the PFA3 gene in pREZ337, double-crossover recombination occurs such that codon-optimized Thraustochytrium sp. ATCC PTA-10212 PFA3 (SEQ ID NO:122) is inserted into the native orfC locus. Recombination with codon-optimized Thraustochytrium sp. ATCC PTA-10212 PFA3 (SEQ ID NO:122) restores PUPA production in the Schizochytrium sp. ATCC 20888 mutant lacking oifC.

The Schizochytrium sp. ATCC 20888 and daughter strain mutants lacking functional oifC are also transformed with pREZ337 containing PFA3, such that PFA3 is randomly integrated in the mutants and restores PUPA production in each of the mutants.

Example 14

Any two or all three of the orfA, orfB, and orfC genes in Schizochytrium sp. ATCC 20888 are replaced by homologous recombination following transformation with vectors containing either the Zeocin™ or paromomycin resistance marker surrounded by sequences from the appropriate orf flanking region. Mutant strains are generated lacking functional genes for any two or all three of 01fA, orfB, and orfC. The mutant strains are auxotrophic and require PUPA supplementation for growth.

The Schizochytrium sp. ATCC 20888 mutants lacking functional orf genes are transformed with one or more expression vectors containing corresponding PFA genes (one or more of SEQ ID NOs: 1, 3, 5, 120, 121, or 122). Based on homologous regions flanking the Zeocin$_{IM}$ or paromomycin resistance markers in the mutants and flanking the PF,4 genes in the respective expression vectors, double-crossover recombination can occur such that PFA genes are inserted into the native 01f loci. Random integration of these expression vectors can also occur with the selection of transformants based solely on the restoration of PUPA production. Homologous recombination with PFA genes restores PUPA production in the mutants, such that native PUPA profiles are restored or altered based on the combination of PFA genes inserted into the mutants.

In one performed experiment, the Schizochytrium sp. ATCC 20888 strain from Example 12 lacking a functional orfC gene and containing randomly integrated Schizochytrium sp. ATCC PTA-9695 PFA3 (SEQ ID NO:5) was used for replacement of the orfA and orfB genes. The native orfA and orfB genes in the strain were replaced by homologous recombination following transformation with a vector containing the Zeocin™ resistance marker surrounded by sequences from the orfA and orfB flanking regions. A strain was generated lacking functional orfA, orfB, and orfC, and containing randomly integrated Schizochytrium sp. ATCC PTA-9695 PFA3. The strain was transformed with pREZ345 containing codon-optimized Schizochytrium sp. ATCC PTA-9695 PF,41 (SEQ ID NO:1) and pREZ331 containing codon-optimized Schizochytrium sp. ATCC PTA-9695 PFA2 (SEQ ID NO:3) such that random integration of PFAJ and PFA2 occurred. The resulting recombinant strain lacked functional orfA, orfB, and orfC and contained random integrations of Schizochytrium sp. ATCC PTA-9695 PFAJ, PFA2, and PFA3. Cells were grown and analyzed for PAMEs as described in Example 7. The EPA content of the recombinant strain was 6.6% of FAME, the DPA n-3 content was 0.8%, the DPA n-6 content was 1.6%, and the DHA content was 20.9%.

In another performed experiment, the daughter strain from Example 12 lacking a functional orfC gene and containing *Schizochytrium* sp. ATCC PTA-9695 PFA3 (SEQ ID NO:5) inserted into the native o,fC locus was used for replacement of the orfA and orfB genes. The native o,f,4 and orfB genes in the strain were replaced by homologous recombination following transformation with a vector containing the paromomycin resistance marker surrounded by sequences from the orfA and orfB flanking regions. A strain was generated lacking functional o,fA, o,fB, and o,fC, and containing *Schizochytrium* sp. ATCC PTA-9695 PFA3 inserted into the native 01fC locus. The strain was transformed with pREZ345 containing codon-optimized *Schizochytrium* sp. ATCC PTA-9695 PFAJ (SEQ ID NO:1) and pREZ331 containing codon-optimized *Schizochytrium* sp. ATCC PTA-9695 PFA2 (SEQ ID NO:3). Double-crossover recombinations occurred such that *Schizochytrium* sp. ATCC PTA-9695 PFAJ was inserted into the native orfA locus and *Schizochytrium* sp. ATCC PTA-9695 PFA2 was inserted into the native o,fB locus of the strain. The resulting recombinant strain lacked functional orfA, orfB, and o,fC and contained *Schizochytrium* sp. ATCC PTA-9695 PF,41, PFA2, and PFA3 inserted into the respective orfA, o,fB, and o,fC loci. Cells were grown and analyzed for FAMEs as described in Example 7. The EPA content of the recombinant strain was 7.3% of FAME, the DPA n-3 content was 0.4%, the DPA n-6 content was 1.5%, and the DHA content was 23.9%.

In another performed experiment, the daughter strain from Example 12 lacking a functional orfC gene and containing randomly integrated *Schizochytrium* sp. ATCC PTA-9695 PFA3 (SEQ ID NO:5) was used for replacement of the orfA and orfB genes. The native orfA and orfB genes in the strain were replaced by homologous recombination following transformation with a vector containing the Zeocin™ resistance marker surrounded by sequences from the orfA and o,fB flanking regions. A strain was generated lacking functional 01fA, o,fB, and orfC, and containing randomly integrated *Schizochytrium* sp. ATCC PTA-9695 PFA3. The strain was transformed with pREZ345 containing codon-optimized Schizochytrium sp. ATCC PTA-9695 PFAJ (SEQ ID NO:1) and pREZ331 containing codon-optimized *Schizochytrium* sp. ATCC PTA-9695 PFA2 (SEQ ID NO:3) such that random integration of PFAJ and PFA2 occurred. The resulting recombinant strain lacked functional orfA, orfB, and orfC and contained random integrations of *Schizochytrium* sp. ATCC PTA-9695 PFAJ, PFA2, and PFA3. Cells were grown and analyzed for FAMEs as described in Example 7. The EPA content of the recombinant strain was 6.2% of FAME, the DPA n-3 content was 1.3%, the DPA n-6 content was 0.9%, and the DHA content was 16.6%.

In another performed experiment, the daughter strain from Example 13 lacking a functional orfC gene and containing *Schizochytrium* sp. ATCC PTA-10212 PFA3 (SEQ ID NO:122) inserted into the native orfC locus was used for replacement of the orfA and orfB genes. The native orfA and orfB genes in the strain were replaced by homologous recombination following transformation with a vector containing the paromomycin resistance marker surrounded by sequences from the orf,4 and orfB flanking regions. A strain was generated lacking functional orfA, orfB, and orfC, and containing *Schizochytrium* sp. ATCC PTA-10212 PFA3 inserted into the native orfC locus. The strain was transformed with pLR95 containing codon-optimized *Schizochytrium* sp. ATCC PTA-10212 PFAJ (SEQ ID NO:120) and pLR85 containing codon-optimized *Schizochytrium* sp. ATCC PTA-10212 PFA2 (SEQ ID NO:121). Double-crossover recombinations occurred such that *Schizochytrium* sp. ATCC PTA-10212 PFAJ was inserted into the native orfA locus and *Schizochytrium* sp. ATCC PTA-10212 PFA2 was inserted into the native 01fB locus of the strain. The resulting recombinant strain lacked functional orfA, orfB, and orfC and contained *Schizochytrium* sp. ATCC PTA-10212 PFAJ, PFA2, and PFA3 inserted into the respective orfA, orfB, and 01fC loci. Cells were grown and analyzed for FAMEs as described in Example 7. The EPA content of the recombinant strain was 5.2% of FAME, the DPA n-3 content was 0.6%, the DPA n-6 content was 2.1%, and the DHA content was 47.1%.

In another performed experiment, the daughter strain from Example 13 lacking a functional orfC gene and containing randomly integrated *Schizochytrium* sp. ATCC PTA-10212 PFA3 (SEQ ID NO:122) was used for replacement of the orfA and orfB genes. The native orfA and orfB genes in the strain were replaced by homologous recombination following transformation with a vector containing the Zeocin$_{IM}$ resistance marker surrounded by sequences from the orfA and orfB flanking regions. A strain was generated lacking functional orfA, orfB, and orfC, and containing randomly integrated *Schizochytrium* sp. ATCC PTA-10212 PFA3. The strain was transformed with pLR95 containing codon-optimized *Schizochytrium* sp. ATCC PTA-10212 PFAJ (SEQ ID NO:120) and pLR85 containing codon-optimized *Schizochytrium* sp. ATCC PTA-10212 PFA.2 (SEQ ID NO:121) such that random integration of PFAJ and PFA2 occurred. The resulting recombinant strain lacked functional orfA, 01fB, and 01fC and contained random integrations of *Schizochytrium* sp. ATCC PTA-10212 PFAJ, PFA2, and PFA3. Cells were grown and analyzed for FAMEs as described in Example 7. The EPA content of the recombinant strain was 1.8% of FAME, the DPA n-3 content was 1.8%, the DPA n-6 content was 2.3%, and the DHA content was 34.1%.

Example 15

The orfA, oifB, and o,fC genes from *Schizochytrium* sp. ATCC 20888 were cloned into a series of Duet vectors (Novagen). The Duet expression vectors are a set of compatible plasmids in which multiple target genes are cloned and co-expressed from the T7 inducible promoter in *E. coli*. Duet plasmid pREZ91 contained *Schizochytrium* sp. ATCC 20888 orfA in pETDuet-1; duet plasmid pREZ96 contained *Schizochytrium* sp. ATCC 20888 orfB in pCDFDuet-1; and duet plasmid pREZ1O1 contained *Schizochytrium* sp. ATCC 20888 o,fC in pCOLADuet-1. Duet plasmids pREZ91, pREZ96, and pREZ1O1, along with plasmid pJK737, which contained the required accessory gene Hetl (described in U.S. Pat. No. 7,217,856, incorporated by reference herein in its entirety), were transformed into *E. coli* strain BLR(DE3), which contains an inducible T7 RNA polymerase gene. Upon cell growth and addition of IPTG, according to manufacturer's instructions (Novagen), DHA and DPA n-6 were produced. Briefly, 1 mM IPTG was added for induction when cells reached an optical density of about 0.5 at 600 nm. Cells were the grown for 12 hours at 30° C. in Luria broth and harvested. The fatty acids were converted to methylesters using standard techniques. Fatty acid profiles were determined using gas chromatography with flame ionization detection (GC-FID) as fatty acid methyl esters (FAME).

81

The *Schizochytrium* sp. ATCC PTA-9695 PFAJ (SEQ ID NO:1) gene was cloned into the expression vector pETDuet-1, generating pREZ346. Duet plasmids pREZ346 (containing *Schizochytrium* sp. ATCC PTA-9695 PFAJ), pREZ96 (containing 01fB), and pREZ101 (containing orfC) were transformed into *E. coli* strain BLR(DE3) along with pJK737 (containing Hetl). The *Schizochytrium* sp. ATCC PTA-9695 PFAJ gene was coexpressed with the *Schizochytrium* sp. ATCC 20888 01fB and o,fC genes. The expression of *Schizochytrium* sp. ATCC PTA-9695 PFAJ, in combination with *Schizochytrium* sp. ATCC 20888 o,fB and 01fC, supported DHA production in *E. coli* under induction conditions. The DHA content of the transformed *E. coli* was 2.8% of FAME, the DPA n-6 content was 1.1%, the DPA n-3 content was 0.6%, and the EPA content was 3.7%.

Example 16

The codon-optimized *Thraustochytrium* sp. ATCC PTA-10212 PFAJ (SEQ ID NO:120) gene was cloned into the expression vector pETDuet-1, generating pLR100. Duet plasmids pLR100 (containing codon-optimized *Thraustochytrium* sp. ATCC PTA-10212 PFAJ), pREZ96 (containing *Schizochytrium* sp. ATCC 20888 o,fB), and pREZ101 (containing *Schizochytrium* sp. ATCC 20888 orfC) are transformed into *E. coli* strain BLR(DE3) along with pJK737 (containing Hetl). See Example 15. The *Thraustochytrium* sp. ATCC PTA-10212 PFAJ gene is coexpressed with the *Schizochytrium* sp. ATCC 20888 orfB and o,fC genes. The expression of *Thraustochytrium* sp. ATCC PTA-10212 PFAJ, in combination with *Schizochytrium* sp. ATCC 20888 o,fB and orfC, supports DHA and EPA production in *E. coli* under induction conditions.

Example 17

The *Schizochytrium* sp. ATCC PTA-9695 PFA3 (SEQ ID NO:5) gene was cloned into the expression vector pCOLADuet-1, generating pREZ326. Duet plasmids pREZ326 (containing *Schizochytrium* sp. ATCC PTA-9695 PFA3), pREZ91 (containing *Schizochytrium* sp. ATCC 20888 o,fA), and pREZ96 (containing *Schizochytrium* sp. ATCC 20888 o,fB) were transformed into *E. coli* strain BLR(DE3) along with pJK737 (containing Hetl). See Example 15. The expression of *Schizochytrium* sp. ATCC PTA-9695 PFA3, in combination with *Schizochytrium* sp. ATCC 20888 o,fA and orfB, supported DHA production in *E. coli* under induction conditions. Cells were grown and analyzed for FAMEs as described in Example 15. The DHA content of the transformed *E. coli* was 0.3% of FAME.

Example 18

The codon-optimized *Thraustochytrium* sp. ATCC PTA-10212 PFA3 (SEQ ID NO:122) gene was cloned into the expression vector pCOLADuet-1, generating pREZ348. Duet plasmids pREZ348 (containing codon-optimized *Thraustochytrium* sp. ATCC PTA-10212 PFA3), pREZ91 (containing *Schizochytrium* sp. ATCC 20888 oif4), and pREZ96 (containing *Schizochytrium* sp. ATCC 20888 orfB) were transformed into *E. coli* strain BLR(DE3) along with pJK737 (containing Hetl). See Example 15. The expression of *Thraustochytrium* sp. ATCC PTA-10212 PFA3, in combination with *Schizochytrium* sp. ATCC 20888 orfA and orfB, supported DHA production in *E. coli* under induction conditions. Cells were grown and analyzed for FAMEs as described in Example 15. The DHA content of the transformed *E. coli* was 2.9% of FAME and the DPA n-6 content was 0.4%.

Example 19

The *Schizochytrium* sp. ATCC PTA-9695 PFA2 (SEQ ID NO:3) gene was cloned into the expression vector pCDF-Duet-1, generating pREZ330. Duet plasmids pREZ330 (containing *Schizochytrium* sp. ATCC PTA-9695 PFA2), pREZ326 (containing *Schizochytrium* sp. ATCC PTA-9695 PFA3), and pREZ91 (containing *Schizochytrium* sp. ATCC 20888 orfA), were transformed into *E. coli* strain BLR(DE3) along with pJK737 (containing Hetl). See Example 9. The expression of *Schizochytrium* sp. ATCC PTA-9695 PFA2 and PFA3, in combination with *Schizochytrium* sp. ATCC 20888 oif4, supported DHA production in *E. coli* under induction conditions. Cells were grown and analyzed for FAMEs as described in Example 15. The DHA content of the transformed *E. coli* was 0.8% of FAME and the DPA n-6 content was 0.2%.

Example 20

The codon-optimized *Thraustochytrium* sp. ATCC PTA-10212 PFA2 (SEQ ID NO:121) gene was cloned into the expression vector pCDFDuet-1, generating pLR87. Duet plasmids pLR87 (containing codon-optimized *Thraustochytrium* sp. ATCC PTA-10212 PFA2), pREZ348 (containing codon-optimized *Thraustochytrium* sp. ATCC PTA-10212 PFA3), and pREZ91 (containing *Schizochytrium* sp. ATCC 20888 oifA), were transformed into *E. coli* strain BLR(DE3) along with pJK737 (containing Hetl). See Example 15. The expression of codon-optimized *Thraustochytrium* sp. ATCC PTA-10212 PFA2 and PFA3, in combination with *Schizochytrium* sp. ATCC 20888 orfA, supported DHA and low levels of EPA production in *E. coli* under induction conditions. Cells were grown and analyzed for FAMEs as described in Example 15. The DHA content of the transformed *E. coli* was 4.4% of FAME, the DPA n-6 content was 1.1%, and the EPA content was 0.1%.

Example 21

Duet plasmids pREZ346 (containing *Schizochytrium* sp. ATCC PTA-9695 PF,AJ), pREZ330 (containing *Schizochytrium* sp. ATCC PTA-9695 PFA2), and pREZ326 (containing *Schizochytrium* sp. ATCC PTA-9695 PFA3) were transformed into *E. coli* strain BLR(DE3) along with pJK737 (containing Hetl). See Example 15. The expression of *Schizochytrium* sp. ATCC PTA-9695 PFAJ, PFA2, and PFA3 supported DHA production in *E. coli* under induction conditions. Cells were grown and analyzed for FAMEs as described in Example 15. The DHA content of the transformed *E. coli* was 0.3% of FAME and the EPA content was 0.3%.

Example 22

Duet plasmids pLR100 (containing codon-optimized *Thraustochytrium* sp. ATCC PTA-10212 PFAJ), pLR87 (containing codon-optimized *Thraustochytrium* sp. ATCC PTA-10212 PFA2), and pREZ348 (containing codon-optimized *Thraustochytrium* sp. ATCC PTA-10212 PFA3) are transformed into *E. coli* strain BLR(DE3) along with pJK737 (containing Hetl). See Example 15. The expression of codon-optimized *Thraustochytrium* sp. ATCC PTA- 10212 PFAJ, PFA2, and PFA3 supports DHA and EPA production in *E. coli* under induction conditions.

Example 23

Duet plasmids pREZ330 (containing *Schizochytrium* sp. ATCC PTA-9695 PFA2), pREZ91 (containing *Schizochytrium* sp. ATCC 20888 01fA), and pREZ101 (containing *Schizochytrium* sp. ATCC 20888 oifC) were transformed into *E. coli* strain BLR(DE3) along with pJK737 (containing Het/). See Example 15. The expression of *Schizochytrium* sp. ATCC PTA-9695 PFA2, in combination with *Schizochytrium* sp. ATCC 20888 oifA and orfC, supported DHA production in *E. coli* under induction conditions. Cells were grown and analyzed for FAMEs as described in Example 15. The DHA content of the transformed *E. coli* was 0.6% of FAME and the DPA n-6 content was 0.3%.

Example 24

Duet plasmids pLR87 (containing codon-optimized *Thraustochytrium* sp. ATCC PTA-10212 PFA2), pREZ91 (containing *Schizochytrium* sp. ATCC 20888 orfA), and pREZ101 (containing *Schizochytrium* sp. ATCC 20888 01fC) were transformed into *E. coli* strain BLR(DE3) along with pJK737 (containing Het/). See Example 15. The expression of codon-optimized *Thraustochytrium* sp. ATCC PTA-10212 PFA2, in combination with *Schizochytrium* sp. ATCC 20888 orfA and 01fC, supported DHA and low levels of EPA production in *E. coli* under induction conditions. Cells were grown and analyzed for FAMEs as described in Example 15. The DHA content of the transformed *E. coli* was 1.7% of FAME, the DPA n-6 content was 0.9%, and the EPA content was 0.1%.

Example 25

Duet plasmids pREZ346 (containing *Schizochytrium* sp. ATCC PTA-9695 PFAJ), pREZ330 (containing *Schizochytrium* sp. ATCC PTA-9695 PFA2), and pREZ101 (containing *Schizochytrium* sp. ATCC 20888 orfC) were transformed into *E. coli* strain BLR(DE3) along with pJK737 (containing Het/). See Example 15. The expression of PFAJ and PFA2, in combination with *Schizochytrium* 5p. ATCC 20888 orfC, supported DHA production in *E. coli* under induction conditions. Cells were grown and analyzed for FAMEs as described in Example 15. The DHA content of the transformed *E. coli* was 0.3% of FAME, the DPA n-6 content was 0.1%, and the EPA content was 0.5%.

Example 26

Duet plasmids pLR100 (containing codon-optimized *Thraustochytrium* sp. ATCC PTA-10212 PFAJ), pLR87 (containing codon-optimized *Thraustochytrium* sp. ATCC PTA-10212 PFA2), and pREZ101 (containing *Schizochytrium* sp. ATCC 20888 orfC) are transformed into *E. coli* strain BLR(DE3) along with pJK737 (containing Het1). See Example 15. The expression of codon-optimized *Thraustochytrium* sp. ATCC PTA-10212 PFAJ and PFA2, in combination with *Schizochytrium* sp. ATCC 20888 oifC, supports DHA and EPA production in *E. coli* under induction conditions.

Example 27

Duet plasmids pREZ346 (containing *Schizochytrium* sp. ATCC PTA-9695 PF,AJ), pREZ96 (containing *Schizochytrium* sp. ATCC 20888 orfB), and pREZ326 (containing *Schizochytrium* sp. ATCC PTA-9695 PFA3) were transformed into *E. coli* strain BLR(DE3) along with pJK737 (containing Hell). See Example 15. The expression of *Schizochytrium* sp. ATCC PTA-9695 PFAJ and PFA3, in combination with *Schizochytrium* sp. ATCC 20888 orfB, supported DHA production in *E. coli* under induction conditions. Cells were grown and analyzed for FAMEs as described in Example 15. The DHA content of the transformed *E. coli* was 0.1% of FAME and the EPA content was 0.1%.

Example 28

Duet plasmids pLR100 (containing codon-optimized *Thraustochytrium* sp. ATCC PTA-10212 PFAJ), pREZ96 (containing *Schizochytrium* sp. ATCC 20888 orfB), and pREZ348 (containing codon-optimized *Thraustochytrium* sp. ATCC PTA-10212 PFA3) are transformed into *E. coli* strain BLR(DE3) along with pJK737 (containing Het1). See Example 15. The expression of codon-optimized *Thraustochytrium* sp. ATCC PTA-10212 PFAJ and PFA3, in combination with *Schizochytrium* sp. ATCC 20888 orfB, supports DHA and EPA production in *E. coli* under induction conditions.

Example 29

Pfa1p, Pfa2p, and Pfa3p PUFA synthase activities in *Schizochytrium* 0.5p. ATCC PTA-9695 and *Thraustochytrium* sp. ATCC PTA-10212 are individually knocked-out by standard procedures. See, e.g., U.S. Pat. No. 7,217,856, incorporated by reference herein in its entirety.

The Zeocin™, hygromycin, blasticidin, or other appropriate resistance marker is inserted into a restriction site of the PFAJ gene (SEQ ID NO:1 or SEQ ID NO:68) that is contained in a plasmid. Following insertion of the resistance marker, the plasmid is introduced into *Schizochytrium* sp. ATCC PTA-9695 or *Thraustochytrium* sp. ATCC PTA-10212, respectively, by particle bombardment, electroporation, or other appropriate transformation method. Homologous recombination occurs, generating mutants in which the native PFAJ gene is either replaced or disrupted by the Zeocin™, hygromycin, blasticidin, or other appropriate resistance marker. Transformants are selected on plates containing Zeocin™, hygromycin, blasticidin, or other appropriate selection agent, supplemented with PUFAs. Colonies are further examined for the capacity to grow in the absence of PUFA supplementation. Genomic DNA is isolated from the colonies that are resistant to the selection agent and unable to grow in the absence of PUFA supplementation. PCR and Southern Blot analysis of the DNA is performed to demonstrate that the PFAJ gene is either deleted or disrupted.

PFA2 is knocked-out by similar procedures. Resultant knock-out mutants requiring PUFA supplementation are found to lack full-length PFA2.

PFA3 is knocked-out by similar procedures. Resultant knock-out mutants requiring PUFA supplementation are found to lack full-length PFA3.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A recombinant nucleic acid molecule comprising a polynucleotide sequence at least 90% identical to SEQ ID NO:1 and a transcription control sequence, wherein the polynucleotide sequence encodes a polypeptide comprising beta-keto acyl-ACP synthase (KS) activity, malonyl-CoA: ACP acyltransferase (MAT) activity, acyl carrier protein (ACP) activity, ketoreductase (KR) activity, and beta-hydroxyacyl-ACP dehydrase (DH) activity, wherein said polynucleotide sequence is heterologous to said transcription control sequence.

2. The recombinant nucleic acid molecule of claim 1, wherein the polynucleotide sequence is at least 95% identical to SEQ ID NO:1.

3. The recombinant nucleic acid molecule of claim 1, wherein the nucleic acid molecule comprises the polynucleotide sequence sequences of SEQ ID NO:1.

4. A recombinant nucleic acid molecule comprising a polynucleotide sequence encoding a polypeptide and a transcription control sequence, wherein the polypeptide comprises an amino acid sequence at least 90% identical to SEQ ID NO:2, wherein the polypeptide comprises beta-keto acyl-ACP synthase (KS) activity, malonyl-CoA: ACP acyltransferase (MAT) activity, acyl carrier protein (ACP) activity, ketoreductase (KR) activity, and beta-hydroxyacyl-ACP dehydrase (DH) activity, wherein said polynucleotide sequence is heterologous to said transcription control sequence.

5. The recombinant nucleic acid molecule of claim 4, wherein the amino acid sequence is at least 95% identical to SEQ ID NO:2.

6. The recombinant nucleic acid molecule of claim 4, wherein the polypeptide comprises the amino acid sequence of SEQ ID NO:2.

7. A host cell that expresses the nucleic acid molecule of claim 1 or claim 4, wherein said nucleic acid molecule is heterologous to the host cell, and wherein said host cell is not a human cell.

8. The host cell of claim 7, wherein the host cell is selected from the group consisting of a plant cell, a microbial cell, and an isolated animal cell.

9. A method to produce at least one polyunsaturated fatty acid (PUFA), comprising: expressing a PUFA synthase gene in a host cell under conditions effective to produce PUFA, wherein the PUFA synthase gene comprises a nucleic acid molecule comprising a polynucleotide sequence at least 90% identical to SEQ ID NO: 1 or a polynucleotide sequence encoding a polypeptide which comprises an amino acid sequence at least 90% identical to SEQ ID NO:2, wherein said nucleic acid molecule is heterologous to the host cell, wherein said polynucleotide sequence encodes a PUFA synthase polypeptide comprising beta-keto acyl-ACP synthase (KS) activity, malonyl-CoA: ACP acyltransferase (MAT) activity, acyl carrier protein (ACP) activity, ketoreductase (KR) activity, and beta-hydroxyacyl-ACP dehydrase (DH) activity, and wherein at least one PUFA is produced.

10. A method to produce lipids enriched for docosahexaenoic acid (DHA), eicosapentaenoic acid (EPA), or a combination thereof as compared to a host cell not expressing a polyunsaturated fatty acid (PUFA) synthase gene as claimed, comprising: expressing a PUFA synthase gene in a host cell under conditions effective to produce lipids, wherein the PUFA synthase gene comprises a nucleic acid molecule comprising a polynucleotide sequence at least 90% identical to SEQ ID NO:1 or a polynucleotide sequence encoding a polypeptide which comprises an amino acid sequence at least 90% identical to SEQ ID NO: 2, wherein said nucleic acid molecule is heterologous to the host cell, wherein said polynucleotide sequence encodes a PUFA synthase polypeptide comprising beta-hydroxyacyl-ACP dehydrase (DH) activity and enoyl-ACP reductase (ER) activity, beta-keto acyl-ACP synthase (KS) activity, malonyl-CoA: ACP acyltransferase (MAT) activity, acyl carrier protein (ACP) activity, ketoreductase (KR) activity, and beta-hydroxyacyl-ACP dehydrase (DH) activity, and wherein lipids enriched with DHA, EPA, or a combination thereof are produced.

11. A method of increasing production of docosahexaenoic acid (DHA), eicosapentaenoic acid (EPA), or a combination thereof in an organism having polyunsaturated fatty acid (PUFA) synthase activity, comprising: expressing the recombinant nucleic acid molecule of claim 1 or claim 4 in the organism under conditions effective to produce DHA, EPA, or a combination thereof, wherein the PUFA synthase activity replaces an inactive or deleted activity, introduces a new activity, or enhances an existing activity in the organism, and wherein production of DHA, EPA, or a combination thereof in the organism is increased.

* * * * *

SEQUENCE LISTING

<160> NUMBER OF SEQ ID NOS: 127

<210> SEQ ID NO 1
<211> LENGTH: 7824
<212> TYPE: DNA
<213> ORGANISM: Schizochytrium sp.

<400> SEQUENCE: 1

| | | | | | | |
|---|---|---|---|---|---|---|
| atggatactc | gcatcgcgat | cgtggggatg | tcggcgatcc | tgccgagcgg | ggagaacgtg | 60 |
| cgcgagagct | gggaggcgat | ccgcgatggg | ctggattgcc | tgagcgatct | gccggcggac | 120 |
| cgcgtggacg | tgacggccta | ctacaacccg | gagaagacga | ccaaggacaa | gatctactgc | 180 |
| aagcgcggcg | ggttcatccc | ggagtacgac | ttcgacgcgc | gtgagttcgg | gctcaacatg | 240 |
| ttccagatgg | aggactcgga | cgccaaccag | acgatctcgc | tgctcaaggt | gaaggaggcg | 300 |
| ctgacggacg | ccaacatccc | ggcgttctcg | agcggtaaga | gaacatcgg | ctgcgtgctg | 360 |
| ggcatcggcg | gcggccagaa | ggcgagccac | gagttctact | cgcggctcaa | ctacgtggtc | 420 |
| gtggacaagg | tgctgcgcaa | gatgggcctg | ccggaggaag | acgtggcggc | ggcggtggac | 480 |
| aagtacaagg | cgagtttccc | cgagtggcgc | ctcgactctt | tccccgggtt | cctgggcaac | 540 |
| gtcacggcgg | ggcgctgctg | caataccttc | aacatggagg | gcatgaactg | cgtcgtggac | 600 |
| gcggcctgcg | cgtcgtcgct | gatcgcggtc | aaagtggcga | tcgaggagct | gctctacggc | 660 |
| gactgcgatg | cgatgatcgc | gggtgccacc | tgcacggaca | actcgatcgg | gatgtacatg | 720 |
| gccttctcca | agacgcccgt | gttttccacg | gacccgagcg | tcaaggcgta | cgacgccgcc | 780 |
| accaaaggca | tgctcatcgg | cgagggctcg | gcgatgctcg | tgctgaagcg | ctacgcggac | 840 |
| gccgtgcgcg | acggcgacac | cgtgcacgcc | gtcatcaagg | ggtgcgcgtc | ctcgagcgac | 900 |
| ggcaaggcgg | cgggcatcta | cacgccgaca | atctcgggcc | aggaggaggc | cctgcgccgc | 960 |
| gcctacgccc | cgccaatgt | cgacccgccc | actgtgacgc | tggtggaggg | ccacggcacg | 1020 |
| ggtacgccgg | tgggcgacaa | gatcgagctg | acggcgctga | gcaacctctt | ctccaaggcg | 1080 |
| ttttctgcca | acggtggcgg | cgcggaggaa | gcagagcagg | tggcggtggg | cagcatcaag | 1140 |
| tcgcagatcg | ggcacctcaa | ggcggtggcc | gggctggccg | ggctggtcaa | ggtggtgctg | 1200 |
| gcgctcaagc | acaagacgct | gccgcagacg | atcaacgtcg | acaagccgcc | gtcgctggtg | 1260 |
| gacgggaccc | cgatccagca | gtcgccgctg | tacgtcaaca | cgatgaaccg | ccctggttc | 1320 |
| acgcccgtag | gggtgccgcg | ccgcgccggc | gtgtcgtcgt | ttgggtttgg | cggtgccaac | 1380 |
| taccacgccg | tgctggagga | gtttgagccc | gagcacgaga | gcgcgtaccg | gtacaacaac | 1440 |
| ctgccgcagg | tggcgctgct | gcacgcgggg | gacgtcgcga | ccttggcggc | gacggttcgc | 1500 |
| gccaagctgg | cgctggccac | cgccgagcag | gaagaggcgc | gtgtggtgaa | gaacgcggac | 1560 |
| tacatcgcgt | accaccggtt | cctggacgag | tgcaagttgc | gcggcgctgt | gccgcaggcg | 1620 |
| cacgcgcggg | tgggactgct | cgtacgggac | ctgagctcgc | tcatcgccgt | gctcgaggcc | 1680 |
| gctgccgcca | agctcgcggg | cgaagagagc | gcgacggagt | ggacggtcag | cgttgctacg | 1740 |
| ggcgaggcg | ccttccgcgt | gcgcggtgtg | gctacggagg | ccaacgtggc | ggcgctgttc | 1800 |
| tcgggccagg | gcgcgcagta | cacgcacatg | ttcagcgacg | tggcgatgaa | ctggcccccg | 1860 |
| ttccgcgaga | gcgtcgccgc | catgaccgcg | gcccagcgcg | agcgcttcgg | gcggcctgcc | 1920 |
| aagcgcgtga | gcagcgtgct | gtacccgcgc | aagccgtacg | cgacgaaccc | gcggcaggac | 1980 |
| cacaaggaga | tctcgcaaac | gcgctactcg | cagcccgcaa | cgctcgcgtg | ctcggtcggc | 2040 |
| gcctttgaca | tcttcaaagc | ggcgggactg | gcgccgagct | ttgcggcggg | ccactcgctg | 2100 |

-continued

```
ggcgagtttg cggcgctcta cgcggccggg tcgctcgatc gcgacgccgt cttcgacctg    2160
gtctgcgcgc gcgccaaggc catgagcgac ttcacggccc aggccagcag cagcggtggc    2220
gccatggcgg ccgtgattgg cgccaaggcg accagctct cgctgggtgg cgcgcccgac     2280
gtgtggctcg ccaacagcaa ctcgccctcg cagaccgtga tcacgggaac cgccgaagca    2340
gtggctgcgg cctctgacaa gttgcgctgc agcggcaact tccgcgtcgt gcctctggcc    2400
tgcgaggcgg ccttccactc gccgcacatg cgcggcgcgg agcagacgtt tgcgtcggcg    2460
ctcgcgcagg cgcccgtgtc ggcaccggcg gctgctcggt tctactctaa cgtgacgggg    2520
ggcgccgcgg taacctcgcc cgcggacgtc aaaacgaacc tgggcaagca catgacgagc    2580
cctgtgcagt tcgtgcagca ggtgcgagcc atgcacgcgg cgggcgcgcg tgtgtttgtg    2640
gagtttgggc ccaagcaggt cctgtcgcgc tcgtcaagg agacccttgg cgaggccggc     2700
gacgtggtca cggtcgccgt caacccagac tcggccaagg acagcgacac gcagctgcgc    2760
caggcggcgc tcacgttggc ggtcgccggc gtgccgctca aggactttga ccgctggcag    2820
ctgccggatg ccacgcgcct cgagcctgtc aagaagaaga agaccacgtt gcggctctcg    2880
gcagccacct acgtctccgc caagacgttg cgccagcgcg aggccgtgct caacgacggc    2940
tacactgtca gtggtgccac ggcggtagtc aaggaagtgg acacggccaa cgaggagcgt    3000
ctcgtccgcc aagcccagga tctccagcgc cagctcgcgg aggcctcgac ggcagcccag    3060
gcggcgcagt ccaaggtcgc ggagctcgag cgcacgatcc aggacttgga gcgcaaggtg    3120
cagcagcagc agcaagagaa gggtgagaac tcagacagca acgctgccgc cgaagtgctg    3180
cggcgccaca aggagctgct ccagcgcatg ctgcaggact gtgacgagca ggcagtgccc    3240
gtagccacgg tggttccgac acctacgtcc tccccgacgc ctacatcctc acccgtatcc    3300
ggcaacagca agagcactcg tggcagtgct gatctgcaag cgctgctggc caaggcggag    3360
actgtggtga tggctgtgct ggctgccaag actggctacg aggccgacat ggttgaggcg    3420
gacatggacc tggaggccga gctcggcatc gactcgatca agcgcgtgga gatcctttcc    3480
gaggtgcagg gccagctggg cgtcgaggcc aaggacgtgg atgcgctgag ccgcacgcgc    3540
acggtcggtg aggttgtgga cgccatgaag gcggagatcg tggctgcctc tggtggtagt    3600
gctcctgcgg ttccttcggc gcccgctgct tctgcagctc cgactcccgc tgcttcgact    3660
gcgccttctg ctgatctgca agcgctgctg tccaaggcgg agactgtggt gatggctgtg    3720
ctggcggcca agactggcta cgaggccgac atggtcgagg cggacatgga cctggaggcc    3780
gagctcggca tcgactcgat caagcgcgtg gagatcctct cggaggtgca gggccagctg    3840
ggcgtcgagg ccaaggacgt ggatgcgctg agccgcacgc gcacggtcgg tgaggttgtg    3900
gatgccatga aggcggaaat cgtggctgcc tctgctggta gtgctcctgc tcctgctgtt    3960
ccttcggcgc ccgctgcttc tgcagctccg actcccgctg cttcgactgc gccttctgct    4020
gatctgcaag cgctgctgtc caaggcggag acggtggtga tggctgtgct ggcggccaag    4080
actggctacg aggccgacat ggtcgaggcg gacatggacc tggaggccga gctcggcatc    4140
gactcgatca agcgcgtgga gatcctctcg gaggtgcagg gccagctggg cgtcgaggcc    4200
aaggacgtgg atgcgctgag ccgcacgcgc acggtcggtg aggttgtgga tgccatgaag    4260
gcggaaatcg tggctgcctc tgctggtagt gctcctgctc tgcggttcc ttcggcgccc     4320 gctgcttctg cagctccgac tcccgcggct gcgacagcgc cttctgctga tctgcaagcg    4380
ctgctggcca aggcggagac tgtggtgatg gctgtgctgg cggccaagac tggctacgag    4440
```

```
gccgacatgg tcgaggcgga catggacctg gaggccgagc tcggcatcga ctcgatcaag    4500
cgcgtggaga tcctttccga ggtgcagggc cagctgggcg tcgaggccaa ggacgtagat    4560
gcgctgagcc gcacgcgcac ggtcggtgag gttgtggatg ccatgaaggc ggagatcgtg    4620
gctgcctctg ctggtagtgc tcctgctcct gctgttcctt cggcgcccgc tgcttctgca    4680
gctccgactc ccgctgcttc gactgcgcct tctgctgatc tgcaagcgct gctgtccaag    4740
gcggagactg tggtgatggc tgtgctggcg gccaagactg gctacgaggc cgacatggtc    4800
gaggcggaca tggacctgga ggccgagctc ggcatcgact cgatcaagcg cgtggagatc    4860
ctctcggagg tgcagggcca gctgggcgtc gaggccaagg acgtggatgc gctgagccgc    4920
acgcgcacgg tcggtgaggt tgtggatgcc atgaaggcgg aaatcgtggc tgcctctggt    4980
ggtagtgctc ctgctgctgc tgttccttcg gcgcccgctg cttctgcagc tccgactcct    5040
gcgactgcgc cttctgctga tctgcaagcg ctgctgtcca aggcggagac tgtggtgatg    5100
gctgtgctgg cggccaagac tggctacgag gccgacatgg tcgaggcgga catggacctg    5160
gaggccgagc tcggcatcga ctcgatcaag cgcgtggaga tcctttccga ggtgcagggc    5220
cagctgggcg tcgaggccaa ggacgtagat gcgctgagcc gcacgcgcac ggtcggtgaa    5280
gtggtggacg ccatgaaggc ggagatcgtg gctgcctctg gtggtagtgc tcctgctgct    5340
ccttcggcgc ccgcgcttct tccaacgctg tttggttccg agtgcgagga cctgtctctg    5400
acctttcccg tgataacgac cctgccgctt cctgcagagc ttgtgctggc cgagggcggc    5460
gctcgccctg tagtcgtggt ggatgatgga tctgcactca cctcgtcgct ggtgtcctcg    5520
ctcggcgatc gtgcggtgct gctgcaggtg cagtcttcct ctgcctgctc gccgcgctcg    5580
accacgcaca agttggtgac cgtagcagac cgctctgaag cggcgctaca ggcggcgctc    5640
acgtccgtcg aggcgcagtt cggcaaggtg ggtggctttg tgttccagtt cggcgacgac    5700
gacgtgcaag cgcagctcgg ctgggcgctg ctcgcggcca agcacctcaa aacttcgctg    5760
tcagaacaga tcgagggcgg tcgcaccttt ttcgtggccg tcgcgcggct cgacggccag    5820
ctggggctct ccggcaagtc gacgaccgct accgttgatc tctcccgcgc gcagcagggc    5880
agcgtgttcg gcctgtgcaa gacactcgac ctggagtggc ccgctgtctt ctgccgcgga    5940
atcgacctgg ccgccgacct cgacgccgca caggccgcgc ggtgcctgct gggcgagctg    6000
tcagaccccg acgtggccgt gcgcgagtct ggttactccg cctcgggcca gcgctgcacg    6060
acaactacga agtcgctgac tacgggcaag ccgcaccagc cgatctcctc gtcggacctc    6120
tttctggtgt cgggcggcgc gcgcggcatc accccgctgt gcgtgcgcga gctggcgcag    6180
cgcgtgggcg gcggcacgta cgtgctcatc ggccgctcgg agctgccgac gacggagcct    6240
gcctgggcgg tcggcgtgga gtctggcaag ccgctggaga aggccgcgct ggcgttcctg    6300
aaggcggagt ttgcagcggg ccgcggggcc aagccgacgc cgatgctgca caagaagctc    6360
gtgggcgccg tggtcggagc gcgcgaggtg cgagcctcgc tcgccgagat cactgcacag    6420
ggcgccacgg ctgtgtacga gtcgtgcgac gtgagctctg ccgccaaggt gcgtgagatg    6480
gtagagcgcg tgcagcagca gggcgggcgg cgcgtgtcgg gcgtgttcca cgcgtcgggc    6540
gtgctgcgcg acaagctcgt ggagaacaag tcgctggcgg acttcagcgc cgtgtacgac    6600
accaaggtgg gcggcctcat caacctgctg gcctgcgtgg acctggcgca gctgcgtcac    6660
ctcgtgctct tcagctcgct cgcgggcttc cacggcaacg tcgggcagtc ggactacgca    6720
atggccaacg aggcgctcaa caagctggcg gcgcacctgt cggcggtgca cccgcagctg    6780
tgcgcgcgct cgatctgctt cggaccgtgg gacggcggca tggtgacccc cgcgctcaag    6840
```

```
gccaacttca tccgcatggg catccagatc atcccgcgcc aaggcggcgc gcagaccgtc      6900
gccaacatgc tcgtcagtag ctcccccggt cagctgctcg tgggcaactg gggcgtgcca      6960
cccgtcgtgc cgagtgccac cgagcacacc gtgctgcaga cgctccgcca gagcgacaac      7020
cccttcctcg actcgcacgt gatccagggc cgccgcgtgc tgcccatgac cctggccgtg      7080
ggctacatgg cgcaccaggc gcagagcatc tacgcgggcc accagctgtg gccgtcgag       7140
gacgcccagc tcttcaaggg catcgccatc gacaatggcg ccgacgtgcc cgtgcgcgtg      7200
gagctgtcgc gccgcaagga ggagcaggag gacgccggca aggtcaaggt caaggtgcag      7260
gtgctgctca atcgcaggt caacggcaag tcggtgcccg cgtacaaggc gaccgtcgtg       7320
ctgtcccctg cgccgcgccc cagcgtcatc acgcgtgact tcgacctcac cccggacccg      7380
gcctgcacgg agcacgacct ctacgacggc aagacgctct ccacggcaa ggccttccag       7440
ggcatcgagc aggtgctctc ggcgacgccc aagcagctca ccgccaagtg ccgcaatttg      7500
ccctcacgc ccgagcagcg cggccagttc gtcgttaacc tcagccagca ggacccgttc       7560
caggcggaca ttgcgttcca ggcgatgctc gtctgggcgc gcatgctgcg ccaatcggcg      7620
gccctgccca caactgcga gcgcttcgac ttttacaagc cgatggcccc gggcgccacc       7680
tactacacgt cggtcaagct ggcctcggcc tcacccttgg tggactctgt gtgcaagtgc      7740
accgtggcga tgcacgatga gcaaggtgag gtgtactttt ctgctcgtgc cagcgtcgtc      7800
ctcaacaaga ccctcacgta ctaa                                            7824
```

<210> SEQ ID NO 2
<211> LENGTH: 2607
<212> TYPE: PRT
<213> ORGANISM: Schizochytrium sp.

<400> SEQUENCE: 2

Met Asp Thr Arg Ile Ala Ile Val Gly Met Ser Ala Ile Leu Pro Ser
1               5                   10                  15

Gly Glu Asn Val Arg Glu Ser Trp Glu Ala Ile Arg Asp Gly Leu Asp
            20                  25                  30

Cys Leu Ser Asp Leu Pro Ala Asp Arg Val Asp Val Thr Ala Tyr Tyr
        35                  40                  45

Asn Pro Glu Lys Thr Thr Lys Asp Lys Ile Tyr Cys Lys Arg Gly Gly
    50                  55                  60

Phe Ile Pro Glu Tyr Asp Phe Asp Ala Arg Glu Phe Gly Leu Asn Met
65                  70                  75                  80

Phe Gln Met Glu Asp Ser Asp Ala Asn Gln Thr Ile Ser Leu Leu Lys
                85                  90                  95

Val Lys Glu Ala Leu Thr Asp Ala Asn Ile Pro Ala Phe Ser Ser Gly
            100                 105                 110

Lys Lys Asn Ile Gly Cys Val Leu Gly Ile Gly Gly Gly Gln Lys Ala
        115                 120                 125

Ser His Glu Phe Tyr Ser Arg Leu Asn Tyr Val Val Asp Lys Val
    130                 135                 140

Leu Arg Lys Met Gly Leu Pro Glu Glu Asp Val Ala Ala Val Asp
145                 150                 155                 160

Lys Tyr Lys Ala Ser Phe Pro Glu Trp Arg Leu Asp Ser Phe Pro Gly
                165                 170                 175

Phe Leu Gly Asn Val Thr Ala Gly Arg Cys Cys Asn Thr Phe Asn Met
            180                 185                 190

```
Glu Gly Met Asn Cys Val Val Asp Ala Ala Cys Ala Ser Ser Leu Ile
            195                 200                 205
Ala Val Lys Val Ala Ile Glu Glu Leu Leu Tyr Gly Asp Cys Asp Ala
210                 215                 220
Met Ile Ala Gly Ala Thr Cys Thr Asp Asn Ser Ile Gly Met Tyr Met
225                 230                 235                 240
Ala Phe Ser Lys Thr Pro Val Phe Ser Thr Asp Pro Ser Val Lys Ala
            245                 250                 255
Tyr Asp Ala Ala Thr Lys Gly Met Leu Ile Gly Glu Gly Ser Ala Met
                260                 265                 270
Leu Val Leu Lys Arg Tyr Ala Asp Ala Val Arg Asp Gly Asp Thr Val
275                 280                 285
His Ala Val Ile Lys Gly Cys Ala Ser Ser Ser Asp Gly Lys Ala Ala
            290                 295                 300
Gly Ile Tyr Thr Pro Thr Ile Ser Gly Gln Glu Glu Ala Leu Arg Arg
305                 310                 315                 320
Ala Tyr Ala Arg Ala Asn Val Asp Pro Ala Thr Val Thr Leu Val Glu
            325                 330                 335
Gly His Gly Thr Gly Thr Pro Val Gly Asp Lys Ile Glu Leu Thr Ala
                340                 345                 350
Leu Ser Asn Leu Phe Ser Lys Ala Phe Ser Ala Asn Gly Gly Gly Ala
            355                 360                 365
Glu Glu Ala Glu Gln Val Ala Val Gly Ser Ile Lys Ser Gln Ile Gly
                370                 375                 380
His Leu Lys Ala Val Ala Gly Leu Ala Gly Leu Val Lys Val Val Leu
385                 390                 395                 400
Ala Leu Lys His Lys Thr Leu Pro Gln Thr Ile Asn Val Asp Lys Pro
                405                 410                 415
Pro Ser Leu Val Asp Gly Thr Pro Ile Gln Gln Ser Pro Leu Tyr Val
            420                 425                 430
Asn Thr Met Asn Arg Pro Trp Phe Thr Pro Val Gly Val Pro Arg Arg
                435                 440                 445
Ala Gly Val Ser Ser Phe Gly Phe Gly Gly Ala Asn Tyr His Ala Val
450                 455                 460
Leu Glu Glu Phe Glu Pro Glu His Glu Ser Ala Tyr Arg Tyr Asn Asn
465                 470                 475                 480
Leu Pro Gln Val Ala Leu Leu His Ala Gly Asp Val Ala Thr Leu Ala
            485                 490                 495
Ala Thr Val Arg Ala Lys Leu Ala Leu Ala Thr Ala Glu Gln Glu Glu
                500                 505                 510
Ala Arg Val Val Lys Asn Ala Asp Tyr Ile Ala Tyr His Arg Phe Leu
            515                 520                 525
Asp Glu Cys Lys Leu Arg Gly Ala Val Pro Gln Ala His Ala Arg Val
530                 535                 540
Gly Leu Leu Val Arg Asp Leu Ser Ser Leu Ile Ala Val Leu Glu Ala
545                 550                 555                 560
Ala Ala Ala Lys Leu Ala Gly Glu Glu Ser Ala Thr Glu Trp Thr Val
                565                 570                 575
Ser Val Ala Thr Gly Glu Ala Ala Phe Arg Val Arg Gly Val Ala Thr
            580                 585                 590
Glu Ala Asn Val Ala Ala Leu Phe Ser Gln Gly Ala Gln Tyr Thr
            595                 600                 605
His Met Phe Ser Asp Val Ala Met Asn Trp Pro Pro Phe Arg Glu Ser
```

```
                610                 615                 620
Val Ala Ala Met Asp Arg Ala Gln Arg Glu Arg Phe Gly Arg Pro Ala
625                 630                 635                 640

Lys Arg Val Ser Ser Val Leu Tyr Pro Arg Pro Tyr Gly Asp Glu
                645                 650                 655

Pro Arg Gln Asp His Lys Glu Ile Ser Gln Thr Arg Tyr Ser Gln Pro
                660                 665                 670

Ala Thr Leu Ala Cys Ser Val Gly Ala Phe Asp Ile Phe Lys Ala Ala
                675                 680                 685

Gly Leu Ala Pro Ser Phe Ala Ala Gly His Ser Leu Gly Glu Phe Ala
            690                 695                 700

Ala Leu Tyr Ala Ala Gly Ser Leu Asp Arg Asp Ala Val Phe Asp Leu
705                 710                 715                 720

Val Cys Ala Arg Ala Lys Ala Met Ser Asp Phe Thr Ala Gln Ala Ser
                725                 730                 735

Ser Ser Gly Gly Ala Met Ala Ala Val Ile Gly Ala Lys Ala Asp Gln
            740                 745                 750

Leu Ser Leu Gly Gly Ala Pro Asp Val Trp Leu Ala Asn Ser Asn Ser
            755                 760                 765

Pro Ser Gln Thr Val Ile Thr Gly Thr Ala Glu Ala Val Ala Ala Ala
770                 775                 780

Ser Asp Lys Leu Arg Cys Ser Gly Asn Phe Arg Val Pro Leu Ala
785                 790                 795                 800

Cys Glu Ala Ala Phe His Ser Pro His Met Arg Gly Ala Glu Gln Thr
                805                 810                 815

Phe Ala Ser Ala Leu Ala Gln Ala Pro Val Ser Ala Pro Ala Ala Ala
                820                 825                 830

Arg Phe Tyr Ser Asn Val Thr Gly Gly Ala Ala Val Thr Ser Pro Ala
                835                 840                 845

Asp Val Lys Thr Asn Leu Gly Lys His Met Thr Ser Pro Val Gln Phe
850                 855                 860

Val Gln Gln Val Arg Ala Met His Ala Ala Gly Ala Arg Val Phe Val
865                 870                 875                 880

Glu Phe Gly Pro Lys Gln Val Leu Ser Arg Leu Val Lys Glu Thr Leu
                885                 890                 895

Gly Glu Ala Gly Asp Val Thr Val Ala Val Asn Pro Asp Ser Ala
            900                 905                 910

Lys Asp Ser Asp Thr Gln Leu Arg Gln Ala Ala Leu Thr Leu Ala Val
            915                 920                 925

Ala Gly Val Pro Leu Lys Asp Phe Asp Arg Trp Gln Leu Pro Asp Ala
930                 935                 940

Thr Arg Leu Glu Pro Val Lys Lys Lys Thr Thr Leu Arg Leu Ser
945                 950                 955                 960

Ala Ala Thr Tyr Val Ser Ala Lys Thr Leu Arg Gln Arg Glu Ala Val
                965                 970                 975

Leu Asn Asp Gly Tyr Thr Val Ser Gly Ala Thr Ala Val Lys Glu
            980                 985                 990

Val Asp Thr Ala Asn Glu Glu Arg Leu Val Arg Gln Ala Gln Asp Leu
            995                 1000                1005

Gln Arg Gln Leu Ala Glu Ala Ser Thr Ala Ala Gln Ala Ala Gln
    1010                1015                1020

Ser Lys Val Ala Glu Leu Glu Arg Thr Ile Gln Asp Leu Glu Arg
    1025                1030                1035
```

```
Lys Val Gln Gln Gln Gln Glu Lys Gly Glu Asn Ser Asp Ser
    1040            1045            1050

Asn Ala Ala Ala Glu Val Leu Arg Arg His Lys Glu Leu Leu Gln
    1055            1060            1065

Arg Met Leu Gln Asp Cys Asp Glu Gln Ala Val Pro Val Ala Thr
    1070            1075            1080

Val Val Pro Thr Pro Thr Ser Ser Pro Thr Pro Thr Ser Ser Pro
    1085            1090            1095

Val Ser Gly Asn Ser Lys Ser Thr Arg Gly Ser Ala Asp Leu Gln
    1100            1105            1110

Ala Leu Leu Ala Lys Ala Glu Thr Val Val Met Ala Val Leu Ala
    1115            1120            1125

Ala Lys Thr Gly Tyr Glu Ala Asp Met Val Glu Ala Asp Met Asp
    1130            1135            1140

Leu Glu Ala Glu Leu Gly Ile Asp Ser Ile Lys Arg Val Glu Ile
    1145            1150            1155

Leu Ser Glu Val Gln Gly Gln Leu Gly Val Glu Ala Lys Asp Val
    1160            1165            1170

Asp Ala Leu Ser Arg Thr Arg Thr Val Gly Glu Val Val Asp Ala
    1175            1180            1185

Met Lys Ala Glu Ile Val Ala Ala Ser Gly Gly Ser Ala Pro Ala
    1190            1195            1200

Val Pro Ser Ala Pro Ala Ala Ser Ala Ala Pro Thr Pro Ala Ala
    1205            1210            1215

Ser Thr Ala Pro Ser Ala Asp Leu Gln Ala Leu Leu Ser Lys Ala
    1220            1225            1230

Glu Thr Val Val Met Ala Val Leu Ala Ala Lys Thr Gly Tyr Glu
    1235            1240            1245

Ala Asp Met Val Glu Ala Asp Met Asp Leu Glu Ala Glu Leu Gly
    1250            1255            1260

Ile Asp Ser Ile Lys Arg Val Glu Ile Leu Ser Glu Val Gln Gly
    1265            1270            1275

Gln Leu Gly Val Glu Ala Lys Asp Val Asp Ala Leu Ser Arg Thr
    1280            1285            1290

Arg Thr Val Gly Glu Val Val Asp Ala Met Lys Ala Glu Ile Val
    1295            1300            1305

Ala Ala Ser Ala Gly Ser Ala Pro Ala Pro Ala Val Pro Ser Ala
    1310            1315            1320

Pro Ala Ala Ser Ala Ala Pro Thr Pro Ala Ala Ser Thr Ala Pro
    1325            1330            1335

Ser Ala Asp Leu Gln Ala Leu Leu Ser Lys Ala Glu Thr Val Val
    1340            1345            1350

Met Ala Val Leu Ala Ala Lys Thr Gly Tyr Glu Ala Asp Met Val
    1355            1360            1365

Glu Ala Asp Met Asp Leu Glu Ala Glu Leu Gly Ile Asp Ser Ile
    1370            1375            1380

Lys Arg Val Glu Ile Leu Ser Glu Val Gln Gly Gln Leu Gly Val
    1385            1390            1395

Glu Ala Lys Asp Val Asp Ala Leu Ser Arg Thr Arg Thr Val Gly
    1400            1405            1410

Glu Val Val Asp Ala Met Lys Ala Glu Ile Val Ala Ala Ser Gly
    1415            1420            1425
```

-continued

```
Gly Ser Ala Pro Ala Pro Ala Val Pro Ser Ala Pro Ala Ala Ser
    1430                1435                1440

Ala Ala Pro Thr Pro Ala Ala Ala Thr Ala Pro Ser Ala Asp Leu
    1445                1450                1455

Gln Ala Leu Leu Ala Lys Ala Glu Thr Val Val Met Ala Val Leu
    1460                1465                1470

Ala Ala Lys Thr Gly Tyr Glu Ala Asp Met Val Glu Ala Asp Met
    1475                1480                1485

Asp Leu Glu Ala Glu Leu Gly Ile Asp Ser Ile Lys Arg Val Glu
    1490                1495                1500

Ile Leu Ser Glu Val Gln Gly Gln Leu Gly Val Glu Ala Lys Asp
    1505                1510                1515

Val Asp Ala Leu Ser Arg Thr Arg Thr Val Gly Glu Val Val Asp
    1520                1525                1530

Ala Met Lys Ala Glu Ile Val Ala Ala Ser Ala Gly Ser Ala Pro
    1535                1540                1545

Ala Pro Ala Val Pro Ser Ala Pro Ala Ala Ser Ala Ala Pro Thr
    1550                1555                1560

Pro Ala Ala Ser Thr Ala Pro Ser Ala Asp Leu Gln Ala Leu Leu
    1565                1570                1575

Ser Lys Ala Glu Thr Val Val Met Ala Val Leu Ala Ala Lys Thr
    1580                1585                1590

Gly Tyr Glu Ala Asp Met Val Glu Ala Asp Met Asp Leu Glu Ala
    1595                1600                1605

Glu Leu Gly Ile Asp Ser Ile Lys Arg Val Glu Ile Leu Ser Glu
    1610                1615                1620

Val Gln Gly Gln Leu Gly Val Glu Ala Lys Asp Val Asp Ala Leu
    1625                1630                1635

Ser Arg Thr Arg Thr Val Gly Glu Val Val Asp Ala Met Lys Ala
    1640                1645                1650

Glu Ile Val Ala Ala Ser Gly Gly Ser Ala Pro Ala Ala Ala Val
    1655                1660                1665

Pro Ser Ala Pro Ala Ala Ser Ala Ala Pro Thr Pro Ala Thr Ala
    1670                1675                1680

Pro Ser Ala Asp Leu Gln Ala Leu Leu Ser Lys Ala Glu Thr Val
    1685                1690                1695

Val Met Ala Val Leu Ala Ala Lys Thr Gly Tyr Glu Ala Asp Met
    1700                1705                1710

Val Glu Ala Asp Met Asp Leu Glu Ala Glu Leu Gly Ile Asp Ser
    1715                1720                1725

Ile Lys Arg Val Glu Ile Leu Ser Glu Val Gln Gly Gln Leu Gly
    1730                1735                1740

Val Glu Ala Lys Asp Val Asp Ala Leu Ser Arg Thr Arg Thr Val
    1745                1750                1755

Gly Glu Val Val Asp Ala Met Lys Ala Glu Ile Val Ala Ala Ser
    1760                1765                1770

Gly Gly Ser Ala Pro Ala Ala Pro Ser Ala Pro Ala Leu Leu Pro
    1775                1780                1785

Thr Leu Phe Gly Ser Glu Cys Glu Asp Leu Ser Leu Thr Phe Pro
    1790                1795                1800

Val Ile Thr Thr Leu Pro Leu Pro Ala Glu Leu Val Leu Ala Glu
    1805                1810                1815

Gly Gly Ala Arg Pro Val Val Val Val Asp Asp Gly Ser Ala Leu
```

-continued

```
            1820                1825                1830
Thr Ser Ser Leu Val Ser Ser Leu Gly Asp Arg Ala Val Leu Leu
            1835                1840                1845

Gln Val Gln Ser Ser Ser Ala Cys Ser Pro Arg Ser Thr Thr His
            1850                1855                1860

Lys Leu Val Thr Val Ala Asp Arg Ser Glu Ala Ala Leu Gln Ala
            1865                1870                1875

Ala Leu Thr Ser Val Glu Ala Gln Phe Gly Lys Val Gly Gly Phe
            1880                1885                1890

Val Phe Gln Phe Gly Asp Asp Val Gln Ala Gln Leu Gly Trp
            1895                1900                1905

Ala Leu Leu Ala Ala Lys His Leu Lys Thr Ser Leu Ser Glu Gln
            1910                1915                1920

Ile Glu Gly Gly Arg Thr Phe Phe Val Ala Val Ala Arg Leu Asp
            1925                1930                1935

Gly Gln Leu Gly Leu Ser Gly Lys Ser Thr Thr Ala Thr Val Asp
            1940                1945                1950

Leu Ser Arg Ala Gln Gln Gly Ser Val Phe Gly Leu Cys Lys Thr
            1955                1960                1965

Leu Asp Leu Glu Trp Pro Ala Val Phe Cys Arg Gly Ile Asp Leu
            1970                1975                1980

Ala Ala Asp Leu Asp Ala Ala Gln Ala Ala Arg Cys Leu Leu Gly
            1985                1990                1995

Glu Leu Ser Asp Pro Asp Val Ala Val Arg Glu Ser Gly Tyr Ser
            2000                2005                2010

Ala Ser Gly Gln Arg Cys Thr Thr Thr Lys Ser Leu Thr Thr
            2015                2020                2025

Gly Lys Pro His Gln Pro Ile Ser Ser Ser Asp Leu Phe Leu Val
            2030                2035                2040

Ser Gly Gly Ala Arg Gly Ile Thr Pro Leu Cys Val Arg Glu Leu
            2045                2050                2055

Ala Gln Arg Val Gly Gly Gly Thr Tyr Val Leu Ile Gly Arg Ser
            2060                2065                2070

Glu Leu Pro Thr Thr Glu Pro Ala Trp Ala Val Gly Val Glu Ser
            2075                2080                2085

Gly Lys Pro Leu Glu Lys Ala Ala Leu Ala Phe Leu Lys Ala Glu
            2090                2095                2100

Phe Ala Ala Gly Arg Gly Ala Lys Pro Thr Pro Met Leu His Lys
            2105                2110                2115

Lys Leu Val Gly Ala Val Val Gly Ala Arg Glu Val Arg Ala Ser
            2120                2125                2130

Leu Ala Glu Ile Thr Ala Gln Gly Ala Thr Ala Val Tyr Glu Ser
            2135                2140                2145

Cys Asp Val Ser Ser Ala Ala Lys Val Arg Glu Met Val Glu Arg
            2150                2155                2160

Val Gln Gln Gln Gly Gly Arg Arg Val Ser Gly Val Phe His Ala
            2165                2170                2175

Ser Gly Val Leu Arg Asp Lys Leu Val Glu Asn Lys Ser Leu Ala
            2180                2185                2190

Asp Phe Ser Ala Val Tyr Asp Thr Lys Val Gly Gly Leu Ile Asn
            2195                2200                2205

Leu Leu Ala Cys Val Asp Leu Ala Gln Leu Arg His Leu Val Leu
            2210                2215                2220
```

-continued

Phe Ser Ser Leu Ala Gly Phe His Gly Asn Val Gly Gln Ser Asp
2225                2230                2235

Tyr Ala Met Ala Asn Glu Ala Leu Asn Lys Leu Ala Ala His Leu
2240                2245                2250

Ser Ala Val His Pro Gln Leu Cys Ala Arg Ser Ile Cys Phe Gly
2255                2260                2265

Pro Trp Asp Gly Gly Met Val Thr Pro Ala Leu Lys Ala Asn Phe
2270                2275                2280

Ile Arg Met Gly Ile Gln Ile Ile Pro Arg Gln Gly Gly Ala Gln
2285                2290                2295

Thr Val Ala Asn Met Leu Val Ser Ser Pro Gly Gln Leu Leu
2300                2305                2310

Val Gly Asn Trp Gly Val Pro Pro Val Val Pro Ser Ala Thr Glu
2315                2320                2325

His Thr Val Leu Gln Thr Leu Arg Gln Ser Asp Asn Pro Phe Leu
2330                2335                2340

Asp Ser His Val Ile Gln Gly Arg Arg Val Leu Pro Met Thr Leu
2345                2350                2355

Ala Val Gly Tyr Met Ala His Gln Ala Gln Ser Ile Tyr Ala Gly
2360                2365                2370

His Gln Leu Trp Ala Val Glu Asp Ala Gln Leu Phe Lys Gly Ile
2375                2380                2385

Ala Ile Asp Asn Gly Ala Asp Val Pro Val Arg Val Glu Leu Ser
2390                2395                2400

Arg Arg Lys Glu Glu Gln Glu Asp Ala Gly Lys Val Lys Val Lys
2405                2410                2415

Val Gln Val Leu Leu Lys Ser Gln Val Asn Gly Lys Ser Val Pro
2420                2425                2430

Ala Tyr Lys Ala Thr Val Val Leu Ser Pro Ala Pro Arg Pro Ser
2435                2440                2445

Val Ile Thr Arg Asp Phe Asp Leu Thr Pro Asp Pro Ala Cys Thr
2450                2455                2460

Glu His Asp Leu Tyr Asp Gly Lys Thr Leu Phe His Gly Lys Ala
2465                2470                2475

Phe Gln Gly Ile Glu Gln Val Leu Ser Ala Thr Pro Lys Gln Leu
2480                2485                2490

Thr Ala Lys Cys Arg Asn Leu Pro Leu Thr Pro Glu Gln Arg Gly
2495                2500                2505

Gln Phe Val Val Asn Leu Ser Gln Gln Asp Pro Phe Gln Ala Asp
2510                2515                2520

Ile Ala Phe Gln Ala Met Leu Val Trp Ala Arg Met Leu Arg Gln
2525                2530                2535

Ser Ala Ala Leu Pro Asn Asn Cys Glu Arg Phe Asp Phe Tyr Lys
2540                2545                2550

Pro Met Ala Pro Gly Ala Thr Tyr Tyr Thr Ser Val Lys Leu Ala
2555                2560                2565

Ser Ala Ser Pro Leu Val Asp Ser Val Cys Lys Cys Thr Val Ala
2570                2575                2580

Met His Asp Glu Gln Gly Glu Val Tyr Phe Ser Ala Arg Ala Ser
2585                2590                2595

Val Val Leu Asn Lys Thr Leu Thr Tyr
2600                2605

<210> SEQ ID NO 3
<211> LENGTH: 5778
<212> TYPE: DNA
<213> ORGANISM: Schizochytrium sp.

<400> SEQUENCE: 3

| | |
|---|---|
| atgccgtgcg ataacattgc ggtcgtgggc atggcggtgc agtatgccgg atgcaagaac | 60 |
| caggacgagt tctgggatac gctgatgcgt aaggagatca actcgagccc gatctcggcg | 120 |
| gagcgcctcg gtacgcgcta ccgcgacctc cacttccacc cgcagcgcag caagtacgcc | 180 |
| gacaccttct gcaacgatcg ctacggctgc gtcgatgcca cgtcgacaa cgagcacgac | 240 |
| ctcctcgccg acctggcccg gcgcgccctg ctcgacgccg aattaaccct cgacgacgcc | 300 |
| agcaccaccg ccaacctacg cgacttcggc atcgtgagcg gctgcctgtc gttcccatg | 360 |
| gacaatctgc agggcgagct gctcaatctg taccaagtgc atgtggagaa ccgcgtgggc | 420 |
| gcccagcgct ccgcgactc gcgccctgg tcggagcgcc cgcgcgctgt ctcgcccgag | 480 |
| gccagcgacc cgcgcgtgta ctccgacccg gcgtccttcg tggccaacca gctcggcctg | 540 |
| gggcccgtgc gctacagcct cgatgcagcc tgcgcgtcgg cgctgtactg cctcaagctg | 600 |
| gcgtccgacc acttgctctc gcgcagcgcg gacgtgatgc tgtgcggcgc cacatgcttt | 660 |
| ccggacccgt tcttcattct ctcggggttc tccaccttcc aggcgatgcc gctgggcgga | 720 |
| ccggacgata acccactgtc cgtgccgctg cggcagggca gccagggcct gacgcccgga | 780 |
| gagggcggcg ccatcatggt gctgaagcgc ctcgaggacg ccgtgcgcga cggcgaccgc | 840 |
| atctacggca ccttgctcgg cacgagtctg agcaacgccg ggtgcggcct gccgctgagc | 900 |
| ccgcacctgc cgagcgagaa gtcgtgcatg gaggacctgt acacgagcgt cggcatcgac | 960 |
| ccaagcgagg tgcagtacgt ggagtgccac gccacgggca ctccgcaggg cgacgtcgtg | 1020 |
| gaggtagagg cgctgcgcca ctgctttcga ggtaacacgg accaccgcc gcgcatgggc | 1080 |
| tccaccaagg gcaactttgg ccacactctc gtggcggccg ggttcgcagg catgccaag | 1140 |
| gtgctgctgt cgatgcagca cggcacgatc ccgcccacgc ccggtgtcga ccgctccaac | 1200 |
| tgcatcgacc cgctcgtcgt ggacgaggcc atcccttggc cgtactcgtc ggcgcaggcg | 1260 |
| cgggcaggca aaccaggcga tgagctcaag tgcgcctcgc tctccgcctt tggctttggt | 1320 |
| ggaaccaacg cgcactgtgt cttccgtgag caccgccaaa ttgctgctac tgcgacagcc | 1380 |
| tcgccggtgc ttcccgaggt gactcctgga ccgattgcca tcatcgggat ggacgcgacg | 1440 |
| tttggtaccc tcaagggcct ggacgcgttt gagcaggcca tctacaaggg cacggacggc | 1500 |
| gccagcgacc tgccgagcaa cgctggcgg ttcctgggcg ccgacacgga cttcttgacc | 1560 |
| gccatgggcc tcgacgccgt gccgcgcggg tgctacgtgc gcgacgtgga cgtggactac | 1620 |
| aagcggctgc ggtcgccgat gatccctgag gacgtcctgc gcccgcaaca gctgctggcg | 1680 |
| gtggctacga tggaccgcgc gctgcaggac gctggaatgg cgacgggagg caaggtggcg | 1740 |
| gtgctggtgg ggctcggcac ggacaccgag ctgtaccggc accgcgcgcg cgtgacactc | 1800 |
| aaggagcggc tcgacccggc cgcgttctcg cccgagcagg tgcaggagat gatggactac | 1860 |
| atcaacgact gcggcacctc gacgtcgtac acgtcgtaca tcgcaacct cgtggccacg | 1920 |
| cgcgtgtcct cgcagtgggg ctttacgggc ccgtccttca ccgtcaccga aggcgcaaac | 1980 |
| tcggtctacc gctgcctcga gctgggcaag ttcctgctcg acacgcacca ggtggacgcc | 2040 |
| gtcgtggtgg ccggcgtcga cctctgtgcc accgccgaga acctttacct caaggcgcgc | 2100 |
| cgctccgcca tcagccgaca ggaccaccct cgcgccaact tgaggccag cgccgacggg | 2160 |

```
tactttgccg gcgagggcag cggcgccctg gtcctcaagc gccaggccga cgttggctca    2220
gacgacaagg tctacgccag tgtcgcgggc ctcacgtgcg ccgcgcagcc cgctgaagcc    2280
gtgtcgccgc tactactcca agtccacaac gacgacaacg agaagagggt ggtggagatg    2340
gtggagctcg ccgccgactc gggtcgccat gcgccgcact ggccaactc gccgctgagc     2400 gccgagtcgc agctggagca agtgtccaag ttgctcgcgc accaggtgcc gggctcggtg    2460
gccatcggca gcgtgcgcgc caacgtggga gacgtcgggt acgcctcggg cgccgcgagc    2520
ctcatcaaga cggcgctgtg cctccacaac cgctacctcc cggccaaccc gcagtgggag    2580
cggccggtgg cgccggtctc cgaggcgctg tttacttgcc cgcgctcgcg tgcctggctg    2640
aagaacccgg gcgagtcgcg actggcggct gtcgccagtg cctccgagag cgggtcctgc    2700
tttggcgtgc tcctcacaga cgagtacgcc actcatgaga gcagcaaccg cctctcgctg    2760
gatgacgccg cccccaagct catcgcgatc cgtggcgaca ccgttgacga tatcatggcc    2820
aaggtcaacg ccgagctggc gctcctccga gcgcacgccg aaaccgggtc tgctactgac    2880
gacgacccag ctgctgctgt cgctttcact gctcatcgct tgcgcttttt gcggctcgta    2940
ggggagacgt ggctagtca cggtgccacg gcgaccttgt gtttggccct gctgacaacg     3000
ccggagaagc tggagaagga gttggagctg gcagccaagg gtgtaccgcg aagcgccaag    3060
gccgggcgca actggatgtc gccatcgggc agcgcctttg cgccgacacc tgtgaccagc    3120
gaccgcgtcg cgttcatgta cggcgagggc cgcagcccct actacggcgt cgggctcgac    3180
ctgcaccgcc tgtggccggc tttgcacgag cgcatcaacg acaagaccgc ggcgctgtgg    3240
gagaacggcg actcgtggct catgccgcgc gcggtggatg ccgactcgca gcgcgccgtg    3300
cagacggcct ttgacgcgga ccagatcgag atgttccgca cgggcatctt cgtgtccatc    3360
tgcctcaccg actacgcgcg cgacgtgctc ggggtgcagc ccaaggcgtg cttcggcctc    3420
agcctcggcg agatctccat gctctttgcg ctgtcgcgac gcaactgcgg cctgtcggac    3480
cagctcacgc agcgcctacg cacctcgccg gtgtggtcga cacagctggc ggtggagttc    3540
caggccttgc gcaagctatg gaacgtgccg gcggacgccc ccgtggagtc cttctggcag    3600
ggctacttgg ttcgcgccag ccgcgccgaa atcgagaagg cgatcgggcc cgacaaccgc    3660
ttcgtgcgcc tgctgatcgt caacgactcg agcagcgcgc tgatcgccgg caaacctgcc    3720
gagtgtctgc gcgtgctgga gcgcctgggc gggcggttgc cgccgatgcc cgtcaagcaa    3780
ggcatgattg ggcactgccc cgaagtggcg ccctacacgc cgggcatcgc gcacatccac    3840
gagatttttg agattccgga cagccccgtc aagatgtaca cctcggtcac caacgccgag    3900
ctgcgcgggg gcagcaacag cagcatcacc gagttcgtgc agaagttgta cacgcgcatc    3960
gccgactttc cgggcatcgt cgacaaggtc agccgtgacg gccacgatgt cttcgtcgag    4020
gtggggccga caacatgcg ctccgccgcg gtcagtgaca ttcttggcaa ggctgccacc     4080
ccgcatgtct ccgtggcgct ggaccgcccc agtgagtcgg cgtggacgca gaccctcaag    4140
tcgctggcgc tgctgaccgc ccaccgcgtg ccctgcaca acccgactct gtttgcggac     4200
ctgtaccacc ccacgttcct gacggctatc gactctgcga tgcaggagcc cccgcccaag    4260
cccaaccgct tccttcgcag cgtagaggtc aacgggtact tttgccccga cggcatcagc    4320
aagcaggttg ctgctgcaag tgccaaaccc tcgacgcatt gcatggttcg tttgcaccca    4380
gccaaggcag ttgtggttgc tgctgctggt gctgtggttg ctgattcgac gcccgtggtc    4440
aaggccaagc agacgtcgtc gtcgttgttg gttggggatg acgcctttct gcgctgctac    4500
```

```
gacgtggact ggccgctcta catgggcgcc atggcggaag gcatctcgtc ggtagacctg    4560
gtggtcgctg ccgccgaggc ccgcatgctg catcattcg gagcggcccg cttgcctatg     4620
gaccaggtgg aactccagat ccgtgagatc cagcaacgca cctccaacgc ctttgctgtc    4680
aacctgatgc cgggtcctga cgaggccgcg acggtggacg cgctgctgcg cacgggcgtc    4740
tcaatcgtcg aggcatcggg ctacaccggc gcgctctctg cagacctggt gcgctaccgt    4800
gtcacgggtc tgcgacgaac tagttgcggt gcttctgtgt cggcgactca ccgtgtggtc    4860
gccaaggtgt cgcgcaccga ggtggccgag cactttctgc gcccggcgcc ggccgccgta    4920
ctagaggctt tggtcgccgc caaacagatt acgcccgagc aggccgcgct ggccagccgc    4980
gtcgccatgg ccgacgacgt cgcggtggag ccgactcgg gcgggcacac cgacaaccga     5040
ccgatccacg tgctgctgcc gctcgtggtg gcgcagcgca accgctggcg ccacctggtg    5100
gacacgccag tgcgcgtcgg cgccggcggc gggatcgcct gtccgcgcgc cgcgctgctc    5160
gccttttccc tgggcgccgc ctttgtggtc accgggtccg tcaaccaact ggcccgcgag    5220
gctggcacca gcgacgcggt ccgactactg ctggcgacgg ccacctactc ggacgtggcc    5280
atggcgccgg gcggcgtcca ggtgctcaag aagcagacca tgttcgccgc gcgggccacg    5340
atgctcgccc agctgcaggc caagttcggc tcctttgacg ccgtgccgga ccgcagctg     5400 cgcaagctcg agcgctccgt gttcaagcag tccgtggcgg acgtgtgggc tgctgcacgc    5460
gaaaagtttg tgtcgacgc taccgctgca agtccgcagg agaggatggc gctctgtgtg     5520
cgctggtaca tgtcgcagtc gtcgcgatgg gctaccgagg cgacgtccgc gcgcaaggcg    5580
gactaccaga tctggtgcgg ccccgccatc ggcagcttca acgacttcgt tcgcggcacc    5640
aagctggacg cgaccgctgg caccggcgag tttccgcgcg tcgtggacat caaccagcac    5700
atcctcctcg gagcctcgca ctaccgccgc gtgcagcaac aacaacagga cgacgacgta    5760
gaatacatca tcgtataa                                                  5778
```

<210> SEQ ID NO 4
<211> LENGTH: 1925
<212> TYPE: PRT
<213> ORGANISM: Schizochytrium sp.

<400> SEQUENCE: 4

```
Met Pro Cys Asp Asn Ile Ala Val Val Gly Met Ala Val Gln Tyr Ala
1               5                   10                  15

Gly Cys Lys Asn Gln Asp Glu Phe Trp Asp Thr Leu Met Arg Lys Glu
            20                  25                  30

Ile Asn Ser Ser Pro Ile Ser Ala Glu Arg Leu Gly Thr Arg Tyr Arg
        35                  40                  45

Asp Leu His Phe His Pro Gln Arg Ser Lys Tyr Ala Asp Thr Phe Cys
    50                  55                  60

Asn Asp Arg Tyr Gly Cys Val Asp Ala Ser Val Asp Asn Glu His Asp
65                  70                  75                  80

Leu Leu Ala Asp Leu Ala Arg Arg Ala Leu Asp Ala Gly Ile Asn
            85                  90                  95

Leu Asp Asp Ala Ser Thr Thr Ala Asn Leu Arg Asp Phe Gly Ile Val
            100                 105                 110

Ser Gly Cys Leu Ser Phe Pro Met Asp Asn Leu Gln Gly Glu Leu Leu
        115                 120                 125

Asn Leu Tyr Gln Val His Val Glu Asn Arg Val Gly Ala Gln Arg Phe
    130                 135                 140
```

-continued

Arg Asp Ser Arg Pro Trp Ser Glu Arg Pro Arg Ala Val Ser Pro Glu
145                 150                 155                 160

Ala Ser Asp Pro Arg Val Tyr Ser Asp Pro Ala Ser Phe Val Ala Asn
            165                 170                 175

Gln Leu Gly Leu Gly Pro Val Arg Tyr Ser Leu Asp Ala Ala Cys Ala
            180                 185                 190

Ser Ala Leu Tyr Cys Leu Lys Leu Ala Ser Asp His Leu Leu Ser Arg
            195                 200                 205

Ser Ala Asp Val Met Leu Cys Gly Ala Thr Cys Phe Pro Asp Pro Phe
            210                 215                 220

Phe Ile Leu Ser Gly Phe Ser Thr Phe Gln Ala Met Pro Leu Gly Gly
225                 230                 235                 240

Pro Asp Asp Asn Pro Leu Ser Val Pro Leu Arg Gln Gly Ser Gln Gly
            245                 250                 255

Leu Thr Pro Gly Glu Gly Gly Ala Ile Met Val Leu Lys Arg Leu Glu
            260                 265                 270

Asp Ala Val Arg Asp Gly Asp Arg Ile Tyr Gly Thr Leu Leu Gly Thr
            275                 280                 285

Ser Leu Ser Asn Ala Gly Cys Gly Leu Pro Leu Ser Pro His Leu Pro
            290                 295                 300

Ser Glu Lys Ser Cys Met Glu Asp Leu Tyr Thr Ser Val Gly Ile Asp
305                 310                 315                 320

Pro Ser Glu Val Gln Tyr Val Glu Cys His Ala Thr Gly Thr Pro Gln
            325                 330                 335

Gly Asp Val Val Glu Val Glu Ala Leu Arg His Cys Phe Arg Gly Asn
            340                 345                 350

Thr Asp His Pro Pro Arg Met Gly Ser Thr Lys Gly Asn Phe Gly His
            355                 360                 365

Thr Leu Val Ala Ala Gly Phe Ala Gly Met Ala Lys Val Leu Leu Ser
            370                 375                 380

Met Gln His Gly Thr Ile Pro Pro Thr Pro Gly Val Asp Arg Ser Asn
385                 390                 395                 400

Cys Ile Asp Pro Leu Val Val Asp Glu Ala Ile Pro Trp Pro Tyr Ser
            405                 410                 415

Ser Ala Gln Ala Arg Ala Gly Lys Pro Gly Asp Glu Leu Lys Cys Ala
            420                 425                 430

Ser Leu Ser Ala Phe Gly Phe Gly Gly Thr Asn Ala His Cys Val Phe
            435                 440                 445

Arg Glu His Arg Gln Ile Ala Thr Ala Thr Ala Ser Pro Val Leu
            450                 455                 460

Pro Glu Val Thr Pro Gly Pro Ile Ala Ile Gly Met Asp Ala Thr
465                 470                 475                 480

Phe Gly Thr Leu Lys Gly Leu Asp Ala Phe Glu Gln Ala Ile Tyr Lys
            485                 490                 495

Gly Thr Asp Gly Ala Ser Asp Leu Pro Ser Lys Arg Trp Arg Phe Leu
            500                 505                 510

Gly Ala Asp Thr Asp Phe Leu Thr Ala Met Gly Leu Asp Ala Val Pro
            515                 520                 525

Arg Gly Cys Tyr Val Arg Asp Val Asp Val Asp Tyr Lys Arg Leu Arg
            530                 535                 540

Ser Pro Met Ile Pro Glu Asp Val Leu Arg Pro Gln Gln Leu Leu Ala
545                 550                 555                 560

Val Ala Thr Met Asp Arg Ala Leu Gln Asp Ala Gly Met Ala Thr Gly

-continued

```
                565                 570                 575
Gly Lys Val Ala Val Leu Val Gly Leu Gly Thr Asp Thr Glu Leu Tyr
            580                 585                 590
Arg His Arg Ala Arg Val Thr Leu Lys Glu Arg Leu Asp Pro Ala Ala
            595                 600                 605
Phe Ser Pro Glu Gln Val Gln Glu Met Met Asp Tyr Ile Asn Asp Cys
610                 615                 620
Gly Thr Ser Thr Ser Tyr Thr Ser Tyr Ile Gly Asn Leu Val Ala Thr
625                 630                 635                 640
Arg Val Ser Ser Gln Trp Gly Phe Thr Gly Pro Ser Phe Thr Val Thr
            645                 650                 655
Glu Gly Ala Asn Ser Val Tyr Arg Cys Leu Glu Leu Gly Lys Phe Leu
            660                 665                 670
Leu Asp Thr His Gln Val Asp Ala Val Val Ala Gly Val Asp Leu
            675                 680                 685
Cys Ala Thr Ala Glu Asn Leu Tyr Leu Lys Ala Arg Arg Ser Ala Ile
690                 695                 700
Ser Arg Gln Asp His Pro Arg Ala Asn Phe Glu Ala Ser Ala Asp Gly
705                 710                 715                 720
Tyr Phe Ala Gly Glu Gly Ser Gly Ala Leu Val Leu Lys Arg Gln Ala
                725                 730                 735
Asp Val Gly Ser Asp Lys Val Tyr Ala Ser Val Ala Gly Leu Thr
                740                 745                 750
Cys Ala Ala Gln Pro Ala Glu Ala Val Ser Pro Leu Leu Gln Val
            755                 760                 765
His Asn Asp Asp Asn Glu Lys Arg Val Val Glu Met Val Glu Leu Ala
770                 775                 780
Ala Asp Ser Gly Arg His Ala Pro His Leu Ala Asn Ser Pro Leu Ser
785                 790                 795                 800
Ala Glu Ser Gln Leu Glu Gln Val Ser Lys Leu Leu Ala His Gln Val
            805                 810                 815
Pro Gly Ser Val Ala Ile Gly Ser Val Arg Ala Asn Val Gly Asp Val
            820                 825                 830
Gly Tyr Ala Ser Gly Ala Ala Ser Leu Ile Lys Thr Ala Leu Cys Leu
            835                 840                 845
His Asn Arg Tyr Leu Pro Ala Asn Pro Gln Trp Glu Arg Pro Val Ala
            850                 855                 860
Pro Val Ser Glu Ala Leu Phe Thr Cys Pro Arg Ser Arg Ala Trp Leu
865                 870                 875                 880
Lys Asn Pro Gly Glu Ser Arg Leu Ala Ala Val Ala Ser Ala Ser Glu
                885                 890                 895
Ser Gly Ser Cys Phe Gly Val Leu Leu Thr Asp Glu Tyr Ala Thr His
                900                 905                 910
Glu Ser Ser Asn Arg Leu Ser Leu Asp Asp Ala Ala Pro Lys Leu Ile
            915                 920                 925
Ala Ile Arg Gly Asp Thr Val Asp Asp Ile Met Ala Lys Val Asn Ala
            930                 935                 940
Glu Leu Ala Leu Leu Arg Ala His Ala Glu Thr Gly Ser Ala Thr Asp
945                 950                 955                 960
Asp Asp Pro Ala Ala Val Ala Phe Thr Ala His Arg Leu Arg Phe
                965                 970                 975
Leu Arg Leu Val Gly Glu Thr Val Ala Ser His Gly Ala Thr Ala Thr
            980                 985                 990
```

-continued

Leu Cys Leu Ala Leu Leu Thr Thr Pro Glu Lys Leu Glu Lys Glu Leu
        995                 1000                    1005

Glu Leu Ala Ala Lys Gly Val Pro Arg Ser Ala Lys Ala Gly Arg
    1010                1015                1020

Asn Trp Met Ser Pro Ser Gly Ser Ala Phe Ala Pro Thr Pro Val
    1025                1030                1035

Thr Ser Asp Arg Val Ala Phe Met Tyr Gly Glu Gly Arg Ser Pro
    1040                1045                1050

Tyr Tyr Gly Val Gly Leu Asp Leu His Arg Leu Trp Pro Ala Leu
    1055                1060                1065

His Glu Arg Ile Asn Asp Lys Thr Ala Ala Leu Trp Glu Asn Gly
    1070                1075                1080

Asp Ser Trp Leu Met Pro Arg Ala Val Asp Ala Asp Ser Gln Arg
    1085                1090                1095

Ala Val Gln Thr Ala Phe Asp Ala Asp Gln Ile Glu Met Phe Arg
    1100                1105                1110

Thr Gly Ile Phe Val Ser Ile Cys Leu Thr Asp Tyr Ala Arg Asp
    1115                1120                1125

Val Leu Gly Val Gln Pro Lys Ala Cys Phe Gly Leu Ser Leu Gly
    1130                1135                1140

Glu Ile Ser Met Leu Phe Ala Leu Ser Arg Arg Asn Cys Gly Leu
    1145                1150                1155

Ser Asp Gln Leu Thr Gln Arg Leu Arg Thr Ser Pro Val Trp Ser
    1160                1165                1170

Thr Gln Leu Ala Val Glu Phe Gln Ala Leu Arg Lys Leu Trp Asn
    1175                1180                1185

Val Pro Ala Asp Ala Pro Val Glu Ser Phe Trp Gln Gly Tyr Leu
    1190                1195                1200

Val Arg Ala Ser Arg Ala Glu Ile Glu Lys Ala Ile Gly Pro Asp
    1205                1210                1215

Asn Arg Phe Val Arg Leu Leu Ile Val Asn Asp Ser Ser Ser Ala
    1220                1225                1230

Leu Ile Ala Gly Lys Pro Ala Glu Cys Leu Arg Val Leu Glu Arg
    1235                1240                1245

Leu Gly Gly Arg Leu Pro Pro Met Pro Val Lys Gln Gly Met Ile
    1250                1255                1260

Gly His Cys Pro Glu Val Ala Pro Tyr Thr Pro Gly Ile Ala His
    1265                1270                1275

Ile His Glu Ile Leu Glu Ile Pro Asp Ser Pro Val Lys Met Tyr
    1280                1285                1290

Thr Ser Val Thr Asn Ala Glu Leu Arg Gly Gly Ser Asn Ser Ser
    1295                1300                1305

Ile Thr Glu Phe Val Gln Lys Leu Tyr Thr Arg Ile Ala Asp Phe
    1310                1315                1320

Pro Gly Ile Val Asp Lys Val Ser Arg Asp Gly His Asp Val Phe
    1325                1330                1335

Val Glu Val Gly Pro Asn Asn Met Arg Ser Ala Ala Val Ser Asp
    1340                1345                1350

Ile Leu Gly Lys Ala Ala Thr Pro His Val Ser Val Ala Leu Asp
    1355                1360                1365

Arg Pro Ser Glu Ser Ala Trp Thr Gln Thr Leu Lys Ser Leu Ala
    1370                1375                1380

```
Leu Leu Thr Ala His Arg Val Pro Leu His Asn Pro Thr Leu Phe
    1385                1390                1395

Ala Asp Leu Tyr His Pro Thr Phe Leu Thr Ala Ile Asp Ser Ala
1400                1405                1410

Met Gln Glu Pro Pro Lys Pro Asn Arg Phe Leu Arg Ser Val
    1415                1420                1425

Glu Val Asn Gly Tyr Phe Cys Pro Asp Gly Ile Ser Lys Gln Val
    1430                1435                1440

Ala Ala Ala Ser Ala Lys Pro Ser Thr His Cys Met Val Arg Leu
    1445                1450                1455

His Pro Ala Lys Ala Val Val Ala Ala Ala Gly Ala Val Val
    1460                1465                1470

Ala Asp Ser Thr Pro Val Val Lys Ala Lys Gln Thr Ser Ser Ser
    1475                1480                1485

Leu Leu Val Gly Asp Asp Ala Phe Leu Arg Cys Tyr Asp Val Asp
    1490                1495                1500

Trp Pro Leu Tyr Met Gly Ala Met Ala Glu Gly Ile Ser Ser Val
    1505                1510                1515

Asp Leu Val Val Ala Ala Glu Ala Arg Met Leu Ala Ser Phe
    1520                1525                1530

Gly Ala Ala Arg Leu Pro Met Asp Gln Val Glu Leu Gln Ile Arg
    1535                1540                1545

Glu Ile Gln Gln Arg Thr Ser Asn Ala Phe Ala Val Asn Leu Met
    1550                1555                1560

Pro Gly Pro Asp Glu Ala Ala Thr Val Asp Ala Leu Leu Arg Thr
    1565                1570                1575

Gly Val Ser Ile Val Glu Ala Ser Gly Tyr Thr Gly Ala Leu Ser
    1580                1585                1590

Ala Asp Leu Val Arg Tyr Arg Val Thr Gly Leu Arg Arg Thr Ser
    1595                1600                1605

Cys Gly Ala Ser Val Ser Ala Thr His Arg Val Val Ala Lys Val
    1610                1615                1620

Ser Arg Thr Glu Val Ala Glu His Phe Leu Arg Pro Ala Pro Ala
    1625                1630                1635

Ala Val Leu Glu Ala Leu Val Ala Ala Lys Gln Ile Thr Pro Glu
    1640                1645                1650

Gln Ala Ala Leu Ala Ser Arg Val Ala Met Ala Asp Asp Val Ala
    1655                1660                1665

Val Glu Ala Asp Ser Gly Gly His Thr Asp Asn Arg Pro Ile His
    1670                1675                1680

Val Leu Leu Pro Leu Val Val Ala Gln Arg Asn Arg Trp Arg His
    1685                1690                1695

Leu Val Asp Thr Pro Val Arg Val Gly Ala Gly Gly Ile Ala
    1700                1705                1710

Cys Pro Arg Ala Ala Leu Leu Ala Phe Ser Leu Gly Ala Ala Phe
    1715                1720                1725

Val Val Thr Gly Ser Val Asn Gln Leu Ala Arg Glu Ala Gly Thr
    1730                1735                1740

Ser Asp Ala Val Arg Leu Leu Ala Thr Ala Thr Tyr Ser Asp
    1745                1750                1755

Val Ala Met Ala Pro Gly Gly Val Gln Val Leu Lys Lys Gln Thr
    1760                1765                1770

Met Phe Ala Ala Arg Ala Thr Met Leu Ala Gln Leu Gln Ala Lys
```

```
               1775                1780                1785
Phe Gly Ser Phe Asp Ala Val Pro Glu Pro Gln Leu Arg Lys Leu
    1790                1795                1800

Glu Arg Ser Val Phe Lys Gln Ser Val Ala Asp Val Trp Ala Ala
    1805                1810                1815

Ala Arg Glu Lys Phe Gly Val Asp Ala Thr Ala Ala Ser Pro Gln
    1820                1825                1830

Glu Arg Met Ala Leu Cys Val Arg Trp Tyr Met Ser Gln Ser Ser
    1835                1840                1845

Arg Trp Ala Thr Glu Ala Thr Ser Ala Arg Lys Ala Asp Tyr Gln
    1850                1855                1860

Ile Trp Cys Gly Pro Ala Ile Gly Ser Phe Asn Asp Phe Val Arg
    1865                1870                1875

Gly Thr Lys Leu Asp Ala Thr Ala Gly Thr Gly Glu Phe Pro Arg
    1880                1885                1890

Val Val Asp Ile Asn Gln His Ile Leu Leu Gly Ala Ser His Tyr
    1895                1900                1905

Arg Arg Val Gln Gln Gln Gln Asp Asp Asp Val Glu Tyr Ile
    1910                1915                1920

Ile Val
    1925

<210> SEQ ID NO 5
<211> LENGTH: 4308
<212> TYPE: DNA
<213> ORGANISM: Schizochytrium sp.

<400> SEQUENCE: 5
atgacatcat cgaagaagac tcccgtgtgg gagatgagca aggaggagct gctggacggc      60
aagacggtgg tcttcgacta caacgagctg ctcgaattcg ccgagggcga cgtgggccaa     120
gtgttcggac ccgagttcga catcatcgac aagtaccggc gtcgcgtgcg gctgccggcg     180
cgcgagtacc tgctcgtgtc gcgcgtgacg ctgatggacg ccgaggtgaa caacttccgc     240
gtcgggtcgc gcatggtgac cgagtacgac gtgcccgtga cggggagct gtcggagggc      300 ggggacgtgc cgtgggcggt gctggtggag tcggggcagt gcgacctgat gctcatctcg     360
tacatgggca tcgacttcca gtgcaagggc gaccgcgtgt accgcctgct caacacatcg     420
ctcaccttct tcggggtggc gcacgagggc gagacgctgg tgtacgacat ccgcgtcacg     480
gggttcgcca agggcgcggg cggggagatc tcgatgttct tcttcgagta cgactgcttc     540
gtggacggcc gcctgctgat cgagatgcgc gacgggtgcg ccgggttctt cacggacgcc     600
gagctggccg ccggcaaggg cgtgcttaag accaaggcgg agctggcggc gcgcgcgcag     660
atccagaagc aggacatcgc gcccttgcg ccggcgccgt gctcgcacaa gacctcgctg      720
gacgcgcgcg agatgcggct gctcgtggac cgccagtggg cgcgcgtctt cggcagcggc     780
atggcgggca tcgactacaa gttgtgcgct cgcaagatgc tcatgatcga ccgcgtcacg     840
cacctcgacc cgcgcggcgg cgcgcacggc ctcgggctgc tgatcgggga aggtgctg      900 gagcgcgacc actggtactt ccctgccac tttgtgcgcg acgaggtgat ggccgggtcg     960
ctggtcagcg acggctgctc gcagctcctc aaggtgtaca tgctgtggct cggcctgcac    1020
acgaccgtgg gcgcgttcga ctttcgtccc gtgagcgggc acgccaacaa ggtgcggtgc    1080
cgcgggcaga tctcaccgca aagggcaag ctcgtgtacg tgatggagat caaggaaatg     1140
ggctttgacg cgaagacggg cgatccgttt gcgatcgcgg acgtggacat catcgacgtc    1200
```

-continued

```
aacttcgagg agggacaggc gtttgcggga gtggaagacc tgcacagcta cggccagggc   1260
gacctccgca agaagatcgt cgtcgacttc aagggcatcg cgctctccct gcagaagcgg   1320
aaggagcagc agaaggaaag catgaccgtg actacgacga cgacgacgac gagccgggtg   1380
attgcgccgc ccagcgggtg cctcaagggc gacccgacgg cgccgacgag cgtgacgtgg   1440
cacccgatgg cggagggcaa cggcgggccc ggaccgacgc cgtcgttctc gccgtccgcg   1500
tacccgccgc gggcggtgtg cttctcgccg ttccccaaca acccgcttga caacgaccac   1560
acgccgggcc agatgccgtt gacctggttc aacatgtccg aattcatgtg cggcaaagtg   1620
tccaactgcc tgggccccga gtttgcgcgc ttcgacgcga gcaagacgag ccgcagcccg   1680
gcctttgacc tggcgctcgt gacgcgggtg acgagcgtgg cggacatgga gcacgggccg   1740
ttctacaacg tggacgtcaa cccgggccag ggcacgatgg tgggcgagtt cgactgtccc   1800
gcggacgcgt ggttcttcgg cgcctcgagc cgcgacgacc acatgccgta ctcgatcctg   1860
atggagatcg cgctgcagac gtcgggcgtc ctcacctcgg tgctcaaggc gccgctgacg   1920
atggacaagg acgacatcct cttccgcaac ctcgacgcag acgccgagct cgtgggcgac   1980
gccatgccgg acgtgcgcgg caagacgatc cgcaacttca ccaagtgcac aggctacagc   2040
atgctcggca agatgggcat ccaccgcttc acctttgagc tcagcgtcga cggcgccgtc   2100
ttctacaagg gcagcacctc gtttggctgg ttcgtcccgc aggtcttcga gtcgcagacc   2160
ggtctcgaca acggcaagcc gcgcctgcct tggtaccgcg agaacaacgt cgccgtcgac   2220
acgctctccg cgcccgcctc cgcttcctcc gcgcaaggtc agctgcagct gcagcgacgc   2280
gggtcgcagg cgcagttcct ggacacaatc cacctggcgg gcagcggcgc cggcgtgcac   2340
ggccagggct acgcgcacgg ggagaaggcc gtgaacaagc aagattggtt cttctcgtgc   2400
cacttctggt tcgaccccgt gatgcccggg tccctgggca tcgagtcgat gttccagctc   2460
gtcgaggcgt ggtgcgtgaa gcagggactc gcggcgcggc acggcatcgc tcacccagtg   2520
ttcgcgcacg cgcccggggc cacgagctgg aagtaccgcg ggcagctaac ccccaagaac   2580
gaccgcatgg acagcgaggt gcacatcaag tcggtggcgg ccttctcctc ctgggtcgac   2640
gtcgtcgcgg acgggttcct cttcgtcgac ggcctccgcg tctactcggc agacaacctc   2700
cgcgtccgca tccagaccgg cgccggccac gttgaagagc aagaggttgc tgccaaggcc   2760
acaaccaaga acagcagtat tgctgatgtg gacgtggcgg acctgcaagc gctcaagcag   2820
gcgttgctga cgctggagcg accgctgcag ctggacgcgg ggagcgaggt gcccgcctgc   2880
gcggtgagcg acctgggcga taggggcttc atggagacgt acggggtggt ggcgccgctg   2940
tacagcgggg cgatggccaa gggcatcgcg tcggcggacc tggtgatcgc gatgggccag   3000
cgcaagatgc tggggtcgtt tggcgcgggc gggctcccga tgcacgtcgt gcgcgcgggg   3060
attgagaaga tccaggcagc gctgccagcg gggccatacg cggtcaacct gattcactcg   3120
ccttttgacg ccaacctgga gaagggcaac gtggacctct tcctggagaa gggcgtgcgc   3180
gtcgtggagg cgtcggcctt catggagctc acgccccagg tggtgcgcta ccgcgcgacg   3240
ggcctctctc gcgacgcgcg cggcggctcc gtgcgcacgg cccacaagat catccggcaag  3300
gtcagccgca ccgagctggc cgagatgttt atccggcccg cgccgcaagc cattctcgac   3360
aagcttgtgg cgtccggcga gatcacccccc gagcaggcgg cgctggcgct cgaggtgccc   3420
atggcggacg acatcgccgt cgaggccgat tcggcgggc acaccgacaa ccgcccccatc   3480
cacgtcatcc tgcccctcat cctcagcctg cgcaaccgcc tccagcgcga gctcaagtac   3540
```

```
cctgcgcgac accgcgtgcg cgtcggcgcc ggggcggca tcgggtgccc gcaagcggct    3600
ctgggcgcct tccacatggg cgccgcgttt gtggtgacgg gcacggtcaa ccagctgagc    3660
cggcaggccg ggacatgcga caatgtgcgg cggcagctgt cgcgcgcgac gtactcggac    3720
atcacgatgg cgccggcggc ggacatgttc gagcagggcg tcgagctgca ggtgctcaag    3780
aagggcacga tgtttccctc gcgcgccaag aagctgttcg agctgtttca caagtacgac    3840
tcgttcgagg cgatgccggc ggacgagctg gcgcgcgtcg agaagcgcat cttcagcaag    3900
tcactcgccg aggtgtgggc cgagaccaag gacttctaca tcacgcggct caacaacccg    3960
gagaagatcc gcaaggcgga gaacgaggac cccaagctca agatgtcact ctgcttccgc    4020
tggtacctcg ggctcagctc gttctgggcc aacaacggca tcgcggaccg cacgatggac    4080
taccagatct ggtgcggccc tgccatcggc gccttcaacg acttcatcgc cgactcgtac    4140
ctcgacgtgg ccgtctcggg cgagttcccc gacgtcgtgc agatcaacct gcagatcctg    4200
tcgggcgcag cctacctcca gcgcctcctc tccgtcaagc tcgcaccgcg gatcgacgtc    4260
gacaccgagg acgacctctt cacctaccgc cccgaccacg cactctaa                 4308
```

<210> SEQ ID NO 6
<211> LENGTH: 1435
<212> TYPE: PRT
<213> ORGANISM: Schizochytrium sp.

<400> SEQUENCE: 6

```
Met Thr Ser Ser Lys Lys Thr Pro Val Trp Glu Met Ser Lys Glu Glu
1               5                   10                  15

Leu Leu Asp Gly Lys Thr Val Val Phe Asp Tyr Asn Glu Leu Leu Glu
            20                  25                  30

Phe Ala Glu Gly Asp Val Gly Gln Val Phe Gly Pro Glu Phe Asp Ile
        35                  40                  45

Ile Asp Lys Tyr Arg Arg Arg Val Arg Leu Pro Ala Arg Glu Tyr Leu
    50                  55                  60

Leu Val Ser Arg Val Thr Leu Met Asp Ala Glu Val Asn Asn Phe Arg
65                  70                  75                  80

Val Gly Ser Arg Met Val Thr Glu Tyr Asp Val Pro Val Asn Gly Glu
                85                  90                  95

Leu Ser Glu Gly Gly Asp Val Pro Trp Ala Val Leu Val Glu Ser Gly
            100                 105                 110

Gln Cys Asp Leu Met Leu Ile Ser Tyr Met Gly Ile Asp Phe Gln Cys
        115                 120                 125

Lys Gly Asp Arg Val Tyr Arg Leu Leu Asn Thr Ser Leu Thr Phe Phe
    130                 135                 140

Gly Val Ala His Glu Gly Glu Thr Leu Val Tyr Asp Ile Arg Val Thr
145                 150                 155                 160

Gly Phe Ala Lys Gly Ala Gly Glu Ile Ser Met Phe Phe Glu
                165                 170                 175

Tyr Asp Cys Phe Val Asp Gly Arg Leu Leu Ile Glu Met Arg Asp Gly
            180                 185                 190

Cys Ala Gly Phe Phe Thr Asp Ala Glu Leu Ala Ala Gly Lys Gly Val
        195                 200                 205

Leu Lys Thr Lys Ala Glu Leu Ala Ala Arg Ala Gln Ile Gln Lys Gln
    210                 215                 220

Asp Ile Ala Pro Phe Ala Pro Ala Pro Cys Ser His Lys Thr Ser Leu
225                 230                 235                 240
```

```
Asp Ala Arg Glu Met Arg Leu Leu Val Asp Arg Gln Trp Ala Arg Val
            245                 250                 255

Phe Gly Ser Gly Met Ala Gly Ile Asp Tyr Lys Leu Cys Ala Arg Lys
        260                 265                 270

Met Leu Met Ile Asp Arg Val Thr His Leu Asp Pro Arg Gly Gly Ala
    275                 280                 285

His Gly Leu Gly Leu Leu Ile Gly Glu Lys Val Leu Glu Arg Asp His
290                 295                 300

Trp Tyr Phe Pro Cys His Phe Val Arg Asp Glu Val Met Ala Gly Ser
305                 310                 315                 320

Leu Val Ser Asp Gly Cys Ser Gln Leu Leu Lys Val Tyr Met Leu Trp
                325                 330                 335

Leu Gly Leu His Thr Thr Val Gly Ala Phe Asp Phe Arg Pro Val Ser
            340                 345                 350

Gly His Ala Asn Lys Val Arg Cys Arg Gly Gln Ile Ser Pro His Lys
        355                 360                 365

Gly Lys Leu Val Tyr Val Met Glu Ile Lys Glu Met Gly Phe Asp Ala
    370                 375                 380

Lys Thr Gly Asp Pro Phe Ala Ile Ala Asp Val Asp Ile Ile Asp Val
385                 390                 395                 400

Asn Phe Glu Glu Gly Gln Ala Phe Ala Gly Val Glu Asp Leu His Ser
                405                 410                 415

Tyr Gly Gln Gly Asp Leu Arg Lys Lys Ile Val Val Asp Phe Lys Gly
            420                 425                 430

Ile Ala Leu Ser Leu Gln Lys Arg Lys Glu Gln Gln Lys Glu Ser Met
        435                 440                 445

Thr Val Thr Thr Thr Thr Thr Thr Ser Arg Val Ile Ala Pro Pro
    450                 455                 460

Ser Gly Cys Leu Lys Gly Asp Pro Thr Ala Pro Thr Ser Val Thr Trp
465                 470                 475                 480

His Pro Met Ala Glu Gly Asn Gly Gly Pro Gly Pro Thr Pro Ser Phe
                485                 490                 495

Ser Pro Ser Ala Tyr Pro Pro Arg Ala Val Cys Phe Ser Pro Phe Pro
            500                 505                 510

Asn Asn Pro Leu Asp Asn Asp His Thr Pro Gly Gln Met Pro Leu Thr
        515                 520                 525

Trp Phe Asn Met Ser Glu Phe Met Cys Gly Lys Val Ser Asn Cys Leu
    530                 535                 540

Gly Pro Glu Phe Ala Arg Phe Asp Ala Ser Lys Thr Ser Arg Ser Pro
545                 550                 555                 560

Ala Phe Asp Leu Ala Leu Val Thr Arg Val Thr Ser Val Ala Asp Met
                565                 570                 575

Glu His Gly Pro Phe Tyr Asn Val Asp Val Asn Pro Gly Gln Gly Thr
            580                 585                 590

Met Val Gly Glu Phe Asp Cys Pro Ala Asp Ala Trp Phe Phe Gly Ala
        595                 600                 605

Ser Ser Arg Asp Asp His Met Pro Tyr Ser Ile Leu Met Glu Ile Ala
    610                 615                 620

Leu Gln Thr Ser Gly Val Leu Thr Ser Val Leu Lys Ala Pro Leu Thr
625                 630                 635                 640

Met Asp Lys Asp Ile Leu Phe Arg Asn Leu Asp Ala Asp Ala Glu
                645                 650                 655

Leu Val Gly Asp Ala Met Pro Asp Val Arg Gly Lys Thr Ile Arg Asn
```

-continued

```
              660                 665                 670
Phe Thr Lys Cys Thr Gly Tyr Ser Met Leu Gly Lys Met Gly Ile His
            675                 680                 685
Arg Phe Thr Phe Glu Leu Ser Val Asp Gly Ala Val Phe Tyr Lys Gly
            690                 695                 700
Ser Thr Ser Phe Gly Trp Phe Val Pro Glu Val Phe Glu Ser Gln Thr
705                 710                 715                 720
Gly Leu Asp Asn Gly Lys Pro Arg Leu Pro Trp Tyr Arg Glu Asn Asn
                725                 730                 735
Val Ala Val Asp Thr Leu Ser Ala Pro Ala Ser Ser Ala Gln
                740                 745                 750
Gly Gln Leu Gln Leu Gln Arg Arg Gly Ser Gln Ala Gln Phe Leu Asp
            755                 760                 765
Thr Ile His Leu Ala Gly Ser Gly Ala Gly Val His Gly Gln Gly Tyr
            770                 775                 780
Ala His Gly Glu Lys Ala Val Asn Lys Gln Asp Trp Phe Phe Ser Cys
785                 790                 795                 800
His Phe Trp Phe Asp Pro Val Met Pro Gly Ser Leu Gly Ile Glu Ser
                805                 810                 815
Met Phe Gln Leu Val Glu Ala Trp Cys Val Lys Gln Gly Leu Ala Ala
                820                 825                 830
Arg His Gly Ile Ala His Pro Val Phe Ala His Ala Pro Gly Ala Thr
            835                 840                 845
Ser Trp Lys Tyr Arg Gly Gln Leu Thr Pro Lys Asn Asp Arg Met Asp
            850                 855                 860
Ser Glu Val His Ile Lys Ser Val Ala Ala Phe Ser Ser Trp Val Asp
865                 870                 875                 880
Val Val Ala Asp Gly Phe Leu Phe Val Asp Gly Leu Arg Val Tyr Ser
                885                 890                 895
Ala Asp Asn Leu Arg Val Arg Ile Gln Thr Gly Ala Gly His Val Glu
                900                 905                 910
Glu Gln Glu Val Ala Ala Lys Ala Thr Thr Lys Asn Ser Ser Ile Ala
            915                 920                 925
Asp Val Asp Val Ala Asp Leu Gln Ala Leu Lys Gln Ala Leu Leu Thr
            930                 935                 940
Leu Glu Arg Pro Leu Gln Leu Asp Ala Gly Ser Glu Val Pro Ala Cys
945                 950                 955                 960
Ala Val Ser Asp Leu Gly Asp Arg Gly Phe Met Glu Thr Tyr Gly Val
                965                 970                 975
Val Ala Pro Leu Tyr Ser Gly Ala Met Ala Lys Gly Ile Ala Ser Ala
                980                 985                 990
Asp Leu Val Ile Ala Met Gly Gln Arg Lys Met Leu Gly Ser Phe Gly
            995                 1000                1005
Ala Gly Gly Leu Pro Met His Val Val Arg Ala Gly Ile Glu Lys
            1010                1015                1020
Ile Gln Ala Ala Leu Pro Ala Gly Pro Tyr Ala Val Asn Leu Ile
            1025                1030                1035
His Ser Pro Phe Asp Ala Asn Leu Glu Lys Gly Asn Val Asp Leu
            1040                1045                1050
Phe Leu Glu Lys Gly Val Arg Val Val Glu Ala Ser Ala Phe Met
            1055                1060                1065
Glu Leu Thr Pro Gln Val Val Arg Tyr Arg Ala Thr Gly Leu Ser
            1070                1075                1080
```

Arg Asp Ala Arg Gly Gly Ser Val Arg Thr Ala His Lys Ile Ile
1085                1090                1095

Gly Lys Val Ser Arg Thr Glu Leu Ala Glu Met Phe Ile Arg Pro
1100                1105                1110

Ala Pro Gln Ala Ile Leu Asp Lys Leu Val Ala Ser Gly Glu Ile
1115                1120                1125

Thr Pro Glu Gln Ala Ala Leu Ala Leu Glu Val Pro Met Ala Asp
1130                1135                1140

Asp Ile Ala Val Glu Ala Asp Ser Gly Gly His Thr Asp Asn Arg
1145                1150                1155

Pro Ile His Val Ile Leu Pro Leu Ile Leu Ser Leu Arg Asn Arg
1160                1165                1170

Leu Gln Arg Glu Leu Lys Tyr Pro Ala Arg His Arg Val Arg Val
1175                1180                1185

Gly Ala Gly Gly Gly Ile Gly Cys Pro Gln Ala Ala Leu Gly Ala
1190                1195                1200

Phe His Met Gly Ala Ala Phe Val Val Thr Gly Thr Val Asn Gln
1205                1210                1215

Leu Ser Arg Gln Ala Gly Thr Cys Asp Asn Val Arg Arg Gln Leu
1220                1225                1230

Ser Arg Ala Thr Tyr Ser Asp Ile Thr Met Ala Pro Ala Ala Asp
1235                1240                1245

Met Phe Glu Gln Gly Val Glu Leu Gln Val Leu Lys Lys Gly Thr
1250                1255                1260

Met Phe Pro Ser Arg Ala Lys Lys Leu Phe Glu Leu Phe His Lys
1265                1270                1275

Tyr Asp Ser Phe Glu Ala Met Pro Ala Asp Glu Leu Ala Arg Val
1280                1285                1290

Glu Lys Arg Ile Phe Ser Lys Ser Leu Ala Glu Val Trp Ala Glu
1295                1300                1305

Thr Lys Asp Phe Tyr Ile Thr Arg Leu Asn Asn Pro Glu Lys Ile
1310                1315                1320

Arg Lys Ala Glu Asn Glu Asp Pro Lys Leu Lys Met Ser Leu Cys
1325                1330                1335

Phe Arg Trp Tyr Leu Gly Leu Ser Ser Phe Trp Ala Asn Asn Gly
1340                1345                1350

Ile Ala Asp Arg Thr Met Asp Tyr Gln Ile Trp Cys Gly Pro Ala
1355                1360                1365

Ile Gly Ala Phe Asn Asp Phe Ile Ala Asp Ser Tyr Leu Asp Val
1370                1375                1380

Ala Val Ser Gly Glu Phe Pro Asp Val Val Gln Ile Asn Leu Gln
1385                1390                1395

Ile Leu Ser Gly Ala Ala Tyr Leu Gln Arg Leu Leu Ser Val Lys
1400                1405                1410

Leu Ala Pro Arg Ile Asp Val Asp Thr Glu Asp Asp Leu Phe Thr
1415                1420                1425

Tyr Arg Pro Asp His Ala Leu
1430                1435

<210> SEQ ID NO 7
<211> LENGTH: 1395
<212> TYPE: DNA
<213> ORGANISM: Schizochytrium sp.

```
<400> SEQUENCE: 7
actcgcatcg cgatcgtggg gatgtcggcg atcctgccga gcggggagaa cgtgcgcgag      60
agctgggagg cgatccgcga tgggctggat tgcctgagcg atctgccggc ggaccgcgtg     120
gacgtgacgg cctactacaa cccggagaag acgaccaagg acaagatcta ctgcaagcgc     180
ggcgggttca tcccggagta cgacttcgac gcgcgtgagt tcgggctcaa catgttccag     240
atggaggact cggacgccaa ccagacgatc tcgctgctca aggtgaagga ggcgctgacg     300
gacgccaaca tcccggcgtt ctcgagcggt aagaagaaca tcggctgcgt gctgggcatc     360
ggcggcggcc agaaggcgag ccacgagttc tactcgcggc tcaactacgt ggtcgtggac     420
aaggtgctgc gcaagatggg cctgccggag gaagacgtgg cggcggcggt ggacaagtac     480
aaggcgagtt tccccgagtg gcgcctcgac tctttccccg ggttcctggg caacgtcacg     540
gcggggcgct gctgcaatac cttcaacatg gagggcatga actgcgtcgt ggacgcggcc     600
tgcgcgtcgt cgctgatcgc ggtcaaagtg gcgatcgagg agctgctcta cggcgactgc     660
gatgcgatga tcgcgggtgc cacctgcacg gacaactcga tcgggatgta catggccttc     720
tccaagacgc ccgtgttttc cacggacccg agcgtcaagg cgtacgacgc cgccaccaaa     780
ggcatgctca tcggcgaggg ctcggcgatg ctcgtgctga gcgctacgc ggacgccgtg     840 cgcgacggcg acaccgtgca cgccgtcatc aaggggtgcg cgtcctcgag cgacggcaag     900
gcggcgggca tctacacgcc gacaatctcg ggccaggagg aggccctgcg ccgcgcctac     960
gcccgcgcca atgtcgaccc ggccactgtg acgctggtgg agggccacgg cacgggtacg    1020
ccggtgggcg acaagatcga gctgacggcg ctgagcaacc tcttctccaa ggcgttttct    1080
gccaacggtg gcggcgcgga ggaagcagag caggtggcgg tgggcagcat caagtcgcag    1140
atcgggcacc tcaaggcggt ggccgggctg gccgggctgg tcaaggtggt gctggcgctc    1200
aagcacaaga cgctgccgca gacgatcaac gtcgacaagc cgccgtcgct ggtggacggg    1260
accccgatcc agcagtcgcc gctgtacgtc aacacgatga accgcccctg gttcacgccc    1320
gtaggggtgc cgcgccgcgc cggcgtgtcg tcgtttgggt ttggcggtgc caactaccac    1380
gccgtgctgg aggag                                                   1395
```

<210> SEQ ID NO 8
<211> LENGTH: 465
<212> TYPE: PRT
<213> ORGANISM: Schizochytrium sp.

<400> SEQUENCE: 8

```
Thr Arg Ile Ala Ile Val Gly Met Ser Ala Ile Leu Pro Ser Gly Glu
1               5                   10                  15

Asn Val Arg Glu Ser Trp Glu Ala Ile Arg Asp Gly Leu Asp Cys Leu
            20                  25                  30

Ser Asp Leu Pro Ala Asp Arg Val Asp Val Thr Ala Tyr Tyr Asn Pro
        35                  40                  45

Glu Lys Thr Thr Lys Asp Lys Ile Tyr Cys Lys Arg Gly Gly Phe Ile
    50                  55                  60

Pro Glu Tyr Asp Phe Asp Ala Arg Glu Phe Gly Leu Asn Met Phe Gln
65                  70                  75                  80

Met Glu Asp Ser Asp Ala Asn Gln Thr Ile Ser Leu Leu Lys Val Lys
                85                  90                  95

Glu Ala Leu Thr Asp Ala Asn Ile Pro Ala Phe Ser Ser Gly Lys Lys
            100                 105                 110
```

Asn Ile Gly Cys Val Leu Gly Ile Gly Gly Gln Lys Ala Ser His
        115                 120                 125

Glu Phe Tyr Ser Arg Leu Asn Tyr Val Val Asp Lys Val Leu Arg
130                 135                 140

Lys Met Gly Leu Pro Glu Asp Val Ala Ala Val Asp Lys Tyr
145                 150                 155                 160

Lys Ala Ser Phe Pro Glu Trp Arg Leu Asp Ser Phe Pro Gly Phe Leu
                165                 170                 175

Gly Asn Val Thr Ala Gly Arg Cys Cys Asn Thr Phe Asn Met Glu Gly
            180                 185                 190

Met Asn Cys Val Val Asp Ala Ala Cys Ala Ser Ser Leu Ile Ala Val
        195                 200                 205

Lys Val Ala Ile Glu Glu Leu Leu Tyr Gly Asp Cys Asp Ala Met Ile
210                 215                 220

Ala Gly Ala Thr Cys Thr Asp Asn Ser Ile Gly Met Tyr Met Ala Phe
225                 230                 235                 240

Ser Lys Thr Pro Val Phe Ser Thr Asp Pro Ser Val Lys Ala Tyr Asp
                245                 250                 255

Ala Ala Thr Lys Gly Met Leu Ile Gly Glu Gly Ser Ala Met Leu Val
            260                 265                 270

Leu Lys Arg Tyr Ala Asp Ala Val Arg Asp Gly Asp Thr Val His Ala
        275                 280                 285

Val Ile Lys Gly Cys Ala Ser Ser Asp Gly Lys Ala Ala Gly Ile
290                 295                 300

Tyr Thr Pro Thr Ile Ser Gly Gln Glu Ala Leu Arg Arg Ala Tyr
305                 310                 315                 320

Ala Arg Ala Asn Val Asp Pro Ala Thr Val Thr Leu Val Glu Gly His
                325                 330                 335

Gly Thr Gly Thr Pro Val Gly Asp Lys Ile Glu Leu Thr Ala Leu Ser
            340                 345                 350

Asn Leu Phe Ser Lys Ala Phe Ser Ala Asn Gly Gly Ala Glu Glu
        355                 360                 365

Ala Glu Gln Val Ala Val Gly Ser Ile Lys Ser Gln Ile Gly His Leu
370                 375                 380

Lys Ala Val Ala Gly Leu Ala Gly Leu Val Lys Val Leu Ala Leu
385                 390                 395                 400

Lys His Lys Thr Leu Pro Gln Thr Ile Asn Val Asp Lys Pro Pro Ser
                405                 410                 415

Leu Val Asp Gly Thr Pro Ile Gln Gln Ser Pro Leu Tyr Val Asn Thr
            420                 425                 430

Met Asn Arg Pro Trp Phe Thr Pro Val Gly Val Pro Arg Arg Ala Gly
        435                 440                 445

Val Ser Ser Phe Gly Phe Gly Gly Ala Asn Tyr His Ala Val Leu Glu
450                 455                 460

Glu
465

<210> SEQ ID NO 9
<211> LENGTH: 903
<212> TYPE: DNA
<213> ORGANISM: Schizochytrium sp.

<400> SEQUENCE: 9
ttctcgggcc agggcgcgca gtacacgcac atgttcagcg acgtggcgat gaactggccc      60

```
ccgttccgcg agagcgtcgc cgccatggac cgcgcccagc gcgagcgctt cgggcggcct    120
gccaagcgcg tgagcagcgt gctgtacccg cgcaagccgt acggcgacga accgcggcag    180
gaccacaagg agatctcgca aacgcgctac tcgcagcccg caacgctcgc gtgctcggtc    240
ggcgcctttg acatcttcaa agcggcggga ctggcgccga gctttgcggc gggccactcg    300
ctgggcgagt ttgcggcgct ctacgcggcc gggtcgctcg atcgcgacgc cgtcttcgac    360
ctggtctgcg cgcgcgccaa ggccatgagc gacttcacgg cccaggccag cagcagcggt    420
ggcgccatgg cggccgtgat tggcgccaag gcggaccagc tctcgctggg tggcgcgccc    480
gacgtgtggc tcgccaacag caactcgccc tcgcagaccg tgatcacggg aaccgccgaa    540
gcagtggctg cggcctctga caagttgcgc tgcagcggca acttccgcgt cgtgcctctg    600
gcctgcgagg cggccttcca ctcgccgcac atgcgcggcg cggagcagac gtttgcgtcg    660
gcgctcgcgc aggcgcccgt gtcggcaccg gcggctgctc ggttctactc taacgtgacg    720
gggggcgccg cggtaacctc gcccgcggac gtcaaaacga acctgggcaa gcacatgacg    780
agccctgtgc agttcgtgca gcaggtgcga gccatgcacg cggcgggcgc cgtgtgtttt    840
gtggagtttg ggcccaagca ggtcctgtcg cgcctcgtca aggagaccct tggcgaggcc    900
ggc                                                                   903
```

<210> SEQ ID NO 10
<211> LENGTH: 301
<212> TYPE: PRT
<213> ORGANISM: Schizochytrium sp.

<400> SEQUENCE: 10

```
Phe Ser Gly Gln Gly Ala Gln Tyr Thr His Met Phe Ser Asp Val Ala
1               5                   10                  15

Met Asn Trp Pro Pro Phe Arg Glu Ser Val Ala Ala Met Asp Arg Ala
            20                  25                  30

Gln Arg Glu Arg Phe Gly Arg Pro Ala Lys Arg Val Ser Ser Val Leu
        35                  40                  45

Tyr Pro Arg Lys Pro Tyr Gly Asp Glu Pro Arg Gln Asp His Lys Glu
    50                  55                  60

Ile Ser Gln Thr Arg Tyr Ser Gln Pro Ala Thr Leu Ala Cys Ser Val
65                  70                  75                  80

Gly Ala Phe Asp Ile Phe Lys Ala Ala Gly Leu Ala Pro Ser Phe Ala
                85                  90                  95

Ala Gly His Ser Leu Gly Glu Phe Ala Ala Leu Tyr Ala Ala Gly Ser
            100                 105                 110

Leu Asp Arg Asp Ala Val Phe Asp Leu Val Cys Ala Arg Ala Lys Ala
        115                 120                 125

Met Ser Asp Phe Thr Ala Gln Ala Ser Ser Ser Gly Gly Ala Met Ala
    130                 135                 140

Ala Val Ile Gly Ala Lys Ala Asp Gln Leu Ser Leu Gly Gly Ala Pro
145                 150                 155                 160

Asp Val Trp Leu Ala Asn Ser Asn Ser Pro Ser Gln Thr Val Ile Thr
                165                 170                 175

Gly Thr Ala Glu Ala Val Ala Ala Ser Asp Lys Leu Arg Cys Ser
            180                 185                 190

Gly Asn Phe Arg Val Val Pro Leu Ala Cys Glu Ala Ala Phe His Ser
        195                 200                 205

Pro His Met Arg Gly Ala Glu Gln Thr Phe Ala Ser Ala Leu Ala Gln
    210                 215                 220
```

| Ala | Pro | Val | Ser | Ala | Pro | Ala | Ala | Arg | Phe | Tyr | Ser | Asn | Val | Thr |
| 225 | | | | 230 | | | | | 235 | | | | | 240 |

| Gly | Gly | Ala | Ala | Val | Thr | Ser | Pro | Ala | Asp | Val | Lys | Thr | Asn | Leu | Gly |
| | | | | 245 | | | | | 250 | | | | | 255 | |

| Lys | His | Met | Thr | Ser | Pro | Val | Gln | Phe | Val | Gln | Gln | Val | Arg | Ala | Met |
| | | | 260 | | | | | 265 | | | | | 270 | | |

| His | Ala | Ala | Gly | Ala | Arg | Val | Phe | Val | Glu | Phe | Gly | Pro | Lys | Gln | Val |
| | 275 | | | | | 280 | | | | | 285 | | | | |

| Leu | Ser | Arg | Leu | Val | Lys | Glu | Thr | Leu | Gly | Glu | Ala | Gly |
| 290 | | | | | 295 | | | | | 300 | | |

<210> SEQ ID NO 11
<211> LENGTH: 2103
<212> TYPE: DNA
<213> ORGANISM: Schizochytrium sp.

<400> SEQUENCE: 11

| | | | | | |
|---|---|---|---|---|---|
| tccggcaaca | gcaagagcac | tcgtggcagt | gctgatctgc | aagcgctgct | ggccaaggcg | 60 |
| gagactgtgg | tgatggctgt | gctggctgcc | aagactggct | acgaggccga | catggttgag | 120 |
| gcggacatgg | acctggaggc | cgagctcggc | atcgactcga | tcaagcgcgt | ggagatcctt | 180 |
| tccgaggtgc | agggccagct | gggcgtcgag | gccaaggacg | tggatgcgct | gagccgcacg | 240 |
| cgcacggtcg | gtgaggttgt | ggacgccatg | aaggcggaga | tcgtggctgc | ctctggtggt | 300 |
| agtgctcctg | cggttccttc | ggcgcccgct | gcttctgcag | ctccgactcc | cgctgcttcg | 360 |
| actgcgcctt | ctgctgatct | gcaagcgctg | ctgtccaagg | cggagactgt | ggtgatggct | 420 |
| gtgctggcgg | ccaagactgg | ctacgaggcc | gacatggtcg | aggcggacat | ggacctggag | 480 |
| gccgagctcg | gcatcgactc | gatcaagcgc | gtggagatcc | tctcggaggt | gcagggccag | 540 |
| ctgggcgtcg | aggccaagga | cgtggatgcg | ctgagccgca | cgcgcacggt | cggtgaggtt | 600 |
| gtggatgcca | tgaaggcgga | aatcgtggct | gcctctgctg | gtagtgctcc | tgctcctgct | 660 |
| gttccttcgg | cgcccgctgc | ttctgcagct | ccgactcccg | ctgcttcgac | tgcgccttct | 720 |
| gctgatctgc | aagcgctgct | gtccaaggcg | gagacggtgg | tgatggctgt | gctggcggcc | 780 |
| aagactggct | acgaggccga | catggtcgag | gcggacatgg | acctggaggc | cgagctcggc | 840 |
| atcgactcga | tcaagcgcgt | ggagatcctc | tcggaggtgc | agggccagct | gggcgtcgag | 900 |
| gccaaggacg | tggatgcgct | gagccgcacg | cgcacggtcg | gtgaggttgt | ggatgccatg | 960 |
| aaggcggaaa | tcgtggctgc | ctctggtggt | agtgctcctg | ctcctgcggt | tccttcggcg | 1020 |
| cccgctgctt | ctgcagctcc | gactcccgcg | gctgcgacag | cgccttctgc | tgatctgcaa | 1080 |
| gcgctgctgg | ccaaggcgga | gactgtggtg | atggctgtgc | tggcggccaa | gactggctac | 1140 |
| gaggccgaca | tggtcgaggc | ggacatggac | ctggaggccg | agctcggcat | cgactcgatc | 1200 |
| aagcgcgtgg | agatcctttc | gaggtgcagg | gccagctggg | cgtcgaggc | caaggacgta | 1260 |
| gatgcgctga | gccgcacgcg | cacggtcggt | gaggttgtgg | atgccatgaa | ggcggagatc | 1320 |
| gtggctgcct | ctgctggtag | tgctcctgct | cctgctgttc | cttcggcgcc | cgctgcttct | 1380 |
| gcagctccga | ctcccgctgc | ttcgactgcg | ccttctgctg | atctgcaagc | gctgctgtcc | 1440 |
| aaggcggaga | ctgtggtgat | ggctgtgctg | gcggccaaga | ctggctacga | ggccgacatg | 1500 |
| gtcgaggcgg | acatggacct | ggaggccgag | ctcggcatcg | actcgatcaa | gcgcgtggag | 1560 |
| atcctctcgg | aggtgcaggg | ccagctgggc | gtcgaggcca | aggacgtgga | tgcgctgagc | 1620 |
| cgcacgcgca | cggtcggtga | ggttgtggat | gccatgaagg | cggaaatcgt | ggctgcctct | 1680 |

```
ggtggtagtg ctcctgctgc tgctgttcct tcggcgcccg ctgcttctgc agctccgact    1740
cctgcgactg cgccttctgc tgatctgcaa gcgctgctgt ccaaggcgga gactgtggtg    1800
atggctgtgc tggcggccaa gactggctac gaggccgaca tggtcgaggc ggacatggac    1860
ctggaggccg agctcggcat cgactcgatc aagcgcgtgg agatcctttc cgaggtgcag    1920
ggccagctgg gcgtcgaggc caaggacgta gatgcgctga ccgcacgcg cacggtcggt     1980 gaagtggtgg acgccatgaa ggcggagatc gtggctgcct ctggtggtag tgctcctgct    2040
gctccttcgg cgcccgcgct tcttccaacg ctgtttggtt ccgagtgcga ggacctgtct    2100
ctg                                                                  2103
```

<210> SEQ ID NO 12
<211> LENGTH: 701
<212> TYPE: PRT
<213> ORGANISM: Schizochytrium sp.

<400> SEQUENCE: 12

```
Ser Gly Asn Ser Lys Ser Thr Arg Gly Ser Ala Asp Leu Gln Ala Leu
1               5                   10                  15

Leu Ala Lys Ala Glu Thr Val Val Met Ala Val Leu Ala Ala Lys Thr
            20                  25                  30

Gly Tyr Glu Ala Asp Met Val Glu Ala Asp Met Asp Leu Glu Ala Glu
        35                  40                  45

Leu Gly Ile Asp Ser Ile Lys Arg Val Glu Ile Leu Ser Glu Val Gln
    50                  55                  60

Gly Gln Leu Gly Val Glu Ala Lys Asp Val Asp Ala Leu Ser Arg Thr
65                  70                  75                  80

Arg Thr Val Gly Glu Val Val Asp Ala Met Lys Ala Glu Ile Val Ala
                85                  90                  95

Ala Ser Gly Gly Ser Ala Pro Ala Val Pro Ser Ala Pro Ala Ala Ser
            100                 105                 110

Ala Ala Pro Thr Pro Ala Ala Ser Thr Ala Pro Ser Ala Asp Leu Gln
        115                 120                 125

Ala Leu Leu Ser Lys Ala Glu Thr Val Val Met Ala Val Leu Ala Ala
    130                 135                 140

Lys Thr Gly Tyr Glu Ala Asp Met Val Glu Ala Asp Met Asp Leu Glu
145                 150                 155                 160

Ala Glu Leu Gly Ile Asp Ser Ile Lys Arg Val Glu Ile Leu Ser Glu
                165                 170                 175

Val Gln Gly Gln Leu Gly Val Glu Ala Lys Asp Val Asp Ala Leu Ser
            180                 185                 190

Arg Thr Arg Thr Val Gly Glu Val Val Asp Ala Met Lys Ala Glu Ile
        195                 200                 205

Val Ala Ala Ser Ala Gly Ser Ala Pro Ala Pro Ala Val Pro Ser Ala
    210                 215                 220

Pro Ala Ala Ser Ala Ala Pro Thr Pro Ala Ala Ser Thr Ala Pro Ser
225                 230                 235                 240

Ala Asp Leu Gln Ala Leu Leu Ser Lys Ala Glu Thr Val Val Met Ala
                245                 250                 255

Val Leu Ala Ala Lys Thr Gly Tyr Glu Ala Asp Met Val Glu Ala Asp
            260                 265                 270

Met Asp Leu Glu Ala Glu Leu Gly Ile Asp Ser Ile Lys Arg Val Glu
        275                 280                 285
```

-continued

```
Ile Leu Ser Glu Val Gln Gly Gln Leu Gly Val Glu Ala Lys Asp Val
            290                 295                 300

Asp Ala Leu Ser Arg Thr Arg Thr Val Gly Glu Val Val Asp Ala Met
305                 310                 315                 320

Lys Ala Glu Ile Val Ala Ala Ser Gly Gly Ser Ala Pro Ala Pro Ala
                        325                 330                 335

Val Pro Ser Ala Pro Ala Ala Ser Ala Ala Pro Thr Pro Ala Ala Ala
                340                 345                 350

Thr Ala Pro Ser Ala Asp Leu Gln Ala Leu Leu Ala Lys Ala Glu Thr
            355                 360                 365

Val Val Met Ala Val Leu Ala Ala Lys Thr Gly Tyr Glu Ala Asp Met
370                 375                 380

Val Glu Ala Asp Met Asp Leu Glu Ala Glu Leu Gly Ile Asp Ser Ile
385                 390                 395                 400

Lys Arg Val Glu Ile Leu Ser Glu Val Gln Gly Gln Leu Gly Val Glu
                        405                 410                 415

Ala Lys Asp Val Asp Ala Leu Ser Arg Thr Arg Thr Val Gly Glu Val
                420                 425                 430

Val Asp Ala Met Lys Ala Glu Ile Val Ala Ala Ser Ala Gly Ser Ala
            435                 440                 445

Pro Ala Pro Ala Val Pro Ser Ala Pro Ala Ala Ser Ala Ala Pro Thr
450                 455                 460

Pro Ala Ala Ser Thr Ala Pro Ser Ala Asp Leu Gln Ala Leu Leu Ser
465                 470                 475                 480

Lys Ala Glu Thr Val Val Met Ala Val Leu Ala Ala Lys Thr Gly Tyr
                        485                 490                 495

Glu Ala Asp Met Val Glu Ala Asp Met Asp Leu Glu Ala Glu Leu Gly
                500                 505                 510

Ile Asp Ser Ile Lys Arg Val Glu Ile Leu Ser Glu Val Gln Gly Gln
            515                 520                 525

Leu Gly Val Glu Ala Lys Asp Val Asp Ala Leu Ser Arg Thr Arg Thr
530                 535                 540

Val Gly Glu Val Val Asp Ala Met Lys Ala Glu Ile Val Ala Ala Ser
545                 550                 555                 560

Gly Gly Ser Ala Pro Ala Ala Val Pro Ser Ala Pro Ala Ala Ser
                        565                 570                 575

Ala Ala Pro Thr Pro Ala Thr Ala Pro Ser Ala Asp Leu Gln Ala Leu
                580                 585                 590

Leu Ser Lys Ala Glu Thr Val Val Met Ala Val Leu Ala Ala Lys Thr
            595                 600                 605

Gly Tyr Glu Ala Asp Met Val Glu Ala Asp Met Asp Leu Glu Ala Glu
610                 615                 620

Leu Gly Ile Asp Ser Ile Lys Arg Val Glu Ile Leu Ser Glu Val Gln
625                 630                 635                 640

Gly Gln Leu Gly Val Glu Ala Lys Asp Val Asp Ala Leu Ser Arg Thr
                        645                 650                 655

Arg Thr Val Gly Glu Val Val Asp Ala Met Lys Ala Glu Ile Val Ala
                660                 665                 670

Ala Ser Gly Gly Ser Ala Pro Ala Pro Ala Pro Ser Ala Pro Ala Leu Leu
            675                 680                 685

Pro Thr Leu Phe Gly Ser Glu Cys Glu Asp Leu Ser Leu
690                 695                 700
```

<210> SEQ ID NO 13
<211> LENGTH: 276
<212> TYPE: DNA
<213> ORGANISM: Schizochytrium sp.

<400> SEQUENCE: 13

```
agtgctgatc tgcaagcgct gctggccaag gcggagactg tggtgatggc tgtgctggct    60
gccaagactg gctacgaggc cgacatggtt gaggcggaca tggacctgga ggccgagctc   120
ggcatcgact cgatcaagcg cgtggagatc ctttccgagg tgcagggcca gctgggcgtc   180
gaggccaagg acgtggatgc gctgagccgc acgcgcacgg tcggtgaggt tgtggacgcc   240
atgaaggcgg agatcgtggc tgcctctggt ggtagt                             276
```

<210> SEQ ID NO 14
<211> LENGTH: 92
<212> TYPE: PRT
<213> ORGANISM: Schizochytrium sp.

<400> SEQUENCE: 14

```
Ser Ala Asp Leu Gln Ala Leu Leu Ala Lys Ala Glu Thr Val Val Met
1               5                   10                  15
Ala Val Leu Ala Ala Lys Thr Gly Tyr Glu Ala Asp Met Val Glu Ala
            20                  25                  30
Asp Met Asp Leu Glu Ala Glu Leu Gly Ile Asp Ser Ile Lys Arg Val
        35                  40                  45
Glu Ile Leu Ser Glu Val Gln Gly Gln Leu Gly Val Glu Ala Lys Asp
    50                  55                  60
Val Asp Ala Leu Ser Arg Thr Arg Thr Val Gly Val Val Asp Ala
65                  70                  75                  80
Met Lys Ala Glu Ile Val Ala Ala Ser Gly Gly Ser
            85                  90
```

<210> SEQ ID NO 15
<211> LENGTH: 276
<212> TYPE: DNA
<213> ORGANISM: Schizochytrium sp.

<400> SEQUENCE: 15

```
tctgctgatc tgcaagcgct gctgtccaag gcggagactg tggtgatggc tgtgctggcg    60
gccaagactg gctacgaggc cgacatggtc gaggcggaca tggacctgga ggccgagctc   120
ggcatcgact cgatcaagcg cgtggagatc ctctcggagg tgcagggcca gctgggcgtc   180
gaggccaagg acgtggatgc gctgagccgc acgcgcacgg tcggtgaggt tgtggatgcc   240
atgaaggcgg aaatcgtggc tgcctctgct ggtagt                             276
```

<210> SEQ ID NO 16
<211> LENGTH: 92
<212> TYPE: PRT
<213> ORGANISM: Schizochytrium sp.

<400> SEQUENCE: 16

```
Ser Ala Asp Leu Gln Ala Leu Leu Ser Lys Ala Glu Thr Val Val Met
1               5                   10                  15
Ala Val Leu Ala Ala Lys Thr Gly Tyr Glu Ala Asp Met Val Glu Ala
            20                  25                  30
Asp Met Asp Leu Glu Ala Glu Leu Gly Ile Asp Ser Ile Lys Arg Val
        35                  40                  45
Glu Ile Leu Ser Glu Val Gln Gly Gln Leu Gly Val Glu Ala Lys Asp
```

```
                        50                  55                  60

Val Asp Ala Leu Ser Arg Thr Arg Thr Val Gly Glu Val Val Asp Ala
 65                  70                  75                  80

Met Lys Ala Glu Ile Val Ala Ala Ser Ala Gly Ser
                 85                  90

<210> SEQ ID NO 17
<211> LENGTH: 276
<212> TYPE: DNA
<213> ORGANISM: Schizochytrium sp.

<400> SEQUENCE: 17
tctgctgatc tgcaagcgct gctgtccaag gcggagacgg tggtgatggc tgtgctggcg      60
gccaagactg gctacgaggc cgacatggtc gaggcggaca tggacctgga ggccgagctc     120
ggcatcgact cgatcaagcg cgtggagatc ctctcggagg tgcagggcca gctgggcgtc     180
gaggccaagg acgtggatgc gctgagccgc acgcgcacgg tcggtgaggt tgtggatgcc     240
atgaaggcgg aaatcgtggc tgcctctggt ggtagt                              276

<210> SEQ ID NO 18
<211> LENGTH: 92
<212> TYPE: PRT
<213> ORGANISM: Schizochytrium sp.

<400> SEQUENCE: 18

Ser Ala Asp Leu Gln Ala Leu Leu Ser Lys Ala Glu Thr Val Val Met
 1               5                  10                  15

Ala Val Leu Ala Ala Lys Thr Gly Tyr Glu Ala Asp Met Val Glu Ala
                 20                  25                  30

Asp Met Asp Leu Glu Ala Glu Leu Gly Ile Asp Ser Ile Lys Arg Val
             35                  40                  45

Glu Ile Leu Ser Glu Val Gln Gly Gln Leu Gly Val Glu Ala Lys Asp
         50                  55                  60

Val Asp Ala Leu Ser Arg Thr Arg Thr Val Gly Glu Val Val Asp Ala
 65                  70                  75                  80

Met Lys Ala Glu Ile Val Ala Ala Ser Gly Gly Ser
                 85                  90

<210> SEQ ID NO 19
<211> LENGTH: 276
<212> TYPE: DNA
<213> ORGANISM: Schizochytrium sp.

<400> SEQUENCE: 19
tctgctgatc tgcaagcgct gctggccaag gcggagactg tggtgatggc tgtgctggcg      60
gccaagactg gctacgaggc cgacatggtc gaggcggaca tggacctgga ggccgagctc     120
ggcatcgact cgatcaagcg cgtggagatc ctttccgagg tgcagggcca gctgggcgtc     180
gaggccaagg acgtagatgc gctgagccgc acgcgcacgg tcggtgaggt tgtggatgcc     240
atgaaggcgg agatcgtggc tgcctctgct ggtagt                              276

<210> SEQ ID NO 20
<211> LENGTH: 92
<212> TYPE: PRT
<213> ORGANISM: Schizochytrium sp.

<400> SEQUENCE: 20

Ser Ala Asp Leu Gln Ala Leu Leu Ala Lys Ala Glu Thr Val Val Met
```

```
                 1               5                   10                  15
Ala Val Leu Ala Ala Lys Thr Gly Tyr Glu Ala Asp Met Val Glu Ala
                20                  25                  30

Asp Met Asp Leu Glu Ala Glu Leu Gly Ile Asp Ser Ile Lys Arg Val
            35                  40                  45

Glu Ile Leu Ser Glu Val Gln Gly Gln Leu Gly Val Glu Ala Lys Asp
        50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Ala Gly Ser
                85                  90

<210> SEQ ID NO 21
<211> LENGTH: 276
<212> TYPE: DNA
<213> ORGANISM: Schizochytrium sp.

<400> SEQUENCE: 21
tctgctgatc tgcaagcgct gctgtccaag gcggagactg tggtgatggc tgtgctggcg    60
gccaagactg gctacgaggc cgacatggtc gaggcggaca tggacctgga ggccgagctc   120
ggcatcgact cgatcaagcg cgtggagatc ctctcggagg tgcagggcca gctgggcgtc   180
gaggccaagg acgtggatgc gctgagccgc acgcgcacgg tcggtgaggt tgtggatgcc   240
atgaaggcgg aaatcgtggc tgcctctggt ggtagt                             276

<210> SEQ ID NO 22
<211> LENGTH: 92
<212> TYPE: PRT
<213> ORGANISM: Schizochytrium sp.

<400> SEQUENCE: 22

Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
                20                  25                  30

Asp Met Asp Leu Glu Ala Glu Leu Gly Ile Asp Ser Ile Lys Arg Val
            35                  40                  45

Glu Ile Leu Ser Glu Val Gln Gly Gln Leu Gly Val Glu Ala Lys Asp
        50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Gly Gly Ser
                85                  90

<210> SEQ ID NO 23
<211> LENGTH: 276
<212> TYPE: DNA
<213> ORGANISM: Schizochytrium sp.

<400> SEQUENCE: 23
tctgctgatc tgcaagcgct gctgtccaag gcggagactg tggtgatggc tgtgctggcg    60
gccaagactg gctacgaggc cgacatggtc gaggcggaca tggacctgga ggccgagctc   120
ggcatcgact cgatcaagcg cgtggagatc ctttccgagg tgcagggcca gctgggcgtc   180
gaggccaagg acgtagatgc gctgagccgc acgcgcacgg tcggtgaagt ggtggacgcc   240
atgaaggcgg agatcgtggc tgcctctggt ggtagt                             276
```

<210> SEQ ID NO 24
<211> LENGTH: 92
<212> TYPE: PRT
<213> ORGANISM: Schizochytrium sp.

<400> SEQUENCE: 24

```
Ser Ala Asp Leu Gln Ala Leu Leu Ser Lys Ala Glu Thr Val Val Met
1               5                   10                  15

Ala Val Leu Ala Ala Lys Thr Gly Tyr Glu Ala Asp Met Val Glu Ala
            20                  25                  30

Asp Met Asp Leu Glu Ala Glu Leu Gly Ile Asp Ser Ile Lys Arg Val
        35                  40                  45

Glu Ile Leu Ser Glu Val Gln Gly Gln Leu Gly Val Glu Ala Lys Asp
    50                  55                  60

Val Asp Ala Leu Ser Arg Thr Arg Thr Val Gly Glu Val Val Asp Ala
65                  70                  75                  80

Met Lys Ala Glu Ile Val Ala Ala Ser Gly Gly Ser
                85                  90
```

<210> SEQ ID NO 25
<211> LENGTH: 2178
<212> TYPE: DNA
<213> ORGANISM: Schizochytrium sp.

<400> SEQUENCE: 25

```
gcgctacagg cggcgctcac gtccgtcgag gcgcagttcg gcaaggtggg tggctttgtg      60
ttccagttcg cgacgacga cgtgcaagcg cagctcggct gggcgctgct cgcggccaag     120
cacctcaaaa cttcgctgtc agaacagatc gagggcggtc gcacctttttt cgtggccgtc    180
gcgcggctcg acgccagct ggggctctcc ggcaagtcga cgaccgctac cgttgatctc      240
tcccgcgcgc agcagggcag cgtgttcggc ctgtgcaaga cactcgacct ggagtggccc     300
gctgtcttct gccgcggaat cgacctggcc gccgacctcg acgccgcaca ggccgcgcgg    360
tgcctgctgg gcgagctgtc agaccccgac gtggccgtgc gcgagtctgg ttactccgcc    420
tcgggccagc gctgcacgac aactacgaag tcgctgacta cgggcaagcc gcaccagccg    480
atctcctcgt cggacctctt tctggtgtcg ggcggcgcgc gcggcatcac ccgctgtgc     540
gtgcgcgagc tggcgcagcg cgtgggcggc ggcacgtacg tgctcatcgg ccgctcggag     600
ctgcccacga cggagcctgc ctgggcggtc ggcgtggagt ctggcaagcc gctggagaag    660
gccgcgctgg cgttcctgaa ggcggagttt gcagcgggcc gcggggccaa gccgacgccg    720
atgctgcaca agaagctcgt gggcgccgtg gtcggagcgc gcgaggtgcg agcctcgctc    780
gccgagatca ctgcacaggg cgccacggct gtgtacgagt cgtgcgacgt gagctctgcc    840
gccaaggtgc gtgagatggt agagcgcgtg cagcagcagg gcgggcggcg cgtgtcgggc    900
gtgttccacg cgtcgggcgt gctgcgcgac aagctcgtgg agaacaagtc gctggcggac    960
ttcagcgccg tgtacgacac caaggtgggc ggcctcatca acctgctggc ctgcgtggac   1020
ctggcgcagc tgcgtcacct cgtgctcttc agctcgctcg cgggcttcca cggcaacgtc   1080
gggcagtcgg actacgcaat ggccaacgag gcgctcaaca agctggcggc cacctgtcg    1140
gcggtgcacc cgcagctgtg cgcgcgctcg atctgcttcg gaccgtggga cggcggcatg   1200
gtgacccccg cgctcaaggc caacttcatc gcatgggca tccagatcat cccgcgccaa    1260
ggcggcgcgc agaccgtcgc caacatgctc gtcagtagct ccccccggtca gctgctcgtg   1320
ggcaactggg gcgtgccacc cgtcgtgccg agtgccaccg agcacaccgt gctgcagacg   1380
```

```
ctccgccaga gcgacaaccc cttcctcgac tcgcacgtga tccagggccg ccgcgtgctg    1440
cccatgaccc tggccgtggg ctacatggcg caccaggcgc agagcatcta cgcgggccac    1500
cagctgtggg ccgtcgagga cgcccagctc ttcaagggca tcgccatcga caatggcgcc    1560
gacgtgcccg tgcgcgtgga gctgtcgcgc gcaaggagg agcaggagga cgccggcaag    1620
gtcaaggtca aggtgcaggt gctgctcaaa tcgcaggtca acggcaagtc ggtgcccgcg    1680
tacaaggcga ccgtcgtgct gtcccctgcg ccgcgcccca gcgtcatcac gcgtgacttc    1740
gacctcaccc cggacccggc ctgcacggag cacgacctct acgacggcaa gacgctcttc    1800
cacggcaagg ccttccaggg catcgagcag gtgctctcgg cgacgcccaa gcagctcacc    1860
gccaagtgcc gcaatttgcc cctcacgccc gagcagcgcg ccagttcgt cgttaacctc    1920 agccagcagg acccgttcca ggcggacatt gcgttccagg cgatgctcgt ctgggcgcgc    1980
atgctgcgcc aatcggcggc cctgcccaac aactgcgagc gcttcgactt ttacaagccg    2040
atggccccgg cgccaccta ctacacgtcg gtcaagctgg cctcggcctc acccttggtg    2100
gactctgtgt gcaagtgcac cgtggcgatg cacgatgagc aaggtgaggt gtacttttct    2160
gctcgtgcca gcgtcgtc                                                   2178
```

<210> SEQ ID NO 26
<211> LENGTH: 726
<212> TYPE: PRT
<213> ORGANISM: Schizochytrium sp.

<400> SEQUENCE: 26

```
Ala Leu Gln Ala Ala Leu Thr Ser Val Glu Ala Gln Phe Gly Lys Val
1               5                   10                  15

Gly Gly Phe Val Phe Gln Phe Gly Asp Asp Val Gln Ala Gln Leu
            20                  25                  30

Gly Trp Ala Leu Leu Ala Ala Lys His Leu Lys Thr Ser Leu Ser Glu
        35                  40                  45

Gln Ile Glu Gly Gly Arg Thr Phe Phe Val Ala Val Ala Arg Leu Asp
    50                  55                  60

Gly Gln Leu Gly Leu Ser Gly Lys Ser Thr Thr Ala Thr Val Asp Leu
65                  70                  75                  80

Ser Arg Ala Gln Gln Gly Ser Val Phe Gly Leu Cys Lys Thr Leu Asp
                85                  90                  95

Leu Glu Trp Pro Ala Val Phe Cys Arg Gly Ile Asp Leu Ala Ala Asp
            100                 105                 110

Leu Asp Ala Ala Gln Ala Ala Arg Cys Leu Leu Gly Glu Leu Ser Asp
        115                 120                 125

Pro Asp Val Ala Val Arg Glu Ser Gly Tyr Ser Ala Ser Gly Gln Arg
    130                 135                 140

Cys Thr Thr Thr Thr Lys Ser Leu Thr Gly Lys Pro His Gln Pro
145                 150                 155                 160

Ile Ser Ser Ser Asp Leu Phe Leu Val Ser Gly Gly Ala Arg Gly Ile
                165                 170                 175

Thr Pro Leu Cys Val Arg Glu Leu Ala Gln Arg Val Gly Gly Gly Thr
            180                 185                 190

Tyr Val Leu Ile Gly Arg Ser Glu Leu Pro Thr Thr Glu Pro Ala Trp
        195                 200                 205

Ala Val Gly Val Glu Ser Gly Lys Pro Leu Glu Lys Ala Ala Leu Ala
    210                 215                 220
```

```
Phe Leu Lys Ala Glu Phe Ala Ala Gly Arg Gly Ala Lys Pro Thr Pro
225                 230                 235                 240

Met Leu His Lys Lys Leu Val Gly Ala Val Gly Ala Arg Glu Val
                245                 250                 255

Arg Ala Ser Leu Ala Glu Ile Thr Ala Gln Gly Ala Thr Ala Val Tyr
            260                 265                 270

Glu Ser Cys Asp Val Ser Ala Ala Lys Val Arg Glu Met Val Glu
        275                 280                 285

Arg Val Gln Gln Gln Gly Arg Arg Val Ser Gly Val Phe His Ala
290                 295                 300

Ser Gly Val Leu Arg Asp Lys Leu Val Glu Asn Lys Ser Leu Ala Asp
305                 310                 315                 320

Phe Ser Ala Val Tyr Asp Thr Lys Val Gly Gly Leu Ile Asn Leu Leu
                325                 330                 335

Ala Cys Val Asp Leu Ala Gln Leu Arg His Leu Val Leu Phe Ser Ser
            340                 345                 350

Leu Ala Gly Phe His Gly Asn Val Gly Gln Ser Asp Tyr Ala Met Ala
        355                 360                 365

Asn Glu Ala Leu Asn Lys Leu Ala Ala His Leu Ser Ala Val His Pro
370                 375                 380

Gln Leu Cys Ala Arg Ser Ile Cys Phe Gly Pro Trp Asp Gly Gly Met
385                 390                 395                 400

Val Thr Pro Ala Leu Lys Ala Asn Phe Ile Arg Met Gly Ile Gln Ile
                405                 410                 415

Ile Pro Arg Gln Gly Gly Ala Gln Thr Val Ala Asn Met Leu Val Ser
            420                 425                 430

Ser Ser Pro Gly Gln Leu Leu Val Gly Asn Trp Gly Val Pro Pro Val
        435                 440                 445

Val Pro Ser Ala Thr Glu His Thr Val Leu Gln Thr Leu Arg Gln Ser
450                 455                 460

Asp Asn Pro Phe Leu Asp Ser His Val Ile Gln Gly Arg Arg Val Leu
465                 470                 475                 480

Pro Met Thr Leu Ala Val Gly Tyr Met Ala His Gln Ala Gln Ser Ile
                485                 490                 495

Tyr Ala Gly His Gln Leu Trp Ala Val Glu Asp Ala Gln Leu Phe Lys
            500                 505                 510

Gly Ile Ala Ile Asp Asn Gly Ala Asp Val Pro Val Arg Val Glu Leu
        515                 520                 525

Ser Arg Arg Lys Glu Gln Glu Asp Ala Gly Lys Val Lys Val Lys
530                 535                 540

Val Gln Val Leu Leu Lys Ser Gln Val Asn Gly Lys Ser Val Pro Ala
545                 550                 555                 560

Tyr Lys Ala Thr Val Val Leu Ser Pro Ala Arg Pro Ser Val Ile
                565                 570                 575

Thr Arg Asp Phe Asp Leu Thr Pro Asp Pro Ala Cys Thr Glu His Asp
            580                 585                 590

Leu Tyr Asp Gly Lys Thr Leu Phe His Gly Lys Ala Phe Gln Gly Ile
        595                 600                 605

Glu Gln Val Leu Ser Ala Thr Pro Lys Gln Leu Thr Ala Lys Cys Arg
610                 615                 620

Asn Leu Pro Leu Thr Pro Glu Gln Arg Gly Gln Phe Val Val Asn Leu
625                 630                 635                 640

Ser Gln Gln Asp Pro Phe Gln Ala Asp Ile Ala Phe Gln Ala Met Leu
```

```
                    645                 650                 655
Val Trp Ala Arg Met Leu Arg Gln Ser Ala Ala Leu Pro Asn Asn Cys
                660                 665                 670

Glu Arg Phe Asp Phe Tyr Lys Pro Met Ala Pro Gly Ala Thr Tyr Tyr
            675                 680                 685

Thr Ser Val Lys Leu Ala Ser Ala Ser Pro Leu Val Asp Ser Val Cys
        690                 695                 700

Lys Cys Thr Val Ala Met His Asp Glu Gln Gly Glu Val Tyr Phe Ser
705                 710                 715                 720

Ala Arg Ala Ser Val Val
                725

<210> SEQ ID NO 27
<211> LENGTH: 39
<212> TYPE: DNA
<213> ORGANISM: Schizochytrium sp.

<400> SEQUENCE: 27
ctcgactcgc acgtgatcca gggccgccgc gtgctgccc                              39

<210> SEQ ID NO 28
<211> LENGTH: 13
<212> TYPE: PRT
<213> ORGANISM: Schizochytrium sp.

<400> SEQUENCE: 28

Leu Asp Ser His Val Ile Gln Gly Arg Arg Val Leu Pro
1               5                   10

<210> SEQ ID NO 29
<211> LENGTH: 1341
<212> TYPE: DNA
<213> ORGANISM: Schizochytrium sp.

<400> SEQUENCE: 29
gataacattg cggtcgtggg catggcggtg cagtatgccg atgcaagaa ccaggacgag       60 ttctgggata cgctgatgcg taaggagatc aactcgagcc cgatctcggc ggagcgcctc     120
ggtacgcgct accgcgacct ccacttccac ccgcagcgca gcaagtacgc cgacaccttc     180
tgcaacgatc gctacggctg cgtcgatgcc agcgtcgaca acgagcacga cctcctcgcc     240
gacctggccc ggcgcgccct gctcgacgcc ggaattaacc tcgacgacgc cagcaccacc     300
gccaacctac gcgacttcgg catcgtgagc ggctgcctgt cgttccccat ggacaatctg     360
cagggcgagc tgctcaatct gtaccaagtg catgtggaga accgcgtggg cgcccagcgc     420
ttccgcgact cgcgccccctg gtcggagcgc ccgcgcgctg tctcgcccga ggccagcgac     480
ccgcgcgtgt actccgaccc ggcgtccttc gtggccaacc agctcggcct ggggcccgtg     540
cgctacagcc tcgatgcagc ctgcgcgtcg gcgctgtact gcctcaagct ggcgtccgac     600
cacttgctct cgcgcagcgc ggacgtgatg ctgtgcggcg ccacatgctt ccggacccg      660 ttcttcattc tctcgggggtt ctccaccttc caggcgatgc cgctgggcgg accggacgat    720
aacccactgt ccgtgccgct gcggcagggc agccagggcc tgacgcccgg agagggcggc    780
gccatcatgg tgctgaagcg cctcgaggac gccgtgcgcg acggcgaccg catctacggc    840
accttgctcg gcacgagtct gagcaacgcc gggtgcggcc tgccgctgag cccgcacctg    900
ccgagcgaga agtcgtgcat ggaggacctg tacacgagcg tcggcatcga cccaagcgag    960
gtgcagtacg tggagtgcca cgccacgggc actccgcagg gcgacgtcgt ggaggtagag   1020
```

```
gcgctgcgcc actgctttcg aggtaacacg gaccacccgc cgcgcatggg ctccaccaag      1080
ggcaactttg ccacactct  cgtggcggcc gggttcgcag gcatggccaa ggtgctgctg      1140
tcgatgcagc acggcacgat cccgcccacg cccggtgtcg accgctccaa ctgcatcgac      1200
ccgctcgtcg tggacgaggc catcccttgg ccgtactcgt cggcgcaggc gcgggcaggc      1260
aaaccaggcg atgagctcaa gtgcgcctcg ctctccgcct ttggctttgg tggaaccaac      1320
gcgcactgtg tcttccgtga g                                                1341
```

<210> SEQ ID NO 30
<211> LENGTH: 447
<212> TYPE: PRT
<213> ORGANISM: Schizochytrium sp.

<400> SEQUENCE: 30

```
Asp Asn Ile Ala Val Gly Met Ala Val Gln Tyr Ala Gly Cys Lys
1               5                  10                  15

Asn Gln Asp Glu Phe Trp Asp Thr Leu Met Arg Lys Glu Ile Asn Ser
            20                  25                  30

Ser Pro Ile Ser Ala Glu Arg Leu Gly Thr Arg Tyr Arg Asp Leu His
        35                  40                  45

Phe His Pro Gln Arg Ser Lys Tyr Ala Asp Thr Phe Cys Asn Asp Arg
    50                  55                  60

Tyr Gly Cys Val Asp Ala Ser Val Asp Asn Glu His Asp Leu Leu Ala
65                  70                  75                  80

Asp Leu Ala Arg Arg Ala Leu Leu Asp Ala Gly Ile Asn Leu Asp Asp
                85                  90                  95

Ala Ser Thr Thr Ala Asn Leu Arg Asp Phe Gly Ile Val Ser Gly Cys
            100                 105                 110

Leu Ser Phe Pro Met Asp Asn Leu Gln Gly Glu Leu Leu Asn Leu Tyr
        115                 120                 125

Gln Val His Val Glu Asn Arg Val Gly Ala Gln Arg Phe Arg Asp Ser
    130                 135                 140

Arg Pro Trp Ser Glu Arg Pro Arg Ala Val Ser Pro Glu Ala Ser Asp
145                 150                 155                 160

Pro Arg Val Tyr Ser Asp Pro Ala Ser Phe Val Ala Asn Gln Leu Gly
                165                 170                 175

Leu Gly Pro Val Arg Tyr Ser Leu Asp Ala Ala Cys Ala Ser Ala Leu
            180                 185                 190

Tyr Cys Leu Lys Leu Ala Ser Asp His Leu Leu Ser Arg Ser Ala Asp
        195                 200                 205

Val Met Leu Cys Gly Ala Thr Cys Phe Pro Asp Pro Phe Phe Ile Leu
    210                 215                 220

Ser Gly Phe Ser Thr Phe Gln Ala Met Pro Leu Gly Gly Pro Asp Asp
225                 230                 235                 240

Asn Pro Leu Ser Val Pro Leu Arg Gln Gly Ser Gln Gly Leu Thr Pro
                245                 250                 255

Gly Glu Gly Gly Ala Ile Met Val Leu Lys Arg Leu Glu Asp Ala Val
            260                 265                 270

Arg Asp Gly Asp Arg Ile Tyr Gly Thr Leu Leu Gly Thr Ser Leu Ser
        275                 280                 285

Asn Ala Gly Cys Gly Leu Pro Leu Ser Pro His Leu Pro Ser Glu Lys
    290                 295                 300

Ser Cys Met Glu Asp Leu Tyr Thr Ser Val Gly Ile Asp Pro Ser Glu
```

| | | | | | | 305 | | | 310 | | | | | 315 | | | | | 320 |
|---|---|---|---|---|---|---|---|---|---|---|---|---|---|---|---|---|---|---|---|
| Val | Gln | Tyr | Val | Glu | Cys | His | Ala | Thr | Gly | Thr | Pro | Gln | Gly | Asp | Val |
| | | | | 325 | | | | | 330 | | | | | 335 | |

Val Glu Val Glu Ala Leu Arg His Cys Phe Arg Gly Asn Thr Asp His
 340 345 350

Pro Pro Arg Met Gly Ser Thr Lys Gly Asn Phe Gly His Thr Leu Val
 355 360 365

Ala Ala Gly Phe Ala Gly Met Ala Lys Val Leu Leu Ser Met Gln His
 370 375 380

Gly Thr Ile Pro Pro Thr Pro Gly Val Asp Arg Ser Asn Cys Ile Asp
385 390 395 400

Pro Leu Val Val Asp Glu Ala Ile Pro Trp Pro Tyr Ser Ser Ala Gln
 405 410 415

Ala Arg Ala Gly Lys Pro Gly Asp Glu Leu Lys Cys Ala Ser Leu Ser
 420 425 430

Ala Phe Gly Phe Gly Gly Thr Asn Ala His Cys Val Phe Arg Glu
 435 440 445

<210> SEQ ID NO 31
<211> LENGTH: 1293
<212> TYPE: DNA
<213> ORGANISM: Schizochytrium sp.

<400> SEQUENCE: 31

| ggaccgattg ccatcatcgg gatggacgcg acgtttggta ccctcaaggg cctggacgcg | 60 |
|---|---|
| tttgagcagg ccatctacaa gggcacggac ggcgccagcg acctgccgag caagcgctgg | 120 |
| cggttcctgg gcgccgacac ggacttcttg accgccatgg gcctcgacgc cgtgccgcgc | 180 |
| gggtgctacg tgcgcgacgt ggacgtggac tacaagcggc tgcggtcgcc gatgatccct | 240 |
| gaggacgtcc tgcgcccgca cagctgctg gcggtggcta cgatggaccg cgcgctgcag | 300 |
| gacgctggaa tggcgacggg aggcaaggtg gcggtgctgg tggggctcgg cacggacacc | 360 |
| gagctgtacc ggcaccgcgc gcgcgtgaca ctcaaggagc ggctcgaccc ggccgcgttc | 420 |
| tcgcccgagc aggtgcagga gatgatggac tacatcaacg actgcggcac ctcgacgtcg | 480 |
| tacacgtcgt acatcggcaa cctcgtggcc acgcgcgtgt cctcgcagtg gggctttacg | 540 |
| ggcccgtcct tcaccgtcac cgaaggcgca aactcggtct accgctgcct cgagctgggc | 600 |
| aagttcctgc tcgacacgca ccaggtggac gccgtcgtgg tggccggcgt cgacctctgt | 660 |
| gccaccgccg agaacccttta cctcaaggcg cgccgctccg ccatcagccg acaggaccac | 720 |
| cctcgcgcca actttgaggc cagcgccgac gggtactttg ccggcgaggg cagcggcgcc | 780 |
| ctggtcctca gcgccaggc cgacgttggc tcagacgaca aggtctacgc cagtgtcgcg | 840 |
| ggcctcacgt gcgccgcgca gcccgctgaa gccgtgtcgc cgctactact ccaagtccac | 900 |
| aacgacgaca cgagaagag ggtggtggag atggtggagc tcgccgccga ctcgggtcgc | 960 |
| catgcgccgc acttggccaa ctcgccgctg agcgccgagt cgcagctgga gcaagtgtcc | 1020 |
| aagttgctcg cgcaccaggt gccgggctcg gtggccatcg gcagcgtgcg cgccaacgtg | 1080 |
| ggagacgtcg ggtacgcctc gggcgccgcg agcctcatca agacggcgct gtgcctccac | 1140 |
| aaccgctacc tcccggccaa cccgcagtgg gagcggccgg tggcgccggt ctccgaggcg | 1200 |
| ctgtttactt gcccgcgctc gcgtgcctgg ctgaagaacc cgggcgagtc gcgactggcg | 1260 |
| gctgtcgcca gtgcctccga gagcgggtcc tgc | 1293 |

-continued

```
<210> SEQ ID NO 32
<211> LENGTH: 431
<212> TYPE: PRT
<213> ORGANISM: Schizochytrium sp.

<400> SEQUENCE: 32
```

| | | | | | | | | | | | | | | | |
|---|---|---|---|---|---|---|---|---|---|---|---|---|---|---|---|
| Gly | Pro | Ile | Ala | Ile | Gly | Met | Asp | Ala | Thr | Phe | Gly | Thr | Leu | Lys | |
| 1 | | | | 5 | | | | | 10 | | | | | 15 | |
| Gly | Leu | Asp | Ala | Phe | Glu | Gln | Ala | Ile | Tyr | Lys | Gly | Thr | Asp | Gly | Ala |
| | | | 20 | | | | | 25 | | | | | 30 | | |
| Ser | Asp | Leu | Pro | Ser | Lys | Arg | Trp | Arg | Phe | Leu | Gly | Ala | Asp | Thr | Asp |
| | | 35 | | | | | 40 | | | | | 45 | | | |
| Phe | Leu | Thr | Ala | Met | Gly | Leu | Asp | Ala | Val | Pro | Arg | Gly | Cys | Tyr | Val |
| | 50 | | | | | 55 | | | | | 60 | | | | |
| Arg | Asp | Val | Asp | Val | Asp | Tyr | Lys | Arg | Leu | Arg | Ser | Pro | Met | Ile | Pro |
| 65 | | | | | 70 | | | | | 75 | | | | | 80 |
| Glu | Asp | Val | Leu | Arg | Pro | Gln | Gln | Leu | Leu | Ala | Val | Ala | Thr | Met | Asp |
| | | | | 85 | | | | | 90 | | | | | 95 | |
| Arg | Ala | Leu | Gln | Asp | Ala | Gly | Met | Ala | Thr | Gly | Gly | Lys | Val | Ala | Val |
| | | | 100 | | | | | 105 | | | | | 110 | | |
| Leu | Val | Gly | Leu | Gly | Thr | Asp | Thr | Glu | Leu | Tyr | Arg | His | Arg | Ala | Arg |
| | | 115 | | | | | 120 | | | | | 125 | | | |
| Val | Thr | Leu | Lys | Glu | Arg | Leu | Asp | Pro | Ala | Ala | Phe | Ser | Pro | Glu | Gln |
| | 130 | | | | | 135 | | | | | 140 | | | | |
| Val | Gln | Glu | Met | Met | Asp | Tyr | Ile | Asn | Asp | Cys | Gly | Thr | Ser | Thr | Ser |
| 145 | | | | | 150 | | | | | 155 | | | | | 160 |
| Tyr | Thr | Ser | Tyr | Ile | Gly | Asn | Leu | Val | Ala | Thr | Arg | Val | Ser | Ser | Gln |
| | | | | 165 | | | | | 170 | | | | | 175 | |
| Trp | Gly | Phe | Thr | Gly | Pro | Ser | Phe | Thr | Val | Thr | Glu | Gly | Ala | Asn | Ser |
| | | | 180 | | | | | 185 | | | | | 190 | | |
| Val | Tyr | Arg | Cys | Leu | Glu | Leu | Gly | Lys | Phe | Leu | Leu | Asp | Thr | His | Gln |
| | | 195 | | | | | 200 | | | | | 205 | | | |
| Val | Asp | Ala | Val | Val | Val | Ala | Gly | Val | Asp | Leu | Cys | Ala | Thr | Ala | Glu |
| | 210 | | | | | 215 | | | | | 220 | | | | |
| Asn | Leu | Tyr | Leu | Lys | Ala | Arg | Arg | Ser | Ala | Ile | Ser | Arg | Gln | Asp | His |
| 225 | | | | | 230 | | | | | 235 | | | | | 240 |
| Pro | Arg | Ala | Asn | Phe | Glu | Ala | Ser | Ala | Asp | Gly | Tyr | Phe | Ala | Gly | Glu |
| | | | | 245 | | | | | 250 | | | | | 255 | |
| Gly | Ser | Gly | Ala | Leu | Val | Leu | Lys | Arg | Gln | Ala | Asp | Val | Gly | Ser | Asp |
| | | | 260 | | | | | 265 | | | | | 270 | | |
| Asp | Lys | Val | Tyr | Ala | Ser | Val | Ala | Gly | Leu | Thr | Cys | Ala | Ala | Gln | Pro |
| | | 275 | | | | | 280 | | | | | 285 | | | |
| Ala | Glu | Ala | Val | Ser | Pro | Leu | Leu | Gln | Val | His | Asn | Asp | Asp | Asn | |
| | 290 | | | | | 295 | | | | | 300 | | | | |
| Glu | Lys | Arg | Val | Val | Glu | Met | Val | Glu | Leu | Ala | Ala | Asp | Ser | Gly | Arg |
| 305 | | | | | 310 | | | | | 315 | | | | | 320 |
| His | Ala | Pro | His | Leu | Ala | Asn | Ser | Pro | Leu | Ser | Ala | Glu | Ser | Gln | Leu |
| | | | | 325 | | | | | 330 | | | | | 335 | |
| Glu | Gln | Val | Ser | Lys | Leu | Leu | Ala | His | Gln | Val | Pro | Gly | Ser | Val | Ala |
| | | | 340 | | | | | 345 | | | | | 350 | | |
| Ile | Gly | Ser | Val | Arg | Ala | Asn | Val | Gly | Asp | Val | Gly | Tyr | Ala | Ser | Gly |
| | | 355 | | | | | 360 | | | | | 365 | | | |
| Ala | Ala | Ser | Leu | Ile | Lys | Thr | Ala | Leu | Cys | Leu | His | Asn | Arg | Tyr | Leu |
| | 370 | | | | | 375 | | | | | 380 | | | | |

Pro Ala Asn Pro Gln Trp Glu Arg Pro Val Ala Val Ser Glu Ala
385                 390                 395                 400

Leu Phe Thr Cys Pro Arg Ser Arg Ala Trp Leu Lys Asn Pro Gly Glu
            405                 410                 415

Ser Arg Leu Ala Ala Val Ala Ser Ala Ser Glu Ser Gly Ser Cys
            420                 425                 430

<210> SEQ ID NO 33
<211> LENGTH: 1203
<212> TYPE: DNA
<213> ORGANISM: Schizochytrium sp.

<400> SEQUENCE: 33
acgccggaga agctggagaa ggagttggag ctggcagcca agggtgtacc gcgaagcgcc      60
aaggccgggc gcaactggat gtcgccatcg ggcagcgcct ttgcgccgac acctgtgacc     120
agcgaccgcg tcgcgttcat gtacggcgag ggccgcagcc cctactacgg cgtcgggctc     180
gacctgcacc gcctgtggcc ggctttgcac gagcgcatca cgacaagac cgcggcgctg     240 tgggagaacg gcgactcgtg gctcatgccg cgcgcggtgg atgccgactc gcagcgcgcc     300
gtgcagacgg cctttgacgc ggaccagatc gagatgttcc gcacgggcat cttcgtgtcc     360
atctgcctca ccgactacgc gcgcgacgtg ctcggggtgc agcccaaggc gtgcttcggc     420
ctcagcctcg gcgagatctc catgctcttt gcgctgtcgc gacgcaactg cggcctgtcg     480
gaccagctca cgcagcgcct acgcacctcg ccggtgtggt cgacacagct ggcggtggag     540
ttccaggcct tgcgcaagct atggaacgtg ccggcggacg ccccgtgga gtccttctgg     600 cagggctact tggttcgcgc cagccgcgcc gaaatcgaga aggcgatcgg gcccgacaac     660
cgcttcgtgc gcctgctgat cgtcaacgac tcgagcagcg cgctgatcgc cggcaaacct     720
gccgagtgtc tgcgcgtgct ggagcgcctg ggcgggcggt tgccgccgat gcccgtcaag     780
caaggcatga ttgggcactg ccccgaagtg gcgccctaca cgcccgggcat cgcgcacatc     840 cacgagattt tggagattcc ggacagcccc gtcaagatgt acacctcggt caccaacgcc     900
gagctgcgcg ggggcagcaa cagcagcatc accgagttcg tgcagaagtt gtacacgcgc     960
atcgccgact ttccgggcat cgtcgacaag gtcagccgtg acggccacga tgtcttcgtc    1020
gaggtggggc cgaacaacat gcgctccgcc gcggtcagtg acattcttgg caaggctgcc    1080
accccgcatg tctccgtggc gctggaccgc cccagtgagt cggcgtggac gcagaccctc    1140
aagtcgctgg cgctgctgac cgcccaccgc gtgcccctgc acaacccgac tctgtttgcg    1200
gac                                                                  1203

<210> SEQ ID NO 34
<211> LENGTH: 401
<212> TYPE: PRT
<213> ORGANISM: Schizochytrium sp.

<400> SEQUENCE: 34

Thr Pro Glu Lys Leu Glu Lys Glu Leu Glu Leu Ala Ala Lys Gly Val
1               5                   10                  15

Pro Arg Ser Ala Lys Ala Gly Arg Asn Trp Met Ser Pro Ser Gly Ser
            20                  25                  30

Ala Phe Ala Pro Thr Pro Val Thr Ser Asp Arg Val Ala Phe Met Tyr
        35                  40                  45

Gly Glu Gly Arg Ser Pro Tyr Tyr Gly Val Gly Leu Asp Leu His Arg
    50                  55                  60

```
Leu Trp Pro Ala Leu His Glu Arg Ile Asn Asp Lys Thr Ala Ala Leu
 65                  70                  75                  80

Trp Glu Asn Gly Asp Ser Trp Leu Met Pro Arg Ala Val Asp Ala Asp
                 85                  90                  95

Ser Gln Arg Ala Val Gln Thr Ala Phe Asp Ala Asp Gln Ile Glu Met
            100                 105                 110

Phe Arg Thr Gly Ile Phe Val Ser Ile Cys Leu Thr Asp Tyr Ala Arg
        115                 120                 125

Asp Val Leu Gly Val Gln Pro Lys Ala Cys Phe Gly Leu Ser Leu Gly
    130                 135                 140

Glu Ile Ser Met Leu Phe Ala Leu Ser Arg Arg Asn Cys Gly Leu Ser
145                 150                 155                 160

Asp Gln Leu Thr Gln Arg Leu Arg Thr Ser Pro Val Trp Ser Thr Gln
                165                 170                 175

Leu Ala Val Glu Phe Gln Ala Leu Arg Lys Leu Trp Asn Val Pro Ala
            180                 185                 190

Asp Ala Pro Val Glu Ser Phe Trp Gln Gly Tyr Leu Val Arg Ala Ser
        195                 200                 205

Arg Ala Glu Ile Glu Lys Ala Ile Gly Pro Asp Asn Arg Phe Val Arg
    210                 215                 220

Leu Leu Ile Val Asn Asp Ser Ser Ala Leu Ile Ala Gly Lys Pro
225                 230                 235                 240

Ala Glu Cys Leu Arg Val Leu Glu Arg Leu Gly Gly Arg Leu Pro Pro
                245                 250                 255

Met Pro Val Lys Gln Gly Met Ile Gly His Cys Pro Glu Val Ala Pro
            260                 265                 270

Tyr Thr Pro Gly Ile Ala His Ile His Glu Ile Leu Glu Ile Pro Asp
        275                 280                 285

Ser Pro Val Lys Met Tyr Thr Ser Val Thr Asn Ala Glu Leu Arg Gly
    290                 295                 300

Gly Ser Asn Ser Ser Ile Thr Glu Phe Val Gln Lys Leu Tyr Thr Arg
305                 310                 315                 320

Ile Ala Asp Phe Pro Gly Ile Val Asp Lys Val Ser Arg Asp Gly His
                325                 330                 335

Asp Val Phe Val Glu Val Gly Pro Asn Asn Met Arg Ser Ala Ala Val
            340                 345                 350

Ser Asp Ile Leu Gly Lys Ala Ala Thr Pro His Val Ser Val Ala Leu
        355                 360                 365

Asp Arg Pro Ser Glu Ser Ala Trp Thr Gln Thr Leu Lys Ser Leu Ala
    370                 375                 380

Leu Leu Thr Ala His Arg Val Pro Leu His Asn Pro Thr Leu Phe Ala
385                 390                 395                 400

Asp
```

<210> SEQ ID NO 35
<211> LENGTH: 1273
<212> TYPE: DNA
<213> ORGANISM: Schizochytrium sp.

<400> SEQUENCE: 35

```
tacgacgtgg actggccgct ctacatgggc gccatggcgg aaggcatctc gtcggtagac    60
ctggtggtcg ctgccgccga ggcccgcatg ctggcatcat tcggagcggc ccgcttgcct   120
atggaccagg tggaactcca gatccgtgag atccagcaac gcacctccaa cgcctttgct   180
```

-continued

```
gtcaacctga tgccgggtcc tgacgaggcc gcgacggtgg acgcgctgct gcgcacgggc       240
gtctcaatcg tcgaggcatc gggctacacc ggcgcgctct ctgcagacct ggtgcgctac       300
cgtgtcacgg gtctgcgacg aactagttgc ggtgcttctg tgtcggcgac tcaccgtgtg       360
gtcgccaagg tgtcgcgcac cgaggtggcc gagcactttc tgcgcccggc gccggccgcc       420
gtactagagg ctttggtcgc cgccaaacag attacgcccg agcaggccgc gctggccagc       480
cgcgtcgcca tggccgacga cgtcgcggtg gaggccgact cgggcgggca caccgacaac       540
cgaccgatcc acgtgctgct gccgctcgtg gtggcgcagc gcaaccgctg cgccacctg        600 gtggacacgc cagtgcgcgt cggcgccggc ggcgggatcg cctgtccgcg cgccgcgctg       660
ctcgcctttt ccctgggcgc cgcctttgtg gtcaccgggt ccgtcaacca actggcccgc       720
gaggctggca ccagcgacgc ggtccgacta ctgctggcga cggccaccta ctcggacgtg       780
gccatggcgc cgggcggcgt ccaggtgctc aagaagcaga ccatgttcgc cgcgcgggcc       840
acgatgctcg cccagctgca ggccaagttc ggctcctttg acgccgtgcc ggagccgcag       900
ctgcgcaagc tcgagcgctc cgtgttcaag cagtccgtgg cggacgtgtg ggctgctgca       960
cgcgaaaagt ttggtgtcga cgctaccgct gcaagtccgc aggagaggat ggcgctctgt      1020
gtgcgctggt acatgtcgca gtcgtcgcga tgggctaccg aggcgacgtc cgcgcgcaag      1080
gcggactacc agatctggtg cggccccgcc atcggcagct tcaacgactt cgttcgcggc      1140
accaagctgg acgcgaccgc tggcaccggc gagtttccgc gcgtcgtgga catcaaccag      1200
cacatcctcc tcggagcctc gcactaccgc cgcgtgcagc aacaacaaca ggacgacgac      1260
gtagaataca tca                                                         1273
```

<210> SEQ ID NO 36
<211> LENGTH: 401
<212> TYPE: PRT
<213> ORGANISM: Schizochytrium sp.

<400> SEQUENCE: 36

```
Tyr Asp Val Asp Trp Pro Leu Tyr Met Gly Ala Met Ala Glu Gly Ile
 1               5                  10                  15

Ser Ser Val Asp Leu Val Val Ala Ala Ala Glu Ala Arg Met Leu Ala
            20                  25                  30

Ser Phe Gly Ala Ala Arg Leu Pro Met Asp Gln Val Glu Leu Gln Ile
        35                  40                  45

Arg Glu Ile Gln Gln Arg Thr Ser Asn Ala Phe Ala Val Asn Leu Met
    50                  55                  60

Pro Gly Pro Asp Glu Ala Ala Thr Val Asp Ala Leu Leu Arg Thr Gly
65                  70                  75                  80

Val Ser Ile Val Glu Ala Ser Gly Tyr Thr Gly Ala Leu Ser Ala Asp
                85                  90                  95

Leu Val Arg Tyr Arg Val Thr Gly Leu Arg Arg Thr Ser Cys Gly Ala
            100                 105                 110

Ser Val Ser Ala Thr His Arg Val Ala Lys Val Ser Arg Thr Glu
        115                 120                 125

Val Ala Glu His Phe Leu Arg Pro Ala Pro Ala Val Leu Glu Ala
    130                 135                 140

Leu Val Ala Ala Lys Gln Ile Thr Pro Glu Gln Ala Ala Leu Ala Ser
145                 150                 155                 160

Arg Val Ala Met Ala Asp Asp Val Ala Val Glu Ala Asp Ser Gly Gly
                165                 170                 175
```

```
His Thr Asp Asn Arg Pro Ile His Val Leu Leu Pro Leu Val Val Ala
                180                 185                 190

Gln Arg Asn Arg Trp Arg His Leu Val Asp Thr Pro Val Arg Val Gly
            195                 200                 205

Ala Gly Gly Gly Ile Ala Cys Pro Arg Ala Ala Leu Leu Ala Phe Ser
        210                 215                 220

Leu Gly Ala Ala Phe Val Val Thr Gly Ser Val Asn Gln Leu Ala Arg
225                 230                 235                 240

Glu Ala Gly Thr Ser Asp Ala Val Arg Leu Leu Ala Thr Ala Thr
                245                 250                 255

Tyr Ser Asp Val Ala Met Ala Pro Gly Gly Val Gln Val Leu Lys Lys
            260                 265                 270

Gln Thr Met Phe Ala Ala Arg Ala Thr Met Leu Ala Gln Leu Gln Ala
        275                 280                 285

Lys Phe Gly Ser Phe Asp Ala Val Pro Glu Pro Gln Leu Arg Lys Leu
        290                 295                 300

Glu Arg Ser Val Phe Lys Gln Ser Val Ala Asp Val Trp Ala Ala Ala
305                 310                 315                 320

Arg Glu Lys Phe Gly Val Asp Ala Thr Ala Ala Ser Pro Gln Glu Arg
                325                 330                 335

Met Ala Leu Cys Val Arg Trp Tyr Met Ser Gln Ser Ser Arg Trp Ala
            340                 345                 350

Thr Glu Ala Thr Ser Ala Arg Lys Ala Asp Tyr Gln Ile Trp Cys Gly
        355                 360                 365

Pro Ala Ile Gly Ser Phe Asn Asp Phe Val Arg Gly Thr Lys Leu Asp
        370                 375                 380

Ala Thr Ala Gly Thr Gly Glu Phe Pro Arg Val Val Asp Ile Asn Gln
385                 390                 395                 400

His

<210> SEQ ID NO 37
<211> LENGTH: 1350
<212> TYPE: DNA
<213> ORGANISM: Schizochytrium sp.

<400> SEQUENCE: 37
atgacatcat cgaagaagac tcccgtgtgg gagatgagca aggaggagct gctggacggc      60
aagacggtgg tcttcgacta caacgagctg ctcgaattcg ccgagggcga cgtgggccaa     120
gtgttcggac ccgagttcga catcatcgac aagtaccggc gtcgcgtgcg gctgccggcg     180
cgcgagtacc tgctcgtgtc gcgcgtgacg ctgatggacg ccgaggtgaa caacttccgc     240
gtcgggtcgc gcatggtgac cgagtacgac gtgcccgtga acggggagct gtcggagggc     300
ggggacgtgc cgtgggcggt gctggtggag tcggggcagt gcgacctgat gctcatctcg     360
tacatgggca tcgacttcca gtgcaagggc gaccgcgtgt accgcctgct caacacatcg     420
ctcaccttct tcggggtggc gcacgagggc gagacgctgg tgtacgacat ccgcgtcacg     480
gggttcgcca agggcgcggg cggggagatc tcgatgttct tcttcgagta cgactgcttc     540
gtggacggcc gctgctgat cgagatgcgc gacgggtgcg ccgggttctt cacggacgcc     600
gagctggccg ccggcaaggg cgtgcttaag accaaggcgg agctggcggc gcgcgcgcag     660
atccagaagc aggacatcgc gcccttgcg ccggcgccgt gctcgcacaa gacctcgctg     720
gacgcgcgcg agatgcggct gctcgtggac cgccagtggg cgcgcgtctt cggcagcggc     780
atggcgggca tcgactacaa gttgtgcgct cgcaagatgc tcatgatcga ccgcgtcacg     840
```

```
cacctcgacc cgcgcggcgg cgcgcacggc ctcgggctgc tgatcgggga gaaggtgctg    900
gagcgcgacc actggtactt ccctgccac tttgtgcgcg acgaggtgat ggccgggtcg    960
ctggtcagcg acggctgctc gcagctcctc aaggtgtaca tgctgtggct cggcctgcac   1020
acgaccgtgg gcgcgttcga ctttcgtccc gtgagcgggc acgccaacaa ggtgcggtgc   1080
cgcgggcaga tctcaccgca aagggcaag ctcgtgtacg tgatggagat caaggaaatg   1140
ggctttgacg cgaagacggg cgatccgttt gcgatcgcgg acgtggacat catcgacgtc   1200
aacttcgagg agggacaggc gtttgcggga gtggaagacc tgcacagcta cggccagggc   1260
gacctccgca agaagatcgt cgtcgacttc aagggcatcg cgctctccct gcagaagcgg   1320
aaggagcagc agaaggaaag catgaccgtg                                    1350
```

<210> SEQ ID NO 38
<211> LENGTH: 450
<212> TYPE: PRT
<213> ORGANISM: Schizochytrium sp.

<400> SEQUENCE: 38

```
Met Thr Ser Ser Lys Lys Thr Pro Val Trp Glu Met Ser Lys Glu Glu
1               5                   10                  15

Leu Leu Asp Gly Lys Thr Val Val Phe Asp Tyr Asn Glu Leu Leu Glu
            20                  25                  30

Phe Ala Glu Gly Asp Val Gly Gln Val Phe Gly Pro Glu Phe Asp Ile
        35                  40                  45

Ile Asp Lys Tyr Arg Arg Val Arg Leu Pro Ala Arg Glu Tyr Leu
    50                  55                  60

Leu Val Ser Arg Val Thr Leu Met Asp Ala Glu Val Asn Asn Phe Arg
65                  70                  75                  80

Val Gly Ser Arg Met Val Thr Glu Tyr Asp Val Pro Val Asn Gly Glu
                85                  90                  95

Leu Ser Glu Gly Gly Asp Val Pro Trp Ala Val Leu Val Glu Ser Gly
            100                 105                 110

Gln Cys Asp Leu Met Leu Ile Ser Tyr Met Gly Ile Asp Phe Gln Cys
        115                 120                 125

Lys Gly Asp Arg Val Tyr Arg Leu Leu Asn Thr Ser Leu Thr Phe Phe
    130                 135                 140

Gly Val Ala His Glu Gly Glu Thr Leu Val Tyr Asp Ile Arg Val Thr
145                 150                 155                 160

Gly Phe Ala Lys Gly Ala Gly Glu Ile Ser Met Phe Phe Glu
                165                 170                 175

Tyr Asp Cys Phe Val Asp Gly Arg Leu Leu Ile Glu Met Arg Asp Gly
            180                 185                 190

Cys Ala Gly Phe Phe Thr Asp Ala Glu Leu Ala Ala Gly Lys Gly Val
        195                 200                 205

Leu Lys Thr Lys Ala Glu Leu Ala Ala Arg Ala Gln Ile Gln Lys Gln
    210                 215                 220

Asp Ile Ala Pro Phe Ala Pro Ala Pro Cys Ser His Lys Thr Ser Leu
225                 230                 235                 240

Asp Ala Arg Glu Met Arg Leu Leu Val Asp Arg Gln Trp Ala Arg Val
                245                 250                 255

Phe Gly Ser Gly Met Ala Gly Ile Asp Tyr Lys Leu Cys Ala Arg Lys
            260                 265                 270

Met Leu Met Ile Asp Arg Val Thr His Leu Asp Pro Arg Gly Gly Ala
```

```
                275                 280                 285
His Gly Leu Gly Leu Leu Ile Gly Glu Lys Val Leu Glu Arg Asp His
    290                 295                 300

Trp Tyr Phe Pro Cys His Phe Val Arg Asp Glu Val Met Ala Gly Ser
305                 310                 315                 320

Leu Val Ser Asp Gly Cys Ser Gln Leu Leu Lys Val Tyr Met Leu Trp
                325                 330                 335

Leu Gly Leu His Thr Thr Val Gly Ala Phe Asp Phe Arg Pro Val Ser
                340                 345                 350

Gly His Ala Asn Lys Val Arg Cys Arg Gly Gln Ile Ser Pro His Lys
                355                 360                 365

Gly Lys Leu Val Tyr Val Met Glu Ile Lys Glu Met Gly Phe Asp Ala
    370                 375                 380

Lys Thr Gly Asp Pro Phe Ala Ile Ala Asp Val Asp Ile Ile Asp Val
385                 390                 395                 400

Asn Phe Glu Glu Gly Gln Ala Phe Ala Gly Val Glu Asp Leu His Ser
                405                 410                 415

Tyr Gly Gln Gly Asp Leu Arg Lys Lys Ile Val Asp Phe Lys Gly
                420                 425                 430

Ile Ala Leu Ser Leu Gln Lys Arg Lys Glu Gln Gln Lys Glu Ser Met
                435                 440                 445

Thr Val
    450

<210> SEQ ID NO 39
<211> LENGTH: 1200
<212> TYPE: DNA
<213> ORGANISM: Schizochytrium sp.

<400> SEQUENCE: 39
tacccgccgc gggcggtgtg cttctcgccg ttccccaaca cccgcttga caacgaccac      60 acgccgggcc agatgccgtt gacctggttc aacatgtccg aattcatgtg cggcaaagtg     120
tccaactgcc tgggccccga gtttgcgcgc ttcgacgcga gcaagacgag ccgcagcccg     180
gcctttgacc tggcgctcgt gacgcgggtg acgagcgtgg cggacatgga gcacgggccg     240
ttctacaacg tggacgtcaa cccgggccag ggcacgatgg tgggcgagtt cgactgtccc     300
gcggacgcgt ggttcttcgg cgcctcgagc cgcgacgacc acatgccgta ctcgatcctg     360
atggagatcg cgctgcagac gtcgggcgtc ctcacctcgg tgctcaaggc gccgctgacg     420
atggacaagg acgacatcct cttccgcaac ctcgacgcag acgccgagct cgtgggcgac     480
gccatgccgg acgtgcgcgg caagacgatc cgcaacttca ccaagtgcac aggctacagc     540
atgctcggca agatgggcat ccaccgcttc acctttgagc tcagcgtcga cggcgccgtc     600
ttctacaagg gcagcaccct cgtttggctgg ttcgtccccg aggtcttcga gtcgcagacc     660
ggtctcgaca cggcaagcc gcgcctgcct tggtaccgcg agaacaacgt cgccgtcgac     720
acgctctccg cgcccgcctc cgcttcctcc gcgcaaggtc agctgcagct gcagcgacgc     780
gggtcgcagg cgcagttcct ggacacaatc cacctggcgg gcagcggcgc cggcgtgcac     840
ggccagggct acgcgcacgg ggagaaggcc gtgaacaagc aagattggtt cttctcgtgc     900
cacttctggt cgaccccgt gatgcccggg tccctgggca tcgagtcgat gttccagctc     960
gtcgaggcgt ggtgcgtgaa gcagggactc gcggcgcggc acggcatcgc tcacccagtg    1020
ttcgcgcacg cgcccggggc cacgagctgg aagtaccgcg ggcagctaac ccccaagaac    1080
```

-continued

```
gaccgcatgg acagcgaggt gcacatcaag tcggtggcgg ccttctcctc ctgggtcgac   1140
gtcgtcgcgg acgggttcct cttcgtcgac ggcctccgcg tctactcggc agacaacctc   1200
```

<210> SEQ ID NO 40
<211> LENGTH: 400
<212> TYPE: PRT
<213> ORGANISM: Schizochytrium sp.

<400> SEQUENCE: 40

| Tyr | Pro | Pro | Arg | Ala | Val | Cys | Phe | Ser | Pro | Phe | Pro | Asn | Asn | Pro | Leu |
|---|---|---|---|---|---|---|---|---|---|---|---|---|---|---|---|
| 1 | | | | 5 | | | | | 10 | | | | | 15 | |

| Asp | Asn | Asp | His | Thr | Pro | Gly | Gln | Met | Pro | Leu | Thr | Trp | Phe | Asn | Met |
|---|---|---|---|---|---|---|---|---|---|---|---|---|---|---|---|
| | | | | 20 | | | | | 25 | | | | | 30 | |

| Ser | Glu | Phe | Met | Cys | Gly | Lys | Val | Ser | Asn | Cys | Leu | Gly | Pro | Glu | Phe |
|---|---|---|---|---|---|---|---|---|---|---|---|---|---|---|---|
| | | | 35 | | | | | 40 | | | | | 45 | | |

| Ala | Arg | Phe | Asp | Ala | Ser | Lys | Thr | Ser | Arg | Ser | Pro | Ala | Phe | Asp | Leu |
|---|---|---|---|---|---|---|---|---|---|---|---|---|---|---|---|
| | 50 | | | | | 55 | | | | | 60 | | | | |

| Ala | Leu | Val | Thr | Arg | Val | Thr | Ser | Val | Ala | Asp | Met | Glu | His | Gly | Pro |
|---|---|---|---|---|---|---|---|---|---|---|---|---|---|---|---|
| 65 | | | | | 70 | | | | | 75 | | | | | 80 |

| Phe | Tyr | Asn | Val | Asp | Val | Asn | Pro | Gly | Gln | Gly | Thr | Met | Val | Gly | Glu |
|---|---|---|---|---|---|---|---|---|---|---|---|---|---|---|---|
| | | | | 85 | | | | | 90 | | | | | 95 | |

| Phe | Asp | Cys | Pro | Ala | Asp | Ala | Trp | Phe | Phe | Gly | Ala | Ser | Ser | Arg | Asp |
|---|---|---|---|---|---|---|---|---|---|---|---|---|---|---|---|
| | | | 100 | | | | | 105 | | | | | 110 | | |

| Asp | His | Met | Pro | Tyr | Ser | Ile | Leu | Met | Glu | Ile | Ala | Leu | Gln | Thr | Ser |
|---|---|---|---|---|---|---|---|---|---|---|---|---|---|---|---|
| | | | 115 | | | | | 120 | | | | | 125 | | |

| Gly | Val | Leu | Thr | Ser | Val | Leu | Lys | Ala | Pro | Leu | Thr | Met | Asp | Lys | Asp |
|---|---|---|---|---|---|---|---|---|---|---|---|---|---|---|---|
| | 130 | | | | | 135 | | | | | 140 | | | | |

| Asp | Ile | Leu | Phe | Arg | Asn | Leu | Asp | Ala | Asp | Ala | Glu | Leu | Val | Gly | Asp |
|---|---|---|---|---|---|---|---|---|---|---|---|---|---|---|---|
| 145 | | | | | 150 | | | | | 155 | | | | | 160 |

| Ala | Met | Pro | Asp | Val | Arg | Gly | Lys | Thr | Ile | Arg | Asn | Phe | Thr | Lys | Cys |
|---|---|---|---|---|---|---|---|---|---|---|---|---|---|---|---|
| | | | | 165 | | | | | 170 | | | | | 175 | |

| Thr | Gly | Tyr | Ser | Met | Leu | Gly | Lys | Met | Gly | Ile | His | Arg | Phe | Thr | Phe |
|---|---|---|---|---|---|---|---|---|---|---|---|---|---|---|---|
| | | | | 180 | | | | | 185 | | | | | 190 | |

| Glu | Leu | Ser | Val | Asp | Gly | Ala | Val | Phe | Tyr | Lys | Gly | Ser | Thr | Ser | Phe |
|---|---|---|---|---|---|---|---|---|---|---|---|---|---|---|---|
| | | 195 | | | | | 200 | | | | | 205 | | | |

| Gly | Trp | Phe | Val | Pro | Glu | Val | Phe | Glu | Ser | Gln | Thr | Gly | Leu | Asp | Asn |
|---|---|---|---|---|---|---|---|---|---|---|---|---|---|---|---|
| 210 | | | | | 215 | | | | | 220 | | | | | |

| Gly | Lys | Pro | Arg | Leu | Pro | Trp | Tyr | Arg | Glu | Asn | Asn | Val | Ala | Val | Asp |
|---|---|---|---|---|---|---|---|---|---|---|---|---|---|---|---|
| 225 | | | | | 230 | | | | | 235 | | | | | 240 |

| Thr | Leu | Ser | Ala | Pro | Ala | Ser | Ala | Ser | Ser | Ala | Gln | Gly | Gln | Leu | Gln |
|---|---|---|---|---|---|---|---|---|---|---|---|---|---|---|---|
| | | | | 245 | | | | | 250 | | | | | 255 | |

| Leu | Gln | Arg | Arg | Gly | Ser | Gln | Ala | Gln | Phe | Leu | Asp | Thr | Ile | His | Leu |
|---|---|---|---|---|---|---|---|---|---|---|---|---|---|---|---|
| | | | 260 | | | | | 265 | | | | | 270 | | |

| Ala | Gly | Ser | Gly | Ala | Gly | Val | His | Gly | Gln | Gly | Tyr | Ala | His | Gly | Glu |
|---|---|---|---|---|---|---|---|---|---|---|---|---|---|---|---|
| | | 275 | | | | | 280 | | | | | 285 | | | |

| Lys | Ala | Val | Asn | Lys | Gln | Asp | Trp | Phe | Phe | Ser | Cys | His | Phe | Trp | Phe |
|---|---|---|---|---|---|---|---|---|---|---|---|---|---|---|---|
| | 290 | | | | | 295 | | | | | 300 | | | | |

| Asp | Pro | Val | Met | Pro | Gly | Ser | Leu | Gly | Ile | Glu | Ser | Met | Phe | Gln | Leu |
|---|---|---|---|---|---|---|---|---|---|---|---|---|---|---|---|
| 305 | | | | | 310 | | | | | 315 | | | | | 320 |

| Val | Glu | Ala | Trp | Cys | Val | Lys | Gln | Gly | Leu | Ala | Ala | Arg | His | Gly | Ile |
|---|---|---|---|---|---|---|---|---|---|---|---|---|---|---|---|
| | | | | 325 | | | | | 330 | | | | | 335 | |

| Ala | His | Pro | Val | Phe | Ala | His | Ala | Pro | Gly | Ala | Thr | Ser | Trp | Lys | Tyr |
|---|---|---|---|---|---|---|---|---|---|---|---|---|---|---|---|
| | | | | 340 | | | | | 345 | | | | | 350 | |

| Arg | Gly | Gln | Leu | Thr | Pro | Lys | Asn | Asp | Arg | Met | Asp | Ser | Glu | Val | His |
|---|---|---|---|---|---|---|---|---|---|---|---|---|---|---|---|

```
                355                 360                 365
Ile Lys Ser Val Ala Ala Phe Ser Ser Trp Val Asp Val Ala Asp
            370                 375                 380
Gly Phe Leu Phe Val Asp Gly Leu Arg Val Tyr Ser Ala Asp Asn Leu
385                 390                 395                 400
```

<210> SEQ ID NO 41
<211> LENGTH: 1353
<212> TYPE: DNA
<213> ORGANISM: Schizochytrium sp.

<400> SEQUENCE: 41

```
cagctggacg cggggagcga ggtgcccgcc tgcgcggtga gcgacctggg cgatagggc      60
ttcatggaga cgtacggggt ggtggcgccg ctgtacagcg gggcgatggc caagggcatc    120
gcgtcggcgg acctggtgat cgcgatgggc cagcgcaaga tgctggggtc gtttggcgcg    180
ggcgggctcc cgatgcacgt cgtgcgcgcg gggattgaga agatccaggc agcgctgcca    240
gcggggccat acgcggtcaa cctgattcac tcgccttttg acgccaacct ggagaagggc    300
aacgtggacc tcttcctgga aagggcgtg cgcgtcgtgg aggcgtcggc cttcatggag    360
ctcacgcccc aggtggtgcg ctaccgcgcg acgggcctct ctcgcgacgc gcgcggcggc    420
tccgtgcgca cggcccacaa gatcatcggc aaggtcagcc gcaccgagct ggccgagatg    480
tttatccggc ccgcgccgca agccattctc gacaagcttg tggcgtccgg cgagatcacc    540
cccgagcagg cggcgctggc gctcgaggtg cccatggcgg acgacatcgc cgtcgaggcc    600
gattcgggcg gcacaccga caaccgcccc atccacgtca cctgccccct catcctcagc    660
ctgcgcaacc gcctccagcg cgagctcaag taccctgcgc gacaccgcgt gcgcgtcggc    720
gccggggggcg gcatcgggtg cccgcaagcg gctctgggcg ccttccacat gggcgccgcg    780
tttgtggtga cgggcacggt caaccagctg agccggcagg ccgggacatg cgacaatgtg    840
cggcggcagc tgtcgcgcgc gacgtactcg gacatcacga tggcgccggc ggcggacatg    900
ttcgagcagg gcgtcgagct gcaggtgctc aagaagggca cgatgttcc ctcgcgcgcc    960
aagaagctgt cgagctgttt cacaagtac gactcgttcg aggcgatgcc ggcggacgag   1020
ctggcgcgcg tcgagaagcg catcttcagc aagtcactcg ccgaggtgtg ggccgagacc   1080
aaggacttct acatcacgcg gctcaacaac ccggagaaga tccgcaaggc ggagaacgag   1140
gaccccaagc tcaagatgtc actctgcttc cgctggtacc tcgggctcag ctcgttctgg   1200
gccaacaacg gcatcgcgga ccgcacgatg gactaccaga tctggtgcgg ccctgccatc   1260
ggcgccttca cgacttcat cgccgactcg tacctcgacg tggccgtctc gggcgagttc   1320
cccgacgtcg tgcagatcaa cctgcagatc ctg                               1353
```

<210> SEQ ID NO 42
<211> LENGTH: 451
<212> TYPE: PRT
<213> ORGANISM: Schizochytrium sp.

<400> SEQUENCE: 42

```
Gln Leu Asp Ala Gly Ser Glu Val Pro Ala Cys Ala Val Ser Asp Leu
1               5                   10                  15
Gly Asp Arg Gly Phe Met Glu Thr Tyr Gly Val Val Ala Pro Leu Tyr
            20                  25                  30
Ser Gly Ala Met Ala Lys Gly Ile Ala Ser Ala Asp Leu Val Ile Ala
        35                  40                  45
```

```
Met Gly Gln Arg Lys Met Leu Gly Ser Phe Gly Ala Gly Gly Leu Pro
    50                  55                  60
Met His Val Val Arg Ala Gly Ile Glu Lys Ile Gln Ala Ala Leu Pro
65                  70                  75                  80
Ala Gly Pro Tyr Ala Val Asn Leu Ile His Ser Pro Phe Asp Ala Asn
                85                  90                  95
Leu Glu Lys Gly Asn Val Asp Leu Phe Leu Glu Lys Gly Val Arg Val
            100                 105                 110
Val Glu Ala Ser Ala Phe Met Glu Leu Thr Pro Gln Val Val Arg Tyr
            115                 120                 125
Arg Ala Thr Gly Leu Ser Arg Asp Ala Arg Gly Gly Ser Val Arg Thr
130                 135                 140
Ala His Lys Ile Ile Gly Lys Val Ser Arg Thr Glu Leu Ala Glu Met
145                 150                 155                 160
Phe Ile Arg Pro Ala Pro Gln Ala Ile Leu Asp Lys Leu Val Ala Ser
                165                 170                 175
Gly Glu Ile Thr Pro Glu Gln Ala Ala Leu Ala Leu Glu Val Pro Met
            180                 185                 190
Ala Asp Asp Ile Ala Val Glu Ala Asp Ser Gly Gly His Thr Asp Asn
            195                 200                 205
Arg Pro Ile His Val Ile Leu Pro Leu Ile Leu Ser Leu Arg Asn Arg
210                 215                 220
Leu Gln Arg Glu Leu Lys Tyr Pro Ala Arg His Arg Val Arg Val Gly
225                 230                 235                 240
Ala Gly Gly Gly Ile Gly Cys Pro Gln Ala Ala Leu Gly Ala Phe His
                245                 250                 255
Met Gly Ala Ala Phe Val Val Thr Gly Thr Val Asn Gln Leu Ser Arg
            260                 265                 270
Gln Ala Gly Thr Cys Asp Asn Val Arg Arg Gln Leu Ser Arg Ala Thr
            275                 280                 285
Tyr Ser Asp Ile Thr Met Ala Pro Ala Ala Asp Met Phe Glu Gln Gly
            290                 295                 300
Val Glu Leu Gln Val Leu Lys Lys Gly Thr Met Phe Pro Ser Arg Ala
305                 310                 315                 320
Lys Lys Leu Phe Glu Leu Phe His Lys Tyr Asp Ser Phe Glu Ala Met
                325                 330                 335
Pro Ala Asp Glu Leu Ala Arg Val Glu Lys Arg Ile Phe Ser Lys Ser
            340                 345                 350
Leu Ala Glu Val Trp Ala Glu Thr Lys Asp Phe Tyr Ile Thr Arg Leu
            355                 360                 365
Asn Asn Pro Glu Lys Ile Arg Lys Ala Glu Asn Glu Asp Pro Lys Leu
370                 375                 380
Lys Met Ser Leu Cys Phe Arg Trp Tyr Leu Gly Leu Ser Ser Phe Trp
385                 390                 395                 400
Ala Asn Asn Gly Ile Ala Asp Arg Thr Met Asp Tyr Gln Ile Trp Cys
                405                 410                 415
Gly Pro Ala Ile Gly Ala Phe Asn Asp Phe Ile Ala Asp Ser Tyr Leu
            420                 425                 430
Asp Val Ala Val Ser Gly Glu Phe Pro Asp Val Val Gln Ile Asn Leu
            435                 440                 445
Gln Ile Leu
    450
```

```
<210> SEQ ID NO 43
<211> LENGTH: 4
<212> TYPE: PRT
<213> ORGANISM: Schizochytrium sp.
<220> FEATURE:
<221> NAME/KEY: misc_feature
<222> LOCATION: (2)..(2)
<223> OTHER INFORMATION: Xaa can be any naturally occurring amino acid

<400> SEQUENCE: 43

Asp Xaa Ala Cys
1

<210> SEQ ID NO 44
<211> LENGTH: 4
<212> TYPE: PRT
<213> ORGANISM: Schizochytrium sp.

<400> SEQUENCE: 44

Gly Phe Gly Gly
1

<210> SEQ ID NO 45
<211> LENGTH: 12
<212> TYPE: DNA
<213> ORGANISM: Schizochytrium sp.

<400> SEQUENCE: 45
gggtttggcg gt                                                         12

<210> SEQ ID NO 46
<211> LENGTH: 5
<212> TYPE: PRT
<213> ORGANISM: Schizochytrium sp.

<400> SEQUENCE: 46

Gly Phe Ser Leu Gly
1               5

<210> SEQ ID NO 47
<211> LENGTH: 5
<212> TYPE: PRT
<213> ORGANISM: Schizochytrium sp.

<400> SEQUENCE: 47

Leu Gly Ile Asp Ser
1               5

<210> SEQ ID NO 48
<211> LENGTH: 903
<212> TYPE: DNA
<213> ORGANISM: Schizochytrium sp.

<400> SEQUENCE: 48
ctgtcagacc cgacgtggc cgtgcgcgag tctggttact ccgcctcggg ccagcgctgc      60
acgacaacta cgaagtcgct gactacgggc aagccgcacc agccgatctc ctcgtcggac    120
ctctttctgg tgtcgggcgg cgcgcgcggc atcaccccgc tgtgcgtgcg cgagctggcg    180
cagcgcgtgg gcggcggcac gtacgtgctc atcggccgct cggagctgcc cacgacggag    240
cctgcctggg cggtcggcgt ggagtctggc aagccgctgg agaaggccgc gctggcgttc    300
ctgaaggcgg agtttgcagc gggccgcggg gccaagccga cgccgatgct gcacaagaag    360
ctcgtgggcg ccgtggtcgg agcgcgcgag gtgcgagcct cgctcgccga gatcactgca    420
```

-continued

```
cagggcgcca cggctgtgta cgagtcgtgc gacgtgagct ctgccgccaa ggtgcgtgag    480
atggtagagc gcgtgcagca gcagggcggg cggcgcgtgt cgggcgtgtt ccacgcgtcg    540
ggcgtgctgc gcgacaagct cgtggagaac aagtcgctgg cggacttcag cgccgtgtac    600
gacaccaagg tgggcggcct catcaacctg ctggcctgcg tggacctggc gcagctgcgt    660
cacctcgtgc tcttcagctc gctcgcgggc ttccacggca acgtcgggca gtcggactac    720
gcaatggcca acgaggcgct caacaagctg gcggcgcacc tgtcggcggt gcacccgcag    780
ctgtgcgcgc gctcgatctg cttcggaccg tgggacggcg gcatggtgac ccccgcgctc    840
aaggccaact tcatccgcat gggcatccag atcatcccgc gccaaggcgg cgcgcagacc    900
gtc                                                                 903
```

<210> SEQ ID NO 49
<211> LENGTH: 301
<212> TYPE: PRT
<213> ORGANISM: Schizochytrium sp.

<400> SEQUENCE: 49

```
Leu Ser Asp Pro Asp Val Ala Val Arg Glu Ser Gly Tyr Ser Ala Ser
 1               5                  10                  15

Gly Gln Arg Cys Thr Thr Thr Lys Ser Leu Thr Thr Gly Lys Pro
            20                  25                  30

His Gln Pro Ile Ser Ser Ser Asp Leu Phe Leu Val Ser Gly Gly Ala
        35                  40                  45

Arg Gly Ile Thr Pro Leu Cys Val Arg Glu Leu Ala Gln Arg Val Gly
    50                  55                  60

Gly Gly Thr Tyr Val Leu Ile Gly Arg Ser Glu Leu Pro Thr Thr Glu
65                  70                  75                  80

Pro Ala Trp Ala Val Gly Val Glu Ser Gly Lys Pro Leu Glu Lys Ala
                85                  90                  95

Ala Leu Ala Phe Leu Lys Ala Glu Phe Ala Ala Gly Arg Gly Ala Lys
            100                 105                 110

Pro Thr Pro Met Leu His Lys Lys Leu Val Gly Ala Val Gly Ala
        115                 120                 125

Arg Glu Val Arg Ala Ser Leu Ala Glu Ile Thr Ala Gln Gly Ala Thr
    130                 135                 140

Ala Val Tyr Glu Ser Cys Asp Val Ser Ser Ala Ala Lys Val Arg Glu
145                 150                 155                 160

Met Val Glu Arg Val Gln Gln Gln Gly Gly Arg Arg Val Ser Gly Val
                165                 170                 175

Phe His Ala Ser Gly Val Leu Arg Asp Lys Leu Val Glu Asn Lys Ser
            180                 185                 190

Leu Ala Asp Phe Ser Ala Val Tyr Asp Thr Lys Val Gly Gly Leu Ile
        195                 200                 205

Asn Leu Leu Ala Cys Val Asp Leu Ala Gln Leu Arg His Leu Val Leu
    210                 215                 220

Phe Ser Ser Leu Ala Gly Phe His Gly Asn Val Gly Gln Ser Asp Tyr
225                 230                 235                 240

Ala Met Ala Asn Glu Ala Leu Asn Lys Leu Ala Ala His Leu Ser Ala
                245                 250                 255

Val His Pro Gln Leu Cys Ala Arg Ser Ile Cys Phe Gly Pro Trp Asp
            260                 265                 270

Gly Gly Met Val Thr Pro Ala Leu Lys Ala Asn Phe Ile Arg Met Gly
        275                 280                 285
```

Ile Gln Ile Ile Pro Arg Gln Gly Gly Ala Gln Thr Val
    290                 295                 300

<210> SEQ ID NO 50
<211> LENGTH: 13
<212> TYPE: PRT
<213> ORGANISM: Schizochytrium sp.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid

<400> SEQUENCE: 50

Leu Xaa Xaa His Xaa Xaa Xaa Gly Xaa Xaa Xaa Xaa Pro
1               5                   10

<210> SEQ ID NO 51
<211> LENGTH: 12
<212> TYPE: DNA
<213> ORGANISM: Schizochytrium sp.

<400> SEQUENCE: 51
ggctttggtg ga                                                          12

<210> SEQ ID NO 52
<211> LENGTH: 5
<212> TYPE: PRT
<213> ORGANISM: Schizochytrium sp.
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 52

Gly Xaa Ser Xaa Gly
1               5

<210> SEQ ID NO 53
<211> LENGTH: 5
<212> TYPE: PRT
<213> ORGANISM: Schizochytrium sp.
<220> FEATURE:
<221> NAME/KEY: misc_feature
<222> LOCATION: (2)..(3)
<223> OTHER INFORMATION: Xaa can be any naturally occurring amino acid

<400> SEQUENCE: 53

Phe Xaa Xaa His Phe
1               5

<210> SEQ ID NO 54
<211> LENGTH: 2910
<212> TYPE: PRT
<213> ORGANISM: Schizochytrium sp.

<400> SEQUENCE: 54

-continued

```
Met Ala Ala Arg Leu Gln Glu Gln Lys Gly Glu Met Asp Thr Arg
1               5                   10                  15

Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45

Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
            100                 105                 110

Leu Gln Asp Ala Gly Ile Asp Ala Leu Gly Lys Glu Lys Lys Asn Ile
        115                 120                 125

Gly Cys Val Leu Gly Ile Gly Gly Gln Lys Ser Ser His Glu Phe
    130                 135                 140

Tyr Ser Arg Leu Asn Tyr Val Val Glu Lys Val Leu Arg Lys Met
145                 150                 155                 160

Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
            180                 185                 190

Val Thr Ala Gly Arg Cys Thr Asn Thr Phe Asn Leu Asp Gly Met Asn
        195                 200                 205

Cys Val Val Asp Ala Ala Cys Ala Ser Ser Leu Ile Ala Val Lys Val
    210                 215                 220

Ala Ile Asp Glu Leu Leu Tyr Gly Asp Cys Asp Met Met Val Thr Gly
225                 230                 235                 240

Ala Thr Cys Thr Asp Asn Ser Ile Gly Met Tyr Met Ala Phe Ser Lys
                245                 250                 255

Thr Pro Val Phe Ser Thr Asp Pro Ser Val Arg Ala Tyr Asp Glu Lys
            260                 265                 270

Thr Lys Gly Met Leu Ile Gly Glu Gly Ser Ala Met Leu Val Leu Lys
        275                 280                 285

Arg Tyr Ala Asp Ala Val Arg Asp Gly Asp Glu Ile His Ala Val Ile
    290                 295                 300

Arg Gly Cys Ala Ser Ser Asp Gly Lys Ala Ala Gly Ile Tyr Thr
305                 310                 315                 320

Pro Thr Ile Ser Gly Gln Glu Glu Ala Leu Arg Arg Ala Tyr Asn Arg
                325                 330                 335

Ala Cys Val Asp Pro Ala Thr Val Thr Leu Val Glu Gly His Gly Thr
            340                 345                 350

Gly Thr Pro Val Gly Asp Arg Ile Glu Leu Thr Ala Leu Arg Asn Leu
        355                 360                 365

Phe Asp Lys Ala Tyr Gly Glu Gly Asn Thr Glu Lys Val Ala Val Gly
    370                 375                 380

Ser Ile Lys Ser Ser Ile Gly His Leu Lys Ala Val Ala Gly Leu Ala
385                 390                 395                 400

Gly Met Ile Lys Val Ile Met Ala Leu Lys His Lys Thr Leu Pro Gly
                405                 410                 415

Thr Ile Asn Val Asp Asn Pro Pro Asn Leu Tyr Asp Asn Thr Pro Ile
```

```
                420             425             430
Asn Glu Ser Ser Leu Tyr Ile Asn Thr Met Asn Arg Pro Trp Phe Pro
            435             440             445
Pro Pro Gly Val Pro Arg Arg Ala Gly Ile Ser Ser Phe Gly Phe Gly
        450             455             460
Gly Ala Asn Tyr His Ala Val Leu Glu Glu Ala Glu Pro Glu His Thr
465             470             475             480
Thr Ala Tyr Arg Leu Asn Lys Arg Pro Gln Pro Val Leu Met Met Ala
            485             490             495
Ala Thr Pro Ala Ala Leu Gln Ser Leu Cys Glu Ala Gln Leu Lys Glu
        500             505             510
Phe Glu Ala Ala Ile Lys Glu Asn Glu Thr Val Lys Asn Thr Ala Tyr
        515             520             525
Ile Lys Cys Val Lys Phe Gly Glu Gln Phe Lys Phe Pro Gly Ser Ile
        530             535             540
Pro Ala Thr Asn Ala Arg Leu Gly Phe Leu Val Lys Asp Ala Glu Asp
545             550             555             560
Ala Cys Ser Thr Leu Arg Ala Ile Cys Ala Gln Phe Ala Lys Asp Val
            565             570             575
Thr Lys Glu Ala Trp Arg Leu Pro Arg Glu Gly Val Ser Phe Arg Ala
            580             585             590
Lys Gly Ile Ala Thr Asn Gly Ala Val Ala Ala Leu Phe Ser Gly Gln
        595             600             605
Gly Ala Gln Tyr Thr His Met Phe Ser Glu Val Ala Met Asn Trp Pro
        610             615             620
Gln Phe Arg Gln Ser Ile Ala Ala Met Asp Ala Ala Gln Ser Lys Val
625             630             635             640
Ala Gly Ser Asp Lys Asp Phe Glu Arg Val Ser Gln Val Leu Tyr Pro
            645             650             655
Arg Lys Pro Tyr Glu Arg Glu Pro Glu Gln Asn Pro Lys Lys Ile Ser
            660             665             670
Leu Thr Ala Tyr Ser Gln Pro Ser Thr Leu Ala Cys Ala Leu Gly Ala
        675             680             685
Phe Glu Ile Phe Lys Glu Ala Gly Phe Thr Pro Asp Phe Ala Ala Gly
        690             695             700
His Ser Leu Gly Glu Phe Ala Ala Leu Tyr Ala Ala Gly Cys Val Asp
705             710             715             720
Arg Asp Glu Leu Phe Glu Leu Val Cys Arg Arg Ala Arg Ile Met Gly
            725             730             735
Gly Lys Asp Ala Pro Ala Thr Pro Lys Gly Cys Met Ala Ala Val Ile
            740             745             750
Gly Pro Asn Ala Glu Asn Ile Lys Val Gln Ala Ala Asn Val Trp Leu
        755             760             765
Gly Asn Ser Asn Ser Pro Ser Gln Thr Val Ile Thr Gly Ser Val Glu
        770             775             780
Gly Ile Gln Ala Glu Ser Ala Arg Leu Gln Lys Glu Gly Phe Arg Val
785             790             795             800
Val Pro Leu Ala Cys Glu Ser Ala Phe His Ser Pro Gln Met Glu Asn
            805             810             815
Ala Ser Ser Ala Phe Lys Asp Val Ile Ser Lys Val Ser Phe Arg Thr
            820             825             830
Pro Lys Ala Glu Thr Lys Leu Phe Ser Asn Val Ser Gly Glu Thr Tyr
        835             840             845
```

-continued

```
Pro Thr Asp Ala Arg Glu Met Leu Thr Gln His Met Thr Ser Ser Val
    850                 855                 860

Lys Phe Leu Thr Gln Val Arg Asn Met His Gln Ala Gly Ala Arg Ile
865                 870                 875                 880

Phe Val Glu Phe Gly Pro Lys Gln Val Leu Ser Lys Leu Val Ser Glu
                885                 890                 895

Thr Leu Lys Asp Asp Pro Ser Val Val Thr Val Ser Val Asn Pro Ala
            900                 905                 910

Ser Gly Thr Asp Ser Asp Ile Gln Leu Arg Asp Ala Ala Val Gln Leu
            915                 920                 925

Val Val Ala Gly Val Asn Leu Gln Gly Phe Asp Lys Trp Asp Ala Pro
    930                 935                 940

Asp Ala Thr Arg Met Gln Ala Ile Lys Lys Arg Thr Thr Leu Arg
945                 950                 955                 960

Leu Ser Ala Ala Thr Tyr Val Ser Asp Lys Thr Lys Lys Val Arg Asp
                965                 970                 975

Ala Ala Met Asn Asp Gly Arg Cys Val Thr Tyr Leu Lys Gly Ala Ala
                980                 985                 990

Pro Leu Ile Lys Ala Pro Glu Pro  Val Val Asp Glu Ala  Ala Lys Arg
            995                 1000                1005

Glu Ala  Glu Arg Leu Gln Lys  Glu Leu Gln Asp Ala  Gln Arg Gln
    1010                1015                1020

Leu Asp  Asp Ala Lys Arg Ala  Ala Ala Glu Ala Asn  Ser Lys Leu
    1025                1030                1035

Ala Ala  Ala Lys Glu Glu Ala  Lys Thr Ala Ala Ala  Ser Ala Lys
    1040                1045                1050

Pro Ala  Val Asp Thr Ala Val  Val Glu Lys His Arg  Ala Ile Leu
    1055                1060                1065

Lys Ser  Met Leu Ala Glu Leu  Asp Gly Tyr Gly Ser  Val Asp Ala
    1070                1075                1080

Ser Ser  Leu Gln Gln Gln Gln  Gln Gln Gln Thr Ala  Pro Ala Pro
    1085                1090                1095

Val Lys  Ala Ala Ala Pro Ala  Ala Pro Val Ala Ser  Ala Pro Ala
    1100                1105                1110

Pro Ala  Val Ser Asn Glu Leu  Leu Glu Lys Ala Glu  Thr Val Val
    1115                1120                1125

Met Glu  Val Leu Ala Ala Lys  Thr Gly Tyr Glu Thr  Asp Met Ile
    1130                1135                1140

Glu Ala  Asp Met Glu Leu Glu  Thr Glu Leu Gly Ile  Asp Ser Ile
    1145                1150                1155

Lys Arg  Val Glu Ile Leu Ser  Glu Val Gln Ala Met  Leu Asn Val
    1160                1165                1170

Glu Ala  Lys Asp Val Asp Ala  Leu Ser Arg Thr Arg  Thr Val Gly
    1175                1180                1185

Glu Val  Val Asn Ala Met Lys  Ala Glu Ile Ala Gly  Ser Ser Ala
    1190                1195                1200

Pro Ala  Pro Ala Ala Ala Ala  Pro Ala Pro Ala Lys  Ala Ala Pro
    1205                1210                1215

Ala Ala  Ala Ala Pro Ala Val  Ser Asn Glu Leu Leu  Glu Lys Ala
    1220                1225                1230

Glu Thr  Val Val Met Glu Val  Leu Ala Ala Lys Thr  Gly Tyr Glu
    1235                1240                1245
```

-continued

```
Thr Asp Met Ile Glu Ser Asp Met Glu Leu Glu Thr Glu Leu Gly
    1250                1255                1260

Ile Asp Ser Ile Lys Arg Val Glu Ile Leu Ser Glu Val Gln Ala
    1265                1270                1275

Met Leu Asn Val Glu Ala Lys Asp Val Asp Ala Leu Ser Arg Thr
    1280                1285                1290

Arg Thr Val Gly Glu Val Val Asn Ala Met Lys Ala Glu Ile Ala
    1295                1300                1305

Gly Gly Ser Ala Pro Ala Pro Ala Ala Ala Ala Pro Gly Pro Ala
    1310                1315                1320

Ala Ala Ala Pro Ala Pro Ala Ala Ala Ala Pro Ala Val Ser Asn
    1325                1330                1335

Glu Leu Leu Glu Lys Ala Glu Thr Val Val Met Glu Val Leu Ala
    1340                1345                1350

Ala Lys Thr Gly Tyr Glu Thr Asp Met Ile Glu Ser Asp Met Glu
    1355                1360                1365

Leu Glu Thr Glu Leu Gly Ile Asp Ser Ile Lys Arg Val Glu Ile
    1370                1375                1380

Leu Ser Glu Val Gln Ala Met Leu Asn Val Glu Ala Lys Asp Val
    1385                1390                1395

Asp Ala Leu Ser Arg Thr Arg Thr Val Gly Glu Val Val Asp Ala
    1400                1405                1410

Met Lys Ala Glu Ile Ala Gly Gly Ser Ala Pro Ala Pro Ala Ala
    1415                1420                1425

Ala Ala Pro Ala Pro Ala Ala Ala Ala Pro Ala Pro Ala Ala Pro
    1430                1435                1440

Ala Pro Ala Val Ser Ser Glu Leu Leu Glu Lys Ala Glu Thr Val
    1445                1450                1455

Val Met Glu Val Leu Ala Ala Lys Thr Gly Tyr Glu Thr Asp Met
    1460                1465                1470

Ile Glu Ser Asp Met Glu Leu Glu Thr Glu Leu Gly Ile Asp Ser
    1475                1480                1485

Ile Lys Arg Val Glu Ile Leu Ser Glu Val Gln Ala Met Leu Asn
    1490                1495                1500

Val Glu Ala Lys Asp Val Asp Ala Leu Ser Arg Thr Arg Thr Val
    1505                1510                1515

Gly Glu Val Val Asp Ala Met Lys Ala Glu Ile Ala Gly Gly Ser
    1520                1525                1530

Ala Pro Ala Pro Ala Ala Ala Pro Ala Pro Ala Ala Ala Ala
    1535                1540                1545

Pro Ala Pro Ala Ala Pro Pro Ala Ala Pro Ala Pro Ala Val
    1550                1555                1560

Ser Ser Glu Leu Leu Glu Lys Ala Glu Thr Val Val Met Glu Val
    1565                1570                1575

Leu Ala Ala Lys Thr Gly Tyr Glu Thr Asp Met Ile Glu Ser Asp
    1580                1585                1590

Met Glu Leu Glu Thr Glu Leu Gly Ile Asp Ser Ile Lys Arg Val
    1595                1600                1605

Glu Ile Leu Ser Glu Val Gln Ala Met Leu Asn Val Glu Ala Lys
    1610                1615                1620

Asp Val Asp Ala Leu Ser Arg Thr Arg Thr Val Gly Glu Val Val
    1625                1630                1635

Asp Ala Met Lys Ala Glu Ile Ala Gly Ser Ser Ala Ser Ala Pro
```

```
                  1640                1645                1650

Ala  Ala  Ala  Ala  Pro  Ala  Pro  Ala  Ala  Ala  Pro  Ala  Pro  Ala
     1655                1660                1665

Ala  Ala  Ala  Pro  Ala  Val  Ser  Asn  Glu  Leu  Leu  Glu  Lys  Ala  Glu
     1670                1675                1680

Thr  Val  Val  Met  Glu  Val  Leu  Ala  Ala  Lys  Thr  Gly  Tyr  Glu  Thr
     1685                1690                1695

Asp  Met  Ile  Glu  Ser  Asp  Met  Glu  Leu  Glu  Thr  Glu  Leu  Gly  Ile
     1700                1705                1710

Asp  Ser  Ile  Lys  Arg  Val  Glu  Ile  Leu  Ser  Glu  Val  Gln  Ala  Met
     1715                1720                1725

Leu  Asn  Val  Glu  Ala  Lys  Asp  Val  Asp  Ala  Leu  Ser  Arg  Thr  Arg
     1730                1735                1740

Thr  Val  Gly  Glu  Val  Val  Asp  Ala  Met  Lys  Ala  Glu  Ile  Ala  Gly
     1745                1750                1755

Gly  Ser  Ala  Pro  Ala  Pro  Ala  Ala  Ala  Pro  Ala  Pro  Ala  Ala
     1760                1765                1770

Ala  Ala  Pro  Ala  Val  Ser  Asn  Glu  Leu  Leu  Glu  Lys  Ala  Glu  Thr
     1775                1780                1785

Val  Val  Met  Glu  Val  Leu  Ala  Ala  Lys  Thr  Gly  Tyr  Glu  Thr  Asp
     1790                1795                1800

Met  Ile  Glu  Ser  Asp  Met  Glu  Leu  Glu  Thr  Glu  Leu  Gly  Ile  Asp
     1805                1810                1815

Ser  Ile  Lys  Arg  Val  Glu  Ile  Leu  Ser  Glu  Val  Gln  Ala  Met  Leu
     1820                1825                1830

Asn  Val  Glu  Ala  Lys  Asp  Val  Asp  Ala  Leu  Ser  Arg  Thr  Arg  Thr
     1835                1840                1845

Val  Gly  Glu  Val  Val  Asp  Ala  Met  Lys  Ala  Glu  Ile  Ala  Gly  Ser
     1850                1855                1860

Ser  Ala  Pro  Ala  Pro  Ala  Ala  Ala  Pro  Ala  Pro  Ala  Ala  Ala
     1865                1870                1875

Ala  Pro  Ala  Pro  Ala  Ala  Ala  Pro  Ala  Val  Ser  Ser  Glu  Leu
     1880                1885                1890

Leu  Glu  Lys  Ala  Glu  Thr  Val  Val  Met  Glu  Val  Leu  Ala  Ala  Lys
     1895                1900                1905

Thr  Gly  Tyr  Glu  Thr  Asp  Met  Ile  Glu  Ser  Asp  Met  Glu  Leu  Glu
     1910                1915                1920

Thr  Glu  Leu  Gly  Ile  Asp  Ser  Ile  Lys  Arg  Val  Glu  Ile  Leu  Ser
     1925                1930                1935

Glu  Val  Gln  Ala  Met  Leu  Asn  Val  Glu  Ala  Lys  Asp  Val  Asp  Ala
     1940                1945                1950

Leu  Ser  Arg  Thr  Arg  Thr  Val  Gly  Glu  Val  Val  Asp  Ala  Met  Lys
     1955                1960                1965

Ala  Glu  Ile  Ala  Gly  Gly  Ser  Ala  Pro  Ala  Pro  Ala  Ala  Ala
     1970                1975                1980

Pro  Ala  Pro  Ala  Ala  Ala  Pro  Ala  Val  Ser  Asn  Glu  Leu  Leu
     1985                1990                1995

Glu  Lys  Ala  Glu  Thr  Val  Val  Met  Glu  Val  Leu  Ala  Ala  Lys  Thr
     2000                2005                2010

Gly  Tyr  Glu  Thr  Asp  Met  Ile  Glu  Ser  Asp  Met  Glu  Leu  Glu  Thr
     2015                2020                2025

Glu  Leu  Gly  Ile  Asp  Ser  Ile  Lys  Arg  Val  Glu  Ile  Leu  Ser  Glu
     2030                2035                2040
```

```
Val Gln Ala Met Leu Asn Val Glu Ala Lys Asp Val Asp Ala Leu
    2045                2050                2055

Ser Arg Thr Arg Thr Val Gly Glu Val Val Asp Ala Met Lys Ala
    2060                2065                2070

Glu Ile Ala Gly Gly Ser Ala Pro Ala Pro Ala Ala Ala Ala Pro
    2075                2080                2085

Ala Ser Ala Gly Ala Ala Pro Ala Val Lys Ile Asp Ser Val His
    2090                2095                2100

Gly Ala Asp Cys Asp Asp Leu Ser Leu Met His Ala Lys Val Val
    2105                2110                2115

Asp Ile Arg Arg Pro Asp Glu Leu Ile Leu Glu Arg Pro Glu Asn
    2120                2125                2130

Arg Pro Val Leu Val Val Asp Asp Gly Ser Glu Leu Thr Leu Ala
    2135                2140                2145

Leu Val Arg Val Leu Gly Ala Cys Ala Val Val Leu Thr Phe Glu
    2150                2155                2160

Gly Leu Gln Leu Ala Gln Arg Ala Gly Ala Ala Ala Ile Arg His
    2165                2170                2175

Lys Ala Ile Lys Glu Ala Glu Gln Arg Phe Gly Ala Leu Gly Gly
    2180                2185                2190

Phe Ile Ser Gln Gln Ala Glu Arg Phe Glu Pro Ala Glu Ile Leu
    2195                2200                2205

Gly Phe Thr Leu Met Cys Ala Lys Phe Ala Lys Ala Ser Leu Cys
    2210                2215                2220

Thr Ala Val Ala Gly Val Leu Ala Lys Asp Leu Ser Ala Glu Ser
    2225                2230                2235

Ala Glu Gly Arg Pro Ala Phe Ile Gly Val Ala Arg Leu Asp Gly
    2240                2245                2250

Arg Leu Gly Phe Thr Ser Gln Gly Thr Ser Asp Ala Leu Lys Arg
    2255                2260                2265

Ala Gln Arg Gly Ala Ile Phe Gly Leu Cys Lys Thr Ile Gly Leu
    2270                2275                2280

Glu Trp Ser Glu Ser Asp Val Phe Ser Arg Gly Val Asp Ile Ala
    2285                2290                2295

Gln Gly Met His Pro Glu Asp Ala Ala Val Ala Ile Val Arg Glu
    2300                2305                2310

Met Ala Cys Ala Asp Ile Arg Ile Arg Glu Val Gly Ile Gly Ala
    2315                2320                2325

Asn Gln Gln Arg Cys Thr Ile Arg Ala Ala Lys Leu Glu Thr Gly
    2330                2335                2340

Asn Pro Gln Arg Gln Ile Ala Lys Asp Asp Val Leu Leu Val Ser
    2345                2350                2355

Gly Gly Ala Arg Gly Ile Thr Pro Leu Cys Ile Arg Glu Ile Thr
    2360                2365                2370

Arg Gln Ile Ala Gly Gly Lys Tyr Ile Leu Leu Gly Arg Ser Lys
    2375                2380                2385

Val Ser Ala Ser Glu Pro Ala Trp Cys Ala Gly Ile Thr Asp Glu
    2390                2395                2400

Lys Ala Val Gln Lys Ala Ala Thr Gln Glu Leu Lys Arg Ala Phe
    2405                2410                2415

Ser Ala Gly Glu Gly Pro Lys Pro Thr Pro Arg Ala Val Thr Lys
    2420                2425                2430
```

```
Leu Val Gly Ser Val Leu Gly Ala Arg Glu Val Arg Ser Ser Ile
    2435            2440                2445

Ala Ala Ile Glu Ala Leu Gly Gly Lys Ala Ile Tyr Ser Ser Cys
    2450            2455                2460

Asp Val Asn Ser Ala Ala Asp Val Ala Lys Ala Val Arg Asp Ala
    2465            2470                2475

Glu Ser Gln Leu Gly Ala Arg Val Ser Gly Ile Val His Ala Ser
    2480            2485                2490

Gly Val Leu Arg Asp Arg Leu Ile Glu Lys Lys Leu Pro Asp Glu
    2495            2500                2505

Phe Asp Ala Val Phe Gly Thr Lys Val Thr Gly Leu Glu Asn Leu
    2510            2515                2520

Leu Ala Ala Val Asp Arg Ala Asn Leu Lys His Met Val Leu Phe
    2525            2530                2535

Ser Ser Leu Ala Gly Phe His Gly Asn Val Gly Gln Ser Asp Tyr
    2540            2545                2550

Ala Met Ala Asn Glu Ala Leu Asn Lys Met Gly Leu Glu Leu Ala
    2555            2560                2565

Lys Asp Val Ser Val Lys Ser Ile Cys Phe Gly Pro Trp Asp Gly
    2570            2575                2580

Gly Met Val Thr Pro Gln Leu Lys Lys Gln Phe Gln Glu Met Gly
    2585            2590                2595

Val Gln Ile Ile Pro Arg Glu Gly Gly Ala Asp Thr Val Ala Arg
    2600            2605                2610

Ile Val Leu Gly Ser Ser Pro Ala Glu Ile Leu Val Gly Asn Trp
    2615            2620                2625

Arg Thr Pro Ser Lys Lys Val Gly Ser Asp Thr Ile Thr Leu His
    2630            2635                2640

Arg Lys Ile Ser Ala Lys Ser Asn Pro Phe Leu Glu Asp His Val
    2645            2650                2655

Ile Gln Gly Arg Arg Val Leu Pro Met Thr Leu Ala Ile Gly Ser
    2660            2665                2670

Leu Ala Glu Thr Cys Leu Gly Leu Phe Pro Gly Tyr Ser Leu Trp
    2675            2680                2685

Ala Ile Asp Asp Ala Gln Leu Phe Lys Gly Val Thr Val Asp Gly
    2690            2695                2700

Asp Val Asn Cys Glu Val Thr Leu Thr Pro Ser Thr Ala Pro Ser
    2705            2710                2715

Gly Arg Val Asn Val Gln Ala Thr Leu Lys Thr Phe Ser Ser Gly
    2720            2725                2730

Lys Leu Val Pro Ala Tyr Arg Ala Val Ile Val Leu Ser Asn Gln
    2735            2740                2745

Gly Ala Pro Pro Ala Asn Ala Thr Met Gln Pro Pro Ser Leu Asp
    2750            2755                2760

Ala Asp Pro Ala Leu Gln Gly Ser Val Tyr Asp Gly Lys Thr Leu
    2765            2770                2775

Phe His Gly Pro Ala Phe Arg Gly Ile Asp Asp Val Leu Ser Cys
    2780            2785                2790

Thr Lys Ser Gln Leu Val Ala Lys Cys Ser Ala Val Pro Gly Ser
    2795            2800                2805

Asp Ala Ala Arg Gly Glu Phe Ala Thr Asp Thr Asp Ala His Asp
    2810            2815                2820

Pro Phe Val Asn Asp Leu Ala Phe Gln Ala Met Leu Val Trp Val
```

```
                    2825                2830                2835
Arg Arg  Thr Leu Gly Gln Ala  Ala Leu Pro Asn Ser  Ile Gln Arg
        2840                2845                2850

Ile Val  Gln His Arg Pro Val  Pro Gln Asp Lys Pro  Phe Tyr Ile
        2855                2860                2865

Thr Leu  Arg Ser Asn Gln Ser  Gly Gly His Ser Gln  His Lys His
        2870                2875                2880

Ala Leu  Gln Phe His Asn Glu  Gln Gly Asp Leu Phe  Ile Asp Val
        2885                2890                2895

Gln Ala  Ser Val Ile Ala Thr  Asp Ser Leu Ala Phe
        2900                2905                2910

<210> SEQ ID NO 55
<211> LENGTH: 2895
<212> TYPE: PRT
<213> ORGANISM: Thraustochytrium aureum

<400> SEQUENCE: 55

Arg Lys Cys Ile Arg Pro Ser Leu Gly His His Trp Ala Ile Ile Gly
1               5                   10                  15

Val Leu Gly Arg Ala Leu Arg Ile Val Arg Pro Ile Arg Tyr Glu Ala
            20                  25                  30

Thr Asn Leu Arg Arg Leu Pro Arg Ser Gly Trp Leu Val Ala Leu Gly
        35                  40                  45

Leu Phe Cys Asp Leu Ser Ser Cys Ala Gly Lys Leu Asp Leu Gln Thr
    50                  55                  60

Arg Asp Thr Ala Lys Asp Pro Cys Cys Lys Arg Lys Trp Ser Ala Ser
65                  70                  75                  80

Arg Ala Pro Pro Arg Pro Arg Ala Glu Ala Asp Lys Ala Ser Asn Glu
                85                  90                  95

Met Glu Thr Lys Asp Asp Arg Val Ala Ile Val Gly Met Ser Ala Ile
            100                 105                 110

Leu Pro Cys Gly Glu Ser Val Arg Glu Ser Trp Glu Ala Ile Arg Glu
        115                 120                 125

Gly Leu Asp Cys Leu Gln Asp Leu Pro Ala Asp Arg Val Asp Ile Thr
    130                 135                 140

Ala Tyr Tyr Asp Pro Asn Lys Thr Thr Lys Asp Lys Ile Tyr Cys Lys
145                 150                 155                 160

Arg Gly Gly Phe Ile Pro Glu Tyr Asp Phe Asp Ala Arg Glu Phe Gly
                165                 170                 175

Leu Asn Met Phe Gln Met Glu Asp Ser Asp Ala Asn Gln Thr Val Thr
            180                 185                 190

Leu Leu Lys Val Lys Glu Ala Leu Glu Asp Ala Gly Val Glu Pro Phe
        195                 200                 205

Thr Lys Lys Lys Lys Asn Ile Gly Cys Val Leu Gly Ile Gly Gly Gly
    210                 215                 220

Gln Lys Ala Ser His Glu Phe Tyr Ser Arg Leu Asn Tyr Val Val Val
225                 230                 235                 240

Glu Lys Val Leu Arg Lys Met Asn Leu Pro Asp Glu Val Val Glu Ala
                245                 250                 255

Ala Val Glu Lys Tyr Lys Ala Asn Phe Pro Glu Trp Arg Leu Asp Ser
            260                 265                 270

Phe Pro Gly Phe Leu Gly Asn Val Thr Ala Gly Arg Cys Ser Asn Val
        275                 280                 285
```

```
Phe Asn Met Glu Gly Met Asn Cys Val Val Asp Ala Ala Cys Ala Ser
    290                 295                 300

Ser Leu Ile Ala Ile Lys Val Ala Ile Asp Glu Leu Leu His Gly Asp
305                 310                 315                 320

Cys Asp Thr Met Ile Ala Gly Ala Thr Cys Thr Asp Asn Ser Ile Gly
                325                 330                 335

Met Tyr Met Ala Phe Ser Lys Thr Pro Val Phe Ser Thr Asp Gln Ser
                340                 345                 350

Val Lys Ala Tyr Asp Ala Lys Thr Lys Gly Met Leu Ile Gly Glu Gly
            355                 360                 365

Ser Ala Met Val Val Leu Lys Arg Tyr Ala Asp Ala Val Arg Asp Gly
370                 375                 380

Asp Glu Ile His Ala Val Ile Arg Ala Cys Ala Ser Ser Asp Gly
385                 390                 395                 400

Lys Ala Ala Gly Ile Tyr Ala Pro Thr Val Ser Gly Gln Glu Glu Ala
                405                 410                 415

Leu Arg Arg Ala Tyr Ala Arg Ala Gly Val Asp Pro Ser Thr Val Thr
            420                 425                 430

Leu Val Glu Gly His Gly Thr Gly Thr Pro Val Gly Asp Arg Ile Glu
435                 440                 445

Leu Thr Ala Leu Arg Asn Val Phe Asp Ala Ala Asn Lys Gly Arg Lys
450                 455                 460

Glu Thr Val Ala Val Gly Ser Ile Lys Ser Gln Ile Gly His Leu Lys
465                 470                 475                 480

Ala Val Ala Gly Phe Ala Gly Leu Val Lys Val Val Met Ala Leu Lys
                485                 490                 495

His Lys Thr Leu Pro Gln Thr Ile Asn Val His Asp Pro Ala Leu
                500                 505                 510

His Asp Gly Ser Pro Ile Gln Asp Ser Ser Leu Tyr Ile Asn Thr Met
            515                 520                 525

Asn Arg Pro Trp Phe Thr Ala Pro Gly Val Pro Arg Arg Ala Gly Ile
530                 535                 540

Ser Ser Phe Gly Phe Gly Gly Ala Asn Tyr His Ala Val Leu Glu Glu
545                 550                 555                 560

Ala Glu Pro Glu His Ala Lys Pro Tyr Arg Met Asn Gln Val Pro Gln
                565                 570                 575

Pro Val Leu Leu His Ala Ser Ala Ser Ala Leu Ala Ser Ile Cys
            580                 585                 590

Asp Ala Gln Ala Asp Ala Leu Gln Ala Val Ser Pro Glu Ala Ser
            595                 600                 605

Lys His Ala Asp Tyr Arg Ala Ile Val Ala Phe His Glu Ala Phe Lys
            610                 615                 620

Leu Arg Ala Gly Val Pro Ala Gly His Ala Arg Ile Gly Phe Val Ser
625                 630                 635                 640

Gly Ser Ala Ala Ala Thr Leu Ala Val Leu Arg Ala Ala Ser Ala Lys
                645                 650                 655

Leu Lys Gln Ser Ser Ala Thr Leu Glu Trp Thr Leu Leu Arg Glu Gly
                660                 665                 670

Val Thr Tyr Arg Ser Ala Ala Met His Thr Pro Gly Ser Val Ala Ala
            675                 680                 685

Leu Phe Ala Gly Gln Gly Ala Gln Tyr Thr His Met Phe Ala Asp Val
690                 695                 700

Ala Met Asn Trp Pro Pro Phe Arg Ser Ala Val Gln Glu Met Asp Ala
```

```
                705                 710                 715                 720
Ala Gln Val Thr Ala Ala Pro Lys Arg Leu Ser Glu Val Leu Tyr
                    725                 730                 735

Pro Arg Lys Pro Tyr Ala Ala Glu Pro Glu Gln Asp Asn Lys Ala Ile
                    740                 745                 750

Ser Met Thr Ile Asn Ser Gln Pro Ala Leu Met Ala Cys Ala Ala Gly
                    755                 760                 765

Ala Phe Glu Val Phe Arg Gln Ala Gly Leu Ala Pro Asp His Val Ala
                    770                 775                 780

Gly His Ser Leu Gly Glu Phe Gly Ala Leu Ala Ala Gly Cys Ala
785                 790                 795                 800

Ser Arg Glu Glu Leu Phe Arg Leu Val Cys Ser Arg Ala Lys Ala Met
                    805                 810                 815

Gln Asp Val Pro Gln Gly Asp Gly Ala Trp Leu Ala Asn Cys Asn Ser
                    820                 825                 830

Pro Ser Gln Val Val Ile Ser Gly Asp Lys Thr Ala Val Glu Arg Glu
                    835                 840                 845

Ser Ser Arg Leu Ala Gly Leu Gly Phe Arg Ile Ile Pro Leu Ala Cys
                    850                 855                 860

Glu Gly Ala Phe His Ser Pro His Met Thr Ala Ala Gln Ala Thr Phe
865                 870                 875                 880

Gln Ala Ala Leu Asp Ser Leu Lys Ile Ser Thr Pro Thr Asn Gly Ala
                    885                 890                 895

Arg Leu Tyr Asn Asn Val Ser Gly Lys Thr Cys Arg Ser Leu Gly Glu
                    900                 905                 910

Leu Arg Asp Cys Leu Gly Lys His Met Thr Ser Pro Val Leu Phe Gln
                    915                 920                 925

Ala Gln Val Glu Asn Met Tyr Ala Ala Gly Ala Arg Ile Phe Val Glu
                    930                 935                 940

Phe Gly Pro Lys Gln Val Leu Ser Lys Leu Val Gly Glu Ile Leu Ala
945                 950                 955                 960

Asp Lys Ser Asp Phe Val Thr Val Ala Val Asn Ser Ser Ser Ser Lys
                    965                 970                 975

Asp Ser Asp Val Gln Leu Arg Glu Ala Ala Ala Lys Leu Ala Val Leu
                    980                 985                 990

Gly Val Pro Leu Ala Asn Phe Asp Pro Trp Glu Leu Cys Asp Ala Arg
                    995                 1000                1005

Arg Leu Arg Glu Cys Pro Arg Ser Lys Thr Thr Leu Arg Leu Ser
    1010                1015                1020

Ala Ala Thr Tyr Val Ser Asn Lys Thr Leu Ala Ala Arg Glu Lys
    1025                1030                1035

Val Met Glu Asp Asn Cys Asp Phe Ser Leu Phe Ala Ser Gly
    1040                1045                1050

Pro Ala Ser Gln Glu Met Glu Arg Glu Ile Ala Asn Leu Arg Ala
    1055                1060                1065

Glu Leu Glu Ala Ala Gln Arg Gln Leu Asp Thr Ala Lys Thr Gln
    1070                1075                1080

Leu Ala Arg Lys Gln Val Gln Asp Pro Thr Ala Asp Arg Gln Arg
    1085                1090                1095

Asp Met Ile Ala Lys His Arg Ser Thr Leu Ala Ala Met Val Lys
    1100                1105                1110

Glu Phe Glu Ala Leu Ala Ser Gly Ser Pro Cys Ala Val Pro Phe
    1115                1120                1125
```

-continued

```
Ala Pro Val Val Asp Thr Ala Val Glu Asp Val Pro Phe Ala Asp
    1130               1135               1140

Lys Val Ser Thr Pro Pro Gln Val Thr Ser Ala Pro Ile Ala
    1145               1150               1155

Glu Leu Ala Arg Ala Glu Ala Val Val Met Glu Val Leu Ala Ala
    1160               1165               1170

Lys Thr Gly Tyr Glu Val Asp Met Ile Glu Ala Asp Met Leu Leu
    1175               1180               1185

Asp Ala Glu Leu Gly Ile Asp Ser Val Lys Arg Ile Glu Ile Leu
    1190               1195               1200

Ala Ala Val Gln Ala Gln Leu Gly Val Glu Ala Lys Asp Val Asp
    1205               1210               1215

Ala Leu Ser Arg Thr Arg Thr Val Gly Glu Val Val Asp Ala Met
    1220               1225               1230

Lys Ala Glu Ile Gly Gly Gln Ala Thr Ser Ala Pro Ser Pro Met
    1235               1240               1245

Ala Gln Pro Gln Ala Ser Ala Pro Ser Pro Ser Pro Thr Ala Ser
    1250               1255               1260

Val Leu Pro Lys Pro Val Ala Leu Pro Ala Ser Val Asp Pro Ala
    1265               1270               1275

Lys Leu Ala Arg Ala Glu Ala Val Val Met Glu Val Leu Ala Ala
    1280               1285               1290

Lys Thr Gly Tyr Glu Val Asp Met Ile Glu Ala Asp Met Leu Leu
    1295               1300               1305

Asp Ala Glu Leu Gly Ile Asp Ser Val Lys Arg Ile Glu Ile Leu
    1310               1315               1320

Ala Ala Val Gln Ala Gln Leu Gly Val Glu Ala Lys Asp Val Asp
    1325               1330               1335

Ala Leu Ser Arg Thr Arg Thr Val Gly Glu Val Val Asp Ala Met
    1340               1345               1350

Lys Ala Glu Ile Gly Gly Gln Ala Thr Ser Ala Pro Ala Ser Val
    1355               1360               1365

Ala Gln Pro Gln Ala Ser Ala Pro Ser Pro Ser Ala Thr Thr Ala
    1370               1375               1380

Ser Val Leu Pro Lys Pro Val Ala Ala Pro Thr Ser Ala Asp Pro
    1385               1390               1395

Ala Lys Leu Ala Arg Ala Glu Ala Val Val Met Glu Val Leu Ala
    1400               1405               1410

Ala Lys Thr Gly Tyr Glu Val Asp Met Ile Glu Ala Asp Met Leu
    1415               1420               1425

Leu Asp Ala Glu Leu Gly Ile Asp Ser Val Lys Arg Ile Glu Ile
    1430               1435               1440

Leu Ala Ala Val Gln Ala Gln Leu Gly Val Glu Ala Lys Asp Val
    1445               1450               1455

Asp Ala Leu Ser Arg Thr Arg Thr Val Gly Glu Val Val Glu Ala
    1460               1465               1470

Met Lys Ala Glu Ile Gly Gly Gln Ala Thr Ser Ala Pro Ala Ser
    1475               1480               1485

Val Ala Gln Pro Gln Ile Ser Val Ser Pro Thr Pro Leu Ala Ala
    1490               1495               1500

Ser Pro Ser Ala Asp Pro Ala Lys Leu Ala Arg Ala Glu Ala Val
    1505               1510               1515
```

```
Val Met Glu Val Leu Ala Ala Lys Thr Gly Tyr Glu Val Asp Met
    1520                1525                1530

Ile Glu Ala Asp Met Leu Leu Asp Ala Glu Leu Gly Ile Asp Ser
    1535                1540                1545

Val Lys Arg Ile Glu Ile Leu Ala Ala Val Gln Ala Gln Leu Gly
    1550                1555                1560

Val Glu Ala Lys Asp Val Asp Ala Leu Ser Arg Thr Arg Thr Val
    1565                1570                1575

Gly Glu Val Val Asp Ala Met Lys Ala Glu Ile Gly Gly Gln Ala
    1580                1585                1590

Thr Ser Ala Pro Ala Ser Val Ala Gln Pro Gln Ala Ser Ala Pro
    1595                1600                1605

Ser Pro Ser Ala Thr Ala Ser Val Leu Pro Lys Pro Val Ala Ala
    1610                1615                1620

Pro Thr Ser Ala Asp Pro Ala Lys Leu Ala Arg Ala Glu Ala Val
    1625                1630                1635

Val Met Glu Val Leu Ala Ala Lys Thr Gly Tyr Glu Val Asp Met
    1640                1645                1650

Ile Glu Ala Asp Met Leu Leu Asp Ala Glu Leu Gly Ile Asp Ser
    1655                1660                1665

Val Lys Arg Ile Glu Ile Leu Ala Ala Val Gln Ala Gln Leu Gly
    1670                1675                1680

Val Glu Ala Lys Asp Val Asp Ala Leu Ser Arg Thr Arg Thr Val
    1685                1690                1695

Gly Glu Val Val Glu Ala Met Lys Ala Glu Ile Gly Gly Gln Ala
    1700                1705                1710

Thr Ser Ala Pro Ala Ser Met Ala Gln Pro Gln Ile Ser Val Ser
    1715                1720                1725

Pro Thr Pro Leu Ala Ala Ser Pro Ser Ala Asp Pro Ala Lys Leu
    1730                1735                1740

Ala Arg Ala Glu Ala Val Val Met Glu Val Leu Ala Ala Lys Thr
    1745                1750                1755

Gly Tyr Glu Val Asp Met Ile Glu Ala Asp Met Leu Leu Asp Ala
    1760                1765                1770

Glu Leu Gly Ile Asp Ser Val Lys Arg Ile Glu Ile Leu Ala Ala
    1775                1780                1785

Val Gln Ala Gln Leu Gly Val Glu Ala Lys Asp Val Asp Ala Leu
    1790                1795                1800

Ser Arg Thr Arg Thr Val Gly Glu Val Val Asp Ala Met Lys Ala
    1805                1810                1815

Glu Ile Gly Gly Gln Ala Thr Ser Ala Pro Ala Ser Val Ala Gln
    1820                1825                1830

Pro Gln Ala Ser Ala Pro Ser Pro Ser Ala Thr Ala Ser Ala Pro
    1835                1840                1845

Val Thr Pro Leu Ala Ala Pro Ala Ser Val Asp Pro Ala Lys Leu
    1850                1855                1860

Ala Arg Ala Glu Ala Val Val Met Glu Val Leu Ala Ala Lys Thr
    1865                1870                1875

Gly Tyr Glu Val Asp Met Ile Glu Ala Asp Met Leu Leu Asp Ala
    1880                1885                1890

Glu Leu Gly Ile Asp Ser Val Lys Arg Ile Glu Ile Leu Ala Ala
    1895                1900                1905

Val Gln Ala Gln Leu Gly Val Glu Ala Lys Asp Val Asp Ala Leu
```

-continued

```
                1910                1915                1920
Ser Arg Thr Arg Thr Val Gly Glu Val Val Asp Ala Met Lys Ala
    1925                1930                1935
Glu Ile Gly Gly Gln Ala Thr Ser Ala Pro Ala Ser Val Ala Gln
    1940                1945                1950
Pro Gln Ala Ser Ala Pro Ser Pro Ser Ala Thr Ala Ser Val Leu
    1955                1960                1965
Pro Lys Pro Val Ala Ser Pro Ala Ser Val Asp Pro Ala Lys Leu
    1970                1975                1980
Ala Arg Ala Glu Ala Val Val Met Glu Val Leu Ala Ala Lys Thr
    1985                1990                1995
Gly Tyr Glu Val Asp Met Ile Asp Ala Asp Met Leu Leu Asp Ala
    2000                2005                2010
Glu Leu Gly Ile Asp Ser Val Lys Arg Ile Glu Ile Leu Ala Ala
    2015                2020                2025
Val Gln Ala Gln Leu Gly Val Glu Ala Lys Asp Val Asp Ala Leu
    2030                2035                2040
Ser Arg Thr Arg Thr Val Gly Glu Val Val Glu Ala Met Lys Ala
    2045                2050                2055
Glu Ile Gly Ala Ala Gly Pro Asn Asp Ala Gln Ala Ala Ser Gly
    2060                2065                2070
His Leu Phe Gly Thr Gly Cys Glu Asp Leu Ser Leu Cys Ser Ala
    2075                2080                2085
Ser Val Val Glu Ile Ala Arg Cys Ser Glu Leu Ala Leu Glu Arg
    2090                2095                2100
Pro Met Asp Arg Pro Ile Leu Ile Val Ser Asp Gly Ser Ala Leu
    2105                2110                2115
Pro Ala Ala Leu Ala Ser Arg Leu Gly Ser Cys Ala Val Ile Leu
    2120                2125                2130
Thr Thr Ala Gly Glu Thr Asp Gln Ser Val Arg Ser Thr Lys His
    2135                2140                2145
Val Asp Met Glu Gly Trp Gly Glu Ala Asp Leu Val Arg Ala Leu
    2150                2155                2160
Glu Ala Val Glu Ser Arg Phe Gly Val Pro Gly Gly Val Val Val
    2165                2170                2175
Leu Glu Arg Ala Ser Glu Thr Ala Arg Asp Gln Leu Gly Phe Ala
    2180                2185                2190
Leu Leu Leu Ala Lys His Ser Ser Lys Ala Leu Asn Gln Gln Ile
    2195                2200                2205
Pro Gly Gly Arg Ala Cys Phe Val Gly Val Ser Arg Ile Asp Gly
    2210                2215                2220
Lys Leu Gly Leu Ser Gly Ala Cys Ala Lys Gly Lys Gly Trp Ala
    2225                2230                2235
Glu Ala Ala Glu Ile Ala Gln Gln Gly Ala Val Ala Gly Leu Cys
    2240                2245                2250
Lys Thr Leu Asp Leu Glu Trp Pro His Val Phe Ala Arg Ser Ile
    2255                2260                2265
Asp Ile Glu Leu Gly Ala Asn Glu Glu Thr Ala Ala Gln Ala Ile
    2270                2275                2280
Phe Glu Glu Leu Ser Cys Pro Asp Leu Thr Val Arg Glu Ala Gly
    2285                2290                2295
Tyr Thr Lys Asp Gly Lys Arg Trp Thr Thr Glu Ala Arg Pro Val
    2300                2305                2310
```

-continued

Gly Leu Gly Lys Pro Lys Gln Ala Leu Arg Ser Ser Asp Val Phe
2315                2320                2325

Leu Val Ser Gly Gly Ala Arg Gly Ile Thr Pro Val Cys Val Arg
2330                2335                2340

Glu Leu Ala Lys Ser Ile Ser Gly Gly Thr Phe Val Leu Leu Gly
2345                2350                2355

Arg Ser Pro Leu Ala Asp Asp Pro Ala Trp Ala Cys Gly Val Glu
2360                2365                2370

Glu Ala Asn Ile Gly Thr Ala Ala Met Ala His Leu Lys Ala Glu
2375                2380                2385

Phe Ala Ala Gly Arg Gly Pro Lys Pro Thr Pro Lys Ala His Lys
2390                2395                2400

Ala Leu Val Gly Ser Val Leu Gly Ala Arg Glu Val Leu Gly Ser
2405                2410                2415

Leu Glu Ser Ile Arg Ala Gln Gly Ala Arg Ala Glu Tyr Val Ser
2420                2425                2430

Cys Asp Val Ser Cys Ala Glu Arg Val Lys Ala Val Val Asp Asp
2435                2440                2445

Leu Glu Arg Arg Val Gly Ala Val Thr Gly Val Val His Ala Ser
2450                2455                2460

Gly Val Leu Arg Asp Lys Ser Val Glu Arg Leu Glu Leu Ala Asp
2465                2470                2475

Phe Glu Val Val Tyr Gly Thr Lys Val Asp Gly Leu Leu Asn Leu
2480                2485                2490

Leu Gln Ala Val Asp Arg Pro Lys Leu Arg His Leu Val Leu Phe
2495                2500                2505

Ser Ser Leu Ala Gly Phe His Gly Asn Thr Gly Gln Ala Val Tyr
2510                2515                2520

Ala Met Ala Asn Glu Ala Leu Asn Lys Met Ala Phe His Leu Glu
2525                2530                2535

Thr Ala Met Pro Gly Leu Ser Val Lys Thr Ile Gly Phe Gly Pro
2540                2545                2550

Trp Asp Gly Gly Met Val Asn Asp Ala Leu Lys Ala His Phe Ala
2555                2560                2565

Ser Met Gly Val Gln Ile Ile Pro Leu Asp Gly Gly Ala Glu Thr
2570                2575                2580

Val Ser Arg Ile Ile Gly Ala Cys Ser Pro Thr Gln Val Leu Val
2585                2590                2595

Gly Asn Trp Gly Leu Pro Pro Val Val Pro Asn Ala Ser Val His
2600                2605                2610

Lys Ile Thr Val Arg Leu Gly Gly Glu Ser Ala Asn Pro Phe Leu
2615                2620                2625

Ser Ser His Thr Ile Gln Gly Arg Lys Val Leu Pro Met Thr Val
2630                2635                2640

Ala Leu Gly Leu Leu Ala Glu Ala Ala Arg Gly Leu Tyr Val Gly
2645                2650                2655

His Gln Val Val Gly Ile Glu Asp Ala Gln Val Phe Gln Gly Val
2660                2665                2670

Val Leu Asp Lys Gly Ala Thr Cys Glu Val Gln Leu Arg Arg Glu
2675                2680                2685

Ser Ser Thr Ala Ser Pro Ser Glu Val Val Leu Ser Ala Ser Leu
2690                2695                2700

-continued

```
Asn Val Phe Ala Ala Gly Lys Val Val Pro Ala Tyr Arg Ala His
    2705                2710                2715

Val Val Leu Gly Ala Ser Gly Pro Arg Thr Gly Val Gln Leu
2720                2725                2730

Glu Leu Lys Asp Leu Gly Val Asp Ala Asp Pro Ala Cys Ser Val
2735                2740                2745

Gly Lys Gly Ala Leu Tyr Asp Gly Arg Thr Leu Phe His Gly Pro
    2750                2755                2760

Ala Phe Gln Tyr Met Asp Glu Val Leu Arg Cys Ser Pro Ala Glu
2765                2770                2775

Leu Ala Val Arg Cys Arg Val Val Pro Ser Ala Ala Gln Asp Arg
    2780                2785                2790

Gly Gln Phe Val Ser Arg Gly Val Leu Tyr Asp Pro Phe Leu Asn
2795                2800                2805

Asp Thr Val Phe Gln Ala Leu Leu Val Trp Ala Arg Leu Val Arg
    2810                2815                2820

Asp Ser Ala Ser Leu Pro Ser Asn Val Glu Arg Ile Ser Phe His
2825                2830                2835

Gly Gln Pro Pro Ser Glu Gly Glu Val Phe Tyr Thr Thr Leu Lys
    2840                2845                2850

Leu Asp Ser Ala Ala Ser Gly Pro Leu Asp Pro Ile Ala Lys Ala
2855                2860                2865

Gln Phe Phe Leu His Arg Ala Cys Gly Ala Val Phe Ala Ser Gly
    2870                2875                2880

Arg Ala Ser Val Val Leu Asn Lys Ala Leu Ser Phe
2885                2890                2895

<210> SEQ ID NO 56
<211> LENGTH: 2811
<212> TYPE: PRT
<213> ORGANISM: Thraustochytrium sp.

<400> SEQUENCE: 56

Met Lys Asp Met Glu Asp Arg Arg Val Ala Ile Val Gly Met Ser Ala
1               5                   10                  15

His Leu Pro Cys Gly Thr Asp Val Lys Glu Ser Trp Gln Ala Ile Arg
                20                  25                  30

Asp Gly Ile Asp Cys Leu Ser Asp Leu Pro Ala Asp Arg Leu Asp Val
            35                  40                  45

Thr Ala Tyr Tyr Asn Pro Asn Lys Ala Thr Lys Asp Lys Ile Tyr Cys
        50                  55                  60

Lys Arg Gly Gly Phe Ile Pro Asn Tyr Asp Phe Asp Pro Arg Glu Phe
65                  70                  75                  80

Gly Leu Asn Met Phe Gln Met Glu Asp Ser Ala Asn Gln Thr Leu
                85                  90                  95

Thr Leu Leu Lys Val Lys Gln Ala Leu Glu Asp Ala Ser Ile Glu Pro
            100                 105                 110

Phe Thr Lys Glu Lys Asn Ile Gly Cys Val Leu Gly Ile Gly Gly
        115                 120                 125

Gly Gln Lys Ala Ser His Glu Phe Tyr Ser Arg Leu Asn Tyr Val Val
    130                 135                 140

Val Glu Lys Val Leu Arg Lys Met Gly Leu Pro Asp Ala Asp Val Glu
145                 150                 155                 160

Glu Ala Val Glu Lys Tyr Lys Ala Asn Phe Pro Glu Trp Arg Leu Asp
                165                 170                 175
```

```
Ser Phe Pro Gly Phe Leu Gly Asn Val Thr Ala Gly Arg Cys Ser Asn
            180                 185                 190

Thr Phe Asn Met Glu Gly Met Asn Cys Val Val Asp Ala Ala Cys Ala
        195                 200                 205

Ser Ser Leu Ile Ala Ile Lys Val Ala Val Glu Glu Leu Leu Phe Gly
    210                 215                 220

Asp Cys Asp Thr Met Ile Ala Gly Ala Thr Cys Thr Asp Asn Ser Leu
225                 230                 235                 240

Gly Met Tyr Met Ala Phe Ser Lys Thr Pro Val Phe Ser Thr Asp Pro
                245                 250                 255

Ser Val Arg Ala Tyr Asp Glu Lys Thr Lys Gly Met Leu Ile Gly Glu
            260                 265                 270

Gly Ser Ala Met Phe Val Leu Lys Arg Tyr Ala Asp Ala Val Arg Asp
        275                 280                 285

Gly Asp Thr Ile His Ala Val Leu Arg Ser Cys Ser Ser Ser Ser Asp
    290                 295                 300

Gly Lys Ala Ala Gly Ile Tyr Thr Pro Thr Ile Ser Gly Gln Glu Glu
305                 310                 315                 320

Ala Leu Arg Arg Ala Tyr Ala Arg Ala Gly Val Cys Pro Ser Thr Ile
                325                 330                 335

Gly Leu Val Glu Gly His Gly Thr Gly Thr Pro Val Gly Asp Arg Ile
            340                 345                 350

Glu Leu Thr Ala Leu Arg Asn Leu Phe Asp Lys Ala Phe Gly Ser Lys
        355                 360                 365

Lys Glu Gln Ile Ala Val Gly Ser Ile Lys Ser Gln Ile Gly His Leu
    370                 375                 380

Lys Ser Val Ala Gly Phe Ala Gly Leu Val Lys Ala Val Leu Ala Leu
385                 390                 395                 400

Lys His Lys Thr Leu Pro Gly Ser Ile Asn Val Asp Gln Pro Pro Leu
                405                 410                 415

Leu Tyr Asp Gly Thr Gln Ile Gln Asp Ser Ser Leu Tyr Ile Asn Lys
            420                 425                 430

Thr Asn Arg Pro Trp Phe Thr Gln Asn Lys Leu Pro Arg Arg Ala Gly
        435                 440                 445

Val Ser Ser Phe Gly Phe Gly Gly Ala Asn Tyr His Ala Val Leu Glu
    450                 455                 460

Glu Phe Glu Pro Glu His Glu Lys Pro Tyr Arg Leu Asn Thr Val Gly
465                 470                 475                 480

His Pro Val Leu Leu Tyr Ala Pro Ser Val Glu Ala Leu Lys Val Leu
                485                 490                 495

Cys Asn Asp Gln Leu Ala Glu Leu Thr Ile Ala Leu Glu Glu Ala Lys
            500                 505                 510

Thr His Lys Asn Val Asp Lys Val Cys Gly Tyr Lys Phe Ile Asp Glu
        515                 520                 525

Phe Gln Leu Gln Gly Ser Cys Pro Pro Glu Asn Pro Arg Val Gly Phe
    530                 535                 540

Leu Ala Thr Leu Pro Thr Ser Asn Ile Ile Val Ala Leu Lys Ala Ile
545                 550                 555                 560

Leu Ala Gln Leu Asp Ala Lys Pro Asp Ala Lys Lys Trp Asp Leu Pro
                565                 570                 575

His Lys Lys Ala Phe Gly Ala Thr Phe Ala Ser Ser Ser Val Lys Gly
            580                 585                 590
```

```
Ser Val Ala Ala Leu Phe Ala Gly Gln Gly Thr Gln Tyr Leu Asn Met
        595                 600                 605

Phe Ser Asp Val Ala Met Asn Trp Pro Pro Phe Arg Asp Ser Ile Val
610                 615                 620

Ala Met Glu Glu Ala Gln Thr Glu Val Phe Glu Gly Gln Val Glu Pro
625                 630                 635                 640

Ile Ser Lys Val Leu Phe Pro Arg Glu Arg Tyr Ala Ser Glu Ser Glu
                645                 650                 655

Gln Gly Asn Glu Leu Leu Cys Leu Thr Glu Tyr Ser Gln Pro Thr Thr
                660                 665                 670

Ile Ala Ala Ala Val Gly Ala Phe Asp Ile Phe Lys Ala Ala Gly Phe
                675                 680                 685

Lys Pro Asp Met Val Gly Gly His Ser Leu Gly Glu Phe Ala Ala Leu
690                 695                 700

Tyr Ala Ala Gly Ser Ile Ser Arg Asp Asp Leu Tyr Lys Leu Val Cys
705                 710                 715                 720

Lys Arg Ala Lys Ala Met Ala Asn Ala Ser Asp Gly Ala Met Ala Ala
                725                 730                 735

Val Ile Gly Pro Asp Ala Arg Leu Val Thr Pro Gln Asn Ser Asp Val
                740                 745                 750

Tyr Val Ala Asn Phe Asn Ser Ala Thr Gln Val Val Ile Ser Gly Thr
                755                 760                 765

Val Gln Gly Val Lys Glu Glu Ser Lys Leu Leu Ile Ser Lys Gly Phe
                770                 775                 780

Arg Val Leu Pro Leu Lys Cys Gln Gly Ala Phe His Ser Pro Leu Met
785                 790                 795                 800

Gly Pro Ser Glu Asp Ser Phe Lys Ser Leu Val Glu Thr Cys Thr Ile
                805                 810                 815

Ser Pro Pro Lys Asn Val Lys Phe Phe Cys Asn Val Ser Gly Lys Glu
                820                 825                 830

Ser Pro Asn Pro Lys Gln Thr Leu Lys Ser His Met Thr Ser Ser Val
                835                 840                 845

Gln Phe Glu Glu Gln Ile Arg Asn Met Tyr Asp Ala Gly Ala Arg Val
850                 855                 860

Phe Leu Glu Phe Gly Pro Arg Gln Val Leu Ala Lys Leu Ile Ala Glu
865                 870                 875                 880

Met Phe Pro Ser Cys Thr Ala Ile Ser Val Asn Pro Ala Ser Ser Gly
                885                 890                 895

Asp Ser Asp Val Gln Leu Arg Leu Ala Ala Val Lys Phe Ala Val Ser
                900                 905                 910

Gly Ala Ala Leu Ser Thr Phe Asp Pro Trp Glu Tyr Arg Lys Pro Gln
                915                 920                 925

Asp Leu Leu Ile Arg Lys Pro Arg Lys Thr Ala Leu Val Leu Ser Ala
                930                 935                 940

Ala Thr Tyr Val Ser Pro Lys Thr Leu Ala Glu Arg Lys Lys Ala Met
945                 950                 955                 960

Glu Asp Ile Lys Leu Val Ser Ile Thr Pro Arg Asp Ser Met Val Ser
                965                 970                 975

Ile Gly Lys Ile Ala Gln Glu Val Arg Thr Ala Lys Gln Pro Leu Glu
                980                 985                 990

Thr Glu Ile Arg Arg Leu Asn Lys Glu Leu Glu His Leu Lys Arg Glu
                995                 1000                1005

Leu Ala Ala Ala Lys Ala Ser Val Lys Ser Ala Ser Lys Ser Ser
```

```
                 1010                1015                1020
Lys Glu Arg Ser Val Leu Ser Lys His Arg Ala Leu Leu Gln Asn
         1025                1030                1035
Ile Leu Gln Asp Tyr Asp Asp Leu Arg Val Val Pro Phe Ala Val
         1040                1045                1050
Arg Ser Val Ala Val Asp Asn Thr Ala Pro Tyr Ala Asp Gln Val
         1055                1060                1065
Ser Thr Pro Ala Ser Glu Arg Ser Ala Ser Pro Leu Phe Glu Lys
         1070                1075                1080
Arg Ser Ser Val Ser Ser Ala Arg Leu Ala Glu Ala Glu Ala Ala
         1085                1090                1095
Val Leu Ser Val Leu Ala Asp Lys Thr Gly Tyr Asp Ser Ser Met
         1100                1105                1110
Ile Glu Met Asp Met Asp Leu Glu Ser Glu Leu Gly Val Asp Ser
         1115                1120                1125
Ile Lys Arg Val Glu Ile Met Ser Glu Val Gln Thr Leu Leu Ser
         1130                1135                1140
Val Glu Val Ser Asp Val Asp Ala Leu Ser Arg Thr Lys Thr Val
         1145                1150                1155
Gly Asp Val Ile Glu Ala Met Lys Leu Glu Leu Gly Gly Pro Gln
         1160                1165                1170
Gly Gln Thr Leu Thr Ala Glu Ser Ile Arg Gln Pro Pro Val Ser
         1175                1180                1185
Glu Pro Ala Val Pro Thr Ser Ser Ser Ser Ile Ala Asn Val
         1190                1195                1200
Ser Ser Ala Arg Leu Ala Glu Ala Glu Ala Ala Val Leu Ser Val
         1205                1210                1215
Leu Ala Asp Lys Thr Gly Tyr Asp Ser Ser Met Ile Glu Met Asp
         1220                1225                1230
Met Asp Leu Glu Ser Glu Leu Gly Val Asp Ser Ile Lys Arg Val
         1235                1240                1245
Glu Ile Met Ser Glu Val Gln Thr Leu Leu Ser Val Glu Val Ser
         1250                1255                1260
Asp Val Asp Ala Leu Ser Arg Thr Lys Thr Val Gly Asp Val Ile
         1265                1270                1275
Glu Ala Met Lys Leu Glu Leu Gly Gly Pro Gln Gly Gln Thr Leu
         1280                1285                1290
Thr Ala Glu Ser Ile Arg Gln Pro Pro Val Ser Glu Pro Ala Val
         1295                1300                1305
Pro Thr Ser Ser Ser Ser Ile Ala Asn Val Ser Ser Ala Arg
         1310                1315                1320
Leu Ala Glu Ala Glu Ala Ala Val Leu Ser Val Leu Ala Asp Lys
         1325                1330                1335
Thr Gly Tyr Asp Ser Ser Met Ile Glu Met Asp Met Asp Leu Glu
         1340                1345                1350
Ser Glu Leu Gly Val Asp Ser Ile Lys Arg Val Glu Ile Met Ser
         1355                1360                1365
Glu Val Gln Thr Leu Leu Ser Val Glu Val Ser Asp Val Asp Ala
         1370                1375                1380
Leu Ser Arg Thr Lys Thr Val Gly Asp Val Ile Glu Ala Met Lys
         1385                1390                1395
Leu Glu Leu Gly Gly Pro Gln Gly Gln Thr Leu Thr Ala Glu Ser
         1400                1405                1410
```

```
Ile Arg Gln Pro Pro Val Ser Glu Pro Ala Val Pro Thr Ser Ser
1415                1420                1425

Ser Ser Ser Ile Ala Asn Val Ser Ala Arg Leu Ala Glu Ala
1430                1435                1440

Glu Ala Ala Val Leu Ser Val Leu Ala Asp Lys Thr Gly Tyr Asp
1445                1450                1455

Ser Ser Met Ile Glu Met Asp Met Asp Leu Glu Ser Glu Leu Gly
1460                1465                1470

Val Asp Ser Ile Lys Arg Val Glu Ile Met Ser Glu Val Gln Thr
1475                1480                1485

Leu Leu Ser Val Glu Val Ser Asp Val Asp Ala Leu Ser Arg Thr
1490                1495                1500

Lys Thr Val Gly Asp Val Ile Glu Ala Met Lys Leu Glu Leu Gly
1505                1510                1515

Gly Pro Gln Gly Gln Thr Leu Thr Ala Glu Ser Ile Arg Gln Pro
1520                1525                1530

Pro Val Ser Glu Pro Ala Val Pro Thr Ser Ser Ser Ser Ile
1535                1540                1545

Ala Asn Val Ser Ser Ala Arg Leu Ala Glu Ala Glu Ala Ala Val
1550                1555                1560

Leu Ser Val Leu Ala Asp Lys Thr Gly Tyr Asp Ser Ser Met Ile
1565                1570                1575

Glu Met Asp Met Asp Leu Glu Ser Glu Leu Gly Val Asp Ser Ile
1580                1585                1590

Lys Arg Val Glu Ile Met Ser Glu Val Gln Thr Leu Leu Ser Val
1595                1600                1605

Glu Val Ser Asp Val Asp Ala Leu Ser Arg Thr Lys Thr Val Gly
1610                1615                1620

Asp Val Ile Glu Ala Met Lys Leu Glu Leu Gly Gly Pro Gln Gly
1625                1630                1635

Gln Thr Leu Thr Ser Glu Pro Ile His Gln Pro Pro Val Ser Glu
1640                1645                1650

Pro Ala Val Pro Thr Ser Ser Ser Ser Ile Ala Asn Val Ser
1655                1660                1665

Ser Ala Arg Leu Ala Glu Ala Glu Ala Ala Val Leu Ser Val Leu
1670                1675                1680

Ala Asp Lys Thr Gly Tyr Asp Ser Ser Met Ile Glu Met Asp Met
1685                1690                1695

Asp Leu Glu Ser Glu Leu Gly Val Asp Ser Ile Lys Arg Val Glu
1700                1705                1710

Ile Met Ser Glu Val Gln Thr Leu Leu Ser Val Glu Val Ser Asp
1715                1720                1725

Val Asp Ala Leu Ser Arg Thr Lys Thr Val Gly Asp Val Ile Glu
1730                1735                1740

Ala Met Lys Met Glu Leu Gly Gly Pro Gln Gly Gln Thr Leu Thr
1745                1750                1755

Ala Glu Ser Ile Arg Gln Pro Pro Val Ser Glu Pro Ala Val Pro
1760                1765                1770

Thr Ser Ser Ser Ser Ser Ile Ala Asn Val Ser Ser Ala Arg Leu
1775                1780                1785

Ala Glu Ala Glu Ala Ala Val Leu Ser Val Leu Ala Asp Lys Thr
1790                1795                1800
```

```
Gly Tyr Asp Ser Ser Met Ile Glu Met Asp Met Asp Leu Glu Ser
    1805                1810                1815

Glu Leu Gly Val Asp Ser Ile Lys Arg Val Glu Ile Met Ser Glu
    1820                1825                1830

Val Gln Ala Leu Leu Ser Val Glu Val Ser Asp Val Asp Ala Leu
    1835                1840                1845

Ser Arg Thr Lys Thr Val Gly Asp Val Ile Glu Ala Met Lys Met
    1850                1855                1860

Glu Leu Gly Gly Pro Gln Gln Thr Leu Thr Ala Glu Ser Ile
    1865                1870                1875

Arg Glu Pro Pro Val Ser Glu Pro Ala Val Pro Thr Ser Ser Ser
    1880                1885                1890

Ser Ser Ile Ala Asn Val Ser Ala Arg Leu Ala Glu Ala Glu
    1895                1900                1905

Ala Ala Val Leu Ser Val Leu Ala Asp Lys Thr Gly Tyr Asp Ser
    1910                1915                1920

Ser Met Ile Glu Met Asp Met Asp Leu Glu Ser Glu Leu Gly Val
    1925                1930                1935

Asp Ser Ile Lys Arg Val Glu Ile Met Ser Glu Val Gln Thr Leu
    1940                1945                1950

Leu Ser Val Glu Val Ser Asp Val Asp Ala Leu Ser Arg Thr Lys
    1955                1960                1965

Thr Val Gly Asp Val Ile Glu Ala Met Lys Leu Glu Leu Gly Glu
    1970                1975                1980

Ser Ser Ser Ile Glu Thr Leu Asn Cys Thr Glu Val Glu His Thr
    1985                1990                1995

Ser Tyr Lys Ser Val Lys Ala Ser Gly Cys Glu Asn Val Asp Thr
    2000                2005                2010

Arg Phe Ala Lys Val Val Gln Ile Ser Leu Pro Ser Lys Leu Lys
    2015                2020                2025

Ser Thr Val Ser His Asp Arg Pro Val Ile Val Val Asp Asp Gly
    2030                2035                2040

Thr Pro Leu Thr Thr Glu Leu Cys Lys Ile Leu Gly Gly Asn Ile
    2045                2050                2055

Val Val Leu Ser Tyr Gln Gly Lys Pro Ala Gly Pro Arg Gly Val
    2060                2065                2070

Glu Val Pro Asp Leu Ser Glu Glu Ala Leu Ile Gln Ala Leu Ala
    2075                2080                2085

Leu Ile Arg Ser Thr Tyr Gly Val Pro Ile Gly Phe Ile Cys Gln
    2090                2095                2100

Gln Val Ser Asn Val Ser Thr Lys Ala Gln Leu Cys Trp Ala Leu
    2105                2110                2115

Leu Ala Ala Lys His Leu Lys Lys Asp Leu Asn Ala Val Leu Pro
    2120                2125                2130

Asp Ser Arg Ser Phe Phe Val Gly Val Val Arg Leu Asn Gly Lys
    2135                2140                2145

Leu Gly Thr Phe Glu Asn Ile Ser Asp Phe Ser Lys Phe Asp Leu
    2150                2155                2160

Thr Lys Ala Leu Asp Tyr Gly Gln Arg Gly Ser Leu Leu Gly Leu
    2165                2170                2175

Cys Lys Ser Leu Asp Leu Glu Trp Glu Gln Val Phe Cys Arg Gly
    2180                2185                2190

Ile Asp Leu Ala Cys Asp Leu Met Pro Leu Gln Ala Ala Arg Ile
```

-continued

```
            2195                2200                2205

Leu Arg Asn Glu Leu Gln Cys Pro Asn Met Arg Leu Arg Glu Val
    2210                2215                2220

Gly Tyr Asp Ile Ser Gly Ala Arg Tyr Thr Ile Ser Thr Asp Asp
    2225                2230                2235

Leu Leu Cys Gly Pro Ser Lys Ala Lys Val Glu Ala Ala Asp Leu
    2240                2245                2250

Phe Leu Val Thr Gly Gly Ala Arg Gly Ile Thr Pro His Cys Val
    2255                2260                2265

Arg Glu Ile Ala Ser Arg Ser Pro Gly Thr Thr Phe Val Leu Val
    2270                2275                2280

Gly Arg Ser Glu Met Ser Asp Glu Pro Asp Trp Ala Val Gly His
    2285                2290                2295

Tyr Asn Lys Asp Leu Asp Gln Ser Thr Met Lys His Leu Lys Ala
    2300                2305                2310

Thr His Ala Ala Gly Gly Val Lys Pro Thr Pro Lys Ala His Arg
    2315                2320                2325

Ala Leu Val Asn Arg Val Thr Gly Ser Arg Glu Val Arg Glu Ser
    2330                2335                2340

Leu Arg Ala Ile Gln Glu Ala Gly Ala Asn Val Glu Tyr Ile Ala
    2345                2350                2355

Cys Asp Val Ser Asp Glu Asn Lys Val Arg Gln Leu Val Gln Arg
    2360                2365                2370

Val Glu Gln Lys Tyr Gly Cys Glu Ile Thr Gly Ile Trp His Ala
    2375                2380                2385

Ser Gly Val Leu Arg Asp Lys Leu Val Glu Gln Lys Thr Thr Asp
    2390                2395                2400

Asp Phe Glu Ala Val Phe Gly Thr Lys Val Thr Gly Leu Val Asn
    2405                2410                2415

Ile Val Ser Gln Val Asn Met Ser Lys Leu Arg His Phe Ile Leu
    2420                2425                2430

Phe Ser Ser Leu Ala Gly Phe His Gly Asn Lys Gly Gln Thr Asp
    2435                2440                2445

Tyr Ala Ile Ala Asn Glu Ala Leu Asn Lys Ile Ala His Thr Leu
    2450                2455                2460

Ser Ala Phe Leu Pro Lys Leu Asn Ala Lys Val Leu Asp Phe Gly
    2465                2470                2475

Pro Trp Val Gly Ser Gly Met Val Thr Glu Thr Leu Glu Lys His
    2480                2485                2490

Phe Lys Ala Met Gly Val Gln Thr Ile Pro Leu Glu Pro Gly Ala
    2495                2500                2505

Arg Thr Val Ala Gln Ile Ile Leu Ala Ser Ser Pro Pro Gln Ser
    2510                2515                2520

Leu Leu Gly Asn Trp Gly Phe Pro Ala Thr Lys Pro Leu Gln Arg
    2525                2530                2535

Ser Asn Val Val Thr Gly Thr Leu Ser Pro Glu Glu Ile Glu Phe
    2540                2545                2550

Ile Ala Asp His Lys Ile Gln Gly Arg Lys Val Leu Pro Met Met
    2555                2560                2565

Ala Ala Ile Gly Phe Met Ala Ser Ile Ala Glu Gly Leu Tyr Pro
    2570                2575                2580

Gly Tyr Asn Leu Gln Gly Val Glu Asn Ala Gln Leu Phe Gln Gly
    2585                2590                2595
```

-continued

```
Leu Thr Ile Asn Gln Glu Thr Lys Phe Gln Ile Thr Leu Ile Glu
    2600                2605                2610

Glu His Asn Ser Glu Glu Asn Leu Asp Val Leu Thr Ser Leu Gly
    2615                2620                2625

Val Met Leu Glu Ser Gly Lys Val Leu Pro Ala Tyr Arg Cys Val
    2630                2635                2640

Val Cys Leu Asn Thr Thr Gln Gln Pro Lys Leu Ser Pro Lys
    2645                2650                2655

Ile Leu Asn Leu Glu Val Asp Pro Ala Cys Glu Val Asn Pro Tyr
    2660                2665                2670

Asp Gly Lys Ser Leu Phe His Gly Pro Leu Leu Gln Phe Val Gln
    2675                2680                2685

Gln Val Leu His Ser Ser Thr Lys Gly Leu Val Ala Lys Cys Arg
    2690                2695                2700

Ala Leu Pro Ile Lys Glu Ala Ile Arg Gly Pro Phe Ile Lys Gln
    2705                2710                2715

Thr Leu His Asp Pro Ile Leu Asp Asp Val Ile Phe Gln Leu Met
    2720                2725                2730

Leu Val Trp Cys Arg Asn Ala Leu Gly Ser Ala Ser Leu Pro Asn
    2735                2740                2745

Arg Ile Glu Lys Met Ser Tyr Phe Gly Asn Val Ser Glu Gly Ser
    2750                2755                2760

Thr Phe Phe Ala Ser Val Thr Pro Val Gly Pro Arg Val Pro Lys
    2765                2770                2775

Asp Pro Val Ile Lys Met Gln Phe Leu Leu Gln Asp Glu Ser Gly
    2780                2785                2790

Asn Thr Phe Ser Ser Gly Glu Gly Ser Val Val Leu Ser Asp Glu
    2795                2800                2805

Leu Val Phe
    2810

<210> SEQ ID NO 57
<211> LENGTH: 2059
<212> TYPE: PRT
<213> ORGANISM: Schizochytrium sp.

<400> SEQUENCE: 57

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
```

```
            130                 135                 140
Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
                180                 185                 190

Asp Ala Ala Cys Ala Thr Ala Leu Tyr Val Leu Arg Leu Ala Gln Asp
                195                 200                 205

His Leu Val Ser Gly Ala Ala Asp Val Met Leu Cys Gly Ala Thr Cys
                210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Ser Ile Met Val Leu Lys
                260                 265                 270

Arg Leu Asp Asp Ala Ile Arg Asp Gly Asp His Ile Tyr Gly Thr Leu
                275                 280                 285

Leu Gly Ala Asn Val Ser Asn Ser Gly Thr Gly Leu Pro Leu Lys Pro
                290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
                340                 345                 350

Glu Gly Lys Val Pro Arg Phe Gly Thr Thr Lys Gly Asn Phe Gly His
                355                 360                 365

Thr Leu Val Ala Ala Gly Phe Ala Gly Met Cys Lys Val Leu Leu Ser
                370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
                405                 410                 415

Thr Asn Gly Glu Pro Lys Arg Ala Gly Leu Ser Ala Phe Gly Phe Gly
                420                 425                 430

Gly Thr Asn Ala His Ala Val Phe Glu Glu His Asp Pro Ser Asn Ala
                435                 440                 445

Ala Cys Thr Gly His Asp Ser Ile Ser Ala Leu Ser Ala Arg Cys Gly
                450                 455                 460

Gly Glu Ser Asn Met Arg Ile Ala Ile Thr Gly Met Asp Ala Thr Phe
465                 470                 475                 480

Gly Ala Leu Lys Gly Leu Asp Ala Phe Glu Arg Ala Ile Tyr Thr Gly
                485                 490                 495

Ala His Gly Ala Ile Pro Leu Pro Glu Lys Arg Trp Arg Phe Leu Gly
                500                 505                 510

Lys Asp Lys Asp Phe Leu Asp Leu Cys Gly Val Lys Ala Thr Pro His
                515                 520                 525

Gly Cys Tyr Ile Glu Asp Val Glu Val Asp Phe Gln Arg Leu Arg Thr
                530                 535                 540

Pro Met Thr Pro Glu Asp Met Leu Leu Pro Gln Gln Leu Leu Ala Val
545                 550                 555                 560
```

```
Thr Thr Ile Asp Arg Ala Ile Leu Asp Ser Gly Met Lys Lys Gly Gly
                565                 570                 575

Asn Val Ala Val Phe Val Gly Leu Gly Thr Asp Leu Glu Leu Tyr Arg
            580                 585                 590

His Arg Ala Arg Val Ala Leu Lys Glu Arg Val Arg Pro Glu Ala Ser
        595                 600                 605

Lys Lys Leu Asn Asp Met Met Gln Tyr Ile Asn Asp Cys Gly Thr Ser
    610                 615                 620

Thr Ser Tyr Thr Ser Tyr Ile Gly Asn Leu Val Ala Thr Arg Val Ser
625                 630                 635                 640

Ser Gln Trp Gly Phe Thr Gly Pro Ser Phe Thr Ile Thr Glu Gly Asn
                645                 650                 655

Asn Ser Val Tyr Arg Cys Ala Glu Leu Gly Lys Tyr Leu Leu Glu Thr
            660                 665                 670

Gly Glu Val Asp Gly Val Val Ala Gly Val Asp Leu Cys Gly Ser
        675                 680                 685

Ala Glu Asn Leu Tyr Val Lys Ser Arg Arg Phe Lys Val Ser Thr Ser
    690                 695                 700

Asp Thr Pro Arg Ala Ser Phe Asp Ala Ala Asp Gly Tyr Phe Val
705                 710                 715                 720

Gly Glu Gly Cys Gly Ala Phe Val Leu Lys Arg Glu Thr Ser Cys Thr
                725                 730                 735

Lys Asp Asp Arg Ile Tyr Ala Cys Met Asp Ala Ile Val Pro Gly Asn
            740                 745                 750

Val Pro Ser Ala Cys Leu Arg Glu Ala Leu Asp Gln Ala Arg Val Lys
        755                 760                 765

Pro Gly Asp Ile Glu Met Leu Glu Leu Ser Ala Asp Ser Ala Arg His
    770                 775                 780

Leu Lys Asp Pro Ser Val Leu Pro Lys Glu Leu Thr Ala Glu Glu
785                 790                 795                 800

Ile Gly Gly Leu Gln Thr Ile Leu Arg Asp Asp Lys Leu Pro Arg
                805                 810                 815

Asn Val Ala Thr Gly Ser Val Lys Ala Thr Val Gly Asp Thr Gly Tyr
            820                 825                 830

Ala Ser Gly Ala Ala Ser Leu Ile Lys Ala Ala Leu Cys Ile Tyr Asn
        835                 840                 845

Arg Tyr Leu Pro Ser Asn Gly Asp Asp Trp Asp Glu Pro Ala Pro Glu
    850                 855                 860

Ala Pro Trp Asp Ser Thr Leu Phe Ala Cys Gln Thr Ser Arg Ala Trp
865                 870                 875                 880

Leu Lys Asn Pro Gly Glu Arg Arg Tyr Ala Ala Val Ser Gly Val Ser
                885                 890                 895

Glu Thr Arg Ser Cys Tyr Ser Val Leu Leu Ser Glu Ala Glu Gly His
            900                 905                 910

Tyr Glu Arg Glu Asn Arg Ile Ser Leu Asp Glu Glu Ala Pro Lys Leu
        915                 920                 925

Ile Val Leu Arg Ala Asp Ser His Glu Glu Ile Leu Gly Arg Leu Asp
    930                 935                 940

Lys Ile Arg Glu Arg Phe Leu Gln Pro Thr Gly Ala Ala Pro Arg Glu
945                 950                 955                 960

Ser Glu Leu Lys Ala Gln Ala Arg Arg Ile Phe Leu Glu Leu Leu Gly
                965                 970                 975
```

```
Glu Thr Leu Ala Gln Asp Ala Ala Ser Ser Gly Ser Gln Lys Pro Leu
            980                 985                 990

Ala Leu Ser Leu Val Ser Thr Pro  Ser Lys Leu Gln Arg Glu Val Glu
        995                 1000                1005

Leu Ala Ala Lys Gly Ile Pro Arg Cys Leu Lys Met  Arg Arg Asp
    1010                1015                1020

Trp Ser Ser Pro Ala Gly Ser Arg Tyr Ala Pro Glu  Pro Leu Ala
    1025                1030                1035

Ser Asp Arg Val Ala Phe Met Tyr Gly Glu Gly Arg  Ser Pro Tyr
    1040                1045                1050

Tyr Gly Ile Thr Gln Asp Ile His Arg Ile Trp Pro  Glu Leu His
    1055                1060                1065

Glu Val Ile Asn Glu Lys Thr Asn Arg Leu Trp Ala  Glu Gly Asp
    1070                1075                1080

Arg Trp Val Met Pro Arg Ala Ser Phe Lys Ser Glu  Leu Glu Ser
    1085                1090                1095

Gln Gln Gln Glu Phe Asp Arg Asn Met Ile Glu Met  Phe Arg Leu
    1100                1105                1110

Gly Ile Leu Thr Ser Ile Ala Phe Thr Asn Leu Ala  Arg Asp Val
    1115                1120                1125

Leu Asn Ile Thr Pro Lys Ala Ala Phe Gly Leu Ser  Leu Gly Glu
    1130                1135                1140

Ile Ser Met Ile Phe Ala Phe Ser Lys Lys Asn Gly  Leu Ile Ser
    1145                1150                1155

Asp Gln Leu Thr Lys Asp Leu Arg Glu Ser Asp Val  Trp Asn Lys
    1160                1165                1170

Ala Leu Ala Val Glu Phe Asn Ala Leu Arg Glu Ala  Trp Gly Ile
    1175                1180                1185

Pro Gln Ser Val Pro Lys Asp Glu Phe Trp Gln Gly  Tyr Ile Val
    1190                1195                1200

Arg Gly Thr Lys Gln Asp Ile Glu Ala Ala Ile Ala  Pro Asp Ser
    1205                1210                1215

Lys Tyr Val Arg Leu Thr Ile Ile Asn Asp Ala Asn  Thr Ala Leu
    1220                1225                1230

Ile Ser Gly Lys Pro Asp Ala Cys Lys Ala Ala Ile  Ala Arg Leu
    1235                1240                1245

Gly Gly Asn Ile Pro Ala Leu Pro Val Thr Gln Gly  Met Cys Gly
    1250                1255                1260

His Cys Pro Glu Val Gly Pro Tyr Thr Lys Asp Ile  Ala Lys Ile
    1265                1270                1275

His Ala Asn Leu Glu Phe Pro Val Val Asp Gly Leu  Asp Leu Trp
    1280                1285                1290

Thr Thr Ile Asn Gln Lys Arg Leu Val Pro Arg Ala  Thr Gly Ala
    1295                1300                1305

Lys Asp Glu Trp Ala Pro Ser Ser Phe Gly Glu Tyr  Ala Gly Gln
    1310                1315                1320

Leu Tyr Glu Lys Gln Ala Asn Phe Pro Gln Ile Val  Glu Thr Ile
    1325                1330                1335

Tyr Lys Gln Asn Tyr Asp Val Phe Val Glu Val Gly  Pro Asn Asn
    1340                1345                1350

His Arg Ser Thr Ala Val Arg Thr Thr Leu Gly Pro  Gln Arg Asn
    1355                1360                1365

His Leu Ala Gly Ala Ile Asp Lys Gln Asn Glu Asp  Ala Trp Thr
```

-continued

```
            1370               1375               1380
Thr Ile Val Lys Leu Val Ala Ser Leu Lys Ala His Leu Val Pro
    1385               1390               1395
Gly Val Thr Ile Ser Pro Leu Tyr His Ser Lys Leu Val Ala Glu
    1400               1405               1410
Ala Gln Ala Cys Tyr Ala Ala Leu Cys Lys Gly Glu Lys Pro Lys
    1415               1420               1425
Lys Asn Lys Phe Val Arg Lys Ile Gln Leu Asn Gly Arg Phe Asn
    1430               1435               1440
Ser Lys Ala Asp Pro Ile Ser Ser Ala Asp Leu Ala Ser Phe Pro
    1445               1450               1455
Pro Ala Asp Pro Ala Ile Glu Ala Ala Ile Ser Arg Ile Met
    1460               1465               1470
Lys Pro Val Ala Pro Lys Phe Tyr Ala Arg Leu Asn Ile Asp Glu
    1475               1480               1485
Gln Asp Glu Thr Arg Asp Pro Ile Leu Asn Lys Asp Asn Ala Pro
    1490               1495               1500
Ser Ser Ser Ser Ser Ser Ser Ser Ser Ser Ser Ser Ser
    1505               1510               1515
Pro Ser Pro Ala Pro Ser Ala Pro Val Gln Lys Lys Ala Ala Pro
    1520               1525               1530
Ala Ala Glu Thr Lys Ala Val Ala Ser Ala Asp Ala Leu Arg Ser
    1535               1540               1545
Ala Leu Leu Asp Leu Asp Ser Met Leu Ala Leu Ser Ser Ala Ser
    1550               1555               1560
Ala Ser Gly Asn Leu Val Glu Thr Ala Pro Ser Asp Ala Ser Val
    1565               1570               1575
Ile Val Pro Pro Cys Asn Ile Ala Asp Leu Gly Ser Arg Ala Phe
    1580               1585               1590
Met Lys Thr Tyr Gly Val Ser Ala Pro Leu Tyr Thr Gly Ala Met
    1595               1600               1605
Ala Lys Gly Ile Ala Ser Ala Asp Leu Val Ile Ala Ala Gly Arg
    1610               1615               1620
Gln Gly Ile Leu Ala Ser Phe Gly Ala Gly Gly Leu Pro Met Gln
    1625               1630               1635
Val Val Arg Glu Ser Ile Glu Lys Ile Gln Ala Ala Leu Pro Asn
    1640               1645               1650
Gly Pro Tyr Ala Val Asn Leu Ile His Ser Pro Phe Asp Ser Asn
    1655               1660               1665
Leu Glu Lys Gly Asn Val Asp Leu Phe Leu Glu Lys Gly Val Thr
    1670               1675               1680
Phe Val Glu Ala Ser Ala Phe Met Thr Leu Thr Pro Gln Val Val
    1685               1690               1695
Arg Tyr Arg Ala Ala Gly Leu Thr Arg Asn Ala Asp Gly Ser Val
    1700               1705               1710
Asn Ile Arg Asn Arg Ile Ile Gly Lys Val Ser Arg Thr Glu Leu
    1715               1720               1725
Ala Glu Met Phe Met Arg Pro Ala Pro Glu His Leu Leu Gln Lys
    1730               1735               1740
Leu Ile Ala Ser Gly Glu Ile Asn Gln Glu Gln Ala Glu Leu Ala
    1745               1750               1755
Arg Arg Val Pro Val Ala Asp Asp Ile Ala Val Glu Ala Asp Ser
    1760               1765               1770
```

Gly Gly His Thr Asp Asn Arg Pro Ile His Val Ile Leu Pro Leu
            1775                1780                1785

Ile Ile Asn Leu Arg Asp Arg Leu His Arg Glu Cys Gly Tyr Pro
        1790                1795                1800

Ala Asn Leu Arg Val Arg Val Gly Ala Gly Gly Ile Gly Cys
        1805                1810                1815

Pro Gln Ala Ala Leu Ala Thr Phe Asn Met Gly Ala Ser Phe Ile
    1820                1825                1830

Val Thr Gly Thr Val Asn Gln Val Ala Lys Gln Ser Gly Thr Cys
    1835                1840                1845

Asp Asn Val Arg Lys Gln Leu Ala Lys Ala Thr Tyr Ser Asp Val
    1850                1855                1860

Cys Met Ala Pro Ala Ala Asp Met Phe Glu Glu Gly Val Lys Leu
    1865                1870                1875

Gln Val Leu Lys Lys Gly Thr Met Phe Pro Ser Arg Ala Asn Lys
    1880                1885                1890

Leu Tyr Glu Leu Phe Cys Lys Tyr Asp Ser Phe Glu Ser Met Pro
    1895                1900                1905

Pro Ala Glu Leu Ala Arg Val Glu Lys Arg Ile Phe Ser Arg Ala
    1910                1915                1920

Leu Glu Glu Val Trp Asp Glu Thr Lys Asn Phe Tyr Ile Asn Arg
    1925                1930                1935

Leu His Asn Pro Glu Lys Ile Gln Arg Ala Glu Arg Asp Pro Lys
    1940                1945                1950

Leu Lys Met Ser Leu Cys Phe Arg Trp Tyr Leu Ser Leu Ala Ser
    1955                1960                1965

Arg Trp Ala Asn Thr Gly Ala Ser Asp Arg Val Met Asp Tyr Gln
    1970                1975                1980

Val Trp Cys Gly Pro Ala Ile Gly Ser Phe Asn Asp Phe Ile Lys
    1985                1990                1995

Gly Thr Tyr Leu Asp Pro Ala Val Ala Asn Glu Tyr Pro Cys Val
    2000                2005                2010

Val Gln Ile Asn Lys Gln Ile Leu Arg Gly Ala Cys Phe Leu Arg
    2015                2020                2025

Arg Leu Glu Ile Leu Arg Asn Ala Arg Leu Ser Asp Gly Ala Ala
    2030                2035                2040

Ala Leu Val Ala Ser Ile Asp Asp Thr Tyr Val Pro Ala Glu Lys
    2045                2050                2055

Leu

<210> SEQ ID NO 58
<211> LENGTH: 1935
<212> TYPE: PRT
<213> ORGANISM: Thraustochytrium sp.

<400> SEQUENCE: 58

Met Gln Leu Pro Pro Ala His Ser Ala Asp Glu Asn Arg Ile Ala Val
1               5                   10                  15

Val Gly Met Ala Val Lys Tyr Ala Gly Cys Asp Asn Lys Glu Glu Phe
            20                  25                  30

Trp Lys Thr Leu Met Asn Gly Ser Ile Asn Thr Lys Ser Ile Ser Ala
        35                  40                  45

Ala Arg Leu Gly Ser Asn Lys Arg Asp Glu His Tyr Val Pro Glu Arg
    50                  55                  60

```
Ser Lys Tyr Ala Asp Thr Phe Cys Asn Glu Arg Tyr Gly Cys Ile Gln
 65                  70                  75                  80

Gln Gly Thr Asp Asn Glu His Asp Leu Leu Gly Leu Ala Gln Glu
                 85                  90                  95

Ala Leu Ala Asp Ala Ala Gly Arg Met Glu Lys Gln Pro Ser Glu Ala
            100                 105                 110

Phe Asp Leu Glu Asn Thr Gly Ile Val Ser Gly Cys Leu Ser Phe Pro
            115                 120                 125

Met Asp Asn Leu Gln Gly Glu Leu Leu Asn Leu Tyr Gln Ser His Val
130                 135                 140

Glu Lys Gln Leu Pro Pro Ser Ala Leu Val Glu Ala Val Lys Leu Trp
145                 150                 155                 160

Ser Glu Arg Gln Lys Ser Thr Lys Ala His Ala Gly Asp Lys Arg Arg
                165                 170                 175

Phe Ile Asp Pro Ala Ser Phe Val Ala Asp Lys Leu Asn Leu Gly Pro
            180                 185                 190

Leu His Tyr Ala Ile Asp Ala Ala Cys Ala Ser Ala Leu Tyr Val Leu
            195                 200                 205

Lys Leu Ala Gln Asp His Leu Val Ser Gly Ala Val Asp Met Met Leu
210                 215                 220

Cys Gly Ala Thr Cys Phe Pro Glu Pro Phe Phe Ile Leu Ser Gly Phe
225                 230                 235                 240

Ser Thr Phe Gln Ala Met Pro Val Gly Ala Asp Gly Val Ser Leu Pro
                245                 250                 255

Leu His Lys Thr Ser Ala Gly Leu Thr Pro Gly Glu Gly Gly Ser Ile
            260                 265                 270

Met Val Leu Lys Arg Leu Lys Asp Ala Ile Arg Asp Gly Asn His Ile
            275                 280                 285

Tyr Gly Val Leu Leu Glu Ala Asn Leu Ser Asn Ala Gly Cys Gly Leu
            290                 295                 300

Pro Leu Ser Pro His Leu Pro Ser Glu Glu Ser Cys Ile Arg Asp Thr
305                 310                 315                 320

Tyr Arg Arg Ala Gly Val Ala Ala Asp Gln Ser Ile Gln Tyr Ile Glu
                325                 330                 335

Cys His Ala Thr Gly Thr Pro Arg Gly Asp Val Val Glu Ile Glu Ala
            340                 345                 350

Val Glu Arg Val Phe Lys Lys Asn Val Pro Arg Leu Gly Ser Thr Lys
            355                 360                 365

Gly Asn Phe Gly His Ser Leu Val Ala Ala Gly Phe Ala Gly Met Ala
            370                 375                 380

Lys Leu Leu Leu Ala Met Glu His Gly Val Ile Pro Pro Thr Pro Gly
385                 390                 395                 400

Leu Asp Ala Ser Asn Gln Ala Ser Glu His Val Val Thr Lys Ala Ile
                405                 410                 415

Thr Trp Pro Glu Thr His Gly Ala Pro Lys Arg Ala Gly Leu Ser Ala
            420                 425                 430

Phe Gly Phe Gly Gly Thr Asn Ala His Ala Leu Phe Glu Glu Phe Asn
            435                 440                 445

Ala Glu Gly Ile Ser Tyr Arg Pro Gly Lys Pro Val Glu Ser Asn
            450                 455                 460

Thr Arg Pro Ser Val Val Ile Thr Gly Met Asp Cys Thr Phe Gly Ser
465                 470                 475                 480
```

```
Leu Glu Gly Ile Asp Ala Phe Glu Thr Ala Leu Tyr Glu Gly Arg Asp
                485                 490                 495

Ala Ala Arg Asp Leu Pro Ala Lys Arg Trp Arg Phe Leu Gly Glu Asp
            500                 505                 510

Leu Glu Phe Leu Arg Ala Ile Arg Leu Lys Glu Lys Pro Arg Gly Cys
            515                 520                 525

Phe Val Glu Ser Val Asp Val Asn Phe Arg Arg Leu Lys Thr Pro Leu
            530                 535                 540

Thr Pro Glu Asp Met Leu Arg Pro Gln Gln Leu Leu Ala Val Ser Thr
545                 550                 555                 560

Met Asp Arg Ala Ile Ile Asp Ala Gly Leu Lys Lys Gly Gln His Val
                565                 570                 575

Ala Val Leu Val Gly Leu Gly Thr Asp Leu Glu Leu Tyr Arg His Arg
            580                 585                 590

Ala Arg Val Ala Leu Lys Glu Val Leu His Pro Ser Leu Lys Ser Asp
            595                 600                 605

Thr Ala Ile Leu Gln Lys Ile Met Gln Tyr Val Asn Asp Ala Gly Thr
610                 615                 620

Ser Thr Ser Tyr Thr Ser Tyr Ile Gly Asn Leu Val Ala Thr Arg Ile
625                 630                 635                 640

Ser Ser Gln Trp Gly Phe Thr Gly Pro Ser Phe Thr Val Thr Glu Gly
            645                 650                 655

Asn Asn Ser Val Tyr Arg Cys Ala Gln Leu Ala Lys Asp Met Leu Gln
            660                 665                 670

Val Asn Arg Val Asp Ala Val Ile Ala Gly Val Asp Leu Asn Gly
            675                 680                 685

Ser Ala Glu Ser Phe Phe Val Arg Ala Asn Arg Gln Lys Ile Ser Lys
690                 695                 700

Leu Ser His Pro Cys Ala Ser Phe Asp Arg Asp Ala Asp Gly Phe Phe
705                 710                 715                 720

Ala Gly Glu Gly Cys Gly Ala Leu Val Phe Lys Arg Leu Glu Asp Cys
            725                 730                 735

Ala Pro Gln Glu Lys Ile Tyr Ala Ser Ile Asp Ser Ile Ala Ile Asp
            740                 745                 750

Lys Glu Pro Thr Ser Ser Ala Val Lys Ala Val Tyr Gln Ser Asp Ser
            755                 760                 765

Ser Leu Ser Asp Ile Glu Leu Leu Glu Ile Ser Gly Asp Ser Lys Arg
            770                 775                 780

Phe Ala Ala Phe Glu Gly Ala Val Glu Ile Gln Ser Ser Val Glu Ala
785                 790                 795                 800

Gln Leu Lys Gly Leu Ser Lys Val Leu Glu Pro Ala Lys Gly Gln Gly
            805                 810                 815

Val Ala Val Gly Ser Thr Arg Ala Thr Val Gly Asp Ile Gly Tyr Ala
            820                 825                 830

Thr Gly Ala Ala Ser Leu Ile Lys Thr Ala Leu Cys Leu Tyr Asn Arg
            835                 840                 845

Tyr Leu Pro Ala Leu Ala Asn Trp Ser Gly Pro Cys Glu Gln Ser Ala
850                 855                 860

Trp Gly Ser Asn Met Phe Val Cys His Glu Thr Arg Pro Trp Met Lys
865                 870                 875                 880

Asn Gln Asn Glu Lys Arg Cys Ala Leu Ile Ser Gly Thr Asp Pro Ser
            885                 890                 895

His Thr Cys Phe Ser Leu Val Leu Ser Asp Thr Gly Cys Tyr Glu Glu
```

-continued

```
              900             905             910
His Asn Arg Thr Cys Phe Asp Val Gln Ala Pro Gln Leu Val Leu Ile
        915             920             925

His Gly Phe Asp Gly Lys Thr Ile Val Arg Arg Leu Glu Gly Tyr Leu
        930             935             940

Leu Glu Leu Val Glu Gly His Ala Ser Pro Ser Glu Tyr Phe His Lys
945             950             955             960

Leu Ile Gly Gln Ser Leu Leu Glu Asn Ser Lys Glu Ser Lys Leu Thr
                965             970             975

Leu Ser Leu Val Cys Asn Pro Asn Gln Leu Gln Lys Glu Leu Met Leu
                980             985             990

Ala Ile Lys Gly Val Gln Arg Ser Met Leu Thr Gly Lys Asp Trp Val
        995             1000            1005

Ser Pro Ser Gly Ser Cys Phe Ala Pro Asn Pro Leu Ser Ser Ala
    1010            1015            1020

Lys Val Ala Phe Met Tyr Gly Glu Gly Arg Ser Pro Tyr Cys Gly
    1025            1030            1035

Val Gly Leu Gly Leu His Arg Leu Trp Pro Gly Leu His Glu Asn
    1040            1045            1050

Val Asn Asn Lys Thr Val Asp Leu Trp Thr Glu Gly Asp Gly Trp
    1055            1060            1065

Leu Tyr Pro Arg Thr Leu Thr Arg Glu Glu His Thr Lys Ala Ile
    1070            1075            1080

Glu Ser Phe Asn Ala Asn Gln Ile Glu Met Phe Arg Ala Gly Ile
    1085            1090            1095

Phe Ile Ser Met Cys Gln Thr Asp Tyr Val Met Asn Val Leu Gly
    1100            1105            1110

Val Gln Pro Lys Ala Gly Phe Gly Leu Ser Leu Gly Glu Ile Ser
    1115            1120            1125

Met Leu Phe Ala Met Ser Lys Glu Asn Cys Arg Gln Ser Gln Glu
    1130            1135            1140

Met Thr Asn Arg Leu Arg Gly Ser Pro Val Trp Ser Asn Glu Leu
    1145            1150            1155

Ala Ile Asn Phe Asn Ala Ile Arg Lys Leu Trp Lys Ile Pro Arg
    1160            1165            1170

Gly Ala Pro Leu Glu Ser Phe Trp Gln Gly Tyr Leu Val His Gly
    1175            1180            1185

Thr Arg Glu Glu Val Glu His Ala Ile Gly Leu Ser Glu Pro Tyr
    1190            1195            1200

Val Arg Leu Leu Ile Val Asn Asp Ser Arg Ser Ala Leu Ile Ala
    1205            1210            1215

Gly Lys Pro Asp Ala Cys Gln Ala Val Ile Ser Arg Leu Asn Ser
    1220            1225            1230

Lys Phe Pro Ser Leu Pro Val Lys Gln Gly Met Ile Gly His Cys
    1235            1240            1245

Pro Glu Val Arg Ala Phe Ile Lys Asp Ile Gly Tyr Ile His Glu
    1250            1255            1260

Thr Leu Arg Ile Ser Asn Asp Tyr Ser Asp Cys Gln Leu Phe Ser
    1265            1270            1275

Ala Val Thr Lys Gly Ala Leu Asp Ser Ser Thr Met Glu Ile Lys
    1280            1285            1290

His Phe Val Gly Glu Val Tyr Ser Arg Ile Ala Asp Phe Pro Gln
    1295            1300            1305
```

-continued

```
Ile Val Asn Thr Val His Ser Ala Gly Tyr Asp Val Phe Leu Glu
1310            1315                1320

Leu Gly Cys Asp Ala Ser Arg Ser Ala Ala Val Gln Asn Ile Leu
1325            1330                1335

Gly Gly Gln Gly Lys Phe Leu Ser Thr Ala Ile Asp Lys Lys Gly
1340            1345                1350

His Ser Ala Trp Ser Gln Val Leu Arg Ala Thr Ala Ser Leu Ala
1355            1360                1365

Ala His Arg Val Pro Gly Ile Ser Ile Leu Asp Leu Phe His Pro
1370            1375                1380

Asn Phe Arg Glu Met Cys Cys Thr Met Ala Thr Thr Pro Lys Val
1385            1390                1395

Glu Asp Lys Phe Leu Arg Thr Ile Gln Ile Asn Gly Arg Phe Glu
1400            1405                1410

Lys Glu Met Ile His Leu Glu Asp Thr Thr Leu Ser Cys Leu Pro
1415            1420                1425

Ala Pro Ser Glu Ala Asn Ile Ala Ala Ile Gln Ser Arg Ser Ile
1430            1435                1440

Arg Ser Ala Ala Ala Arg Ser Gly Gln Ser His Asp Cys Ala Ser
1445            1450                1455

His Ser His Glu Glu Asn Lys Asp Ser Cys Pro Glu Lys Leu Lys
1460            1465                1470

Leu Asp Ser Val Ser Val Ala Ile Asn Phe Asp Asn Asp Asp Arg
1475            1480                1485

Ile Gln Leu Gly His Ala Gly Phe Arg Glu Met Tyr Asn Thr Arg
1490            1495                1500

Tyr Ser Leu Tyr Thr Gly Ala Met Ala Lys Gly Ile Ala Ser Ala
1505            1510                1515

Asp Leu Val Ile Ala Ala Gly Lys Glu Gly Ile Leu Ala Ser Tyr
1520            1525                1530

Gly Ala Gly Gly Leu Pro Leu Ala Thr Val Arg Lys Gly Ile Asp
1535            1540                1545

Lys Ile Gln Gln Ala Leu Pro Ser Gly Pro Tyr Ala Val Asn Leu
1550            1555                1560

Ile His Ser Pro Phe Asp Gly Asn Leu Glu Gln Gly Asn Val Asp
1565            1570                1575

Leu Phe Leu Glu Lys Asn Val Arg Val Ala Glu Cys Ser Ala Phe
1580            1585                1590

Thr Thr Leu Thr Val Pro Val Val His Tyr Arg Ala Ala Gly Leu
1595            1600                1605

Val Arg Arg Gln Asp Gly Ser Ile Leu Ile Lys Asn Arg Ile Ile
1610            1615                1620

Ala Lys Val Ser Arg Thr Glu Leu Ala Glu Met Phe Leu Arg Pro
1625            1630                1635

Ala Pro Gln Ile Ile Leu Glu Lys Leu Val Ala Ala Glu Ile Ile
1640            1645                1650

Ser Ser Asp Gln Ala Arg Met Ala Ala Lys Val Pro Met Ala Asp
1655            1660                1665

Asp Ile Ala Val Glu Ala Asp Ser Gly Gly His Thr Asp Asn Arg
1670            1675                1680

Pro Met His Val Ile Leu Pro Leu Ile Ile Gln Leu Arg Asn Thr
1685            1690                1695
```

```
Ile Leu Ala Glu Tyr Gly Cys Ala Thr Ala Phe Arg Thr Arg Ile
    1700                1705                1710

Gly Ala Gly Gly Gly Ile Gly Cys Pro Ser Ala Ala Leu Ala Ala
    1715                1720                1725

Phe Asp Met Gly Ala Ser Phe Val Val Thr Gly Ser Ile Asn Gln
    1730                1735                1740

Ile Cys Arg Glu Ala Gly Thr Cys Asp Thr Val Arg Glu Leu Leu
    1745                1750                1755

Ala Asn Ser Ser Tyr Ser Asp Val Thr Met Ala Pro Ala Ala Asp
    1760                1765                1770

Met Phe Asp Gln Gly Val Lys Leu Gln Val Leu Lys Arg Gly Thr
    1775                1780                1785

Met Phe Pro Ser Arg Ala Asn Lys Leu Arg Lys Leu Phe Val Asn
    1790                1795                1800

Tyr Glu Ser Leu Glu Thr Leu Pro Ser Lys Glu Leu Lys Tyr Leu
    1805                1810                1815

Glu Asn Ile Ile Phe Lys Gln Ala Val Asp Gln Val Trp Glu Glu
    1820                1825                1830

Thr Lys Arg Phe Tyr Cys Glu Lys Leu Asn Asn Pro Asp Lys Ile
    1835                1840                1845

Ala Arg Ala Met Lys Asp Pro Lys Leu Lys Met Ser Leu Cys Phe
    1850                1855                1860

Arg Trp Tyr Leu Ser Lys Ser Ser Gly Trp Ala Asn Ala Gly Ile
    1865                1870                1875

Lys Ser Arg Ala Leu Asp Tyr Gln Ile Trp Cys Gly Pro Ala Met
    1880                1885                1890

Gly Ser Phe Asn Asn Phe Ala Ser Gly Thr Ser Leu Asp Trp Lys
    1895                1900                1905

Val Thr Gly Val Phe Pro Gly Val Ala Glu Val Asn Met Ala Ile
    1910                1915                1920

Leu Asp Gly Ala Arg Glu Leu Ala Ala Lys Arg Asn
    1925                1930                1935

<210> SEQ ID NO 59
<211> LENGTH: 2037
<212> TYPE: PRT
<213> ORGANISM: Thraustochytrium aureum

<400> SEQUENCE: 59

Gln Ala Ile Gly His Arg Ala Ala Arg Trp Ser Cys Arg Ser Lys Ser
1               5                   10                  15

Lys Ala Arg Gly His Lys Ala Gln Lys Glu Met Asn Gln Gly Gly Arg
                20                  25                  30

Asn Asp Glu Gly Val Ser Val Ala Arg Ala Asp Pro Cys Pro Asp Thr
            35                  40                  45

Arg Ile Ala Val Val Gly Met Ala Val Glu Tyr Ala Gly Cys Arg Gly
        50                  55                  60

Lys Glu Ala Phe Trp Asp Thr Leu Met Asn Gly Lys Ile Asn Ser Ala
65                  70                  75                  80

Cys Ile Ser Asp Asp Arg Leu Gly Ser Ala Arg Arg Glu Glu His Tyr
                85                  90                  95

Ala Pro Glu Arg Ser Lys Tyr Ala Asp Thr Phe Cys Asn Glu Arg Tyr
            100                 105                 110

Gly Cys Ile Asp Pro Lys Val Asp Asn Glu His Asp Leu Leu Leu Gly
        115                 120                 125
```

```
Leu Ala Ala Ala Leu Gln Asp Ala Gln Asp Arg Arg Ser Asp Gly
    130             135             140
Gly Lys Phe Asp Pro Ala Gln Leu Lys Arg Cys Gly Ile Val Ser Gly
145             150             155                         160
Cys Leu Ser Phe Pro Met Asp Asn Leu Gln Gly Glu Leu Leu Asn Leu
                165             170             175
Tyr Gln Ala His Ala Glu Arg Arg Ile Gly Lys His Cys Phe Ala Asp
            180             185             190
Gln Thr Pro Trp Ser Thr Arg Thr Arg Ala Leu His Pro Leu Pro Gly
        195             200             205
Asp Pro Arg Thr His Arg Asp Pro Ala Ser Phe Val Ala Gly Gln Leu
    210             215             220
Gly Leu Gly Pro Leu His Tyr Ser Leu Asp Ala Ala Cys Ala Ser Ala
225             230             235             240
Leu Tyr Val Leu Arg Leu Ala Gln Asp His Leu Leu Ser Gly Glu Ala
                245             250             255
Asp Leu Met Leu Cys Gly Ala Thr Cys Phe Pro Glu Pro Phe Phe Ile
            260             265             270
Leu Thr Gly Phe Ser Thr Phe His Ala Met Pro Val Gly Glu Asn Gly
        275             280             285
Val Ser Met Pro Phe His Arg Asp His Leu Leu Ser Gly Glu Ala Asp
    290             295             300
Leu Met Leu Cys Gly Ala Thr Cys Phe Pro Glu Pro Phe Phe Ile Leu
305             310             315             320
Thr Gly Phe Ser Thr Phe His Ala Met Pro Val Gly Glu Asn Gly Val
                325             330             335
Ser Met Pro Phe His Arg Gln Pro Ser Glu Glu Ala Cys Leu Lys Ala
            340             345             350
Thr Tyr Glu Leu Val Gly Val Pro Pro Arg Asp Val Gln Tyr Val Glu
        355             360             365
Cys His Ala Thr Gly Thr Pro Gln Gly Asp Thr Val Glu Leu Gln Ala
    370             375             380
Val Lys Ala Cys Phe Glu Gly Ala Ser Pro Arg Ile Gly Ser Thr Lys
385             390             395             400
Gly Asn Phe Gly His Thr Leu Val Ala Ala Gly Phe Ala Gly Met Cys
                405             410             415
Lys Val Leu Leu Ala Met Glu Arg Gly Val Ile Pro Pro Thr Pro Gly
            420             425             430
Val Asp Ser Gly Thr Gln Ile Asp Pro Leu Val Val Thr Ala Ala Leu
        435             440             445
Pro Trp Pro Asp Thr Arg Gly Gly Pro Lys Arg Ala Gly Leu Ser Ala
    450             455             460
Phe Gly Phe Gly Gly Thr Asn Ala His Ala Val Phe Glu Glu His Ile
465             470             475             480
Pro Ser Arg Ala Pro Pro Ala Val Leu Cys Gln Pro Arg Leu Gly Ser
                485             490             495
Gly Pro Asn Arg Lys Leu Ala Ile Val Gly Met Asp Ala Thr Phe Gly
            500             505             510
Ser Leu Lys Gly Leu Ser Ala Leu Glu Ala Ala Leu Tyr Glu Ala Arg
        515             520             525
His Ala Ala Arg Pro Leu Pro Ala Lys Arg Trp Arg Phe Leu Gly Gly
    530             535             540
```

-continued

```
Asp Glu Ser Phe Leu His Glu Ile Gly Leu Glu Cys Ser Pro His Gly
545                 550                 555                 560

Cys Tyr Ile Glu Asp Val Asp Val Asp Phe Lys Arg Leu Arg Thr Pro
                565                 570                 575

Met Val Pro Glu Asp Leu Leu Arg Pro Gln Gln Leu Leu Ala Val Ser
            580                 585                 590

Thr Ile Asp Lys Ala Ile Leu Asp Ser Gly Leu Ala Lys Gly Gly Asn
        595                 600                 605

Val Ala Val Leu Val Gly Leu Gly Thr Asp Leu Glu Leu Tyr Arg His
    610                 615                 620

Arg Ala Arg Val Ala Leu Lys Glu Arg Leu Gln Gly Leu Val Arg Ser
625                 630                 635                 640

Ala Glu Gly Gly Ala Leu Thr Ser Arg Leu Met Asn Tyr Ile Asn Asp
                645                 650                 655

Ser Gly Thr Ser Thr Ser Tyr Thr Ser Tyr Ile Gly Asn Leu Val Ala
                660                 665                 670

Thr Arg Val Ser Ser Gln Trp Gly Phe Thr Gly Pro Ser Phe Thr Val
            675                 680                 685

Thr Glu Gly Ala Asn Ser Val His Arg Cys Ala Gln Leu Ala Lys Tyr
        690                 695                 700

Met Leu Asp Arg Gly Glu Val Asp Ala Val Val Ala Gly Val Asp
705                 710                 715                 720

Leu Cys Gly Ser Ala Glu Ala Phe Phe Val Arg Ser Arg Met Gln
                725                 730                 735

Ile Ser Lys Ser Gln Arg Pro Ala Ala Pro Phe Asp Arg Ala Ala Asp
                740                 745                 750

Gly Phe Phe Ala Gly Glu Gly Cys Gly Ala Leu Val Phe Lys Arg Leu
            755                 760                 765

Thr Asp Cys Val Ser Gly Glu Arg Ile Tyr Ala Ser Leu Asp Ser Val
        770                 775                 780

Val Val Ala Thr Thr Pro Arg Ala Ala Leu Arg Ala Ala Gly Ser
785                 790                 795                 800

Ala Arg Val Asp Pro Ala Ser Ile Asp Met Val Glu Leu Ser Ala Asp
                805                 810                 815

Ser His Arg Phe Val Arg Ala Pro Gly Thr Val Ala Gln Pro Leu Thr
            820                 825                 830

Ala Glu Val Glu Val Gly Ala Val Arg Glu Val Ile Gly Thr Ala Gly
        835                 840                 845

Arg Gly Ser Arg Ser Val Ala Val Gly Ser Val Arg Ala Asn Val Gly
    850                 855                 860

Asp Ala Gly Phe Ala Ser Gly Ala Ala Ala Leu Val Lys Thr Ala Leu
865                 870                 875                 880

Cys Leu His Asn Arg Tyr Leu Ala Ala Thr Pro Gly Trp Asp Ala Pro
                885                 890                 895

Ala Ala Gly Val Asp Phe Gly Ala Glu Leu Tyr Val Cys Arg Glu Ser
            900                 905                 910

Arg Ala Trp Val Lys Asn Ala Gly Val Ala Arg His Ala Ala Ile Ser
        915                 920                 925

Gly Val Asp Glu Gly Gly Ser Cys Tyr Gly Leu Val Leu Ser Asp Val
    930                 935                 940

Pro Gly Gln Tyr Glu Thr Gly Asn Arg Ile Ser Leu Gln Ala Glu Ser
945                 950                 955                 960

Pro Lys Leu Leu Leu Leu Ser Ala Pro Asp His Ala Ala Leu Leu Asp
```

Lys Val Ala Ala Glu Leu Ala Ala Leu Glu Gln Ala Asp Gly Leu Ser
Ala Ala Ala Ala Ala Val Asp Arg Leu Leu Gly Glu Ser Leu Val Gly
Cys Ala Ala Gly Ser Gly Gly Leu Thr Leu Cys Leu Val Ala Ser
Pro Ala Ser Leu His Lys Glu Leu Ala Leu Ala His Arg Gly Ile
Pro Arg Cys Ile Lys Ala Arg Arg Asp Trp Ala Ser Pro Ala Gly
Ser Tyr Phe Ala Pro Glu Pro Ile Ala Ser Asp Arg Val Ala Phe
Met Tyr Gly Glu Gly Arg Ser Pro Tyr Cys Gly Val Gly Arg Asp
Leu His Arg Ile Trp Pro Ala Leu His Glu Arg Val Asn Ala Lys
Thr Val Asn Leu Trp Gly Asp Gly Asp Ala Trp Leu Leu Pro Arg
Ala Thr Ser Ala Glu Glu Glu Gln Leu Cys Arg Asn Phe Asp
Ser Asn Gln Val Glu Met Phe Arg Thr Gly Val Tyr Ile Ser Met
Cys Leu Thr Asp Leu Ala Arg Ser Leu Ile Gly Leu Gly Pro Lys
Ala Ser Phe Gly Leu Ser Leu Gly Glu Val Ser Met Leu Phe Ala
Leu Ser Glu Ser Asn Cys Arg Leu Ser Glu Glu Met Thr Arg Arg
Leu Arg Ala Ser Pro Val Trp Asn Ser Glu Leu Ala Val Glu Phe
Asn Ala Leu Arg Lys Leu Trp Gly Val Ala Pro Gly Ala Pro Val
Asp Ser Phe Trp Gln Gly Tyr Val Val Arg Ala Thr Arg Ala Gln
Val Glu Gln Ala Ile Gly Glu Asp Asn Gln Phe Val Arg Leu Leu
Ile Val Asn Asp Ser Gln Ser Val Leu Ile Ala Gly Lys Pro Ala
Ala Cys Glu Ala Val Ile Ala Arg Ile Gly Ser Ile Leu Pro Pro
Leu Gln Val Ser Gln Gly Met Val Gly His Cys Ala Glu Val Leu
Pro Tyr Thr Ser Glu Ile Gly Arg Ile His Asn Met Leu Arg Phe
Pro Ser Gln Asp Glu Thr Gly Gly Cys Lys Met Tyr Ser Ser Val
Ser Asn Ser Arg Ile Gly Pro Val Glu Glu Ser Gln Met Gly Pro
Gly Thr Glu Leu Val Phe Ser Pro Ser Met Glu Asp Phe Val Ala
Gln Leu Tyr Ser Arg Val Ala Asp Phe Pro Ala Ile Thr Glu Ala

```
Val Tyr Gln Gln Gly His Asp Val Phe Val Glu Val Gly Pro Asp
    1370                1375                1380

His Ser Arg Ser Ala Ala Val Arg Ser Thr Leu Gly Pro Thr Arg
    1385                1390                1395

Arg His Ile Ala Val Ala Met Asp Arg Lys Gly Glu Ser Ala Trp
    1400                1405                1410

Ser Gln Leu Leu Lys Met Leu Ala Thr Leu Ala Ser His Arg Val
    1415                1420                1425

Pro Gly Leu Asp Leu Ser Ser Met Tyr His Pro Ala Val Val Glu
    1430                1435                1440

Arg Cys Arg Leu Ala Leu Ala Ala Gln Arg Ser Gly Gln Pro Glu
    1445                1450                1455

Gln Arg Asn Lys Phe Leu Arg Thr Ile Glu Val Asn Gly Phe Tyr
    1460                1465                1470

Asp Pro Ala Asp Ala Thr Ile Pro Glu Ala Val Ala Thr Ile Leu
    1475                1480                1485

Pro Ala Thr Ala Ala Ile Ser Pro Pro Lys Leu Gly Ala Pro His
    1490                1495                1500

Asp Ser Gln Pro Glu Ala Glu Ala Arg Pro Val Gly Glu Ala Ser
    1505                1510                1515

Val Pro Arg Arg Ala Thr Ser Ser Ser Lys Leu Ala Arg Thr Leu
    1520                1525                1530

Ala Ile Asp Ala Cys Asp Ser Asp Val Arg Ala Ala Leu Leu Asp
    1535                1540                1545

Leu Asp Ala Pro Ile Ala Val Gly Gly Ser Ser Arg Ala Gln Val
    1550                1555                1560

Pro Pro Cys Pro Val Ser Ala Leu Gly Ser Ala Ala Phe Arg Ala
    1565                1570                1575

Ala His Gly Val Asp Tyr Ala Leu Tyr Met Gly Ala Met Ala Lys
    1580                1585                1590

Gly Val Ala Ser Ala Glu Met Val Ile Ala Ala Gly Lys Ala Arg
    1595                1600                1605

Met Leu Ala Ser Phe Gly Ala Gly Gly Leu Pro Leu Gly Glu Val
    1610                1615                1620

Glu Glu Ala Leu Asp Lys Ile Gln Ala Ala Leu Pro Glu Gly Pro
    1625                1630                1635

Phe Ala Val Asn Leu Ile His Ser Pro Phe Asp Pro Asn Leu Glu
    1640                1645                1650

Glu Gly Asn Val Glu Leu Phe Leu Arg Arg Gly Ile Arg Leu Val
    1655                1660                1665

Glu Ala Ser Ala Phe Met Ser Val Thr Pro Ser Leu Val Arg Tyr
    1670                1675                1680

Arg Val Ala Gly Leu Glu Arg Gly Pro Gly Gly Thr Ala Arg Val
    1685                1690                1695

Leu Asn Arg Val Ile Gly Lys Val Ser Arg Ala Glu Leu Ala Glu
    1700                1705                1710

Met Phe Met Arg Pro Pro Ala Ala Ile Val Ser Lys Leu Leu
    1715                1720                1725

Ala Gln Gly Leu Val Thr Glu Glu Gln Ala Ser Leu Ala Glu Ile
    1730                1735                1740

Val Pro Leu Val Asp Asp Val Ala Ile Glu Ala Asp Ser Gly Gly
    1745                1750                1755
```

-continued

His Thr Asp Asn Arg Pro Ile His Val Val Leu Pro Val Val Leu
    1760                1765                1770

Ala Leu Arg Asp Arg Val Met Arg Glu Cys Lys Tyr Pro Ala Ala
    1775                1780                1785

Asn Arg Val Arg Val Gly Ala Gly Gly Gly Ile Gly Cys Pro Ala
    1790                1795                1800

Ala Ala Arg Ala Ala Phe Asp Met Gly Ala Ala Phe Val Leu Thr
    1805                1810                1815

Gly Ser Ile Asn Gln Leu Thr Arg Gln Ala Gly Thr Ser Asp Ser
    1820                1825                1830

Val Arg Ala Ala Leu Ala Arg Ala Thr Tyr Ser Asp Val Thr Met
    1835                1840                1845

Ala Pro Ala Ala Asp Met Phe Asp Gln Gly Val Lys Leu Gln Val
    1850                1855                1860

Leu Lys Arg Gly Thr Met Phe Pro Ala Arg Ala Asn Lys Leu Tyr
    1865                1870                1875

Glu Leu Phe Thr Thr Tyr Gln Ser Leu Asp Ala Ile Pro Arg Ala
    1880                1885                1890

Glu Leu Ala Arg Leu Glu Lys Arg Val Phe Arg Met Ser Ile Asp
    1895                1900                1905

Glu Val Trp Asn Glu Thr Lys Gln Phe Tyr Glu Thr Arg Leu Asn
    1910                1915                1920

Asn Pro Ala Lys Val Ala Arg Ala Glu Arg Asp Pro Lys Leu Lys
    1925                1930                1935

Met Ser Leu Cys Phe Arg Trp Tyr Leu Ser Lys Ser Ser Lys Trp
    1940                1945                1950

Ala Ser Thr Gly Gln Val Gly Arg Glu Leu Asp Tyr Gln Val Trp
    1955                1960                1965

Cys Gly Pro Thr Ile Gly Ala Phe Asn Glu Phe Val Lys Gly Ser
    1970                1975                1980

Ser Leu Asp Ala Glu Ala Cys Gly Gly Arg Phe Pro Cys Val Val
    1985                1990                1995

Arg Val Asn Gln Glu Ile Leu Cys Gly Ala Ala Tyr Glu Gln Arg
    2000                2005                2010

Leu Ala Arg Phe Met Leu Leu Ala Gly Arg Glu Ser Ala Asp Ala
    2015                2020                2025

Leu Ala Tyr Thr Val Ala Glu Ala Arg
    2030                2035

<210> SEQ ID NO 60
<211> LENGTH: 1470
<212> TYPE: PRT
<213> ORGANISM: Thraustochytrium sp.

<400> SEQUENCE: 60

Met Gly Pro Arg Val Ala Ser Gly Lys Val Pro Ala Trp Glu Met Ser
1               5                   10                  15

Lys Ser Glu Leu Cys Asp Asp Arg Thr Val Val Phe Asp Tyr Glu Glu
                20                  25                  30

Leu Leu Glu Phe Ala Glu Gly Asp Ile Ser Lys Val Phe Gly Pro Glu
            35                  40                  45

Phe Lys Val Val Asp Gly Phe Arg Arg Val Arg Leu Pro Ala Arg
        50                  55                  60

Glu Tyr Leu Leu Val Thr Arg Val Thr Leu Met Asp Ala Glu Val Gly
65                  70                  75                  80

```
Asn Phe Arg Val Gly Ala Arg Met Val Thr Glu Tyr Asp Val Pro Val
                 85                  90                  95

Asn Gly Glu Leu Ser Glu Gly Gly Asp Val Pro Trp Ala Val Leu Val
            100                 105                 110

Glu Ala Gly Gln Cys Asp Leu Leu Ile Ser Tyr Met Gly Ile Asp
            115                 120                 125

Phe Gln Cys Lys Gly Glu Arg Val Tyr Arg Leu Leu Asn Thr Thr Leu
    130                 135                 140

Thr Phe Phe Gly Val Ala Lys Glu Gly Glu Thr Leu Val Tyr Asp Ile
145                 150                 155                 160

Arg Val Thr Gly Phe Ala Lys Arg Pro Asp Gly Asp Ile Ser Met Phe
                165                 170                 175

Phe Phe Glu Tyr Asp Cys Tyr Cys Asn Gly Lys Leu Leu Ile Glu Met
            180                 185                 190

Arg Asp Gly Ser Ala Gly Phe Phe Thr Asp Glu Glu Leu Ala Ala Gly
            195                 200                 205

Lys Gly Val Val Val Thr Arg Ala Gln Gln Asn Met Arg Asp Lys Ile
    210                 215                 220

Val Arg Gln Ser Ile Glu Pro Phe Ala Leu Ala Ala Cys Thr His Lys
225                 230                 235                 240

Thr Thr Leu Asn Glu Ser Asp Met Gln Ser Leu Val Glu Arg Asn Trp
                245                 250                 255

Ala Asn Val Phe Gly Thr Ser Asn Lys Met Ala Glu Leu Asn Tyr Lys
            260                 265                 270

Ile Cys Ala Arg Lys Met Leu Met Ile Asp Arg Val Thr His Ile Asp
            275                 280                 285

His His Gly Gly Ala Tyr Gly Leu Gly Leu Leu Val Gly Glu Lys Ile
    290                 295                 300

Leu Asp Arg Asn His Trp Tyr Phe Pro Cys His Phe Val Asn Asp Gln
305                 310                 315                 320

Val Met Ala Gly Ser Leu Val Ser Asp Gly Cys Ser Gln Leu Leu Lys
                325                 330                 335

Leu Tyr Met Ile Trp Leu Gly Leu His Leu Lys Met Glu Glu Phe Asp
            340                 345                 350

Phe Leu Pro Val Ser Gly His Lys Asn Lys Val Arg Cys Arg Gly Gln
    355                 360                 365

Ile Ser Pro His Lys Gly Lys Leu Val Tyr Val Met Glu Ile Lys Lys
    370                 375                 380

Met Gly Tyr Asp Gln Ala Ser Gly Ser Pro Tyr Ala Ile Ala Asp Val
385                 390                 395                 400

Asp Ile Ile Asp Val Asn Glu Glu Leu Gly Gln Ser Phe Asp Ile Asn
                405                 410                 415

Asp Leu Ala Ser Tyr Gly Lys Gly Asp Leu Ser Lys Lys Ile Val Val
            420                 425                 430

Asp Phe Lys Gly Ile Ala Leu Gln Leu Lys Gly Arg Ala Phe Ser Arg
    435                 440                 445

Met Ser Ser Ser Ser Leu Asn Glu Gly Trp Gln Cys Val Pro Lys
    450                 455                 460

Pro Ser Gln Arg Met Glu His Glu Gln Pro Ala His Cys Leu Ala
465                 470                 475                 480

Ser Asp Pro Glu Ala Pro Ser Thr Val Thr Trp His Pro Met Ser Lys
                485                 490                 495
```

```
Leu Pro Gly Asn Pro Thr Pro Phe Phe Ser Pro Ser Tyr Pro Pro
            500                 505                 510

Arg Ala Ile Cys Phe Ile Pro Phe Pro Gly Asn Pro Leu Asp Asn Asn
            515                 520                 525

Cys Lys Ala Gly Glu Met Pro Leu Asn Trp Tyr Asn Met Ser Glu Phe
            530                 535                 540

Met Cys Gly Lys Val Ser Asn Cys Leu Gly Pro Glu Phe Ala Arg Phe
545                 550                 555                 560

Asp Lys Ser Asn Thr Ser Arg Ser Pro Ala Phe Asp Leu Ala Leu Val
                565                 570                 575

Thr Arg Val Val Glu Val Thr Asn Met Glu His Gly Lys Phe Leu Asn
            580                 585                 590

Val Asp Cys Asn Pro Ser Lys Gly Thr Met Val Gly Glu Phe Asp Cys
            595                 600                 605

Pro Gln Asp Ala Trp Phe Phe Asp Gly Ser Cys Asn Asp Gly His Met
            610                 615                 620

Pro Tyr Ser Ile Ile Met Glu Ile Gly Leu Gln Thr Ser Gly Val Leu
625                 630                 635                 640

Thr Ser Val Leu Lys Ala Pro Leu Thr Met Asp Lys Asp Asp Ile Leu
                645                 650                 655

Phe Arg Asn Leu Asp Ala Ser Ala Glu Met Val Arg Pro Asp Val Asp
                660                 665                 670

Val Arg Gly Lys Thr Ile Arg Asn Val Thr Lys Cys Thr Gly Tyr Ala
            675                 680                 685

Met Leu Gly Lys Met Gly Ile His Arg Phe Thr Phe Glu Leu Ser Val
690                 695                 700

Asp Gly Val Val Phe Tyr Lys Gly Ser Thr Ser Phe Gly Trp Phe Thr
705                 710                 715                 720

Pro Glu Val Phe Ala Gln Ala Gly Leu Asp Asn Gly Lys Lys Thr
                725                 730                 735

Glu Pro Trp Cys Lys Thr Asn Asn Thr Ser Val Arg Arg Val Glu Ile
            740                 745                 750

Ala Ser Ala Lys Gly Lys Glu Gln Leu Thr Glu Lys Leu Pro Asp Ala
            755                 760                 765

Thr Asn Ala Gln Val Leu Arg Arg Ser Glu Gln Cys Glu Tyr Leu Asp
            770                 775                 780

Tyr Leu Asn Ile Ala Pro Asp Ser Gly Leu His Gly Lys Gly Tyr Ala
785                 790                 795                 800

His Gly His Lys Asp Val Asn Pro Gln Asp Trp Phe Phe Ser Cys His
                805                 810                 815

Phe Trp Phe Asp Pro Val Met Pro Gly Ser Leu Gly Ile Glu Ser Met
            820                 825                 830

Phe Gln Leu Ile Glu Ala Phe Ala Val Asp Gln Asn Ile Pro Gly Glu
            835                 840                 845

Tyr Asn Val Ser Asn Pro Thr Phe Ala His Ala Pro Gly Lys Thr Ala
            850                 855                 860

Trp Lys Tyr Arg Gly Gln Leu Thr Pro Lys Asn Arg Ala Met Asp Cys
865                 870                 875                 880

Glu Val His Ile Val Ser Ile Thr Ala Ser Pro Glu Asn Gly Gly Tyr
                885                 890                 895

Val Asp Ile Val Ala Asp Gly Ala Leu Trp Val Asp Gly Leu Arg Val
            900                 905                 910

Tyr Glu Ala Lys Glu Leu Arg Val Arg Val Ser Ala Lys Pro Gln
```

-continued

```
                915                 920                 925
Ala Ile Pro Asp Val Gln Gln Gln Pro Pro Ser Ala Lys Ala Asp Pro
    930                 935                 940

Gly Lys Thr Gly Val Ala Leu Ser Pro Thr Gln Leu Arg Asp Val Leu
945                 950                 955                 960

Leu Glu Val Asp Asn Pro Leu Tyr Leu Gly Val Glu Asn Ser Asn Leu
                965                 970                 975

Val Gln Phe Glu Ser Lys Pro Ala Thr Ser Ser Arg Ile Val Ser Ile
            980                 985                 990

Lys Pro Cys Ser Ile Ser Asp Leu  Gly Asp Lys Ser Phe  Met Glu Thr
            995                 1000                1005

Tyr Asn  Val Ser Ala Pro Leu  Tyr Thr Gly Ala Met  Ala Lys Gly
    1010                1015                1020

Ile Ala  Ser Ala Asp Leu Val  Ile Ala Ala Gly Lys  Arg Lys Ile
    1025                1030                1035

Leu Gly  Ser Phe Gly Ala Gly  Gly Leu Pro Ile Ser  Ile Val Arg
    1040                1045                1050

Glu Ala  Leu Glu Lys Ile Gln  Gln His Leu Pro His  Gly Pro Tyr
    1055                1060                1065

Ala Val  Asn Leu Ile His Ser  Pro Phe Asp Ser Asn  Leu Glu Lys
    1070                1075                1080

Gly Asn  Val Asp Leu Phe Leu  Glu Met Gly Val Thr  Val Val Glu
    1085                1090                1095

Cys Ser  Ala Phe Met Glu Leu  Thr Ala Gln Val Val  Arg Tyr Arg
    1100                1105                1110

Ala Ser  Gly Leu Ser Lys Ser  Ala Asp Gly Ser Ile  Arg Ile Ala
    1115                1120                1125

His Arg  Ile Ile Gly Lys Val  Ser Arg Thr Glu Leu  Ala Glu Met
    1130                1135                1140

Phe Ile  Arg Pro Ala Pro Gln  His Leu Leu Gln Lys  Leu Val Ala
    1145                1150                1155

Ser Gly  Glu Leu Thr Ala Glu  Gln Ala Glu Leu Ala  Thr Gln Val
    1160                1165                1170

Pro Val  Ala Asp Asp Ile Ala  Val Glu Ala Asp Ser  Gly Gly His
    1175                1180                1185

Thr Asp  Asn Arg Pro Ile His  Val Ile Leu Pro Leu  Ile Ile Asn
    1190                1195                1200

Leu Arg  Asn Arg Leu His Lys  Glu Leu Asp Tyr Pro  Ser His Leu
    1205                1210                1215

Arg Val  Arg Val Gly Ala Gly  Gly Gly Ile Gly Cys  Pro Gln Ala
    1220                1225                1230

Ala Leu  Ala Ala Phe Gln Met  Gly Ala Ala Phe Leu  Ile Thr Gly
    1235                1240                1245

Thr Val  Asn Gln Leu Ala Arg  Glu Ser Gly Thr Cys  Asp Asn Val
    1250                1255                1260

Arg Leu  Gln Leu Ser Lys Ala  Thr Tyr Ser Asp Val  Cys Met Ala
    1265                1270                1275

Pro Ala  Ala Asp Met Phe Asp  Gln Gly Val Glu Leu  Gln Val Leu
    1280                1285                1290

Lys Lys  Gly Thr Leu Phe Pro  Ser Arg Ala Lys Lys  Leu Tyr Glu
    1295                1300                1305

Leu Phe  Cys Lys Tyr Asp Ser  Phe Glu Ala Met Pro  Ala Glu Glu
    1310                1315                1320
```

-continued

Leu Gln Arg Val Glu Lys Arg Ile Phe Gln Lys Ser Leu Ala Glu
    1325                1330                1335

Val Trp Gln Glu Thr Ser Asp Phe Tyr Ile His Arg Ile Lys Asn
    1340                1345                1350

Pro Glu Lys Ile Asn Arg Ala Ala Ser Asp Gly Lys Leu Lys Met
    1355                1360                1365

Ser Leu Cys Phe Arg Trp Tyr Leu Gly Leu Ser Ser Phe Trp Ala
    1370                1375                1380

Asn Ser Gly Ala Gln Asp Arg Val Met Asp Tyr Gln Ile Trp Cys
    1385                1390                1395

Gly Pro Ala Ile Gly Ala Phe Asn Asp Phe Thr Lys Gly Thr Tyr
    1400                1405                1410

Leu Asp Val Thr Val Ala Lys Ser Tyr Pro Cys Val Ala Gln Ile
    1415                1420                1425

Asn Leu Gln Ile Leu Gln Gly Ala Ala Tyr Leu Lys Arg Leu Gly
    1430                1435                1440

Val Ile Arg Phe Asp Arg Met Leu Leu Gln Ala Val Asp Ile Asp
    1445                1450                1455

Asp Pro Val Phe Thr Tyr Val Pro Thr Gln Pro Leu
    1460                1465                1470

<210> SEQ ID NO 61
<211> LENGTH: 1503
<212> TYPE: PRT
<213> ORGANISM: Schizochytrium sp.

<400> SEQUENCE: 61

Met Ala Leu Arg Val Lys Thr Asn Lys Lys Pro Cys Trp Glu Met Thr
1               5                   10                  15

Lys Glu Glu Leu Thr Ser Gly Lys Thr Glu Val Phe Asn Tyr Glu Glu
                20                  25                  30

Leu Leu Glu Phe Ala Glu Gly Asp Ile Ala Lys Val Phe Gly Pro Glu
            35                  40                  45

Phe Ala Val Ile Asp Lys Tyr Pro Arg Arg Val Arg Leu Pro Ala Arg
        50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
        115                 120                 125

Phe Gln Asn Gln Gly Asp Arg Val Tyr Arg Leu Leu Asn Thr Thr Leu
    130                 135                 140

Thr Phe Tyr Gly Val Ala His Glu Gly Glu Thr Leu Glu Tyr Asp Ile
145                 150                 155                 160

Arg Val Thr Gly Phe Ala Lys Arg Leu Asp Gly Gly Ile Ser Met Phe
                165                 170                 175

Phe Phe Glu Tyr Asp Cys Tyr Val Asn Gly Arg Leu Leu Ile Glu Met
            180                 185                 190

Arg Asp Gly Cys Ala Gly Phe Phe Thr Asn Glu Glu Leu Asp Ala Gly
        195                 200                 205

Lys Gly Val Val Phe Thr Arg Gly Asp Leu Ala Ala Arg Ala Lys Ile

-continued

```
            210                 215                 220
Pro Lys Gln Asp Val Ser Pro Tyr Ala Val Ala Pro Cys Leu His Lys
225                 230                 235                 240

Thr Lys Leu Asn Glu Lys Met Gln Thr Leu Val Asp Lys Asp Trp
                245                 250                 255

Ala Ser Val Phe Gly Ser Lys Asn Gly Met Pro Glu Ile Asn Tyr Lys
                260                 265                 270

Leu Cys Ala Arg Lys Met Leu Met Ile Asp Arg Val Thr Ser Ile Asp
                275                 280                 285

His Lys Gly Gly Val Tyr Gly Leu Gly Gln Leu Val Gly Glu Lys Ile
                290                 295                 300

Leu Glu Arg Asp His Trp Tyr Phe Pro Cys His Phe Val Lys Asp Gln
305                 310                 315                 320

Val Met Ala Gly Ser Leu Val Ser Asp Gly Cys Ser Gln Met Leu Lys
                325                 330                 335

Met Tyr Met Ile Trp Leu Gly Leu His Leu Thr Thr Gly Pro Phe Asp
                340                 345                 350

Phe Arg Pro Val Asn Gly His Pro Asn Lys Val Arg Cys Arg Gly Gln
                355                 360                 365

Ile Ser Pro His Lys Gly Lys Leu Val Tyr Val Met Glu Ile Lys Glu
                370                 375                 380

Met Gly Phe Asp Glu Asp Asn Asp Pro Tyr Ala Ile Ala Asp Val Asn
385                 390                 395                 400

Ile Ile Asp Val Asp Phe Glu Lys Gly Gln Asp Phe Ser Leu Asp Arg
                405                 410                 415

Ile Ser Asp Tyr Gly Lys Gly Asp Leu Asn Lys Lys Ile Val Val Asp
                420                 425                 430

Phe Lys Gly Ile Ala Leu Lys Met Gln Lys Arg Ser Thr Asn Lys Asn
                435                 440                 445

Pro Ser Lys Val Gln Pro Val Phe Ala Asn Gly Ala Ala Thr Val Gly
                450                 455                 460

Pro Glu Ala Ser Lys Ala Ser Ser Gly Ala Ser Ala Ser Ala Ser Ala
465                 470                 475                 480

Ala Pro Ala Lys Pro Ala Phe Ser Ala Asp Val Leu Ala Pro Lys Pro
                485                 490                 495

Val Ala Leu Pro Glu His Ile Leu Lys Gly Asp Ala Leu Ala Pro Lys
                500                 505                 510

Glu Met Ser Trp His Pro Met Ala Arg Ile Pro Gly Asn Pro Thr Pro
                515                 520                 525

Ser Phe Ala Pro Ser Ala Tyr Lys Pro Arg Asn Ile Ala Phe Thr Pro
                530                 535                 540

Phe Pro Gly Asn Pro Asn Asp Asn Asp His Thr Pro Gly Lys Met Pro
545                 550                 555                 560

Leu Thr Trp Phe Asn Met Ala Glu Phe Met Ala Gly Lys Val Ser Met
                565                 570                 575

Cys Leu Gly Pro Glu Phe Ala Lys Phe Asp Asp Ser Asn Thr Ser Arg
                580                 585                 590

Ser Pro Ala Trp Asp Leu Ala Leu Val Thr Arg Ala Val Ser Val Ser
                595                 600                 605

Asp Leu Lys His Val Asn Tyr Arg Asn Ile Asp Leu Asp Pro Ser Lys
                610                 615                 620

Gly Thr Met Val Gly Glu Phe Asp Cys Pro Ala Asp Ala Trp Phe Tyr
625                 630                 635                 640
```

```
Lys Gly Ala Cys Asn Asp Ala His Met Pro Tyr Ser Ile Leu Met Glu
                645                 650                 655

Ile Ala Leu Gln Thr Ser Gly Val Leu Thr Ser Val Leu Lys Ala Pro
                660                 665                 670

Leu Thr Met Glu Lys Asp Asp Ile Leu Phe Arg Asn Leu Asp Ala Asn
                675                 680                 685

Ala Glu Phe Val Arg Ala Asp Leu Asp Tyr Arg Gly Lys Thr Ile Arg
            690                 695                 700

Asn Val Thr Lys Cys Thr Gly Tyr Ser Met Leu Gly Glu Met Gly Val
705                 710                 715                 720

His Arg Phe Thr Phe Glu Leu Tyr Val Asp Val Leu Phe Tyr Lys
                725                 730                 735

Gly Ser Thr Ser Phe Gly Trp Phe Val Pro Glu Val Phe Ala Ala Gln
                740                 745                 750

Ala Gly Leu Asp Asn Gly Arg Lys Ser Glu Pro Trp Phe Ile Glu Asn
                755                 760                 765

Lys Val Pro Ala Ser Gln Val Ser Ser Phe Asp Val Arg Pro Asn Gly
                770                 775                 780

Ser Gly Arg Thr Ala Ile Phe Ala Asn Ala Pro Ser Gly Ala Gln Leu
785                 790                 795                 800

Asn Arg Arg Thr Asp Gln Gly Gln Tyr Leu Asp Ala Val Asp Ile Val
                805                 810                 815

Ser Gly Ser Gly Lys Lys Ser Leu Gly Tyr Ala His Gly Ser Lys Thr
                820                 825                 830

Val Asn Pro Asn Asp Trp Phe Phe Ser Cys His Phe Trp Phe Asp Ser
                835                 840                 845

Val Met Pro Gly Ser Leu Gly Val Glu Ser Met Phe Gln Leu Val Glu
                850                 855                 860

Ala Ile Ala Ala His Glu Asp Leu Ala Gly Lys Ala Arg His Cys Gln
865                 870                 875                 880

Pro His Leu Cys Ala Arg Pro Arg Ala Arg Ser Ser Trp Lys Tyr Arg
                885                 890                 895

Gly Gln Leu Thr Pro Lys Ser Lys Lys Met Asp Ser Glu Val His Ile
                900                 905                 910

Val Ser Val Asp Ala His Asp Gly Val Val Asp Leu Val Ala Asp Gly
                915                 920                 925

Phe Leu Trp Ala Asp Ser Leu Arg Val Tyr Ser Val Ser Asn Ile Arg
930                 935                 940

Val Arg Ile Ala Ser Gly Glu Ala Pro Ala Ala Ser Ser Ala Ala
945                 950                 955                 960

Ser Val Gly Ser Ser Ala Ser Ser Val Glu Arg Thr Arg Ser Ser Pro
                965                 970                 975

Ala Val Ala Ser Gly Pro Ala Gln Thr Ile Asp Leu Lys Gln Leu Lys
                980                 985                 990

Thr Glu Leu Leu Glu Leu Asp Ala Pro Leu Tyr Leu Ser Gln Asp Pro
            995                 1000                1005

Thr Ser Gly Gln Leu Lys Lys His Thr Asp Val Ala Ser Gly Gln
            1010                1015                1020

Ala Thr Ile Val Gln Pro Cys Thr Leu Gly Asp Leu Gly Asp Arg
            1025                1030                1035

Ser Phe Met Glu Thr Tyr Gly Val Val Ala Pro Leu Tyr Thr Gly
            1040                1045                1050
```

```
Ala Met Ala Lys Gly Ile Ala Ser Ala Asp Leu Val Ile Ala Ala
    1055                1060            1065

Gly Lys Arg Lys Ile Leu Gly Ser Phe Gly Ala Gly Gly Leu Pro
    1070                1075            1080

Met His His Val Arg Ala Ala Leu Glu Lys Ile Gln Ala Ala Leu
    1085                1090            1095

Pro Gln Gly Pro Tyr Ala Val Asn Leu Ile His Ser Pro Phe Asp
    1100                1105            1110

Ser Asn Leu Glu Lys Gly Asn Val Asp Leu Phe Leu Glu Lys Gly
    1115                1120            1125

Val Thr Val Val Glu Ala Ser Ala Phe Met Thr Leu Thr Pro Gln
    1130                1135            1140

Val Val Arg Tyr Arg Ala Ala Gly Leu Ser Arg Asn Ala Asp Gly
    1145                1150            1155

Ser Val Asn Ile Arg Asn Arg Ile Ile Gly Lys Val Ser Arg Thr
    1160                1165            1170

Glu Leu Ala Glu Met Phe Ile Arg Pro Ala Pro Glu His Leu Leu
    1175                1180            1185

Glu Lys Leu Ile Ala Ser Gly Glu Ile Thr Gln Glu Gln Ala Glu
    1190                1195            1200

Leu Ala Arg Arg Val Pro Val Ala Asp Ile Ala Val Glu Ala
    1205                1210            1215

Asp Ser Gly Gly His Thr Asp Asn Arg Pro Ile His Val Ile Leu
    1220                1225            1230

Pro Leu Ile Ile Asn Leu Arg Asn Arg Leu His Arg Glu Cys Gly
    1235                1240            1245

Tyr Pro Ala His Leu Arg Val Arg Val Gly Ala Gly Gly Gly Val
    1250                1255            1260

Gly Cys Pro Gln Ala Ala Ala Ala Leu Thr Met Gly Ala Ala
    1265                1270            1275

Phe Ile Val Thr Gly Thr Val Asn Gln Val Ala Lys Gln Ser Gly
    1280                1285            1290

Thr Cys Asp Asn Val Arg Lys Gln Leu Ser Gln Ala Thr Tyr Ser
    1295                1300            1305

Asp Ile Cys Met Ala Pro Ala Ala Asp Met Phe Glu Glu Gly Val
    1310                1315            1320

Lys Leu Gln Val Leu Lys Lys Gly Thr Met Phe Pro Ser Arg Ala
    1325                1330            1335

Asn Lys Leu Tyr Glu Leu Phe Cys Lys Tyr Asp Ser Phe Asp Ser
    1340                1345            1350

Met Pro Pro Ala Glu Leu Glu Arg Ile Glu Lys Arg Ile Phe Lys
    1355                1360            1365

Arg Ala Leu Gln Glu Val Trp Glu Glu Thr Lys Asp Phe Tyr Ile
    1370                1375            1380

Asn Gly Leu Lys Asn Pro Glu Lys Ile Gln Arg Ala Glu His Asp
    1385                1390            1395

Pro Lys Leu Lys Met Ser Leu Cys Phe Arg Trp Tyr Leu Gly Leu
    1400                1405            1410

Ala Ser Arg Trp Ala Asn Met Gly Ala Pro Asp Arg Val Met Asp
    1415                1420            1425

Tyr Gln Val Trp Cys Gly Pro Ala Ile Gly Ala Phe Asn Asp Phe
    1430                1435            1440

Ile Lys Gly Thr Tyr Leu Asp Pro Ala Val Ser Asn Glu Tyr Pro
```

-continued

```
                    1445                1450                1455

Cys Val  Val Gln Ile Asn  Leu Gln Ile Leu  Arg Gly Ala Cys Tyr
        1460                1465                1470

Leu Arg  Arg Leu Asn Ala  Leu Arg Asn Asp  Pro Arg Ile Asp Leu
        1475                1480                1485

Glu Thr  Glu Asp Ala Ala  Phe Val Tyr Glu  Pro Thr Asn Ala Leu
        1490                1495                1500

<210> SEQ ID NO 62
<211> LENGTH: 27
<212> TYPE: DNA
<213> ORGANISM: Artificial
<220> FEATURE:
<223> OTHER INFORMATION: Synthetic Primer prDS173
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 62
gatctactgc aagcgcggng gnttyat                                        27

<210> SEQ ID NO 63
<211> LENGTH: 21
<212> TYPE: DNA
<213> ORGANISM: Artificial
<220> FEATURE:
<223> OTHER INFORMATION: Synthetic Primer prDS174
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 63
ggcgcaggcg gcrtcnacna c                                              21

<210> SEQ ID NO 64
<211> LENGTH: 23
<212> TYPE: DNA
<213> ORGANISM: Artificial
<220> FEATURE:
<223> OTHER INFORMATION: Synthetic Primer JGM190
<220> FEATURE:
<221> NAME/KEY: misc_feature
<222> LOCATION: (15)..(15)
<223> OTHER INFORMATION: n is a, c, g, or t

<400> SEQUENCE: 64
caytggtayt tyccntgyca ytt                                            23

<210> SEQ ID NO 65
<211> LENGTH: 17
<212> TYPE: DNA
<213> ORGANISM: Artificial
<220> FEATURE:
<223> OTHER INFORMATION: Synthetic Primer BLR242
<220> FEATURE:
<221> NAME/KEY: misc_feature
<222> LOCATION: (3)..(3)
<223> OTHER INFORMATION: n is a, c, g, or t
<220> FEATURE:
```

```
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 65
ccnggcatna cnggrtc                                                  17

<210> SEQ ID NO 66
<211> LENGTH: 27
<212> TYPE: DNA
<213> ORGANISM: Artificial
<220> FEATURE:
<223> OTHER INFORMATION: Synthetic Primer CAX055

<400> SEQUENCE: 66
gtcatgattg aacaagatgg attgcac                                       27

<210> SEQ ID NO 67
<211> LENGTH: 27
<212> TYPE: DNA
<213> ORGANISM: Artificial
<220> FEATURE:
<223> OTHER INFORMATION: Synthetic Primer CAX056

<400> SEQUENCE: 67
ccacgtgtca gaagaactcg tcaagaa                                       27

<210> SEQ ID NO 68
<211> LENGTH: 8976
<212> TYPE: DNA
<213> ORGANISM: Thraustochytrium sp.

<400> SEQUENCE: 68
atggaagatc aaagaattgc tattgttgga ttatctgcga ttttaccaag tggtgaaaat    60
gttagagaat cttgggaagc aatacgtgat ggtttgaatt gtttaagtga tttacctgcg   120
gatcgtgttg atgttactgc gtattataat ccaacaaaag gtgtaaagga taaaatttat   180
tgtaaacgtg gtgggtttat tcctgaatat gaatttgatt ctagagaatt tggacttaat   240
atgttacaaa tggaagattc tgatgctaat caaacgttaa ctttattaaa ggttaaagaa   300
gcattagatg atgctaatat acctgcattt actaatgaga aaaaaaatat tggttgtgtt   360
cttggtattg gtggtggtca aaaagcatct catgaatttt attcaagact taattatgtt   420
gttgtggata agttttaag aaaaatggga ttacctgatg aggatgttga aactgctgtt   480
gaaaagttta agctaatttt cctgaatgg agattagatt cctttcctgg ttttcttggt   540
aatgttactg ctggccgttg tactaataca ttcaatatgg aaggtatgaa ttgtgttgta   600
gatgctgctt gtgctagttc tttaattgct attaaagttg ctattgatga attattacat   660
ggtgattgtg atgcaatgat tgctggtgca acttgtactg ataacgctct tggtatgtat   720
atggcatttt caaaacacc tgttttttca actgatcaaa gttgtcttgc atatgatgaa   780
aaaacaaaag gtatgcttat tggtgaaggt tcagctatgt ttgttttaaa acgttatgct   840
gacgcagtga gagatggtga tactgtacat gctgttatac gttcatgttc atcatcatct   900
gacggtaaag catctggtat ttatacacca actatttctg gtcaagaaga agctattctt   960
agagcatatc gtagagctgg tgtatcacca aatactatta ctttagttga aggacatggt  1020
actggtacac cagtgggtga taaaattgaa ttaacagctt tacgcaatgt atttgataaa  1080
```

```
gcatatggtc ctggtcataa ggaagaagtt gctgttggaa gtattaaaag tcaaattggt    1140
catttgaaag ctgttgctgg ttgtgctggt cttgtgaaat tggttatggc attgaaacat    1200
aaaacactac ctcaaagtat taatgttgaa aatccaccta atttagtgga tggtactgtc    1260
attagtgata ctactttata tattaataca atgaatcgtc catggattac taagcctggt    1320
gttccaagaa gagctggtat atctagtttc ggatttggtg gtgcaaatta tcatgctgtt    1380
ttagaagaat ttgagccgga acaaactaaa ccatatagat tgaatgtatc tgcacaacca    1440
atgcttcttc atgcggtaaa tgcaaattca ttacaaaagc tatgtgaaga tcaattaaaa    1500
cttttgaaag aatcaagaga aaaatgtgtc aacaccaaaa acactgatta tgttgcgttt    1560
tcaaaatttc aagattcttt taaattgaaa ggttctgttc catcacaaca tgctagagtt    1620
ggttttgcat caaaatctat tgaagatact atttctattt tatctgctat cgttaataga    1680
tttcaaaaag atattacaac aactagttgg gctttaccaa agaaggtgc tatttttaga    1740 tctactgcat tgattaatga caataaaagt gtagctgctt tattttctgg acaaggcgca    1800
caatataccc atatgtttaa tgatgttgca atgcaatggc cacaatttcg tttatgtgta    1860
aatgatatgg agaaagcaca ggaagaagtt atcaatgata aaagtgtgaa acgtatcagt    1920
caagttatgt ttcctcgtaa accatatgca agagaatcac ctttagacaa taaagaaatc    1980
tctaagactg aatattctca acaacaact gtcgctagtt cagtaggttt atttgaaatt    2040
ttccgtgatg ctggtttcgc tcctgctttt gttgctggtc attctttagg tgaatttagt    2100
gcattgtatg cagctggatt gattgatcgc gaagatttat tcaagttggt atgtaatcgt    2160
gcaatggcta tgagagatgc accaaaaaaa tctgctgatg gagcaatggc tgctgttatt    2220
ggtccaaatg cttcttcaat taagctttca gctcctgaag tatgggttgc taacaataac    2280
tctccatctc aaactgttat taccggtgca aattctggtg tacaagctga aacaagtaaa    2340
ttgaaaactc aaggtttccg tgtggttcat ttggcatgtg atgggcatt tcattcgcct    2400 catatggaaa atgctgaaaa gcaatttcaa aaagctcttt cagcagttaa gtttaataaa    2460
ccaactggtt cttctccaaa aatttttcagc aatgtaactg gtggtgtatt tacggatcca    2520
aaaactgctt tgtcaagaca tatgactagt tctgtacaat ttcttactca aattaagaat    2580
atgtacgcgg ctggagctcg tgtctttatt gaatttggac caaaacaagt acttccaaa    2640 ttggtcaatg aaattttcc tggtgataca agcgttttaa ctgtttcggt gaatccagct    2700
agtgctaaag atagtgacat tcaattgcgt caagctgcag ttcaaatggc cgttgctggt    2760
gtagctctta ccgattttga taatgggaa ctcaaagatc ctacccgtat gaaggaattc    2820
ccacgtaaga agactacttt gactttgtct gcagcaactt atgtctccaa gaaaactcta    2880
caggagcgtg aacgaatcat gaatgatggg cgaactgttt catgtgttca acgtattgaa    2940
aacactaata ctggtgagtt ggagaaattg aagaagcaat tgcaagataa agaaaatgag    3000
gttgtaagag ttcaagctct tgcaactcaa gcttcagctg atttgcaaaa taccaaagca    3060
gaattacaaa aagctcaagc aacaaaatct agtaatgcag catctgatgc ggtggtggca    3120
aaacataagg caattttatt ggcaatgtta gaagaacttg aaaccggcaa ggctgtagat    3180
tattcttcat tttcgaaagg tcaagttgca agtccagcta ccgttcgtgt cgtttcagct    3240
cctgttcaag cggctgctcc tgtgcaggta tctgcttctg ttgattctgg tttgttggca    3300
aaagcggaac aagttgtatt ggaagtattg gcatcgaaga ctggttatga gactgagttg    3360
attgaattgg atatggaatt ggaaactgaa cttggtattg attctatcaa gagagtagaa    3420
```

```
attctttctg aagttcaagc tcaattgaat gttgaagcta agatgtagat gctcttagt    3480
agaactcgta ctgttggtga agtgattgat gcaatgaaag ccgaaattgc tggtggtcaa    3540
ccagctgctc ctgttcaagt tgcagctcct actcaagtag ttgctcctgt tcaagcatct    3600
gctcctgttg attctggttt gttagcaaaa gcggaacaag ttgtattgga agtattggca    3660
tcgaagactg gttatgagac tgagttgatt gaattggata tggaattgga aaccgaactt    3720
ggtattgatt ctatcaagag agtagaaatt ctttctgaag ttcaagctca attgagtgtt    3780
gaagctaaag atgtagatgc tcttagtaga actcgtactg ttggtgaagt gattgatgca    3840
atgaaagccg aaattgctgg tggtcaacca gctgctcctg ttcaagttgc agctcctact    3900
caagtagttg ctcctgttca agcatctgct cctgttgatt ctggtttgtt agcaaaagcg    3960
gaacaagttg tattggaagt attggcatcg aagactggtt atgagactga gttgattgaa    4020
ttggatatgg aattggaaac cgaacttggt attgattcta tcaagagagt agaaattctt    4080
tctgaagttc aagctcaatt gagtgttgaa gctaaagatg tagatgctct tagtagaact    4140
cgtactgttg gtgaagtgat tgatgcaatg aaagctgaaa tttctggtgg tcagccagct    4200
gctcctgttc aagttgcagc tcctactcaa atagttgctc ctgttcaagt atccgctcct    4260
gttgattctg gtttgttagc aaaggcggaa caagtagtat ggaagtatt ggcatccaag    4320
actggttatg agactgagtt gattgaattg gatatggaat tggaaactga acttggtatt    4380
gattctatca gagagtagaa aattcttttct gaagttcaag ctcaattgag tgttgaagct    4440
aaagatgtag atgctcttag tagaactcgt actgttggtg aagtgattga tgcaatgaaa    4500
gctgaaattt ctggtggtca accaactgct cctgttcaag ttgcagctcc tactcaaata    4560
gttgctcctg ttcaagtatc tgctcctgtt gattctggtt tgttagcaaa ggcggaacaa    4620
gttgtattgg aagtattggc atcgaagact ggttatgaga ctgagttgat tgaattggat    4680
atggaattgg aaaccgaact tggtattgat tctatcaaga gagtagaaat tctttctgaa    4740
gttcaagctc aattgagtgt tgaagctaaa gatgtagatg ctcttagtag aactcgtact    4800
gttggtgaag tgattgatgc aatgaaagcc gaaatttctg gtggtcagcc agctgctcct    4860
gttcaagttg cagctcctac tcaaatagtt gctcctgttc aagcatctgc tcctgttgat    4920
tctggtttgt tggcaaaagc ggaacaagtt gtattggaag tgttagcatc caagactggt    4980
tatgaaactg agttgattga attagatatg gaattggaaa ccgaacttgg tattgattct    5040
atcaagagag tagaaattct ttctgaagtt caagctcaat tgagtgttga agctaaagat    5100
gtagatgctc ttagtagaac tcgtactgtt ggtgaagtga ttgatgcaat gaaagctgaa    5160
atttctggtg gtcaaccagc tgctcctgtt caagttgcag ctcctactca atagttgct    5220
cctgttcaag tatctgctcc tgttgattct ggtttgttag caaaggcgga acaagttgta    5280
ttggaagtat tggcatctaa gactggttat gagactgagt tgattgaatt ggatatggaa    5340
ttggaaactg aacttggtat tgattctatc aagagagtag aaattctttc tgaagttcaa    5400
gctcaattga tgttgaagc taaagatgta atgctctta gtagaactcg tactgttggt    5460
gaagtgattg atgcaatgaa agccgaaatt gctggtggtc aaccagctgc tcctgttcaa    5520
gttgcagctc ctgctccagt agttgctcct gttcaagtat ctactcctgt tgattctggt    5580
ttgttggcaa aagcggaaca agttgtattg gaagtgttag catgcaagac tggttatgaa    5640
actgagttga ttgaattgga tatgaattg gaaactgaac ttggtattga ttctatcaag    5700
agagtagaaa ttctttctga agttcaagct caattgagtt tgaagctaa agatgtagat    5760
gctcttagta gaactcgtac tgttggtgaa gtgattgatg caatgaaagc cgaaatttct    5820
```

```
ggtggtcaac caactgctcc tgttcaagtt gcagctccta ctcaagtagt tgctcctgtt   5880
aaagtatcta ctcctgttga ttctggtttg ttagcaaagg cggaacaagt agtattggaa   5940
gtattggcat ctaagactgg ttatgaaact gagttgattg aattagatat ggaattggaa   6000
actgaacttg gtattgattc tatcaagaga gtagaaattc tttctgaagt tcaagctcaa   6060
ttgaatgtgg aagctaaaga tgtggatgct cttagtagaa ctcgtactgt tggtgaagtg   6120
attgatgcaa tgaaagccga aattgctggt gatcaacctg ctccagctgt agttccagtt   6180
caagctaaga gtggtgtagc caaccctgca cttttggcaa aggcggaaca agtagtattg   6240
gaagtattgg catccaagac cggttatgaa actgagctga ttgaattgga tatggaattg   6300
gaaactgaac ttggtattga ttcaatcaag agagtagaaa ttctgtccga agttcaagca   6360
gaattgagtg ttgaagcaaa agatgtagac gctctaagta aacccgtac tgttggggaa   6420 gtgatcgatg caatgaaagc tgaaattgct ggcagtgctg tcacggttgc aactttggat   6480
gattcaacaa ttatggagga gacagatgat gaagatgaag actttatttt atacgatcat   6540
gtatacggaa gcgaatgtga agatcttagt ctgagttttt catccgtaaa gagcatcccg   6600
cgcgctgata aacttttgtt ggataacatt gctgaaaggc caattgttat tgtggattgt   6660
ggaacaaagc ttacaactga acttgcaaaa gctattggag aacgtgccgt ggttgctaca   6720
ttcagtgcac agagcttggt atcccgtgga ttcgttggta aatcatttac tctaggaaat   6780
acagaagaaa gtgagatcga aaagatggtt tcaagcattg aatcttcgta tggaaaaatt   6840
ggtggctttg tttatcaaca ttttcatgat agcgactatg gtatgcaact tggatgggcg   6900
ttaatggcag cgaaacattt gaaagagtcc ctcaacgacc cgattaagaa tggaagaacc   6960
ttctttttgg ctgttgcgcg tatgaatggt aaacttggta tggacaatgc ttcagttcat   7020
gatcaaggaa tagtggaatc atgcggtatc gccgaacgtg gtgctatctt tggtttgtgc   7080
aaaactttgg atttgaatg gcctaatgtt tttgctcgtg gtgttgatat tgctgaaggt   7140
atgagttata gtttggctgc ggaattgatt gttgatgaga tttcttgtgc aaatctttcc   7200
attcgggaat ctggttacac gattagcgga gaaagattca caactgaagc tcacaaattg   7260
gttactggaa agcctcatgc tccgattaag aagaaggatg ctttcctagt atctggtggt   7320
gctcgtggta ttactccact ttgtattcgt gaaattgcta aagcagtgaa aggtggcact   7380 tacatttga tgggtcgatc agcttttggct gatgaaccct tgtgggctaa tggtaaatcc   7440
ggaaaagatt tagataaagc tggtttggca ttttttgaagg aagagtttgc agctgggcgt   7500
ggtagtaaac caactccaaa agttcacaaa tctttgattg ataaagtgct cggtattagg   7560
gaggttagag catctattgc aaatatagaa gcccatggag caaaagctat atatttgtct   7620
tgcgatgtat cttccgctga gaaagtaaag gctgcagtgc aaaaagttga aaaggagcat   7680
ctagttcgta ttactggtat tgtgcatgca tcaggcgttt tgagggataa attggttgag   7740
aacaaaactt tggatgattt caacgcagta tatggaacca agtaactgg actagtaaac   7800 ttgctgtcag cagtgaacat gaattttgtt cgtcatttgg ttatgtttag ttctttggct   7860
ggatatcatg gaaatgttgg tcaatctgat tatgcaatgg ctaacgaatc acttaacaag   7920
attggtttta gattgggtgc agcttattct caattgtgtg ttaaatctat ttgttttgga   7980
ccttgggatg gtggaatggt aactccagct ttgaaaaaac aatttcaatc aatgggtgtc   8040
cagattattc ctcgtgaagg tggcgcggag actgttgcaa gaatagtctt atcttccaaat   8100 ccttctcaag ttttagttgg caactggggt gttcctccag tttcaccttt gtcaaaatcg   8160
```

| | | |
|---|---|---|
| gcaactattg ttcaaacttt taccccctgag ttaaatccat ttctaaagtc tcatcaaatt | 8220 |
| catggtaaaa atgttttgcc tatgactgta gcaattggat atcttgctca cttggttaag | 8280 |
| aattttatg ctggtcatca tttgtgggga gttgaagatg ctcaattgtt cagtggtgtt | 8340 |
| gtaattgacc atgcggtgca agctcaagtg aaattaacgg aacagagttt ggatgatgat | 8400 |
| ggcaaggtaa aagttcaagc tgttctgact gcttcaaacg ataatggaaa aatggtacct | 8460 |
| gcatacaaag cagtgattgt tttgggaaaa acaagtagac ctgcgtttat tttgaaagat | 8520 |
| ttttcattgc aagaatctaa ttctcgcagt gctgatgagt tgtatgatgg taaaactttg | 8580 |
| tttcatggtc cattatttcg tggaattacc aagttgttga atgtatctga tacttcacta | 8640 |
| acaactcaat gtaccaatat tgatttgact gctactgaac gtggtcaatt tgcggatatc | 8700 |
| gaacctgtga atcctttat ggcggatgct gcatttcaag ctatgcttgt atgggttaga | 8760 |
| aatttaagga atagtgcatc tttaccaaac aattgtgaaa gagtagatat ctataaacca | 8820 |
| atagcacctg gtgaaaagta ttacactact ttgcaagctt tgggtaatac ctccggttct | 8880 |
| gttctcaagt ctgtattta tatgcacgat gaacaaggag aagtatttct atctggaaga | 8940 |
| gctagtgttg ttgtgaatga caagatggag ttttag | 8976 |

<210> SEQ ID NO 69
<211> LENGTH: 2991
<212> TYPE: PRT
<213> ORGANISM: Thraustochytrium sp.

<400> SEQUENCE: 69

Met Glu Asp Gln Arg Ile Ala Ile Val Gly Leu Ser Ala Ile Leu Pro
1               5                   10                  15

Ser Gly Glu Asn Val Arg Glu Ser Trp Glu Ala Ile Arg Asp Gly Leu
            20                  25                  30

Asn Cys Leu Ser Asp Leu Pro Ala Asp Arg Val Asp Val Thr Ala Tyr
        35                  40                  45

Tyr Asn Pro Thr Lys Gly Val Lys Asp Lys Ile Tyr Cys Lys Arg Gly
    50                  55                  60

Gly Phe Ile Pro Glu Tyr Glu Phe Asp Ser Arg Glu Phe Gly Leu Asn
65                  70                  75                  80

Met Leu Gln Met Glu Asp Ser Asp Ala Asn Gln Thr Leu Thr Leu Leu
                85                  90                  95

Lys Val Lys Glu Ala Leu Asp Asp Ala Asn Ile Pro Ala Phe Thr Asn
            100                 105                 110

Glu Lys Lys Asn Ile Gly Cys Val Leu Gly Ile Gly Gly Gly Gln Lys
        115                 120                 125

Ala Ser His Glu Phe Tyr Ser Arg Leu Asn Tyr Val Val Val Asp Lys
    130                 135                 140

Val Leu Arg Lys Met Gly Leu Pro Asp Glu Asp Val Glu Thr Ala Val
145                 150                 155                 160

Glu Lys Phe Lys Ala Asn Phe Pro Glu Trp Arg Leu Asp Ser Phe Pro
                165                 170                 175

Gly Phe Leu Gly Asn Val Thr Ala Gly Arg Cys Thr Asn Thr Phe Asn
            180                 185                 190

Met Glu Gly Met Asn Cys Val Val Asp Ala Ala Cys Ala Ser Ser Leu
        195                 200                 205

Ile Ala Ile Lys Val Ala Ile Asp Glu Leu Leu His Gly Asp Cys Asp
    210                 215                 220

Ala Met Ile Ala Gly Ala Thr Cys Thr Asp Asn Ala Leu Gly Met Tyr

-continued

```
              225                 230                 235                 240
         Met Ala Phe Ser Lys Thr Pro Val Phe Ser Thr Asp Gln Ser Cys Leu
                             245                 250                 255

Ala Tyr Asp Glu Lys Thr Lys Gly Met Leu Ile Gly Glu Gly Ser Ala
                         260                 265                 270

Met Phe Val Leu Lys Arg Tyr Ala Asp Ala Val Arg Asp Gly Asp Thr
                     275                 280                 285

Val His Ala Val Ile Arg Ser Cys Ser Ser Ser Asp Gly Lys Ala
                 290                 295                 300

Ser Gly Ile Tyr Thr Pro Thr Ile Ser Gly Gln Glu Glu Ala Ile Leu
         305                 310                 315                 320

Arg Ala Tyr Arg Arg Ala Gly Val Ser Pro Asn Thr Ile Thr Leu Val
                         325                 330                 335

Glu Gly His Gly Thr Gly Thr Pro Val Gly Asp Lys Ile Glu Leu Thr
                     340                 345                 350

Ala Leu Arg Asn Val Phe Asp Lys Ala Tyr Gly Pro Gly His Lys Glu
                 355                 360                 365

Glu Val Ala Val Gly Ser Ile Lys Ser Gln Ile Gly His Leu Lys Ala
             370                 375                 380

Val Ala Gly Cys Ala Gly Leu Val Lys Leu Val Met Ala Leu Lys His
         385                 390                 395                 400

Lys Thr Leu Pro Gln Ser Ile Asn Val Glu Asn Pro Asn Leu Val
                         405                 410                 415

Asp Gly Thr Val Ile Ser Asp Thr Thr Leu Tyr Ile Asn Thr Met Asn
                     420                 425                 430

Arg Pro Trp Ile Thr Lys Pro Gly Val Pro Arg Arg Ala Gly Ile Ser
                 435                 440                 445

Ser Phe Gly Phe Gly Gly Ala Asn Tyr His Ala Val Leu Glu Glu Phe
             450                 455                 460

Glu Pro Glu Gln Thr Lys Pro Tyr Arg Leu Asn Val Ser Ala Gln Pro
         465                 470                 475                 480

Met Leu Leu His Ala Val Asn Ala Asn Ser Leu Gln Lys Leu Cys Glu
                         485                 490                 495

Asp Gln Leu Lys Leu Leu Lys Glu Ser Arg Glu Lys Cys Val Asn Thr
                     500                 505                 510

Lys Asn Thr Asp Tyr Val Ala Phe Ser Lys Phe Gln Asp Ser Phe Lys
                 515                 520                 525

Leu Lys Gly Ser Val Pro Ser Gln His Ala Arg Val Gly Phe Ala Ser
             530                 535                 540

Lys Ser Ile Glu Asp Thr Ile Ser Ile Leu Ser Ala Ile Val Asn Arg
         545                 550                 555                 560

Phe Gln Lys Asp Ile Thr Thr Thr Ser Trp Ala Leu Pro Lys Glu Gly
                         565                 570                 575

Ala Ile Phe Arg Ser Thr Ala Leu Ile Asn Asp Asn Lys Ser Val Ala
                     580                 585                 590

Ala Leu Phe Ser Gly Gln Gly Ala Gln Tyr Thr His Met Phe Asn Asp
                 595                 600                 605

Val Ala Met Gln Trp Pro Gln Phe Arg Leu Cys Val Asn Asp Met Glu
             610                 615                 620

Lys Ala Gln Glu Glu Val Ile Asn Asp Lys Ser Val Lys Arg Ile Ser
         625                 630                 635                 640

Gln Val Met Phe Pro Arg Lys Pro Tyr Ala Arg Glu Ser Pro Leu Asp
                         645                 650                 655
```

```
Asn Lys Glu Ile Ser Lys Thr Glu Tyr Ser Gln Thr Thr Val Ala
            660                 665                 670

Ser Ser Val Gly Leu Phe Glu Ile Phe Arg Asp Ala Gly Phe Ala Pro
        675                 680                 685

Ala Phe Val Ala Gly His Ser Leu Gly Glu Phe Ser Ala Leu Tyr Ala
690                 695                 700

Ala Gly Leu Ile Asp Arg Glu Asp Leu Phe Lys Leu Val Cys Asn Arg
705                 710                 715                 720

Ala Met Ala Met Arg Asp Ala Pro Lys Lys Ser Ala Asp Gly Ala Met
                725                 730                 735

Ala Ala Val Ile Gly Pro Asn Ala Ser Ser Ile Lys Leu Ser Ala Pro
                740                 745                 750

Glu Val Trp Val Ala Asn Asn Ser Pro Ser Gln Thr Val Ile Thr
        755                 760                 765

Gly Ala Asn Ser Gly Val Gln Ala Glu Thr Ser Lys Leu Lys Thr Gln
        770                 775                 780

Gly Phe Arg Val Val His Leu Ala Cys Asp Gly Ala Phe His Ser Pro
785                 790                 795                 800

His Met Glu Asn Ala Glu Lys Gln Phe Gln Lys Ala Leu Ser Ala Val
                805                 810                 815

Lys Phe Asn Lys Pro Thr Gly Ser Ser Pro Lys Ile Phe Ser Asn Val
                820                 825                 830

Thr Gly Gly Val Phe Thr Asp Pro Lys Thr Ala Leu Ser Arg His Met
                835                 840                 845

Thr Ser Ser Val Gln Phe Leu Thr Gln Ile Lys Asn Met Tyr Ala Ala
        850                 855                 860

Gly Ala Arg Val Phe Ile Glu Phe Gly Pro Lys Gln Val Leu Ser Lys
865                 870                 875                 880

Leu Val Asn Glu Ile Phe Pro Gly Asp Thr Ser Val Leu Thr Val Ser
                885                 890                 895

Val Asn Pro Ala Ser Ala Lys Asp Ser Asp Ile Gln Leu Arg Gln Ala
        900                 905                 910

Ala Val Gln Met Ala Val Ala Gly Val Ala Leu Thr Asp Phe Asp Lys
        915                 920                 925

Trp Glu Leu Lys Asp Pro Thr Arg Met Lys Glu Phe Pro Arg Lys Lys
    930                 935                 940

Thr Thr Leu Thr Leu Ser Ala Ala Thr Tyr Val Ser Lys Lys Thr Leu
945                 950                 955                 960

Gln Glu Arg Glu Arg Ile Met Asn Asp Gly Arg Thr Val Ser Cys Val
                965                 970                 975

Gln Arg Ile Glu Asn Thr Asn Thr Gly Glu Leu Glu Lys Leu Lys Lys
                980                 985                 990

Gln Leu Gln Asp Lys Glu Asn Glu  Val Val Arg Val Gln  Ala Leu Ala
        995                 1000                1005

Thr Gln  Ala Ser Ala Asp Leu  Gln Asn Thr Lys Ala  Glu Leu Gln
    1010                1015                1020

Lys Ala  Gln Ala Thr Lys Ser  Ser Asn Ala Ala Ser  Asp Ala Val
    1025                1030                1035

Val Ala  Lys His Lys Ala Ile  Leu Leu Ala Met Leu  Glu Glu Leu
    1040                1045                1050

Glu Thr  Gly Lys Ala Val Asp  Tyr Ser Ser Phe Ser  Lys Gly Gln
    1055                1060                1065
```

```
Val Ala Ser Pro Ala Thr Val Arg Val Ser Ala Pro Val Gln
    1070                1075            1080

Ala Ala Ala Pro Val Gln Val Ser Ala Ser Val Asp Ser Gly Leu
    1085                1090            1095

Leu Ala Lys Ala Glu Gln Val Val Leu Glu Val Leu Ala Ser Lys
    1100                1105            1110

Thr Gly Tyr Glu Thr Glu Leu Ile Glu Leu Asp Met Glu Leu Glu
    1115                1120            1125

Thr Glu Leu Gly Ile Asp Ser Ile Lys Arg Val Glu Ile Leu Ser
    1130                1135            1140

Glu Val Gln Ala Gln Leu Asn Val Glu Ala Lys Asp Val Asp Ala
    1145                1150            1155

Leu Ser Arg Thr Arg Thr Val Gly Glu Val Ile Asp Ala Met Lys
    1160                1165            1170

Ala Glu Ile Ala Gly Gly Gln Pro Ala Ala Pro Val Gln Val Ala
    1175                1180            1185

Ala Pro Thr Gln Val Val Ala Pro Val Gln Ala Ser Ala Pro Val
    1190                1195            1200

Asp Ser Gly Leu Leu Ala Lys Ala Glu Gln Val Val Leu Glu Val
    1205                1210            1215

Leu Ala Ser Lys Thr Gly Tyr Glu Thr Glu Leu Ile Glu Leu Asp
    1220                1225            1230

Met Glu Leu Glu Thr Glu Leu Gly Ile Asp Ser Ile Lys Arg Val
    1235                1240            1245

Glu Ile Leu Ser Glu Val Gln Ala Gln Leu Ser Val Glu Ala Lys
    1250                1255            1260

Asp Val Asp Ala Leu Ser Arg Thr Arg Thr Val Gly Glu Val Ile
    1265                1270            1275

Asp Ala Met Lys Ala Glu Ile Ala Gly Gly Gln Pro Ala Ala Pro
    1280                1285            1290

Val Gln Val Ala Ala Pro Thr Gln Val Val Ala Pro Val Gln Ala
    1295                1300            1305

Ser Ala Pro Val Asp Ser Gly Leu Leu Ala Lys Ala Glu Gln Val
    1310                1315            1320

Val Leu Glu Val Leu Ala Ser Lys Thr Gly Tyr Glu Thr Glu Leu
    1325                1330            1335

Ile Glu Leu Asp Met Glu Leu Glu Thr Glu Leu Gly Ile Asp Ser
    1340                1345            1350

Ile Lys Arg Val Glu Ile Leu Ser Glu Val Gln Ala Gln Leu Ser
    1355                1360            1365

Val Glu Ala Lys Asp Val Asp Ala Leu Ser Arg Thr Arg Thr Val
    1370                1375            1380

Gly Glu Val Ile Asp Ala Met Lys Ala Glu Ile Ser Gly Gly Gln
    1385                1390            1395

Pro Ala Ala Pro Val Gln Val Ala Ala Pro Thr Gln Ile Val Ala
    1400                1405            1410

Pro Val Gln Val Ser Ala Pro Val Asp Ser Gly Leu Leu Ala Lys
    1415                1420            1425

Ala Glu Gln Val Val Leu Glu Val Leu Ala Ser Lys Thr Gly Tyr
    1430                1435            1440

Glu Thr Glu Leu Ile Glu Leu Asp Met Glu Leu Glu Thr Glu Leu
    1445                1450            1455

Gly Ile Asp Ser Ile Lys Arg Val Glu Ile Leu Ser Glu Val Gln
```

-continued

```
                1460                1465                1470

Ala Gln Leu Ser Val Glu Ala Lys Asp Val Asp Ala Leu Ser Arg
    1475                1480                1485

Thr Arg Thr Val Gly Glu Val Ile Asp Ala Met Lys Ala Glu Ile
    1490                1495                1500

Ser Gly Gly Gln Pro Thr Ala Pro Val Gln Val Ala Ala Pro Thr
    1505                1510                1515

Gln Ile Val Ala Pro Val Gln Val Ser Ala Pro Val Asp Ser Gly
    1520                1525                1530

Leu Leu Ala Lys Ala Glu Gln Val Val Leu Glu Val Leu Ala Ser
    1535                1540                1545

Lys Thr Gly Tyr Glu Thr Glu Leu Ile Glu Leu Asp Met Glu Leu
    1550                1555                1560

Glu Thr Glu Leu Gly Ile Asp Ser Ile Lys Arg Val Glu Ile Leu
    1565                1570                1575

Ser Glu Val Gln Ala Gln Leu Ser Val Glu Ala Lys Asp Val Asp
    1580                1585                1590

Ala Leu Ser Arg Thr Arg Thr Val Gly Glu Val Ile Asp Ala Met
    1595                1600                1605

Lys Ala Glu Ile Ser Gly Gly Gln Pro Ala Ala Pro Val Gln Val
    1610                1615                1620

Ala Ala Pro Thr Gln Ile Val Ala Pro Val Gln Ala Ser Ala Pro
    1625                1630                1635

Val Asp Ser Gly Leu Leu Ala Lys Ala Glu Gln Val Val Leu Glu
    1640                1645                1650

Val Leu Ala Ser Lys Thr Gly Tyr Glu Thr Glu Leu Ile Glu Leu
    1655                1660                1665

Asp Met Glu Leu Glu Thr Glu Leu Gly Ile Asp Ser Ile Lys Arg
    1670                1675                1680

Val Glu Ile Leu Ser Glu Val Gln Ala Gln Leu Ser Val Glu Ala
    1685                1690                1695

Lys Asp Val Asp Ala Leu Ser Arg Thr Arg Thr Val Gly Glu Val
    1700                1705                1710

Ile Asp Ala Met Lys Ala Glu Ile Ser Gly Gly Gln Pro Ala Ala
    1715                1720                1725

Pro Val Gln Val Ala Ala Pro Thr Gln Ile Val Ala Pro Val Gln
    1730                1735                1740

Val Ser Ala Pro Val Asp Ser Gly Leu Leu Ala Lys Ala Glu Gln
    1745                1750                1755

Val Val Leu Glu Val Leu Ala Ser Lys Thr Gly Tyr Glu Thr Glu
    1760                1765                1770

Leu Ile Glu Leu Asp Met Glu Leu Glu Thr Glu Leu Gly Ile Asp
    1775                1780                1785

Ser Ile Lys Arg Val Glu Ile Leu Ser Glu Val Gln Ala Gln Leu
    1790                1795                1800

Asn Val Glu Ala Lys Asp Val Asp Ala Leu Ser Arg Thr Arg Thr
    1805                1810                1815

Val Gly Glu Val Ile Asp Ala Met Lys Ala Glu Ile Ala Gly Gly
    1820                1825                1830

Gln Pro Ala Ala Pro Val Gln Val Ala Ala Pro Ala Pro Val Val
    1835                1840                1845

Ala Pro Val Gln Val Ser Thr Pro Val Asp Ser Gly Leu Leu Ala
    1850                1855                1860
```

```
Lys Ala Glu Gln Val Val Leu Glu Val Leu Ala Cys Lys Thr Gly
1865                1870                1875

Tyr Glu Thr Glu Leu Ile Glu Leu Asp Met Glu Leu Glu Thr Glu
1880                1885                1890

Leu Gly Ile Asp Ser Ile Lys Arg Val Glu Ile Leu Ser Glu Val
1895                1900                1905

Gln Ala Gln Leu Ser Val Glu Ala Lys Asp Val Asp Ala Leu Ser
1910                1915                1920

Arg Thr Arg Thr Val Gly Glu Val Ile Asp Ala Met Lys Ala Glu
1925                1930                1935

Ile Ser Gly Gly Gln Pro Thr Ala Pro Val Gln Val Ala Ala Pro
1940                1945                1950

Thr Gln Val Val Ala Pro Val Lys Val Ser Thr Pro Val Asp Ser
1955                1960                1965

Gly Leu Leu Ala Lys Ala Glu Gln Val Val Leu Glu Val Leu Ala
1970                1975                1980

Ser Lys Thr Gly Tyr Glu Thr Glu Leu Ile Glu Leu Asp Met Glu
1985                1990                1995

Leu Glu Thr Glu Leu Gly Ile Asp Ser Ile Lys Arg Val Glu Ile
2000                2005                2010

Leu Ser Glu Val Gln Ala Gln Leu Asn Val Glu Ala Lys Asp Val
2015                2020                2025

Asp Ala Leu Ser Arg Thr Arg Thr Val Gly Glu Val Ile Asp Ala
2030                2035                2040

Met Lys Ala Glu Ile Ala Gly Asp Gln Pro Ala Pro Ala Val Val
2045                2050                2055

Pro Val Gln Ala Lys Ser Gly Val Ala Asn Pro Ala Leu Leu Ala
2060                2065                2070

Lys Ala Glu Gln Val Val Leu Glu Val Leu Ala Ser Lys Thr Gly
2075                2080                2085

Tyr Glu Thr Glu Leu Ile Glu Leu Asp Met Glu Leu Glu Thr Glu
2090                2095                2100

Leu Gly Ile Asp Ser Ile Lys Arg Val Glu Ile Leu Ser Glu Val
2105                2110                2115

Gln Ala Glu Leu Ser Val Glu Ala Lys Asp Val Asp Ala Leu Ser
2120                2125                2130

Arg Thr Arg Thr Val Gly Glu Val Ile Asp Ala Met Lys Ala Glu
2135                2140                2145

Ile Ala Gly Ser Ala Val Thr Val Ala Thr Leu Asp Asp Ser Thr
2150                2155                2160

Ile Met Glu Glu Thr Asp Asp Glu Asp Glu Asp Phe Ile Leu Tyr
2165                2170                2175

Asp His Val Tyr Gly Ser Glu Cys Glu Asp Leu Ser Leu Ser Phe
2180                2185                2190

Ser Ser Val Lys Ser Ile Pro Arg Ala Asp Lys Leu Leu Leu Asp
2195                2200                2205

Asn Ile Ala Glu Arg Pro Ile Val Ile Val Asp Cys Gly Thr Lys
2210                2215                2220

Leu Thr Thr Glu Leu Ala Lys Ala Ile Gly Glu Arg Ala Val Val
2225                2230                2235

Ala Thr Phe Ser Ala Gln Ser Leu Val Ser Arg Gly Phe Val Gly
2240                2245                2250
```

```
Lys Ser Phe Thr Leu Gly Asn Thr Glu Glu Ser Glu Ile Glu Lys
    2255                2260                2265

Met Val Ser Ser Ile Glu Ser Ser Tyr Gly Lys Ile Gly Gly Phe
    2270                2275                2280

Val Tyr Gln His Phe His Asp Ser Asp Tyr Gly Met Gln Leu Gly
    2285                2290                2295

Trp Ala Leu Met Ala Ala Lys His Leu Lys Glu Ser Leu Asn Asp
    2300                2305                2310

Pro Ile Lys Asn Gly Arg Thr Phe Phe Leu Ala Val Ala Arg Met
    2315                2320                2325

Asn Gly Lys Leu Gly Met Asp Asn Ala Ser Val His Asp Gln Gly
    2330                2335                2340

Ile Val Glu Ser Cys Gly Ile Ala Glu Arg Gly Ala Ile Phe Gly
    2345                2350                2355

Leu Cys Lys Thr Leu Asp Leu Glu Trp Pro Asn Val Phe Ala Arg
    2360                2365                2370

Gly Val Asp Ile Ala Glu Gly Met Ser Tyr Ser Leu Ala Ala Glu
    2375                2380                2385

Leu Ile Val Asp Glu Ile Ser Cys Ala Asn Leu Ser Ile Arg Glu
    2390                2395                2400

Ser Gly Tyr Thr Ile Ser Gly Glu Arg Phe Thr Thr Glu Ala His
    2405                2410                2415

Lys Leu Val Thr Gly Lys Pro His Ala Pro Ile Lys Lys Lys Asp
    2420                2425                2430

Ala Phe Leu Val Ser Gly Gly Ala Arg Gly Ile Thr Pro Leu Cys
    2435                2440                2445

Ile Arg Glu Ile Ala Lys Ala Val Lys Gly Gly Thr Tyr Ile Leu
    2450                2455                2460

Met Gly Arg Ser Ala Leu Ala Asp Glu Pro Leu Trp Ala Asn Gly
    2465                2470                2475

Lys Ser Gly Lys Asp Leu Asp Lys Ala Gly Leu Ala Phe Leu Lys
    2480                2485                2490

Glu Glu Phe Ala Ala Gly Arg Gly Ser Lys Pro Thr Pro Lys Val
    2495                2500                2505

His Lys Ser Leu Ile Asp Lys Val Leu Gly Ile Arg Glu Val Arg
    2510                2515                2520

Ala Ser Ile Ala Asn Ile Glu Ala His Gly Ala Lys Ala Ile Tyr
    2525                2530                2535

Leu Ser Cys Asp Val Ser Ser Ala Glu Lys Val Lys Ala Ala Val
    2540                2545                2550

Gln Lys Val Glu Lys Glu His Leu Val Arg Ile Thr Gly Ile Val
    2555                2560                2565

His Ala Ser Gly Val Leu Arg Asp Lys Leu Val Glu Asn Lys Thr
    2570                2575                2580

Leu Asp Asp Phe Asn Ala Val Tyr Gly Thr Lys Val Thr Gly Leu
    2585                2590                2595

Val Asn Leu Leu Ser Ala Val Asn Met Asn Phe Val Arg His Leu
    2600                2605                2610

Val Met Phe Ser Ser Leu Ala Gly Tyr His Gly Asn Val Gly Gln
    2615                2620                2625

Ser Asp Tyr Ala Met Ala Asn Glu Ser Leu Asn Lys Ile Gly Phe
    2630                2635                2640

Arg Leu Gly Ala Ala Tyr Ser Gln Leu Cys Val Lys Ser Ile Cys
```

| | | 2645 | | | 2650 | | | 2655 | | |
|---|---|---|---|---|---|---|---|---|---|---|

Phe Gly Pro Trp Asp Gly Gly Met Val Thr Pro Ala Leu Lys Lys
            2660                2665                2670

Gln Phe Gln Ser Met Gly Val Gln Ile Ile Pro Arg Glu Gly Gly
    2675                2680                2685

Ala Glu Thr Val Ala Arg Ile Val Leu Ser Ser Asn Pro Ser Gln
2690                2695                2700

Val Leu Val Gly Asn Trp Gly Val Pro Pro Val Ser Pro Leu Ser
    2705                2710                2715

Lys Ser Ala Thr Ile Val Gln Thr Phe Thr Pro Glu Leu Asn Pro
2720                2725                2730

Phe Leu Lys Ser His Gln Ile His Gly Lys Asn Val Leu Pro Met
    2735                2740                2745

Thr Val Ala Ile Gly Tyr Leu Ala His Leu Val Lys Asn Phe Tyr
2750                2755                2760

Ala Gly His His Leu Trp Gly Val Glu Asp Ala Gln Leu Phe Ser
    2765                2770                2775

Gly Val Val Ile Asp His Ala Val Gln Ala Gln Val Lys Leu Thr
2780                2785                2790

Glu Gln Ser Leu Asp Asp Asp Gly Lys Val Lys Val Gln Ala Val
    2795                2800                2805

Leu Thr Ala Ser Asn Asp Asn Gly Lys Met Val Pro Ala Tyr Lys
2810                2815                2820

Ala Val Ile Val Leu Gly Lys Thr Ser Arg Pro Ala Phe Ile Leu
    2825                2830                2835

Lys Asp Phe Ser Leu Gln Glu Ser Asn Ser Arg Ser Ala Asp Glu
2840                2845                2850

Leu Tyr Asp Gly Lys Thr Leu Phe His Gly Pro Leu Phe Arg Gly
    2855                2860                2865

Ile Thr Lys Leu Leu Asn Val Ser Asp Thr Ser Leu Thr Thr Gln
2870                2875                2880

Cys Thr Asn Ile Asp Leu Thr Ala Thr Glu Arg Gly Gln Phe Ala
    2885                2890                2895

Asp Ile Glu Pro Val Asn Pro Phe Met Ala Asp Ala Ala Phe Gln
2900                2905                2910

Ala Met Leu Val Trp Val Arg Asn Leu Arg Asn Ser Ala Ser Leu
    2915                2920                2925

Pro Asn Asn Cys Glu Arg Val Asp Ile Tyr Lys Pro Ile Ala Pro
2930                2935                2940

Gly Glu Lys Tyr Tyr Thr Thr Leu Gln Ala Leu Gly Asn Thr Ser
    2945                2950                2955

Gly Ser Val Leu Lys Ser Val Phe Tyr Met His Asp Glu Gln Gly
2960                2965                2970

Glu Val Phe Leu Ser Gly Arg Ala Ser Val Val Val Asn Asp Lys
    2975                2980                2985

Met Glu Phe
    2990

<210> SEQ ID NO 70
<211> LENGTH: 5880
<212> TYPE: DNA
<213> ORGANISM: Thraustochytrium sp.

<400> SEQUENCE: 70

-continued

| | | | | | |
|---|---|---|---|---|---|
| atggtgaaat | taagtgttgg | tgataatatt | tgtcatgatc | aacgtgttgc | tgttgttggt | 60 |
| atggctgtta | tgtatgctgg | ttgtcaaaat | caacatgaat | tttggcaatc | tttacaaggt | 120 |
| aaaaatatga | attcaaaatc | gatttcacaa | aatcgtttag | gttctgagta | tagagaagaa | 180 |
| cattttaaac | ctgaaagaag | taaatattcc | gataccttt | gtaatgaaag | atatggttgt | 240 |
| attgatgaga | atgttcaaag | tgaacatgaa | cttttattaa | aacttgcaaa | agatgctatt | 300 |
| gcggatacaa | aaggttctat | tgatttgaat | aaaaccggaa | tcgttagtgg | ttgcttatct | 360 |
| tttccaatgg | ataatttaca | aggtgattta | ttaaatttgt | atcaatgtca | cattgaaaag | 420 |
| aaaattgggc | caaatgcatt | aaaagatgtg | aatttatggt | ctaaaagaac | caccaacgga | 480 |
| aaagatgata | aaaaagctta | ttttgatcct | gcctctttcg | tagctgaaca | attagatatg | 540 |
| ggaccattac | attatagttt | agatgctgct | tgtgcgtctg | cactttatgt | attaagactt | 600 |
| gctcaagatc | atttattaag | tggtgctgct | gatacaatgt | tatgtggtgc | atcttgttta | 660 |
| cctgaacctt | tttttatttt | atctggtttt | tctactttc | atgcaatgcc | attatctggt | 720 |
| gatgtttctg | ctcctttgca | taaaacttca | caaggtctta | cacctggtga | aggtggtgct | 780 |
| attatggtac | ttaaacgatt | aaatgatgca | atccgtgatg | gtgatagaat | ttatggtact | 840 |
| ttacttggtg | ctgaattaag | taatgctggt | tgtggtttac | cattgagtcc | acatatgcca | 900 |
| agtgaatttg | attgtatgga | aaaagcttta | caaagagtac | acagattacc | atcatctatt | 960 |
| caatatgttg | agtgtcatgc | aactggtaca | ccacaaggtg | ataaagttga | aattgatgct | 1020 |
| atgacaaaat | gttttggtga | acatttacca | aggtttggtt | caacgaaagg | gaattttggt | 1080 |
| catacacttg | ttgctgctgg | ttttgctggt | atgtgtaaag | ttttattatc | aatgcaatat | 1140 |
| ggtgaaatac | caccaactcc | aggtcttgaa | aatccagaca | atattatgca | tgatttagtt | 1200 |
| gttactgaaa | caattccatg | gcctaataca | aatggtgatt | tgaaacgtgc | atgtttatct | 1260 |
| gcttttggat | tcggtggtac | taatgcacat | gctgtatttg | aagagtatcg | ttcagattta | 1320 |
| caagcaaata | aaactcttga | aaatgaaagt | aaaagtcatg | aaatcttttc | ttcatttaaa | 1380 |
| attgctattg | ttggtatgga | atctgaattt | ggtactttga | aggattaca | agaatttgaa | 1440 |
| cgtgctattt | acaatggtgg | tcatggtgca | tgtgatttac | ctgaaaatag | atggagattt | 1500 |
| cttggagaag | ataaagaatt | tttacaagct | tgtggtttac | aaaaattacc | aagaggttgt | 1560 |
| tatattaaag | aagtggaaac | tgattttaaa | aggttacgtt | taccaatgat | acaggaggat | 1620 |
| attctaagac | ctttacagtt | gttagctgtt | tcgattatcg | acagagcact | taacgcatct | 1680 |
| ggtgttaaac | caaatggcaa | agttgcagtt | ttagttggat | taggtactga | tcttgaatta | 1740 |
| tatcgtcatc | gtgctcgtgt | tgcattaaag | gaacgcctcc | aaactgcggt | caaagaagat | 1800 |
| attccttttac | ttgaaaagtt | aatgaactat | gtcaatgata | gaggtacaag | tacatcatat | 1860 |
| acatcttata | ttggaaattt | ggttgcaact | cgagtttcat | cattatgggg | ttttactggt | 1920 |
| ccatcattca | cgattactga | aggtgaaaat | tccgtatatc | gttgtcttga | tttgggaaga | 1980 |
| tggttcttag | ctaatggtga | agtagatgct | gttgttgttg | ccggggttga | tttatgtggt | 2040 |
| agtgctgaaa | atctttttgt | aaaatctcgt | agaagtaaag | tttccacaca | aaatgaacca | 2100 |
| tttgcaaatt | ttgaatcaaa | tgctgatgga | tattttgctg | gagatggttg | tggagctttg | 2160 |
| gttttgaaac | gattgagtga | ttgtacggat | tcaactgaaa | aaatttatgc | aacggtggat | 2220 |
| tcaattgctg | ttggtgatga | agttggccca | actattaaac | aagctttgaa | gaatgcatcc | 2280 |
| atagcagcga | aagatattga | actggcagag | ctatcagcaa | gttcaggcaa | acatcattct | 2340 |
| ggtagaatca | cttgtgaaga | tgaactaaat | gaactgggtg | aaattttcaa | tgaaggtata | 2400 |

-continued

```
caaagagttg caattggtag tgtgaaagct aatgttggag atgttggata tgcatctggt   2460
gcagcaagtt taatcaaaac ggctttgtgc ctgtacaacc gatatttacc aaagttacca   2520
aattggaata agccaacgaa agatgttgaa tggtccaaat cattttttgt atgtgaacat   2580
tctagagcat ggttgaaaaa tgttgatgaa aatagacatg ctgtcgtttc tggagtttgc   2640
gaaaatggtt cgtgttatgg aatcgtaatg tctgatgtac aaggacatca tgaagaatcg   2700
aatcttgtta gtttagacaa aaatgaacca aaagtactgg gtatttacgg agattcagtt   2760
gatgatatcc tagttcagct caacaaatat cttgaaaaat tccttcaaga aactggaacg   2820
gctgcggctg cacaaaaagt taaatcacct acaatagata ttgactccaa tgtgtttgct   2880
gagatgctta atctaccgca ggataaaaac aaaaaatttg cggtcgcatt ggttaccaca   2940
ccaaataaac tccagcgtga aatagaactt gctgtgaagg gtattccacg ttgcgtaaaa   3000
gcaaaagag attggtgttc tccatctgga agtattttg cttgtaatcc actcaaaagt   3060
gataatattg catttatgta tggtgaaggc cgaagcccat atgctggact gggatatgat   3120
ttgcatcgaa tttggcctat gctacacgag ttggttaaca atagaactac agaactttgg   3180
gatcaaggtg atagttggta tttacctcga tctagctctg ttgctgaaaa agaaaaagtc   3240
ttcggagatt ttgataagaa tcaaattgaa atgtttagat tgggtatttt tgtatcaatg   3300
tgtttcactg atatggccac tgaacttttg ggttttaaaac ccaaagccgc gtttggttta   3360
agtttgggtg aaatatctat gcttttttgca ttttctaaaa gaataccaa gttgtccaaa   3420
gaattgaccc gtcgtctaaa agaagcaaaa gtttgggcat cacaattagc tgttgaattt   3480
gcagctattc gagatttgtg gaatattcca gctgataaat ctattgatga attttggcaa   3540
gggtattttg tttacgcaaa tcgaaccctg gtcgagaaca caattgggga gaataaattt   3600
gttcgtttgt tgattgtaaa tgattcgcaa agttgtctaa ttgccgggaa accagatgaa   3660
tgtcaaaaag ttattgagaa gcttcatttg aagctaccgg cggttccagt aactcagggt   3720
atgatcggtc attgcccaga agcaattcct tatctagatc aaatcagtca tattcatgaa   3780
atgcttgaaa ttccaaaacc cgaaaatgtg aaattgttta caactagtga aaacagagaa   3840
ttagtgtcga tgaaagattc cgtgtcaaaa ttggttgctg agatttatca gcatgttgct   3900
gattttccaa acatcgtgaa caaggttaaa gaaacttgca aaactgatat atttattgaa   3960
ttgggatcga acaattatcg atctggagct gtcaaaacaa ttttaggtcc agaaatcgtt   4020
tctgttgcaa ttgataggca aaatgaaact gcatggggtc aactaatgaa gatggttgca   4080
tcgttgataa gtcatcgagt tccgggtgtt gaattgaaaa aactctatca tcctgaattg   4140
ctgaaatttg atccacaggc aaaaccgaat cgtttcatca gaaatataga actgaatgga   4200
ttttttgatc gtacgaatat tattgttgat aagcaactat cccctgcgga tccgaaactc   4260
gctgaaattg tgaacaatcg aaatatgcct aaagataatg tttatgtacc aattgaacgg   4320
gtgaaaacga tgataaaggc ggaaccagct aatttacaag tcagcgtggg aagtaaacca   4380
gttgttactg aaagaattag ttcggacgat aatctatttg aaaagttgtc agaaattaca   4440
aaatcttttg atggtgtaaa tgcgtgtact gaagcaatgt tgggagactc tggatttctc   4500
aaaacatatg aggttgacta tcctttgtac acaggtgcca tggctaaagg aattgcgtct   4560
gctgatttgg ttattgctgc tggtaaatca aagatcttgg catcatttgg agctggtggg   4620
ttggccttac aagtggtaga agatgccatt aaacaaatta agctgaatt ggggaacggt   4680
ccgtttgctg taaatttgat tcattcacca ttcgatccta gcttggagaa gggtaacgtt   4740
```

-continued

```
gatcttttc taaaatataa cgttcgattt gttgaagtat ccgcatttat gtcattaacc    4800
cctcaggttg tacgatacag agccgctggt ttggccaaag caagagatgg atctgtgaaa    4860
attcaaaatc gtattattgc caaaatttca agaacagagt tagcggaact gttcttgaaa    4920
ccagcaccca aaaatatttt agatgcattg gttgcggatg gatctattag tcaagaacaa    4980
gcccaacttg cattacttgt gccaatggct gatgatatta ctgtggaagc tgattctggt    5040
gggcatactg acaatcgacc aattcatgtt ttgttacctt tgataattca gcaaagaaat    5100
agaatttgta acaataccc aaaacattta aaagttcgaa tcggagcagc tggtggtatt    5160
ggatgcccga aggcagcatt tgctgcgttt gagatgggtg ctgcatacat tgcaactgga    5220
acggtaaatc aactttcaaa ggaagcaggt acttgtgact atgtacgtaa agtattgaat    5280
aaagctacat attcggatgt taccatggct ccagccgcag atatgttcga tcatggtgtt    5340
gaattacaag ttttgaagaa aggtactatg tttccttcac gtgctaaaaa actatacgat    5400
ttgttcaaaa aatacaaatc gattgaggaa ttaccagcag atgaggtgaa aaaacttgag    5460
caaaagtttt tcaaaaagtc gtttgatgaa gtatgggatg agaccaagaa ttactatatt    5520
aatcgtttac attctcccga aaaaattgaa cgtgctgaaa gagatgcaaa acttaaaatg    5580
tcgttatgtt ttcgttggta tttgtcgaag tcttccagat gggctaatac cggtgaatct    5640
ggaagagtgc aggattatca aatttggtgt ggtccagcaa ttgggtcata taatgatttt    5700
gcgaaaggat caccatgttt ggatcctgag attttgggta gttttccaag tgttgttcag    5760
attaataaac atattttacg tggtgcttgt ttctatcaaa gactctctca gttgaaatat    5820
ctgaatttta actatgagga attagatacg ttaacatact ctgcatcgaa ttttatttaa    5880
```

<210> SEQ ID NO 71
<211> LENGTH: 1959
<212> TYPE: PRT
<213> ORGANISM: Thraustochytrium sp.

<400> SEQUENCE: 71

```
Met Val Lys Leu Ser Val Gly Asp Asn Ile Cys His Asp Gln Arg Val
1               5                   10                  15

Ala Val Val Gly Met Ala Val Met Tyr Ala Gly Cys Gln Asn Gln His
            20                  25                  30

Glu Phe Trp Gln Ser Leu Gln Gly Lys Asn Met Asn Ser Lys Ser Ile
        35                  40                  45

Ser Gln Asn Arg Leu Gly Ser Glu Tyr Arg Glu Glu His Phe Lys Pro
    50                  55                  60

Glu Arg Ser Lys Tyr Ser Asp Thr Phe Cys Asn Glu Arg Tyr Gly Cys
65                  70                  75                  80

Ile Asp Glu Asn Val Gln Ser Glu His Glu Leu Leu Lys Leu Ala
                85                  90                  95

Lys Asp Ala Ile Ala Asp Thr Lys Gly Ser Ile Asp Leu Asn Lys Thr
            100                 105                 110

Gly Ile Val Ser Gly Cys Leu Ser Phe Pro Met Asp Asn Leu Gln Gly
        115                 120                 125

Asp Leu Leu Asn Leu Tyr Gln Cys His Ile Glu Lys Lys Ile Gly Pro
    130                 135                 140

Asn Ala Leu Lys Asp Val Asn Leu Trp Ser Lys Arg Thr Thr Asn Gly
145                 150                 155                 160

Lys Asp Asp Lys Lys Ala Tyr Phe Asp Pro Ala Ser Phe Val Ala Glu
                165                 170                 175
```

```
Gln Leu Asp Met Gly Pro Leu His Tyr Ser Leu Asp Ala Ala Cys Ala
            180                 185                 190

Ser Ala Leu Tyr Val Leu Arg Leu Ala Gln Asp His Leu Leu Ser Gly
        195                 200                 205

Ala Ala Asp Thr Met Leu Cys Gly Ala Ser Cys Leu Pro Glu Pro Phe
    210                 215                 220

Phe Ile Leu Ser Gly Phe Ser Thr Phe His Ala Met Pro Leu Ser Gly
225                 230                 235                 240

Asp Val Ser Ala Pro Leu His Lys Thr Ser Gln Gly Leu Thr Pro Gly
                245                 250                 255

Glu Gly Gly Ala Ile Met Val Leu Lys Arg Leu Asn Asp Ala Ile Arg
            260                 265                 270

Asp Gly Asp Arg Ile Tyr Gly Thr Leu Leu Gly Ala Glu Leu Ser Asn
        275                 280                 285

Ala Gly Cys Gly Leu Pro Leu Ser Pro His Met Pro Ser Glu Phe Asp
    290                 295                 300

Cys Met Glu Lys Ala Leu Gln Arg Val His Arg Leu Pro Ser Ser Ile
305                 310                 315                 320

Gln Tyr Val Glu Cys His Ala Thr Gly Thr Pro Gln Gly Asp Lys Val
                325                 330                 335

Glu Ile Asp Ala Met Thr Lys Cys Phe Gly Glu His Leu Pro Arg Phe
            340                 345                 350

Gly Ser Thr Lys Gly Asn Phe Gly His Thr Leu Val Ala Ala Gly Phe
        355                 360                 365

Ala Gly Met Cys Lys Val Leu Leu Ser Met Gln Tyr Gly Glu Ile Pro
    370                 375                 380

Pro Thr Pro Gly Leu Glu Asn Pro Asp Asn Ile Met His Asp Leu Val
385                 390                 395                 400

Val Thr Glu Thr Ile Pro Trp Pro Asn Thr Asn Gly Asp Leu Lys Arg
                405                 410                 415

Ala Cys Leu Ser Ala Phe Gly Phe Gly Gly Thr Asn Ala His Ala Val
            420                 425                 430

Phe Glu Glu Tyr Arg Ser Asp Leu Gln Ala Asn Lys Thr Leu Glu Asn
        435                 440                 445

Glu Ser Lys Ser His Glu Ile Phe Ser Ser Phe Lys Ile Ala Ile Val
    450                 455                 460

Gly Met Glu Ser Glu Phe Gly Thr Leu Lys Gly Leu Gln Glu Phe Glu
465                 470                 475                 480

Arg Ala Ile Tyr Asn Gly Gly His Gly Ala Cys Asp Leu Pro Glu Asn
                485                 490                 495

Arg Trp Arg Phe Leu Gly Glu Asp Lys Glu Phe Leu Gln Ala Cys Gly
            500                 505                 510

Leu Gln Lys Leu Pro Arg Gly Cys Tyr Ile Lys Glu Val Glu Thr Asp
        515                 520                 525

Phe Lys Arg Leu Arg Leu Pro Met Ile Gln Glu Asp Ile Leu Arg Pro
    530                 535                 540

Leu Gln Leu Leu Ala Val Ser Ile Ile Asp Arg Ala Leu Asn Ala Ser
545                 550                 555                 560

Gly Val Lys Pro Asn Gly Lys Val Ala Val Leu Val Gly Leu Gly Thr
                565                 570                 575

Asp Leu Glu Leu Tyr Arg His Arg Ala Arg Val Ala Leu Lys Glu Arg
            580                 585                 590

Leu Gln Thr Ala Val Lys Glu Asp Ile Pro Leu Leu Glu Lys Leu Met
```

```
                595                 600                 605
Asn Tyr Val Asn Asp Arg Gly Thr Ser Thr Ser Tyr Thr Ser Tyr Ile
        610                 615                 620
Gly Asn Leu Val Ala Thr Arg Val Ser Ser Leu Trp Gly Phe Thr Gly
625                 630                 635                 640
Pro Ser Phe Thr Ile Thr Glu Gly Glu Asn Ser Val Tyr Arg Cys Leu
                645                 650                 655
Asp Leu Gly Arg Trp Phe Leu Ala Asn Gly Glu Val Asp Ala Val Val
                660                 665                 670
Val Ala Gly Val Asp Leu Cys Gly Ser Ala Glu Asn Leu Phe Val Lys
        675                 680                 685
Ser Arg Arg Ser Lys Val Ser Thr Gln Asn Glu Pro Phe Ala Asn Phe
        690                 695                 700
Glu Ser Asn Ala Asp Gly Tyr Phe Ala Gly Asp Gly Cys Gly Ala Leu
705                 710                 715                 720
Val Leu Lys Arg Leu Ser Asp Cys Thr Asp Ser Thr Glu Lys Ile Tyr
                725                 730                 735
Ala Thr Val Asp Ser Ile Ala Val Gly Asp Glu Val Gly Pro Thr Ile
                740                 745                 750
Lys Gln Ala Leu Lys Asn Ala Ser Ile Ala Ala Lys Asp Ile Glu Leu
        755                 760                 765
Ala Glu Leu Ser Ala Ser Ser Gly Lys His His Ser Gly Arg Ile Thr
770                 775                 780
Cys Glu Asp Glu Leu Asn Glu Leu Gly Glu Ile Phe Asn Glu Gly Ile
785                 790                 795                 800
Gln Arg Val Ala Ile Gly Ser Val Lys Ala Asn Val Gly Asp Val Gly
                805                 810                 815
Tyr Ala Ser Gly Ala Ala Ser Leu Ile Lys Thr Ala Leu Cys Leu Tyr
                820                 825                 830
Asn Arg Tyr Leu Pro Lys Leu Pro Asn Trp Asn Lys Pro Thr Lys Asp
        835                 840                 845
Val Glu Trp Ser Lys Ser Phe Phe Val Cys Glu His Ser Arg Ala Trp
850                 855                 860
Leu Lys Asn Val Asp Glu Asn Arg His Ala Val Val Ser Gly Val Cys
865                 870                 875                 880
Glu Asn Gly Ser Cys Tyr Gly Ile Val Met Ser Asp Val Gln Gly His
                885                 890                 895
His Glu Glu Ser Asn Leu Val Ser Leu Asp Lys Asn Glu Pro Lys Val
                900                 905                 910
Leu Gly Ile Tyr Gly Asp Ser Val Asp Asp Ile Leu Val Gln Leu Asn
        915                 920                 925
Lys Tyr Leu Glu Lys Phe Gln Glu Thr Gly Thr Ala Ala Ala Ala
        930                 935                 940
Gln Lys Val Lys Ser Pro Thr Ile Asp Ile Asp Ser Asn Val Phe Ala
945                 950                 955                 960
Glu Met Leu Asn Leu Pro Gln Asp Lys Asn Lys Phe Ala Val Ala
                965                 970                 975
Leu Val Thr Thr Pro Asn Lys Leu Gln Arg Glu Ile Glu Leu Ala Val
                980                 985                 990
Lys Gly Ile Pro Arg Cys Val Lys Ala Lys Arg Asp Trp Cys Ser Pro
        995                 1000                1005
Ser Gly Ser Ile Phe Ala Cys Asn Pro Leu Lys Ser Asp Asn Ile
        1010                1015                1020
```

```
Ala Phe Met Tyr Gly Glu Gly Arg Ser Pro Tyr Ala Gly Leu Gly
    1025                1030                1035

Tyr Asp Leu His Arg Ile Trp Pro Met Leu His Glu Leu Val Asn
    1040                1045                1050

Asn Arg Thr Thr Glu Leu Trp Asp Gln Gly Asp Ser Trp Tyr Leu
    1055                1060                1065

Pro Arg Ser Ser Ser Val Ala Glu Lys Glu Lys Val Phe Gly Asp
    1070                1075                1080

Phe Asp Lys Asn Gln Ile Glu Met Phe Arg Leu Gly Ile Phe Val
    1085                1090                1095

Ser Met Cys Phe Thr Asp Met Ala Thr Glu Leu Leu Gly Leu Lys
    1100                1105                1110

Pro Lys Ala Ala Phe Gly Leu Ser Leu Gly Glu Ile Ser Met Leu
    1115                1120                1125

Phe Ala Phe Ser Lys Lys Asn Thr Lys Leu Ser Lys Glu Leu Thr
    1130                1135                1140

Arg Arg Leu Lys Glu Ala Lys Val Trp Ala Ser Gln Leu Ala Val
    1145                1150                1155

Glu Phe Ala Ala Ile Arg Asp Leu Trp Asn Ile Pro Ala Asp Lys
    1160                1165                1170

Ser Ile Asp Glu Phe Trp Gln Gly Tyr Phe Val Tyr Ala Asn Arg
    1175                1180                1185

Thr Leu Val Glu Asn Thr Ile Gly Glu Asn Lys Phe Val Arg Leu
    1190                1195                1200

Leu Ile Val Asn Asp Ser Gln Ser Cys Leu Ile Ala Gly Lys Pro
    1205                1210                1215

Asp Glu Cys Gln Lys Val Ile Glu Lys Leu His Leu Lys Leu Pro
    1220                1225                1230

Ala Val Pro Val Thr Gln Gly Met Ile Gly His Cys Pro Glu Ala
    1235                1240                1245

Ile Pro Tyr Leu Asp Gln Ile Ser His Ile His Glu Met Leu Glu
    1250                1255                1260

Ile Pro Lys Pro Glu Asn Val Lys Leu Phe Thr Thr Ser Glu Asn
    1265                1270                1275

Arg Glu Leu Val Ser Met Lys Asp Ser Val Ser Lys Leu Val Ala
    1280                1285                1290

Glu Ile Tyr Gln His Val Ala Asp Phe Pro Asn Ile Val Asn Lys
    1295                1300                1305

Val Lys Glu Thr Cys Lys Thr Asp Ile Phe Ile Glu Leu Gly Ser
    1310                1315                1320

Asn Asn Tyr Arg Ser Gly Ala Val Lys Thr Ile Leu Gly Pro Glu
    1325                1330                1335

Ile Val Ser Val Ala Ile Asp Arg Gln Asn Glu Thr Ala Trp Gly
    1340                1345                1350

Gln Leu Met Lys Met Val Ala Ser Leu Ile Ser His Arg Val Pro
    1355                1360                1365

Gly Val Glu Leu Lys Lys Leu Tyr His Pro Glu Leu Leu Lys Phe
    1370                1375                1380

Asp Pro Gln Ala Lys Pro Asn Arg Phe Ile Arg Asn Ile Glu Leu
    1385                1390                1395

Asn Gly Phe Phe Asp Arg Thr Asn Ile Ile Val Asp Lys Gln Leu
    1400                1405                1410
```

```
Ser Pro Ala Asp Pro Lys Leu Ala Glu Ile Val Asn Asn Arg Asn
    1415            1420                1425

Met Pro Lys Asp Asn Val Tyr Val Pro Ile Glu Arg Val Lys Thr
    1430            1435                1440

Met Ile Lys Ala Glu Pro Ala Asn Leu Gln Val Ser Val Gly Ser
    1445            1450                1455

Lys Pro Val Val Thr Glu Arg Ile Ser Ser Asp Asp Asn Leu Phe
    1460            1465                1470

Glu Lys Leu Ser Glu Ile Thr Lys Ser Phe Asp Gly Val Asn Ala
    1475            1480                1485

Cys Thr Glu Ala Met Leu Gly Asp Ser Gly Phe Leu Lys Thr Tyr
    1490            1495                1500

Glu Val Asp Tyr Pro Leu Tyr Thr Gly Ala Met Ala Lys Gly Ile
    1505            1510                1515

Ala Ser Ala Asp Leu Val Ile Ala Ala Gly Lys Ser Lys Ile Leu
    1520            1525                1530

Ala Ser Phe Gly Ala Gly Gly Leu Ala Leu Gln Val Val Glu Asp
    1535            1540                1545

Ala Ile Lys Gln Ile Lys Ala Glu Leu Gly Asn Gly Pro Phe Ala
    1550            1555                1560

Val Asn Leu Ile His Ser Pro Phe Asp Pro Ser Leu Glu Lys Gly
    1565            1570                1575

Asn Val Asp Leu Phe Leu Lys Tyr Asn Val Arg Phe Val Glu Val
    1580            1585                1590

Ser Ala Phe Met Ser Leu Thr Pro Gln Val Val Arg Tyr Arg Ala
    1595            1600                1605

Ala Gly Leu Ala Lys Ala Arg Asp Gly Ser Val Lys Ile Gln Asn
    1610            1615                1620

Arg Ile Ile Ala Lys Ile Ser Arg Thr Glu Leu Ala Glu Leu Phe
    1625            1630                1635

Leu Lys Pro Ala Pro Lys Asn Ile Leu Asp Ala Leu Val Ala Asp
    1640            1645                1650

Gly Ser Ile Ser Gln Glu Gln Ala Gln Leu Ala Leu Leu Val Pro
    1655            1660                1665

Met Ala Asp Asp Ile Thr Val Glu Ala Asp Ser Gly Gly His Thr
    1670            1675                1680

Asp Asn Arg Pro Ile His Val Leu Leu Pro Leu Ile Ile Gln Gln
    1685            1690                1695

Arg Asn Arg Ile Cys Lys Gln Tyr Pro Lys His Leu Lys Val Arg
    1700            1705                1710

Ile Gly Ala Ala Gly Gly Ile Gly Cys Pro Lys Ala Ala Phe Ala
    1715            1720                1725

Ala Phe Glu Met Gly Ala Ala Tyr Ile Ala Thr Gly Thr Val Asn
    1730            1735                1740

Gln Leu Ser Lys Glu Ala Gly Thr Cys Asp Tyr Val Arg Lys Val
    1745            1750                1755

Leu Asn Lys Ala Thr Tyr Ser Asp Val Thr Met Ala Pro Ala Ala
    1760            1765                1770

Asp Met Phe Asp His Gly Val Glu Leu Gln Val Leu Lys Lys Gly
    1775            1780                1785

Thr Met Phe Pro Ser Arg Ala Lys Lys Leu Tyr Asp Leu Phe Lys
    1790            1795                1800

Lys Tyr Lys Ser Ile Glu Glu Leu Pro Ala Asp Glu Val Lys Lys
```

| | | | | | | | | | | |
|---|---|---|---|---|---|---|---|---|---|---|
| | | 1805 | | | 1810 | | | | 1815 | |
| Leu | Glu | Gln | Lys | Val | Phe | Lys | Lys | Ser | Phe | Asp | Glu | Val | Trp | Asp |
| | | 1820 | | | | 1825 | | | | 1830 | |
| Glu | Thr | Lys | Asn | Tyr | Tyr | Ile | Asn | Arg | Leu | His | Ser | Pro | Glu | Lys |
| | | 1835 | | | | 1840 | | | | 1845 | |
| Ile | Glu | Arg | Ala | Glu | Arg | Asp | Ala | Lys | Leu | Lys | Met | Ser | Leu | Cys |
| | | 1850 | | | | 1855 | | | | 1860 | |
| Phe | Arg | Trp | Tyr | Leu | Ser | Lys | Ser | Ser | Arg | Trp | Ala | Asn | Thr | Gly |
| | | 1865 | | | | 1870 | | | | 1875 | |
| Glu | Ser | Gly | Arg | Val | Gln | Asp | Tyr | Gln | Ile | Trp | Cys | Gly | Pro | Ala |
| | | 1880 | | | | 1885 | | | | 1890 | |
| Ile | Gly | Ser | Tyr | Asn | Asp | Phe | Ala | Lys | Gly | Ser | Pro | Cys | Leu | Asp |
| | | 1895 | | | | 1900 | | | | 1905 | |
| Pro | Glu | Ile | Leu | Gly | Ser | Phe | Pro | Ser | Val | Val | Gln | Ile | Asn | Lys |
| | | 1910 | | | | 1915 | | | | 1920 | |
| His | Ile | Leu | Arg | Gly | Ala | Cys | Phe | Tyr | Gln | Arg | Leu | Ser | Gln | Leu |
| | | 1925 | | | | 1930 | | | | 1935 | |
| Lys | Tyr | Leu | Asn | Phe | Asn | Tyr | Glu | Glu | Leu | Asp | Thr | Leu | Thr | Tyr |
| | | 1940 | | | | 1945 | | | | 1950 | |
| Ser | Ala | Ser | Asn | Phe | Ile |
| | | 1955 | |

```
<210> SEQ ID NO 72
<211> LENGTH: 4368
<212> TYPE: DNA
<213> ORGANISM: Thraustochytrium sp.

<400> SEQUENCE: 72
atggttggtt tacaaatgaa aaagaaacca gtatgggaga tgagtaagga agaacaaagt      60
tctggaaaga atgttgtatt tgactatgat gaattgttgg aatttgctga aggtgatatt     120
ggtaaagtct ttggacctaa gtttgatatt atcgataagt atagtcgacg tgtacgttta     180
cctgcgagag aatatcttct agttaccaga gttactttga tggatgctga agttgggaat     240
ttcagagttg gatctagaat ggttactgaa tatgatgttc cagtaaatgg tgaactttca     300
caaggtggtg atgttccatg ggctgttctt gttgaatctg acaatgtgat cttatgttta     360
atatccttata tgggtattga ttttcaatgt aaaggtgatc gtgtctatcg attattaaat     420
actacgttga cgttttacgg tgttgctcat gagggtgaaa cactagtata cgatattcgt     480
gtaactggat ttgcaaaagg tatgcacggt gaaatctcca tgttttttt tgaatatgat     540
tgttatgtga atggacgatt attaatcgaa atgagagatg gttgtgcggg atttttact     600
gatgaagaac ttgcagcagg taaggagtt attaaaactg ttgctgaact tcataaaaga     660
aaatctattg ttccaaaatc cattaaacct tttgctctaa atccagcagt acacaaaaca     720
atgtttctg aaaatgatat ggaaaaattg tgtgagcgtc aatgggaaaa tgtattgggt     780
agtggacttc aaggtattga ctacaagtta tgtgcacgga aaatgcttat gattgatcgt     840
attactaaaa tacaacataa tggtggtgca tatggtcttg gattattggt tggcgaaaaa     900
attcttgaac gtgatcattg gtattttcca tgccattttg taaaggatca agttatggct     960
ggctcacttg ttagtgatgg ttgcagtcag ctactaaaac tttatatgtt atggttgggt    1020
ttacatgatg tggttccaga ttttcaattt cgtccagttc ctggacaacc aaataaagtt    1080
cgttgccgtg acaaattag tccacatcgt ggtaaacttg tttatgttat ggaaataaga    1140
gaaatgggat tcaatgaatc aactggacaa ccatatgcta ttgctgatgt tgatattatt    1200
```

-continued

```
gatgtaaact atgaacttgg tcaatcattt gatatggctg atattgatag ttatggacgt    1260
ggtaatttgt caaagaaaat tgtggttgat tttaaaggaa ttgctttgca aatggaaggt    1320
accgtgaaat catcaaatat cattgattct tcaccaaaat caactattat acaaccacct    1380
ccaaattgtc ttcgtggtga tccactggca ccatcacaag ttacatggca tccaatggca    1440
ggagttaatg gggcaccagc tccttcattt agtccatctg attatccacc acgtgctgtt    1500
tgcttcaaac catttcctgg taatccttta gataacgatc atacacctgg taaaatgcct    1560
ttaacatggt ttaatatgtc cgagtttatg tgtggtaaag tatcaaattg tcttggacca    1620
gaatttaaga gatttgataa ctctaaaaca tccagaagtc ctgcctttga tcttgcactt    1680
gttacacgtg ttgtgagtgt atcagatatg gaatttaaac ctcatttaaa tattgatgtt    1740
aatccaagta agggtacaat gataggtgaa tttgattgcc ctgcagatgc gtggttttt    1800 caaggatcat gtaacgatgg tcatatgccg tattctattg ttatggaaat tgctcttcaa    1860
acttctggtg tattaacttc agttttgaaa gcacctttga ctatggataa agatgatatt    1920
cttttccgca atttggatgc cactgctgaa atggttcgaa gtgatgttga ttgtagaggt    1980
aaaactatca aaactttac tcaatgtacc ggttacagta tgctcggaaa atgggaatt    2040 catagattca catttgaatt atctgttgat gatgtagttt tctacaaagg atcaacatct    2100
tttggttggt tcaccccctga agtattcgag tcacaagttg gtcttgataa tggtaaaaaa    2160
gtacaaccat ggtatttgga acaaaaatca tctaatgtag taacttatga cgttgcgtcc    2220
actgctggca aggataagtt attttcaaag attggatcta aggatgcaca agttcaaaga    2280
agaaatacac aatgtgagtt tctagatact atgcatatta ttccaaatac tggaaagtac    2340
aacaaaggtt atgctcatgg agaaaagaaa gttaatccaa acgactggtt cttttcctgt    2400
catttctggt ttgatcctgt gatgcctggt tcattaggta ttgaaagtat gtttcaactc    2460
attgaagcat tttcaattga tcaaggaatc gcttcaaaac atggtattgt gaatccaact    2520
tttgctcatt ccaatggaaa aacttcttgg aaatacagag gtcaattgaa taacaaaggt    2580
aaacgaatgg atagtgaaat tcatatcaaa gatattgtca aaaatgctga tggtactgtt    2640
gatttgattg ctgatggatt tttattggtt gattcactaa gagtatactc tgcagatgat    2700
cttcgcgtaa aaattgtacc gggaaccaaa gctgcaccta atcagtagc tgctgctcca    2760 agacatgttg caacaccaat tccaggagtg ccttcgaata caagcagtgt tgaaatcagt    2820
ttggaatctt tgaagaaaga attgttaaat cttgagaaac cattgtatct tgaaacttcc    2880
aatcatattg taaaacaatt cggtgacgtt aacaatggcc aagcatccgt tattccacca    2940
tgcaccatca atgatttggg tgagcgtagt tttatggaaa catacaatgt tgttgcacca    3000
ctttacactg gagccatggc taaaggtatt gcatctgctg atttggtaat tgcagctggt    3060
aaaagaaaaa ttttgggttc ttttggcgct ggaggcttac caatgcactt ggttcgtgct    3120
tctgttgaaa aaatccaagc cgcacttcca gaaggtccat acgctgtcaa cttgattcat    3180
agtccattcg actcaaatct tgaaaaggga atgtagatc tattttgga aaaggtgtt    3240 catgttgttg aagcatctgc attcactgct ctgaccactc aagtagttcg ttaccgtgca    3300 tgtggttat ctcgggctaa agacggatct gtattgatca aaaatagaat catcggtaaa    3360
gtttcaagaa ccgaattggc tgaaatgtttt ttcagacctg caccacaaaa cttgcttgac    3420
aagcttattg ctagtggaga aatcactaaa gaacaagctt cattggcttt ggaagtacca    3480
atggctgatg atgtagctgt tgaagctgat agcggtggac atactgataa tagaccaatt    3540
```

```
catgtaatcc tacctttgat tatcaatcta cgaaatagaa ttcataaaga atgtggtttt      3600
cctgctgctt tgagagttcg cgttggtgct ggtggtggaa ttggttgtcc aagtgctgca      3660
gttgctgcat tcaatatggg agctgcattc ttgattactg gcagcgtcaa ccaagttagc      3720
aaacaatctg gtacgtgtga tatcgttaga aagcaattat ctgaagcttc gtattcagat      3780
attaccatgg caccagcggc tgatatgttt gatcaaggag tcgagcttca agtattaaaa      3840
aaaggaacta tgtttccatc tcgtgcaaag aaattgtatg aattattctg tatgtacaac      3900
tcatttgatg acatgccaaa aagcgaactt caaagactag agaagcgaat ttttcaaaaa      3960
tcgcttgcgg aagtttggga agaaactaaa gatttttata tcaatcgttt gaataatcct      4020
gagaagattg aacatgctga agaaaagat ccaagttga agatgtcatt atgctttaga       4080
tggtatttgg gtttaagttc attttgggca aacaatggaa ttaaagaaag atcaatggac      4140
tatcaaattt ggtgtggtcc agcgattggt tcatacaatg attttgtaaa aggaacttat      4200
ttggatcctg cagtagcagg ttcatatcca tgtgttgttc aaattaacat gcaaattcta      4260
cgcggtgctt gttttcttca acgagttcgt gcaatcaagc acgatccacg attggatatt      4320
gatgtcgatg aagatgtatt tacctatcgt ccagaatcaa ccctatag                  4368
```

<210> SEQ ID NO 73
<211> LENGTH: 1455
<212> TYPE: PRT
<213> ORGANISM: Thraustochytrium sp.

<400> SEQUENCE: 73

```
Met Val Gly Leu Gln Met Lys Lys Pro Val Trp Glu Met Ser Lys
1               5                   10                  15

Glu Glu Gln Ser Ser Gly Lys Asn Val Val Phe Asp Tyr Asp Glu Leu
            20                  25                  30

Leu Glu Phe Ala Glu Gly Asp Ile Gly Lys Val Phe Gly Pro Lys Phe
        35                  40                  45

Asp Ile Ile Asp Lys Tyr Ser Arg Arg Val Arg Leu Pro Ala Arg Glu
    50                  55                  60

Tyr Leu Leu Val Thr Arg Val Thr Leu Met Asp Ala Glu Val Gly Asn
65                  70                  75                  80

Phe Arg Val Gly Ser Arg Met Val Thr Glu Tyr Asp Val Pro Val Asn
                85                  90                  95

Gly Glu Leu Ser Gln Gly Gly Asp Val Pro Trp Ala Val Leu Val Glu
            100                 105                 110

Ser Gly Gln Cys Asp Leu Met Leu Ile Ser Tyr Met Gly Ile Asp Phe
        115                 120                 125

Gln Cys Lys Gly Asp Arg Val Tyr Arg Leu Leu Asn Thr Thr Leu Thr
    130                 135                 140

Phe Tyr Gly Val Ala His Glu Gly Glu Thr Leu Val Tyr Asp Ile Arg
145                 150                 155                 160

Val Thr Gly Phe Ala Lys Gly Met His Gly Glu Ile Ser Met Phe Phe
                165                 170                 175

Phe Glu Tyr Asp Cys Tyr Val Asn Gly Arg Leu Leu Ile Glu Met Arg
            180                 185                 190

Asp Gly Cys Ala Gly Phe Thr Asp Glu Glu Leu Ala Gly Lys
        195                 200                 205

Gly Val Ile Lys Thr Val Ala Glu Leu His Lys Arg Lys Ser Ile Val
    210                 215                 220

Pro Lys Ser Ile Lys Pro Phe Ala Leu Asn Pro Ala Val His Lys Thr
```

```
            225                 230                 235                 240
        Met Phe Ser Glu Asn Asp Met Glu Lys Leu Cys Glu Arg Gln Trp Glu
                            245                 250                 255
        Asn Val Leu Gly Ser Gly Leu Gln Gly Ile Asp Tyr Lys Leu Cys Ala
                            260                 265                 270
        Arg Lys Met Leu Met Ile Asp Arg Ile Thr Lys Ile Gln His Asn Gly
                            275                 280                 285
        Gly Ala Tyr Gly Leu Gly Leu Leu Val Gly Glu Lys Ile Leu Glu Arg
                            290                 295                 300
        Asp His Trp Tyr Phe Pro Cys His Phe Val Lys Asp Gln Val Met Ala
        305                 310                 315                 320
        Gly Ser Leu Val Ser Asp Gly Cys Ser Gln Leu Leu Lys Leu Tyr Met
                            325                 330                 335
        Leu Trp Leu Gly Leu His Asp Val Val Pro Asp Phe Gln Phe Arg Pro
                            340                 345                 350
        Val Pro Gly Gln Pro Asn Lys Val Arg Cys Arg Gly Gln Ile Ser Pro
                            355                 360                 365
        His Arg Gly Lys Leu Val Tyr Val Met Glu Ile Arg Glu Met Gly Phe
                            370                 375                 380
        Asn Glu Ser Thr Gly Gln Pro Tyr Ala Ile Ala Asp Val Asp Ile Ile
        385                 390                 395                 400
        Asp Val Asn Tyr Glu Leu Gly Gln Ser Phe Asp Met Ala Asp Ile Asp
                            405                 410                 415
        Ser Tyr Gly Arg Gly Asn Leu Ser Lys Lys Ile Val Val Asp Phe Lys
                            420                 425                 430
        Gly Ile Ala Leu Gln Met Glu Gly Thr Val Lys Ser Ser Asn Ile Ile
                            435                 440                 445
        Asp Ser Ser Pro Lys Ser Thr Ile Ile Gln Pro Pro Asn Cys Leu
                            450                 455                 460
        Arg Gly Asp Pro Leu Ala Pro Ser Gln Val Thr Trp His Pro Met Ala
        465                 470                 475                 480
        Gly Val Asn Gly Ala Pro Ala Pro Ser Phe Ser Pro Ser Asp Tyr Pro
                            485                 490                 495
        Pro Arg Ala Val Cys Phe Lys Pro Phe Pro Gly Asn Pro Leu Asp Asn
                            500                 505                 510
        Asp His Thr Pro Gly Lys Met Pro Leu Thr Trp Phe Asn Met Ser Glu
                            515                 520                 525
        Phe Met Cys Gly Lys Val Ser Asn Cys Leu Gly Pro Glu Phe Lys Arg
                            530                 535                 540
        Phe Asp Asn Ser Lys Thr Ser Arg Ser Pro Ala Phe Asp Leu Ala Leu
        545                 550                 555                 560
        Val Thr Arg Val Val Ser Val Ser Asp Met Glu Phe Lys Pro His Leu
                            565                 570                 575
        Asn Ile Asp Val Asn Pro Ser Lys Gly Thr Met Ile Gly Glu Phe Asp
                            580                 585                 590
        Cys Pro Ala Asp Ala Trp Phe Phe Gln Gly Ser Cys Asn Asp Gly His
                            595                 600                 605
        Met Pro Tyr Ser Ile Val Met Glu Ile Ala Leu Gln Thr Ser Gly Val
                            610                 615                 620
        Leu Thr Ser Val Leu Lys Ala Pro Leu Thr Met Asp Lys Asp Asp Ile
        625                 630                 635                 640
        Leu Phe Arg Asn Leu Asp Ala Thr Ala Glu Met Val Arg Ser Asp Val
                            645                 650                 655
```

Asp Cys Arg Gly Lys Thr Ile Lys Asn Phe Thr Gln Cys Thr Gly Tyr
              660                 665                 670

Ser Met Leu Gly Lys Met Gly Ile His Arg Phe Thr Phe Glu Leu Ser
              675                 680                 685

Val Asp Asp Val Val Phe Tyr Lys Gly Ser Thr Ser Phe Gly Trp Phe
690                 695                 700

Thr Pro Glu Val Phe Glu Ser Gln Val Gly Leu Asp Asn Gly Lys Lys
705                 710                 715                 720

Val Gln Pro Trp Tyr Leu Glu Gln Lys Ser Ser Asn Val Val Thr Tyr
                  725                 730                 735

Asp Val Ala Ser Thr Ala Gly Lys Asp Lys Leu Phe Ser Lys Ile Gly
              740                 745                 750

Ser Lys Asp Ala Gln Val Gln Arg Arg Asn Thr Gln Cys Glu Phe Leu
              755                 760                 765

Asp Thr Met His Ile Ile Pro Asn Thr Gly Lys Tyr Asn Lys Gly Tyr
              770                 775                 780

Ala His Gly Glu Lys Lys Val Asn Pro Asn Asp Trp Phe Phe Ser Cys
785                 790                 795                 800

His Phe Trp Phe Asp Pro Val Met Pro Gly Ser Leu Gly Ile Glu Ser
                  805                 810                 815

Met Phe Gln Leu Ile Glu Ala Phe Ser Ile Asp Gln Gly Ile Ala Ser
              820                 825                 830

Lys His Gly Ile Val Asn Pro Thr Phe Ala His Ser Asn Gly Lys Thr
              835                 840                 845

Ser Trp Lys Tyr Arg Gly Gln Leu Asn Asn Lys Gly Lys Arg Met Asp
              850                 855                 860

Ser Glu Ile His Ile Lys Asp Ile Val Lys Asn Ala Asp Gly Thr Val
865                 870                 875                 880

Asp Leu Ile Ala Asp Gly Phe Leu Leu Val Asp Ser Leu Arg Val Tyr
                  885                 890                 895

Ser Ala Asp Asp Leu Arg Val Lys Ile Val Pro Gly Thr Lys Ala Ala
              900                 905                 910

Pro Lys Ser Val Ala Ala Pro Arg His Val Ala Thr Pro Ile Pro
              915                 920                 925

Gly Val Pro Ser Asn Thr Ser Ser Val Glu Ile Ser Leu Glu Ser Leu
930                 935                 940

Lys Lys Glu Leu Leu Asn Leu Glu Lys Pro Leu Tyr Leu Glu Thr Ser
945                 950                 955                 960

Asn His Ile Val Lys Gln Phe Gly Asp Val Asn Asn Gly Gln Ala Ser
                  965                 970                 975

Val Ile Pro Pro Cys Thr Ile Asn Asp Leu Gly Glu Arg Ser Phe Met
              980                 985                 990

Glu Thr Tyr Asn Val Val Ala Pro Leu Tyr Thr Gly Ala Met Ala Lys
              995                 1000                1005

Gly Ile Ala Ser Ala Asp Leu Val Ile Ala Ala Gly Lys Arg Lys
         1010                1015                1020

Ile Leu Gly Ser Phe Gly Ala Gly Gly Leu Pro Met His Leu Val
         1025                1030                1035

Arg Ala Ser Val Glu Lys Ile Gln Ala Ala Leu Pro Glu Gly Pro
         1040                1045                1050

Tyr Ala Val Asn Leu Ile His Ser Pro Phe Asp Ser Asn Leu Glu
         1055                1060                1065

```
Lys Gly Asn Val Asp Leu Phe Leu Glu Lys Gly Val His Val Val
    1070            1075            1080

Glu Ala Ser Ala Phe Thr Ala Leu Thr Thr Gln Val Val Arg Tyr
    1085            1090            1095

Arg Ala Cys Gly Leu Ser Arg Ala Lys Asp Gly Ser Val Leu Ile
    1100            1105            1110

Lys Asn Arg Ile Ile Gly Lys Val Ser Arg Thr Glu Leu Ala Glu
    1115            1120            1125

Met Phe Phe Arg Pro Ala Pro Gln Asn Leu Leu Asp Lys Leu Ile
    1130            1135            1140

Ala Ser Gly Glu Ile Thr Lys Glu Gln Ala Ser Leu Ala Leu Glu
    1145            1150            1155

Val Pro Met Ala Asp Asp Val Ala Val Glu Ala Asp Ser Gly Gly
    1160            1165            1170

His Thr Asp Asn Arg Pro Ile His Val Ile Leu Pro Leu Ile Ile
    1175            1180            1185

Asn Leu Arg Asn Arg Ile His Lys Glu Cys Gly Phe Pro Ala Ala
    1190            1195            1200

Leu Arg Val Arg Val Gly Ala Gly Gly Gly Ile Gly Cys Pro Ser
    1205            1210            1215

Ala Ala Val Ala Ala Phe Asn Met Gly Ala Ala Phe Leu Ile Thr
    1220            1225            1230

Gly Ser Val Asn Gln Val Ser Lys Gln Ser Gly Thr Cys Asp Ile
    1235            1240            1245

Val Arg Lys Gln Leu Ser Glu Ala Ser Tyr Ser Asp Ile Thr Met
    1250            1255            1260

Ala Pro Ala Ala Asp Met Phe Asp Gln Gly Val Glu Leu Gln Val
    1265            1270            1275

Leu Lys Lys Gly Thr Met Phe Pro Ser Arg Ala Lys Lys Leu Tyr
    1280            1285            1290

Glu Leu Phe Cys Met Tyr Asn Ser Phe Asp Asp Met Pro Lys Ser
    1295            1300            1305

Glu Leu Gln Arg Leu Glu Lys Arg Ile Phe Gln Lys Ser Leu Ala
    1310            1315            1320

Glu Val Trp Glu Glu Thr Lys Asp Phe Tyr Ile Asn Arg Leu Asn
    1325            1330            1335

Asn Pro Glu Lys Ile Glu His Ala Glu Lys Lys Asp Pro Lys Leu
    1340            1345            1350

Lys Met Ser Leu Cys Phe Arg Trp Tyr Leu Gly Leu Ser Ser Phe
    1355            1360            1365

Trp Ala Asn Asn Gly Ile Lys Glu Arg Ser Met Asp Tyr Gln Ile
    1370            1375            1380

Trp Cys Gly Pro Ala Ile Gly Ser Tyr Asn Asp Phe Val Lys Gly
    1385            1390            1395

Thr Tyr Leu Asp Pro Ala Val Ala Gly Ser Tyr Pro Cys Val Val
    1400            1405            1410

Gln Ile Asn Met Gln Ile Leu Arg Gly Ala Cys Phe Leu Gln Arg
    1415            1420            1425

Val Arg Ala Ile Lys His Asp Pro Arg Leu Asp Ile Asp Val Asp
    1430            1435            1440

Glu Asp Val Phe Thr Tyr Arg Pro Glu Ser Thr Leu
    1445            1450            1455
```

<210> SEQ ID NO 74
<211> LENGTH: 1350
<212> TYPE: DNA
<213> ORGANISM: Thraustochytrium sp.

<400> SEQUENCE: 74

| | | |
|---|---|---|
| agaattgcta ttgttggatt atctgcgatt ttaccaagtg gtgaaaatgt tagagaatct | 60 |
| tgggaagcaa tacgtgatgg tttgaattgt ttaagtgatt tacctgcgga tcgtgttgat | 120 |
| gttactgcgt attataatcc aacaaaaggt gtaaaggata aaatttattg taaacgtggt | 180 |
| gggtttattc ctgaatatga atttgattct agagaatttg gacttaatat gttacaaatg | 240 |
| gaagattctg atgctaatca aacgttaact ttattaaagg ttaaagaagc attagatgat | 300 |
| gctaatatac ctgcatttac taatgagaaa aaaaatattg ttgtgttct tggtattggt | 360 |
| ggtggtcaaa aagcatctca tgaattttat tcaagactta attatgttgt tgtggataaa | 420 |
| gttttaagaa aaatgggatt acctgatgag gatgttgaaa ctgctgttga aaagtttaaa | 480 |
| gctaattttc ctgaatggag attagattcc tttcctggtt ttcttggtaa tgttactgct | 540 |
| ggccgttgta ctaatacatt caatatggaa ggtatgaatt gtgttgtaga tgctgcttgt | 600 |
| gctagttctt taattgctat taagttgct attgatgaat tattacatgg tgattgtgat | 660 |
| gcaatgattg ctggtgcaac ttgtactgat aacgctcttg gtatgtatat ggcattttca | 720 |
| aaaacacctg tttttcaac tgatcaaagt tgtcttgcat atgatgaaaa acaaaaggt | 780 |
| atgcttattg gtgaaggttc agctatgttt gtttaaaac gttatgctga cgcagtgaga | 840 |
| gatggtgata ctgtacatgc tgttatacgt tcatgttcat catcatctga cggtaaagca | 900 |
| tctggtattt atacaccaac tatttctggt caagaagaag ctattcttag agcatatcgt | 960 |
| agagctggtg tatcaccaaa tactattact ttagttgaag acatggtac tggtacacca | 1020 |
| gtgggtgata aaattgaatt aacagcttta cgcaatgtat ttgataaagc atatggtcct | 1080 |
| ggtcataagg aagaagttgc tgttggaagt attaaaagtc aaattggtca tttgaaagct | 1140 |
| gttgctggtt gtgctggtct tgtgaaattg gttatggcat gaaacataa acactacct | 1200 |
| caaagtatta atgttgaaaa tccacctaat ttagtggatg gtactgtcat tagtgatact | 1260 |
| actttatata ttaatacaat gaatcgtcca tggattacta gcctggtgt tccaagaaga | 1320 |
| gctggtatat ctagtttcgg atttggtggt | 1350 |

<210> SEQ ID NO 75
<211> LENGTH: 450
<212> TYPE: PRT
<213> ORGANISM: Thraustochytrium sp.

<400> SEQUENCE: 75

```
Arg Ile Ala Ile Val Gly Leu Ser Ala Ile Leu Pro Ser Gly Glu Asn
1               5                   10                  15

Val Arg Glu Ser Trp Glu Ala Ile Arg Asp Gly Leu Asn Cys Leu Ser
            20                  25                  30

Asp Leu Pro Ala Asp Arg Val Asp Val Thr Ala Tyr Tyr Asn Pro Thr
        35                  40                  45

Lys Gly Val Lys Asp Lys Ile Tyr Cys Lys Arg Gly Gly Phe Ile Pro
    50                  55                  60

Glu Tyr Glu Phe Asp Ser Arg Glu Phe Gly Leu Asn Met Leu Gln Met
65                  70                  75                  80

Glu Asp Ser Asp Ala Asn Gln Thr Leu Thr Leu Leu Lys Val Lys Glu
                85                  90                  95
```

```
Ala Leu Asp Asp Ala Asn Ile Pro Ala Phe Thr Asn Glu Lys Lys Asn
                100                 105                 110

Ile Gly Cys Val Leu Gly Ile Gly Gly Gln Lys Ala Ser His Glu
        115                 120                 125

Phe Tyr Ser Arg Leu Asn Tyr Val Val Asp Lys Val Leu Arg Lys
    130                 135                 140

Met Gly Leu Pro Asp Glu Asp Val Glu Thr Ala Val Glu Lys Phe Lys
145                 150                 155                 160

Ala Asn Phe Pro Glu Trp Arg Leu Asp Ser Phe Pro Gly Phe Leu Gly
                165                 170                 175

Asn Val Thr Ala Gly Arg Cys Thr Asn Thr Phe Asn Met Glu Gly Met
            180                 185                 190

Asn Cys Val Val Asp Ala Ala Cys Ala Ser Ser Leu Ile Ala Ile Lys
        195                 200                 205

Val Ala Ile Asp Glu Leu Leu His Gly Asp Cys Asp Ala Met Ile Ala
    210                 215                 220

Gly Ala Thr Cys Thr Asp Asn Ala Leu Gly Met Tyr Met Ala Phe Ser
225                 230                 235                 240

Lys Thr Pro Val Phe Ser Thr Asp Gln Ser Cys Leu Ala Tyr Asp Glu
                245                 250                 255

Lys Thr Lys Gly Met Leu Ile Gly Glu Gly Ser Ala Met Phe Val Leu
            260                 265                 270

Lys Arg Tyr Ala Asp Ala Val Arg Asp Gly Asp Thr Val His Ala Val
        275                 280                 285

Ile Arg Ser Cys Ser Ser Ser Asp Gly Lys Ala Ser Gly Ile Tyr
    290                 295                 300

Thr Pro Thr Ile Ser Gly Gln Glu Ala Ile Leu Arg Ala Tyr Arg
305                 310                 315                 320

Arg Ala Gly Val Ser Pro Asn Thr Ile Thr Leu Val Glu His Gly
                325                 330                 335

Thr Gly Thr Pro Val Gly Asp Lys Ile Glu Leu Thr Ala Leu Arg Asn
            340                 345                 350

Val Phe Asp Lys Ala Tyr Gly Pro Gly His Lys Glu Glu Val Ala Val
        355                 360                 365

Gly Ser Ile Lys Ser Gln Ile Gly His Leu Lys Ala Val Ala Gly Cys
    370                 375                 380

Ala Gly Leu Val Lys Leu Val Met Ala Leu Lys His Lys Thr Leu Pro
385                 390                 395                 400

Gln Ser Ile Asn Val Glu Asn Pro Pro Asn Leu Val Asp Gly Thr Val
                405                 410                 415

Ile Ser Asp Thr Thr Leu Tyr Ile Asn Thr Met Asn Arg Pro Trp Ile
            420                 425                 430

Thr Lys Pro Gly Val Pro Arg Arg Ala Gly Ile Ser Ser Phe Gly Phe
        435                 440                 445

Gly Gly
    450

<210> SEQ ID NO 76
<211> LENGTH: 921
<212> TYPE: DNA
<213> ORGANISM: Thraustochytrium sp.

<400> SEQUENCE: 76
ttttctggac aaggcgcaca atatacccat atgtttaatg atgttgcaat gcaatggcca    60
```

```
caatttcgtt tatgtgtaaa tgatatggag aaagcacagg aagaagttat caatgataaa    120
agtgtgaaac gtatcagtca agttatgttt cctcgtaaac catatgcaag agaatcacct    180
ttagacaata aagaaatctc taagactgaa tattctcaaa caacaactgt cgctagttca    240
gtaggtttat ttgaaatttt ccgtgatgct ggtttcgctc ctgcttttgt tgctggtcat    300
tctttaggtg aatttagtgc attgtatgca gctggattga ttgatcgcga agatttattc    360
aagttggtat gtaatcgtgc aatggctatg agagatgcac caaaaaaatc tgctgatgga    420
gcaatggctg ctgttattgg tccaaatgct tcttcaatta agctttcagc tcctgaagta    480
tgggttgcta acaataactc tccatctcaa actgttatta ccggtgcaaa ttctggtgta    540
caagctgaaa caagtaaatt gaaaactcaa ggtttccgtg tggttcattt ggcatgtgat    600
ggggcatttc attcgcctca tatggaaaat gctgaaaagc aatttcaaaa agctctttca    660
gcagttaagt ttaataaacc aactggttct tctccaaaaa ttttcagcaa tgtaactggt    720
ggtgtattta cggatccaaa aactgctttg tcaagacata tgactagttc tgtacaattt    780
cttactcaaa ttaagaatat gtacgcggct ggagctcgtg tctttattga atttggacca    840
aaacaagtac tttccaaatt ggtcaatgaa attttccctg gtgatacaag cgtttttaact    900 gtttcggtga atccagctag t                                              921
```

<210> SEQ ID NO 77
<211> LENGTH: 307
<212> TYPE: PRT
<213> ORGANISM: Thraustochytrium sp.

<400> SEQUENCE: 77

```
Phe Ser Gly Gln Gly Ala Gln Tyr Thr His Met Phe Asn Asp Val Ala
1               5                   10                  15

Met Gln Trp Pro Gln Phe Arg Leu Cys Val Asn Asp Met Glu Lys Ala
            20                  25                  30

Gln Glu Glu Val Ile Asn Asp Lys Ser Val Lys Arg Ile Ser Gln Val
        35                  40                  45

Met Phe Pro Arg Lys Pro Tyr Ala Arg Glu Ser Pro Leu Asp Asn Lys
    50                  55                  60

Glu Ile Ser Lys Thr Glu Tyr Ser Gln Thr Thr Val Ala Ser Ser
65                  70                  75                  80

Val Gly Leu Phe Glu Ile Phe Arg Asp Ala Gly Phe Ala Pro Ala Phe
                85                  90                  95

Val Ala Gly His Ser Leu Gly Glu Phe Ser Ala Leu Tyr Ala Ala Gly
            100                 105                 110

Leu Ile Asp Arg Glu Asp Leu Phe Lys Leu Val Cys Asn Arg Ala Met
        115                 120                 125

Ala Met Arg Asp Ala Pro Lys Lys Ser Ala Asp Gly Ala Met Ala Ala
    130                 135                 140

Val Ile Gly Pro Asn Ala Ser Ser Ile Lys Leu Ser Ala Pro Glu Val
145                 150                 155                 160

Trp Val Ala Asn Asn Asn Ser Pro Ser Gln Thr Val Ile Thr Gly Ala
                165                 170                 175

Asn Ser Gly Val Gln Ala Glu Thr Ser Lys Leu Lys Thr Gln Gly Phe
            180                 185                 190

Arg Val Val His Leu Ala Cys Asp Gly Ala Phe His Ser Pro His Met
        195                 200                 205

Glu Asn Ala Glu Lys Gln Phe Gln Lys Ala Leu Ser Ala Val Lys Phe
    210                 215                 220
```

```
Asn Lys Pro Thr Gly Ser Ser Pro Lys Ile Phe Ser Asn Val Thr Gly
225                 230                 235                 240

Gly Val Phe Thr Asp Pro Lys Thr Ala Leu Ser Arg His Met Thr Ser
            245                 250                 255

Ser Val Gln Phe Leu Thr Gln Ile Lys Asn Met Tyr Ala Ala Gly Ala
        260                 265                 270

Arg Val Phe Ile Glu Phe Gly Pro Lys Gln Val Leu Ser Lys Leu Val
    275                 280                 285

Asn Glu Ile Phe Pro Gly Asp Thr Ser Val Leu Thr Val Ser Val Asn
    290                 295                 300

Pro Ala Ser
305

<210> SEQ ID NO 78
<211> LENGTH: 3303
<212> TYPE: DNA
<213> ORGANISM: Thraustochytrium sp.

<400> SEQUENCE: 78
gcaagtccag ctaccgttcg tgtcgtttca gctcctgttc aagcggctgc tcctgtgcag      60
gtatctgctt ctgttgattc tggtttgttg gcaaaagcgg aacaagttgt attggaagta     120
ttggcatcga agactggtta tgagactgag ttgattgaat ggatatggaa attggaaact     180
gaacttggta ttgattctat caagagagta gaaattcttt ctgaagttca agctcaattg     240
aatgttgaag ctaaagatgt agatgctctt agtagaactc gtactgttgg tgaagtgatt     300
gatgcaatga agccgaaat tgctggtggt caaccagctg ctcctgttca agttgcagct     360
cctactcaag tagttgctcc tgttcaagca tctgctcctg ttgattctgg tttgttagca     420
aaagcggaac aagttgtatt ggaagtattg gcatcgaaga ctggttatga gactgagttg     480
attgaattgg atatggaatt ggaaaccgaa cttggtattg attctatcaa gagagtagaa     540
attctttctg aagttcaagc tcaattgagt gttgaagcta agatgtaga tgctcttagt     600
agaactcgta ctgttggtga agtgattgat gcaatgaaag ccgaaattgc tggtggtcaa     660
ccagctgctc ctgttcaagt tgcagctcct actcaagtag ttgctcctgt tcaagcatct     720
gctcctgttg attctggttt gttagcaaaa gcggaacaag ttgtattgga agtattggca     780
tcgaagactg gttatgagac tgagttgatt gaattggata tggaattgga aaccgaactt     840
ggtattgatt ctatcaagag agtagaaatt ctttctgaag ttcaagctca attgagtgtt     900
gaagctaaag atgtagatgc tcttagtaga actcgtactg ttggtgaagt gattgatgca     960
atgaaagctg aaatttctgg tggtcagcca gctgctcctg ttcaagttgc agctcctact    1020
caaatagttg ctcctgttca gtatccgct cctgttgatt ctggtttgtt agcaaaggcg    1080
gaacaagtag tattggaagt attggcatcc aagactggtt atgagactga gttgattgaa    1140
ttggatatgg aattggaaac tgaacttggt attgattcta tcaagagagt agaaattctt    1200
tctgaagttc aagctcaatt gagtgttgaa gctaaagatg tagatgctct tagtagaact    1260
cgtactgttg gtgaagtgat tgatgcaatg aaagctgaaa tttctggtgg tcaaccaact    1320
gctcctgttc aagttgcagc tcctactcaa atagttgctc ctgttcaagt atctgctcct    1380
gttgattctg gtttgttagc aaaggcggaa caagttgtat tggaagtatt ggcatcgaag    1440
actggttatg agactgagtt gattgaattg gatatggaat tggaaaccga acttggtatt    1500
gattctatca agagagtaga aattcttcct gaagttcaag ctcaattgag tgttgaagct    1560
```

```
aaagatgtag atgctcttag tagaactcgt actgttggtg aagtgattga tgcaatgaaa    1620
gccgaaattt ctggtggtca gccagctgct cctgttcaag ttgcagctcc tactcaaata    1680
gttgctcctg ttcaagcatc tgctcctgtt gattctggtt tgttggcaaa agcggaacaa    1740
gttgtattgg aagtgttagc atccaagact ggttatgaaa ctgagttgat tgaattagat    1800
atggaattgg aaaccgaact tggtattgat tctatcaaga gagtagaaat tctttctgaa    1860
gttcaagctc aattgagtgt tgaagctaaa gatgtagatg ctcttagtag aactcgtact    1920
gttggtgaag tgattgatgc aatgaaagct gaaatttctg gtggtcaacc agctgctcct    1980
gttcaagttg cagctcctac tcaaatagtt gctcctgttc aagtatctgc tcctgttgat    2040
tctggtttgt tagcaaaggc ggaacaagtt gtattggaag tattggcatc taagactggt    2100
tatgagactg agttgattga attggatatg aattggaaa ctgaacttgg tattgattct    2160
atcaagagag tagaaattct ttctgaagtt caagctcaat gaatgttga agctaaagat    2220 gtagatgctc ttagtagaac tcgtactgtt ggtgaagtga ttgatgcaat gaaagccgaa    2280
attgctggtg gtcaaccagc tgctcctgtt caagttgcag ctcctgctcc agtagttgct    2340
cctgttcaag tatctactcc tgttgattct ggtttgttgg caaaagcgga acaagttgta    2400
ttggaagtgt tagcatgcaa gactggttat gaaactgagt tgattgaatt ggatatggaa    2460
ttggaaactg aacttggtat tgattctatc aagagagtag aaattctttc tgaagttcaa    2520
gctcaattga gtgttgaagc taagatgta atgctctta gtagaactcg tactgttggt    2580
gaagtgattg atgcaatgaa agccgaaatt tctggtggtc aaccaactgc tcctgttcaa    2640
gttgcagctc ctactcaagt agttgctcct gttaaagtat ctactcctgt tgattctggt    2700
ttgttagcaa aggcggaaca agtagtattg aagtattgg catctaagac tggttatgaa    2760
actgagttga ttgaattaga tatggaattg gaaactgaac ttggtattga ttctatcaag    2820
agagtagaaa ttctttctga agttcaagct caattgaatg tggaagctaa agatgtggat    2880
gctcttagta gaactcgtac tgttggtgaa gtgattgatg caatgaaagc cgaaattgct    2940
ggtgatcaac ctgctccagc tgtagttcca gttcaagcta agagtggtgt agccaaccct    3000
gcacttttgg caaaggcgga acaagtagta ttggaagtat tggcatccaa gaccggttat    3060
gaaactgagc tgattgaatt ggatatggaa ttggaaactg aacttggtat tgattcaatc    3120
aagagagtag aaattctgtc cgaagttcaa gcagaattga gtgttgaagc aaaagatgta    3180
gacgctctaa gtagaacccg tactgttggg gaagtgatcg atgcaatgaa agctgaaatt    3240
gctggcagtg ctgtcacggt tgcaactttg gatgattcaa caattatgga ggagacagat    3300
gat                                                                  3303
```

<210> SEQ ID NO 79
<211> LENGTH: 1101
<212> TYPE: PRT
<213> ORGANISM: Thraustochytrium sp.

<400> SEQUENCE: 79

Ala Ser Pro Ala Thr Val Arg Val Val Ser Ala Pro Val Gln Ala Ala
1               5                   10                  15

Ala Pro Val Gln Val Ser Ala Ser Val Asp Ser Gly Leu Leu Ala Lys
            20                  25                  30

Ala Glu Gln Val Val Leu Glu Val Leu Ala Ser Lys Thr Gly Tyr Glu
        35                  40                  45

Thr Glu Leu Ile Glu Leu Asp Met Glu Leu Glu Thr Glu Leu Gly Ile
    50                  55                  60

-continued

```
Asp Ser Ile Lys Arg Val Glu Ile Leu Ser Glu Val Gln Ala Gln Leu
 65                  70                  75                  80

Asn Val Glu Ala Lys Asp Val Asp Ala Leu Ser Arg Thr Arg Thr Val
                 85                  90                  95

Gly Glu Val Ile Asp Ala Met Lys Ala Glu Ile Ala Gly Gly Gln Pro
            100                 105                 110

Ala Ala Pro Val Gln Val Ala Ala Pro Thr Gln Val Val Ala Pro Val
        115                 120                 125

Gln Ala Ser Ala Pro Val Asp Ser Gly Leu Leu Ala Lys Ala Glu Gln
130                 135                 140

Val Val Leu Glu Val Leu Ala Ser Lys Thr Gly Tyr Glu Thr Glu Leu
145                 150                 155                 160

Ile Glu Leu Asp Met Glu Leu Glu Thr Glu Leu Gly Ile Asp Ser Ile
                165                 170                 175

Lys Arg Val Glu Ile Leu Ser Glu Val Gln Ala Gln Leu Ser Val Glu
            180                 185                 190

Ala Lys Asp Val Asp Ala Leu Ser Arg Thr Arg Thr Val Gly Glu Val
        195                 200                 205

Ile Asp Ala Met Lys Ala Glu Ile Ala Gly Gly Gln Pro Ala Ala Pro
210                 215                 220

Val Gln Val Ala Ala Pro Thr Gln Val Val Ala Pro Val Gln Ala Ser
225                 230                 235                 240

Ala Pro Val Asp Ser Gly Leu Leu Ala Lys Ala Glu Gln Val Val Leu
                245                 250                 255

Glu Val Leu Ala Ser Lys Thr Gly Tyr Glu Thr Glu Leu Ile Glu Leu
            260                 265                 270

Asp Met Glu Leu Glu Thr Glu Leu Gly Ile Asp Ser Ile Lys Arg Val
        275                 280                 285

Glu Ile Leu Ser Glu Val Gln Ala Gln Leu Ser Val Glu Ala Lys Asp
290                 295                 300

Val Asp Ala Leu Ser Arg Thr Arg Thr Val Gly Glu Val Ile Asp Ala
305                 310                 315                 320

Met Lys Ala Glu Ile Ser Gly Gly Gln Pro Ala Ala Pro Val Gln Val
                325                 330                 335

Ala Ala Pro Thr Gln Ile Val Ala Pro Val Gln Val Ser Ala Pro Val
            340                 345                 350

Asp Ser Gly Leu Leu Ala Lys Ala Glu Gln Val Val Leu Glu Val Leu
        355                 360                 365

Ala Ser Lys Thr Gly Tyr Glu Thr Glu Leu Ile Glu Leu Asp Met Glu
370                 375                 380

Leu Glu Thr Glu Leu Gly Ile Asp Ser Ile Lys Arg Val Glu Ile Leu
385                 390                 395                 400

Ser Glu Val Gln Ala Gln Leu Ser Val Glu Ala Lys Asp Val Asp Ala
                405                 410                 415

Leu Ser Arg Thr Arg Thr Val Gly Glu Val Ile Asp Ala Met Lys Ala
            420                 425                 430

Glu Ile Ser Gly Gly Gln Pro Thr Ala Pro Val Gln Val Ala Ala Pro
        435                 440                 445

Thr Gln Ile Val Ala Pro Val Gln Val Ser Ala Pro Val Asp Ser Gly
450                 455                 460

Leu Leu Ala Lys Ala Glu Gln Val Val Leu Glu Val Leu Ala Ser Lys
465                 470                 475                 480
```

```
Thr Gly Tyr Glu Thr Glu Leu Ile Glu Leu Asp Met Glu Leu Glu Thr
                    485                 490                 495

Glu Leu Gly Ile Asp Ser Ile Lys Arg Val Glu Ile Leu Ser Glu Val
            500                 505                 510

Gln Ala Gln Leu Ser Val Glu Ala Lys Asp Val Asp Ala Leu Ser Arg
        515                 520                 525

Thr Arg Thr Val Gly Glu Val Ile Asp Ala Met Lys Ala Glu Ile Ser
    530                 535                 540

Gly Gly Gln Pro Ala Ala Pro Val Gln Val Ala Ala Pro Thr Gln Ile
545                 550                 555                 560

Val Ala Pro Val Gln Ala Ser Ala Pro Val Asp Ser Gly Leu Leu Ala
                565                 570                 575

Lys Ala Glu Gln Val Val Leu Glu Val Leu Ala Ser Lys Thr Gly Tyr
            580                 585                 590

Glu Thr Glu Leu Ile Glu Leu Asp Met Glu Leu Glu Thr Glu Leu Gly
        595                 600                 605

Ile Asp Ser Ile Lys Arg Val Glu Ile Leu Ser Glu Val Gln Ala Gln
610                 615                 620

Leu Ser Val Glu Ala Lys Asp Val Asp Ala Leu Ser Arg Thr Arg Thr
625                 630                 635                 640

Val Gly Glu Val Ile Asp Ala Met Lys Ala Glu Ile Ser Gly Gly Gln
                645                 650                 655

Pro Ala Ala Pro Val Gln Val Ala Ala Pro Thr Gln Ile Val Ala Pro
            660                 665                 670

Val Gln Val Ser Ala Pro Val Asp Ser Gly Leu Leu Ala Lys Ala Glu
        675                 680                 685

Gln Val Val Leu Glu Val Leu Ala Ser Lys Thr Gly Tyr Glu Thr Glu
    690                 695                 700

Leu Ile Glu Leu Asp Met Glu Leu Glu Thr Glu Leu Gly Ile Asp Ser
705                 710                 715                 720

Ile Lys Arg Val Glu Ile Leu Ser Glu Val Gln Ala Gln Leu Asn Val
                725                 730                 735

Glu Ala Lys Asp Val Asp Ala Leu Ser Arg Thr Arg Thr Val Gly Glu
            740                 745                 750

Val Ile Asp Ala Met Lys Ala Glu Ile Ala Gly Gly Gln Pro Ala Ala
        755                 760                 765

Pro Val Gln Val Ala Ala Pro Ala Pro Val Val Ala Pro Val Gln Val
    770                 775                 780

Ser Thr Pro Val Asp Ser Gly Leu Leu Ala Lys Ala Glu Gln Val Val
785                 790                 795                 800

Leu Glu Val Leu Ala Cys Lys Thr Gly Tyr Glu Thr Glu Leu Ile Glu
                805                 810                 815

Leu Asp Met Glu Leu Glu Thr Glu Leu Gly Ile Asp Ser Ile Lys Arg
            820                 825                 830

Val Glu Ile Leu Ser Glu Val Gln Ala Gln Leu Ser Val Glu Ala Lys
        835                 840                 845

Asp Val Asp Ala Leu Ser Arg Thr Arg Thr Val Gly Glu Val Ile Asp
    850                 855                 860

Ala Met Lys Ala Glu Ile Ser Gly Gly Gln Pro Thr Ala Pro Val Gln
865                 870                 875                 880

Val Ala Ala Pro Thr Gln Val Val Ala Pro Val Lys Val Ser Thr Pro
                885                 890                 895

Val Asp Ser Gly Leu Leu Ala Lys Ala Glu Gln Val Val Leu Glu Val
```

```
                  900               905               910
Leu Ala Ser Lys Thr Gly Tyr Glu Thr Glu Leu Ile Glu Leu Asp Met
            915               920               925

Glu Leu Glu Thr Glu Leu Gly Ile Asp Ser Ile Lys Arg Val Glu Ile
        930               935               940

Leu Ser Glu Val Gln Ala Gln Leu Asn Val Glu Ala Lys Asp Val Asp
945               950               955               960

Ala Leu Ser Arg Thr Arg Thr Val Gly Glu Val Ile Asp Ala Met Lys
            965               970               975

Ala Glu Ile Ala Gly Asp Gln Pro Ala Pro Ala Val Val Pro Val Gln
        980               985               990

Ala Lys Ser Gly Val Ala Asn Pro  Ala Leu Leu Ala Lys  Ala Glu Gln
        995               1000              1005

Val Val  Leu Glu Val Leu Ala  Ser Lys Thr Gly Tyr  Glu Thr Glu
     1010              1015              1020

Leu Ile  Glu Leu Asp Met Glu  Leu Glu Thr Glu Leu  Gly Ile Asp
     1025              1030              1035

Ser Ile  Lys Arg Val Glu Ile  Leu Ser Glu Val Gln  Ala Glu Leu
     1040              1045              1050

Ser Val  Glu Ala Lys Asp Val  Asp Ala Leu Ser Arg  Thr Arg Thr
     1055              1060              1065

Val Gly  Glu Val Ile Asp Ala  Met Lys Ala Glu Ile  Ala Gly Ser
     1070              1075              1080

Ala Val  Thr Val Ala Thr Leu  Asp Asp Ser Thr Ile  Met Glu Glu
     1085              1090              1095

Thr Asp  Asp
     1100

<210> SEQ ID NO 80
<211> LENGTH: 255
<212> TYPE: DNA
<213> ORGANISM: Thraustochytrium sp.

<400> SEQUENCE: 80
gttgattctg gtttgttggc aaaagcggaa caagttgtat tggaagtatt ggcatcgaag      60
actggttatg agactgagtt gattgaattg gatatggaat tggaaactga acttggtatt     120
gattctatca agagagtaga aattctttct gaagttcaag ctcaattgaa tgttgaagct     180
aaagatgtag atgctcttag tagaactcgt actgttggtg aagtgattga tgcaatgaaa     240
gccgaaattg ctggt                                                     255

<210> SEQ ID NO 81
<211> LENGTH: 85
<212> TYPE: PRT
<213> ORGANISM: Thraustochytrium sp.

<400> SEQUENCE: 81

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Asn Val Glu Ala Lys Asp Val Asp
    50                  55                  60
```

Ala Leu Ser Arg Thr Arg Thr Val Gly Glu Val Ile Asp Ala Met Lys
65                  70                  75                  80

Ala Glu Ile Ala Gly
            85

<210> SEQ ID NO 82
<211> LENGTH: 255
<212> TYPE: DNA
<213> ORGANISM: Thraustochytrium sp.

<400> SEQUENCE: 82
gttgattctg gtttgttagc aaaagcggaa caagttgtat tggaagtatt ggcatcgaag      60
actggttatg agactgagtt gattgaattg gatatggaat tggaaaccga acttggtatt     120
gattctatca agagagtaga aattctttct gaagttcaag ctcaattgag tgttgaagct     180
aaagatgtag atgctcttag tagaactcgt actgttggtg aagtgattga tgcaatgaaa     240
gccgaaattg ctggt                                                     255

<210> SEQ ID NO 83
<211> LENGTH: 85
<212> TYPE: PRT
<213> ORGANISM: Thraustochytrium sp.

<400> SEQUENCE: 83

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
            85

<210> SEQ ID NO 84
<211> LENGTH: 252
<212> TYPE: DNA
<213> ORGANISM: Thraustochytrium sp.

<400> SEQUENCE: 84
gttgattctg gtttgttagc aaaagcggaa caagttgtat tggaagtatt ggcatcgaag      60
actggttatg agactgagtt gattgaattg gatatggaat tggaaaccga acttggtatt     120
gattctatca agagagtaga aattctttct gaagttcaag ctcaattgag tgttgaagct     180
aaagatgtag atgctcttag tagaactcgt actgttggtg aagtgattga tgcaatgaaa     240
gctgaaattt ct                                                        252

<210> SEQ ID NO 85
<211> LENGTH: 85
<212> TYPE: PRT
<213> ORGANISM: Thraustochytrium sp.

<400> SEQUENCE: 85

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ser Gly
            85

<210> SEQ ID NO 86
<211> LENGTH: 255
<212> TYPE: DNA
<213> ORGANISM: Thraustochytrium sp.

<400> SEQUENCE: 86
gttgattctg gtttgttagc aaaggcggaa caagtagtat tggaagtatt ggcatccaag     60
actggttatg agactgagtt gattgaattg gatatggaat tggaaactga acttggtatt    120
gattctatca agagagtaga aattctttct gaagttcaag ctcaattgag tgttgaagct    180
aaagatgtag atgctcttag tagaactcgt actgttggtg aagtgattga tgcaatgaaa    240
gctgaaattt ctggt                                                    255

<210> SEQ ID NO 87
<211> LENGTH: 85
<212> TYPE: PRT
<213> ORGANISM: Thraustochytrium sp.

<400> SEQUENCE: 87

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ser Gly
            85

<210> SEQ ID NO 88
<211> LENGTH: 254
<212> TYPE: DNA
<213> ORGANISM: Thraustochytrium sp.

<400> SEQUENCE: 88
ttgattctgg tttgttagca aaggcggaac aagttgtatt ggaagtattg gcatcgaaga     60
ctggttatga gactgagttg attgaattgg atatggaatt ggaaaccgaa cttggtattg    120
attctatcaa gagagtagaa attctttctg aagttcaagc tcaattgagt gttgaagcta    180
agatgtagat gctcttagta gaactcgtac tgttggtgaa gtgattgatg caatgaaag    240 ccgaaatttc tggt                                                    254

<210> SEQ ID NO 89

```
<211> LENGTH: 85
<212> TYPE: PRT
<213> ORGANISM: Thraustochytrium sp.

<400> SEQUENCE: 89

Val Asp Ser Gly Leu Leu Ala Lys Ala Glu Gln Val Val Leu Glu Val
1               5                   10                  15
Leu Ala Ser Lys Thr Gly Tyr Glu Thr Glu Leu Ile Glu Leu Asp Met
            20                  25                  30
Glu Leu Glu Thr Glu Leu Gly Ile Asp Ser Ile Lys Arg Val Glu Ile
        35                  40                  45
Leu Ser Glu Val Gln Ala Gln Leu Ser Val Glu Ala Lys Asp Val Asp
    50                  55                  60
Ala Leu Ser Arg Thr Arg Thr Val Gly Glu Val Ile Asp Ala Met Lys
65                  70                  75                  80
Ala Glu Ile Ser Gly
                85

<210> SEQ ID NO 90
<211> LENGTH: 255
<212> TYPE: DNA
<213> ORGANISM: Thraustochytrium sp.

<400> SEQUENCE: 90
gttgattctg gtttgttggc aaaagcggaa caagttgtat tggaagtgtt agcatccaag     60
actggttatg aaactgagtt gattgaatta gatatggaat tggaaaccga acttggtatt    120
gattctatca agagagtaga aattctttct gaagttcaag ctcaattgag tgttgaagct    180
aaagatgtag atgctcttag tagaactcgt actgttggtg aagtgattga tgcaatgaaa    240
gctgaaattt ctggt                                                     255

<210> SEQ ID NO 91
<211> LENGTH: 85
<212> TYPE: PRT
<213> ORGANISM: Thraustochytrium sp.

<400> SEQUENCE: 91

Val Asp Ser Gly Leu Leu Ala Lys Ala Glu Gln Val Val Leu Glu Val
1               5                   10                  15
Leu Ala Ser Lys Thr Gly Tyr Glu Thr Glu Leu Ile Glu Leu Asp Met
            20                  25                  30
Glu Leu Glu Thr Glu Leu Gly Ile Asp Ser Ile Lys Arg Val Glu Ile
        35                  40                  45
Leu Ser Glu Val Gln Ala Gln Leu Ser Val Glu Ala Lys Asp Val Asp
    50                  55                  60
Ala Leu Ser Arg Thr Arg Thr Val Gly Glu Val Ile Asp Ala Met Lys
65                  70                  75                  80
Ala Glu Ile Ser Gly
                85

<210> SEQ ID NO 92
<211> LENGTH: 255
<212> TYPE: DNA
<213> ORGANISM: Thraustochytrium sp.

<400> SEQUENCE: 92
gttgattctg gtttgttagc aaaggcggaa caagttgtat tggaagtatt ggcatctaag     60
actggttatg agactgagtt gattgaattg gatatggaat tggaaactga acttggtatt    120
```

```
gattctatca agagagtaga aattctttct gaagttcaag ctcaattgaa tgttgaagct      180
aaagatgtag atgctcttag tagaactcgt actgttggtg aagtgattga tgcaatgaaa      240
gccgaaattg ctggt                                                       255
```

<210> SEQ ID NO 93
<211> LENGTH: 85
<212> TYPE: PRT
<213> ORGANISM: Thraustochytrium sp.

<400> SEQUENCE: 93

```
Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Asn Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
                85
```

<210> SEQ ID NO 94
<211> LENGTH: 255
<212> TYPE: DNA
<213> ORGANISM: Thraustochytrium sp.

<400> SEQUENCE: 94

```
gttgattctg gtttgttggc aaaagcggaa caagttgtat tggaagtgtt agcatgcaag       60
actggttatg aaactgagtt gattgaattg gatatggaat tggaaactga acttggtatt      120
gattctatca agagagtaga aattctttct gaagttcaag ctcaattgag tgttgaagct      180
aaagatgtag atgctcttag tagaactcgt actgttggtg aagtgattga tgcaatgaaa      240
gccgaaattt ctggt                                                       255
```

<210> SEQ ID NO 95
<211> LENGTH: 85
<212> TYPE: PRT
<213> ORGANISM: Thraustochytrium sp.

<400> SEQUENCE: 95

```
Val Asp Ser Gly Leu Leu Ala Lys Ala Glu Gln Val Val Leu Glu Val
1               5                   10                  15

Leu Ala Cys Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Ser Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ser Gly
                85
```

<210> SEQ ID NO 96

```
<211> LENGTH: 255
<212> TYPE: DNA
<213> ORGANISM: Thraustochytrium sp.

<400> SEQUENCE: 96
gttgattctg gtttgttagc aaaggcggaa caagtagtat tggaagtatt ggcatctaag      60
actggttatg aaactgagtt gattgaatta gatatggaat tggaaactga acttggtatt    120
gattctatca agagagtaga aattctttct gaagttcaag ctcaattgaa tgtggaagct    180
aaagatgtgg atgctcttag tagaactcgt actgttggtg aagtgattga tgcaatgaaa    240
gccgaaattg ctggt                                                      255

<210> SEQ ID NO 97
<211> LENGTH: 85
<212> TYPE: PRT
<213> ORGANISM: Thraustochytrium sp.

<400> SEQUENCE: 97

Val Asp Ser Gly Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Gln Leu Asn Val Glu Ala Lys Asp Val Asp
    50                  55                  60

Ala Leu Ser Arg Thr Arg Thr Val Gly Glu Val Ile Asp Ala Met Lys
65                  70                  75                  80

Ala Glu Ile Ala Gly
                85

<210> SEQ ID NO 98
<211> LENGTH: 255
<212> TYPE: DNA
<213> ORGANISM: Thraustochytrium sp.

<400> SEQUENCE: 98
gccaaccctg cacttttggc aaaggcggaa caagtagtat tggaagtatt ggcatccaag      60
accggttatg aaactgagct gattgaattg gatatggaat tggaaactga acttggtatt    120
gattcaatca agagagtaga aattctgtcc gaagttcaag cagaattgag tgttgaagca    180
aaagatgtag acgctctaag tagaacccgt actgttgggg aagtgatcga tgcaatgaaa    240
gctgaaattg ctggc                                                      255

<210> SEQ ID NO 99
<211> LENGTH: 85
<212> TYPE: PRT
<213> ORGANISM: Thraustochytrium sp.

<400> SEQUENCE: 99

Ala Asn Pro Ala Leu Leu Ala Lys Ala Glu Gln Val Val Leu Glu Val
1               5                   10                  15

Leu Ala Ser Lys Thr Gly Tyr Glu Thr Glu Leu Ile Glu Leu Asp Met
            20                  25                  30

Glu Leu Glu Thr Glu Leu Gly Ile Asp Ser Ile Lys Arg Val Glu Ile
        35                  40                  45

Leu Ser Glu Val Gln Ala Glu Leu Ser Val Glu Ala Lys Asp Val Asp
    50                  55                  60
```

```
Ala Leu Ser Arg Thr Arg Thr Val Gly Glu Val Ile Asp Ala Met Lys
65                  70                  75                  80

Ala Glu Ile Ala Gly
                85

<210> SEQ ID NO 100
<211> LENGTH: 2151
<212> TYPE: DNA
<213> ORGANISM: Thraustochytrium sp.

<400> SEQUENCE: 100
gtttcaagca ttgaatcttc gtatggaaaa attggtggct ttgtttatca acattttcat      60
gatagcgact atggtatgca acttggatgg gcgttaatgg cagcgaaaca tttgaaagag     120
tccctcaacg acccgattaa gaatggaaga accttctttt tggctgttgc gcgtatgaat     180
ggtaaacttg gtatggacaa tgcttcagtt catgatcaag aatagtggaa tcatgcggt      240
atcgccgaac gtggtgctat ctttggtttg tgcaaaactt tggatttgga atggcctaat     300
gttttgctc gtggtgttga tattgctgaa ggtatgagtt atagtttggc tgcggaattg     360
attgttgatg agatttcttg tgcaaatctt tccattcggg aatctggtta cacgattagc     420
ggagaaagat tcacaactga agctcacaaa ttggttactg aaagcctca tgctccgatt      480
aagaagaagg atgctttcct agtatctggt ggtgctcgtg gtattactcc actttgtatt     540
cgtgaaattg ctaaagcagt gaaggtggc acttacattt tgatgggtcg atcagctttg      600
gctgatgaac ccttgtgggc taatggtaaa tccggaaaag atttagataa agctggtttg     660
gcatttttga aggaagagtt tgcagctggg cgtggtagta aaccaactcc aaaagttcac     720
aaatctttga ttgataaagt gctcggtatt agggaggtta gagcatctat tgcaaatata     780
gaagcccatg gagcaaaagc tatatatttg tcttgcgatg tatcttccgc tgagaaagta     840
aaggctgcag tgcaaaaagt tgaaaaggag catctagttc gtattactgg tattgtgcat     900
gcatcaggcg ttttgaggga taaattggtt gagaacaaaa ctttggatga tttcaacgca     960
gtatatggaa ccaaagtaac tggactagta aacttgctgt cagcagtgaa catgaatttt    1020
gttcgtcatt tggttatgtt tagttctttg gctggatatc atggaaatgt tggtcaatct    1080
gattatgcaa tggctaacga atcacttaac aagattggtt ttagattggg tgcagcttat    1140
tctcaattgt gtgttaaatc tatttgtttt ggaccttggg atggtggaat ggtaactcca    1200
gctttgaaaa aacaatttca atcaatgggt gtccagatta ttcctcgtga aggtggcgcg    1260
gagactgttg caagaatagt cttatcttca aatccttctc aagttttagt tggcaactgg    1320
ggtgttcctc cagtttcacc tttgtcaaaa tcggcaacta ttgttcaaac ttttaccct    1380
gagttaaatc catttctaaa gtctcatcaa attcatggta aaaatgtttt gcctatgact    1440
gtagcaattg gatatcttgc tcacttggtt aagaattttt atgctggtca tcatttgtgg    1500
ggagttgaag atgctcaatt gttcagtggt gttgtaattg accatgcggt gcaagctcaa    1560
gtgaaattaa cggaacagag tttggatgat gatggcaagg taaagttca agctgttctg    1620
actgcttcaa cgataatgg aaaaatggta cctgcataca aagcagtgat tgttttggga    1680
aaaacaagta gacctgcgtt tattttgaaa gattttcat tgcaagaatc taattctcgc    1740
agtgctgatg agttgtatga tggtaaaaact ttgtttcatg gtccattatt tcgtggaatt    1800
accaagttgt tgaatgtatc tgatacttca ctaacaactc aatgtaccaa tattgatttg    1860
actgctactg aacgtggtca atttgcggat atcgaacctg tgaatccttt tatggcggat    1920
```

```
gctgcatttc aagctatgct tgtatgggtt agaaatttaa ggaatagtgc atctttacca    1980
aacaattgtg aaagagtaga tatctataaa ccaatagcac ctggtgaaaa gtattacact    2040
actttgcaag ctttgggtaa tacctccggt tctgttctca agtctgtatt ttatatgcac    2100
gatgaacaag gagaagtatt tctatctgga agagctagtg ttgttgtgaa t             2151
```

<210> SEQ ID NO 101
<211> LENGTH: 717
<212> TYPE: PRT
<213> ORGANISM: Thraustochytrium sp.

<400> SEQUENCE: 101

```
Val Ser Ser Ile Glu Ser Ser Tyr Gly Lys Ile Gly Gly Phe Val Tyr
1               5                   10                  15

Gln His Phe His Asp Ser Asp Tyr Gly Met Gln Leu Gly Trp Ala Leu
            20                  25                  30

Met Ala Ala Lys His Leu Lys Glu Ser Leu Asn Asp Pro Ile Lys Asn
        35                  40                  45

Gly Arg Thr Phe Phe Leu Ala Val Ala Arg Met Asn Gly Lys Leu Gly
    50                  55                  60

Met Asp Asn Ala Ser Val His Asp Gln Gly Ile Val Glu Ser Cys Gly
65                  70                  75                  80

Ile Ala Glu Arg Gly Ala Ile Phe Gly Leu Cys Lys Thr Leu Asp Leu
                85                  90                  95

Glu Trp Pro Asn Val Phe Ala Arg Gly Val Asp Ile Ala Glu Gly Met
            100                 105                 110

Ser Tyr Ser Leu Ala Ala Glu Leu Ile Val Asp Glu Ile Ser Cys Ala
        115                 120                 125

Asn Leu Ser Ile Arg Glu Ser Gly Tyr Thr Ile Ser Gly Glu Arg Phe
    130                 135                 140

Thr Thr Glu Ala His Lys Leu Val Thr Gly Lys Pro His Ala Pro Ile
145                 150                 155                 160

Lys Lys Lys Asp Ala Phe Leu Val Ser Gly Ala Arg Gly Ile Thr
                165                 170                 175

Pro Leu Cys Ile Arg Glu Ile Ala Lys Ala Val Lys Gly Thr Tyr
            180                 185                 190

Ile Leu Met Gly Arg Ser Ala Leu Ala Asp Glu Pro Leu Trp Ala Asn
        195                 200                 205

Gly Lys Ser Gly Lys Asp Leu Asp Lys Ala Gly Leu Ala Phe Leu Lys
    210                 215                 220

Glu Glu Phe Ala Ala Gly Arg Gly Ser Lys Pro Thr Pro Lys Val His
225                 230                 235                 240

Lys Ser Leu Ile Asp Lys Val Leu Gly Ile Arg Glu Val Arg Ala Ser
                245                 250                 255

Ile Ala Asn Ile Glu Ala His Gly Ala Lys Ala Ile Tyr Leu Ser Cys
            260                 265                 270

Asp Val Ser Ser Ala Glu Lys Val Lys Ala Ala Val Gln Lys Val Glu
        275                 280                 285

Lys Glu His Leu Val Arg Ile Thr Gly Ile Val His Ala Ser Gly Val
    290                 295                 300

Leu Arg Asp Lys Leu Val Glu Asn Lys Thr Leu Asp Asp Phe Asn Ala
305                 310                 315                 320

Val Tyr Gly Thr Lys Val Thr Gly Leu Val Asn Leu Leu Ser Ala Val
                325                 330                 335
```

Asn Met Asn Phe Val Arg His Leu Val Met Phe Ser Ser Leu Ala Gly
            340                 345                 350

Tyr His Gly Asn Val Gly Gln Ser Asp Tyr Ala Met Ala Asn Glu Ser
            355                 360                 365

Leu Asn Lys Ile Gly Phe Arg Leu Gly Ala Ala Tyr Ser Gln Leu Cys
            370                 375                 380

Val Lys Ser Ile Cys Phe Gly Pro Trp Asp Gly Met Val Thr Pro
385                 390                 395                 400

Ala Leu Lys Lys Gln Phe Gln Ser Met Gly Val Gln Ile Ile Pro Arg
            405                 410                 415

Glu Gly Gly Ala Glu Thr Val Ala Arg Ile Val Leu Ser Ser Asn Pro
            420                 425                 430

Ser Gln Val Leu Val Gly Asn Trp Gly Val Pro Pro Val Ser Pro Leu
            435                 440                 445

Ser Lys Ser Ala Thr Ile Val Gln Thr Phe Thr Pro Glu Leu Asn Pro
            450                 455                 460

Phe Leu Lys Ser His Gln Ile His Gly Lys Asn Val Leu Pro Met Thr
465                 470                 475                 480

Val Ala Ile Gly Tyr Leu Ala His Leu Val Lys Asn Phe Tyr Ala Gly
            485                 490                 495

His His Leu Trp Gly Val Glu Asp Ala Gln Leu Phe Ser Gly Val Val
            500                 505                 510

Ile Asp His Ala Val Gln Ala Val Lys Leu Thr Glu Gln Ser Leu
            515                 520                 525

Asp Asp Asp Gly Lys Val Lys Val Gln Ala Val Leu Thr Ala Ser Asn
530                 535                 540

Asp Asn Gly Lys Met Val Pro Ala Tyr Lys Ala Val Ile Val Leu Gly
545                 550                 555                 560

Lys Thr Ser Arg Pro Ala Phe Ile Leu Lys Asp Phe Ser Leu Gln Glu
            565                 570                 575

Ser Asn Ser Arg Ser Ala Asp Glu Leu Tyr Asp Gly Lys Thr Leu Phe
            580                 585                 590

His Gly Pro Leu Phe Arg Gly Ile Thr Lys Leu Leu Asn Val Ser Asp
            595                 600                 605

Thr Ser Leu Thr Thr Gln Cys Thr Asn Ile Asp Leu Thr Ala Thr Glu
            610                 615                 620

Arg Gly Gln Phe Ala Asp Ile Glu Pro Val Asn Pro Phe Met Ala Asp
625                 630                 635                 640

Ala Ala Phe Gln Ala Met Leu Val Trp Val Arg Asn Leu Arg Asn Ser
            645                 650                 655

Ala Ser Leu Pro Asn Asn Cys Glu Arg Val Asp Ile Tyr Lys Pro Ile
            660                 665                 670

Ala Pro Gly Glu Lys Tyr Tyr Thr Thr Leu Gln Ala Leu Gly Asn Thr
            675                 680                 685

Ser Gly Ser Val Leu Lys Ser Val Phe Tyr Met His Asp Glu Gln Gly
            690                 695                 700

Glu Val Phe Leu Ser Gly Arg Ala Ser Val Val Val Asn
705                 710                 715

<210> SEQ ID NO 102
<211> LENGTH: 1311
<212> TYPE: DNA
<213> ORGANISM: Thraustochytrium sp.

<400> SEQUENCE: 102

```
ttaagtgttg gtgataatat ttgtcatgat caacgtgttg ctgttgttgg tatggctgtt      60
atgtatgctg gttgtcaaaa tcaacatgaa ttttggcaat ctttacaagg taaaaatatg     120
aattcaaaat cgatttcaca aaatcgttta ggttctgagt atagagaaga acattttaaa     180
cctgaaagaa gtaaatattc cgatacccttt tgtaatgaaa gatatggttg tattgatgag     240
aatgttcaaa gtgaacatga acttttatta aaacttgcaa agatgctat tgcggataca     300 aaaggttcta ttgatttgaa taaaaccgga atcgttagtg gttgcttatc ttttccaatg     360
gataatttac aaggtgattt attaaatttg tatcaatgtc acattgaaaa gaaaattggg     420
ccaaatgcat taaagatgt gaatttatgg tctaaaagaa ccaccaacgg aaaagatgat     480
aaaaaagctt attttgatcc tgcctctttc gtagctgaac aattagatat gggaccatta     540
cattatagtt tagatgctgc ttgtgcgtct gcactttatg tattaagact tgctcaagat     600
catttattaa gtggtgctgc tgatacaatg ttatgtggtg catcttgttt acctgaacct     660
ttttttattt tatctggttt ttctactttt catgcaatgc cattatctgg tgatgtttct     720
gctcctttgc ataaaacttc acaaggtctt acacctggtg aaggtggtgc tattatggta     780
cttaaacgat taaatgatgc aatccgtgat ggtgatagaa tttatggtac tttacttggt     840
gctgaattaa gtaatgctgg ttgtggttta ccattgagtc cacatatgcc aagtgaattt     900
gattgtatgg aaaaagcttt acaaagagta cacagattac catcatctat tcaatatgtt     960
gagtgtcatg caactggtac accacaaggt gataaagttg aaattgatgc tatgacaaaa    1020
tgttttggtg aacatttacc aaggtttggt tcaacgaaag ggaattttgg tcatacactt    1080
gttgctgctg gttttgctgg tatgtgtaaa gttttattat caatgcaata tggtgaaata    1140
ccaccaactc caggtcttga aaatccagac aatattatgc atgatttagt tgttactgaa    1200
acaattccat ggcctaatac aaatggtgat ttgaaacgtg catgtttatc tgcttttgga    1260
ttcggtggta ctaatgcaca tgctgtattt gaagagtatc gttcagattt a             1311
```

<210> SEQ ID NO 103
<211> LENGTH: 437
<212> TYPE: PRT
<213> ORGANISM: Thraustochytrium sp.

<400> SEQUENCE: 103

```
Leu Ser Val Gly Asp Asn Ile Cys His Asp Gln Arg Val Ala Val Val
 1               5                  10                  15

Gly Met Ala Val Met Tyr Ala Gly Cys Gln Asn Gln His Glu Phe Trp
                20                  25                  30

Gln Ser Leu Gln Gly Lys Asn Met Asn Ser Lys Ser Ile Ser Gln Asn
            35                  40                  45

Arg Leu Gly Ser Glu Tyr Arg Glu Glu His Phe Lys Pro Glu Arg Ser
        50                  55                  60

Lys Tyr Ser Asp Thr Phe Cys Asn Glu Arg Tyr Gly Cys Ile Asp Glu
 65                  70                  75                  80

Asn Val Gln Ser Glu His Glu Leu Leu Leu Lys Leu Ala Lys Asp Ala
                 85                  90                  95

Ile Ala Asp Thr Lys Gly Ser Ile Asp Leu Asn Lys Thr Gly Ile Val
            100                 105                 110

Ser Gly Cys Leu Ser Phe Pro Met Asp Asn Leu Gln Gly Asp Leu Leu
        115                 120                 125

Asn Leu Tyr Gln Cys His Ile Glu Lys Lys Ile Gly Pro Asn Ala Leu
    130                 135                 140
```

```
Lys Asp Val Asn Leu Trp Ser Lys Arg Thr Thr Asn Gly Lys Asp Asp
145                 150                 155                 160

Lys Lys Ala Tyr Phe Asp Pro Ala Ser Phe Val Ala Glu Gln Leu Asp
                165                 170                 175

Met Gly Pro Leu His Tyr Ser Leu Asp Ala Ala Cys Ala Ser Ala Leu
            180                 185                 190

Tyr Val Leu Arg Leu Ala Gln Asp His Leu Leu Ser Gly Ala Ala Asp
        195                 200                 205

Thr Met Leu Cys Gly Ala Ser Cys Leu Pro Glu Pro Phe Phe Ile Leu
210                 215                 220

Ser Gly Phe Ser Thr Phe His Ala Met Pro Leu Ser Gly Asp Val Ser
225                 230                 235                 240

Ala Pro Leu His Lys Thr Ser Gln Gly Leu Thr Pro Gly Glu Gly Gly
                245                 250                 255

Ala Ile Met Val Leu Lys Arg Leu Asn Asp Ala Ile Arg Asp Gly Asp
            260                 265                 270

Arg Ile Tyr Gly Thr Leu Leu Gly Ala Glu Leu Ser Asn Ala Gly Cys
        275                 280                 285

Gly Leu Pro Leu Ser Pro His Met Pro Ser Glu Phe Asp Cys Met Glu
290                 295                 300

Lys Ala Leu Gln Arg Val His Arg Leu Pro Ser Ser Ile Gln Tyr Val
305                 310                 315                 320

Glu Cys His Ala Thr Gly Thr Pro Gln Gly Asp Lys Val Glu Ile Asp
                325                 330                 335

Ala Met Thr Lys Cys Phe Gly Glu His Leu Pro Arg Phe Gly Ser Thr
            340                 345                 350

Lys Gly Asn Phe Gly His Thr Leu Val Ala Ala Gly Phe Ala Gly Met
        355                 360                 365

Cys Lys Val Leu Leu Ser Met Gln Tyr Gly Glu Ile Pro Pro Thr Pro
370                 375                 380

Gly Leu Glu Asn Pro Asp Asn Ile Met His Asp Leu Val Val Thr Glu
385                 390                 395                 400

Thr Ile Pro Trp Pro Asn Thr Asn Gly Asp Leu Lys Arg Ala Cys Leu
                405                 410                 415

Ser Ala Phe Gly Phe Gly Gly Thr Asn Ala His Ala Val Phe Glu Glu
            420                 425                 430

Tyr Arg Ser Asp Leu
        435
```

<210> SEQ ID NO 104
<211> LENGTH: 1323
<212> TYPE: DNA
<213> ORGANISM: Thraustochytrium sp.

<400> SEQUENCE: 104

```
aaaattgcta ttgttggtat ggaatctgaa tttggtactt tgaaaggatt acaagaattt      60
gaacgtgcta tttacaatgg tggtcatggt gcatgtgatt tacctgaaaa tagatggaga     120
tttcttggag aagataaaga atttttacaa gcttgtggtt acaaaaaatt accaagaggt     180
tgttatatta agaagtggaa actgattttt aaaaggttac gtttaccaat gatacaggag     240
gatattctaa gacctttaca gttgttagct gtttcgatta cgacagagc acttaacgca      300 tctggtgtta aaccaaatgg caaagttgca gtttttagttg gattaggtac tgatcttgaa     360
ttatatcgtc atcgtgctcg tgttgcatta aaggaacgcc tccaaactgc ggtcaaagaa     420
```

```
gatattcctt tacttgaaaa gttaatgaac tatgtcaatg atagaggtac aagtacatca    480
tatacatctt atattggaaa tttggttgca actcgagttt catcattatg ggtttttact    540
ggtccatcat tcacgattac tgaaggtgaa aattccgtat atcgttgtct tgatttggga    600
agatggttct tagctaatgg tgaagtagat gctgttgttg ttgccggggt tgatttatgt    660
ggtagtgctg aaaatctttt tgtaaaatct cgtagaagta agtttccac acaaaatgaa     720 ccatttgcaa attttgaatc aaatgctgat ggatattttg ctggagatgg ttgtggagct    780
ttggttttga aacgattgag tgattgtacg gattcaactg aaaaaattta tgcaacggtg    840
gattcaattg ctgttggtga tgaagttggc ccaactatta acaagctttt gaagaatgca    900
tccatagcag cgaaagatat tgaactggca gagctatcag caagttcagg caaacatcat    960
tctggtagaa tcacttgtga agatgaacta aatgaactgg gtgaaatttt caatgaaggt   1020
atacaaagag ttgcaattgg tagtgtgaaa gctaatgttg gagatgttgg atatgcatct   1080
ggtgcagcaa gtttaatcaa aacggctttg tgcctgtaca accgatattt accaaagtta   1140
ccaaattgga ataagccaac gaaagatgtt gaatggtcca atcattttt tgtatgtgaa    1200 cattctagag catggttgaa aaatgttgat gaaaatagac atgctgtcgt ttctggagtt   1260
tgcgaaaatg gttcgtgtta tggaatcgta atgtctgatg tacaaggaca tcatgaagaa   1320
tcg                                                                 1323

<210> SEQ ID NO 105
<211> LENGTH: 441
<212> TYPE: PRT
<213> ORGANISM: Thraustochytrium sp.

<400> SEQUENCE: 105

Lys Ile Ala Ile Val Gly Met Glu Ser Glu Phe Gly Thr Leu Lys Gly
1               5                   10                  15

Leu Gln Glu Phe Glu Arg Ala Ile Tyr Asn Gly Gly His Gly Ala Cys
            20                  25                  30

Asp Leu Pro Glu Asn Arg Trp Arg Phe Leu Gly Glu Asp Lys Glu Phe
        35                  40                  45

Leu Gln Ala Cys Gly Leu Gln Lys Leu Pro Arg Gly Cys Tyr Ile Lys
    50                  55                  60

Glu Val Glu Thr Asp Phe Lys Arg Leu Arg Leu Pro Met Ile Gln Glu
65                  70                  75                  80

Asp Ile Leu Arg Pro Leu Gln Leu Leu Ala Val Ser Ile Ile Asp Arg
                85                  90                  95

Ala Leu Asn Ala Ser Gly Val Lys Pro Asn Gly Lys Val Ala Val Leu
            100                 105                 110

Val Gly Leu Gly Thr Asp Leu Glu Leu Tyr Arg His Arg Ala Arg Val
        115                 120                 125

Ala Leu Lys Glu Arg Leu Gln Thr Ala Val Lys Glu Asp Ile Pro Leu
    130                 135                 140

Leu Glu Lys Leu Met Asn Tyr Val Asn Asp Arg Gly Thr Ser Thr Ser
145                 150                 155                 160

Tyr Thr Ser Tyr Ile Gly Asn Leu Val Ala Thr Arg Val Ser Ser Leu
                165                 170                 175

Trp Gly Phe Thr Gly Pro Ser Phe Thr Ile Thr Glu Gly Glu Asn Ser
            180                 185                 190

Val Tyr Arg Cys Leu Asp Leu Gly Arg Trp Phe Leu Ala Asn Gly Glu
        195                 200                 205
```

Val Asp Ala Val Val Ala Gly Val Asp Leu Cys Gly Ser Ala Glu
    210                 215                 220

Asn Leu Phe Val Lys Ser Arg Arg Ser Lys Val Ser Thr Gln Asn Glu
225                 230                 235                 240

Pro Phe Ala Asn Phe Glu Ser Asn Ala Asp Gly Tyr Phe Ala Gly Asp
                245                 250                 255

Gly Cys Gly Ala Leu Val Leu Lys Arg Leu Ser Asp Cys Thr Asp Ser
                260                 265                 270

Thr Glu Lys Ile Tyr Ala Thr Val Asp Ser Ile Ala Val Gly Asp Glu
    275                 280                 285

Val Gly Pro Thr Ile Lys Gln Ala Leu Lys Asn Ala Ser Ile Ala Ala
    290                 295                 300

Lys Asp Ile Glu Leu Ala Glu Leu Ser Ala Ser Ser Gly Lys His His
305                 310                 315                 320

Ser Gly Arg Ile Thr Cys Glu Asp Glu Leu Asn Glu Leu Gly Glu Ile
                325                 330                 335

Phe Asn Glu Gly Ile Gln Arg Val Ala Ile Gly Ser Val Lys Ala Asn
                340                 345                 350

Val Gly Asp Val Gly Tyr Ala Ser Gly Ala Ala Ser Leu Ile Lys Thr
    355                 360                 365

Ala Leu Cys Leu Tyr Asn Arg Tyr Leu Pro Lys Leu Pro Asn Trp Asn
370                 375                 380

Lys Pro Thr Lys Asp Val Glu Trp Ser Lys Ser Phe Phe Val Cys Glu
385                 390                 395                 400

His Ser Arg Ala Trp Leu Lys Asn Val Asp Glu Asn Arg His Ala Val
                405                 410                 415

Val Ser Gly Val Cys Glu Asn Gly Ser Cys Tyr Gly Ile Val Met Ser
    420                 425                 430

Asp Val Gln Gly His His Glu Glu Ser
    435                 440

<210> SEQ ID NO 106
<211> LENGTH: 1353
<212> TYPE: DNA
<213> ORGANISM: Thraustochytrium sp.

<400> SEQUENCE: 106
cctacaatag atattgactc caatgtgttt gctgagatgc ttaatctacc gcaggataaa      60
aacaaaaaat ttgcggtcgc attggttacc acaccaaata aactccagcg tgaaatagaa     120
cttgctgtga agggtattcc acgttgcgta aaagcaaaaa gagattggtg ttctccatct     180
ggaagtattt ttgcttgtaa tccactcaaa agtgataata ttgcatttat gtatggtgaa     240
ggccgaagcc catatgctgg actgggatat gatttgcatc gaatttggcc tatgctacac     300
gagttggtta acaatagaac tacagaactt tgggatcaag gtgatagttg gtatttacct     360
cgatctagct ctgttgctga aaagaaaaa gtcttcggag attttgataa gaatcaaatt      420
gaaatgttta gattgggtat ttttgtatca atgtgtttca ctgatatggc cactgaactt     480
ttgggtttaa acccaaagc cgcgtttggt ttaagtttgg gtgaaatatc tatgcttttt      540
gcattttcta aaaagaatac caagttgtcc aaagaattga cccgtcgtct aaaagaagca     600
aaagtttggg catcacaatt agctgttgaa tttgcagcta ttcgagattt gtggaatatt     660
ccagctgata atctattga tgaatttttgg caagggtatt ttgtttacgc aaatcgaacc     720
ctggtcgaga acacaattgg ggagaataaa tttgttcgtt tgttgattgt aaatgattcg     780

```
caaagttgtc taattgccgg gaaaccagat gaatgtcaaa aagttattga gaagcttcat    840
ttgaagctac cggcggttcc agtaactcag ggtatgatcg gtcattgccc agaagcaatt    900
ccttatctag atcaaatcag tcatattcat gaaatgcttg aaattccaaa acccgaaaat    960
gtgaaattgt ttacaactag tgaaaacaga gaattagtgt cgatgaaaga ttccgtgtca   1020
aaattggttg ctgagattta tcagcatgtt gctgattttc caaacatcgt gaacaaggtt   1080
aaagaaactt gcaaaactga tatatttatt gaattgggat cgaacaatta tcgatctgga   1140
gctgtcaaaa caattttagg tccagaaatc gtttctgttg caattgatag caaaatgaa    1200 actgcatggg gtcaactaat gaagatggtt gcatcgttga taagtcatcg agttccgggt   1260
gttgaattga aaaaactcta tcatcctgaa ttgctgaaat ttgatccaca ggcaaaaccg   1320
aatcgtttca tcagaaatat agaactgaat gga                                1353
```

<210> SEQ ID NO 107
<211> LENGTH: 451
<212> TYPE: PRT
<213> ORGANISM: Thraustochytrium sp.

<400> SEQUENCE: 107

```
Pro Thr Ile Asp Ile Asp Ser Asn Val Phe Ala Glu Met Leu Asn Leu
1               5                   10                  15

Pro Gln Asp Lys Asn Lys Lys Phe Ala Val Ala Leu Val Thr Thr Pro
            20                  25                  30

Asn Lys Leu Gln Arg Glu Ile Glu Leu Ala Val Lys Gly Ile Pro Arg
        35                  40                  45

Cys Val Lys Ala Lys Arg Asp Trp Cys Ser Pro Ser Gly Ser Ile Phe
    50                  55                  60

Ala Cys Asn Pro Leu Lys Ser Asp Asn Ile Ala Phe Met Tyr Gly Glu
65                  70                  75                  80

Gly Arg Ser Pro Tyr Ala Gly Leu Gly Tyr Asp Leu His Arg Ile Trp
                85                  90                  95

Pro Met Leu His Glu Leu Val Asn Asn Arg Thr Thr Glu Leu Trp Asp
            100                 105                 110

Gln Gly Asp Ser Trp Tyr Leu Pro Arg Ser Ser Val Ala Glu Lys
        115                 120                 125

Glu Lys Val Phe Gly Asp Phe Asp Lys Asn Gln Ile Glu Met Phe Arg
    130                 135                 140

Leu Gly Ile Phe Val Ser Met Cys Phe Thr Asp Met Ala Thr Glu Leu
145                 150                 155                 160

Leu Gly Leu Lys Pro Lys Ala Ala Phe Gly Leu Ser Leu Gly Glu Ile
                165                 170                 175

Ser Met Leu Phe Ala Phe Ser Lys Lys Asn Thr Lys Leu Ser Lys Glu
            180                 185                 190

Leu Thr Arg Arg Leu Lys Glu Ala Lys Val Trp Ala Ser Gln Leu Ala
        195                 200                 205

Val Glu Phe Ala Ala Ile Arg Asp Leu Trp Asn Ile Pro Ala Asp Lys
    210                 215                 220

Ser Ile Asp Glu Phe Trp Gln Gly Tyr Phe Val Tyr Ala Asn Arg Thr
225                 230                 235                 240

Leu Val Glu Asn Thr Ile Gly Glu Asn Lys Phe Val Arg Leu Leu Ile
                245                 250                 255

Val Asn Asp Ser Gln Ser Cys Leu Ile Ala Gly Lys Pro Asp Glu Cys
            260                 265                 270
```

```
Gln Lys Val Ile Glu Lys Leu His Leu Lys Leu Pro Ala Pro Val
        275                 280                 285
Thr Gln Gly Met Ile Gly His Cys Pro Glu Ala Ile Pro Tyr Leu Asp
    290                 295                 300
Gln Ile Ser His Ile His Glu Met Leu Glu Ile Pro Lys Pro Glu Asn
305                 310                 315                 320
Val Lys Leu Phe Thr Thr Ser Glu Asn Arg Glu Leu Val Ser Met Lys
                325                 330                 335
Asp Ser Val Ser Lys Leu Val Ala Glu Ile Tyr Gln His Val Ala Asp
            340                 345                 350
Phe Pro Asn Ile Val Asn Lys Val Lys Glu Thr Cys Lys Thr Asp Ile
        355                 360                 365
Phe Ile Glu Leu Gly Ser Asn Asn Tyr Arg Ser Gly Ala Val Lys Thr
    370                 375                 380
Ile Leu Gly Pro Glu Ile Val Ser Val Ala Ile Asp Arg Gln Asn Glu
385                 390                 395                 400
Thr Ala Trp Gly Gln Leu Met Lys Met Val Ala Ser Leu Ile Ser His
                405                 410                 415
Arg Val Pro Gly Val Glu Leu Lys Leu Tyr His Pro Glu Leu Leu
            420                 425                 430
Lys Phe Asp Pro Gln Ala Lys Pro Asn Arg Phe Ile Arg Asn Ile Glu
        435                 440                 445
Leu Asn Gly
    450

<210> SEQ ID NO 108
<211> LENGTH: 1203
<212> TYPE: DNA
<213> ORGANISM: Thraustochytrium sp.

<400> SEQUENCE: 108
ctcaaaacat atgaggttga ctatcctttg tacacaggtg ccatggctaa aggaattgcg      60
tctgctgatt tggttattgc tgctggtaaa tcaaagatct tggcatcatt tggagctggt     120
gggttggcct acaagtggt  agaagatgcc attaaacaaa ttaaagctga attggggaac     180
ggtccgtttg ctgtaaattt gattcattca ccattcgatc ctagcttgga agggtaac      240 gttgatcttt ttctaaaata taacgttcga tttgttgaag tatccgcatt tatgtcatta     300
acccctcagg ttgtacgata cagagccgct ggtttggcca aagcaagaga tggatctgtg    360
aaaattcaaa atcgtattat tgccaaaatt tcaagaacag agttagcgga actgttcttg    420
aaaccagcac ccaaaaatat tttagatgca ttggttgcgg atggatctat tagtcaagaa    480
caagcccaac ttgcattact ctgtgccaatg gctgatgata ttactgtgga agctgattct    540
ggtgggcata ctgacaatcg accaattcat gttttgttac ctttgataat tcagcaaaga    600
aatagaattt gtaaacaata cccaaaaacat ttaaaagttc gaatcggagc agctggtggt    660
attggatgcc cgaaggcagc atttgctgcg tttgagatgg gtgctgcata cattgcaact    720
ggaacggtaa atcaactttc aaaggaagca ggtacttgtg actatgtacg taaagtattg    780
aataaagcta catattcgga tgttaccatg gctccagccg cagatatgtt cgatcatggt    840
gttgaattac aagttttgaa gaaaggtact atgtttcctt cacgtgctaa aaaactatac    900
gatttgttca aaaatacaa  atcgattgag gaattaccag cagatgaggt gaaaaaactt    960
gagcaaaaag ttttcaaaaa gtcgtttgat gaagtatggg atgagaccaa gaattactat   1020
```

-continued

```
attaatcgtt tacattctcc cgaaaaaatt gaacgtgctg aaagagatgc aaaacttaaa    1080
atgtcgttat gttttcgttg gtatttgtcg aagtcttcca gatgggctaa taccggtgaa    1140
tctggaagag tgcaggatta tcaaatttgg tgtggtccag caattgggtc atataatgat    1200
ttt                                                                  1203
```

<210> SEQ ID NO 109
<211> LENGTH: 401
<212> TYPE: PRT
<213> ORGANISM: Thraustochytrium sp.

<400> SEQUENCE: 109

```
Leu Lys Thr Tyr Glu Val Asp Tyr Pro Leu Tyr Thr Gly Ala Met Ala
1               5                   10                  15

Lys Gly Ile Ala Ser Ala Asp Leu Val Ile Ala Ala Gly Lys Ser Lys
            20                  25                  30

Ile Leu Ala Ser Phe Gly Ala Gly Gly Leu Ala Leu Gln Val Val Glu
        35                  40                  45

Asp Ala Ile Lys Gln Ile Lys Ala Glu Leu Gly Asn Gly Pro Phe Ala
    50                  55                  60

Val Asn Leu Ile His Ser Pro Phe Asp Pro Ser Leu Glu Lys Gly Asn
65                  70                  75                  80

Val Asp Leu Phe Leu Lys Tyr Asn Val Arg Phe Val Glu Val Ser Ala
                85                  90                  95

Phe Met Ser Leu Thr Pro Gln Val Val Arg Tyr Arg Ala Ala Gly Leu
            100                 105                 110

Ala Lys Ala Arg Asp Gly Ser Val Lys Ile Gln Asn Arg Ile Ile Ala
        115                 120                 125

Lys Ile Ser Arg Thr Glu Leu Ala Glu Leu Phe Leu Lys Pro Ala Pro
    130                 135                 140

Lys Asn Ile Leu Asp Ala Leu Val Ala Asp Gly Ser Ile Ser Gln Glu
145                 150                 155                 160

Gln Ala Gln Leu Ala Leu Leu Val Pro Met Ala Asp Ile Thr Val
                165                 170                 175

Glu Ala Asp Ser Gly Gly His Thr Asp Asn Arg Pro Ile His Val Leu
            180                 185                 190

Leu Pro Leu Ile Ile Gln Gln Arg Asn Arg Ile Cys Lys Gln Tyr Pro
        195                 200                 205

Lys His Leu Lys Val Arg Ile Gly Ala Ala Gly Ile Gly Cys Pro
    210                 215                 220

Lys Ala Ala Phe Ala Ala Phe Glu Met Gly Ala Ala Tyr Ile Ala Thr
225                 230                 235                 240

Gly Thr Val Asn Gln Leu Ser Lys Glu Ala Gly Thr Cys Asp Tyr Val
                245                 250                 255

Arg Lys Val Leu Asn Lys Ala Thr Tyr Ser Asp Val Thr Met Ala Pro
            260                 265                 270

Ala Ala Asp Met Phe Asp His Gly Val Glu Leu Gln Val Leu Lys Lys
        275                 280                 285

Gly Thr Met Phe Pro Ser Arg Ala Lys Lys Leu Tyr Asp Leu Phe Lys
    290                 295                 300

Lys Tyr Lys Ser Ile Glu Glu Leu Pro Ala Asp Glu Val Lys Lys Leu
305                 310                 315                 320

Glu Gln Lys Val Phe Lys Lys Ser Phe Asp Glu Val Trp Asp Glu Thr
                325                 330                 335
```

Lys Asn Tyr Tyr Ile Asn Arg Leu His Ser Pro Glu Lys Ile Glu Arg
            340                 345                 350

Ala Glu Arg Asp Ala Lys Leu Lys Met Ser Leu Cys Phe Arg Trp Tyr
        355                 360                 365

Leu Ser Lys Ser Ser Arg Trp Ala Asn Thr Gly Glu Ser Gly Arg Val
    370                 375                 380

Gln Asp Tyr Gln Ile Trp Cys Gly Pro Ala Ile Gly Ser Tyr Asn Asp
385                 390                 395                 400

Phe

<210> SEQ ID NO 110
<211> LENGTH: 1350
<212> TYPE: DNA
<213> ORGANISM: Thraustochytrium sp.

<400> SEQUENCE: 110

```
atggttggtt tacaaatgaa aaagaaacca gtatgggaga tgagtaagga agaacaaagt      60
tctggaaaga atgttgtatt tgactatgat gaattgttgg aatttgctga aggtgatatt     120
ggtaaagtct ttggacctaa gtttgatatt atcgataagt atagtcgacg tgtacgttta     180
cctgcgagag aatatcttct agttaccaga gttactttga tggatgctga agttgggaat     240
ttcagagttg gatctagaat ggttactgaa tatgatgttc cagtaaatgg tgaactttca     300
caaggtggtg atgttccatg gctgttctt gttgaatctg acaatgtga tcttatgtta      360
atatcttata tgggtattga ttttcaatgt aaaggtgatc gtgtctatcg attattaaat     420
actacgttga cgttttacgg tgttgctcat gagggtgaaa cactagtata cgatattcgt     480
gtaactggat ttgcaaaagg tatgcacggt gaaatctcca tgtttttttt tgaatatgat     540
tgttatgtga atggacgatt attaatcgaa atgagagatg ttgtgcggg atttttttact     600
gatgaagaac ttgcagcagg taaggagtt attaaaactg ttgctgaact tcataaaaga     660
aaatctattg ttccaaaatc cattaaacct tttgctctaa atccagcagt acacaaaaca     720
atgttttctg aaaatgatat ggaaaaattg tgtgagcgtc aatgggaaaa tgtattgggt     780
agtggacttc aaggtattga ctacaagtta tgtgcacgga aaatgctat gattgatcgt      840
attactaaaa tacaacataa tggtggtgca tatggtcttg gattattggt tggcgaaaaa     900
attcttgaac gtgatcattg gtattttcca tgccattttg taaaggatca agttatggct     960
ggctcacttg ttagtgatgg ttgcagtcag ctactaaaac tttatatgtt atggttgggt    1020
ttacatgatg tggttccaga ttttcaattt cgtccagttc ctggacaacc aaataaagtt    1080
cgttgccgtg acaaattag tccacatcgt ggtaaacttg tttatgttat ggaaataaga    1140
gaaatgggat tcaatgaatc aactggacaa ccatatgcta ttgctgatgt tgatattatt    1200
gatgtaaact atgaacttgg tcaatcattt gatatggctg atattgatag ttatggacgt    1260
ggtaatttgt caaagaaaat tgtggttgat tttaaaggaa ttgctttgca aatggaaggt    1320
accgtgaaat catcaaatat cattgattct                                     1350
```

<210> SEQ ID NO 111
<211> LENGTH: 450
<212> TYPE: PRT
<213> ORGANISM: Thraustochytrium sp.

<400> SEQUENCE: 111

Met Val Gly Leu Gln Met Lys Lys Lys Pro Val Trp Glu Met Ser Lys
1               5                   10                  15

```
Glu Glu Gln Ser Ser Gly Lys Asn Val Val Phe Asp Tyr Asp Glu Leu
             20                  25                  30

Leu Glu Phe Ala Glu Gly Asp Ile Gly Lys Val Phe Gly Pro Lys Phe
         35                  40                  45

Asp Ile Ile Asp Lys Tyr Ser Arg Arg Val Arg Leu Pro Ala Arg Glu
 50                  55                  60

Tyr Leu Leu Val Thr Arg Val Thr Leu Met Asp Ala Glu Val Gly Asn
 65                  70                  75                  80

Phe Arg Val Gly Ser Arg Met Val Thr Glu Tyr Asp Val Pro Val Asn
             85                  90                  95

Gly Glu Leu Ser Gln Gly Gly Asp Val Pro Trp Ala Val Leu Val Glu
             100                 105                 110

Ser Gly Gln Cys Asp Leu Met Leu Ile Ser Tyr Met Gly Ile Asp Phe
             115                 120                 125

Gln Cys Lys Gly Asp Arg Val Tyr Arg Leu Leu Asn Thr Thr Leu Thr
 130                 135                 140

Phe Tyr Gly Val Ala His Glu Gly Glu Thr Leu Val Tyr Asp Ile Arg
 145                 150                 155                 160

Val Thr Gly Phe Ala Lys Gly Met His Gly Glu Ile Ser Met Phe Phe
             165                 170                 175

Phe Glu Tyr Asp Cys Tyr Val Asn Gly Arg Leu Leu Ile Glu Met Arg
             180                 185                 190

Asp Gly Cys Ala Gly Phe Phe Thr Asp Glu Glu Leu Ala Ala Gly Lys
             195                 200                 205

Gly Val Ile Lys Thr Val Ala Glu Leu His Lys Arg Lys Ser Ile Val
 210                 215                 220

Pro Lys Ser Ile Lys Pro Phe Ala Leu Asn Pro Ala Val His Lys Thr
 225                 230                 235                 240

Met Phe Ser Glu Asn Asp Met Glu Lys Leu Cys Glu Arg Gln Trp Glu
             245                 250                 255

Asn Val Leu Gly Ser Gly Leu Gln Gly Ile Asp Tyr Lys Leu Cys Ala
             260                 265                 270

Arg Lys Met Leu Met Ile Asp Arg Ile Thr Lys Ile Gln His Asn Gly
             275                 280                 285

Gly Ala Tyr Gly Leu Gly Leu Leu Val Gly Glu Lys Ile Leu Glu Arg
             290                 295                 300

Asp His Trp Tyr Phe Pro Cys His Phe Val Lys Asp Gln Val Met Ala
 305                 310                 315                 320

Gly Ser Leu Val Ser Asp Gly Cys Ser Gln Leu Leu Lys Leu Tyr Met
             325                 330                 335

Leu Trp Leu Gly Leu His Asp Val Val Pro Asp Phe Gln Phe Arg Pro
             340                 345                 350

Val Pro Gly Gln Pro Asn Lys Val Arg Cys Arg Gly Gln Ile Ser Pro
             355                 360                 365

His Arg Gly Lys Leu Val Tyr Val Met Glu Ile Arg Glu Met Gly Phe
             370                 375                 380

Asn Glu Ser Thr Gly Gln Pro Tyr Ala Ile Ala Asp Val Asp Ile Ile
 385                 390                 395                 400

Asp Val Asn Tyr Glu Leu Gly Gln Ser Phe Asp Met Ala Asp Ile Asp
             405                 410                 415

Ser Tyr Gly Arg Gly Asn Leu Ser Lys Lys Ile Val Val Asp Phe Lys
             420                 425                 430

Gly Ile Ala Leu Gln Met Glu Gly Thr Val Lys Ser Ser Asn Ile Ile
```

Asp Ser
    450

<210> SEQ ID NO 112
<211> LENGTH: 1200
<212> TYPE: DNA
<213> ORGANISM: Thraustochytrium sp.

<400> SEQUENCE: 112

```
tgcttcaaac catttcctgg taatcctttta gataacgatc atacacctgg taaaatgcct      60
ttaacatggt ttaatatgtc cgagtttatg tgtggtaaag tatcaaattg tcttggacca     120
gaatttaaga gatttgataa ctctaaaaca tccagaagtc ctgcctttga tcttgcactt     180
gttacacgtg ttgtgagtgt atcagatatg gaatttaaac ctcatttaaa tattgatgtt     240
aatccaagta agggtacaat gataggtgaa tttgattgcc ctgcagatgc gtggtttttt     300
caaggatcat gtaacgatgg tcatatgccg tattctattg ttatggaaat tgctcttcaa     360
acttctggtg tattaacttc agttttgaaa gcacctttga ctatggataa agatgatatt     420
cttttccgca atttggatgc cactgctgaa atggttcgaa gtgatgttga ttgtagaggt     480
aaaactatca aaaactttac tcaatgtacc ggttacagta tgctcggaaa aatgggaatt     540
catagattca catttgaatt atctgttgat gatgtagttt tctacaaagg atcaacatct     600
tttggttggt tcacccctga agtattcgag tcacaagttg gtcttgataa tggtaaaaaa     660
gtacaaccat ggtatttgga acaaaaatca tctaatgtag taacttatga cgttgcgtcc     720
actgctggca aggataagtt attttcaaag attggatcta aggatgcaca agttcaagaa     780
agaaatacac aatgtgagtt tctagatact atgcatatta ttccaaatac tggaaagtac     840
aacaaaggtt atgctcatgg agaaaagaaa gttaatccaa cgactggttc ttttcctgt     900
catttctggt tgatcctgt gatgcctggt tcattaggta ttgaaagtat gtttcaactc     960
attgaagcat tttcaattga tcaaggaatc gcttcaaaac atggtattgt gaatccaact    1020
tttgctcatt ccaatggaaa aacttcttgg aaatacagag gtcaattgaa taacaaaggt    1080
aaacgaatgg atagtgaaat tcatatcaaa gatattgtca aaaatgctga tggtactgtt    1140
gatttgattg ctgatggatt tttattggtt gattcactaa gagtatactc tgcagatgat    1200
```

<210> SEQ ID NO 113
<211> LENGTH: 400
<212> TYPE: PRT
<213> ORGANISM: Thraustochytrium sp.

<400> SEQUENCE: 113

Cys Phe Lys Pro Phe Pro Gly Asn Pro Leu Asp Asn Asp His Thr Pro
1               5                   10                  15

Gly Lys Met Pro Leu Thr Trp Phe Asn Met Ser Glu Phe Met Cys Gly
            20                  25                  30

Lys Val Ser Asn Cys Leu Gly Pro Glu Phe Lys Arg Phe Asp Asn Ser
        35                  40                  45

Lys Thr Ser Arg Ser Pro Ala Phe Asp Leu Ala Leu Val Thr Arg Val
    50                  55                  60

Val Ser Val Ser Asp Met Glu Phe Lys Pro His Leu Asn Ile Asp Val
65                  70                  75                  80

Asn Pro Ser Lys Gly Thr Met Ile Gly Glu Phe Asp Cys Pro Ala Asp
                85                  90                  95

```
Ala Trp Phe Phe Gln Gly Ser Cys Asn Asp Gly His Met Pro Tyr Ser
                100                 105                 110

Ile Val Met Glu Ile Ala Leu Gln Thr Ser Gly Val Leu Thr Ser Val
            115                 120                 125

Leu Lys Ala Pro Leu Thr Met Asp Lys Asp Asp Ile Leu Phe Arg Asn
        130                 135                 140

Leu Asp Ala Thr Ala Glu Met Val Arg Ser Val Asp Cys Arg Gly
145                 150                 155                 160

Lys Thr Ile Lys Asn Phe Thr Gln Cys Thr Gly Tyr Ser Met Leu Gly
                165                 170                 175

Lys Met Gly Ile His Arg Phe Thr Phe Glu Leu Ser Val Asp Asp Val
            180                 185                 190

Val Phe Tyr Lys Gly Ser Thr Ser Phe Gly Trp Phe Thr Pro Glu Val
        195                 200                 205

Phe Glu Ser Gln Val Gly Leu Asp Asn Gly Lys Lys Val Gln Pro Trp
    210                 215                 220

Tyr Leu Glu Gln Lys Ser Ser Asn Val Val Thr Tyr Asp Val Ala Ser
225                 230                 235                 240

Thr Ala Gly Lys Asp Lys Leu Phe Ser Lys Ile Gly Ser Lys Asp Ala
                245                 250                 255

Gln Val Gln Arg Arg Asn Thr Gln Cys Glu Phe Leu Asp Thr Met His
            260                 265                 270

Ile Ile Pro Asn Thr Gly Lys Tyr Asn Lys Gly Tyr Ala His Gly Glu
        275                 280                 285

Lys Lys Val Asn Pro Asn Asp Trp Phe Phe Ser Cys His Phe Trp Phe
    290                 295                 300

Asp Pro Val Met Pro Gly Ser Leu Gly Ile Glu Ser Met Phe Gln Leu
305                 310                 315                 320

Ile Glu Ala Phe Ser Ile Asp Gln Gly Ile Ala Ser Lys His Gly Ile
                325                 330                 335

Val Asn Pro Thr Phe Ala His Ser Asn Gly Lys Thr Ser Trp Lys Tyr
            340                 345                 350

Arg Gly Gln Leu Asn Asn Lys Gly Lys Arg Met Asp Ser Glu Ile His
        355                 360                 365

Ile Lys Asp Ile Val Lys Asn Ala Asp Gly Thr Val Asp Leu Ile Ala
    370                 375                 380

Asp Gly Phe Leu Leu Val Asp Ser Leu Arg Val Tyr Ser Ala Asp Asp
385                 390                 395                 400

<210> SEQ ID NO 114
<211> LENGTH: 1729
<212> TYPE: DNA
<213> ORGANISM: Thraustochytrium sp.

<400> SEQUENCE: 114
aggaatcgct tcaaaacatg gtattgtgaa tccaactttt gctcattcca atggaaaaac      60
ttcttggaaa tacagaggtc aattgaataa caaaggtaaa cgaatggata gtgaaattca     120
tatcaaagat attgtcaaaa atgctgatgg tactgttgat ttgattgctg atggattttt     180
attggttgat tcactaagag tatactctgc agatgatctt cgcgtaaaaa ttgtaccggg     240
aaccaaagct gcacctaaat cagtagctgc tgctccaaga catgttgcaa caccaattcc     300
aggagtgcct tcgaatacaa gcagtgttga aatcagtttg gaatctttga agaaagaatt     360
gttaaatctt gagaaaccat tgtatcttga aacttccaat catattgtaa aacaattcgg     420
```

```
tgacgttaac aatggccaag catccgttat tccaccatgc accatcaatg atttgggtga    480
gcgtagtttt atggaaacat acaatgttgt tgcaccactt tacactggag ccatggctaa    540
aggtattgca tctgctgatt tggtaattgc agctggtaaa agaaaaattt tgggttcttt    600
tggcgctgga ggcttaccaa tgcacttggt tcgtgcttct gttgaaaaaa tccaagccgc    660
acttccagaa ggtccatacg ctgtcaactt gattcatagt ccattcgact caaatcttga    720
aaagggaaat gtagatctat ttttggaaaa aggtgttcat gttgttgaag catctgcatt    780
cactgctctg accactcaag tagttcgtta ccgtgcatgt ggtttatctc gggctaaaga    840
cggatctgta ttgatcaaaa atagaatcat cggtaaagtt tcaagaaccg aattggctga    900
aatgtttttc agacctgcac cacaaaactt gcttgacaag cttattgcta gtggagaaat    960
cactaaagaa caagcttcat tggctttgga agtaccaatg gctgatgatg tagctgttga   1020
agctgatagc ggtggacata ctgataatag accaattcat gtaatcctac ctttgattat   1080
caatctacga aatagaattc ataaagaatg tggttttcct gctgctttga gagttcgcgt   1140
tggtgctggt ggtggaattg gttgtccaag tgctgcagtt gctgcattca atatgggagc   1200
tgcattcttg attactggca gcgtcaacca agttagcaaa caatctggta cgtgtgatat   1260
cgttagaaag caattatctg aagcttcgta ttcagatatt accatggcac cagcggctga   1320
tatgtttgat caaggagtcg agcttcaagt attaaaaaaa ggaactatgt ttccatctcg   1380
tgcaaagaaa ttgtatgaat tattctgtat gtacaactca tttgatgaca tgccaaaaag   1440
cgaacttcaa agactagaga agcgaatttt tcaaaaatcg cttgcggaag tttgggaaga   1500
aactaaagat ttttatatca atcgtttgaa taatcctgag aagattgaac atgctgagaa   1560
gaaagatcca agttgaaga tgtcattatg ctttagatgg tatttgggtt aagttcatt   1620 ttgggcaaac aatggaatta agaaagatc aatggactat caaatttggt gtggtccagc   1680
gattggttca tacaatgatt ttgtaaaagg aacttatttg gatcctgca              1729
```

<210> SEQ ID NO 115
<211> LENGTH: 455
<212> TYPE: PRT
<213> ORGANISM: Thraustochytrium sp.

<400> SEQUENCE: 115

```
Asn Leu Glu Lys Pro Leu Tyr Leu Glu Thr Ser Asn His Ile Val Lys
1               5                   10                  15

Gln Phe Gly Asp Val Asn Asn Gly Gln Ala Ser Val Ile Pro Pro Cys
            20                  25                  30

Thr Ile Asn Asp Leu Gly Glu Arg Ser Phe Met Glu Thr Tyr Asn Val
        35                  40                  45

Val Ala Pro Leu Tyr Thr Gly Ala Met Ala Lys Gly Ile Ala Ser Ala
    50                  55                  60

Asp Leu Val Ile Ala Ala Gly Lys Arg Lys Ile Leu Gly Ser Phe Gly
65                  70                  75                  80

Ala Gly Gly Leu Pro Met His Leu Val Arg Ala Ser Val Glu Lys Ile
                85                  90                  95

Gln Ala Ala Leu Pro Glu Gly Pro Tyr Ala Val Asn Leu Ile His Ser
            100                 105                 110

Pro Phe Asp Ser Asn Leu Glu Lys Gly Asn Val Asp Leu Phe Leu Glu
        115                 120                 125

Lys Gly Val His Val Val Glu Ala Ser Ala Phe Thr Ala Leu Thr Thr
    130                 135                 140
```

Gln Val Val Arg Tyr Arg Ala Cys Gly Leu Ser Arg Ala Lys Asp Gly
145                 150                 155                 160

Ser Val Leu Ile Lys Asn Arg Ile Ile Gly Lys Val Ser Arg Thr Glu
            165                 170                 175

Leu Ala Glu Met Phe Phe Arg Pro Ala Pro Gln Asn Leu Leu Asp Lys
        180                 185                 190

Leu Ile Ala Ser Gly Glu Ile Thr Lys Glu Gln Ala Ser Leu Ala Leu
    195                 200                 205

Glu Val Pro Met Ala Asp Asp Val Ala Val Glu Ala Asp Ser Gly Gly
210                 215                 220

His Thr Asp Asn Arg Pro Ile His Val Ile Leu Pro Leu Ile Ile Asn
225                 230                 235                 240

Leu Arg Asn Arg Ile His Lys Glu Cys Gly Phe Pro Ala Ala Leu Arg
                245                 250                 255

Val Arg Val Gly Ala Gly Gly Ile Gly Cys Pro Ser Ala Ala Val
            260                 265                 270

Ala Ala Phe Asn Met Gly Ala Ala Phe Leu Ile Thr Gly Ser Val Asn
        275                 280                 285

Gln Val Ser Lys Gln Ser Gly Thr Cys Asp Ile Val Arg Lys Gln Leu
    290                 295                 300

Ser Glu Ala Ser Tyr Ser Asp Ile Thr Met Ala Pro Ala Ala Asp Met
305                 310                 315                 320

Phe Asp Gln Gly Val Glu Leu Gln Val Leu Lys Lys Gly Thr Met Phe
                325                 330                 335

Pro Ser Arg Ala Lys Lys Leu Tyr Glu Leu Phe Cys Met Tyr Asn Ser
            340                 345                 350

Phe Asp Asp Met Pro Lys Ser Glu Leu Gln Arg Leu Glu Lys Arg Ile
        355                 360                 365

Phe Gln Lys Ser Leu Ala Glu Val Trp Glu Thr Lys Asp Phe Tyr
    370                 375                 380

Ile Asn Arg Leu Asn Asn Pro Glu Lys Ile Glu His Ala Glu Lys Lys
385                 390                 395                 400

Asp Pro Lys Leu Lys Met Ser Leu Cys Phe Arg Trp Tyr Leu Gly Leu
                405                 410                 415

Ser Ser Phe Trp Ala Asn Asn Gly Ile Lys Glu Arg Ser Met Asp Tyr
            420                 425                 430

Gln Ile Trp Cys Gly Pro Ala Ile Gly Ser Tyr Asn Asp Phe Val Lys
        435                 440                 445

Gly Thr Tyr Leu Asp Pro Ala
    450                 455

<210> SEQ ID NO 116
<211> LENGTH: 903
<212> TYPE: DNA
<213> ORGANISM: Thraustochytrium sp.

<400> SEQUENCE: 116
tccattcggg aatctggtta cacgattagc ggagaaagat tcacaactga agctcacaaa      60
ttggttactg gaaagcctca tgctccgatt aagaagaagg atgctttcct agtatctggt     120
ggtgctcgtg gtattactcc actttgtatt cgtgaaattg ctaaagcagt gaaggtggc      180 acttacattt tgatgggtcg atcagctttg gctgatgaac ccttgtgggc taatggtaaa     240
tccggaaaag atttagataa agctggtttg cattttttga ggaagagtt tgcagctggg      300 cgtggtagta aaccaactcc aaaagttcac aaatctttga ttgataaagt gctcggtatt     360

```
agggaggtta gagcatctat tgcaaatata gaagcccatg gagcaaaagc tatatatttg    420
tcttgcgatg tatcttccgc tgagaaagta aaggctgcag tgcaaaaagt tgaaaaggag    480
catctagttc gtattactgg tattgtgcat gcatcaggcg ttttgaggga taaattggtt    540
gagaacaaaa ctttggatga tttcaacgca gtatatggaa ccaaagtaac tggactagta    600
aacttgctgt cagcagtgaa catgaatttt gttcgtcatt tggttatgtt tagttctttg    660
gctggatatc atggaaatgt tggtcaatct gattatgcaa tggctaacga atcacttaac    720
aagattggtt ttagattggg tgcagcttat tctcaattgt gtgttaaatc tatttgttt    780 ggaccttggg atggtggaat ggtaactcca gcttttgaaaa aacaatttca atcaatgggt    840
gtccagatta ttcctcgtga aggtggcgcg gagactgttg caagaatagt cttatcttca    900
aat    903
```

```
<210> SEQ ID NO 117
<211> LENGTH: 201
<212> TYPE: PRT
<213> ORGANISM: Thraustochytrium sp.

<400> SEQUENCE: 117

Ser Ile Arg Glu Ser Gly Tyr Thr Ile Ser Gly Glu Arg Phe Thr Thr
1               5                   10                  15

Glu Ala His Lys Leu Val Thr Gly Lys Pro His Ala Pro Ile Lys Lys
            20                  25                  30

Lys Asp Ala Phe Leu Val Ser Gly Gly Ala Arg Gly Ile Thr Pro Leu
        35                  40                  45

Cys Ile Arg Glu Ile Ala Lys Ala Val Lys Gly Gly Thr Tyr Ile Leu
    50                  55                  60

Met Gly Arg Ser Ala Leu Ala Asp Glu Pro Leu Trp Ala Asn Gly Lys
65                  70                  75                  80

Ser Gly Lys Asp Leu Asp Lys Ala Gly Leu Ala Phe Leu Lys Glu Glu
                85                  90                  95

Phe Ala Ala Gly Arg Gly Ser Lys Pro Thr Pro Lys Val His Lys Ser
            100                 105                 110

Leu Ile Asp Lys Val Leu Gly Ile Arg Glu Val Arg Ala Ser Ile Ala
        115                 120                 125

Asn Ile Glu Ala His Gly Ala Lys Ala Ile Tyr Leu Ser Cys Asp Val
    130                 135                 140

Ser Ser Ala Glu Lys Val Lys Ala Ala Val Gln Lys Val Glu Lys Glu
145                 150                 155                 160

His Leu Val Arg Ile Thr Gly Ile Val His Ala Ser Gly Val Leu Arg
                165                 170                 175

Asp Lys Leu Val Glu Asn Lys Thr Leu Asp Asp Phe Asn Ala Val Tyr
            180                 185                 190

Gly Thr Lys Val Thr Gly Leu Val Asn
        195                 200
```

```
<210> SEQ ID NO 118
<211> LENGTH: 39
<212> TYPE: DNA
<213> ORGANISM: Thraustochytrium sp.

<400> SEQUENCE: 118
ctaaagtctc atcaaattca tggtaaaaat gttttgcct    39
```

<210> SEQ ID NO 119
<211> LENGTH: 13
<212> TYPE: PRT
<213> ORGANISM: Thraustochytrium sp.

<400> SEQUENCE: 119

Leu Lys Ser His Gln Ile His Gly Lys Asn Val Leu Pro
1               5                   10

<210> SEQ ID NO 120
<211> LENGTH: 8976
<212> TYPE: DNA
<213> ORGANISM: Artificial Sequence
<220> FEATURE:
<223> OTHER INFORMATION: Codon-optimized PFA1

<400> SEQUENCE: 120

| | | | | | |
|---|---|---|---|---|---|
| atggaggacc | agcgtattgc | gatcgttggc | cttagcgcga | tccttccctc | gggcgagaac | 60 |
| gtccgcgagt | cgtgggaggc | gatccgtgac | ggcctcaact | gcctttccga | cctgcccgcc | 120 |
| gaccgcgttg | acgtcactgc | ctactacaac | cccacgaagg | cgtcaagga | caagatctac | 180 |
| tgcaagcgtg | gtggcttcat | ccccgagtac | gagtttgact | cgcgcgagtt | cggcctcaac | 240 |
| atgcttcaga | tggaggactc | ggacgccaac | cagaccctca | ccctgctcaa | ggttaaggag | 300 |
| gccctcgacg | acgccaacat | tcccgcgttt | accaacgaga | agaagaacat | cggttgcgtc | 360 |
| ctcggtattg | gcggtggtca | gaaggcctcg | catgagttct | acagccgcct | caactacgtc | 420 |
| gtcgtggata | aggtcctccg | caagatgggc | ctcccggacg | aggacgtcga | gactgctgtc | 480 |
| gagaagttca | aggccaactt | tcccgagtgg | cgccttgact | ccttccccgg | ctttctcggt | 540 |
| aacgtcactg | cgggccgctg | caccaacacc | ttcaacatgg | agggcatgaa | ctgcgtggtc | 600 |
| gatgccgcct | cgcctcgtc | cctcatcgct | atcaaggtcg | ccatcgatga | gctgctccac | 660 |
| ggcgattgcg | acgcgatgat | tgctggcgcg | acgtgcaccg | acaacgccct | tggcatgtac | 720 |
| atggcctttt | ccaagacccc | cgtctttcc | acggaccaga | gctgcctcgc | ctacgacgag | 780 |
| aaaaccaagg | gtatgctcat | tggcgagggt | tccgccatgt | tcgtccttaa | gcgctacgcc | 840 |
| gacgccgtcc | gcgatggcga | caccgtccac | gccgtcatcc | gctcgtgctc | gtcctcctcc | 900 |
| gacggcaagg | cgtcgggtat | ctacaccccg | accatctcgg | gccaggagga | ggccatcctt | 960 |
| cgcgcctacc | gtcgtgccgg | cgtgagcccg | aacacgatca | cccttgtgga | gggccatggc | 1020 |
| accggcaccc | ccgtcggcga | caagatcgag | ctgaccgccc | tccgcaacgt | ctttgacaag | 1080 |
| gcctacggcc | ctggccacaa | ggaggaggtc | gctgtgggct | ccatcaagtc | gcagatcggt | 1140 |
| cacctcaagg | ccgtcgccgg | ctgcgctggc | ctcgtcaagc | tcgtgatggc | tctcaagcat | 1200 |
| aagacgctcc | cgcagtccat | caacgtcgag | aacccgccca | acctcgtcga | tggcactgtc | 1260 |
| atctcggaca | ccacgctcta | catcaacacc | atgaaccgcc | cgtggatcac | caagccgggc | 1320 |
| gtccccgtc | gtgcgggcat | ctccagcttc | ggctttggcg | cgctaacta | ccacgctgtc | 1380 |
| cttgaggagt | cgagcccga | gcagaccaag | ccctaccgcc | tgaacgtttc | ggcccagccg | 1440 |
| atgctcctcc | acgccgtcaa | cgcgaactcg | ctccagaagc | tctgcgagga | ccagctcaag | 1500 |
| ctcctcaagg | agtcccgcga | gaagtgcgtc | aacacgaaga | acaccgacta | cgtcgctttt | 1560 |
| tccaagtttc | aggactcctt | taagctcaag | ggctccgtcc | ccagccagca | cgctcgcgtg | 1620 |
| ggctttgctt | ccaagagcat | cgaggacacg | atttccattc | ttagcgccat | tgtcaaccgc | 1680 |
| ttccagaagg | acatcacgac | caccagctgg | gcgctcccga | aggagggcgc | catctttcgc | 1740 |
| agcaccgccc | tcatcaacga | caacaagtcc | gtggccgccc | tgttctcggg | tcagggcgct | 1800 |

```
cagtacaccc acatgttcaa cgacgtcgcg atgcagtggc cgcagttccg cctctgcgtt   1860
aacgatatgg agaaggccca ggaggaggtg atcaacgaca agtcggttaa gcgcattagc   1920
caggtcatgt ttccccgcaa gccctacgcg cgcgagagcc ccctcgacaa caaggagatc   1980
agcaagaccg agtactcgca gacgacgacc gtcgcctcgt ccgtcggcct ctttgagatt   2040
ttccgcgacg ccggctttgc cccggctttt gttgcgggcc actcgctcgg tgagttctcc   2100 gcccttacg ccgctggcct catcgaccgc gaggacctct ttaagctcgt gtgcaaccgc   2160
gccatggcta tgcgcgacgc ccccaagaag tccgctgacg gcgccatggc tgccgtcatc   2220
ggtccgaacg cctcgtccat caagctctcg gctcccgagg tttgggtcgc gaacaacaac   2280
tcgccctcgc agaccgtcat cactggtgcc aacagcggcg tccaggccga gacttcgaag   2340
ctcaagacgc agggtttccg cgtggtccac ctcgcctgcg acggcgcgtt tcacagcccg   2400
cacatggaga acgccgagaa gcagtttcag aaggccctct cggccgtcaa gttcaacaag   2460
cccaccggct cgtcccccaa gatttttcagc aacgtcaccg gcgtgtcttt accgatcct   2520 aagacggccc tctcccgcca catgactagc tcggtccagt ttctcaccca gatcaagaac   2580
atgtacgccg ctggcgcccg cgtttttcatc gagttcggcc ccaagcaggt cctctcgaag   2640
ctcgtcaacg agatttttccc gggcgacacc agcgtcctca ctgttagcgt gaaccctgcc   2700
tccgccaagg actcggacat ccagctccgc caggcggccg tgcagatggc ggtcgctggc   2760
gtcgctctca ccgactttga taagtgggag cttaaggacc cgacccgcat gaaggagttc   2820
cctcgcaaga aaacgaccct caccctctcc gccgctacct acgttagcaa gaaaacgctc   2880
caggagcgcg agcgtatcat gaacgacggt cgcactgtca gctgcgtgca gcgcatcgag   2940
aacacgaaca cgggcgagct tgagaagctc aagaagcagc tccaggacaa ggagaacgag   3000
gttgtccgcg tccaggccct tgccacccag gccagcgccg accttcagaa caccaaggct   3060
gagcttcaga aggctcaggc caccaagtcg tcgaacgctg cctcggacgc cgtcgtcgcc   3120
aagcacaagg ccatcctcct cgctatgctg gaggagctgg agactggcaa ggccgtcgat   3180
tactccagct ttttccaaggg tcaggttgcc tcccctgcga ccgttcgtgt cgtgtcggct   3240
cccgtgcagg ctgccgcacc ggttcaggtc agcgcctccg tggactcggg cctgctcgcg   3300
aaggcggagc aggtcgtgct tgaggtcctc gcctccaaga ccggctacga gactgagctt   3360
atcgagctgg acatggagct tgagactgag cttggtatcg attcgatcaa gcgcgtcgag   3420 attcttttcgg aggtccaggc ccagctcaac gtggaggcca aggacgttga cgccctgtcg   3480
cgcacccgta cggtcggcga ggtcatcgat gccatgaagg cggagattgc cggcggtcag   3540
cctgctgccc ccgtccaggt cgctgcgccg acgcaggtcg tcgccccggt ccaggcctcc   3600
gcgcctgtcg atagcggcct cctcgccaag gcggagcagg tcgtccttga ggtgctcgct   3660
tccaagactg gttacgagac tgagcttatt gagcttgaca tggagctgga gactgagctt   3720
ggcattgact ccatcaagcg cgtggagatt ctgagcgagg tccaggccca gctcagcgtg   3780
gaggccaagg atgtcgatgc cctctcccgt acgcgcaccg tcggcgaggt cattgacgcg   3840
atgaaggccg agatcgcggg tggtcagccg gccgcccccg tccaggtcgc tgcccctacg   3900
caggtcgtcg ctcccgtcca ggccagcgct cccgtcgact cgggccttct tgctaaggcc   3960
gagcaggtcg tccttgaggt ccttgccagc aagactggct acgagactga gcttattgag   4020
cttgacatgg agcttgagac tgagcttggc atcgactcga ttaagcgcgt cgagatcctc   4080
agcgaggtcc aggcccagct ctccgtcgag gctaaggatg tggatgctct cagccgcacg   4140
```

```
cgcacggtgg gcgaggtcat tgatgccatg aaggcggaga tttccggcgg tcagcccgct    4200
gcccccgtcc aggtcgctgc tccgacccag atcgtcgccc cggtccaggt ttcggctccg    4260
gtggacagcg gcctccttgc caaggccgag caggtcgtcc ttgaggtcct cgccagcaag    4320
accggctacg agactgagct gatcgagctt gacatggagc ttgagactga gctgggcatc    4380
gattccatta agcgcgtcga gatcctctcg gaggtccagg cccagctcag cgtggaggcc    4440
aaggatgtcg atgccctctc gcgtacccgt accgtcggcg aggttatcga tgctatgaag    4500
gccgagatca gcggcggtca gcccacggcg cccgttcagg tcgctgcccc tacgcagatc    4560
gttgccctg tccaggtcag cgctcccgtg acagcggcc tcctcgctaa ggctgagcag    4620
gtggtgctgg aggtcctggc ctccaagacc ggctacgaga ctgagcttat cgagcttgac    4680
atggagcttg agactgagct tggcattgac agcatcaagc gtgtcgagat cctctccgag    4740
gtgcaggccc agctcagcgt ggaggccaag gacgttgacg cgctcagccg tacgcgcacc    4800
gttggcgagg tgatcgacgc catgaaggcc gagattagcg gtggtcagcc cgctgccccg    4860
gttcaggtgg ctgcccctac gcagatcgtc gcccccgtgc aagcttccgc ccctgtggac    4920
agcggccttc tcgccaaggc cgagcaggtc gtccttgagg tgctggcctc caagaccggc    4980
tacgagactg agctgatcga gcttgacatg gagctggaga ctgagcttgg catcgactcg    5040
atcaagcgcg tggagattct ctcggaggtc caggcccagc tctcggtcga ggccaaggac    5100
gtcgatgcgc tctcccgcac ccgcaccgtg gcgaggtca tcgacgctat gaaggcggag    5160
atcagcggcg gtcagccggc ggcccctgtg caggtggccg ctccgaccca gatcgtcgct    5220
cctgtccagg tttccgcccc ggtggactcg ggcctcctgg ctaaggccga gcaggtcgtc    5280
cttgaggtcc tcgcttccaa gaccggctac gagactgagc tgatcgagct ggacatggag    5340
cttgagactg agctgggcat cgattcgatc aagcgcgtcg agattctctc ggaggtccag    5400
gcccagctca acgttgaggc caaggacgtg acgccctct cgcgtactcg caccgttggc    5460
gaggttattg atgctatgaa ggccgagatc gccggtggtc agccggctgc ccctgttcag    5520
gttgctgccc ctgcgccggt ggtcgccccg gtccaggtgt ccacccggt tgacagcggc    5580
ctccttgcca aggccgagca ggttgtgctg gaggtcctcg cctgcaagac gggctacgag    5640
actgagctta tcgagcttga catggagctg gagactgagc ttggcatcga ctccatcaaa    5700
cgcgtcgaga ttctttcgga ggtccaggcc cagctgtcgg tggaggctaa ggatgtcgat    5760
gccctcagcc gcacgcgcac ggtcggtgag gtcatcgatg ctatgaaggc cgagatttcg    5820
ggcggtcagc ccaccgcccc cgtgcaggtc gccgcgccca cccaggtcgt ggccccggtc    5880
aaggtttcca cgcccgtgga ctcgggcctt ctcgccaagg ccgagcaggt cgtgctggag    5940
gttctcgcct ccaagacggg ttacgagact gagctgattg agcttgacat ggagctggag    6000
actgagctgg gcattgactc catcaagcgc gtcgagatcc tctcggaggt ccaggcccag    6060
ctcaacgtcg aggccaagga cgtcgatgcc ctctcgcgca cccgcaccgt cggcgaggtc    6120
attgatgcca tgaaggccga gatcgctggc gatcagcctg ccccggctgt ggtcccggtg    6180
caggccaagt cgggtgtcgc gaaccccgcc ctcctcgcca aggcggagca ggtcgtgctg    6240
gaggtcctgg ccagcaagac gggctacgag actgagctta tcgagcttga catggagctt    6300
gagactgagc ttggtattga ctcgattaag cgcgttgaga tcctttccga ggtccaggcc    6360
gagctgtccg tggaggccaa ggatgtcgat gcgctctccc gcacccgcac ggtgggcgag    6420
gtcatcgacg ctatgaaggc cgagattgcc ggctccgcgg tcactgtcgc tacccttgac    6480
gactcgacca ttatggagga gactgacgac gaggacgagg actttatcct gtacgaccac    6540
```

```
gtctacggct ccgagtgcga ggatctctcg ctctcgttct cgtcggtcaa gtcgattcct    6600
cgcgcggaca agctcctgct ggacaacatt gccgagcgcc ccattgtcat tgtcgattgc    6660
ggcacgaagc tcacgaccga gctggcgaag gccatcggcg agcgcgctgt cgttgccacg    6720
ttctcggccc agtcgctcgt gtcccgtggc ttcgtgggca agagcttcac cctcggcaac    6780
accgaggagt cggagatcga gaagatggtg tcctccatcg agtcgtccta cggcaagatc    6840
ggcggctttg tctaccagca cttccatgac agcgactacg gtatgcagct cggctgggct    6900
ctcatggccg cgaagcacct caaggagtcc ctcaacgacc cgatcaagaa cggccgcacc    6960
tttttcctgg ctgtcgcccg catgaacggc aagctcggca tggacaacgc ctccgtccac    7020
gaccagggca tcgtcgagag ctgcggtatc gctgagcgtg gtgccatctt tggcctctgc    7080
aagaccctgg acctggagtg gcctaacgtg tttgcgcgcg gtgtggacat cgcggagggc    7140
atgtcctact ccctcgcggc cgagctgatc gtcgatgaga tcagctgcgc caacctttcg    7200
atccgcgaga gcggctacac tattagcggc gagcgcttca ccacggaggc gcacaagctc    7260
gtcacgggca agcctcacgc gcccatcaag aagaaggacg cctttctcgt gtcgggtggt    7320
gctcgcggca tcacgcccct gtgcattcgc gagattgcca aggccgtcaa gggtggcacc    7380
tacattctca tgggccgctc ggcgctcgcg gacgagcccc tctgggctaa cggcaagagc    7440
ggcaaggacc tcgacaaggc cggcctcgcc ttccttaagg aggagttcgc tgccggccgt    7500
ggctcgaagc ccaccccccaa ggtccacaag tcgctcatcg acaaggtcct cggcatccgc    7560
gaggttcgcg cgtccatcgc caacatcgag gcgcacggcg ctaaggccat ctacctctcg    7620
tgcgatgtgt cgagcgccga aaggtcaag gctgccgtcc agaaggtcga aaggagcat    7680 ctcgtccgca tcacgggcat cgtgcacgcc tccggcgtcc tgcgcgacaa gctcgtcgag    7740
aacaagaccc tcgacgactt taacgctgtg tacggcacga aggtcacggg cctcgtcaac    7800
ctccttagcg ccgtcaacat gaacttcgtc cgccacctgg tgatgttctc gtcgctcgct    7860
ggttaccacg gcaacgtcgg ccagtcggac tacgctatgg ccaacgagag ccttaacaag    7920
atcggcttcc gtcttggtgc cgcgtactcc cagctctgcg tcaagtccat ctgcttcggc    7980
ccttgggatg gcggcatggt gacgccggcg ctcaagaagc agttccagtc catgggcgtt    8040
cagatcatcc ctcgcgaggg tggcgccgag actgtcgctc gcattgtgct ctcgtccaac    8100
cccagccagg tcctcgtcgg caactggggc gtcccgcccg tcagcccccct ctccaagtcg    8160 gccaccatcg tccagacctt taccccctgag cttaacccct tcctcaagtc ccaccagatc    8220
cacggcaaga acgtcctgcc catgacggtc gccattggtt acctcgccca cctcgtgaag    8280 aactttacg ccggccacca cctctggggc gtggaggacg cgcagctctt ctccggcgtc    8340
gtcatcgacc acgccgtgca ggcccaggtc aagctcactg agcagagcct ggatgacgat    8400
ggcaaggtca aggtccaggc ggtgctcacc gcctcgaacg acaacggcaa gatggtgccg    8460
gcctacaagg ccgtcatcgt gctcggcaag acttcccgtc cggccttcat cctcaaggac    8520
ttttcgctcc aggagtccaa ctcgcgctcg gccgacgagc tgtacgacgg caagaccctg    8580
ttccacggcc cgctgttccg tggcatcacc aagctcctca acgtgtccga cactagcctc    8640
acgacccagt gcaccaacat cgatctcacc gccactgagc gcggcagtt tgccgacatc    8700 gagccggtca acccttttcat ggcggacgcc gccttccagg ccatgctcgt ctgggtccgc    8760
aacctccgta actccgccag ccttccgaac aactgcgagc gcgtcgatat ctacaagccc    8820
atcgcgcccg gcgagaagta ctacaccacg ctgcaggccc tcggcaacac ctccggctcg    8880
```

<210> SEQ ID NO 121
<211> LENGTH: 5880
<212> TYPE: DNA
<213> ORGANISM: Artificial Sequence
<220> FEATURE:
<223> OTHER INFORMATION: Codon-optimized PFA2

<400> SEQUENCE: 121

```
gttctcaagt ccgttttcta catgcatgac gagcagggcg aggtgttcct ctcgggccgc    8940
gccagcgtcg tggtcaacga taagatggaa ttctaa                              8976 atggtgaagc tttccgttgg tgacaacatt tgccacgatc agcgcgtcgc cgtggtcggc      60
atggccgtca tgtacgccgg ctgccagaac cagcacgagt tttggcagag cctccagggt     120
aagaacatga acagcaagag catcagccag aaccgcctgg gctccgagta ccgcgaggag     180
cactttaagc cggagcgctc gaagtacagc gacaccttct gcaacgagcg ttacggctgc     240
atcgacgaga cgtccagag cgagcatgag ctcctcctga gctcgctaa ggacgcgatc     300
gccgatacca agggcagcat cgaccttaac aagaccggca ttgtctccgg ctgcctctcg     360
ttccctatgg ataacctcca gggcgacctt ctcaacctct accagtgcca tattgagaag     420
aagatcggcc cgaacgccct caaggatgtc aacctctggt cgaagcgcac gaccaacggt     480
aaggacgata agaaggccta cttcgatccc gccagcttcg tcgctgagca gcttgacatg     540
ggtccctcc actactcgct cgacgctgcc tgcgcctccg ctctctacgt cctccgcctc     600
gcccaggacc acctcctcag cggtgccgcc gacaccatgc tctgcggcgc ctcgtgcctc     660
ccggagccct ttttcatcct ttcgggcttt tcgaccttcc acgccatgcc cctttcgggt     720
gacgtgtcgg cccctcttca agacgagc agggcctca ctccgggcga gggcggtgct     780
atcatggtcc tgaagcgcct caacgatgcc attcgcgacg cgaccgcat ctacggcacg     840
ctcctgggcg ccgagctttc aacgcgggt tgcgcctcc cgctctcccc gcacatgccg     900
tccgagttcg actgcatgga aaggccctc agcgcgttc accgcctccc gtcctccatc     960
cagtacgtgg agtgccacgc cactggcacc ccgcagggcg acaaggtcga gatcgacgcc    1020
atgacgaagt gcttcggcga gcatctgcct cgcttcggct ccaccaaggg taacttcggc    1080
cacacctcg tggctgctgg cttttgcgggc atgtgcaagg tcctcctctc gatgcagtac    1140
ggtgagattc ctcctacgcc tggcctggag aaccccgaca acattatgca cgatcttgtc    1200
gttaccgaga ctattccctg ccgaacacc aacggcgatc ttaagcgtgc gtgcctcagc    1260
gcctttggct ttggcggtac taacgcccac gccgtgttcg aggagtaccg cagcgacctt    1320
caggccaaca gaccccttga aacgagagc aagtcccacg agatcttttc ctcctttaag    1380
attgccattg ttggcatgga gtccgagttt ggcactctca agggcctcca ggagttcgag    1440
cgtgccatct acaacggcgg ccacggcgcg tgcgaccttc cggagaaccg ctggcgcttt    1500
ctcggtgagg acaaggagtt ctccaggcc tgcggcctcc agaagctccc gcgtggctgc    1560
tacatcaagg aggtcgagac tgactttaag cgccttcgcc tccccatgat ccaggaggac    1620
atcctccgcc cctccagct cctcgccgtg tcgatcatcg accgcgccct caacgccagc    1680
ggcgttaagc ccaacggcaa ggtcgccgtc ctcgtgggcc tcggcaccga tcttgagctc    1740
taccgccacc gcgctcgcgt cgccctgaag gagcgccttc agaccgccgt caaggaggac    1800
atcccctgc tggagaagct catgaactac gtgaacgacc gcggcacctc cacgtcctac    1860
acctcgtaca tcggcaacct cgttgcgacc cgcgtcagct cgctctgggg cttcaccggc    1920
cctagcttca cgatcacgga gggcgagaac tcggtttacc gttgcctcga cctcggccgc    1980
```

```
tggttcctcg ccaacggtga ggtcgatgcc gtggttgtcg ctggcgtgga tctctgcggc    2040
tcggccgaga acctgttcgt caagtcgcgc cgctccaagg tgtccaccca gaacgagccc    2100
tttgctaact ttgagtcgaa cgccgacggc tacttcgccg gcgacggctg cggtgccctc    2160
gttctcaagc gcctttcgga ctgcactgac tccaccgaga gatctacgc gaccgtggac     2220 agcattgctg tcggcgacga ggtgggcccg actattaagc aggccctgaa gaacgcctcg    2280
atcgccgcga aggacatcga gctcgcgag ctctccgcct ccagcggcaa gcaccactcc     2340
ggccgcatca cctgcgagga cgagcttaac gagctcggcg agatcttcaa cgagggcatt    2400
cagcgcgtgg ccatcggcag cgtcaaggcc aacgtcggcg acgtcggcta cgcctccggt    2460
gctgccagcc tcatcaagac ggccctctgc ctctacaacc gctacctccc caagctcccc    2520
aactggaaca gccgaccaa ggacgtcgag tggtcgaaga gcttctttgt ctgcgagcac     2580
tcgcgcgcct ggctcaagaa cgtggacgag aaccgccacg cggtcgtgag cggcgtctgc    2640
gagaacggct cctgctacgg catcgtcatg agcgacgtcc agggccacca tgaggagtcg    2700
aacctcgtgt ccctcgataa gaacgagccc aaggtgctcg gtatctacgg cgattccgtg    2760
gacgatattc tggtccagct gaacaagtac ctggagaagt ccttcaggga gactggcact    2820
gctgcggctg cgcagaaggt gaagagccct accattgaca tcgactcgaa cgtctttgcc    2880
gagatgctga accttcccca ggacaagaac aagaagtttg ccgtcgctct ggtcacgacc    2940
cccaacaagc tccagcgcga gattgagctc gccgttaagg gcatccctcg ctgcgtgaag    3000
gccaagcgcg actggtgctc cccctccggc agcatctttg cgtgcaaccc gctcaagtcg    3060
gacaacattg cctttatgta cggcgagggc cgctcgcctt acgccggcct cggctacgat    3120
ctccaccgca tctggcccat gcttcacgag ctcgtgaaca accgcacgac tgagctgtgg    3180
gaccagggtg actcgtggta cctgccgcgc agctcctccg tggccgagaa ggagaaggtc    3240
tttggcgact tcgacaagaa ccagatcgag atgttccgcc tcggtatttt cgtcagcatg    3300
tgctttaccg acatggcgac ggagctcctc ggccttaagc cgaaggccgc tttcggcctc    3360
tccctcggcg agatcagcat gctctttgct ttctcgaaga gaacaccaa gctctccaag     3420 gagcttactc gccgcctcaa ggaggccaag gtgtgggcgt cgcagctggc cgtcgagttc    3480
gccgccatcc gcgaccttg gaacatcccg gccgacaagt ccatcgatga gttctggcag    3540
ggttacttcg tttacgccaa ccgtacgctc gtggagaaca ccattggcga gaacaagttc    3600
gtccgcctcc ttatcgtcaa cgactcccag tcctgcctca ttgccggtaa gcccgatgag    3660
tgccagaagg tcatcgagaa gctccacctt aagctccccg ccgtcccgt cacccagggc    3720 atgattggcc actgcccgga ggccattccc tacctcgacc agatcagcca catccacgag    3780
atgcttgaga tcccgaagcc tgagaacgtc aagctcttca cgacgtccga gaaccgcgag    3840
cttgtctcga tgaaggactc cgttagcaag ctcgtcgcgg agatctacca gcacgtcgct    3900 gacttccccca acattgtcaa caaggtcaag gagacttgca agacggacat tttcatcgag    3960
ctgggcagca acaactaccg ttccggtgcc gtcaagacta tcctcggtcc ggagatcgtg    4020
agcgttgcca tcgaccgtca gaacgagact gcctgggcc agctcatgaa gatggtcgcc     4080
agcctgatct cccaccgcgt ccccggcgtc gagctcaaga gctgtacca tccgagctc      4140 ctgaagttcg atccccaggc caagcccaac cgctttatcc gcaacatcga gctcaacggc    4200
tttttcgacc gcacgaacat catcgtcgat aagcagcttt cccctgcgga cccgaagctc    4260
gccgagatcg tcaacaaccg caacatgccg aaggataacg tgtacgtccc cattgagcgc    4320
```

```
gtcaagacga tgatcaaggc cgagcccgct aacctccagg tgtccgtcgg ctcgaagccc    4380
gtggtcaccg agcgtatctc gtcggacgac aacctctttg agaagctctc ggagatcact    4440
aagtccttcg acggtgtcaa cgcctgcacc gaggccatgc tcggcgattc gggctttctc    4500
aagacgtacg aggttgacta cccgctctac accggcgcta tggccaaggg tatcgcctcc    4560
gccgacctcg tcattgcggc gggtaagtcg aagatccttg cgtcctttgg tgctggcggc    4620
ctcgctctcc aggtggtcga ggatgccatt aagcagatca aggctgagct tggcaacggt    4680 cccttttgccg tcaacctcat ccactcgcct ttcgaccccct cgcttgagaa gggcaacgtt    4740
gaccttttcc tcaagtacaa cgtccgcttt gtcgaggtga gcgcgttcat gagcctcacc    4800
ccccaggtcg ttcgctaccg cgctgccggc cttgccaagg cccgtgacgg ctcggtcaag    4860
attcagaacc gcatcatcgc caagatttcg cgcacggagc tggccgagct cttcctcaag    4920
cccgctccga gaacatcct cgatgccctc gttgccgacg gctcgatttc ccaggagcag    4980
gctcagctcg cgctcctcgt ccctatggcc gatgacatca ccgttgaggc cgactccggt    5040
ggccacaccg acaaccgccc cattcatgtg ctcctccccc tcatcatcca gcagcgcaac    5100
cgcatttgca gcagtaccc gaagcacctc aaggtccgca tcggcgctgc cggtggcatc    5160
ggttgcccta aggcggcttt tgccgccttt gagatgggtg cggcctacat cgccacgggc    5220
accgttaacc agctctcgaa ggaggccggc acctgcgact acgtgcgcaa ggtgctcaac    5280
aaggccacct actccgacgt cacgatggct cccgctgccg acatgttcga ccacggtgtc    5340
gagctccagg ttctcaagaa gggcaccatg tttccgtcgc gcgccaagaa gctctacgac    5400
ctctttaaga agtacaagtc gatcgaggag ctccctgccg acgaggtcaa gaagctggag    5460
cagaaggttt ttaagaagtc gttcgacgag gtctgggacg agactaagaa ctactacatt    5520
aaccgcctcc actcccctga gaagatcgag cgcgcggagc gtgacgccaa gctgaagatg    5580
tcgctctgct ttcgttggta cctgagcaag tcgtcccgct gggccaacac cggcgagtcg    5640
ggccgtgtcc aggactacca gatctggtgc ggccccgcca tcggctcgta caacgacttc    5700
gcgaagggct cgccctgcct tgaccctgag atccttggct cgttcccgtc ggttgtccag    5760
atcaacaagc atattctgcg cggcgcttgc ttctaccagc gtctttcgca gctcaagtac    5820
cttaacttca actacgagga gctcgatacg ctcacctaca gcgctagcaa ctttatctaa    5880
```

<210> SEQ ID NO 122
<211> LENGTH: 4368
<212> TYPE: DNA
<213> ORGANISM: Codon-optimized PFA3

<400> SEQUENCE: 122

```
atggttggcc tgcagatgaa gaagaagcct gtgtgggaga gtcgaagga ggagcagtcg      60 tccggcaaga acgtcgtctt tgactacgac gagctcctcg aattcgcgga gggtgacatc     120
ggcaaggtgt tcggccccaa gtttgacatc atcgacaagt acagccgccg tgtgcgcctc     180
ccggcccgcg agtacctcct cgtcacccgt gtcacgctct ggatgccgaa ggtcggcaac     240
ttccgcgtcg gctcgcgcat ggtcaccgag tacgacgtcc cggtgaacgg cgagctttcc     300
cagggcggcg acgttccctg gccgtcctc gtcgagtcgg ccagtgcgaa cctcatgctt     360
atctcgtaca tgggcattga ctttcagtgc aagggtgacc gcgtttaccg ccttctcaac     420
acgaccctca cgttctacgg tgtgcccac gagggcgaga ctctcgttta cgacatccgc     480
gtcactggtt tcgccaaggg catgcacggc gagattagca tgttcttctt cgagtacgac     540
tgctacgtca acggccgcct gctcatcgag atgcgcgacg gttgcgctgg cttcttcacg     600
```

-continued

```
gacgaggagc tcgccgcggg caagggcgtc atcaagaccg tcgctgagct ccacaagcgc    660
aagtcgattg tgcccaagtc gatcaagcct tttgccctca accccgccgt ccacaagacg    720
atgttcagcg agaacgacat ggagaagctt tgcgagcgcc agtgggagaa cgtcctcggc    780
tccggcctcc agggcatcga ctacaagctg tgcgcccgca agatgctcat gatcgaccgc    840
atcacgaaga tccagcacaa cggcggtgcg tacggcctcg gcctcctcgt tggcgagaag    900
attcttgagc gcgaccattg gtacttccct tgccacttcg tcaaggacca ggtgatggcg    960
ggctccctcg ttagcgacgg ctgctcgcag ctgctcaagc tttacatgct ttggctcggc   1020
ctccacgacg tggtccccga tttccagttc cgtcctgtcc ctggccagcc caacaaggtg   1080
cgctgccgtg gccagatcag cccccatcgt ggcaagctcg tgtacgtgat ggagattcgc   1140
gagatgggtt tcaacgagtc caccggccag ccctacgcga tcgctgacgt tgacattatc   1200
gatgtgaact acgagctcgg ccagtccttt gacatggccg acatcgactc gtacggccgt   1260
ggcaacctct ccaagaagat tgtcgtcgat ttcaagggca ttgcgctcca gatggagggc   1320
accgtcaaga gctccaacat catcgattcg tcccccaagt ccacgattat ccagccgccg   1380
cccaactgcc tccgcggcga tcctctcgcc ccctcgcagg tcacctggca cccgatggcc   1440
ggtgtcaacg gcgccccgc cccctccttc agcccgtcgg attaccctcc tcgtgccgtt   1500
tgctttaagc ccttcctggg caaccccctc gacaacgatc atacgccggg caagatgccg   1560
ctgacctggt ttaacatgtc ggagtttatg tgcggcaagg tcagcaactg ccttggccct   1620
gagtttaagc gcttcgacaa ctccaagacg agccgctccc cggccttcga cctggccctg   1680
gttacgcgcg tggtgtcggt cagcgatatg gagttcaagc cccacctcaa catcgacgtc   1740
aacccgtcga agggcacgat gattggcgag ttcgactgcc ccgctgacgc ctggttcttt   1800
cagggctcct gcaacgacgg ccacatgccg tacagcatcg tcatggagat cgcccttcag   1860
accagcggtg tcctcacctc cgtcctcaag gccccgctca ctatggacaa ggacgacatt   1920
ctctttcgca acctcgacgc caccgccgag atggtccgtt ccgacgtcga ttgccgcggt   1980
aagaccatca agaacttcac ccagtgcacc ggctacagca tgcttggcaa gatgggcatc   2040
caccgcttca ctttgagct ctcggtcgat gacgtcgtgt tttacaaggg ctcgaccagc   2100
tttggttggt tcacgccgga ggtgtttgag tcgcaggtcg gcctcgataa cggcaagaag   2160
gtccagccgt ggtatctgga gcagaagtcg tcgaacgtgg tgacgtacga tgtcgcctcg   2220
accgccggca aggacaagct cttctcgaag atcggctcga aggacgctca ggtccagcgt   2280
cgcaacaccc agtgcgagtt tctcgacacg atgcacatta ttccgaacac cggcaagtac   2340
aacaagggct acgcgcacgg tgagaagaag gtcaaccca cgactggtt cttctcctgc   2400
cacttttggt tcgacccgt gatgcccggc tccctcggta ttgagtccat gttccagctc   2460
atcgaggcct tttcgattga ccagggtatc gcgtccaagc atggcatcgt gaaccctacc   2520
ttcgcgcact cgaacggcaa gacctcgtgg aagtaccgcg ccagctcaa caacaagggc   2580
aagcgcatgg acagcgagat tcacatcaag gatattgtca gaacgccga cggtactgtc   2640
gatctcatcg ccgatggttt tcttctcgtg gactcgcttc gcgtttacag cgccgatgac   2700
ctccgcgtca agatcgtccc cggcactaag gctgctccca gagcgtcgc ggccgctccg   2760
cgccatgtgg ccactccgat ccccggcgtc ccctccaaca cctcctcggt ggagatctcg   2820
cttgagtccc ttaagaagga gctcctcaac ctggagaagc ccctctacct tgagacttcc   2880
aaccacatcg tcaagcagtt cggcgacgtt aacaacggcc aggcctccgt catccctccg   2940
```

```
tgcaccatta acgatctcgg tgagcgctcg tttatggaga cttacaacgt cgtcgctccc    3000
ctctacaccg gcgcgatggc gaagggcatc gcttcggcgg acctcgtcat cgctgccggt    3060
aagcgcaaga tcctcggcag cttcggcgcc ggtggcctcc cgatgcacct cgtgcgcgcc    3120
tcggtcgaga agatccaggc cgccctcccg gagggcccgt acgcggtcaa cctcatccac    3180
tcgcctttcg actcgaacct tgagaagggt aacgtggacc tctttctgga gaagggcgtc    3240
cacgtggtcg aggcctccgc ctttaccgcc ctcacgaccc aggtcgttcg ctaccgcgcc    3300
tgcggcctct cgcgtgctaa ggacggttcc gtgctgatta agaaccgcat catcggtaag    3360
gtcagccgca cggagcttgc cgagatgttc tttcgccctg ccccccagaa cctcctcgat    3420
aagctcatcg ccagcggcga gatcaccaag gagcaggcgt ccctcgctct tgaggttcct    3480
atggccgacg atgtcgctgt tgaggccgac tccggcggcc acaccgataa ccgtcccatc    3540
cacgtcatcc tcccgctgat tattaacctc cgcaaccgta tccacaagga gtgcggcttt    3600
cctgccgctc tccgcgtccg cgtcggcgct ggtggtggca tcggttgccc ctcggccgct    3660
gtcgccgcct tcaacatggg cgcggccttc ctgatcaccg gctccgttaa ccaggtgagc    3720
aagcagtccg gcacgtgcga cattgtgcgc aagcagctta gcgaggccag ctactccgac    3780
atcacgatgg ctcccgccgc tgacatgttc gaccagggcg tggagctcca ggtcctcaag    3840
aagggtacga tgtttccctc gcgcgccaag aagctctacg agctcttttg catgtacaac    3900
agctttgacg acatgccgaa gtccgagctc cagcgcctgg agaagcgcat tttccagaag    3960
agcctcgccg aggtctggga ggagactaag gacttttaca tcaaccgcct caacaacccg    4020
gagaagatcg agcacgccga agaaggac cccaagctca agatgtccct ttgctttcgc    4080
tggtatctcg gccttctgag cttttgggcc aacaacggca tcaaggagcg cagcatggat    4140
taccagattt ggtgcggccc ggccattggc agctacaacg acttcgtgaa gggcacctac    4200
ctcgaccccg ccgtcgccgg ttcgtacccc tgcgtggtcc agatcaacat gcagatcctc    4260
cgcggtgcgt gcttcctcca gcgcgtccgc gccattaagc acgacccgcg cctcgatatc    4320
gacgttgatg aggacgtctt tacctaccgc cccgagagca ccctctcaa                4368
```

<210> SEQ ID NO 123
<211> LENGTH: 33
<212> TYPE: DNA
<213> ORGANISM: Artificial Sequence
<220> FEATURE:
<223> OTHER INFORMATION: Synthetic Primer pDS233
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (28)..(28)
<223> OTHER INFORMATION: y is c or t

<400> SEQUENCE: 123
tgatatggga ggaatgaatt gtgtngtnga ygc                                33

<210> SEQ ID NO 124
<211> LENGTH: 36
<212> TYPE: DNA
<213> ORGANISM: Artificial Sequence
<220> FEATURE:
<223> OTHER INFORMATION: Synthetic Primer pDS235

```
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (34)..(34)
<223> OTHER INFORMATION: r is a or g

<400> SEQUENCE: 124
ttccataaca aaatgataat tagctccncc raancc                                36

<210> SEQ ID NO 125
<211> LENGTH: 23
<212> TYPE: DNA
<213> ORGANISM: Artificial Sequence
<220> FEATURE:
<223> OTHER INFORMATION: Synthetic Primer prDS183
<220> FEATURE:
<221> NAME/KEY: misc_feature
<222> LOCATION: (15)..(15)
<223> OTHER INFORMATION: y is c or t
<220> FEATURE:
<221> NAME/KEY: misc_feature
<222> LOCATION: (19)..(19)
<223> OTHER INFORMATION: m is a or c
<220> FEATURE:
<221> NAME/KEY: misc_feature
<222> LOCATION: (21)..(21)
<223> OTHER INFORMATION: n is a, c, g, or t

<400> SEQUENCE: 125
ggcggccaca ccgayaaymg ncc                                             23

<210> SEQ ID NO 126
<211> LENGTH: 22
<212> TYPE: DNA
<213> ORGANISM: Artificial Sequence
<220> FEATURE:
<223> OTHER INFORMATION: Synthetic Primer prDS184
<220> FEATURE:
<221> NAME/KEY: misc_feature
<222> LOCATION: (14)..(14)
<223> OTHER INFORMATION: r is a or g

<400> SEQUENCE: 126
cggggccgca ccanayytgr ta                                              22

<210> SEQ ID NO 127
<211> LENGTH: 17
<212> TYPE: DNA
<213> ORGANISM: Synthetic Primer prDS181
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: s is c or g
<220> FEATURE:
<221> NAME/KEY: misc_feature
<222> LOCATION: (15)..(15)
<223> OTHER INFORMATION: n is a, c, g, or t

<400> SEQUENCE: 127
tccttcggng cngsngg                                                    17
```